United States Patent
Berry et al.

(10) Patent No.: US 11,672,834 B2
(45) Date of Patent: *Jun. 13, 2023

(54) PROBIOTIC AND PREBIOTIC COMPOSITIONS, AND METHODS OF USE THEREOF FOR MODULATION OF THE MICROBIOME

(71) Applicant: Evelo Biosciences, Inc., Cambridge, MA (US)

(72) Inventors: David Berry, Waban, MA (US); Noubar B. Afeyan, Lexington, MA (US); Johanne Kaplan, Sherborn, MA (US); Shaila Rahman, Cambridge, MA (US)

(73) Assignee: Evelo Biosciences, Inc., Cambridge, MA (US)

( * ) Notice: Subject to any disclaimer, the term of this patent is extended or adjusted under 35 U.S.C. 154(b) by 132 days.

This patent is subject to a terminal disclaimer.

(21) Appl. No.: 17/214,562

(22) Filed: Mar. 26, 2021

(65) Prior Publication Data

US 2022/0323511 A1 Oct. 13, 2022

Related U.S. Application Data

(63) Continuation of application No. 14/952,891, filed on Nov. 25, 2015, now Pat. No. 10,980,845.

(60) Provisional application No. 62/257,714, filed on Nov. 19, 2015, provisional application No. 62/162,562, filed on May 15, 2015, provisional application No. 62/117,639, filed on Feb. 18, 2015, provisional application No. 62/117,637, filed on Feb. 18, 2015, provisional application No. 62/117,632, filed on Feb. 18, 2015, provisional application No. 62/084,536, filed on Nov. 25, 2014, provisional application No. 62/084,540, filed on Nov. 25, 2014, provisional application No. 62/084,537, filed on Nov. 25, 2014.

(51) Int. Cl.

| | |
|---|---|
| A61K 35/74 | (2015.01) |
| A61K 35/741 | (2015.01) |
| A61K 35/742 | (2015.01) |
| A61K 31/7004 | (2006.01) |
| A61K 35/744 | (2015.01) |
| A61K 31/715 | (2006.01) |
| A61K 38/46 | (2006.01) |
| A61K 35/39 | (2015.01) |
| A61P 29/00 | (2006.01) |
| A61P 37/00 | (2006.01) |
| A61P 43/00 | (2006.01) |
| A61K 9/00 | (2006.01) |
| A61K 35/745 | (2015.01) |
| A61K 35/747 | (2015.01) |
| A61K 9/19 | (2006.01) |
| A61K 31/7016 | (2006.01) |
| A61K 35/00 | (2006.01) |

(52) U.S. Cl.
CPC ............ *A61K 35/74* (2013.01); *A61K 9/0031* (2013.01); *A61K 9/0053* (2013.01); *A61K 9/19* (2013.01); *A61K 31/7004* (2013.01); *A61K 31/7016* (2013.01); *A61K 31/715* (2013.01); *A61K 35/39* (2013.01); *A61K 35/741* (2013.01); *A61K 35/742* (2013.01); *A61K 35/744* (2013.01); *A61K 35/745* (2013.01); *A61K 35/747* (2013.01); *A61K 38/46* (2013.01); *A61P 29/00* (2018.01); *A61P 37/00* (2018.01); *A61P 43/00* (2018.01); *A61K 2035/115* (2013.01); *Y02A 50/30* (2018.01)

(58) Field of Classification Search
None
See application file for complete search history.

(56) References Cited

U.S. PATENT DOCUMENTS

| | | |
|---|---|---|
| 6,506,380 B1 | 1/2003 | Isolauri et al. |
| 7,172,756 B2 | 2/2007 | Isolauri et al. |
| 7,235,395 B2 | 6/2007 | Stadler et al. |
| 7,627,437 B2 | 12/2009 | Forney et al. |
| 7,749,494 B2 | 7/2010 | Renaud et al. |
| 8,318,151 B2 | 11/2012 | Darimont-Nicolau et al. |
| 8,486,668 B2 | 7/2013 | Ritter et al. |
| 9,603,878 B2 | 3/2017 | Berry et al. |
| 9,610,307 B2 | 4/2017 | Berry et al. |
| 9,700,609 B2 | 7/2017 | Larkin et al. |
| 10,869,903 B2 | 12/2020 | Berry et al. |
| 10,980,845 B2 | 4/2021 | Berry et al. |
| 2003/0147858 A1 | 8/2003 | Renaud et al. |
| 2004/0265290 A1 | 12/2004 | Stadler et al. |
| 2005/0180961 A1 | 8/2005 | Pecquet et al. |

(Continued)

FOREIGN PATENT DOCUMENTS

| | | |
|---|---|---|
| CA | 1333564 C | 12/1994 |
| CA | 2966132 A1 | 4/2016 |

(Continued)

OTHER PUBLICATIONS

Tagirasa., "Tnf-α negatively regulates Th2 differentiation in humans," Canadian Journal of Biotechnology, 1: p. 158 (2017).

(Continued)

*Primary Examiner* — Teresa E Knight
(74) *Attorney, Agent, or Firm* — Foley Hoag LLP

(57) ABSTRACT

Probiotic compositions containing non-pathogenic microbial entities, e.g., bacterial entities, are described herein. The probiotic compositions may optionally contain or be used in conjunction with one or more prebiotics. Uses of the probiotic compositions to treat or prevent disorders of the local or systemic microbiome in a subject are also provided.

20 Claims, 99 Drawing Sheets

Specification includes a Sequence Listing.

(56) References Cited

U.S. PATENT DOCUMENTS

| | | |
|---|---|---|
| 2006/0088513 A1 | 4/2006 | Inoue et al. |
| 2007/0128303 A1 | 6/2007 | Chang et al. |
| 2007/0207132 A1 | 9/2007 | Speelmans et al. |
| 2007/0280912 A1 | 12/2007 | Cobb et al. |
| 2008/0254058 A1 | 10/2008 | Glenting et al. |
| 2009/0110664 A1 | 4/2009 | Moore |
| 2009/0148545 A1 | 6/2009 | Falk et al. |
| 2010/0074872 A1 | 3/2010 | Blaser et al. |
| 2010/0310514 A1 | 12/2010 | Cho et al. |
| 2010/0316617 A1 | 12/2010 | Renaud et al. |
| 2011/0097361 A1 | 4/2011 | Tang |
| 2011/0280840 A1 | 11/2011 | Blaser et al. |
| 2011/0287072 A1 | 11/2011 | Ritter et al. |
| 2012/0034322 A1 | 2/2012 | Oda et al. |
| 2012/0149584 A1 | 6/2012 | Olle et al. |
| 2012/0276149 A1 | 11/2012 | Littman et al. |
| 2013/0122147 A1 | 5/2013 | Tissot-Favre et al. |
| 2013/0330414 A1 | 12/2013 | Santamaria |
| 2014/0199281 A1 | 7/2014 | Henn et al. |
| 2014/0271721 A1 | 9/2014 | Walser et al. |
| 2014/0271836 A1 | 9/2014 | Walser et al. |
| 2014/0328803 A1 | 11/2014 | McKenzie et al. |
| 2014/0341921 A1 | 11/2014 | Honda et al. |
| 2014/0363397 A1 | 12/2014 | Allen-Vercoe et al. |
| 2016/0143961 A1 | 5/2016 | Berry et al. |
| 2016/0143962 A1 | 5/2016 | Berry et al. |
| 2016/0193258 A1 | 7/2016 | Berry et al. |
| 2016/0199424 A1 | 7/2016 | Berry et al. |
| 2016/0235792 A1 | 8/2016 | Berry et al. |
| 2016/0271188 A1 | 9/2016 | Berry et al. |
| 2017/0065554 A1 | 3/2017 | Heiman et al. |
| 2017/0151291 A1 | 6/2017 | Henn et al. |
| 2018/0015130 A1 | 1/2018 | Berry et al. |
| 2018/0046774 A1 | 2/2018 | Lindahl et al. |
| 2018/0071344 A1 | 3/2018 | Berry et al. |
| 2018/0169153 A1 | 6/2018 | Berry et al. |
| 2018/0280454 A1 | 10/2018 | Garcia-Rodenas et al. |
| 2019/0336543 A1 | 11/2019 | Berry et al. |
| 2020/0061129 A1 | 2/2020 | Berry et al. |
| 2022/0016185 A1 | 1/2022 | Hsiao et al. |

FOREIGN PATENT DOCUMENTS

| | | |
|---|---|---|
| EP | 2308498 A1 | 4/2011 |
| EP | 2967077 A2 | 1/2016 |
| EP | 3297727 A1 | 3/2018 |
| EP | 3587558 A2 | 1/2020 |
| JP | 2005058092 A | 3/2005 |
| JP | 2006/067881 A | 3/2006 |
| JP | 2006067881 A | 3/2006 |
| JP | 2006104107 A | 4/2006 |
| JP | 2007055986 A | 3/2007 |
| WO | WO-96/11014 A1 | 4/1996 |
| WO | WO-2001/85187 A1 | 11/2001 |
| WO | WO-2006/091103 A2 | 8/2006 |
| WO | WO-2008/031438 A2 | 3/2008 |
| WO | WO-2011/107481 A2 | 9/2011 |
| WO | WO-2011/110918 A1 | 9/2011 |
| WO | WO-2011/152566 A2 | 12/2011 |
| WO | WO-2012/016287 A2 | 2/2012 |
| WO | WO-2012/024638 A2 | 2/2012 |
| WO | WO-2012/142605 A1 | 10/2012 |
| WO | WO-2013/037068 A1 | 3/2013 |
| WO | WO-2013/053836 A1 | 4/2013 |
| WO | WO-2013050792 A1 | 4/2013 |
| WO | WO-2013/080561 A1 | 6/2013 |
| WO | WO-2014/078911 A1 | 5/2014 |
| WO | WO-2014/088982 A1 | 6/2014 |
| WO | WO-2014/121298 A2 | 8/2014 |
| WO | WO-2014/121302 A2 | 8/2014 |
| WO | WO-2014/121304 A1 | 8/2014 |
| WO | WO-2014/145958 A2 | 9/2014 |
| WO | WO-2014/150094 A1 | 9/2014 |
| WO | WO-2014/152338 A1 | 9/2014 |
| WO | WO-2014/153194 A2 | 9/2014 |
| WO | WO-2014/201037 A2 | 12/2014 |
| WO | WO-2015/006355 A2 | 1/2015 |
| WO | WO-2015/077794 A1 | 5/2015 |
| WO | WO-2015/082151 A1 | 6/2015 |
| WO | WO-2015/095241 A2 | 6/2015 |
| WO | WO-2016/033439 A2 | 3/2016 |
| WO | WO-2016/086209 A8 | 6/2016 |
| WO | WO-2016/086206 A8 | 7/2016 |
| WO | WO-2016/203218 A1 | 12/2016 |
| WO | WO-2017/115001 A1 | 7/2017 |
| WO | WO-2017/152137 A2 | 9/2017 |
| WO | WO-2018/106845 A1 | 6/2018 |
| WO | WO-2018/109461 A1 | 6/2018 |

OTHER PUBLICATIONS

Tanabe., "The Effect of Probiotics and Gut Microbiota on Th17 Cells," International Reviews of Immunology, 32: 511-525 (2013).
Certified copy of priority document for Application No. GB 1510466.4 dated Jun. 23, 2016.
Certified copy of priority document for Application No. GB 1520508.1 dated Jun. 23, 2016.
Decision reviewing priority of the Opposed patent for EP 3240554 B1 dated Apr. 4, 2022.
Extract from the Register of European Patents confirming entry of PCT/GB2016/051770 into the EP regional phase (2022).
National Institutue of Health and Care Excellence; "Faecal calprotection diagnostic tests for inflammatory: Diagnostics Guidance," retrieved online: ww.nice.org.uk/guidance/dg11>: 56 pages (Oct. 2, 2013).
Adamu et al., "Bacteriotherapy for the treatment of intestinal dysbiosis caused by Clostridium difficile infection," Current Opinion in Microbiology, 16: 596-601, (2013).
Aguilera et al., "Aga1, the first alpha-Galactosidase from the human bacteria Ruminococcus gnavus E1, efficiently transcribed in gut conditions," Research in Microbiology, 163: 14-21 (2012).
Andermann et al., "Microbiota Manipulation With Prebiotics and Probiotics in Patients Undergoing Stem Cell Transplantation," Current Hematologic Malignancy Reports, 11(1): 19-28 (2016).
Aristilde et al., "Hierarchy in Pentose Sugar Metabolism in Clostridium acetobutylicum," Applied and Environmental Microbiology, 81(4): 1452-1462 (2015).
Arumugam et al., "Enterotypes of the human gut microbiome," Nature, 473(12): 174-180 (2011).
Atarashi et al., "Treg induction by a rationally selected mixture of Clostridia strains from the human microbiota," Nature, 500(7461): 232-236 (2013).
Atarashi et al., "Induction of Colonic Regulatory T Cells by Indigenous Clostridium Species," Science, 331 (6015): 337-341 (2011).
Atarod, S. et al., "Elevated level of HSPA 1L mRNA correlates with graft-versus-host disease," Transplant Immunology 32: 188-194 (2015).
Baxter et al., "Structure of the gut microbiome following colonization with human feces determines colonic tumor burden," Microbiome Journal, 2(20): 1-11 (2014).
Beelen et al., "Influence of Intestinal Bacterial Decontamination Using Metronidazole and Ciprofloxacin or Ciprofloxacin Alone on the Development of Acute Graft-Versus-Host Disease After Marrow Transplantation in Patients With Hematologic Malignancies: Final Results and Long-Term Follow-Up of an Open-Label Prospective Randomized Trial," Blood, 93(10): 3267-3275 (1999).
Belief et al., "Circadian clock regulates the host response to *Salmonella*," PNAS, 110(24):9897-9902 (2013).
Bercik et al., "Microbes and the gut-brain axis," Neurogastroenterology & Motility, 24(5): 405-413, (2012).
Bermudez-Brito et al., "The impact of dietary fibers on dendritic cell responses in vitro is dependent on the differential effects of the fibers on intestinal epithelial cells," Molecular Nutrition Food Research, 59(4): 698-710 (2015).
Bernalier et al., "*Ruminococcus hydrogenotrophicus* sp. nov., a new H2/CO2-utilizing acetogenic bacterium isolated from human feces," Archives of Microbiology, 166: 176-183 (1996).

(56) References Cited

OTHER PUBLICATIONS

Bernard et al., "Dietary Pectin-Derived Acidic Oligosaccharides Improve the Pulmonary Bacterial Clearance of Pseudomonas aeruginosa Lung Infection in Mice by Modulating Intestinal Microbiota and Immunity," J Infectious Diseases, 211: 156-165 (2015).
Biagi et al., "Gut microbiota trajectory in pediatric patients undergoing hematopoietic SCT," Bone Marrow Transplantation, 50: 992-998 (2015).
Biddle et al., "Untangling the Genetic Basis of Fibrolytic Specialization by Lachnospiraceae and Ruminococcaceae in Diverse Gut Communities," Diversity, 5: 627-640 (2013).
Bischoff et al., "Intestinal permeability—a new target for disease prevention and therapy," BMC Gastroenterology, 14: Article 189 (2014).
Blaut, "Gut microbiota and energy balance: role in obesity," Proceedings of the Nutrition Society, 74(3): 227-234 (2015).
Borody et al., "Bacteriotherapy Using Fecal Flora: Toying With Human Motions," Journal of Clinical Gastroenterology, 38(6): 475-483 (2004).
Brown et al., "Extracellular vesicles produced by the gram-positive bacterium bacillus subtilis are disrupted by the lipopeptide surfactin," Molecular Microbiology, 93(1):183-198 (2014).
Buffie et al., "Precision microbiome reconstitution restores bile acid mediated resistance to Clostridium difficile," Nature, 517: 205-208 (2015).
Candon et al., "Antiobiotics in Early Life Alter the Gut Microbiome and Increase Disease Incidence in a Spontaneous Mouse Model of Autoimmune Insulin-Dependent Diabetes," PLOS ONE, 10(5): 1-16 (2015).
Cani et al., "Gut microbiota, enteroendocrine functions and metabolism," Current Opinion on Pharmacology, 13(6):935-940 (2013).
Cassir et al., "Clostridium butyricum Strains and Dysbiosis Linked to Necrotizing Enterocolitis in Preterm Neonates," Clinical Infectious Diseases, 1-9, 2015.
Chambers et al., "Control of appetite and energy intake by SCFA: what are the potential underlying mechanisms?," Proceedings of the Nutrition Society, 74(3): 328-336 (2015).
Chen et al., "Arabinoxylan in Wheat Is More Responsible Than Cellulose for Promoting Intestinal Barrier Function in Weaned Male Piglets," The Journal of Nutrition, 145: 51-58 (2015).
Chen et al., "Diet and Parkinson's disease: A potential role of dairy products in men," Annals of Neurology, 52(6): 793-801 (2002).
Clavel et al., "Phylogeny of human intestinal bacteria that activate the dietary lignan secoisolariciresinal diglucoside," FEMS Microbiol. Ecol., 55: 471-478 (2006).
Cobo, E. et al., "Colonic MUC2 mucin regulates the expression and antimicrobial activity of Beta-defensin 2," Mucosal Immunology, 8: 1360-1372 (2015).
Costello et al., "Bacterial Community Variation in Human Body Habitats Across Space and Time," Science, 326(5960): 1694-1697 (2009).
Crost et al., "Utilisation of Mucin Glycans by the Human Gut Symbiont Ruminococcus gnavus Is Strain-Dependent," Plos One, 8(1): e76341 (2013).
Cuervo et al., "Association of Polyphenols from Oranges and Apples with Specific Intestinal Microorganisms in Systemic Lupus Erythematosus Patients," Nutrients, 7(2): 1301-1317 (2015).
Cuiv et al., "Isolation of Genetically Tractable Most-Wanted Bacteria by Metaparental Mating," Scientific Reports, 5: e13282 (2015).
Cuskin et al., "Human gut Bacteroidetes can utilize yeast mannan through a selfish mechanism," Nature, 517: 165-169 (2015).
Datcu, "Characterization of the vaginal microflora in health and disease," Dan Med J, 61(4): B4830 (2014).
David et al., "Diet rapidly and reproducibly alters the human gut microbiome," Nature, 505: 559-563 (2014).
De Vrese et al., "Probiotics, Prebiotics, and Synbiotics," Adv Biochem Engin/Biotechnol., 111: 1-66 (2008).
Devlin et al., "A biosynthetic pathway for a prominent class of microbiota-derived bile acids," Nature Chemical Biology, 11: 685-690 (2015).

Docampo et al., "Emerging Influence of the Intestinal Microbiota during Allogeneic Hematopoietic Cell Transplantation: Control the Gut and the Body Will Follow," Biology of Blood and Marrow Transplant, 21(8): 1360-1366 (2015).
Donelli et al., "Enteric Toxins from Bacteria Colonizing Human Gut," Microbial Ecology in Health and Disease, Supplement 2: 194-208 (2000).
Dotan et al., "Probiotics in inflammatory bowel disease: possible mechanisms of action," Current Opinion in Gastroenterology, 21(4): 426-430 (2005).
Duncan et al., "Proposal of a neotype strain (A1-86) for Eubacterium rectale. Request for an Opinion," International Journal of Systematic and Evolutionary Microbiology, 58: 1735-1736 (2008).
Edwards et al. "Initiation of sporulation in Clostridium difficile: a twist on the classic model," FEMS Microbiology Letters, 358: 110-118 (2014).
Emanuelsson et al., "Allergens as eukaryotic proteins lacking bacterial homologues," Molecular Immunology, 44:3256-3260 (2007).
Eren et al. "A single genus in the gut microbiome reflects host preference and specificity," The ISME Journal, 9: 90-100 (2015).
Eriguchi et al., "Graft-versus-host disease disrupts intestinal microbial ecology by inhibiting Paneth cell production of a-defensins," Blood, 120(1): 223-231 (2012).
European Food Safery Authority, "Appendix: The 2013 updated list of QPS status recommended biological agents in support of EFSA risk assessments—3rd revision (new additions)," EFSA Journal, 13(12):4331 (2015).
Everard et al., "Gut microbiota and GLP-1," Rev Endocr Metab Disord, 15: 189-196 (2014).
Everard et al., "Responses of Gut Microbiota and Glucose and Lipid Metabolism to Prebiotics in Genetic Obese and Diet-Induced Leptin-Resistant Mice," Diabetes, 60: 2775-2786 and supplementary data pages (2011).
Extended European Search Report for EP Application No. EP 20171785 dated Nov. 6, 2020.
Finegold et al., "Gastrointestinal Microflora Studies in Late-Onset Autism," Clinical Infectious Diseases, 35(1): S6-S16 (2002).
Flynn et al., Bile diversion to the distal small intestine has comparable metabolic benefits to bariatric surgery,: Nat Commun, 6: 7715 <doi: 10.1 038/ncomms8715.> (2015).
Fordtran et al., "Intestinal Absorption of D-Xylose in Man," New England J Med, 267(6): 274-279(1962).
Friedl et al., "Carbon Source Dependence and Photostimulation of Conidiation in Hypocrea atroviridis," Applied and Environmenal Microbiology, 74(1): 245-250 (2008).
Furet et al., "Comparative assessment of human and farm animal faecal microbiota using real-time quantitative PCR," FEMS Microbil. Ecol., 68: 351-362 (2009).
Furuya et al., "Isolation of a novel bacterium, *Blautia glucerasei* sp. nov. hydrolyzing plant glucosylceramide to ceramide," Archives of Microbiology, 192: 365-372 (2010).
Garcia-Rodenas et al., "Nutritional Approach to Restore Impaired Intestinal Barrier Function and Growth After Neonatal Stress in Rats," Journal of Pediatric Gastroenterology and Nutrition, 43(1): 16-24 (2006).
Gerbitz et al., "Probiotic effects on experimental graft-versus host disease: let them eat yougurt," Blood, 103(11): 4365-4367 (2004).
Goodman et al., "Identifying Genetic Determinants Needed to Establish a Human Gut Symbiont in Its Habitat," Cell Host & Microbe, 6: 279-289 (2009).
Goto et al., "Innate lymphoid cells regulate intestinal epithelial cell glycosylation," Science, 345(6202): 12 pages (2014).
Gould <https://blogs.scientificamerican.com/lab-rat/the-bacteria-in-breast-milk/?print=true> (2013).
Grimoud et al., "In vitro screening of probiotics and synbiotics according to anti-inflammatory and anti-proliferative effects," Int J Food Micribol, 144: 42-50 (2010).
Gu et al., "Reconstruction of xylose utilization pathway and regulons in Firmicutes." BMC Genomics, 11(255): 1-14 (2010).
Hakansson et al., "Gut microbiota and inflammation," Nutrients, 3: 637-682 (2011).

(56) References Cited

OTHER PUBLICATIONS

Hansen et al., "Two Cases of Ruminococcus gnavus Bacteremia Associate with Diverticulitis," Journal of Clinical Microbiology, 51(4): 1334-1336 (2013).
Harnicar et al., "Intensified Mycophenolate Mofetil Dosing and Higher Mycophenolic Acid Trough Levels Reduce Severe Acute Graft-versus-Host Disease after Double-Unit Cord Blood Transplantation," Biol Blood Marrow Transplant, 21: 920-925 (2015).
Hartman et al., "Human gut microbiome adopts an alternative state following small bowel transplantation," PNAS, 106(4): 17187-17192 (2009).
Hartvigsen et al., "Postprandial effects of test meals including concentrated arabinoxylan and whole grain rye in subjects with the metabolic syndrome: a randomized study," Eur J Clin Nutrition, 68: 567-574 (2014).
Hayashi et al., "A Single Strain of Clostridium butyricum Induces Intestinal IL-1 0-Producing Macrophages to Supress Acute Experimental Colitis in Mice," Cell Host & Microbe, 13(6): 711-722 (2013).
He et al., "Transmissable microbial and metabolomic remodeling by soluble dietary fiber improves metabolic homeostasis," Sci Rep 5, 10604; <doi: 10.1 038/srep1 0604>: 12 pages (2015).
Heimesaat et al., "MyD88/TLR9 mediated immunopathology and gut microbiota dynamics in a novel murine model of intestinal graft-versus-host disease," Gut, 59: 1079-1087 (2010).
Hennet et al., "Decoding breast milk oligosaccharides," Swiss Med Wkly, 144: w13927 (2014).
Heuvelin et al., "Mechanisms Involved in Alleviation of Intestinal Inflammation by Bifidobacterium Breve Soluble Factors," PLoS One, 4(4): e5184 (2009).
Hooper et al., "Interactions Between the Microbiota and the Immune System," Science, 336: 1268-1273 (2012).
Hougee et al., "Oral Treatment with Probiotics Reduces Allergic Symptoms in Ovalbumin-Sensitized Mice: A Bacterial Strain Comparative Study," International Archives of Allergy and Immunology, 151(2): 107-117 (2010).
Hu et al., "Microbiota-induced activation of epithelial IL-6 signaling links inflammasome-driven inflammation with transmissible cance," PNAS, 110(24): 9862-9867 (2013).
Ingerslev et al., "Resistant starch and arabinoxylan augment SCFA absorption, but affect postprandial glucose and insulin responses differently," Br J Nutrition, 111: 1564-1576 (2014).
International Search Report and Written Opinion for International Application No. PCT/US2015/062805 dated Jul. 4, 2016.
International Search Report and Written Opinion for International Application No. PCT/US2015/062806 dated Mar. 9, 2016.
International Search Report and Written Opinion for International Application No. PCT/US2015/062808 dated Feb. 24, 2016.
International Search Report and Written Opinion for International Application No. PCT/US2015/062809 dated Mar. 7, 2016.
International Search Report and Written Opinion for International Application No. PCT/US2015/062810 dated May 19, 2016.
Ivanov et al., "Induction of Intestinal Th17 Cells by Segmented Filamentous Bacteria," Cell, 139(3): 485-498 (2009).
Jain et al., "Influence of synbiotic containing Lactobacillus acidophilus La5, Bifidobacterium lactis Bb 12, *Streptococcus thermophilus*, Lactobacillus bulgaricus and oligofructose on gut barrier function and sepsis in critically ill patients: a randomised controlled trial," Clinical Nutrition, 23(4): 467-475 (2004).
Jenq et al., "Identification of Intestinal Commensal Bacteria Protective Against GVHD in Mice and Humans," Biol Blood Marrow Transplant, 20: S22-23 (2014).
Jenq et al., "Intestinal Blautia Is Associated with Reduced Death from Graft-versus-Host Disease," Biol Blood Bone Marrow, 21(8): 1373-1383 (2015).
Jenq et al., "Intestinal Microbiota in Bone Marrow Transplantation," Blood, 120(21 ): 51 (2012).
Jenq et al., "Regulation of intestinal inflammation by microbiota following allogeneic bone marrow transplantation," J Exp Med, 209(5): 903-911 (2012).
Jeon et al., "Probiotic Bifidobacterium breve induces IL-10-producing Tr1 cells in the colon," PLoS Pathogens, 8(5): e1002714 (2012).
Johansson et al., "Bacteria penetrate the normally impenetrable inner colon mucus layer in both murine colitis and models and patients with ulcerative colitis," Gut, 63: 281-291 (2014).
Johnson et al., "Xylose utilization and short-chain fatty acid production by selected components of the intestinal microflora of a rodent pollinator (*Aethomys namaqunsis*)," J Comp Physiol B, 176: 631-641 (2006).
Kanai et al., "A breakthrough in probiotics: Clostridium butyricum regulates gut homeostasis and anti-inflammatory response in inflammatory bowel disease," J Gastroenterol, 50: 928-939 (2015).
Kanauchi et al., "Eubacterium limosum (probiotic) and its Metabolites Showed Anti-Inflammatory Effects and Increased Mucosal Barrier Function in Colitis," AGA Abstracts, Abstract S1 912: A-281 (2005).
Kano et al., "Oral administration of milk fermented with *Lactobacillus delbrueckii* ssp. Bulgaricus OLL 1 073R-1 to DBN1 mice inhibits secretion of proinflammatory cytokines," Cytotechnology, 40: 67-73 (2002).
Kanuachi et al., "Eubacterium limosum ameliorates experimental colitis and metabolite of microbe attenuates colonic inflammatory action with increase of mucosal integrity," World J Gastroenterol, 12(7): 1071-1077 (2006).
Keshavarzian et al., "Colonic Bacterial Composition in Parkinson's Disease," Movement Disorders, 30(10): 1351-1360 (2015).
Kim et al., "Extracellular vesicle-derived protein from Bifidobacterium longum alleviates food allergy through mast cell suppression," J Allergy Clin Immunol, 137:507-516(2016).
Kim et al., "Metabolism of Kaempferia parviflora Polymethoxyflavones by Human Interstinal Bacterium *Bautia* sp. MRG-PMF1 ," Journal of Agricultural and Food Chemistry, 62: 12377-12383 (2014).
Kim et al., "Simultaneous consumption of pentose and hexose sugars: an optimal microbial phenotype for efficient fermentation of lignocellulosic biomass," Appl Microbiol Biotechnol, 88: 1077-1085 (2010).
Kinnebrew et al., "Early Clostridium difficile Infection during Allogenic Hematopoietic Stem Cell Transplantation," Plos One, 9(3): 1-9 (2014).
Kohanski et al., "How antibiotics kill bacteria: from targets to networks," Nat Rev Microbiol, 8(6):423-435 (2010).
Kong et al., "Oral Administration of Clostridium butyricum for Modulating Gastrointestinal Microflora in Mice", Current Microbiology, 62: 512-517 (2011).
Kontiokari et al., "Effect of Xylitol on Growth of Nasopharyngeal Bacteria In Vitro," Antimicrobial Agents and Chemotherapy, 39(8): 1820-1823, (1995).
Kreisman et al., "Glycoantigens Induce Human Peripheral Tr1 Cell Differentiation with Gut-homing Specialization," Journal of Biological Chemistry, 286(11): 8810-8 (2011).
La Scola et al., "Aerobic culture of anaerobic bacteria using antioxidants: a preliminary report," European Journal of Clinical Microbiology & Infectious Diseases, 33(1): 1781-1783 (2014).
Langlands et al., "Prebiotic carbohydrates modify the mucosa associated microflora of the human large bowel," Gut, 53: 1610-1616 (2004).
Lawson et al., "Reclassification of Ruminococcus obeum as *S/autia obeum* comb, nov.," Intl J System Evol Microbiol 65: 789-793 (2015).
Lee et al., "Has the Microbiota played a Critical Role in the Evolution of the Adaptive Immune System?" Science, 330: 1768-1773 (2010).
Lee et al., "Transcription facter oB plays an important role in the production of extracellular membrane-derived vesicles in listeria monocytogenes," Plos One, 8(8):e73196 (2013).
Leffler et al., "Clostridium difficile Infection," The New England Journal of Medicine, 372(16): 1539-1548 (2015).
Lehar et al., "Chemical combination effects predict connectivity in biological systems," Mol Sys Biol, 3:80 (2017).
Li et al., "Effect of oral feeding with Clostridium leptum on regulatory T-cell responses and allergic airway inflammation in mice," Ann Allergy Asthma Immunol, 109: 201-207 (2012).

(56) References Cited

OTHER PUBLICATIONS

Li et al., "Human Gut Bacterial Communities Are Altered by Addition of Cruciferous Vegetables to a Controlled Fruit-and Vegetable-Free Diet," The Journal of Nutrition, 1685-1691 (2009).
Li et al., "Intestine-derived clostridium leptum induces murine tolerogenic dentritic cells and regulatory T cells in vitro," Human Immunology, 75:1232-1238 (2014).
Liu et al., "Lactobacillus buchneri strain NRRL B-30929 converts a concentrated mixture of xylose and glucose into ethanol and other products," J Ind Microbial Biotechnol, 35: 75-81 (2008).
Liu et al., "Reclassification of Clostridium coccoides, Ruminococcus hansenii, Ruminococcus hydrogenotrophicus, Ruminococcus luti, Ruminococcus productus and Ruminococcus schinkii as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces," International Journal of Systematic and Evolutionary Microbiology, 58: 1896-1902 (2008).
Lopetuso et al., "Commensal Clostridia: leading players in the maintenance of gut homeostasis," Gut Pathogens, 5(1): 23 (2013).
Lu et al., "Arabinoxylan Fiber from a By-Product of Wheat Flour Processing Behaves Physiologically like a Soluble, Fermentable Fiber in the Large Bowel of Rats," J Nutr, 130: 1984-1990 (2000).
Macfarlane et al., "Review article: prebiotics in the gastrointestinal tract," Alim Pharmacal Ther, 24: 701-714 (2006).
Machiels et al., "Specific members or the predominant gut microbiota predict pouchitis following colectomy and IPAA in UC," Gut Microbia, 0:1-10 (2015).
Macpherson et al., "Induction of Protective IgA by Intestinal Dendritic Cells Carrying Commensal Bacteria," Science, 303: 1662-1665 (2004).
Maroni et al., "Fucosyltransferase 2: A Genetic Risk Factor for Primary Sclerosing Cholangitis and Grahn's Disease—A Comprehensive Review," Clinic Rev Allerg Immunol, 48: 182-191 (2015).
Martin et al., "Role of commensal and probiotic bacteria in human health: a focus on inflammatory bowel disease," Microbial Cell Factories, 12: Article 71 (2013).
Mazmanian et al., "A microbial symbiosis factor prevents intestinal inflammatory disease," Nature, 453: 620-625 (2008).
McBroom et al., "Outer membrane vesicle production by *Escherichia coli* is independent of membrane instability," Journal of Bacteriology, 188(15): 5385-5392 (2006).
McDonald et al., "Evaluation of microbial community reproducibility, stability and composition in a human distal gut chemostat model," Journal of Microbiological Methods, 95: 167-174 (2013).
McLellan et al., "Sewage reflects the distribution of human faecal Lachnospiracease," Environronmental Microbiology, 15(8): 2213-2227 (2013).
Meehan et al., "A Phylogenomic View of Ecological Specialization in the Lachnospiraceae, a Family of Digestive Tract-Associated Bacteria," Genome Biol Evol, 6(3): 703-713 (2014).
Menard et al., "Lactic acid bacteria secrete metabolites retaining anti-inflammatory properties after intestinal transport," Gut, 53(6): 821-8 (2004).
Minikiewicz et al., "The occurrence of sequences identical with epitopes from the allergen pen a 1.0102 among food and non-food proteins," Pol J Food Nutr Sci, 65(1):21-29 (2015).
Mitchell et al., "A Multicenter Pilot Evaluation of the National Institutes of Health Chronic Graftversus-Host Disease (cGVHD) Therapeutic Response Measures: Feasibility, Interrater Reliability, and Minimum Detectable Change," Biology of Blood and Marrow Transplantation, 17(11): 1619-1629 (2011).
Nagano et al., "The induction of Treg cells by gut-indigenous Clostridium," Current Opinion in Immunology, 24: 392-397 (2012).
Natividad et al., "Differential Induction of Antimicrobial REGIII by the Intestinal Microbiota and Bifidobacterium breve NCC2950," Applied Environmental Microbiology, 79(24): 7745-54 (2013).
Newton et al., "Sewage Reflects the Microbiomes of Human Populations," American Society of Microbiology, 6(2): 1-9 (2015).
Neyrinck et al., "Dietary modulation of clostridial cluster XIV a gut bacteria *(Roseburria* spp.) by chitin-glucan fiber improves host metabolic alterations induced by high-fat diet in mice," J Nutritional Biochemsitry, 23: 51-59 (2012).
Neyrinck et al., "Prebiotic Effects of Wheat Arabinoxylan Related to the Increase in Bifidobacteria, Roseburia and Bacteriodes/ Prevotella in Diet-Induced Obese Mice," PLOS One, 6(6): 1-12 (2011).
Neyrinck et al., "Wheat-derived arabinoxylan oligosaccharides with prebiotic effect increase satietogenic gut peptides and reduce metabolic endotoxemia in diet-induced obese mice," Nutrition and Diabetes, 2, e28 <doi:1 0/1 038/nutd.2011.24> (2012).
Nielsen et al., "Diets high in resistant starch and arabinoxylan modulate digestion processes and SCFA pool size in the large intestine and faecal microbial composition in pigs," Br J Nutrition, 112: 1837-1849 (2014).
Nutsch et al., "T Cell tolerance and immunity to commensal bacteria," Current Opinion in Immunology, 24: 385-391 (2012).
Ochoa-Reparaz et al., "A polysaccharide from the human commensal Bacteroides fragilis protects against CNS demyelinating disease," Mucosal Immunology, 3(5): 487-495 (2010).
Ohkohchi et al., "Mechanism of D-Xylose Transport in Human Small Intestine," J Pediatric Gastroenterology and Nutrition, 5: 372-378, (1986).
Ohtsuka et al., "Effects of Bifidobacterium breve on inflammatory gene expression in neonatal and weaning rat intestine," Pediatric Research, 71: 46-53 (2012).
Okazaki et al., "Effect of xylooligosaccharide on the Growth of Bifidobacteria," Bifidobacteria Microflora, 9(2): 77-86 (1990).
Park et al., "*Blautia faecis* sp. nov., isolated from human faeces," Inti J of Systematic and Evol Microbial, 63: 599-603 (2013).
Park et al., "*Blautia stercoris* sp. nov., isolated from human faeces," Inti J of Systematic and Evol Microbial, 62: 776-779 (2012).
Parmar et al., "Association study of FUT2 (rs601338) with celiac disease and inflammatory bowel disease in the Finnish population," Tissue Antigens, 80:488-493 (2012).
Parracho et al., "Differences between the gut microflora of children with austistic spectrum disorders and that of healthy children", Journal of Medical Microbiology, 54: 981-991 (2005).
Penack et al., "Graft-versus-host disease: regulation by microbe-associated molecules and inn nate immune receptors," Blood, 115(1 0): 1865-1872 (2010).
Penack et al., "Inhibition of Neovascularization to Simultaneously Ameliorate Graft-vs-Host Disease and Decrease Tumor Growth," J Natl Cancer Inst, 102: 894-908 (2010).
Penders et al., "The role of the intestinal microbiota in the development of atopic disorders," Allergy, 62:1223-1236 (2007).
Reran et al., "Lactobacillus fermentum, a probiotic capable to release glutathione, prevents colonic inflammation in the TNBS model of rat colitis," Int J Colorectal Dis, 21: 737-746 (2005).
Petnicki-Ocweija et al., "Nod2 is required for the regulation of commensal microbiota in the intestine," PNAS, 106(37): 15813-15818 (2009).
Petrof et al., "Stool substitute transplant therapy for the eradication of Clostridium difficile infection: 'RePOOPulating' the gut," Microbiome, 1: Article 3 (2013).
Pichler, "Adverse side-effects to biological agents," Allergy, 61:912-920 (2006).
Ponce et al., "Graft-versus-Host Disease after Double-Unit Cord Blood Transplantation Has Unique Features and an Association with Engrafting Unit-to-Recipient HLA Match," Biol Blood Marrow Transplant, 19: 904-911 (2013).
Pourabedin et al., "Prebiotics and gut microbiota in chickens," FEMS Microbiology Letters, 362: fnv122, 2015. 8 pages.
Puertollano et al., "Orally administered Lactobacillus plantarum reduces pro-inflammatory interleukin secretion in sera from Listeria monocytogenes infected mice," Br J Nutrit, 99(4): 819-825 (2008).
Randhawa et al., "Bioinformatic analysis for allergenicity assessment of bacillus thuringiensis cry proteins expressed in insect-resistant food crops," Food and Chemical Toxicology, 49:356-362 (2011).
Rappazzo et al., "Recombinant M2e outer membrane vesicle vaccines protect against lethal influenza A challenge in BALB/c mice," Vaccine, (2016).

(56) References Cited

OTHER PUBLICATIONS

Rashid et al., "Determining the Long-term Effect of Antibiotic Administration on the Human Normal Intestinal Microbiota Using Culture and Pyrosequencing Methods," Clinical Infectious Diseases, 60(S2): S77-S84 (2015).
Rayes et al., A Genetic Modifier of the Gut Microbiome Influences the Risk of Graft "A Genetic Modifier of the Gut Microbiome Influences the Risk of Graftversus-Host Disease and Bacteremia After Hematopoietic Stem Cell Transplantation," Biol Blood Marrow Transplant, 22(3): 418-422 (2016).
Reid et al., "Microbiota restoration: natural and supplemented recovery of human microbial communities," Nature, 9: 27-38 (2011).
Rieu-Lesme et al., "A new H2/C02-using acetogenic bacterium from the rumen: Description of *Ruminococcusschinkiisp*. nov.," FEMS Microbiology Letters, 140: 281-286 (1996).
Rivas et al., "A microbiota signature associated with experimental food allergy promotes allergic sensitization and anaphylaxis," J. Allergy Clin. Immunol, 131(1): 201-212 (2013).
Roier et al., "A novel mechanism for the biogenesis of outer membrane vesicles in gram-negative bacteria," Nature Communications, 1-13 (2015).
Roopchand et al., "Dietary polyphenols promote growth of the gut bacterium Akkermansia muciniphila and attenuate high fat diet-induced metabolic syndrome," Diabetes, 64: 2847-2858 (2015).
Rosenthal et al., "Mechanistic insight into the TH1-biased immune response to recombinant subunit vaccines delivered by probiotic bacteria-derived outer membrane vesicles," Plos One, 9(11):e112802 (2014).
Roux et al., "Ruminococcus gnavus Total Hip Arthroplasty Infection in a 62-Year-Old Man with Ulcerative Colitis," Journal of Clinical Microbiology, S3(4): 1428-1430 (2015).
Sagar et al., "The combination of Bifidobacterium breve with non-digestible oligosaccharides suppresses airway inflammation in a murine model for chronic asthma," Biochimica et Biophysica Acta (BBA)—Molecular Basis of Disease, 1842(4): 573-583 (2014).
Salminen et al., "Gut Microflora Interactions with Xylitol in the Mouse, Rat, and Man," Fd Chem Tax, 23(11): 985-990 (1985).
Salvador et al., "Sugar composition of dietary fibre and short-chain fatty acid production during in vitro fermentation by human bacteria," Br J Nutrition, 70:189-197 (2013).
Sandler et al.. "Short-Term Benefit From Oral Vancomycin Treatment of Regressive-Onset Autism," J Child Neurology, 1 S(2): 429-435 (2000).
Santiago et al., "Structutal Differences between human proteins and aero- and microbial allergens define allergenicity," Plos One, 7(7):e40552 (2012).
Saujet et al., "The regulatory network controlling spore formation in Clostridium difficile," FEMS Microbial Letters, 358(1): 1-10 (2014).
Savaiano et al., "Improving lactose digestion and symptoms of lactose intolerance with a novel galacto-oligosaccharide (RP-G28): a randomized, double-blind clinical trial," Nutrition Journal, 12: Article 160 (2013).
Scher et al., "Decreased Bacterial Diversity Characterizes the Altered Gut Microbiota in Patients With Psoriatic Arthritis, Resembling Dysbiosis in Inflammatory Bowel Disease," Arthritis & Rheumatology, 67(1): 128-139 (2015).
Shankar et al., "Species and genus level resolution analysis of gut microbiota in Clostridium difficile patients following fecal microbiota transplantation," Microbiome, 2: Article 13 (2014).
Shima et al., "Differential effects of two probiotic strains with different bacteriological properties on intestinal gene expression, with special reference to indigenous bacteria," FEMS Immunol Med Microbiol, 52: 69-77 (2008).
Shono et al., "Intestinal microbiota-related effects on graft-versus-host disease," Int J Hematol, 101 (S): 428-437 (2015).
Smyth et al., "FUT2 Nonsecretor Status Links Type 1 Diabetes Susceptability and Resistance to Infection," Diabetes, 60: 3081-3084 (2011).
Sokol et al., "Faecalibacterium prausnitzii is ananti-inflammatory commensal bacterium identified by gut microbiota analysis of Crohn disease patients," PNAS, 105(43): 16731-16736 (2008).
Solon-Biet et al., "The Ratio of Macronutrients, Not Caloric Intake, DictatesCardiometabolic Health, Aging, and Longevity in Ad Libitum-Fed Mice," Cell Metabolism, 19: 418-430 (2014).
Sparo et al., "Immunomodulatory properties of cell wall extract from Enterococcus faecalis CEC," The Brazilian Journal of Infection Disease, 18(5): 551-555 (2014).
Suez et al., "Artificial sweeteners induce glucose intolerance by altering the gut microbiota," Nature, 514: 181-186 (2014).
Sun et al., "A novel three-component system-based regulatory model forD-xylose sensing and transport in Clostridium beijerinckii," Molecular Microbiology, 95(4): 576-589 (2015).
Sun et al., "Mature T cell responses are controlled by microRNA-142," J Clin Invest, 125(7): 282S-2840 (2015).
Tailford et al., "Mucin glycan foraging in the human gut microbiome," Frontiers in Genetics, 6: 81 (2015).
Tamura et al. "Xylitol Affects the Intestinal Microbiota and Metabolism of Daidzein in Adult Male Mice," Int J Mol Sci, 14: 23993-24007 (2013).
Tanoue et al., "Immune responses to gut microbiota—commensals and pathogens," Gut Microbes, 1 (4): 224-233 (2010).
Tap et al., "Towards the human intestinal microbiota phylogenetic core," Environmental Microbiology, 11 10): 2574-2584 (2009).
Tapiainen et al., "Effect of Xylitol on Growth of *Streptococcus pneumoniae* in the Presence of Fructose and Sorbitol," Antimicrobial Agents and Chemotherapy, 45(1): 166-169 (2001).
Tateyama et al., "Effect of Xylooligosaccharide Intake on Severe Constipation in Pregnant Women," J Nutr Vitaminol, 51: 445-448 (2005).
Taur et al., "Intestinal Domination and the Risk of Bacteremia in Patients Undergoing Allogeneic Hematopoietic Stem Cell Transplantation," Clinical Infectious Diseases, 55(7): 905-914 (2012).
Taur et al., "The effects of intestinal tract bacterial diversity on mortality following allogeneic hematopoietic stem cell transplantation," Blood, 124(7): 1174-1182 (2014).
Tawara et al., "Influence of Donor Microbiota on the Severity of Experimental Graft-versus-Host-Disease," Biol Blood Marrow Transplant, 19: 161-168 (2013).
Telesford et al., "A commensal symbiotic factor derived from Bacteroides fragilis promotes human CD39+Foxp3+ T cells and Treg function," Gut Microbes, 6(4): 234-42 (2015).
Telesford et al., "Gut commensalism, cytokines, and central nervous system demyelination," Journal of Interferon and Cytokine Research, 34(8): 605-614 (2014).
Temudo et al., "Xylose anaerobic conversion by open-mixed cultures," Appl Microbiol Biotechnol 82: 231-239 (2009).
Thaiss et al., "Transkingdom Control of Microbiota Diurnal Oscillations Promotes Metabolic Homeostasis," Cell, 159: 514-529 (2014).
Torres-Maravilla et al., "Identification of bovel anti-inflammatory probiotic strains isolated from pulque," Appl Microbiol Biotechnol, 100:385-396 (2016).
Tuovinen et al., "Cytokine response of human mononuclear cells induced by intestinal Clostridium species," Anaerobe, 19: 70-76 (2013).
Turnbaugh et al., "A core gut microbiome in obese and lean twins," Nature, 457: 480-485 (2009).
Tvede et al., "Bacteriotherapy for Chronic Relapsing Clostridium Difficile Diarrhoea in Six Patients," The Lancet, May 27, 1989, pp. 1156-1160.
Ubeda et al., "Antibiotics, microbiota, and immune defense," Trends in Immunology, 33(9): 459-466 (2012).
Vaishnava et al., "Paneth cells directly sense gut commensals and maintain homeostasis at the intestinal host-microbial interface," PNAS, 105(52): 20858-20863 (2008).
Valdes et al., "Population Dynamics of Some Relevant Intestinal Microbial Groups in Human Fecal Batch Cultures with Added Fermentable Xylooligosaccharides Obtained from Rice Husks," BioResources, 8(2): 2429-2441 (2013).
Van den Abbeele et al., "Butyrate-producing Clostridium cluster XIV a species specifically colonize mucins in an in vitro gut model," The ISME Journal, 7: 949-961 (2013).

(56) References Cited

OTHER PUBLICATIONS

Van den Abbeele et al., "Different Human Gut Models Reveal the Distinct Fermentation Patterns of Arabinoxylan versus Inolin," J Agric Food Chem, 61: 9819-9827 (2013).

Van den Abbeele et al., "Microbial Community Development in a Dynamic Gut Model Is Reproducible, Colon Region Specific, and Selective for Bacteroidetes and Clostridium Cluster IX," Applied and Environmental Microbiology, 76(15): 5237-5246 (2010).

Vanderhaeghen et al., "Methanogen communities in stool of humans of different age andhealth status and co-occurrence with bacteria," FEMS Microbiology Letters,362(0): fnv092 (2015).

Vasquez et al., "Xylooligosaccharides: manufacture and applications," Trends in Food Science and Technology, 11(11): 387-393 (2000).

Veiga et al., "*Bifidobacterium animalis* subsp. lactis fermented milk product reduces inflammation by altering a niche for colitogenic microbes," PNAS, 107(42): 18132-18137 (2010).

Weber et al., "Low urinary indoxyl sulfate levels early after transplantation reflect adisrupted microbiome and are associated with poor outcome," Blood Journal, 126(14): 1723-1728 (2015).

Wong et al., "Colonic health: fermentation and short chain fatty acids," J Clin Gastroenterol, 40(3): 235-243 (2006).

Wu et al., "Genetic determinants of in vivo fitness and diet responsiveness in multiple human QUI Bacteroides," Science, 350(6256): aac5992-1-8 (2015).

Xin et al., "Preventing non-alcoholic fatty liver disease through Lactobacillus johnsonii BS15 by attenuating inflammation and mitochondrial injury and improving gut environment in obese mice," Appl Microbiol Biotechnol 98: 6817-6829 (2014).

Xu et al., "Fecal microbiota transplantation broadening its application beyond intestinal disorders," World J Gastroenterol, 21(1): 102-111 (2015).

Yadav et al., "Peripherally induced Tregs—role in immune homeostasis and autoimmunity," Frontiers in Immunology, 4(232): 1-12 (2013).

Yang et al., "Xylooligosaccharide supplementation alters gut bacteria in both healthy and prediabetic aults: a pilot study," Frontiers in Physiology, 6:1-11 (2015).

Yaung et al., "Improving microbial fitness in the mammalian gut by in vivo temporal functional metagenomics," Mol Sys Biol, 11: 788 (2015).

Yeun et al., "Effect of oral probiotics (Bifidobacterium lactis AD011 and Lactobacillus acidophilus AD031) administration on ovalbumin-induced food allergy mouse model," J Microbiol Biotechnol, 18(8):1393-1400 (2008).

Yin et al., "Different Dynamic Patterns of B-Lactams Quinolones, Glycopeptides and D Macrolides on Mouse Gut Microbial Diversity," PLOS ONE, 10(5): 1-12 (2015).

Young et al., "Detection of Sialic Acid-Utilising Bacteria in a Caecal Community Batch Culture Using RNA-Based Stable Isotope Probing," Nutrients, 7: 2109-2124 (2015).

Youngster et al., "Oral, Capsulized, Frozen Fecal Microbiota Transplantation for Relapsing Clostridium difficile Infection," The Journal of the American Medical Association, 312(17): 1772-1778 (2014).

Yuasa et al., "Comparative Assessment of D-Xylose Absorption between Small and Large D Intestine," J Pharm Pharmacal, 49: 26-29 (1997).

Zhang et al., "Dynamics of Gut Microbiota in Autoimmune Lupus," Applied and Environmental Microbiology, 80(24): 7551-7560 (2014).

Zhang et al., "Xylan utilization in human gut commensal bacteria is orchestrated by unique t modular organization of polysaccharide-degrading enzymes," PNAS, 111 (35): E3708-E3717 (2014).

Zoppi et al., "Modulation of the Intestinal Ecosystem by Probiotics and Lactulose in children During Treatment with Ceftriaxone," Curr Therap Res, 62(5): 418-435 (2001).

Ermolenko et al., "Influence of Different Probiotic Lactic Acid Bacteria on Microbiota and Metabolism of Rats with Dysbiosis," Bioscience of Microbiota, Food and Health, 32(2): 41-40 (2013).

Hughes et al., "The Gut Microbiota and Dysbiosis in Autism Spectrum Disorders," Curr Neurol Neurosci Rep, 18(11) (22 pages) (2019).

Pascal et al.,"Microbiome and Allergic Diseases," Front Immunol, 9: 1584 (9 pages) (2018).

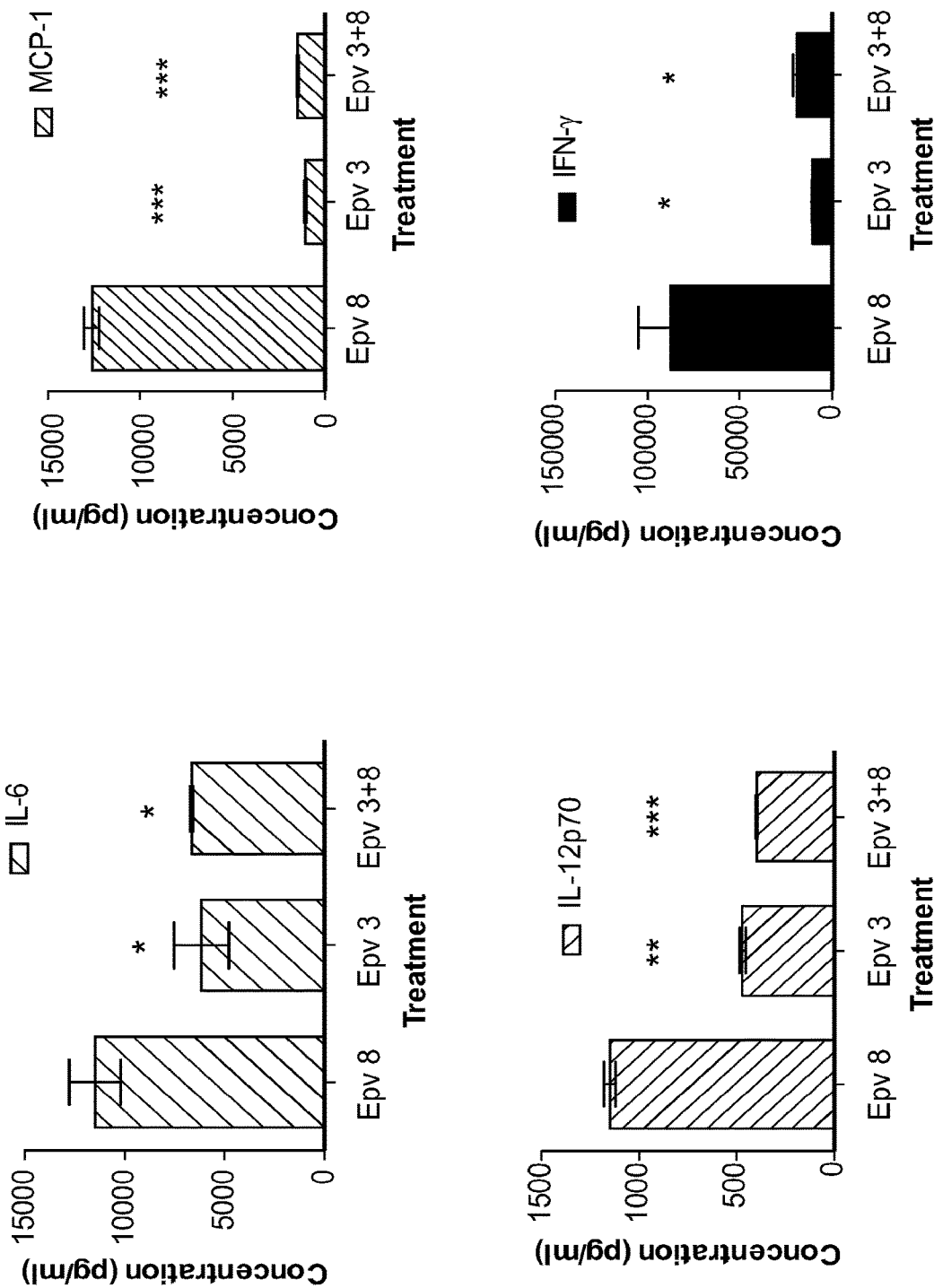
FIG. 11A  EPV3 – Desirable anti-inflammatory profile for GVHD

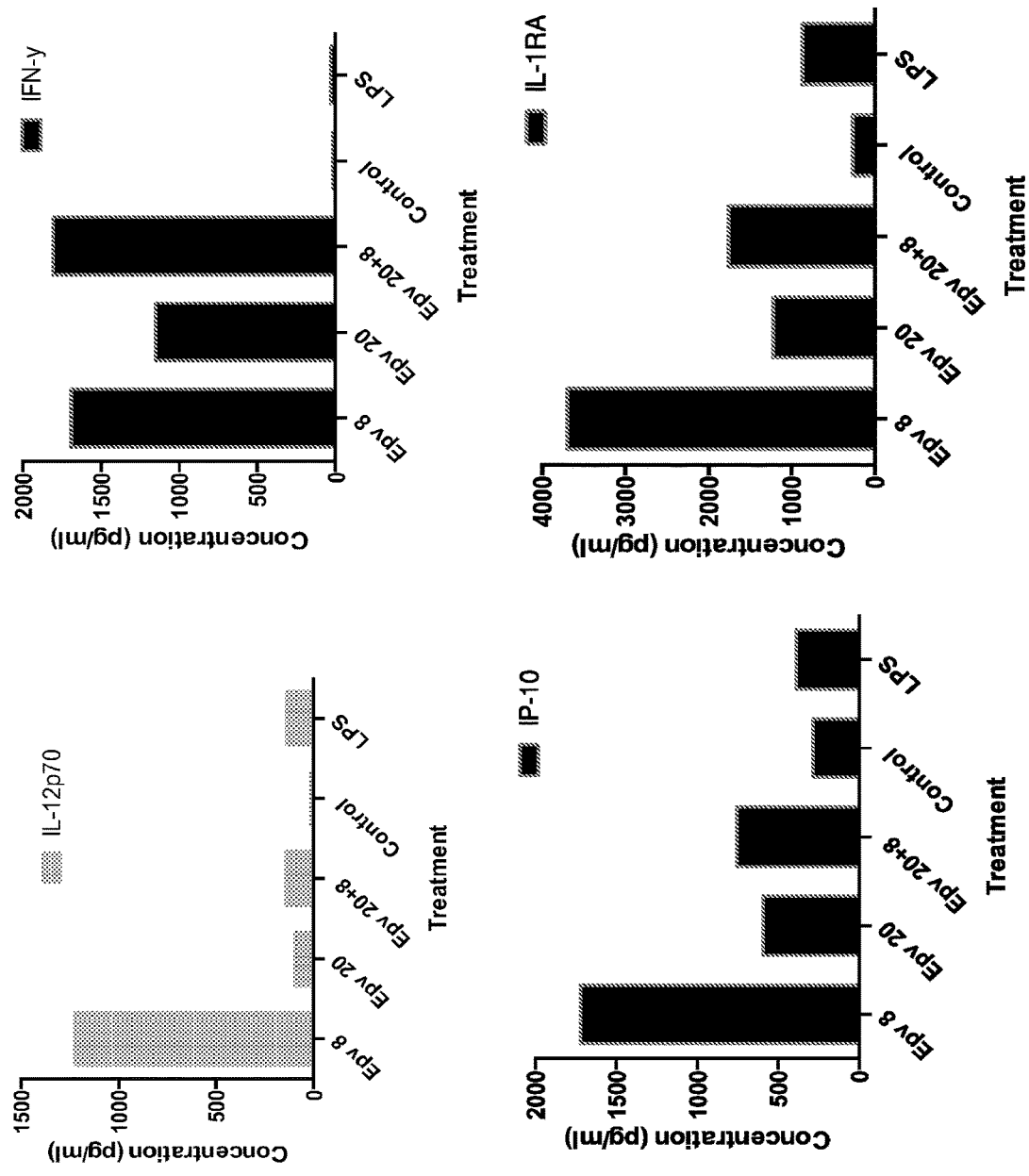
FIG. 14A Epv 20

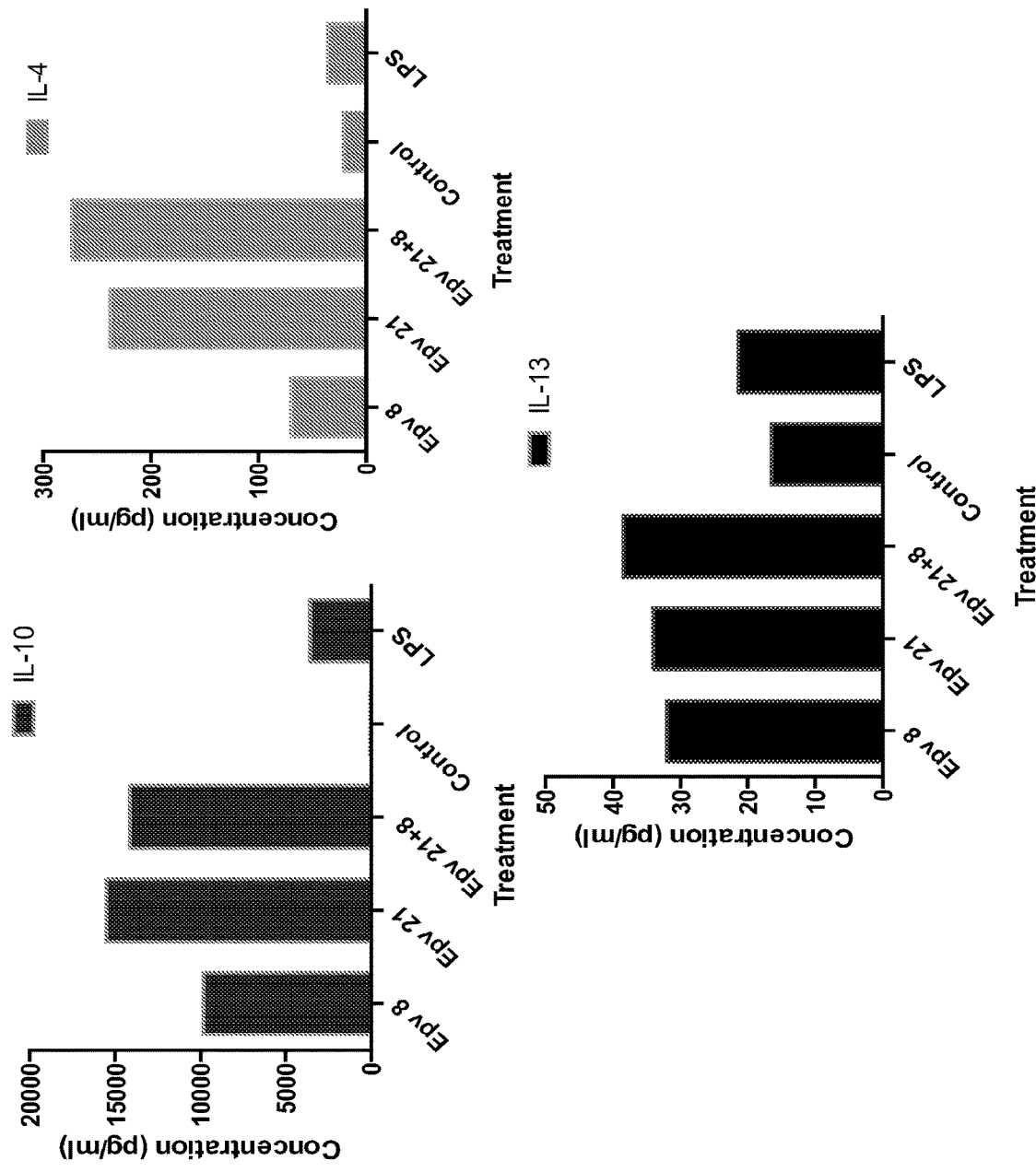
FIG. 15B Epv 21

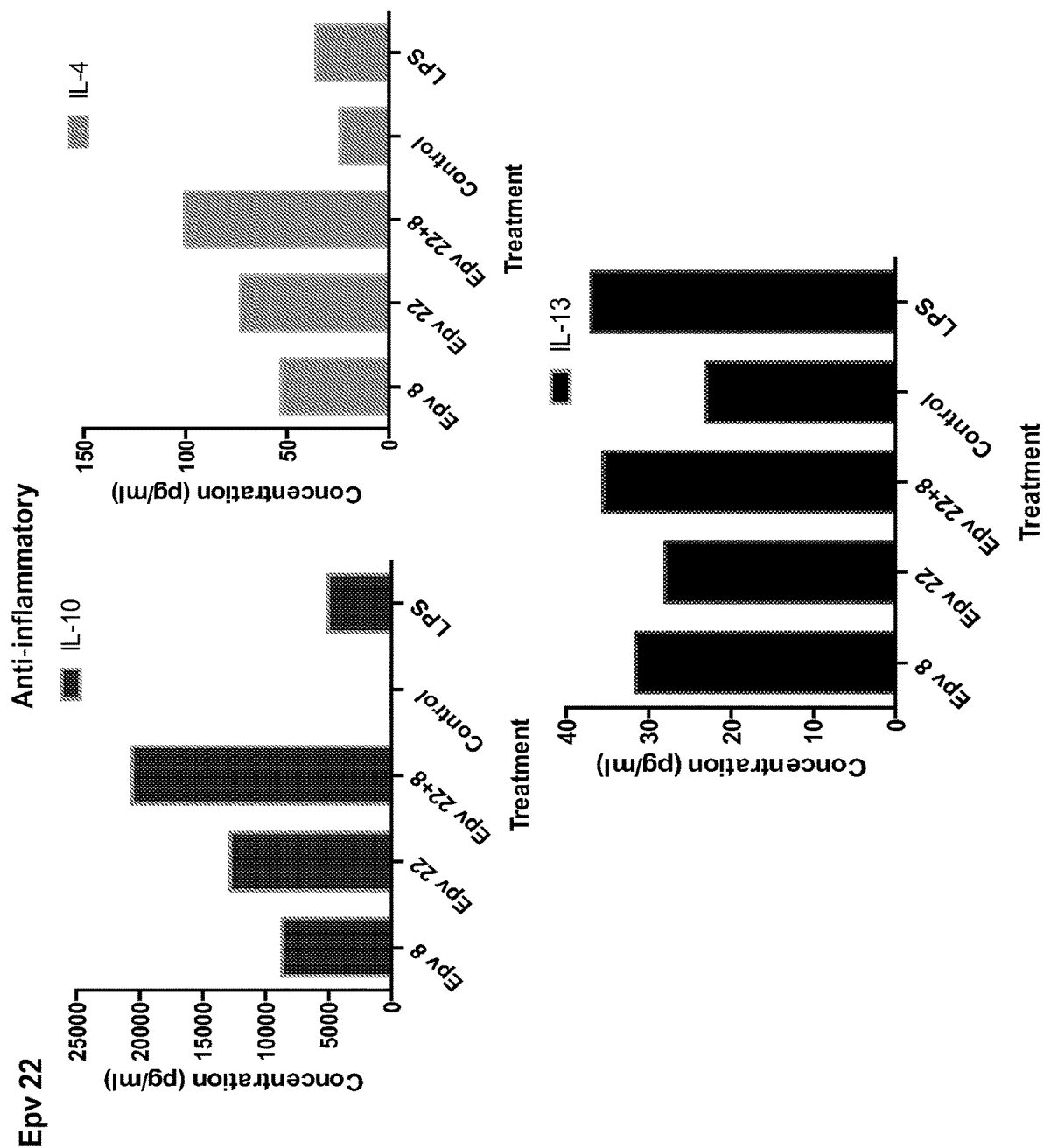

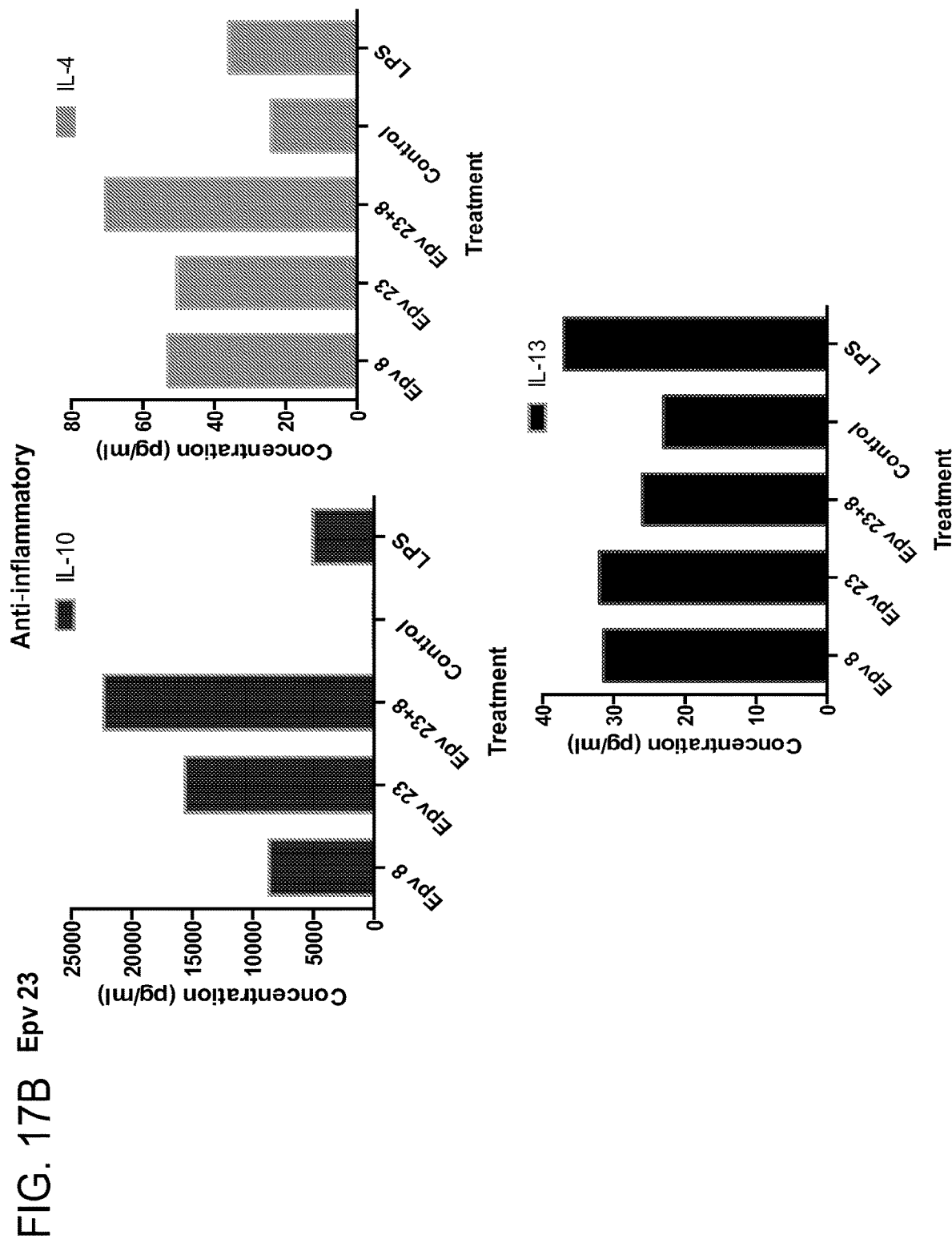
FIG. 17B Epv 23

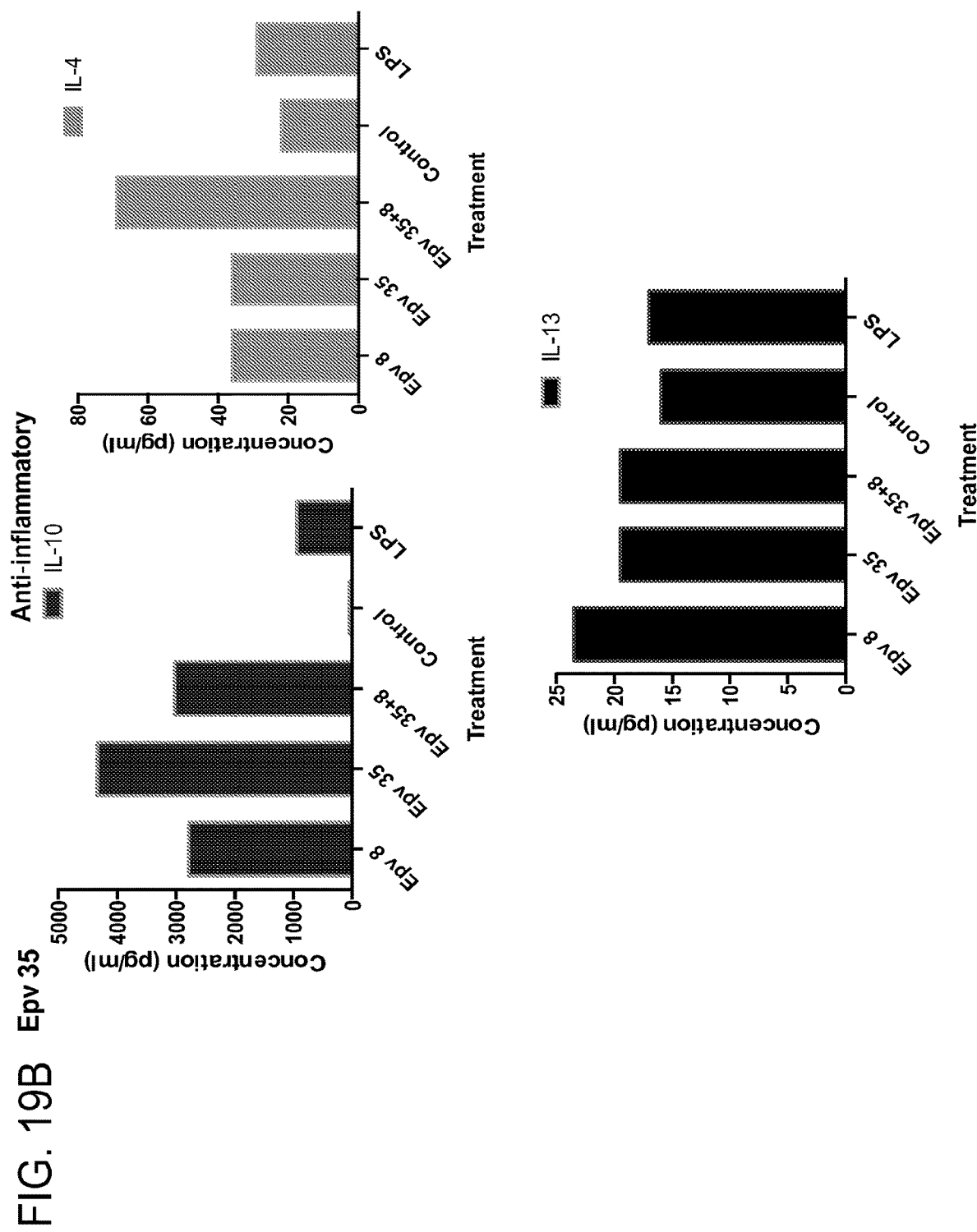

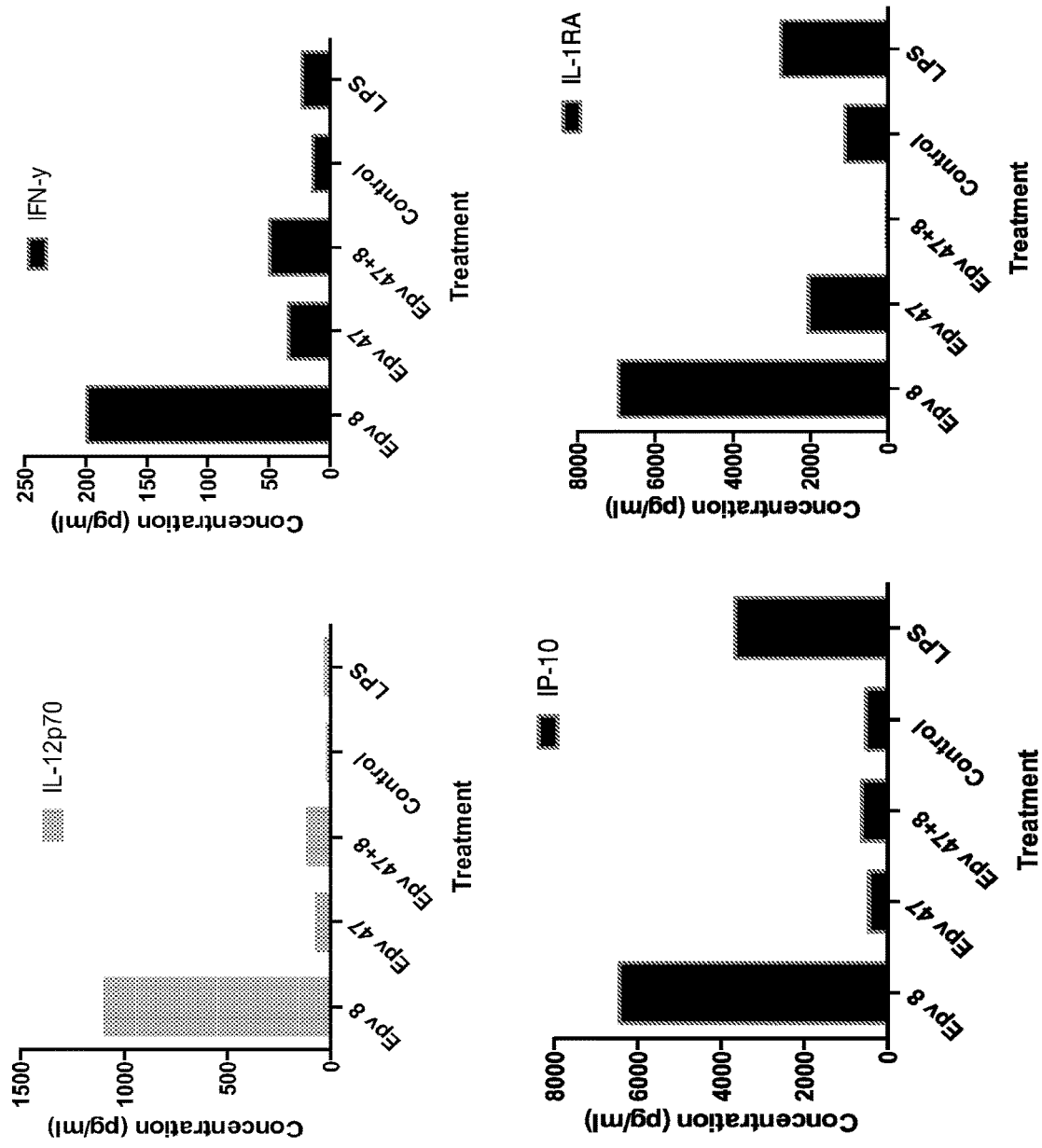
FIG. 20A  Epv 47

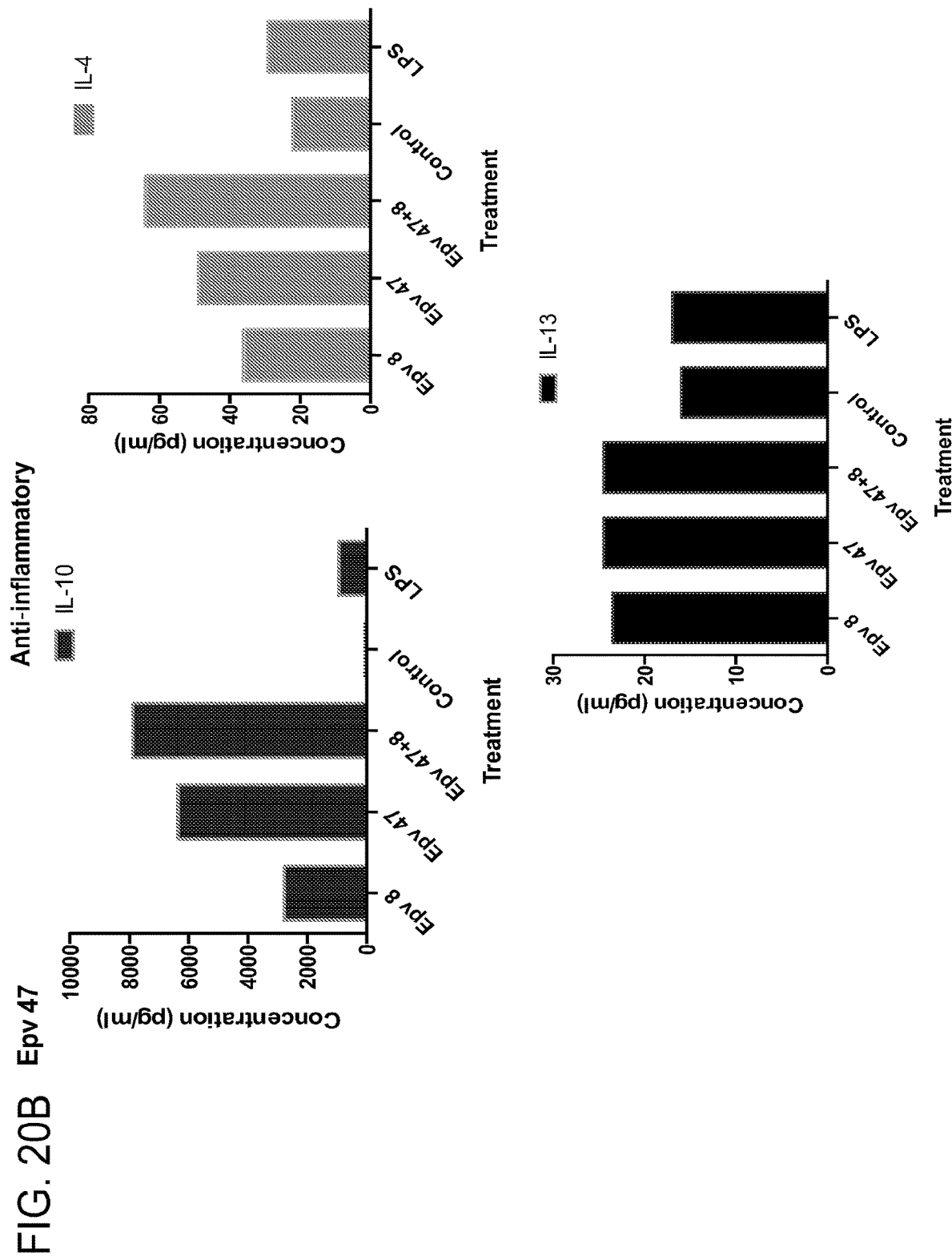

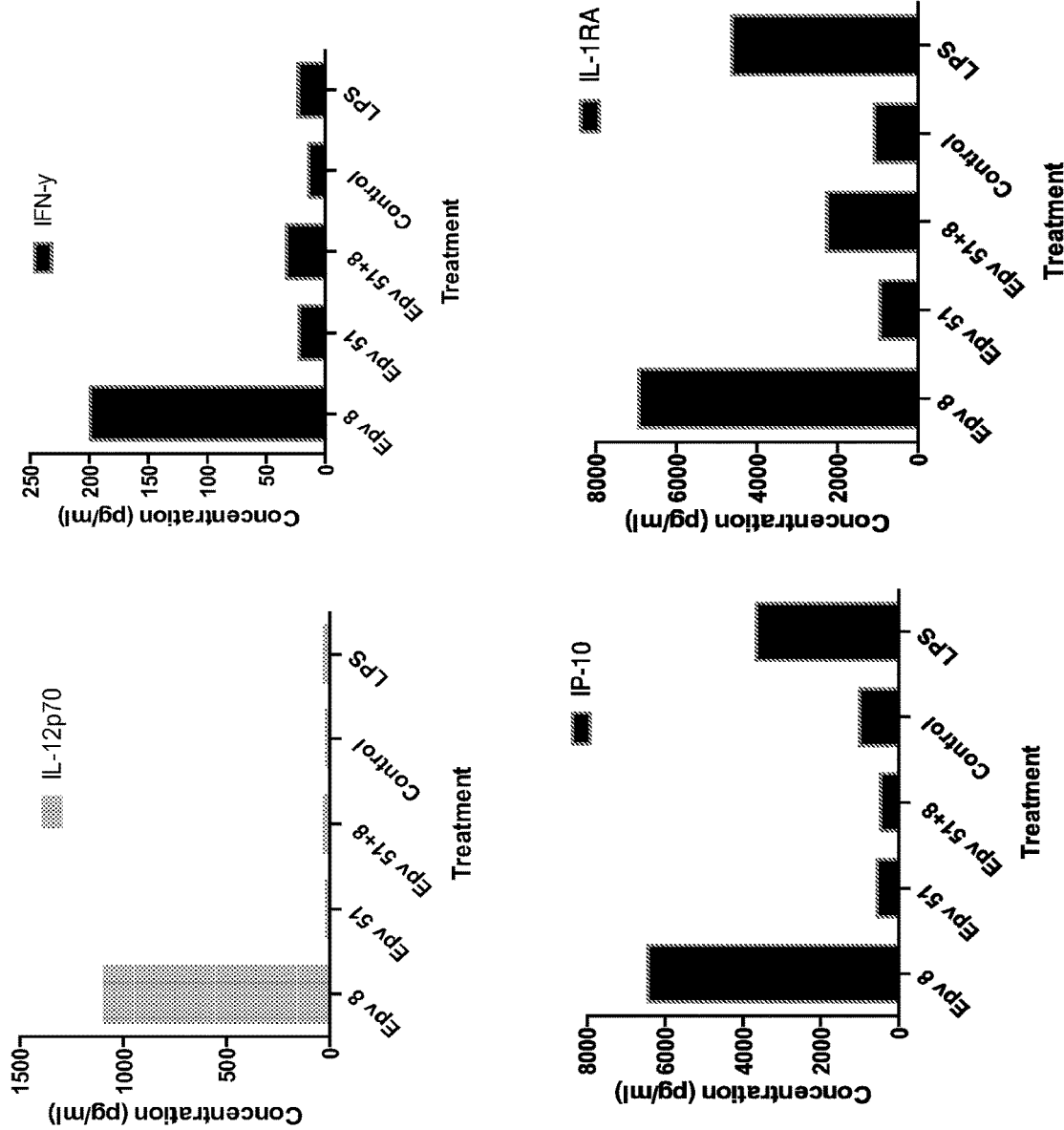
FIG. 21A Epv 51

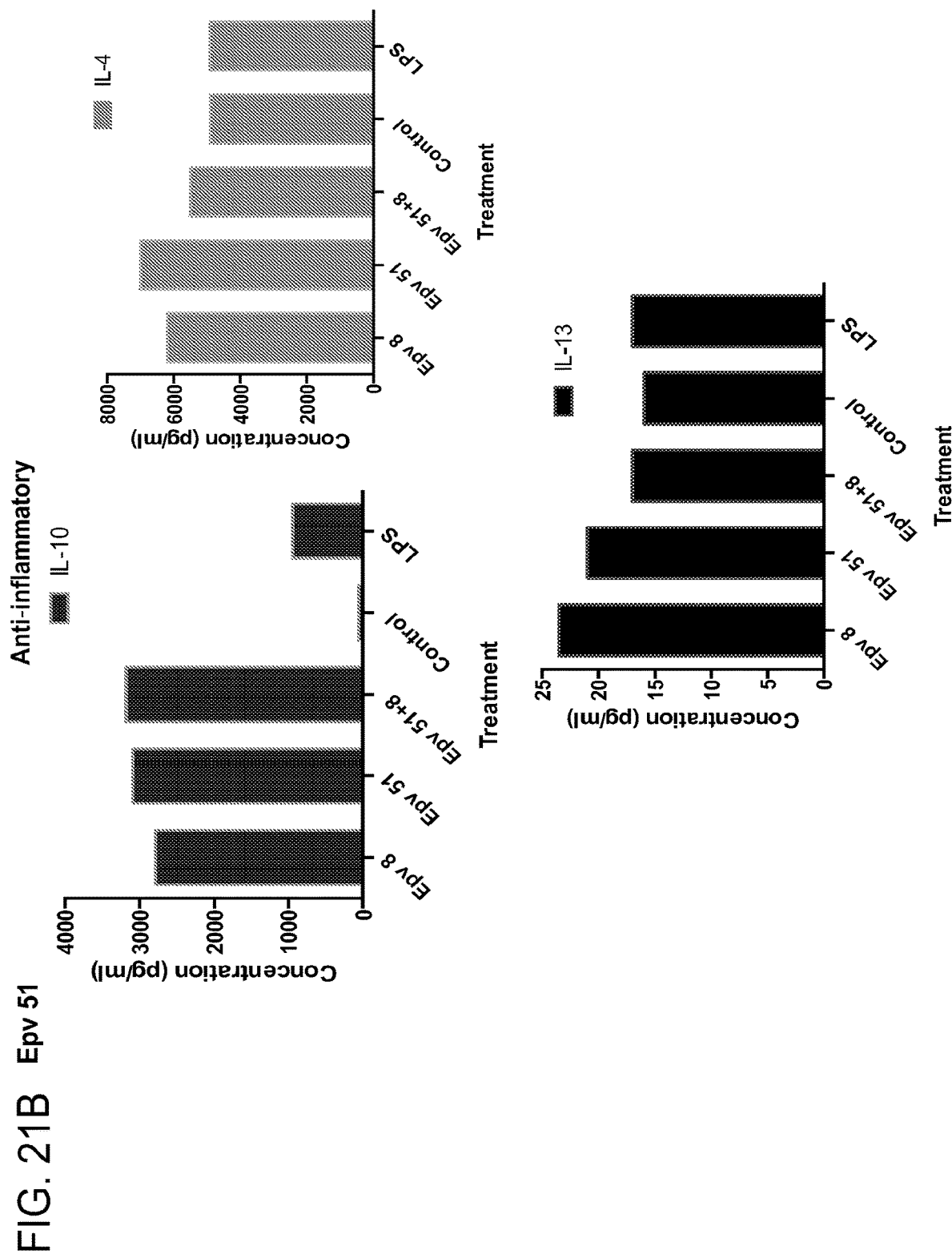
FIG. 21B Epv 51

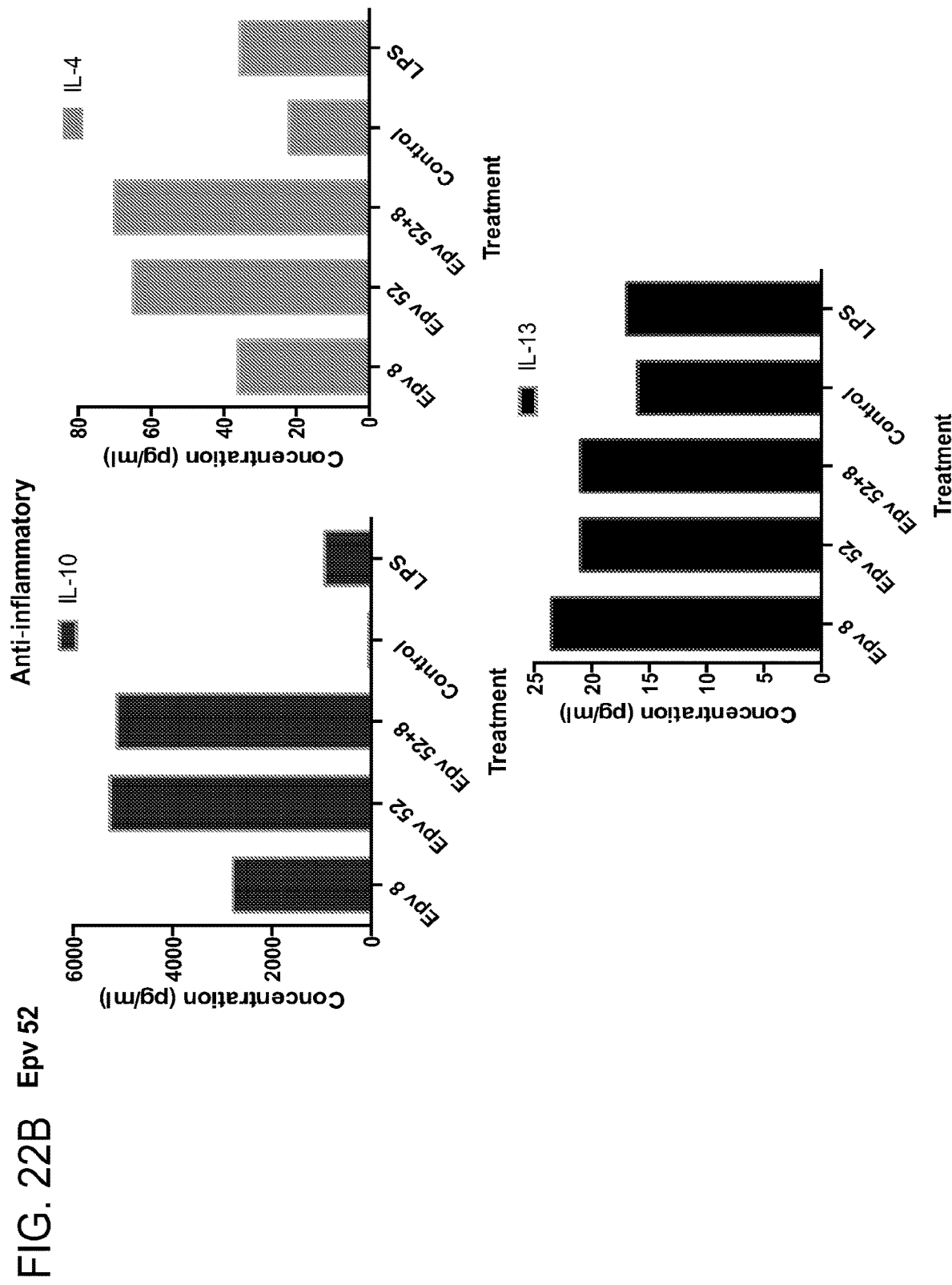
FIG. 22B  Epv 52

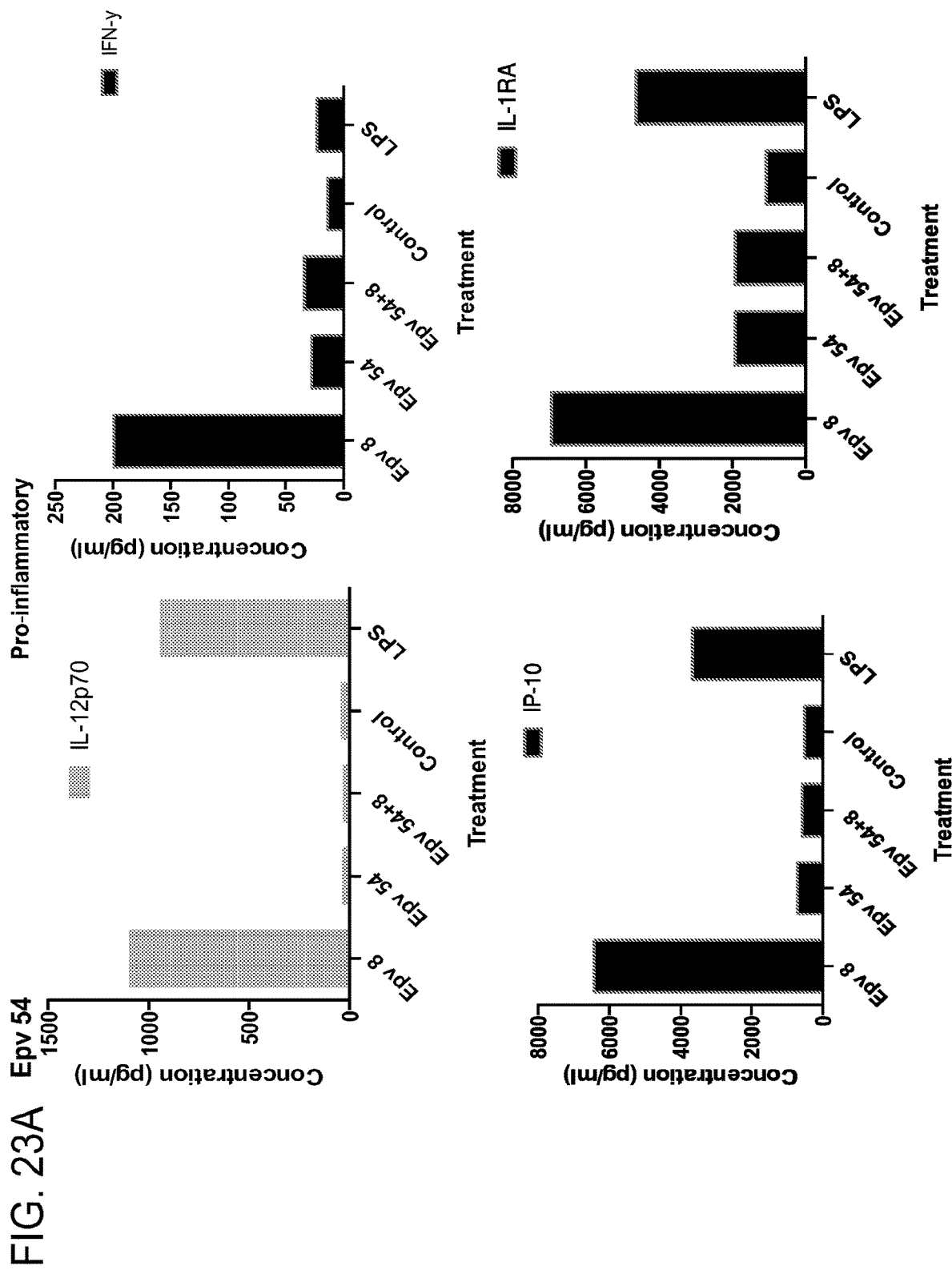

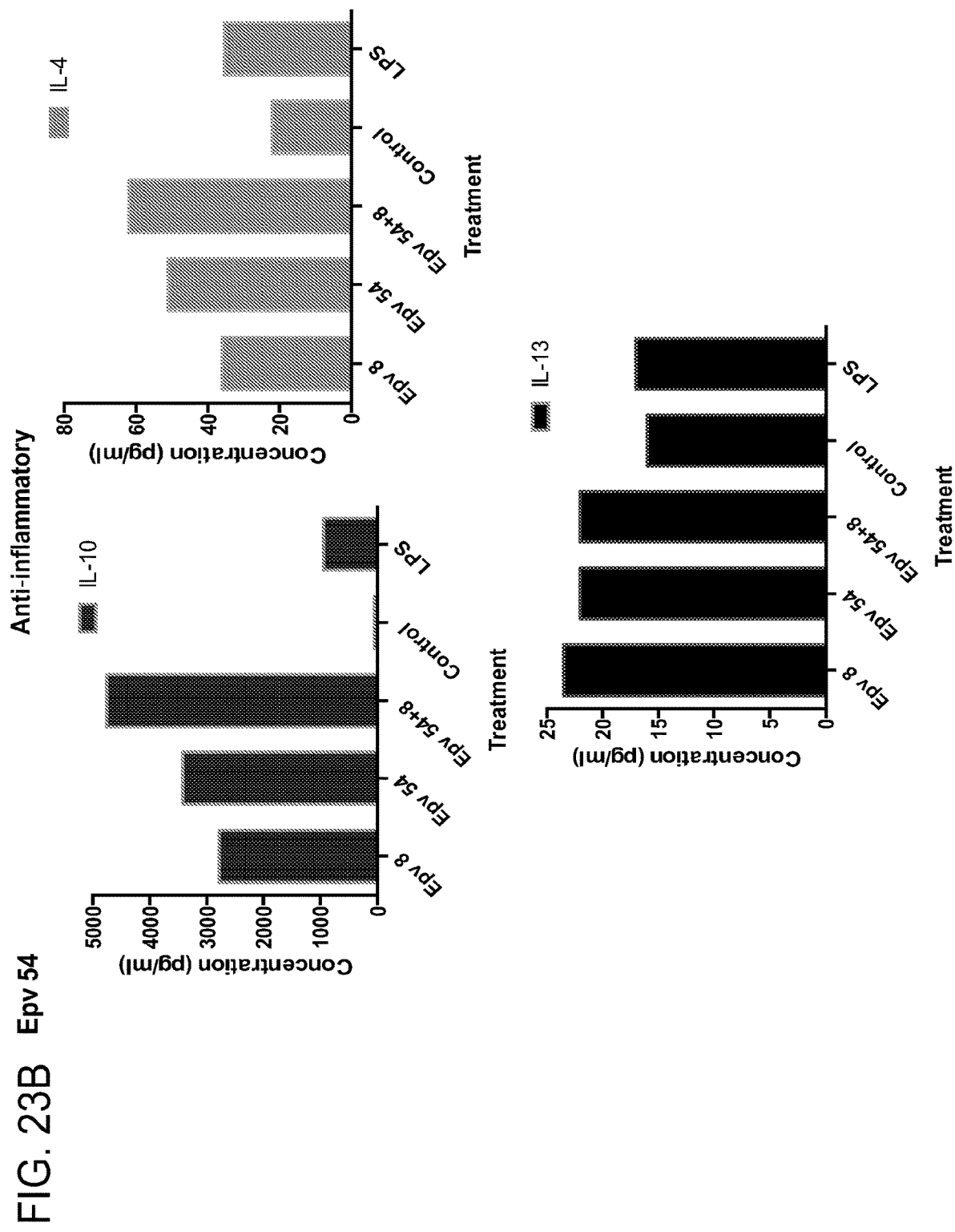
FIG. 23B Epv 54

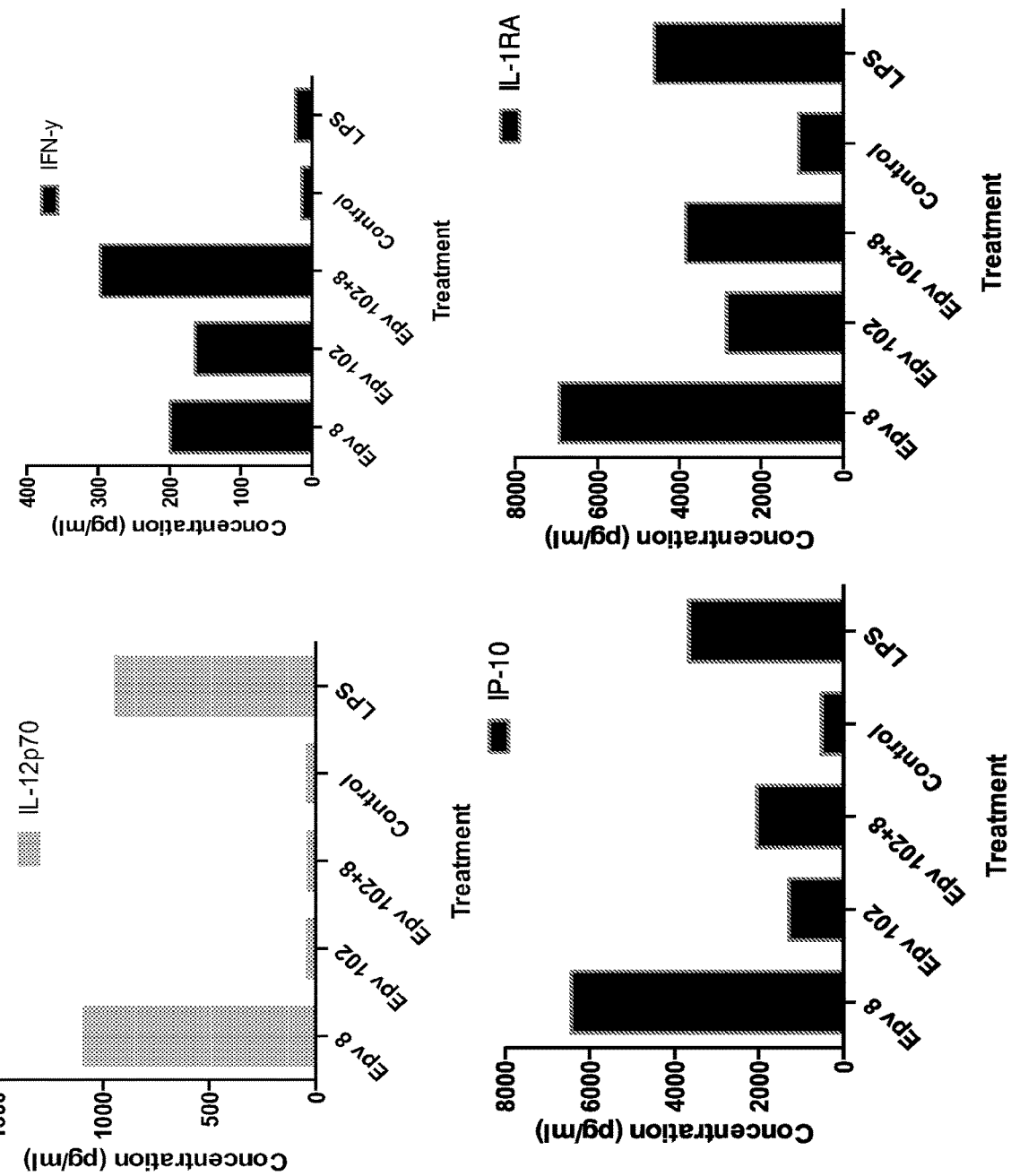
FIG. 26A  Epv 102

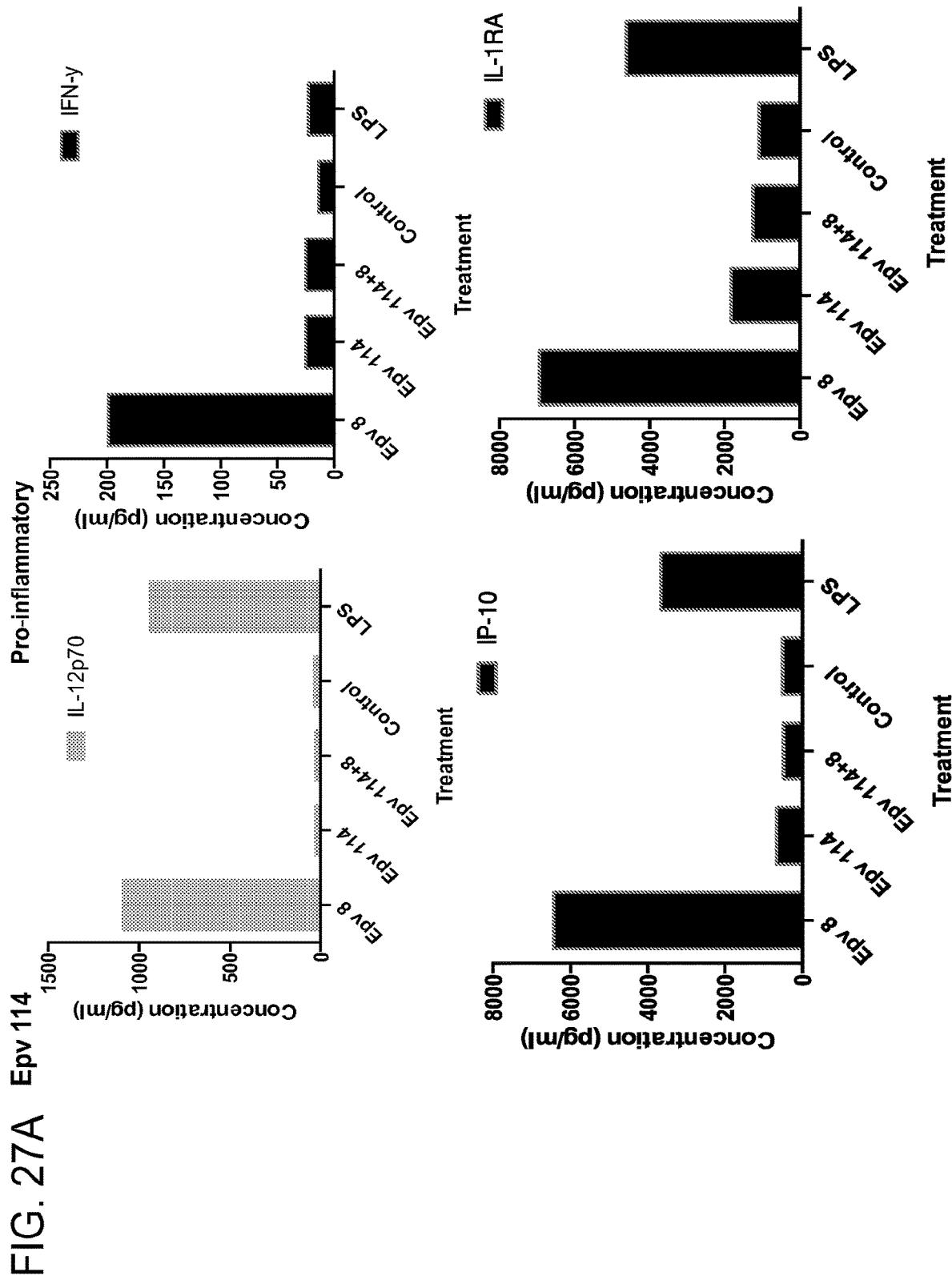
FIG. 27A Epv 114

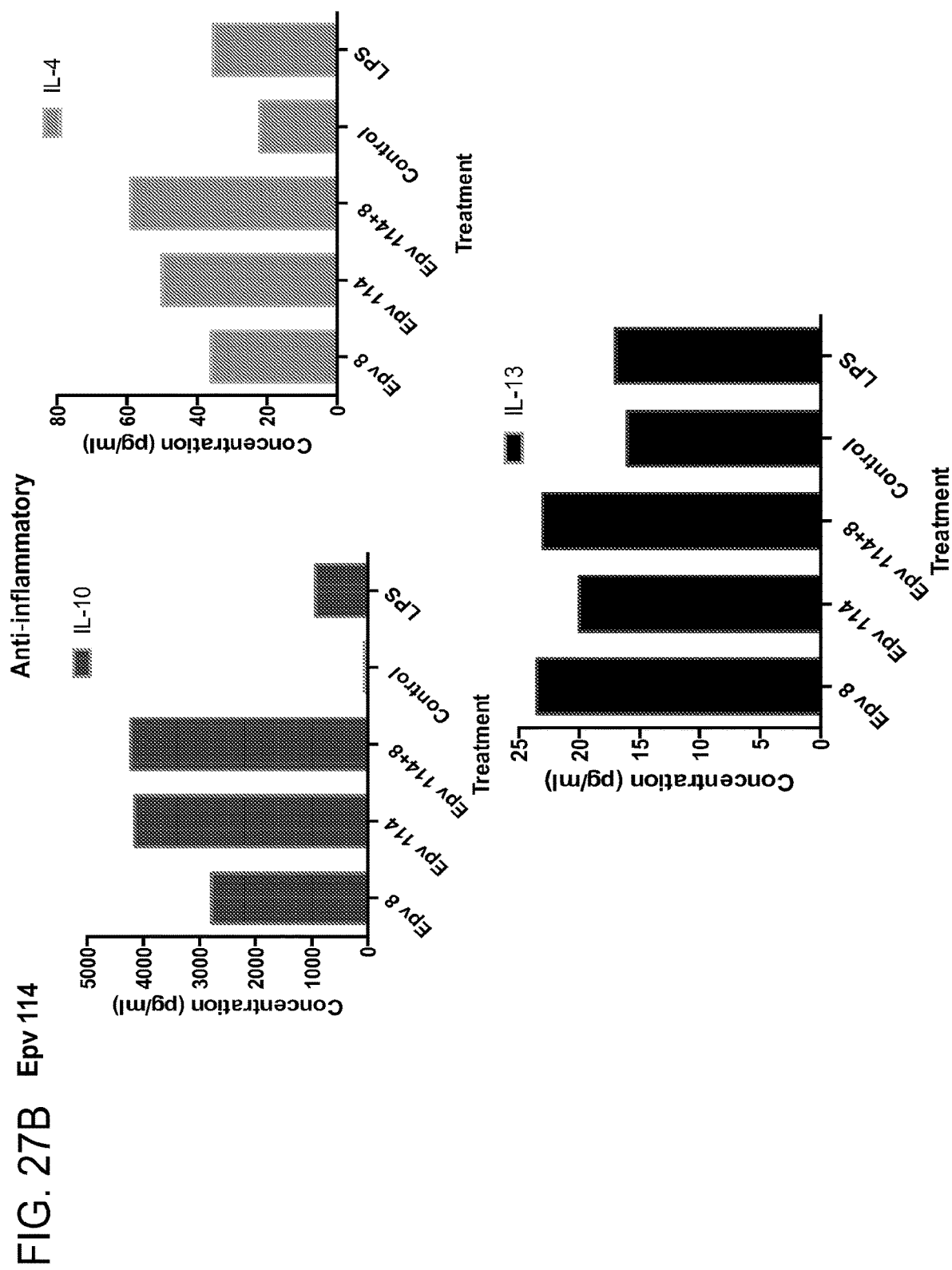
FIG. 27B Epv 114

FIG. 29A
Preferred carbon sources out of 192 different carbon sources tested

| R. gnavus (EPV1) | OD750 |
|---|---|
| Arbutin | 0.525 |
| a-D-Lactose | 0.522 |
| b-Methyl-D-Glucoside | 0.498 |
| Maltose | 0.49 |
| N-Acetyl-D-Glucosamine | 0.49 |
| Maltotriose | 0.478 |
| Gentiobiose | 0.465 |
| Salicin | 0.449 |
| a-D-Glucose | 0.445 |
| D-Fructose | 0.428 |
| L-Fucose | 0.36 |
| D-Galactose | 0.345 |
| L-Arabinose | 0.334 |
| D-Gluconic acid | 0.304 |
| D-Ribose | 0.3 |
| D-Glucosamine | 0.273 |
| D-Arabinose | 0.269 |
| Sucrose | 0.234 |
| D-Xylose | 0.215 |
| Lactulose | 0.143 |
| L-Tartaric acid | 0.141 |
| 3-O-b-D-Galactopyranosyl-D-Arabinose | 0.133 |
| b-Methyl-D-Glucuronic acid | 0.131 |
| D-Mannose | 0.124 |
| L-Rhamnose | 0.101 |
| Uridine | 0.101 |

FIG. 29B
Preferred carbon sources out of 192 different carbon sources tested

| *E. rectale* (EPV2) | OD750 |
|---|---|
| N-Acetyl-D-Glucosamine | 0.174 |
| D-Raffinose | 0.173 |
| Palatinose | 0.157 |
| a-D-Lactose | 0.155 |
| Stachyose | 0.154 |
| g-Cyclodextrin | 0.148 |
| Dextrin | 0.14 |
| Gentiobiose | 0.136 |
| D-Galactose | 0.123 |
| D-Glucosamine | 0.117 |
| D-Melibiose | 0.112 |
| 3-O-b-D-Galactopyranosyl-D-Arabinose | 0.105 |
| b-Methyl-D-Galactoside | 0.103 |

FIG. 29C

| *C. leptum* (EPV6) | OD750 |
|---|---:|
| D-Fructose-6-Phosphate | 0.11 |
| D-Trehalose | 0.109 |

FIG. 29D

Preferred carbon sources out of 192 different carbon sources tested

| *B. luti* (EPV3) | OD750 |
|---|---|
| a-D-Glucose | 0.628 |
| Maltotriose | 0.625 |
| Sucrose | 0.592 |
| Palatinose | 0.588 |
| L-Fucose | 0.576 |
| Stachyose | 0.554 |
| a-D-Lactose | 0.549 |
| D-Fructose | 0.544 |
| D-Melibiose | 0.527 |
| Maltose | 0.523 |
| Salicin | 0.493 |
| D-Raffinose | 0.486 |
| Arbutin | 0.435 |
| D-Mannitol | 0.423 |
| Lactulose | 0.381 |
| D-Lactitol | 0.36 |
| D-Gluconic acid | 0.344 |
| m-Inositol | 0.32 |
| Melibionic acid | 0.29 |
| D-Sorbitol | 0.239 |
| D-Arabinose | 0.183 |
| L-Tartaric acid | 0.178 |
| L-Arabinose | 0.133 |
| Bromosuccinic acid | 0.114 |
| D-Ribose | 0.107 |

FIG. 29E

| B. wexlerae (EPV5) | OD750 |
|---|---|
| a-D-Glucose | 0.988 |
| D-Fructose | 0.964 |
| Stachyose | 0.96 |
| a-D-Lactose | 0.912 |
| Sucrose | 0.84 |
| D-Lactitol | 0.671 |
| L-Fucose | 0.647 |
| Lactulose | 0.566 |
| D-Melibiose | 0.561 |
| D-Raffinose | 0.522 |
| D-Galactose | 0.428 |
| D-Glucosamine | 0.239 |
| b-Methyl-D-Galactoside | 0.206 |
| D-Cellobiose | 0.163 |
| Pectin | 0.109 |
| Inulin | 0.105 |

FIG. 29F
Preferred carbon sources out of 192 different carbon sources tested

| B. faecis (EPV15) | OD750 |
|---|---|
| Arbutin | 0.525 |
| Gentiobiose | 0.465 |
| Salicin | 0.449 |
| D-Glucosamine | 0.273 |
| D-Arabinose | 0.269 |
| D-Sorbitol | 0.227 |
| D-Fructose | 0.213 |
| D-Cellobiose | 0.212 |
| Sucrose | 0.183 |
| Maltose | 0.183 |
| Lactulose | 0.168 |
| a-D-Lactose | 0.164 |
| a-D-Glucose | 0.164 |
| D-Melibiose | 0.163 |
| D-Mannose | 0.143 |
| L-Tartaric acid | 0.141 |
| Bromosuccinic acid | 0.141 |
| 3-O-b-D-Galactopyranosyl-D-Arabinose | 0.133 |
| b-Methyl-D-Glucuronic acid | 0.131 |
| Maltotriose | 0.127 |
| D-Galactose | 0.125 |
| L-Fucose | 0.123 |
| D-Gluconic acid | 0.121 |
| D-Mannitol | 0.117 |
| Thymidine | 0.105 |
| Inosine | 0.102 |

FIG. 29G
Preferred carbon sources out of 192 different carbon sources tested

| B. obeum (EPV20) | OD750 |
|---|---|
| D-Melibiose | 0.588 |
| D-Sorbitol | 0.545 |
| Lactulose | 0.543 |
| D-Lactitol | 0.48 |
| Sucrose | 0.463 |
| L-Arabinose | 0.442 |
| a-D-Glucose | 0.438 |
| D-Galactose | 0.427 |
| D-Mannose | 0.419 |
| D-Fructose | 0.414 |
| Stachyose | 0.405 |
| b-Methyl-D-Galactoside | 0.402 |
| D-Arabinose | 0.395 |
| D-Xylose | 0.377 |
| D-Ribose | 0.376 |
| D-Raffinose | 0.376 |
| D-Fucose | 0.373 |
| Maltose | 0.362 |
| a-D-Lactose | 0.361 |
| Maltotriose | 0.36 |
| 3-O-b-D-Galactopyranosyl-D-Arabinose | 0.352 |
| L-Rhamnose | 0.338 |
| L-Fucose | 0.299 |

FIG. 29H
Preferred carbon sources out of 192 different carbon sources tested

| *B. producta* (EPV21) | OD750 |
|---|---|
| Maltose | 0.199 |
| D-Fructose | 0.193 |
| D-Trehalose | 0.182 |
| a-Methyl-D-Galactoside | 0.179 |
| Stachyose | 0.177 |
| b-Methyl-D-Xyloside | 0.175 |
| Turanose | 0.175 |
| a-D-Glucose | 0.174 |
| Maltotriose | 0.174 |
| D-Galactose | 0.173 |
| b-Methyl-D-Glucoside | 0.17 |
| Maltitol | 0.17 |
| Palatinose | 0.17 |
| D-Arabitol | 0.168 |
| D-Raffinose | 0.167 |
| b-Methyl-D-Galactoside | 0.163 |
| a-D-Lactose | 0.161 |
| Lactulose | 0.156 |
| D-Melibiose | 0.155 |
| Sucrose | 0.153 |
| D-Cellobiose | 0.152 |
| D-Arabinose | 0.148 |
| m-Inositol | 0.146 |

FIG. 29H (cont.)
Preferred carbon sources out of 192 different carbon sources tested

| | |
|---|---|
| 3-O-b-D-Galactopyranosyl-D-Arabinose | 0.146 |
| D-Mannitol | 0.144 |
| a-Methyl-D-Mannoside | 0.142 |
| D-Lactitol | 0.14 |
| Gentiobiose | 0.137 |
| D-Mannose | 0.135 |
| N-Acetyl-Neuraminic acid | 0.134 |
| D-Sorbitol | 0.132 |
| a-Methyl-D-Glucoside | 0.131 |
| L-Rhamnose | 0.129 |
| L-Sorbose | 0.129 |
| L-Arabinose | 0.125 |
| Pyruvic acid | 0.124 |
| Arbutin | 0.118 |
| Salicin | 0.116 |
| Bromosuccinic acid | 0.114 |
| D-Melezitose | 0.113 |
| b-Methyl-D-Glucuronic acid | 0.113 |
| Glucuronamide | 0.107 |
| Amygdalin | 0.107 |
| Pectin | 0.105 |

FIG. 29I

| *B. coccoides* (EPV22) | OD750 |
|---|---|
| D-Sorbitol | 0.468 |
| Lactulose | 0.442 |
| a-D-Lactose | 0.438 |
| D-Raffinose | 0.423 |
| D-Arabitol | 0.417 |
| Stachyose | 0.407 |
| D-Melibiose | 0.403 |
| Maltotriose | 0.401 |

FIG. 29I (cont.)
Preferred carbon sources out of 192 different carbon sources tested

| Sucrose | 0.398 |
|---|---|
| D-Trehalose | 0.394 |
| Palatinose | 0.392 |
| D-Melezitose | 0.388 |
| Turanose | 0.387 |
| Amygdalin | 0.386 |
| b-Methyl-D-Glucoside | 0.384 |
| D-Galactose | 0.381 |
| Maltose | 0.367 |
| D-Lactitol | 0.363 |
| a-D-Glucose | 0.354 |
| D-Fructose | 0.352 |
| b-Methyl-D-Galactoside | 0.345 |
| 3-O-b-D-Galactopyranosyl-D-Arabinose | 0.335 |
| b-Methyl-D-Glucuronic acid | 0.33 |
| Maltitol | 0.326 |
| D-Cellobiose | 0.324 |
| m-Inositol | 0.323 |
| b-Methyl-D-Xyloside | 0.318 |
| N-Acetyl-Neuraminic acid | 0.315 |
| a-Methyl-D-Galactoside | 0.306 |
| D-Mannitol | 0.286 |
| Gentiobiose | 0.256 |
| Salicin | 0.255 |
| Uridine | 0.215 |
| D-Gluconic acid | 0.213 |
| D-Galacturonic acid | 0.2 |

Preferred carbon sources out of 192 different carbon sources tested

FIG. 29J

| B. hydrogenotrophica (EPV23) | OD750 |
|---|---|
| D-Trehalose | 0.445 |
| Palatinose | 0.418 |
| Salicin | 0.412 |
| D-Fructose | 0.377 |
| Arbutin | 0.35 |
| D-Tagatose | 0.341 |
| L-Arabinose | 0.329 |
| Xylitol | 0.301 |
| Maltotriose | 0.287 |
| a-D-Glucose | 0.282 |
| Maltose | 0.248 |
| D-Ribose | 0.218 |
| a-Keto-Valeric acid | 0.208 |
| D-Aspartic acid | 0.182 |
| a-Ketobutyric acid | 0.16 |
| Dextrin | 0.155 |
| L-Leucine | 0.137 |

FIG. 29K

| Blautia hansenii (EPV24) | OD 750 |
|---|---|
|  |  |
| a-D-Glucose | 0.34 |
| Maltose | 0.317 |
| Maltotriose | 0.311 |
| a-D-Lactose | 0.273 |
| Stachyose | 0.258 |
| D-Galactose | 0.254 |
| N-Acetyl-D-Glucosamine | 0.243 |
| D-Raffinose | 0.232 |
| D-Melibiose | 0.216 |
| Chondroitin Sulfate C | 0.214 |
| Inosine | 0.21 |
| Adenosine | 0.161 |
| 2`-Deoxyadenosine | 0.132 |

FIG. 29L
Preferred carbon sources out of 192 different carbon sources tested

| EPV114 (B. luti BlnlX) | OD750 |
|---|---|
| D-Galactose | 0.195 |
| L-Fucose | 0.221 |
| D-Xylose | 0.252 |
| D-Mannitol | 0.169 |
| L-Rhamnose | 0.205 |
| D-Fructose | 0.253 |
| a-D-Glucose | 0.306 |
| Maltose | 0.338 |
| D-Melibiose | 0.288 |
| a-D-Lactose | 0.296 |
| Lactulose | 0.217 |
| Sucrose | 0.295 |
| Maltotriose | 0.352 |
| m-Inositol | 0.18 |
| D-Cellobiose | 0.143 |
| D-Arabinose | 0.181 |
| Arbutin | 0.256 |
| D-Lactitol | 0.252 |
| b-Methyl-D-Galactoside | 0.214 |
| Palatinose | 0.249 |
| D-Raffinose | 0.314 |
| Salicin | 0.292 |
| Stachyose | 0.658 |
| L-Tartaric acid | 0.14 |

FIG. 29M

Preferred carbon sources out of 192 different carbon sources tested

| EPV54 (B. luti ELU) | OD750 |
|---|---|
| D-Galactose | 0.193 |
| L-Fucose | 0.193 |
| D-Xylose | 0.273 |
| D-Mannitol | 0.168 |
| L-Rhamnose | 0.245 |
| D-Fructose | 0.289 |
| a-D-Glucose | 0.431 |
| Maltose | 0.246 |
| D-Melibiose | 0.193 |
| a-D-Lactose | 0.363 |
| Lactulose | 0.177 |
| Sucrose | 0.305 |
| m-Inositol | 0.263 |
| D-Arabinose | 0.196 |
| Arbutin | 0.195 |
| D-Lactitol | 0.204 |
| b-Methyl-D-Galactoside | 0.198 |
| Palatinose | 0.28 |
| D-Raffinose | 0.399 |
| Salicin | 0.257 |
| Stachyose | 0.88 |
| D-Glucosamine | 0.176 |

FIG. 29N

| EPV102 (R. gnavus) | OD750 |
|---|---|
| L-Arabinose | 0.151 |
| N-Acetyl-D-Glucosamine | 0.205 |
| D-Galactose | 0.212 |
| D-Mannose | 0.134 |
| L-Fucose | 0.324 |
| D-Gluconic acid | 0.203 |
| D-Xylose | 0.14 |
| D-Ribose | 0.13 |
| D-Fructose | 0.194 |
| a-D-Glucose | 0.274 |
| Maltose | 0.263 |
| D-Melibiose | 0.194 |
| Sucrose | 0.298 |
| b-Methyl-D-Glucoside | 0.244 |
| Maltotriose | 0.337 |
| b-Cyclodextrin | 0.192 |
| g-Cyclodextrin | 0.14 |
| D-Arabinose | 0.277 |
| Arbutin | 0.307 |
| Gentiobiose | 0.271 |
| D-Raffinose | 0.265 |
| Salicin | 0.266 |
| Stachyose | 0.318 |
| D-Glucosamine | 0.19 |

FIG. 29O

Preferred carbon sources out of 192 different carbon sources tested

| EPV78 (B. faecis) | OD750 |
|---|---|
| L-Fucose | 0.142 |
| D-Xylose | 0.185 |
| D-Ribose | 0.338 |
| L-Rhamnose | 0.227 |
| a-D-Glucose | 0.138 |
| D-Arabinose | 0.132 |
| D-Raffinose | 0.132 |
| Stachyose | 0.146 |

FIG. 29P

| EPV76 (R. torques) | OD750 |
|---|---|
| D-Galactose | 0.223 |
| D-Gluconic acid | 0.166 |
| D-Fructose | 0.244 |
| a-D-Glucose | 0.257 |
| a-D-Lactose | 0.22 |
| Turanose | 0.129 |

FIG. 29Q
Preferred carbon sources out of 192 different carbon sources tested

| EPV64 (B. wexlerae WAL14507) | OD750 |
|---|---|
| L-Arabinose | 0.47 |
| D-Galactose | 0.536 |
| D-Trehalose | 0.472 |
| D-Sorbitol | 0.148 |
| L-Fucose | 0.679 |
| D-Gluconic acid | 0.436 |
| D-Xylose | 0.478 |
| D-Ribose | 0.133 |
| D-Fructose | 0.679 |
| a-D-Glucose | 0.503 |
| Maltose | 0.719 |
| D-Melibiose | 0.747 |
| a-D-Lactose | 0.732 |
| Lactulose | 0.404 |
| Sucrose | 0.572 |
| Maltotriose | 0.617 |
| D-Cellobiose | 0.163 |
| Dextrin | 0.147 |
| Inulin | 0.127 |
| Mannan | 0.127 |
| Pectin | 0.136 |
| D-Arabinose | 0.591 |
| Gentiobiose | 0.566 |
| D-Lactitol | 0.568 |
| D-Melezitose | 0.691 |
| Maltitol | 0.573 |
| b-Methyl-D-Galactoside | 0.281 |
| Palatinose | 0.648 |
| D-Raffinose | 0.783 |
| Stachyose | 0.537 |
| Turanose | 0.57 |
| D-Glucosamine | 0.204 |
| Oxalic acid | 0.125 |
| Oxalomalic acid | 0.126 |
| Quinic acid | 0.148 |
| L-Tartaric acid | 0.146 |

FIG. 29R
Preferred carbon sources out of 192 different carbon sources tested

| EPV52 (B. wexlerae SJTU) | OD750 |
|---|---|
| L-Arabinose | 0.642 |
| D-Galactose | 0.671 |
| D-Trehalose | 0.69 |
| D-Sorbitol | 0.339 |
| L-Fucose | 0.611 |
| D-Xylose | 0.636 |
| D-Mannitol | 0.127 |
| L-Rhamnose | 0.167 |
| D-Fructose | 0.74 |
| a-D-Glucose | 0.524 |
| Maltose | 0.66 |
| D-Melibiose | 0.704 |
| a-D-Lactose | 0.815 |
| Lactulose | 0.701 |
| Sucrose | 0.739 |
| Maltotriose | 0.676 |
| D-Cellobiose | 0.361 |
| Dextrin | 0.116 |
| Inulin | 0.137 |
| Mannan | 0.123 |
| Pectin | 0.123 |
| N-Acetyl-Neuraminic acid | 0.467 |
| D-Arabinose | 0.534 |
| Arbutin | 0.487 |
| Gentiobiose | 0.506 |
| D-Lactitol | 0.71 |
| D-Melezitose | 0.695 |
| Maltitol | 0.658 |
| b-Methyl-D-Galactoside | 0.321 |
| b-Methyl-D-Xyloside | 0.333 |
| Palatinose | 0.666 |
| D-Raffinose | 0.575 |
| Salicin | 0.591 |
| Stachyose | 0.74 |
| Turanose | 0.581 |
| Oxalic acid | 0.123 |
| L-Tartaric acid | 0.259 |

FIG. 29S

Preferred carbon sources out of 192 different carbon sources tested

| EPV51 (SJTU1416) | OD750 |
|---|---|
| D-Trehalose | 0.136 |
| a-D-Glucose | 0.104 |
| Maltose | 0.165 |
| D-Melibiose | 0.115 |
| a-D-Lactose | 0.171 |
| Lactulose | 0.17 |
| Sucrose | 0.18 |
| b-Methyl-D-Glucoside | 0.113 |
| Maltotriose | 0.207 |
| Amygdalin | 0.12 |
| D-Lactitol | 0.137 |
| D-Melezitose | 0.222 |
| b-Methyl-D-Galactoside | 0.142 |
| D-Raffinose | 0.186 |
| Stachyose | 0.199 |
| Turanose | 0.239 |

FIG. 29T
Preferred carbon sources out of 192 different carbon sources tested

| EPV47 (GQ8980099) | OD750 |
|---|---|
| L-Arabinose | 0.336 |
| N-Acetyl-D-Glucosamine | 0.328 |
| D-Saccharic acid | 0.128 |
| D-Galactose | 0.365 |
| L-Fucose | 0.255 |
| D-Xylose | 0.131 |
| L-Rhamnose | 0.286 |
| D-Fructose | 0.466 |
| a-D-Glucose | 0.421 |
| D-Melibiose | 0.428 |
| a-D-Lactose | 0.468 |
| Lactulose | 0.551 |
| Sucrose | 0.475 |
| Mucic acid | 0.153 |
| D-Arabinose | 0.307 |
| Arbutin | 0.389 |
| 3-O-b-D-Galactopyranosyl-D-Arabinose | 0.16 |
| D-Raffinose | 0.408 |
| Salicin | 0.342 |
| Sedoheptulosan | 0.442 |
| Stachyose | 0.516 |
| D-Glucosamine | 0.247 |

FIG. 29U
Preferred carbon sources out of 192 different carbon sources tested

| EPV35 (E rectale) | OD750 |
|---|---|
| L-Arabinose | 0.216 |
| D-Galactose | 0.208 |
| D-Xylose | 0.14 |
| D-Fructose | 0.178 |
| a-D-Glucose | 0.185 |
| Maltose | 0.113 |
| D-Melibiose | 0.173 |
| a-Methyl-D-Galactoside | 0.14 |
| a-D-Lactose | 0.188 |
| Lactulose | 0.112 |
| b-Methyl-D-Glucoside | 0.171 |
| Maltotriose | 0.151 |
| Dextrin | 0.172 |
| Glycogen | 0.144 |
| Gentiobiose | 0.169 |
| a-Methyl-D-Glucoside | 0.165 |
| b-Methyl-D-Galactoside | 0.119 |
| Stachyose | 0.196 |
| Turanose | 0.22 |
| D-Glucosamine | 0.144 |

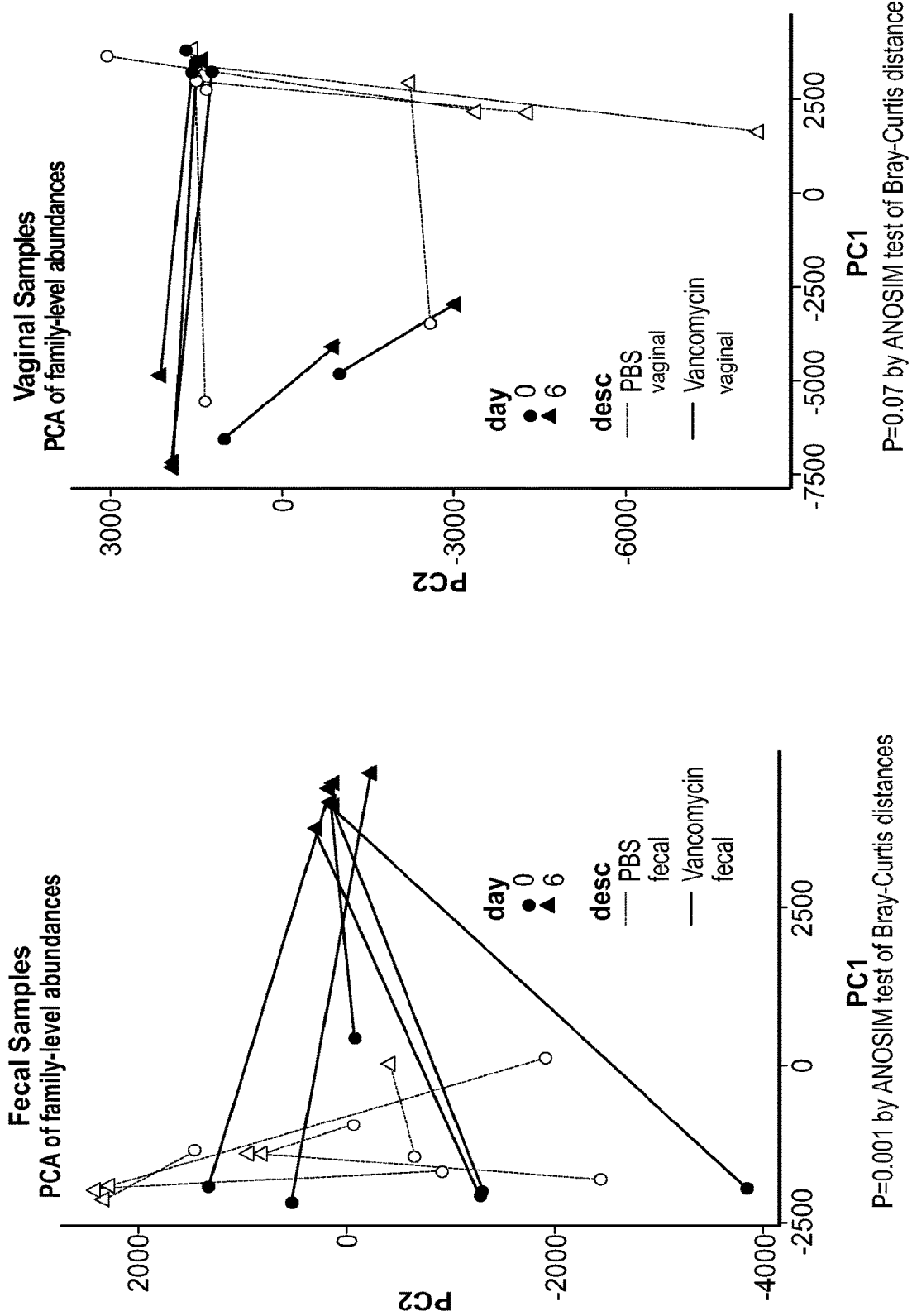
FIG. 32 Shifts in the microbiome of the gut and vagina following treatment with oral vancomycin

PROBIOTIC AND PREBIOTIC COMPOSITIONS, AND METHODS OF USE THEREOF FOR MODULATION OF THE MICROBIOME

RELATED APPLICATIONS

This application is a continuation of U.S. patent application Ser. No. 14/952,891, filed Nov. 25, 2015, which claims priority to U.S. Provisional Patent Application No. 62/084,536, filed Nov. 25, 2014; U.S. Provisional Patent Application No. 62/084,537, filed Nov. 25, 2014; U.S. Provisional Patent Application No. 62/084,540, filed Nov. 25, 2014; U.S. Provisional Patent Application No. 62/117,632, filed Feb. 18, 2015; U.S. Provisional Patent Application No. 62/117,637, filed Feb. 18, 2015; U.S. Provisional patent Application No. 62/117,639, filed Feb. 18, 2015; U.S. Provisional Patent Application No. 62/162,562, filed May 15, 2015; and U.S. Provisional Patent Application No. 62/257,714, filed Nov. 19, 2015. The entire contents of each of the foregoing applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Nov. 25, 2015, is named ETB-07502_SL.txt and is 4,147,450 bytes in size.

BACKGROUND

Humans and other mammals have numerous microbial niches, and interventions to modulate the microbiota thereof have been focused on antibiotics (which effect largely non-specific eradication of the microbiota in an effort to target a pathogen), probiotics (largely in the form of lactic acid-producing bacteria in food products), prebiotics (stimulatory materials, primarily carbohydrates, that increase bacterial growth and/or activity), and synbiotics (combinations of prebiotics and probiotics). See, e.g., WO2011/022542. Autoimmune and inflammatory diseases are characterized by an inappropriate immunological intolerance or an abnormal immune response, and affect up to 50 million Americans. Current treatments for such conditions, such as immunosuppressant drugs, carry a risk of dangerous systemic side effects such as infection, organ damage, and the development of new autoimmunities. There is therefore a need for improved diagnostic and prognostic measures, preventative measures, and treatments for autoimmune and inflammatory diseases.

It is recognized that mammals are colonized by microbes in the gastrointestinal (GI) tract, on the skin, and in other epithelial and tissue niches such as the oral cavity, eye surface and vagina. The gastrointestinal tract, vagina and other niches harbor an abundant and diverse microbial community. It is a complex system, providing an environment or niche for a community of many different species or organisms, including diverse strains of bacteria. Hundreds of different species may form a commensal community in the GI tract or vagina of a healthy person, and this complement of organisms evolves from the time of birth to ultimately form a functionally mature microbial population by about 3 years of age. A substantial diversity of species may form a commensal community in the gut and the vagina in a healthy person. Interactions between microbial strains in these populations, and between microbes and the host, e.g. the host immune system, shape the community structure as well as microbiotal niches distal to the intestinal lumen, with availability of and competition for resources affecting the distribution of microbes. Such resources may be food, location and the availability of space to grow or a physical structure to which the microbe may attach. For example, host diet is involved in shaping the GI tract flora and vaginal flora.

A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. In settings of 'dysbiosis' or disrupted symbiosis, microbiota functions can be lost or deranged, resulting in increased susceptibility to pathogens, altered metabolic profiles, or induction of proinflammatory signals that can result in local or systemic inflammation or autoimmunity. Thus, the intestinal microbiota plays a significant role in the pathogenesis of many diseases and disorders, including a variety of pathogenic infections distal to the gastrointestinal tract. For instance, subjects become more susceptible to pathogenic infections when the normal intestinal microbiota has been disturbed due to use of broad-spectrum antibiotics. Many of these diseases and disorders are chronic conditions that significantly decrease a subject's quality of life and can be ultimately fatal. Thus practitioners have a need for a method of populating a subject's gastrointestinal tract with a diverse and useful selection of microbiota in order to alter a dysbiosis. Also, practitioners have a need for a method of populating a subject's vagina, either directly or indirectly, e.g., through the gastrointestinal tract, with a diverse and useful selection of microbiota in order to alter a dysbiosis. Therefore, in response to the need for durable, efficient, and effective compositions and methods for treatment of immune and inflammatory diseases by way of restoring or enhancing microbiota functions, the present invention provides compositions and methods for treatment and prevention of immune and inflammatory conditions associated with dysbiosis, including dysbiosis distal to the gastrointestinal tract.

Antibiotic resistance is an emerging public health issue (Carlet J, Collignon P, Goldmann D, Goossens H, Gyssens I C, Harbarth S, Jarlier V, Levy S B, N'Doye B, Pittet D, et al. 2011. Society's failure to protect a precious resource: antibiotics. Lancet 378: 369-371). Numerous genera of bacteria harbor species that are developing resistance to antibiotics. These include but are not limited to Vancomycin Resistant Enterococcus (VRE) and Carbapenem resistant Klebsiella (CRKp). *Klebsiella pneumoniae* and *Escherichia coli* strains are becoming resistant to carbapenems and require the use of old antibiotics characterized by high toxicity, such as colistin (Cantón R, Akóva M, Carmen Y, Giske C G, Glupczynski Y, Gniadkowski M, Livermore D M, Miriagou V, Naas T, Rossolini G M, et al, 2012. Rapid evolution and spread of carbapenernases among Enterobacteriaceae in Europe. Clin Microbiol Infect 18: 413-431), Further multiple drug resistant strains of multiple species, including *Pseudomonas aeruginosa, Enterobacter* spp, and *Acinetobacter* spp are observed clinically including isolates that are highly resistant to ceftazidime, carbapenems, and quinolones (European Centre for Disease Prevention and Control: EARSS net database. http//ecdc.europa.eu.). The Centers for Disease Control and Prevention in 2013 released a Threat Report (http://www.cdc.gov/drugresistance/threat-report-2013/) citing numerous bacterial infection threats that included *Clostridium difficile*, Carbapenem-resistant Enterobacteriaceae (CRE), Multidrug-resistant *Acinetobacter*, Drug-resistant *Campylobacter*, Extended spectrum β-lactamase producing Enterobacteriaceae (ESBLs), Vancomycin-resistant *Enterococcus* (VRE), Multidrug-resistant *Pseudomonas aeruginosa*, Drug-resistant Non-typhoidal *Salmonella*, Drug-resistant *Salmonella Typhi*, Drug-resistant *Shigella*, Methicillin-resistant *Staphylococcus aureus* (MRSA), Drug-resistant *Streptococcus pneumoniae*, Vancomycin-resistant *Staphylococcus aureus* (VRSA), Erythromycin-resistant Group A *Streptococcus*, and Clindamycin-resistant Group B *Streptococcus*. The increasing failure of antibiotics due the rise of resistant microbes demands new therapeutics to treat bacterial infections. Administration of a probiotic therapeutic bacterial composition offers potential for such therapies. The gastrointestinal tract is implicated as a reservoir for many of these organisms including VRE, MRSA, *Pseudomonas aeruginosa, Acinetobacter* and the yeast *Candida* (Donskey, Clinical Infectious Diseases 2004 39:214, The Role of the Intestinal Tract as a Reservoir and Source for Transmission of Nosocomial Pathogens), and thus as a source of nosocomial infections. Antibiotic treatment and other decontamination procedures are among the tools in use to reduce colonization of these organisms in susceptible subjects including those who are immunosuppressed. Bacterial-based therapeutics would provide a new tool for decolonization, with a key benefit of not promoting antibiotic resistance as antibiotic therapies do.

There is a need for a safer and reproducible treatment for disorders associated with GI dysbiosis and distal dysbiosis beyond the GI tract, in addition to diseases resulting from an aberrant immune response resulting from, at least in part, the GI or distal dysbiosis.

SUMMARY OF THE INVENTION

Disclosed herein are therapeutic compositions containing probiotic, non-pathogenic bacterial populations and networks thereof, for the prevention, control, and treatment of diseases, disorders and conditions, in particular diseases associated with dysbiosis, e.g., dysbiosis distal to the gastrointestinal tract, and for general nutritional health. In some embodiments, the therapeutic compositions contain prebiotics, e.g., carbohydrates, in conjunction with microbial populations and/or networks thereof. These compositions are advantageous in being suitable for safe administration to humans and other mammalian subjects and are efficacious in numerous dysbiotic diseases, disorders and conditions and in general nutritional health.

In one aspect, the instant invention provides a method of reducing inflammation in a subject, comprising administering to the subject a probiotic composition comprising an isolated, anti-inflammatory bacterial population, such that inflammation in the subject is reduced. In one embodiment of the foregoing aspect, the probiotic composition comprises a pharmaceutically acceptable excipient.

In one embodiment of the foregoing aspect, the subject has an autoimmune or inflammatory disorder. In one embodiment of the foregoing aspect, the autoimmune or inflammatory disorder is selected from the group consisting of graft-versus-host disease (GVHD), an inflammatory bowel disease (IBD), ulterative colitis, Crohn's disease, multiple sclerosis (MS), systemic lupus erythematosus (SLE), type I diabetes, rheumatoid arthritis, Sjögren's syndrome, and Celiac disease.

In one embodiment of the foregoing aspect, administration of the probiotic composition reduces inflammation in the gastrointestinal tract of the subject. In one embodiment of the foregoing aspect, administration of the probiotic composition at a first site reduces inflammation at a distal site in the subject. In one embodiment of the foregoing aspect, the distal site is blood, skin, vagina, liver, spleen, fallopian tubes, uterus, or a combination thereof.

In embodiments of the foregoing aspects, the subject has a dysbiosis. In one embodiment of the foregoing aspect, the dysbiosis is a gastrointestinal dysbiosis. In one embodiment of the foregoing aspect, the dysbiosis is a distal dysbiosis.

In embodiments of the foregoing aspects, the anti-inflammatory bacterial population decreases secretion of pro-inflammatory cytokines and/or increases secretion of anti-inflammatory cytokines by human peripheral blood mononuclear cells (PBMCs). In one embodiment of the foregoing aspect, the anti-inflammatory bacterial population decreases secretion of a pro-inflammatory cytokine selected from the group consisting of IFNγ, IL-12p70, IL-1α, IL-6, IL-8, MCP1, MIP1α, MIP1β, TNFα, and combinations thereof. In one embodiment of the foregoing aspect, the anti-inflammatory bacterial population increases secretion of an anti-inflammatory cytokine selected from the group consisting of IL-10, IL-13, IL-4, IL-5, TGFβ, and combinations thereof.

In embodiments of the foregoing aspects, the anti-inflammatory bacterial population comprises one or more bacterial species of the order Clostridiales. In one embodiment of the foregoing aspect, the bacterial species is from the genus *Blautia, Clostridium*, or *Ruminococcus*. In one embodiment of the foregoing aspect, the bacterial population comprises a single bacterial species set forth in Table 1. In one embodiment of the foregoing aspect, the bacterial population comprises two or more bacterial species set forth in Table 1. In one embodiment of the foregoing aspect, the bacterial population comprises a single bacterial species set forth in Table 1A, Table 1B, Table 1C, Table 1D, Table 1E, or Table 1F. In one embodiment of the foregoing aspect, the bacterial population comprises two or more bacterial species set forth in Table 1A, Table 1B, Table 1C, Table 1D, Table 1E, or Table 1F.

In embodiments of the foregoing aspects, the level of the anti-inflammatory bacteria is augmented in the gastrointestinal tract of the subject. In one embodiment of the foregoing aspect, the anti-inflammatory bacteria engraft in the gastrointestinal tract of the subject.

In embodiments of the foregoing aspects, the level of the anti-inflammatory bacteria is augmented at a site distal to the site of administration in the subject. In one embodiment of the foregoing aspect, the anti-inflammatory bacteria is not detectably present at the site distal to the gastrointestinal tract of the subject prior to administration of the probiotic composition. In one embodiment of the foregoing aspect, the anti-inflammatory bacteria translocate to a distal site within the subject. In one embodiment of the foregoing aspect, the site distal to the gastrointestinal tract is the blood, skin, vagina, liver, spleen, fallopian tubes, uterus, or a combination thereof.

In embodiments of the foregoing aspects, the level of a bacterial species not present in the probiotic composition is augmented in the gastrointestinal tract of the subject. In embodiments of the foregoing aspects, the level of a bacterial species not present in the probiotic composition is augmented at a site distal to the gastrointestinal tract of the subject. In one embodiment of the foregoing aspect, the site distal to the gastrointestinal tract is the blood, skin, vagina, liver, spleen, fallopian tubes, uterus, or a combination thereof.

In embodiments of the foregoing aspects, the methods further comprise administering a prebiotic to the subject. In one embodiment of the foregoing aspect, the prebiotic augments the growth of the anti-inflammatory bacterial population present in the probiotic composition. In one embodiment of the foregoing aspect, the prebiotic comprises a monomer or polymer selected from the group consisting of arabinoxylan, xylose, soluble fiber dextran, soluble corn fiber, polydextrose, lactose, N-acetyl-lactosamine, glucose, and combinations thereof. In one embodiment of the foregoing aspect, the prebiotic comprises a monomer or polymer selected from the group consisting of galactose, fructose, rhamnose, mannose, uronic acids, 3'-fucosyllactose, 3' sialyllactose, 6'-sialyllactose, lacto-N-neotetraose, 2'-2'-fucosyllactose, and combinations thereof. In one embodiment of the foregoing aspect, the prebiotic comprises a monosaccharide selected from the group consisting of arabinose, fructose, fucose, lactose, galactose, glucose, mannose, D-xylose, xylitol, ribose, and combinations thereof. In one embodiment of the foregoing aspect, the prebiotic comprises a disaccharide selected from the group consisting of xylobiose, sucrose, maltose, lactose, lactulose, trehalose, cellobiose, and combinations thereof. In one embodiment of the foregoing aspect, the prebiotic comprises a polysaccharide, wherein the polysaccharide is xylooligosaccharide. In one embodiment of the foregoing aspect, the prebiotic comprises a sugar selected from the group consisting of arabinose, fructose, fucose, lactose, galactose, glucose, mannose, D-xylose, xylitol, ribose, xylobiose, sucrose, maltose, lactose, lactulose, trehalose, cellobiose, xylooligosaccharide, and combinations thereof.

In another aspect, the invention provides a method of treating a distal dysbiosis in a subject, comprising administering to the subject a probiotic composition comprising an isolated bacterial population in an amount sufficient to alter the microbiome at a site distal to the site of administration, engraftment, or colonization, such that the distal dysbiosis is treated.

In one embodiment of the foregoing aspect, the probiotic composition comprises a species of bacteria that is deficient at the site of the distal dysbiosis. In one embodiment of the foregoing aspect, a species of bacteria present in the probiotic composition is augmented at the site of the distal dysbiosis. In one embodiment of the foregoing aspect, the species of bacteria augmented at the site of the distal dysbiosis is not detectably present at the site of the distal dysbiosis prior to administration of the probiotic composition. In one embodiment of the foregoing aspect, the species of bacteria translocates to the site of the distal dysbiosis. In one embodiment of the foregoing aspect, a species of bacteria not present in the probiotic composition is augmented at the site of the distal dysbiosis.

In one embodiment of the foregoing aspect, the site of the distal dysbiosis is the blood, skin, vagina, liver, spleen, fallopian tubes, uterus, or a combination thereof.

In one embodiment of the foregoing aspect, the dysbiosis is caused by a deficiency in microbes that produce short chain fatty acids. In one embodiment of the foregoing aspect, the probiotic composition comprises a species of bacteria that produce short chain fatty acids. In one embodiment of the foregoing aspect, the dysbiosis is caused by a deficiency in microbes that produce lactic acid.

In one embodiment of the foregoing aspect, the probiotic composition comprises a species of bacteria that produce lactic acid. In one embodiment of the foregoing aspect, the probiotic composition reduces inflammation at the site of administration. In one embodiment of the foregoing aspect, the probiotic composition reduces inflammation at a site distal to the site of administration. In one embodiment of the foregoing aspect, the probiotic composition reduces intestinal permeability in the subject.

In one embodiment of the foregoing aspect, the distal dysbiosis is associated with an autoimmune or inflammatory disorder in the subject. In one embodiment of the foregoing aspect, the autoimmune or inflammatory disorder is selected from the group consisting of graft-versus-host disease (GVHD), an inflammatory bowel disease (IBD), ulterative colitis, Crohn's disease, multiple sclerosis (MS), systemic lupus erythematosus (SLE), type I diabetes, rheumatoid arthritis, Sjögren's syndrome, and Celiac disease.

In one embodiment of the foregoing aspect, wherein the distal dysbiosis is associated with increased susceptibility to graft versus host disease (GVHD) in the subject. In one embodiment of the foregoing aspect, the subject is a subject receiving a transplant. In one embodiment of the foregoing aspect, the transplant is a hematopoietic stem cell transplant, a bone marrow transplant, or a solid organ transplant. In one embodiment of the foregoing aspect, the distal dysbiosis is associated with an autoimmune or inflammatory disorder other than graft-versus host disease (GVHD).

In embodiments of the foregoing aspects, the bacterial population comprises one or more bacterial species of the order Clostridiales. In one embodiment of the foregoing aspect, the bacterial population comprises a single bacterial species set forth in Table 1. In one embodiment of the foregoing aspect, the bacterial population comprises two or more bacterial species set forth in Table 1. In one embodiment of the foregoing aspect, the bacterial population comprises a single bacterial species set forth in Table 1A, Table 1B, Table 1C, Table 1D, Table 1E, or Table 1F. In one embodiment of the foregoing aspect, the bacterial population comprises two or more bacterial species set forth in Table 1A, Table 1B, Table 1C, Table 1D, Table 1E, or Table 1F.

In embodiments of the foregoing aspects, the methods further comprise administering a prebiotic to the subject. In one embodiment of the foregoing aspect, the prebiotic augments the growth of the bacterial population present in the probiotic composition. In one embodiment of the foregoing aspect, the prebiotic comprises a monomer or polymer selected from the group consisting of arabinoxylan, xylose, soluble fiber dextran, soluble corn fiber, polydextrose, lactose, N-acetyl-lactosamine, glucose, and combinations thereof. In one embodiment of the foregoing aspect, the prebiotic comprises a monomer or polymer selected from the group consisting of galactose, fructose, rhamnose, mannose, uronic acids, 3'-fucosyllactose, 3' sialylactose, 6'-sialyllactose, lacto-N-neotetraose, 2'-2'-fucosyllactose, and combinations thereof. In one embodiment of the foregoing aspect, the prebiotic comprises a monosaccharide selected from the group consisting of arabinose, fructose, fucose, lactose, galactose, glucose, mannose, D-xylose, xylitol, ribose, and combinations thereof. In one embodiment of the foregoing aspect, the prebiotic comprises a disaccharide selected from the group consisting of xylobiose, sucrose, maltose, lactose, lactulose, trehalose, cellobiose, and combinations thereof. In one embodiment of the foregoing aspect, the prebiotic comprises a polysaccharide, wherein the polysaccharide is xylooligosaccharide. In one embodiment of the foregoing aspect, the prebiotic comprises a sugar selected from the group consisting of arabinose, fructose, fucose, lactose, galactose, glucose, mannose, D-xylose, xylitol, ribose, xylobiose, sucrose, maltose, lactose, lactulose, trehalose, cellobiose, xylooligosaccharide, and combinations thereof.

In another aspect, the invention provides a method of reducing intestinal permeability in a subject, comprising administering to the subject a probiotic composition comprising an isolated bacterial population, wherein administration of the probiotic composition augments a species of bacteria that produces short chain fatty acids, mucin, or a combination thereof, such that the intestinal permeability of the subject is reduced.

In one embodiment of the foregoing aspect, the probiotic composition comprises the species of bacteria that produces short chain fatty acids. In one embodiment of the foregoing aspect, the species of bacteria produces butyrate. In one embodiment of the foregoing aspect, the reduction in intestinal permeability modulates microbial diversity at a site distal to the gastrointestinal tract in the subject.

In embodiments of the foregoing aspects, the bacterial population comprises one or more bacterial species of the order Clostridiales. In one embodiment of the foregoing aspect, the bacterial species is from the genus *Blautia*, *Clostridium*, or *Ruminococcus*. In one embodiment of the foregoing aspect, the bacterial population comprises a single bacterial species set forth in Table 1. In one embodiment of the foregoing aspect, the bacterial population comprises two or more bacterial species set forth in Table 1. In one embodiment of the foregoing aspect, the bacterial population comprises a single bacterial species set forth in Table 1A, Table 1B, Table 1C, Table 1D, Table 1E, or Table 1F. In one embodiment of the foregoing aspect, the bacterial population comprises two or more bacterial species set forth in Table 1A, Table 1B, Table 1C, Table 1D, Table 1E, or Table 1F.

In embodiments of the foregoing aspects, the methods further comprise administering a prebiotic to the subject. In one embodiment of the foregoing aspect, the prebiotic augments the growth of the bacterial population present in the probiotic composition. In one embodiment of the foregoing aspect, the prebiotic comprises a monomer or polymer selected from the group consisting of arabinoxylan, xylose, soluble fiber dextran, soluble corn fiber, polydextrose, lactose, N-acetyl-lactosamine, glucose, and combinations thereof. In one embodiment of the foregoing aspect, the prebiotic comprises a monomer or polymer selected from the group consisting of galactose, fructose, rhamnose, mannose, uronic acids, 3'-fucosyllactose, 3' sialylactose, 6'-sialyllactose, lacto-N-neotetraose, 2'-2'-fucosyllactose, and combinations thereof. In one embodiment of the foregoing aspect, the prebiotic comprises a monosaccharide selected from the group consisting of arabinose, fructose, fucose, lactose, galactose, glucose, mannose, D-xylose, xylitol, ribose, and combinations thereof. In one embodiment of the foregoing aspect, the prebiotic comprises a disaccharide selected from the group consisting of xylobiose, sucrose, maltose, lactose, lactulose, trehalose, cellobiose, and combinations thereof. In one embodiment of the foregoing aspect, the prebiotic comprises a polysaccharide, wherein the polysaccharide is xylooligosaccharide. In one embodiment of the foregoing aspect, the prebiotic comprises a sugar selected from the group consisting of arabinose, fructose, fucose, lactose, galactose, glucose, mannose, D-xylose, xylitol, ribose, xylobiose, sucrose, maltose, lactose, lactulose, trehalose, cellobiose, xylooligosaccharide, and combinations thereof.

In another aspect, the invention provide a method of treating or preventing a disorder associated with a distal dysbiosis in a subject in need thereof, comprising administering to the subject a probiotic composition comprising an isolated bacterial population in an amount sufficient to alter the microbiome at a site distal to the site of administration, engraftment, or colonization, such that the disorder associated with the distal dysbiosis is treated.

In one embodiment of the foregoing aspect, the disorder associated with the distal dysbiosis is an autoimmune or inflammatory disease. In one embodiment of the foregoing aspect, the autoimmune or inflammatory disease is selected from the group consisting of graft-versus-host disease (GVHD), an inflammatory bowel disease (IBD), ulterative colitis, Crohn's disease, multiple sclerosis (MS), systemic lupus erythematosus (SLE), type I diabetes, rheumatoid arthritis, Sjögren's syndrome, and Celiac disease.

In one embodiment of the foregoing aspect, the disorder associated with the distal dysbiosis is a transplant disorder. In one embodiment of the foregoing aspect, the transplant disorder is graft-versus-host-disease. the subject is receiving a hematopoietic stem cell transplant, a bone marrow transplant, or a solid organ transplant. In one embodiment of the foregoing aspect, the solid organ transplant is selected from the group consisting of a kidney transplant, a heart transplant, a lung transplant, a skin transplant, a liver transplant, a pancreas transplant, an intestinal transplant, an endocrine gland transplant, a bladder transplant, and a skeletal muscle transplant.

In one embodiment of the foregoing aspect, the subject has a dysbiosis at a distal site selected from the group consisting of blood, skin, vagina, liver, spleen, fallopian tubes, uterus, and combinations thereof.

In one embodiment of the foregoing aspect, the probiotic composition comprises a species of bacteria that is deficient at the site of the distal dysbiosis. In one embodiment of the foregoing aspect, a species of bacteria present in the probiotic composition is augmented at the site of the distal dysbiosis. In one embodiment of the foregoing aspect, the species of bacteria augmented at the site of the distal dysbiosis is not detectably present at the site of the distal dysbiosis prior to administration of the probiotic composition. In one embodiment of the foregoing aspect, the species of bacteria translocates to the site of the distal dysbiosis. In one embodiment of the foregoing aspect, species of bacteria not present in the probiotic composition is augmented at the site of the distal dysbiosis.

In one embodiment of the foregoing aspect, the dysbiosis is caused by a deficiency in microbes that produce short chain fatty acids. In one embodiment of the foregoing aspect, the probiotic composition comprises a species of bacteria that produce short chain fatty acids. In one embodiment of the foregoing aspect, the dysbiosis is caused by a deficiency in microbes that produce lactic acid. In one embodiment of the foregoing aspect, the probiotic composition comprises a species of bacteria that produce lactic acid.

In one embodiment of the foregoing aspect, the probiotic composition reduces inflammation in the gastrointestinal tract of the subject. In one embodiment of the foregoing aspect, the probiotic composition reduces inflammation at a site distal to the gastrointestinal tract of the subject. In one embodiment of the foregoing aspect, the probiotic composition reduces intestinal permeability in the subject.

In embodiments of the foregoing aspects, the bacterial population comprises one or more bacterial species of the order Clostridiales. In one embodiment of the foregoing aspect, the bacterial population comprises a single bacterial species set forth in Table 1. In one embodiment of the foregoing aspect, the bacterial population comprises two or more bacterial species set forth in Table 1. In one embodiment of the foregoing aspect, the bacterial population comprises a single bacterial species set forth in Table 1A, Table 1B, Table 1C, Table 1D, Table 1E, or Table 1F. In one embodiment of the foregoing aspect, the bacterial population comprises two or more bacterial species set forth in Table 1A, Table 1B, Table 1C, Table 1D, Table 1E, or Table 1F.

In embodiments of the foregoing aspects, the methods further comprise administering a prebiotic to the subject. In one embodiment of the foregoing aspect, the prebiotic augments the growth of the bacterial population present in the probiotic composition. In one embodiment of the foregoing aspect, the prebiotic comprises a monomer or polymer selected from the group consisting of arabinoxylan, xylose, soluble fiber dextran, soluble corn fiber, polydextrose, lactose, N-acetyl-lactosamine, glucose, and combinations thereof. In one embodiment of the foregoing aspect, the prebiotic comprises a monomer or polymer selected from the group consisting of galactose, fructose, rhamnose, mannose, uronic acids, 3'-fucosyllactose, 3' sialylactose, 6'-sialyllactose, lacto-N-neotetraose, 2'-2'-fucosyllactose, and combinations thereof. In one embodiment of the foregoing aspect, the prebiotic comprises a monosaccharide selected from the group consisting of arabinose, fructose, fucose, lactose, galactose, glucose, mannose, D-xylose, xylitol, ribose, and combinations thereof. In one embodiment of the foregoing aspect, the prebiotic comprises a disaccharide selected from the group consisting of xylobiose, sucrose, maltose, lactose, lactulose, trehalose, cellobiose, and combinations thereof. In one embodiment of the foregoing aspect, the prebiotic comprises a polysaccharide, wherein the polysaccharide is xylooligosaccharide. In one embodiment of the foregoing aspect, the prebiotic comprises a sugar selected from the group consisting of arabinose, fructose, fucose, lactose, galactose, glucose, mannose, D-xylose, xylitol, ribose, xylobiose, sucrose, maltose, lactose, lactulose, trehalose, cellobiose, xylooligosaccharide, and combinations thereof.

In another aspect, the invention provides a pharmaceutical composition comprising an isolated anti-inflammatory bacterial population capable of decreasing secretion of pro-inflammatory cytokines and/or increasing secretion of anti-inflammatory cytokines by human peripheral blood mononuclear cells (PBMCs), and a pharmaceutically acceptable excipient.

In one embodiment of the foregoing aspect, the bacterial population comprises one or more bacterial species of the order Clostridiales. In one embodiment of the foregoing aspect, the bacterial population comprises a single bacterial species set forth in Table 1. In one embodiment of the foregoing aspect, the bacterial population comprises two or more bacterial species set forth in Table 1. In one embodiment of the foregoing aspect, the bacterial population comprises a single bacterial species set forth in Table 1A, Table 1B, Table 1C, Table 1D, Table 1E, or Table 1F. In one embodiment of the foregoing aspect, the bacterial population comprises two or more bacterial species set forth in Table 1A, Table 1B, Table 1C, Table 1D, Table 1E, or Table 1F.

In one embodiment of the foregoing aspect, the pharmaceutical composition further comprising a prebiotic. In one embodiment of the foregoing aspect, the prebiotic comprises a monomer or polymer selected from the group consisting of arabinoxylan, xylose, soluble fiber dextran, soluble corn fiber, polydextrose, lactose, N-acetyl-lactosamine, glucose, and combinations thereof. In one embodiment of the foregoing aspect, the prebiotic comprises a monomer or polymer selected from the group consisting of galactose, fructose, rhamnose, mannose, uronic acids, 3'-fucosyllactose, 3' sialylactose, 6'-sialyllactose, lacto-N-neotetraose, 2'-2'-fucosyllactose, and combinations thereof. In one embodiment of the foregoing aspect, the prebiotic comprises a monosaccharide selected from the group consisting of arabinose, fructose, fucose, lactose, galactose, glucose, mannose, D-xylose, xylitol, ribose, and combinations thereof. In one embodiment of the foregoing aspect, the prebiotic comprises a disaccharide selected from the group consisting of xylobiose, sucrose, maltose, lactose, lactulose, trehalose, cellobiose, and combinations thereof. In one embodiment of the foregoing aspect, the prebiotic comprises a polysaccharide, wherein the polysaccharide is xylooligosaccharide. In one embodiment of the foregoing aspect, the prebiotic comprises a sugar selected from the group consisting of arabinose, fructose, fucose, lactose, galactose, glucose, mannose, D-xylose, xylitol, ribose, xylobiose, sucrose, maltose, lactose, lactulose, trehalose, cellobiose, xylooligosaccharide, and combinations thereof.

In a first aspect, the instant invention provides a pharmaceutical formulation comprising a microbial network in an amount effective to populate the gastrointestinal tract in a human subject in need thereof to whom the formulation is administered, under conditions such that i) at least one type of microbe (e.g., one or more microbial species, such as a bacterial species, or more than one strain of a particular microbial species) not detectably present in the microbial network or in the gastrointestinal tract prior to administration is augmented, and ii) the immune system of the human subject is modulated.

In another aspect, the instant invention provides a pharmaceutical formulation comprising a purified bacterial population comprising a plurality of bacterial entities, wherein the bacterial entities are present in an amount effective to induce the formation of a functional microbial network in the gastrointestinal tract in a human subject in need thereof to whom the formulation is administered, under conditions such that the immune system of the human subject is modulated.

In another aspect, the invention relates to a pharmaceutical formulation comprising a purified fungal population comprising a plurality of fungal entities, wherein the fungal entities are present in an amount effective to induce the formation of a functional microbial network in the gastrointestinal tract in a human subject in need thereof to whom the formulation is administered, under conditions such that the immune system of the human subject is modulated.

In another aspect, the instant invention provides a pharmaceutical formulation comprising a purified microbial population comprising a plurality of microbial entities, wherein the microbial entities are present in an amount effective to induce the formation of a functional network in the gastrointestinal tract in a human subject in need thereof to whom the formulation is administered, under conditions such that the immune system of the human subject is modulated.

In some embodiments of the foregoing aspects, the functional network comprises at least one fungal entity and/or one bacterial entity, and separately comprises at least one host gastrointestinal tract cell and/or at least one immune cell.

In another aspect, the instant invention provides a pharmaceutical formulation comprising a microbial augmentation agent, wherein the microbial augmentation agent is capable of augmenting at least one microbial entity when administered to a human subject in need thereof.

In another aspect, the instant invention provides a pharmaceutical formulation comprising a microbial network in an amount effective to correct a distal dysbiosis in a human subject in need thereof to whom the formulation is administered, under conditions such that i) at least one type of microbe not detectably present in the microbial network or in the location of the distal dysbiosis prior to administration is augmented, and ii) the immune system of the human subject is modulated.

In another aspect, the instant invention provides a pharmaceutical formulation comprising a purified bacterial population comprising a plurality of bacterial entities, wherein the bacterial entities are present in an amount effective to induce the formation of a functional microbial network at the location of the distal dysbiosis in a human subject in need thereof to whom the formulation is administered, under conditions such that the immune system of the human subject is modulated.

In another aspect, the instant invention provides a pharmaceutical formulation comprising a purified fungal population comprising a plurality of fungal entities, wherein the fungal entities are present in an amount effective to induce the formation of a functional microbial network at the location of the distal dysbiosis in a human subject in need thereof to whom the formulation is administered, under conditions such that the immune system of the human subject is modulated.

In some embodiments of the foregoing aspects, the functional microbial network comprises a bacterial entity, a fungal entity, or a combination thereof.

In some embodiments of the foregoing aspects, the augmentation produces a functional network in the location of the distal dysbiosis.

In another aspect, the instant invention is directed to a diagnostic composition for the detection of a dysbiosis associated with an immune or inflammatory disease, comprising a first detection moiety capable of detecting a first bacterial entity and a second detection moiety capable of detecting a second bacterial entity, wherein the first and second bacterial entities comprise a network, wherein the absence of at least one of the first and second bacterial entities in a mammalian subject is indicative of a dysbiosis.

In another aspect, the instant invention is directed to a diagnostic device for the detection of a dysbiosis associated with an immune or inflammatory disease, comprising a first detection means capable of detecting a first bacterial entity and optionally a second detection moiety capable of detecting a second bacterial entity, wherein the first and second bacterial entities comprise a network, wherein the absence of at least one of the first and second bacterial entities in a mammalian subject is indicative of a dysbiosis.

In some embodiments of the foregoing aspects, the detection means comprises a magnetic resonance imaging device, wherein the mammalian subject is suffering from or at risk of developing a neurological disorder. In some embodiments, the detection means comprises a endoscopic examination device, wherein the mammalian subject is suffering from or at risk of developing an inflammatory bowel disorder.

In another aspect, the instant invention provides a method of altering a microbiome population present in a human subject, comprising the steps of determining the presence of an incomplete network of microbial entities in a distal microbiota of the human subject, and introducing to the human subject an effective amount of one or more supplemental microbial entities not detectable in the distal microbiota and/or the gastrointestinal tract of the human subject prior to such administration, under conditions such that the incomplete network is completed, thereby altering the microbiome population, wherein the human subject is suffering from or at risk of developing an immune associated disease, disorder or condition if the microbiome population is not altered.

In some embodiments of the foregoing aspects, the one or more supplemental microbial entities become part of the incomplete network, thereby forming a complete network. In some embodiments, the one or more supplemental microbial entities alter the microbiota of the mammalian subject such that one or more additional microbial entities complete the incomplete network. In some embodiments, the one or more supplemental microbial entities comprise a bacterial entity.

In another aspect, the invention is directed to a method for detection and correction of a dysbiosis in a human subject in need thereof, comprising the steps of: providing a fecal sample from the human subject comprising a plurality of bacterial entities; contacting the fecal sample with a first detection moiety capable of detecting a first bacterial entity present in a network; detecting the absence of the first bacterial entity in the fecal sample, thereby detecting a dysbiosis in the human subject; and administering to the human subject a composition comprising an effective amount of the first bacterial entity.

In another aspect, the invention is directed to a method for detection and correction of an immune-associated dysbiosis in a human subject in need thereof, comprising the steps of: providing a biological sample from the human subject comprising an immune-associated analyte; contacting the biological sample with a first detection moiety capable of detecting the immune-associated analyte; detecting the presence of the immune-associated analyte in the biological sample, thereby detecting an immune-associated dysbiosis in the human subject; and administering to the human subject a composition comprising an effective amount of a first microbial entity in an amount effective to correct the immune-associated dysbiosis.

In some embodiments of the foregoing aspects, the steps further comprise confirming that the dysbiosis in the human subject has been corrected.

In some embodiments of the foregoing aspects, the biological sample is selected from the group comprising: whole blood, blood plasma, urine, tears, semen, saliva, buccal mucosa, interstitial fluid, lymph fluid, meningeal fluid, amniotic fluid, glandular fluid, sputum, feces, perspiration, mucous, vaginal secretion, cerebrospinal fluid, hair, skin, fecal material, wound exudate, wound homogenate, and wound fluid.

In some embodiments of the foregoing aspects, the immune-associated analyte is selected from the group consisting of an immune cell, an antibody, or a cytokine. In some embodiments, the immune-associated analyte is IL-1 or TNF-alpha.

In another aspect, the instant invention provides a method of inducing translocation of a bacterial population in a distal microbiota of a human subject, comprising the step of administering to the human subject an orally acceptable pharmaceutical formulation comprising a purified bacterial network, under conditions such that at least i) a subset of the bacterial entities present in the bacterial network sustainably engraft within the gastrointestinal tract, or ii) at least one type of bacteria not present in the therapeutic composition is augmented within the gastrointestinal tract, and wherein at least one bacterial entity present in the bacterial network translocates to a distal microbiota in the human subject.

In another aspect, the instant invention provides a pharmaceutical formulation comprising a microbial network in an amount effective to augment a distal microbiota in a human subject in need thereof to whom the formulation is administered, under conditions such that i) at least one type of microbe not detectably present in the microbial network or in the distal microbiota prior to administration is augmented, and ii) the immune system of the human subject is modulated.

In some embodiments of the foregoing aspects, the pharmaceutical formulation is formulated for oral delivery, rectal delivery, vaginal delivery, intravenous delivery, subdermal delivery or intramuscular delivery.

In another aspect, the instant invention provides a pharmaceutical formulation comprising a purified bacterial population comprising a plurality of bacterial entities, wherein the bacterial entities are present in an amount effective to induce the formation of a functional microbial network in a distal microbiota in a human subject in need thereof to whom the formulation is administered, under conditions such that the immune system of the human subject is modulated.

In another aspect, the instant invention provides a pharmaceutical formulation comprising a purified fungal population comprising a plurality of fungal entities, wherein the fungal entities are present in an amount effective to induce the formation of a functional microbial network in a distal microbiota in a human subject in need thereof to whom the formulation is administered, under conditions such that the immune system of the human subject is modulated.

In some embodiments of the foregoing aspects, the functional microbial network comprises a bacterial entity, a fungal entity, or a combination thereof.

In some embodiments of the foregoing aspects, the human subject is suffering from or at risk of developing a dysbiosis. In some embodiments, the human subject is suffering from or at risk of developing a disease, disorder or condition associated with an aberrant immune response or inflammatory response.

In some embodiments of the foregoing aspects, the augmentation produces a functional network in the gastrointestinal tract.

In some embodiments of the foregoing aspects, the pharmaceutical formulation is provided as i) an oral finished pharmaceutical dosage form including at least one pharmaceutically acceptable carrier, or ii) a finished pharmaceutical dosage form suitable for parenteral administration, including at least one pharmaceutically acceptable carrier.

In some embodiments of the foregoing aspects, mammalian subject suffers from a dysbiosis comprising an autoimmune disease or an autoinflammatory disease, disorder or condition. In some embodiments, the mammalian subject suffers from a gastrointestinal dysbiosis. In other embodiments, the mammalian subject suffers from a distal dysbiosis. In some embodiments, the mammalian subject suffers from a colonization with a pathogen or pathobiont, or infection with a drug-resistant pathogen or pathobiont.

In some embodiments of the foregoing aspects, the microbial network comprises at least one bacterial entity and/or at least one fungal entity purified from a fecal material. In some embodiments, the fecal material is subjected to a culture step and/or a treatment step. In some embodiments, the microbial network is substantially depleted of a detectable level of a first pathogenic material.

In other embodiments of the foregoing aspects, the microbial network produces a first polypeptide capable of catalyzing a first chemical reaction, wherein the first chemical reaction is capable of occurring in the gastrointestinal tract of the human subject under conditions such that a first product of the first chemical reaction, a substance present within said mammalian subject, or a combination of the first product with the substance is used as a substrate in a second chemical reaction to form a second product, wherein the second product induces an immune response. In some embodiments, the immune response comprises increased T cell production.

In some embodiments of the foregoing aspects, the microbial network comprises a network of at least two bacterial entities, wherein the network comprises at least one keystone bacterial entity and at least one non-keystone bacterial entity, wherein the at least two bacterial entities are each provided in amounts effective for the treatment or prevention of an immune disease, disorder or condition in the human subject. In another embodiment, the microbial network comprises at least three bacterial entities. In some embodiments, the microbial network comprises at least three bacterial entities including at least two keystone bacterial entities. In some embodiments of the foregoing aspects, the microbial network comprises at least two keystone bacterial entities capable of forming germination-competent spores, wherein the at least two keystone bacterial entities are each provided in amounts effective for the treatment or prevention of a dysbiosis in the human subject. In other embodiments of the foregoing aspects, the microbial network comprises a network of at least two keystone bacterial entities capable of forming germination-competent spores.

In another aspect, the instant invention provides a pharmaceutical formulation comprising a purified microbial population comprising a plurality of microbial entities, wherein the microbial entities are present in an amount effective to induce the formation of a functional network in a distal microbiota in a human subject in need thereof to whom the formulation is administered, under conditions such that the immune system of the human subject is modulated.

In certain embodiments of the foregoing aspects, the functional network comprises at least one fungal entity and/or one bacterial entity, and separately comprises at least one host gastrointestinal tract cell and/or at least one immune cell.

In another aspect, the instant invention is directed to a pharmaceutical formulation comprising a microbial augmentation agent, wherein the microbial augmentation agent is capable of augmenting at least one microbial entity present in a distal microbiota when administered to a human subject in need thereof.

In some embodiments of the foregoing aspects, the microbial augmentation agent is a small molecule, a polypeptide, an antibody, a bacterial entity, a fungal entity, a viral entity, an isolated mammalian cell, or a combination thereof, and wherein the microbial augmentation agent is capable of augmenting the at least one microbial entity to an amount in the human subject effective to induce the formation of a functional network in the gastrointestinal tract in a human subject in need thereof to whom the formulation is administered, under conditions such that the immune system of the human subject is modulated.

In another aspect, the instant invention is directed to a diagnostic composition for the detection of a dysbiosis associated with an immune or inflammatory disease, comprising a first detection moiety capable of detecting a first bacterial entity present in a distal microbiota.

In some embodiments of the foregoing aspects, the diagnostic composition further comprises a second detection moiety capable of detecting a second bacterial entity. In some embodiments of the foregoing aspects, the first and second bacterial entities comprise a network, wherein the absence of at least one of the first and second bacterial entities in a mammalian subject is indicative of a dysbiosis.

In another aspect, the instant invention is directed to a diagnostic device for the detection of a dysbiosis associated with an immune or inflammatory disease, comprising a first detection means capable of detecting a first bacterial entity present at a distal dysbiosis.

In some embodiments of the foregoing aspects, the diagnostic device further comprises a second detection moiety capable of detecting a second bacterial entity, wherein the first and second bacterial entities comprise a network, wherein the absence of at least one of the first and second bacterial entities in a mammalian subject is indicative of a dysbiosis.

In some embodiments of the foregoing aspects, the detection means comprises a magnetic resonance imaging device, wherein the mammalian subject is suffering from or at risk of developing a neurological disorder. In some embodiments of the foregoing aspects, the detection means comprises an endoscopic examination device, wherein the mammalian subject is suffering from or at risk of developing an inflammatory bowel disorder.

In one aspect, the instant invention is directed to a therapeutic composition comprising a purified population of immunomodulatory bacteria produced by the steps of a) providing a fecal material and b) subjecting the material to a culture step and/or a treatment step resulting in purification of immunomodulatory bacteria and, optionally, c) formulating the purified population for oral administration, wherein the purified population is present in the composition in an amount effective to engraft and/or augment in the gastrointestinal tract in order to treat, prevent or reduce the severity of a symptom of a distal dysbiosis in a mammalian recipient subject to whom the therapeutic composition is administered.

In some embodiments of the foregoing aspect, the population is effective to treat a disease, disorder or condition associated with a gastrointestinal dysbiosis. In some embodiments, the population is effective to treat a disease, disorder or condition associated with a non-gastrointestinal dysbiosis. In some embodiments, the population is effective to reduce the severity of at least one symptom of the distal dysbiosis. In some embodiments, the population is effective to modulate the microbiota diversity present in the mammalian recipient.

In some embodiments of the foregoing aspect, the population comprises a population of bacterial entities. In some embodiments, the population of bacterial entities is isolated from a mammalian source. In some embodiments, the purified population of bacterial entities is isolated from a human source. In some embodiments, the purified population of bacterial entities is isolated from the skin of a human source. In other embodiments, the purified population of bacterial entities is isolated from the gastrointestinal tract of a human source. In some embodiments, the purified population of bacterial entities is isolated from the fecal matter of a subject. In some embodiments, the purified population of bacterial entities is isolated from human fecal matter. In other embodiments, the purified population of bacterial entities is not isolated from fecal matter. In some embodiments, the purified population of bacterial entities is not derived from fecal matter.

In some embodiments of the foregoing aspect, the fecal material is obtained from a healthy mammalian donor subject or a plurality of mammalian donor subjects.

In some embodiments of the foregoing aspect, the treatment step comprises: heating the material above 25 degrees Celsius for at least 30 seconds; contacting the material with a solvent; and or contacting a chemical or physical manipulation of the material. In some embodiments of the foregoing aspect, the culture step comprises replicating the purified population in a liquid suspension and/or a solid medium. In some embodiments of the foregoing aspect, the therapeutic composition comprises removing at least a portion of an acellular component of the fecal material, thereby separating immunomodulatory bacteria from acellular material.

In some embodiments of the foregoing aspect, the population comprises a single bacterial preparation or a combination of bacterial preparations, wherein each bacterial preparation is purified from a fecal material obtained from a single mammalian donor subject. In some embodiments, the population comprises a single bacterial preparation or a combination of bacterial preparations wherein each bacterial preparation is purified from a fecal material obtained from a mammalian donor subject.

In some embodiments of the foregoing aspect, the recipient subject is immunocompromised or immunosuppressed.

In some embodiments of the foregoing aspect, the mammalian subject is suffering from a gastrointestinal disease, disorder or condition selected from the group consisting of *Clostridium difficile*-induced diarrhea, irritable bowel syndrome (IBS), colonization with a pathogen or pathobiont, infection with a drug-resistant pathogen or pathobiont, colitis, and Crohn's Disease.

In some embodiments of the foregoing aspect, the treatment step comprises depleting or inactivating a pathogenic material.

In another aspect, the instant invention is directed to a therapeutic composition comprising a purified population of immunomodulatory bacteria produced by the steps of a) providing a fecal material and b) subjecting the material to a culture step and/or a treatment step resulting in purification of immunomodulatory bacteria and, optionally, c) formulating the purified population for oral administration, wherein the purified population is present in the composition in an amount effective to engraft and/or augment in the gastrointestinal tract in order to treat, prevent or reduce the severity of a symptom of an immune disorder in a mammalian recipient subject to whom the therapeutic composition is administered.

In another aspect, the instant invention provides a therapeutic composition comprising a purified population of immunomodulatory bacteria, in an amount effective to i) treat or prevent an inflammatory condition resulting from a dysbiosis and/or ii) augment at least one type of bacteria not present in the therapeutic composition in a mammalian recipient subject to whom the therapeutic composition is administered, and/or iii) engraft at least one type of bacteria present in the therapeutic composition but not present in a mammalian subject prior to treatment.

In some embodiments of the foregoing aspects, the therapeutic composition comprises a spore population consisting essentially of spores and/or a spore-former population consisting essentially of vegetative cells.

In some embodiments of the foregoing aspects, the population is effective to treat a gastrointestinal dysbiosis or an inflammatory condition associated with the dysbiosis. In some embodiments, the dysbiosis comprises a gastrointestinal disease, disorder or condition selected from the group consisting of *Clostridium difficile*-induced diarrhea, irritable bowel syndrome (IBS), colonization with a pathogen or pathobiont, infection with a drug-resistant pathogen or pathobiont, colitis, and Crohn's Disease. In some embodiments, the dysbiosis comprises a gastrointestinal disease, disorder or condition associated with an immunosuppressive or immunocompromised state of the mammalian subject.

In another aspect, the instant invention is directed to a therapeutic composition comprising a purified population of immunomodulatory bacteria, in an amount effective to i) augment the microbiota diversity present in the mammalian recipient and/or ii) treat or prevent a dysbiosis in a mammalian recipient subject to whom the therapeutic composition is administered, wherein the purified population is obtained by separation of the population apart from at least one residual habitat product in a fecal material obtained from one or a plurality of mammalian donor subjects.

In some embodiments of the foregoing aspects, the purified population is obtained from a miscible solvent treatment of the fecal material or a fraction or derivative thereof. In some embodiments, the purified population comprises a substantial enrichment of bacterial entities present in the fecal material, and wherein the composition optionally comprises a germinant. In some embodiments, the germinant is selected from BHIS oxgall, CaDPA, one or more amino acids, a sugar, a nucleoside, a bile salt, a metal or a metal cation, a fatty acid, and a long-chain alkyl amine, or a combination thereof.

In another aspect, the instant invention provides a method of altering the microbiome of a mammalian subject comprising administering to the subject in need thereof a pharmaceutical composition comprising i) a substantially purified population of Clostridiales bacteria and ii) a stimulatory oligosaccharide, wherein the pharmaceutical composition is formulated for oral administration and wherein the Clostridiales bacteria and the stimulatory oligosaccharide are present in the pharmaceutical composition in an amount effective to alter the gastrointestinal microbiome of the subject to whom the pharmaceutical composition is orally administered.

In some embodiments of the foregoing aspects, the Clostridiales bacteria are substantially in spore form. In some embodiments, the Clostridiales bacteria comprise a first genus and a second genus. In some embodiments, the first genus is selected from the group consisting of *Blautia, Clostridium*, and *Ruminococcus*, and wherein the second genus is not identical to the first genus.

In some embodiments of the foregoing aspects, the Clostridiales bacteria and the stimulatory oligosaccharide synergistically induce an immunomodulatory activity in the subject.

In some embodiments of the foregoing aspects, the immunomodulatory activity comprises modulating the number and/or activity of a CD4+ T cell population in the subject. In some embodiments, the T cell population is associated with the gastrointestinal tract.

In some embodiments of the foregoing aspects, the immunomodulatory activity comprises reducing activation of dendritic cells and/or antigen-presenting cells.

In some embodiments of the foregoing aspects, the immunomodulatory activity comprises reducing the expression and/or activity of an interleukin in the subject. In some embodiments, the interleukin is interleukin-6.

In some embodiments of the foregoing aspects, the immunomodulatory activity comprises an increase in the abundance of innate lymphoid cells. In some embodiments, the innate lymphoid cells comprise interleukin-23-responsive innate lymphoid cells and/or Lgr5+ innate lymphoid cells. In some embodiments, the release of interleukin-22 in the subject is stimulated.

In some embodiments of the foregoing aspects, the release of R-spondin1 in the subject is stimulated, and the released R-spondin1 is present in a location in an amount effective to stimulate Wnt signaling in a population of the subject's intestinal stem cells.

In some embodiments of the foregoing aspects, the Clostriadiales bacteria induce an immunological tolerance in the subject.

In some embodiments of the foregoing aspects, the Clostridiales are capable of modulating the number and/or activity of a population of Paneth cells of the subject. In some embodiments, the Clostridiales are capable of inducing an increase in the number and/or activity of a population of Paneth cells in the host.

In some embodiments of the foregoing aspects, the Clostridiales are capable of increasing a Wnt signaling pathway in a population of intestinal stem cells, as compared to a reference population of intestinal stem cells.

In some embodiments of the foregoing aspects, the pharmaceutical composition induces colonization of at least one bacterial entity in the gastrointestinal tract of the subject. In certain embodiments, the at least one bacterial entity is not detectably present in the pharmaceutical composition and/or is not detectably present in the gastrointestinal tract of the subject prior to administration of the pharmaceutical composition.

In some embodiments of the foregoing aspects, the pharmaceutical composition prevents or reduces the colonization of at least pathogen and/or pathobiont in the gastrointestinal tract of the subject.

In some embodiments of the foregoing aspects, the pharmaceutical composition further comprises an antimicrobial compound in an amount effective to reduce the number, activity and/or viability of at least one pathogen and/or pathobiont present in the gastrointestinal tract of the subject. In certain embodiments, the antimicrobial compound is an antibiotic compound. In certain embodiments, the antimicrobial compound is one or more antibiotic compounds disclosed herein.

In some embodiments of the foregoing aspects, the pharmaceutical composition further comprises an antibacterial compound in an amount effective to prevent or reduce colonization of at least one pathogen and/or pathobiont not present in the gastrointestinal tract of the subject at the time of administration of the pharmaceutical compound. In certain embodiments, the at least one pathogen is a Lactobacilliales bacterium. In certain embodiments, the at least one pathogen is an *Enterococcus* bacterium. In some embodiments, the antibacterial compound does not reduce or prevent colonization of Clostridiales bacteria in the gastrointestinal tract.

In some embodiments of the foregoing aspects, the method of altering a microbiome in a mammalian subject further comprises the step of administering to the subject an effective amount of an antimicrobial compound.

In some embodiments of the foregoing aspects, the Clostridiales bacteria comprise at least one *Blautia* species. In some embodiments, the substantially purified population of Clostridiales bacteria consist essentially of one or more *Blautia* species.

In some embodiments of the foregoing aspects, the method of altering a microbiome in a mammalian subject further comprises the step of administering to the subject, in one or more doses, an oral or gastric nutritional supplement.

In another aspect, the instant invention is directed to a method of preventing or treating a mammalian subject suffering from an autoimmune disease, condition, or disorder, comprising administering to the subject a pharmaceutical composition that substantial increases the relative abundance of at least one Clostridiales bacteria in the gastrointestinal tract of the subject, wherein the mammalian subject has not received a substantial amount of an oral or gastric nutritional supplementation at least 12 hours prior to the administration of the pharmaceutical composition.

In some embodiments of the foregoing aspects, the method of preventing or treating a mammalian subject suffering from an autoimmune disease, condition, or disorder, further comprises the step of administering to the subject, in one or more doses, an oral or gastric nutritional supplement subsequent to administering the pharmaceutical composition.

In another aspect, the instant invention is directed to a method of preventing or treating a mammalian subject suffering from an inflammatory disease, condition, or disorder, comprising administering to the subject a pharmaceutical composition that substantially increases the relative abundance of at least one Clostridiales bacteria in the gastrointestinal tract of the subject, wherein the mammalian subject has not received a substantial amount of an oral or gastric nutritional supplementation at least 12 hours prior to the administration of the pharmaceutical composition.

In some embodiments of the foregoing aspects, the method further comprises the step of administering to the subject, in one or more doses, an oral or gastric nutritional supplement subsequent to the administering of the pharmaceutical composition.

In another aspect, the instant invention is directed to a method of preventing or treating a mammalian subject suffering from or at risk of developing a transplant-associated disease, comprising administering to the subject a pharmaceutical composition that substantial increases the relative abundance of at least one Clostridiales bacteria in the gastrointestinal tract of the subject, wherein the mammalian subject has not received a substantial amount of an oral or gastric nutritional supplementation at least 12 hours prior to the administration of the pharmaceutical composition.

In some embodiments of the foregoing aspects, the method further comprises the step of administering to the subject, in one or more doses, an oral or gastric nutritional supplement subsequent to administering the pharmaceutical composition.

In some embodiments of the foregoing aspects, the method further comprises the step of performing on the subject an allogeneic bone marrow transplantation or an allogeneic stem cell transplantation.

In some embodiments of the foregoing aspects, the Clostridiales bacteria induce an immunomodulatory activity in the subject.

In certain embodiments of the foregoing aspects, the immunomodulatory activity comprises a suppression of innate immunity.

In some embodiments of the foregoing aspects, the immunomodulatory activity comprises a reduction of dendritic cells and/or naïve CD4+ T cells in the subject. In some embodiments, the immunomodulatory activity comprises a reduction in activity of dendritic cells and/or antigen presenting cells. In some embodiments, a T cell level is reduced to or below a level that induces rejection of the allogeneic graft. In some embodiments, a T cell level is reduced to or above a level that induces a graft-versus-tumor response.

In some embodiments of the foregoing aspects, the immunomodulatory activity comprises a reduction of an interleukin activity. In some embodiments, the interleukin activity comprises an interleukin-6 activity.

In some embodiments of the foregoing aspects, the immunomodulatory activity comprises an increase in the abundance of innate lymphoid cells. In some embodiments, the innate lymphoid cells are interleukin-23-responsive innate lymphoid cells or Lgr5+ innate lymphoid cells. In some embodiments, the immunomodulatory activity comprises stimulation of an interleukin activity. In some embodiments, the interleukin activity comprises an interleukin-22 activity.

In some embodiments of the foregoing aspects, the immunomodulatory activity comprises an increase in release of R-spondin1. In some embodiments of the foregoing aspects, the immunomodulatory activity results in an increase in Wnt signaling in intestinal stem cells.

In another aspect, the instant invention provides a method of preventing or treating a mammalian subject suffering from an autoimmune disease, condition, or disorder comprising administering to the subject a pharmaceutical composition that substantially increases the relative abundance of at least one Clostridiales bacteria in the gastrointestinal tract of the subject, wherein the pharmaceutical composition is formulated for oral or gastric administration and comprises a purified bacterial population comprising an effective amount of Clostridiales bacteria.

In some embodiments of the foregoing aspects, the purified bacterial population comprises Clostridiales bacteria in an amount effective to produce one or more metabolites capable of inducing and/or mediating one or more anti-inflammatory effects in the subject. In some embodiments, the one or more metabolites comprise a short chain fatty acid. In some embodiments, the Clostriadiales produce one or more short chain fatty acids in an effective amount to increase the local short chain fatty acid concentration by 2-fold, 4-fold, 5-fold, 10-fold, 50-fold, 100-fold, 1000-fold, or over 1000-fold.

In some embodiments of the foregoing aspects, the purified bacterial population comprises Clostridiales bacteria selected from the genus *Blautia*.

In some embodiments of the foregoing aspects, the method further comprises the step of administering to the subject an effective amount of an antibacterial compound. In some embodiments the pharmaceutical composition further comprises an effective amount of an antibacterial compound.

In another aspect, the instant invention is directed to a method of identifying a subject suitable for treatment with a pharmaceutical composition comprising Clostridiales bacteria, comprising the step of identifying in a fecal material obtained from a human subject suitable for an allogeneic transplant procedure and/or at risk of developing an autoimmune disorder at least one bacterial entity, the presence of which in the fecal sample indicates the suitability of the human subject for treatment with the pharmaceutical composition comprising Clostridiales bacteria.

In another aspect, the instant invention is directed to a method of obtaining a microbiome profile, comprising the steps of: i) providing a fecal material obtained from a human subject suitable for an allogeneic transplant procedure and/or at risk of developing an autoimmune disorder, ii) isolating one or more bacterial entities from the fecal material, iii) isolating one or more nucleic acids from at least one bacterial entity, iv) sequencing the isolated nucleic acids, and v) comparing the sequenced nucleic acids to a reference nucleic acid sequence.

In certain embodiments of the foregoing aspects, the allogeneic transplant procedure is allogeneic bone marrow transplantation or allogeneic stem cell transplantation.

In certain embodiments of the foregoing aspects, the method further comprises at least one of the steps of isolating microbial metabolites, analyzing the metabolites by a technique selected from the group consisting of liquid chromatography, gas chromatography, mass spectrometry, and nuclear magnetic resonance spectroscopy, and comparing the detected metabolites or metabolite fragments to reference metabolite profiles.

In some embodiments of the foregoing aspects, the sequenced nucleic acids comprise one or more 16S nucleic acid sequences.

In some embodiments of the foregoing aspects, the human subject is an allogeneic transplant patient suffering from or at risk of developing acute or chronic graft-versus-host disease, leukemia, lymphoma, or myeloma.

In another aspect, the instant invention provides a pharmaceutical composition comprising i) a substantially purified population of Clostridiales bacteria and ii) a stimulatory oligosaccharide, wherein the pharmaceutical composition is formulated for oral administration and wherein the Clostridiales bacteria and the stimulatory oligosaccharide are present in the pharmaceutical composition in an amount effective to alter the gastrointestinal microbiome of the subject to whom the pharmaceutical composition is orally administered.

In some embodiments of the foregoing aspects, the Clostridiales bacteria and the stimulatory oligosaccharide are capable of synergistically inducing an immunomodulatory activity in the subject. In some embodiments of the foregoing aspects, the Clostridiales bacteria are substantially in spore form.

In some embodiments of the foregoing aspects, the Clostridiales bacteria comprise a first genus and a second genus. In some embodiments, the first genus is selected from the group consisting of Blautia, Clostridium, and Ruminococcus, and wherein the second genus is not identical to the first genus.

In some embodiments of the foregoing aspects, the immunomodulatory activity comprises suppression or reduction of naïve CD4+ T cells.

In some embodiments of the foregoing aspects, the Clostridiales bacteria and the stimulatory oligosaccharide are capable of synergistically inducing colonization of at least one bacterial entity in the gastrointestinal tract of the subject.

In certain embodiments of the foregoing aspects, the Clostridiales bacteria is encapsulated by a polymer of the stimulatory oligosaccharide.

In some embodiments of the foregoing aspects, the pharmaceutical composition comprises an antibacterial compound in an amount effective to reduce the number of at least one pathogen and/or pathobiont present in the gastrointestinal tract of the subject. In some embodiments, the pharmaceutical composition comprises an antibacterial compound in an amount effective to reduce the number of at least one pathogen and/or pathobiont present in the gastrointestinal tract of the subject. In some embodiments, the pharmaceutical composition comprises an antibacterial compound in an amount effective to prevent or reduce colonization of at least one pathogen and/or pathobiont present in the gastrointestinal tract of the subject. In certain embodiments, the at least one pathogen is a Lactobacilliales bacterium. In certain embodiments, the at least one pathogen is an Enterococcus bacterium. In certain embodiments, the administered antibacterial compound does not reduce or prevent colonization of Blautia in the gastrointestinal tract.

In some embodiments of the foregoing aspects, the pharmaceutical composition comprises the stimulatory oligosaccharide in an amount effective to stimulate growth of Blautia bacteria.

In some embodiments of the foregoing aspects, the composition is formulated for oral administration as a solid, semi-solid, gel, or liquid form. In some embodiments, the composition is formulated in the form of a pill, tablet, capsule or lozenge. In some embodiments, the composition comprises an enteric coating.

In some embodiments of the foregoing aspects, the Blautia bacteria are substantially inactive prior to localization in the gastrointestinal tract of the subject.

In some embodiments of the foregoing aspects, the composition further comprises a food or a nutritional supplement effective to stimulate the growth of Clostridiales bacteria present in the gastrointestinal tract of the subject. In some embodiments, the nutritional supplement is produced by a bacterium associated with a healthy human gut microbiome. In certain embodiments, the nutritional supplement is produced by Clostridiales bacteria. In certain embodiments, the nutritional supplement comprises a short chain fatty acid. In certain embodiments, the short chain fatty acid is selected from butyrate, propionate, or a combination thereof. In certain embodiments, the nutritional supplement comprises a nutrient selected from the group of folate, vitamin B6, vitamin B12, vitamin A, thiamine, riboflavin, niacin, ascorbic acid, vitamin D, vitamin E, and vitamin K, or a combination thereof. In certain embodiments, the local concentration of the nutrient in the subject is increased 2 fold, 5 fold, 10 fold, 100 fold, 1000 fold or more than 1000 fold.

In another aspect, the instant invention is directed to a composition of two or more five- or six-carbon sugars, or polymers thereof, capable of modulating the gut microbiome, wherein the composition is formulated for oral administration, wherein the composition is free of detectable amounts of bacteria, wherein the composition is free of detectable amounts of non-comestibles.

In some embodiments of the foregoing aspects, the composition remains within the gut for more than three hours. In some embodiments, the composition is effective for sustaining a modulated gut microbiome for at least 24 hours.

In some embodiments of the foregoing aspects, the composition reduces the intestinal immune response. In some embodiments, the composition increases intestinal integrity.

In some embodiments of the foregoing aspects, the composition augments the abundance or colonization of spore-forming bacteria in the gut.

In some embodiments of the foregoing aspects, the composition prevents or resists bacteremia for at least 24 hours.

In another aspect, the instant invention provides a composition comprising two or more five- or six-carbon sugars, or polymers thereof, capable of augmenting the abundance or colonization or spore-forming bacteria in the liver, wherein the composition is formulated for oral administration, wherein the composition is free of detectable amounts of bacteria, wherein the composition is free of detectable amounts of non-comestibles.

In another aspect, the instant invention provides a composition comprising two or more five- or six-carbon sugars, or polymers thereof, capable of augmenting the abundance or colonization spore-forming bacteria on the skin, wherein the composition is formulated for oral administration, wherein the composition is free of detectable amounts of bacteria, wherein the composition is free of detectable amounts of non-comestibles.

In another aspect, the instant invention provides a method for production of a composition comprising a population of bacterial entities suitable for therapeutic administration to a mammalian subject in need thereof, comprising the steps of: (a) providing a fecal material obtained from a mammalian donor subject; and (b) subjecting the fecal material to at least one purification step and/or at least one culture step under conditions such that a purified population of immunomodulatory bacteria is produced from the fecal material.

In some embodiments of the foregoing aspects, the mammalian donor subject is a healthy human subject. In some embodiments of the foregoing aspects, the method comprises contacting the fecal material or a fraction or derivative thereof with a miscible solvent. In some embodiments of the foregoing aspects, the method comprises a miscible solvent treatment, an immiscible solvent extraction, an elution from a solid medium, a thermal disrupting treatment, a radiation treatment, a filtration treatment, a chromatographic separation treatment, a centrifugation treatment, mechanical disrupting treatment, or a combination thereof.

In another aspect, the instant invention provides a method of treating or preventing a dysbiosis in a human subject, comprising administering to the human subject the composition produced by the method of any of the foregoing aspects.

In some embodiments of the foregoing aspects, the therapeutic administration comprises oral administration of a composition comprising at least about $1\times10^4$ colony forming units of bacterial entities per dose of the composition.

In some embodiments of the foregoing aspects, the bacterial entities comprise bacteria from the genera provided in Table 1.

In some embodiments of the foregoing aspects, the composition comprises at least about 0.1%, 1%, 5%, 10%, 15%, 20%, 25%, 30%, 35%, 40%, 45%, 50% or above 50% spores on a mass basis. In some embodiments, the composition comprises at least about $1\times10^4$ spores per gram or dose. In some embodiments, the composition comprises at least about $1\times10^3$, $1\times10^4$, $1\times10^5$, $1\times10^6$, $1\times10^7$, $1\times10^8$, $1\times10^9$, $1\times10^{10}$, or greater than $1\times10^{10}$ spores per gram or dose.

In another aspect, the instant invention comprises a purified population of bacterial entities comprising at least about $1\times10^3$, $1\times10^4$, $1\times10^5$, or $1\times10^6$ spores, wherein the composition does not exceed about 1 gram in weight, formulated for oral administration to treat or prevent an immune or inflammatory disease induced by a gastrointestinal dysbiosis in a mammalian recipient subject in need thereof.

In some embodiments of the foregoing aspects, the therapeutic composition is formulated to treat or prevent gastrointestinal disease, disorder or condition in a mammalian recipient subject in need thereof.

In some embodiments of the foregoing aspects, the bacterial entities are purified from fecal material obtained from a mammalian donor subject.

In some embodiments of the foregoing aspects, the therapeutic composition is in an amount effective to treat or prevent as a single dose a disorder in a mammalian recipient subject suffering from or at risk of developing such disorder to whom the therapeutic composition is administered.

In some embodiments of the foregoing aspects, the population of bacterial entities is purified from a fecal material obtained from at least one mammalian donor subject, wherein the at least one mammalian donor subject has no clinical history of a metabolic disorder.

In another aspect, the instant invention provides a kit comprising in one or more containers a fecal material collection apparatus and a solvent solution, and instructions for use thereof for generating purified populations of immunomodulatory bacteria.

In some embodiments of the foregoing aspects, the solvent solution comprises a detergent. In some embodiments, the detergent is Triton X-100, Tween 20, Tween 80, Nonidet P40, a pluronic, or a polyol.

In another aspect, the instant invention is directed to a method of modulating the microbiotal population in the gastrointestinal tract of a human subject, comprising the step of administering to the human subject a therapeutic composition comprising a purified population of immunomodulatory bacteria, under conditions such that i) the microbial population present in the gastrointestinal tract, and/or ii) the microbial population present outside the gastrointestinal tract is modulated.

In some embodiments of the foregoing aspects, the modulation comprises reduction or elimination of at least one pathogen and/or pathobiont present in the gastrointestinal tract when the therapeutic composition is administered. In some embodiments, the modulation comprises engraftment of at least one type of immunomodulatory bacteria present in the therapeutic composition. In some embodiments, the modulation comprises augmentation of at least one type of bacteria not present in the therapeutic composition. In some embodiments of the foregoing aspects, the at least one type of immunomodulatory bacteria are not detectably present in gastrointestinal tract when the therapeutic composition is administered. In some embodiments of the foregoing aspects, the modulation comprises augmentation of at least one type of immunomodulatory or non-spore forming bacteria not present in the therapeutic composition. In some embodiments, the at least one type of immunomodulatory bacteria or non-spore forming are increased by at least 2-fold after administration of the therapeutic composition.

In some embodiments of the foregoing aspects, the modulation comprises at least two of: i) reduction or elimination of at least one pathogen and/or pathobiont present in the gastrointestinal tract when the therapeutic composition is administered; ii) engraftment of at least one type of immunomodulatory bacteria present in the therapeutic composition; and iii) augmentation of at least one type of immunomodulatory or non-spore forming bacteria not present in the therapeutic composition. In some embodiments, the modulation comprises reduction or elimination of at least one pathogen and/or pathobiont present in the gastrointestinal tract when the therapeutic composition is administered and at least one of: i) engraftment of at least one type of immunomodulatory bacteria present in the therapeutic composition; and ii) augmentation of at least one type of bacteria not present in the therapeutic composition. In some embodiments, the at least one pathogen and/or pathobiont is present at pathogenic amounts in the gastrointestinal tract when the composition is administered.

In some embodiments of the foregoing aspects, the mammalian subject suffers from or is at risk of developing bacterial overgrowth syndrome (BOS). In some aspects, the modulation comprises reduction or elimination of at least one pathogen and/or pathobiont associated with the BOS. In some aspects, the modulation comprises reduction or elimination of at least one drug resistant pathogen and/or pathobiont.

In another aspect, the instant invention is directed to a method of inducing engraftment of a bacterial population in the gastrointestinal tract of a human subject, comprising the step of administering to the human subject a therapeutic composition comprising a purified population of immunomodulatory bacteria, under conditions such that at least i) a subset of the immunomodulatory bacteria sustainably engraft within the gastrointestinal tract, or ii) at least one type of bacteria not present in the therapeutic composition is augmented within the gastrointestinal tract.

In some embodiments of the foregoing aspects, the population of immunomodulatory bacteria consists essentially of spores, and wherein the spores germinate within the gastrointestinal tract.

In one aspect, the instant invention is directed to a method of treating a vaginal dysbiosis, comprising the steps of: i) identifying a human subject suffering from a disease, disorder or condition associated with a vaginal dysbiosis; and ii) administering one or more times a pharmaceutical formulation comprising an immunomodulatory bacterial composition in an amount effective to treat the vaginal dysbiosis.

In some embodiments of the foregoing aspect, the bacterial composition comprises a synergistic combination of two or more bacterial entities. In some embodiments, the synergistic combination comprises an interaction network. In some embodiments, at least one of the two or more bacterial entities comprises a keystone bacterial entity.

In some embodiments of the forgoing aspect, the bacterial composition comprises an antimicrobial agent. In some embodiments of the foregoing aspect, the bacterial composition comprises an immunosuppressive agent. In some embodiments of the foregoing aspect, the bacterial composition comprises an immunostimulatory agent. In some embodiments of the foregoing aspect, the bacterial composition comprises a prebiotic compound.

In some embodiments of the foregoing aspect, the pharmaceutical formulation is orally administered. In some embodiments of the foregoing aspect, the pharmaceutical formulation is rectally administered. In some embodiments of the foregoing aspect, the pharmaceutical formulation is vaginally administered.

In some embodiments of the foregoing aspect, the method further comprises the steps of a) obtaining a first vaginal material from the human subject prior to a first administration of the pharmaceutical formulation, b) obtaining a second vaginal material from the human subject subsequent to the first administration of the pharmaceutical formulation.

In some embodiments of the foregoing aspect, the method comprises the step of determining at least one alteration in the vaginal microbiota in the first vaginal material versus the second vaginal material. In some embodiments, the at least one alteration comprises the detectable presence of a bacterial entity in the second vaginal material not present in the first vaginal material or the pharmaceutical formulation. In some embodiments, the at least one alteration comprises the detectable increase in the level of a bacterial entity in the second vaginal material present in the first vaginal material. In some embodiments, the at least one alteration comprises the absence of a bacterial entity in the second vaginal material present in the first vaginal material. In some embodiments, the at least one alteration comprises the detectable decrease in the level of a bacterial entity in the second vaginal material present in the first vaginal material. In some embodiments, the at least one alteration comprises detection of an interaction network.

In some embodiments of the foregoing aspect, the method comprises the step of determining at least one alteration in the host immune response in the first vaginal material versus the second vaginal material.

In another aspect, the instant invention is directed to a method of identifying and/or characterizing the incidence and/or risk of a vaginal dysbiosis, comprising: i) providing a reference vaginal microbiotal signature; and ii) determining a microbiotal signature present in a vaginal material from a human subject whose incidence and/or risk of a vaginal dysbiosis is to be identified or characterized.

In another aspect, the instant invention is directed to a method of subject monitoring, comprising the steps of: i) providing a reference vaginal microbiota signature that correlates with extent of severity of a vaginal dysbiosis, and ii) determining a test vaginal microbiota signature in a vaginal material, such that the subject is thereby monitored.

In another aspect, the instant invention provides a library of symbiotic microbiota signatures.

In another aspect, the instant invention provides a therapeutic composition comprising a purified population of immunomodulatory bacteria comprising a Lactobacilli entity and a spore-forming bacterial entity.

In some embodiments of the foregoing aspects, the spore-forming bacterial entity comprises a spore population consisting essentially of spores and/or a spore-former population consisting essentially of vegetative cells.

In another aspect, the instant invention is directed to a therapeutic composition comprising a purified population of immunomodulatory bacteria produced by the steps of a) providing a vaginal or fecal material and b) subjecting the material to a culture step and/or a treatment step resulting in purification of immunomodulatory bacteria and, optionally, c) formulating the purified population for oral administration, wherein the purified population is present in the composition in an amount effective to engraft and/or augment in the gastrointestinal tract in order to treat, prevent or reduce the severity of a symptom of a vaginal dysbiosis in a mammalian recipient subject to whom the therapeutic composition is administered.

In some embodiments of the foregoing aspects, the population is effective to treat a disease, disorder or condition associated with a gastrointestinal dysbiosis.

In some embodiments of the foregoing aspects, the therapeutic composition further comprises a heme group.

In some embodiments of the foregoing aspects, the therapeutic composition further comprises a fatty acid.

In some embodiments of the foregoing aspects, the therapeutic composition is formulated as a gel or a vaginal suppository.

In some embodiments of the foregoing aspects, the therapeutic composition further comprises a hormone selected from estrogen, testosterone, and progesterone, or a combination thereof.

In some embodiments of the foregoing aspects, the therapeutic composition further comprises an estrogen receptor agonist.

In some embodiments of the foregoing aspects, the therapeutic composition further comprises an androgen receptor agonist.

In some embodiments of the foregoing aspects, the therapeutic composition further comprises seminal fluid or a component thereof.

In some embodiments of the foregoing aspects, the population is effective to treat a disease, disorder or condition associated with a vaginal dysbiosis. In some embodiments, the population is effective to reduce the severity of at least one symptom of the vaginal dysbiosis. In some embodiments, the population is effective to modulate the microbiota diversity present in the vagina of the mammalian recipient.

In some embodiments of the foregoing aspects, the population comprises a population of bacterial entities.

In some embodiments of the foregoing aspects, the vaginal or fecal material is obtained from a healthy mammalian donor subject or a plurality of mammalian donor subjects.

In some embodiments of the foregoing aspects, the treatment step comprises: heating the material above 25 degrees Celsius for at least 30 seconds; contacting the material with a solvent; and or contacting a chemical or physical manipulation of the material. In some embodiments, the culture step comprises replicating the purified population in a liquid suspension and/or a solid medium.

In some embodiments of the foregoing aspects, the therapeutic composition comprises removing at least a portion of an acellular component of the vaginal or fecal material, thereby separating immunomodulatory bacteria from acellular material.

In some embodiments of the foregoing aspects, the population comprises a single bacterial preparation or a combination of bacterial preparations, wherein each bacterial preparation is purified from a vaginal or fecal material obtained from a single mammalian donor subject. In some embodiments, the population comprises a single bacterial preparation or a combination of bacterial preparations wherein each bacterial preparation is purified from a vaginal or fecal material obtained from a mammalian donor subject.

In some embodiments of the foregoing aspects, the recipient subject is immunocompromised or immunosuppressed.

In some embodiments of the foregoing aspects, the mammalian subject is suffering from i) a gastrointestinal disease, disorder or condition selected from the group consisting of *Clostridium difficile*-induced diarrhea, irritable bowel syndrome (IBS), colitis, and Crohn's Disease or ii) colonization with a pathogen or pathobiont or infection with a drug-resistant pathogen or pathobiont.

In some embodiments of the foregoing aspects, the treatment step comprises depleting or inactivating a pathogenic material.

In another aspect, the instant invention is directed to a therapeutic composition comprises a purified population of immunomodulatory bacteria produced by the steps of a) providing a fecal material and b) subjecting the material to a culture step and/or a treatment step resulting in purification of immunomodulatory bacteria and, optionally, c) formulating the purified population for oral administration, wherein the purified population is present in the composition in an amount effective to engraft and/or augment in the vagina in order to treat, prevent or reduce the severity of a symptom of an immune disorder in a mammalian recipient subject to whom the therapeutic composition is administered.

In another aspect, the instant invention is directed to a therapeutic composition comprising a purified population of immunomodulatory bacteria, in an amount effective to i) treat or prevent an inflammatory condition resulting from a dysbiosis and/or ii) augment at least one type of bacteria not present in the therapeutic composition in a mammalian recipient subject to whom the therapeutic composition is administered, and/or iii) engraft at least one type of bacteria present in the therapeutic composition but not present in a mammalian subject prior to treatment.

In some embodiments of the foregoing aspects, the therapeutic composition comprises a spore population consisting essentially of spores and/or a spore-former population consisting essentially of vegetative cells.

In some embodiments of the foregoing aspects, the population is effective to treat a gastrointestinal dysbiosis or an inflammatory condition associated with the dysbiosis.

In some embodiments of the foregoing aspects, the dysbiosis comprises a vaginal or gastrointestinal disease, disorder or condition selected from the group consisting of *Clostridium difficile*-induced diarrhea, irritable bowel syndrome (IBS), colonization with a pathogen or pathobiont, infection with a drug-resistant pathogen or pathobiont, colitis, and Crohn's Disease. In some embodiments of the foregoing aspects, the dysbiosis comprises a vaginal or gastrointestinal disease, disorder or condition associated with an immunosuppressive or immunocompromised state of the mammalian subject.

In another aspect, the instant invention is directed to a therapeutic composition comprising a purified population of immunomodulatory bacteria, in an amount effective to i) augment the microbiota diversity present in the mammalian recipient and/or ii) treat or prevent a dysbiosis in a mammalian recipient subject to whom the therapeutic composition is administered, wherein the purified population is obtained by separation of the population apart from at least one residual habitat product in a biological material obtained from one or a plurality of mammalian donor subjects.

In some embodiments of the foregoing aspects, the purified population is obtained from a miscible solvent treatment of the fecal material or a fraction or derivative thereof.

In some embodiments of the foregoing aspects, the purified population comprises a substantial enrichment of bacterial entities present in the fecal material, and wherein the composition optionally comprises a germinant. In some embodiments, the germinant is selected from BHIS oxgall, CaDPA, one or more amino acids, a sugar, a nucleoside, a bile salt, a metal or a metal cation, a fatty acid, and a long-chain alkyl amine, or a combination thereof.

In another aspect, the instant invention is directed to a method of altering the microbiome of a mammalian subject comprising administering to the subject in need thereof a pharmaceutical composition comprising i) a substantially purified population of Lactobacilli bacteria and ii) a stimulatory oligosaccharide, wherein the pharmaceutical composition is formulated for oral administration and wherein the Lactobacilli bacteria and the stimulatory oligosaccharide are present in the pharmaceutical composition in an amount effective to alter the gastrointestinal microbiome of the subject to whom the pharmaceutical composition is orally administered.

In some embodiments of the foregoing aspects, the Lactobacilli bacteria and the stimulatory oligosaccharide synergistically induce an immunomodulatory activity in the subject.

In some embodiments of the foregoing aspects, the immunomodulatory activity comprises modulating the number and/or activity of a CD4+ T cell population in the subject. In some embodiments, the T cell population is associated with the vagina.

In some embodiments of the foregoing aspects, the immunomodulatory activity comprises reducing activation of dendritic cells and/or antigen-presenting cells.

In some embodiments of the foregoing aspects, the immunomodulatory activity comprises reducing the expression and/or activity of an interleukin in the subject. In some embodiments, the interleukin is interleukin-6.

In some embodiments of the foregoing aspects, the immunomodulatory activity comprises an increase in the abundance of innate lymphoid cells. In some embodiments, the innate lymphoid cells comprise interleukin-23-responsive innate lymphoid cells and/or Lgr5+ innate lymphoid cells.

In some embodiments of the foregoing aspects, the release of interleukin-22 in the subject is stimulated.

In some embodiments of the foregoing aspects, the release of R-spondin1 in the subject is stimulated, and the released R-spondin1 is present in a location in an amount effective to stimulate Wnt signaling in a population of the subject's intestinal stem cells.

In some embodiments of the foregoing aspects, the Clostriadiales bacteria induce an immunological tolerance in the subject.

In some embodiments of the foregoing aspects, the Lactobacilli are capable of modulating the number and/or activity of a population of Paneth cells of the subject. In some embodiments, the Lactobacilli are capable of inducing an increase in the number and/or activity of a population of Paneth cells in the host. In some embodiments of the foregoing aspects, the Lactobacilli are capable of increasing a Wnt signaling pathway in a population of intestinal stem cells, as compared to a reference population of intestinal stem cells.

In some embodiments of the foregoing aspects, the pharmaceutical composition induces colonization of at least one bacterial entity in the vagina of the subject. In some embodiments, the at least one bacterial entity is not detectably present in the pharmaceutical composition and/or is not detectably present in the vagina of the subject prior to administration of the pharmaceutical composition.

In some embodiments of the foregoing aspects, the pharmaceutical composition prevents or reduces the colonization of at least pathogen and/or pathobiont in the vagina of the subject.

In some embodiments of the foregoing aspects, the pharmaceutical composition further comprises an antimicrobial compound in an amount effective to reduce the number, activity and/or viability of at least one pathogen and/or pathobiont present in the vagina of the subject. In some embodiments, the antimicrobial compound is an antibiotic compound. In some embodiments, the antimicrobial compound is one or more antibiotic compounds disclosed herein.

In some embodiments of the foregoing aspects, the pharmaceutical composition further comprises an antibacterial compound in an amount effective to prevent or reduce colonization of at least one pathogen and/or pathobiont not present in the vagina of the subject at the time of administration of the pharmaceutical compound.

In some embodiments of the foregoing aspects, the antibacterial compound does not reduce or prevent colonization of bacteria in the gastrointestinal tract.

In some embodiments of the foregoing aspects, the bacteria comprise at least one Lactobacilli species.

In some embodiments of the foregoing aspects, the method further comprises the step of administering to the subject an effective amount of an antimicrobial compound.

In some embodiments of the foregoing aspects, the method further comprises the step of administering to the subject, in one or more doses, an oral or gastric nutritional supplement.

In another aspect, the instant invention is directed to a method of preventing or treating a mammalian subject suffering from an autoimmune disease, condition, or disorder, comprising administering to the subject a pharmaceutical composition that substantial increases the relative abundance of at least one Lactobacilli bacteria in the vagina of the subject, wherein the mammalian subject has not received a substantial amount of an oral or gastric nutritional supplementation at least 12 hours prior to the administration of the pharmaceutical composition.

In another aspect, the instant invention is directed to a method of preventing or treating a mammalian subject suffering from an inflammatory disease, condition, or disorder, comprising administering to the subject a pharmaceutical composition that substantially increases the relative abundance of at least one Lactobacilli bacteria in the vagina of the subject, wherein the mammalian subject has not received a substantial amount of an oral or gastric nutritional supplementation at least 12 hours prior to the administration of the pharmaceutical composition.

In another aspect, the instant invention is directed to a method of preventing or treating a mammalian subject suffering from or at risk of developing a transplant-associated disease, comprising administering to the subject a pharmaceutical composition that substantial increases the relative abundance of at least one Lactobacilli bacteria in the vagina of the subject, wherein the mammalian subject has not received a substantial amount of a oral or gastric nutritional supplementation at least 12 hours prior to the administration of the pharmaceutical composition.

In some embodiments of the foregoing aspects, the method further comprises the step of administering to the subject, in one or more doses, an oral or gastric nutritional supplement subsequent to administering the pharmaceutical composition.

In some embodiments of the foregoing aspects, the method further comprises the step of performing on the subject an allogeneic bone marrow transplantation or an allogeneic stem cell transplantation.

In some embodiments of the foregoing aspects, the Lactobacilli bacteria induce an immunomodulatory activity in the subject.

In some embodiments of the foregoing aspects, the immunomodulatory activity comprises a suppression of innate immunity.

In some embodiments of the foregoing aspects, the immunomodulatory activity comprises a reduction of dendritic cells and/or naïve CD4+ T cells in the subject. In some embodiments, the immunomodulatory activity comprises a reduction in activity of dendritic cells and/or antigen presenting cells. In some embodiments, a T cell level is reduced to or below a level that induces rejection of the allogeneic graft. In some embodiments, a T cell level is reduced to or above a level that induces a graft-versus-tumor response.

In some embodiments of the foregoing aspects, the immunomodulatory activity comprises a reduction of an interleukin activity. In some embodiments, the interleukin activity comprises an interleukin-6 activity.

In some embodiments of the foregoing aspects, the immunomodulatory activity comprises an increase in the abundance of innate lymphoid cells. In some embodiments, the innate lymphoid cells are interleukin-23-responsive innate lymphoid cells or Lgr5+ innate lymphoid cells.

In some embodiments of the foregoing aspects, the immunomodulatory activity comprises stimulation of an interleukin activity. In some embodiments, the interleukin activity comprises an interleukin-22 activity.

In some embodiments of the foregoing aspects, the immunomodulatory activity comprises an increase in release of R-spondin1.

In some embodiments of the foregoing aspects, the immunomodulatory activity results in an increase in Wnt signaling in intestinal stem cells.

In another aspect, the instant invention is directed to a method of preventing or treating a mammalian subject suffering from an autoimmune disease, condition, or disorder comprising administering to the subject a pharmaceutical composition that substantially increases the relative abundance of at least one Lactobacilli bacteria in the vagina of the subject, wherein the pharmaceutical composition is formulated for oral or gastric administration and comprises a purified bacterial population comprising an effective amount of Lactobacilli bacteria.

In some embodiments of the foregoing aspects, the purified bacterial population comprises Lactobacilli bacteria in an amount effective to produce one or more metabolites capable of inducing and/or mediating one or more anti-inflammatory effects in the subject. In some embodiments, the one or more metabolites comprise a short chain fatty acid. In some embodiments, the bacteria produce one or more short chain fatty acids in an effective amount to increase the local short chain fatty acid concentration by 2-fold, 4-fold, 5-fold, 10-fold, 50-fold, 100-fold, 1000-fold, or over 1000-fold.

In some embodiments of the foregoing aspects, the method further comprises the step of administering to the subject an effective amount of an antibacterial compound. In some embodiments, the pharmaceutical composition further comprises an effective amount of an antibacterial compound.

In another aspect, the instant invention provides a method of identifying a subject suitable for treatment with a pharmaceutical composition comprising Lactobacilli bacteria, comprising the step of identifying in a fecal material obtained from a human subject suitable for an allogeneic transplant procedure and/or at risk of developing an autoimmune disorder at least one bacterial entity, the presence of which in the fecal sample indicates the suitability of the human subject for treatment with the pharmaceutical composition comprising Lactobacilli bacteria.

In another aspect, the instant invention provides a method of obtaining a microbiome profile, comprising the steps of: i) providing a fecal material obtained from a human subject suitable for an allogeneic transplant procedure and/or at risk of developing an autoimmune disorder, ii) isolating one or more bacterial entities from the fecal material, iii) isolating one or more nucleic acids from at least one bacterial entity, iv) sequencing the isolated nucleic acids, and v) comparing the sequenced nucleic acids to a reference nucleic acid sequence.

In some embodiments of the foregoing aspects, the allogeneic transplant procedure is allogeneic bone marrow transplantation or allogeneic stem cell transplantation.

In some embodiments of the foregoing aspects, the method further comprises at least one of the steps of isolating microbial metabolites, analyzing the metabolites by a technique selected from the group consisting of liquid chromatography, gas chromatography, mass spectrometry, and nuclear magnetic resonance spectroscopy, and comparing the detected metabolites or metabolite fragments to reference metabolite profiles.

In certain embodiments of the foregoing aspects, the sequenced nucleic acids comprise one or more 16S nucleic acid sequences.

In some embodiments of the foregoing aspects, the human subject is an allogeneic transplant patient suffering from or at risk of developing acute or chronic graft-versus-host disease, leukemia, lymphoma, or myeloma.

In another aspect, the instant invention is directed to a pharmaceutical composition comprising i) a substantially purified population of Lactobacilli bacteria and ii) a stimulatory oligosaccharide, wherein the pharmaceutical composition is formulated for oral administration and wherein the Lactobacilli bacteria and the stimulatory oligosaccharide are present in the pharmaceutical composition in an amount effective to alter the gastrointestinal microbiome of the subject to whom the pharmaceutical composition is orally administered.

In some embodiments of the foregoing aspects, the Lactobacilli bacteria are substantially in spore form. In some embodiments, the Lactobacilli bacteria comprise a first genus and a second genus. In some embodiments of the foregoing aspects, the first genus is selected from the group consisting of *Blautia, Clostridium*, and *Ruminococcus*, and wherein the second genus is not identical to the first genus.

In some embodiments of the foregoing aspects, the Lactobacilli bacteria and the stimulatory oligosaccharide are capable of synergistically inducing an immunomodulatory activity in the subject.

In some embodiments of the foregoing aspects, the immunomodulatory activity comprises suppression or reduction of naïve CD4+ T cells.

In some embodiments of the foregoing aspects, the Lactobacilli bacteria and the stimulatory oligosaccharide are capable of synergistically inducing colonization of at least one bacterial entity in the vagina of the subject. In some embodiments, the Lactobacilli bacteria is encapsulated by a polymer of the stimulatory oligosaccharide.

In some embodiments of the foregoing aspects, the pharmaceutical composition comprises an antibacterial compound in an amount effective to reduce the number of at least one pathogen and/or pathobiont present in the vagina of the subject. In some embodiments, the pharmaceutical composition comprises an antibacterial compound in an amount effective to prevent or reduce colonization of at least one pathogen and/or pathobiont present in the vagina of the subject.

In some embodiments of the foregoing aspects, the at least one pathogen is a Lactobacilliales bacterium. In some embodiments of the foregoing aspects, the at least one pathogen is an *Enterococcus* bacterium.

In some embodiments of the foregoing aspects, the administered antibacterial compound does not reduce or prevent colonization of *Blautia* in the vagina.

In some embodiments of the foregoing aspects, the pharmaceutical composition comprises the stimulatory oligosaccharide in an amount effective to stimulate growth of *Blautia* bacteria.

In some embodiments of the foregoing aspects, the composition is formulated for oral administration as a solid, semi-solid, gel, or liquid form. In some embodiments, the composition is formulated in the form of a pill, tablet, capsule or lozenge. In some embodiments, the composition comprises an enteric coating.

In some embodiments of the foregoing aspects, the *Blautia* bacteria are substantially inactive prior to localization in the vagina of the subject.

In some embodiments of the foregoing aspects, the composition further comprises a food or a nutritional supplement effective to stimulate the growth of Lactobacilli bacteria present in the vagina of the subject. In some embodiments, the nutritional supplement is produced by a bacterium associated with a healthy human gut or vagina microbiome. In some embodiments, the nutritional supplement is produced by Lactobacilli bacteria. In some embodiments of the foregoing aspects, the nutritional supplement comprises a short chain fatty acid. In some embodiments, the short chain fatty acid is selected from butyrate, propionate, or a combination thereof. In some embodiments, the nutritional supplement comprises a nutrient selected from the group of folate, vitamin B6, vitamin B12, vitamin A, thiamine, riboflavin, niacin, ascorbic acid, vitamin D, vitamin E, and vitamin K, or a combination thereof. In some embodiments, the local concentration of the nutrient in the subject is increased 2 fold, 5 fold, 10 fold, 100 fold, 1000 fold or more than 1000 fold.

In another aspect, the instant invention provides a composition of two or more five- or six-carbon sugars, or polymers thereof, capable of modulating the gut or vagina microbiome, wherein the composition is formulated for oral administration, wherein the composition is free of detectable amounts of bacteria, wherein the composition is free of detectable amounts of non-comestibles.

In some embodiments of the foregoing aspects, the composition remains within the gut or vagina for more than three hours. In some embodiments of the foregoing aspects, the composition is effective for sustaining a modulated gut or vagina microbiome for at least 24 hours.

In some embodiments of the foregoing aspects, the composition reduces the intestinal immune response. In some embodiments of the foregoing aspects, the composition increases intestinal integrity.

In some embodiments of the foregoing aspects, the composition augments the abundance or colonization of spore-forming bacteria in the gut or vagina.

In some embodiments of the foregoing aspects, the composition prevents or resists bacteremia for at least 24 hours.

In another aspect, the instant invention is directed to a composition comprising two or more five- or six-carbon sugars, or polymers thereof, capable of augmenting the abundance or colonization or spore-forming bacteria in the liver, wherein the composition is formulated for oral administration, wherein the composition is free of detectable amounts of bacteria, wherein the composition is free of detectable amounts of non-comestibles.

In another aspect, the instant invention is directed to a composition comprising two or more five- or six-carbon sugars, or polymers thereof, capable of augmenting the abundance or colonization spore-forming bacteria on the skin, wherein the composition is formulated for oral administration, wherein the composition is free of detectable amounts of bacteria, wherein the composition is free of detectable amounts of non-comestibles.

In another aspect, the instant invention provides a method for production of a composition comprising a population of bacterial entities suitable for therapeutic administration to a mammalian subject in need thereof, comprising the steps of: (a) providing a fecal material obtained from a mammalian donor subject; and (b) subjecting the fecal material to at least one purification step and/or at least one culture step under conditions such that a purified population of immunomodulatory bacteria is produced from the fecal material.

In some embodiments of the foregoing aspects, the mammalian donor subject is a healthy human subject.

In some embodiments of the foregoing aspects, the method comprises contacting the fecal material or a fraction or derivative thereof with a miscible solvent. In some embodiments, the method comprises a miscible solvent treatment, an immiscible solvent extraction, an elution from a solid medium, a thermal disrupting treatment, a radiation treatment, a filtration treatment, a chromatographic separation treatment, a centrifugation treatment, mechanical disrupting treatment, or a combination thereof.

In another aspect, the instant invention is directed to a method of treating or preventing a dysbiosis in a human subject, comprising administering to the human subject the composition produced by the method of any one of the preceding aspects or embodiments.

In some embodiments of the foregoing aspects, the therapeutic administration comprises oral administration of a composition comprising at least about $1 \times 10^4$ colony forming units of bacterial entities per dose of the composition.

In some embodiments of the foregoing aspects, the bacterial entities comprise bacteria from the genera provided in Table 1.

In some embodiments of the foregoing aspects, the composition comprises at least about 0.1%, 1%, 5%, 10%, 15%, 20%, 25%, 30%, 35%, 40%, 45%, 50% or above 50% spores on a mass basis. In some embodiments of the foregoing aspects, the composition comprises at least about $1 \times 10^4$ spores per gram or dose. In some embodiments of the foregoing aspects, the composition comprises at least about $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, or greater than $1 \times 10^{10}$ spores per gram or dose.

In another aspect, the instant invention is directed to a therapeutic composition comprising a purified population of bacterial entities comprising at least about $1 \times 10^3$, $1 \times 10^4$, $1 \times 10^5$, or $1 \times 10^6$ spores, wherein the composition does not exceed about 1 gram in weight, formulated for oral administration to treat or prevent a immune or inflammatory disease induced by a gastrointestinal dysbiosis in a mammalian recipient subject in need thereof.

In some embodiments of the foregoing aspects, the therapeutic composition is formulated to treat or prevent gastrointestinal disease, disorder or condition in a mammalian recipient subject in need thereof.

In some embodiments of the foregoing aspects, the bacterial entities are purified from fecal material obtained from a mammalian donor subject.

In some embodiments of the foregoing aspects, the therapeutic composition is in an amount effective to treat or prevent as a single dose a disorder in a mammalian recipient subject suffering from or at risk of developing such disorder to whom the therapeutic composition is administered.

In some embodiments of the foregoing aspects, the population of bacterial entities is purified from a fecal material obtained from at least one mammalian donor subject, wherein the at least one mammalian donor subject has no clinical history of a metabolic disorder.

In another aspect, the instant invention provides a kit comprising in one or more containers a fecal material collection apparatus and a solvent solution, and instructions for use thereof for generating purified populations of immunomodulatory bacteria.

In some embodiments of the foregoing aspects, the solvent solution comprises a detergent. In some embodiments, the detergent is Triton X-100, Tween 20, Tween 80, Nonidet P40, a pluronic, or a polyol.

In another aspect, the instant invention provides a method of modulating the microbiotal population in the vagina of a human subject, comprising the step of administering to the human subject a therapeutic composition comprising a purified population of immunomodulatory bacteria, under conditions such that i) the microbial population present in the vagina, and/or ii) the microbial population present outside the vagina is modulated.

In some embodiments of the foregoing aspects, the modulation comprises reduction or elimination of at least one pathogen and/or pathobiont present in the vagina when the therapeutic composition is administered. In some embodiments of the foregoing aspects, the modulation comprises engraftment of at least one type of immunomodulatory bacteria present in the therapeutic composition. In some embodiments of the foregoing aspects, the modulation comprises augmentation of at least one type of bacteria not present in the therapeutic composition.

In some embodiments of the foregoing aspects, the at least one type of immunomodulatory bacteria are not detectably present in vagina when the therapeutic composition is administered.

In some embodiments of the foregoing aspects, the modulation comprises augmentation of at least one type of immunomodulatory or non-spore forming bacteria not present in the therapeutic composition. In some embodiments, the at least one type of immunomodulatory bacteria or non-spore forming are increased by at least 2-fold after administration of the therapeutic composition.

In some embodiments of the foregoing aspects, the modulation comprises at least two of: i) reduction or elimination of at least one pathogen and/or pathobiont present in the vagina when the therapeutic composition is administered; ii) engraftment of at least one type of immunomodulatory bacteria present in the therapeutic composition; and iii) augmentation of at least one type of immunomodulatory or non-spore forming bacteria not present in the therapeutic composition.

In some embodiments of the foregoing aspects, the modulation comprises reduction or elimination of at least one pathogen and/or pathobiont present in the vagina when the therapeutic composition is administered and at least one of: i) engraftment of at least one type of immunomodulatory bacteria present in the therapeutic composition; and ii) augmentation of at least one type of bacteria not present in the therapeutic composition.

In certain embodiments of the foregoing aspects, the at least one pathogen and/or pathobiont is present at pathogenic amounts in the vagina when the composition is administered.

In certain embodiments of the foregoing aspects, the mammalian subject suffers from or is at risk of developing bacterial overgrowth syndrome (BOS). In certain embodiments of the foregoing aspects, the modulation comprises reduction or elimination of at least one pathogen and/or pathobiont associated with the BOS.

In certain embodiments of the foregoing aspects, the modulation comprises reduction or elimination of at least one drug resistant pathogen and/or pathobiont.

In another aspect, the instant invention is directed to a method of inducing engraftment of a bacterial population in the vagina of a human subject, comprising the step of administering to the human subject a therapeutic composition comprising a purified population of immunomodulatory bacteria, under conditions such that at least i) a subset of the immunomodulatory bacteria sustainably engraft within the vagina, or ii) at least one type of bacteria not present in the therapeutic composition is augmented within the vagina.

In certain embodiments of the foregoing aspects, the population of immunomodulatory bacteria consists essentially of spores, and wherein the spores germinate within the vagina.

In one aspect, the instant invention provides a pharmaceutical preparation comprising at least two isolated bacterial populations and a first isolated prebiotic mixture comprising at least one polymer or monomer.

In another aspect, the instant invention provides a pharmaceutical preparation comprising at least one isolated bacterial population that is optionally capable of forming spores and a first isolated prebiotic mixture comprising at least one polymer or monomer.

In another aspect, the instant invention provides a pharmaceutical preparation comprising at least two isolated bacterial populations that are capable of forming spores and an isolated prebiotic mixture comprising at least one polymer or monomer.

In another aspect, the instant invention provides a pharmaceutical preparation comprising a first purified prebiotic mixture comprising at least one polymer or monomer, capable of modulating the bacterial diversity present in a microbial niche in a human subject.

In some embodiments of the foregoing aspects, the preparation further comprises at least one additional isolated prebiotic mixture comprising at least one polymer or monomer.

In some embodiments of the foregoing aspects, at least one bacterial population and one isolated prebiotic mixture are capable of functionally interacting. In some embodiments of the foregoing aspects, at least one bacterial population and one isolated prebiotic mixture are formulated to functionally interact when co-localized in the gastrointestinal tract of a human subject.

In some embodiments of the foregoing aspects, at least one bacterial entity is capable of forming spores.

In some embodiments of the foregoing aspects, at least two bacterial populations form a network.

In some embodiments of the foregoing aspects, a first prebiotic mixture comprises at least one polymer or monomer selected from the group consisting of arabinoxylan, xylose, soluble fiber dextran, soluble corn fiber, polydextrose, lactose, N-acetyl-lactosamine, glucose, and mixtures thereof, and a second prebiotic mixture comprises at least one polymer or monomer selected from the group consisting of galactose, fructose, rhamnose, mannose, uronic acids, 3'-fucosyllactose, 3' sialylactose, 6'-sialyllactose, lacto-N-neotetraose, 2'-2'-fucosyllactose, and mixtures thereof.

In some embodiments of the foregoing aspects, the preparation comprises at least one N-acetyl-oligosaccharide.

In some embodiments of the foregoing aspects, the preparation comprises at least one galactofructose.

In some embodiments of the foregoing aspects, the preparation comprises at least one agricultural product or isolate thereof.

In some embodiments of the foregoing aspects, the preparation comprises at least one synthetic monosaccharide and/or oligosaccharide.

In some embodiments of the foregoing aspects, the preparation comprises at least one mammalian milk isolate.

In some embodiments of the foregoing aspects, the preparation of claim comprises at least one lysate, slurry, powder, or derivative of partly milled grains and seeds, potato, banana, heat-treated starch products, barley, oats, rye, hulls of pea, soya bean meal, sugar-beet pulp, coconut cake, palm cake, apple, sugar-beet pulp, guar gum, rapeseed meal, Jerusalem artichokes, or mixtures thereof.

In some embodiments of the foregoing aspects, the preparation further comprises at least one polyethylene glycol. In some embodiments, the polyethylene glycol is polyethylene glycol 3350 Da.

In some embodiments of the foregoing aspects, at least one bacterial population is vegetative or in a vegetative state.

In some embodiments of the foregoing aspects, the preparation is encapsulated and optionally further comprising an enteric coating.

In some embodiments of the foregoing aspects, the preparation comprises a first prebiotic mixture capable of modulating at least one nucleic acid present in an isolated bacterial population. In certain embodiments, at least one nucleic acid comprises a transcription factor.

In some embodiments of the foregoing aspects, the preparation is suitable for oral or rectal administration.

In some embodiments of the foregoing aspects, at least 90% of at least one bacterial population are endospores or forespores, or a mixture thereof in any proportion, or wherein at least one bacterial population comprises at least $1\times10^4$ colony forming units (CFUs).

In some embodiments of the foregoing aspects, a first isolated bacterial population comprises at least $1\times10^4$ colony forming units (CFUs) and a second isolated bacterial population comprises at least $1\times10^4$ CFUs.

In some embodiments of the foregoing aspects, at least one isolated bacterial population comprises at least $1\times10^4$ CFUs of a bacterial entity comprising a 16S sequence selected from the group consisting of SEQ ID NO 1-2032. In some embodiments of the foregoing aspects, the second isolated bacterial population comprises at least $1\times10^4$ CFUs of a bacterial entity comprising a 16S sequence selected from the group consisting of SEQ ID NO 1-2032. In some embodiments of the foregoing aspects, a first and second isolated bacterial populations independently comprise at least $1\times10^4$ CFUs of a bacterial entity comprising a 16S sequence provided herein.

In some embodiments of the foregoing aspects, the preparation is formulated as a solid, liquid, gel or emulsion.

In some embodiments of the foregoing aspects, at least one isolated bacterial population comprises bacteria that are non-pathogenic, attenuated, or a mixture thereof.

In some embodiments of the foregoing aspects, the preparation further comprises a non-bacterial therapeutic agent. In some embodiments, the therapeutic agent comprises a small molecule, nucleic acid or polypeptide. In some embodiments, the therapeutic agent comprises a fungus, yeast or Archaea. In some embodiments, the therapeutic agent comprises a protein.

In some embodiments of the foregoing aspects, at least one bacterial population comprises an exogenous nucleic acid. In some embodiments, the exogenous nucleic acid comprises a sporulation-associated nucleic acid or a germination-associated amino acid.

In some embodiments of the foregoing aspects, the pharmaceutical preparation further comprises a pharmaceutically acceptable excipient suitable for administration to a mammalian subject in need thereof. In some embodiments, the excipient is suitable for oral administration. In some embodiments, the excipient is suitable for rectal administration.

In another aspect, the instant invention is directed to a method of treating, preventing or reducing the severity of a disease, disorder or condition in a mammalian subject, comprising the step of administering to the mammalian subject the preparation of any of the foregoing aspects and embodiments thereof.

In some embodiments of the foregoing aspects, the disease, disorder or condition is an immune or inflammatory disease, disorder or condition.

In another aspect, the instant invention provides a food product comprising the pharmaceutical preparation of any of the forgoing aspects or embodiments thereof.

In another aspect, the instant invention provides a medical food product comprising a preparation for the treatment of graft-versus-host disease in a mammalian host in need thereof.

In some embodiments of the foregoing aspects, the food product is an infant formula. In some embodiments of the foregoing aspects, the food product is a yogurt. In some embodiments of the foregoing aspects, the food product is a beverage, e.g., chilled beverage.

In another aspect, the instant invention is directed to a method of increasing the titer of a spore-forming bacteria in the intestinal tract of a mammal, the method comprising administering to the mammal an effective amount of the pharmaceutical product of any of the foregoing aspects and embodiments thereof.

In some embodiments of the foregoing aspects, the pharmaceutical product is administered daily.

In some embodiments of the foregoing aspects, the pharmaceutical product is administered through the consumption of a food product comprising the pharmaceutical product.

In another aspect, the instant invention is directed to a method of increasing the titer of a desirable endogenous bacterial population in the intestinal tract of a mammal, the method comprising the administration to the mammal of an effective amount of the pharmaceutical preparation of any of the foregoing aspects and embodiments thereof.

In another aspect, the instant invention is directed to a method of decreasing the titer of an undesirable endogenous bacterial population in the intestinal tract of a mammal, the method comprising the administration to the mammal of an effective amount of the pharmaceutical preparation of any of the foregoing aspects and embodiments thereof.

In some embodiments of the foregoing aspects, the preparation acts by selectively enhancing the growth, division, or sporulation of a competitor strain to the undesirable endogenous bacterial population.

In another aspect, the instant invention is directed to a method of promoting the growth of beneficial microbiota in the gastrointestinal tract of an infant or toddler in need thereof, the method comprising the administration to the infant or toddler the preparation of any of the foregoing aspects or embodiments thereof.

In another aspect, the instant invention is directed to a method of enhancing or promoting the intestinal barrier integrity of an infant or toddler in need thereof, the method comprising the administration to the infant or toddler the preparation of any of the foregoing aspects and embodiments thereof.

In some embodiments of the foregoing aspects, the infant is a neonate delivered by Caesarian section.

In another aspect, the instant invention is directed to a method of stimulating enteric nerve cells in the gastrointestinal tract of an infant or toddler in need thereof, the method comprising the administration to the infant or toddler the preparation of any of the foregoing aspects or embodiments thereof.

In another aspect, the instant invention is directed to a method of treating obesity or facilitating weight loss in a mammalian host in need thereof, the method comprising administering to the mammalian host the preparation of any of the foregoing aspects and embodiments thereof.

In another aspect, the instant invention is directed to a method of treating or alleviating constipation in a mammalian host, the method comprising administering to the mammalian host the preparation of any of the foregoing aspects and embodiments thereof.

In another aspect, the instant invention is directed to a method of reconstituting, modulating, or creating a beneficial bacterial flora in the gastrointestinal tract of a mammalian host, the method comprising administering to the mammalian host the preparation of any of the foregoing aspects and embodiments thereof.

In another aspect, the instant invention is directed to a method of treating hepatic encephalopathy in a mammalian host, the method comprising administering to the mammalian host the preparation of any of the foregoing aspects and embodiments thereof.

In another aspect, the instant invention is directed to a method of preventing or treating one or more immune disorders in a mammalian host, the method comprising administering to the mammalian host the preparation of any of the foregoing aspects and embodiments thereof.

In some embodiments of the foregoing aspects, the immune disorder is an autoimmune disease. In some embodiments, the autoimmune disease is a disease of the gastrointestinal tract. In some embodiments, the autoimmune disease is Crohn's disease or colitis.

In some embodiments of the foregoing aspects, the mammalian host is a human. In some embodiments, the human is an infant or a toddler.

In another aspect, the instant invention is directed to a method of preventing or treating one or more infections in a mammalian host, the method comprising administering to the mammalian host the preparation of any of the foregoing aspects and embodiments thereof.

In some embodiments of the foregoing aspects, the infection being prevented or treated is an infection of the upper respiratory tract.

In some embodiments of the foregoing aspects, the protective effect of the administered preparation stems in part from stimulation of an adaptive immune response.

In another aspect, the instant invention is directed to a method of treating irritable bowel syndrome in a mammalian host in need thereof, the method comprising administering to the mammalian host the preparation of any of the foregoing aspects and embodiments thereof.

In another aspect, the instant invention is directed to a method of restoring or repopulating the gastrointestinal bacterial population of a mammalian host following colonoscopy or endoscopic large bowel examination, the method comprising administering to the mammalian host the preparation of any of the foregoing aspects and embodiments thereof.

In another aspect, the instant invention is directed to a method of treating or preventing allergic disease in an mammalian host in need thereof, the method comprising administering to the mammalian host the preparation of any of the foregoing aspects and embodiments thereof.

In another aspect, the instant invention is directed to a method of treating or preventing lactose intolerance in an mammalian host in need thereof, the method comprising administering to the mammalian host the preparation of any of the foregoing aspects and embodiments thereof.

In another aspect, the instant invention is directed to a method of reducing the infiltration of at least one leukocyte cell population in an allergic legion on a mammalian host in need thereof, the method comprising administering to the mammalian host the preparation of any of the foregoing aspects and embodiments thereof.

In some embodiments of the foregoing aspects, the leukocyte cell population comprises eosinophils, neutrophils, or mononuclear cells.

In another aspect, the instant invention is directed to a method of inhibiting a Th2-type immune response, promoting a Th1-mediated immune response, or exerting both effects simultaneously, the method comprising administering to the mammalian host the preparation of any of the foregoing aspects and embodiments thereof.

In another aspect, the instant invention is directed to a method for improving the growth rate of a mammal, the method comprising administering to the mammal the preparation of any of the foregoing aspects and embodiments thereof.

In another aspect, the instant invention is directed to a method for improving the ability of the animal to extract nutrients from a feedstock, the method comprising administering to the mammal the preparation of any of the foregoing aspects and embodiments thereof.

In some embodiments of the foregoing aspects, the animal is an agricultural animal or a companion animal. In some embodiments, the mammal is a ruminant. In some embodiments, the mammal is a non-ruminant.

In another aspect, the instant invention is directed to a method of increasing the concentration of lactate, acetate, propionate, or butyrate in the gastrointestinal tract of a mammalian host, the method comprising administering to the mammalian host the preparation of any of the foregoing aspects and embodiments thereof.

In another aspect, the instant invention is directed to a method of increasing the biosynthesis or bioavailability of vitamin K in a mammalian host in need thereof, the method comprising administering to the mammalian host the preparation of any of the foregoing aspects and embodiments thereof.

In another aspect, the instant invention is directed to a method for improving the shelf life of a probiotic preparation, the method comprising combining the bacterial populations to be stored with a first isolated prebiotic mixture comprising at least one polymer or monomer, and at least one additional isolated prebiotic comprising at least one polymer or monomer.

In some embodiments of the foregoing aspects, a first isolated prebiotic mixture comprises at least one polymer or monomer selected from the group consisting of arabinoxylan, xylose, soluble fiber dextran, soluble corn fiber, polydextrose, lactose, N-acetyl-lactosamine, glucose, and mixtures thereof, and a second prebiotic mixture comprises at least one polymer or monomer selected from the group consisting of galactose, fructose, rhamnose, mannose, uronic acids, 3'-fucosyllactose, 3'sialyllactose, 6'-sialyllactose, lacto-N-neotetraose, 2'-2'-fucosyllactose, and mixtures thereof.

In another aspect, the instant invention is directed to an assay comprising a detection means for measuring an immune product.

In one aspect, the instant invention provides a pharmaceutical preparation comprising at least two isolated bacterial populations and a first isolated prebiotic mixture comprising at least one polymer or monomer.

In another aspect, the instant invention provides a pharmaceutical preparation comprising at least one isolated bacterial population that is optionally capable of forming spores and a first isolated prebiotic mixture comprising at least one polymer or monomer.

In another aspect, the instant invention provides a pharmaceutical preparation comprising at least two isolated bacterial populations that are capable of forming spores and an isolated prebiotic mixture comprising at least one polymer or monomer.

In another aspect, the instant invention provides a pharmaceutical preparation comprising a first purified prebiotic mixture comprising at least one polymer or monomer, capable of modulating the bacterial diversity present in a microbial niche in a human subject.

In some embodiments of the foregoing aspects, the preparation further comprises at least one additional isolated prebiotic mixture comprising at least one polymer or monomer.

In some embodiments of the foregoing aspects, at least one bacterial population and one isolated prebiotic mixture are capable of functionally interacting. In some embodiments of the foregoing aspects, at least one bacterial population and one isolated prebiotic mixture are formulated to functionally interact when co-localized in the gastrointestinal tract of a human subject.

In some embodiments of the foregoing aspects, the preparation comprises at least one bacterial entity that is capable of forming spores.

In some embodiments of the foregoing aspects, at least two bacterial populations form a network.

In some embodiments of the foregoing aspects, a first prebiotic mixture comprises at least one polymer or monomer selected from the group consisting of arabinoxylan, xylose, soluble fiber dextran, soluble corn fiber, polydextrose, lactose, N-acetyl-lactosamine, glucose, and mixtures thereof, and a second prebiotic mixture comprises at least one polymer or monomer selected from the group consisting of galactose, fructose, rhamnose, mannose, uronic acids, 3'-fucosyllactose, 3' sialylactose, 6'-sialyllactose, lacto-N-neotetraose, 2'-2'-fucosyllactose, and mixtures thereof.

In some embodiments of the foregoing aspects, the preparation comprises at least one N-acetyl-oligosaccharide.

In some embodiments of the foregoing aspects, the preparation comprises at least one galactofructose.

In some embodiments of the foregoing aspects, the preparation comprises at least one agricultural product or isolate thereof.

In some embodiments of the foregoing aspects, the preparation comprises at least one synthetic monosaccharide and/or oligosaccharide.

In some embodiments of the foregoing aspects, the preparation comprises at least one mammalian milk isolate.

In some embodiments of the foregoing aspects, the preparation comprises at least one lysate, slurry, powder, or derivative of partly milled grains and seeds, potato, banana, heat-treated starch products, barley, oats, rye, hulls of pea, soya bean meal, sugar-beet pulp, coconut cake, palm cake, apple, sugar-beet pulp, guar gum, rapeseed meal, Jerusalem artichokes, or mixtures thereof.

In some embodiments of the foregoing aspects, the preparation further comprises at least one polyethylene glycol. In some embodiments, the polyethylene glycol is polyethylene glycol 3350 Da.

In some embodiments of the foregoing aspects, at least one bacterial population is vegetative or in a vegetative state.

In some embodiments of the foregoing aspects, the preparation is encapsulated and optionally further comprises an enteric coating.

In some embodiments of the foregoing aspects, the preparation comprises a first prebiotic mixture capable of modulating at least one nucleic acid present in an isolated bacterial population. In some embodiments, the at least one nucleic acid comprises a transcription factor.

In some embodiments of the foregoing aspects, the preparation is suitable for oral or rectal administration.

In some embodiments of the foregoing aspects, at least 90% of at least one bacterial population are endospores or forespores, or a mixture thereof in any proportion, or wherein at least one bacterial population comprises at least $1\times10^4$ colony forming units (CFUs).

In some embodiments of the foregoing aspects, a first isolated bacterial population comprises at least $1\times10^4$ colony forming units (CFUs) and a second isolated bacterial population comprises at least $1\times10^4$ CFUs.

In some embodiments of the foregoing aspects, at least one isolated bacterial population comprises at least $1\times10^4$ CFUs of a bacterial entity comprising a 16S sequence selected from the group consisting of SEQ ID NO 1-2032.

In some embodiments of the foregoing aspects, the second isolated bacterial population comprises at least $1\times10^4$ CFUs of a bacterial entity comprising a 16S sequence selected from the group consisting of SEQ ID NO 1-2032.

In some embodiments of the foregoing aspects, a first and second isolated bacterial populations independently comprise at least $1\times10^4$ CFUs of a bacterial entity comprising a 16S sequence selected as provided herein.

In some embodiments of the foregoing aspects, the preparation is formulated as a solid, liquid, gel or emulsion.

In some embodiments of the foregoing aspects, at least one isolated bacterial population comprises bacteria that are non-pathogenic, attenuated, or a mixture thereof.

In some embodiments of the foregoing aspects, the preparation further comprises a non-bacterial therapeutic agent. In some embodiments, the therapeutic agent comprises a small molecule, nucleic acid or polypeptide. In some embodiments, the therapeutic agent comprises a fungus, yeast or Archaea. In some embodiments, the therapeutic agent comprises a protein.

In some embodiments of the foregoing aspects, at least one bacterial population comprises an exogenous nucleic acid. In some embodiments, the exogenous nucleic acid comprises a sporulation-associated nucleic acid or a germination-associated amino acid.

In some embodiments of the foregoing aspects, the pharmaceutical preparation further comprises a pharmaceutically acceptable excipient suitable for administration to a mammalian subject in need thereof. In some embodiments, the excipient is suitable for oral administration. In some embodiments, the excipient is suitable for rectal administration.

In another aspect, the instant invention is directed to a method of treating, preventing or reducing the severity of a disease, disorder or condition in a mammalian subject, comprising the step of administering to the mammalian subject the preparation of any of the foregoing aspects and embodiments thereof.

In some embodiments of the foregoing aspects, the disease, disorder or condition is an immune or inflammatory disease, disorder or condition.

In another aspect, the instant invention provides a food product comprising the pharmaceutical preparation of any of the foregoing aspects and embodiments thereof.

In another aspect, the instant invention provides a medical food product comprising a preparation for the treatment of graft-versus-host disease in a mammalian host in need thereof.

In some embodiments of the foregoing aspects, the food product is an infant formula. In some embodiments of the foregoing aspects, the food product is a yogurt. In some embodiments of the foregoing aspects, the food product is a beverage, e.g., chilled beverage.

In another aspect, the instant invention provides a method of increasing the titer of a spore-forming bacteria in the intestinal tract of a mammal, the method comprising administering to the mammal an effective amount of the pharmaceutical product of any of the foregoing aspects and embodiments thereof.

In some embodiments of the foregoing aspects, the pharmaceutical product is administered daily.

In some embodiments of the foregoing aspects, the pharmaceutical product is administered through the consumption of a food product comprising the pharmaceutical product.

In another aspect, the instant invention is directed to a method of increasing the titer of a desirable endogenous bacterial population in the intestinal tract of a mammal, the method comprising the administration to the mammal of an effective amount of the pharmaceutical preparation of any of the foregoing aspects and embodiments thereof.

In another aspect, the instant invention is directed to a method of decreasing the titer of an undesirable endogenous bacterial population in the intestinal tract of a mammal, the method comprising the administration to the mammal of an effective amount of the pharmaceutical preparation of any of the foregoing aspects and embodiments thereof.

In some embodiments of the foregoing aspects, the preparation acts by selectively enhancing the growth, division, or sporulation of a competitor strain to the undesirable endogenous bacterial population.

In another aspect, the instant invention is directed to a method of promoting the growth of beneficial microbiota in the gastrointestinal tract of an infant or toddler in need thereof, the method comprising the administration to the infant or toddler the preparation of any of the foregoing aspects and embodiments thereof.

In another aspect, the instant invention is directed to a method of enhancing or promoting the intestinal barrier integrity of an infant or toddler in need thereof, the method comprising the administration to the infant or toddler the preparation of any of the foregoing aspects and embodiments thereof.

In some embodiments of the foregoing aspects, the infant is a neonate delivered by Caesarian section.

In another aspect, the instant invention is directed to a method of stimulating enteric nerve cells in the gastrointestinal tract of an infant or toddler in need thereof, the method comprising the administration to the infant or toddler the preparation of any of the foregoing aspects and embodiments thereof.

In another aspect, the instant invention is directed to a method of treating obesity or facilitating weight loss in a mammalian host in need thereof, the method comprising administering to the mammalian host the preparation of any of the foregoing aspects and embodiments thereof.

In another aspect, the instant invention is directed to a method of treating or alleviating constipation in a mammalian host, the method comprising administering to the mammalian host the preparation of any of the foregoing aspects and embodiments thereof.

In another aspect, the instant invention is directed to a method of reconstituting, modulating, or creating a beneficial bacterial flora in the gastrointestinal tract of a mammalian host, the method comprising administering to the mammalian host the preparation of any of the foregoing aspects and embodiments thereof.

In another aspect, the instant invention is directed to a method of treating hepatic encephalopathy in a mammalian host, the method comprising administering to the mammalian host the preparation of any of the foregoing aspects and embodiments thereof.

In another aspect, the instant invention is directed to a method of preventing or treating one or more immune disorders in a mammalian host, the method comprising administering to the mammalian host the preparation of any of the foregoing aspects and embodiments thereof.

In some embodiments of the foregoing aspects, the immune disorder is an autoimmune disease. In some embodiments, the autoimmune disease is a disease of the gastrointestinal tract. In some embodiments, the autoimmune disease is Crohn's disease or colitis.

In some embodiments of the foregoing aspects, the mammalian host is a human. In some embodiments, the human is an infant or a toddler.

In another aspect, the instant invention is directed to a method of preventing or treating one or more infections in a mammalian host, the method comprising administering to the mammalian host the preparation of claim 1, 2, 3, or 4.

In some embodiments of the foregoing aspects, the infection being prevented or treated is an infection of the upper respiratory tract.

In some embodiments of the foregoing aspects, the protective effect of the administered preparation stems in part from stimulation of an adaptive immune response.

In another aspect, the instant invention is directed to a method of treating irritable bowel syndrome in a mammalian host in need thereof, the method comprising administering to the mammalian host the preparation of any of the foregoing aspects and embodiments thereof.

In another aspect, the instant invention is directed to a method of restoring or repopulating the gastrointestinal bacterial population of a mammalian host following colonoscopy or endoscopic large bowel examination, the method comprising administering to the mammalian host the preparation of any of the foregoing aspects and embodiments thereof.

In another aspect, the instant invention is directed to a method of treating or preventing allergic disease in an mammalian host in need thereof, the method comprising administering to the mammalian host the preparation of any of the foregoing aspects and embodiments thereof.

In another aspect, the instant invention is directed to a method of treating or preventing lactose intolerance in an mammalian host in need thereof, the method comprising administering to the mammalian host the preparation of any of the foregoing aspects and embodiments thereof.

In another aspect, the instant invention is directed to a method of reducing the infiltration of at least one leukocyte cell population in an allergic legion on a mammalian host in need thereof, the method comprising administering to the mammalian host the preparation of any of the foregoing aspects and embodiments thereof.

In some embodiments of the foregoing aspects, the leukocyte cell population comprises eosinophils, neutrophils, or mononuclear cells.

In another aspect, the instant invention is directed to a method of inhibiting a Th2-type immune response, promoting a Th1-mediated immune response, or exerting both effects simultaneously, the method comprising administering to the mammalian host the preparation of any of the foregoing aspects and embodiments thereof.

In another aspect, the instant invention is directed to a method for improving the growth rate of a mammal, the method comprising administering to the mammal the preparation of some of the foregoing aspects and embodiments thereof.

In another aspect, the instant invention is directed to a method for improving the ability of the animal to extract nutrients from a feedstock, the method comprising administering to the mammal the preparation of any of the foregoing aspects and embodiments thereof.

In some embodiments of the foregoing aspects, the animal is an agricultural animal or a companion animal. In some embodiments, the mammal is a ruminant. In some embodiments, the mammal is a non-ruminant.

In another aspect, the instant invention is directed to a method of increasing the concentration of lactate, acetate, propionate, or butyrate in the gastrointestinal tract of a mammalian host, the method comprising administering to the mammalian host the preparation of any of the foregoing aspects and embodiments thereof.

In another aspect, the instant invention is directed to a method of increasing the biosynthesis or bioavailability of vitamin K in a mammalian host in need thereof, the method comprising administering to the mammalian host the preparation of any of the foregoing aspects and embodiments thereof.

In another aspect, the instant invention is directed to a method for improving the shelf life of a probiotic preparation, the method comprising combining the bacterial populations to be stored with a first isolated prebiotic mixture comprising at least one polymer or monomer, and at least one additional isolated prebiotic comprising at least one polymer or monomer.

In some embodiments of the foregoing aspects, a first isolated prebiotic mixture comprises at least one polymer or monomer selected from the group consisting of arabinoxylan, xylose, soluble fiber dextran, soluble corn fiber, polydextrose, lactose, N-acetyl-lactosamine, glucose, and mixtures thereof, and a second prebiotic mixture comprises at least one polymer or monomer selected from the group consisting of galactose, fructose, rhamnose, mannose, uronic acids, 3'-fucosyllactose, 3'sialylactose, 6'-sialyllactose, lacto-N-neotetraose, 2'-2'-fucosyllactose, and mixtures thereof.

In another aspect, the instant invention is directed to an assay comprising a detection means for measuring an immune product.

In one aspect, the instant invention provides a pharmaceutical preparation comprising at least two isolated bacterial populations and a first isolated prebiotic mixture comprising at least one polymer or monomer.

In another aspect, the instant invention provides a pharmaceutical preparation comprising at least one isolated bacterial population that is optionally capable of forming spores and a first isolated prebiotic mixture comprising at least one polymer or monomer.

In another aspect, the instant invention provides a pharmaceutical preparation comprising at least two isolated bacterial populations that are optionally capable of forming spores and an isolated prebiotic mixture comprising at least one polymer or monomer.

In another aspect, the instant invention provides a pharmaceutical preparation comprising a first purified prebiotic mixture comprising at least one polymer or monomer, capable of modulating the bacterial diversity present in a microbial niche in a human subject.

In some embodiments of the foregoing aspects, the preparation further comprises at least one additional isolated prebiotic mixture comprising at least one polymer or monomer.

In some embodiments of the foregoing aspects, at least one bacterial population and one isolated prebiotic mixture are capable of functionally interacting.

In some embodiments of the foregoing aspects, at least one bacterial population and one isolated prebiotic mixture are formulated to functionally interact when co-localized in the gastrointestinal tract of a human subject.

In some embodiments of the foregoing aspects, the preparation comprises at least one bacterial entity that is capable of forming spores.

In some embodiments of the foregoing aspects, at least two bacterial populations form a network.

In some embodiments of the foregoing aspects, a first prebiotic mixture comprises at least one polymer or monomer selected from the group consisting of arabinoxylan, xylose, soluble fiber dextran, soluble corn fiber, polydextrose, lactose, N-acetyl-lactosamine, glucose, and mixtures thereof, and a second prebiotic mixture comprises at least one polymer or monomer selected from the group consisting of galactose, fructose, rhamnose, mannose, uronic acids, 3'-fucosyllactose, 3' sialylactose, 6'-sialyllactose, lacto-N-neotetraose, 2'-2'-fucosyllactose, and mixtures thereof.

In some embodiments of the foregoing aspects, the preparation comprises at least one N-acetyl-oligosaccharide.

In some embodiments of the foregoing aspects, the preparation comprises at least one galactofructose.

In some embodiments of the foregoing aspects, the preparation comprises at least one agricultural product or isolate thereof.

In some embodiments of the foregoing aspects, the preparation comprises at least one synthetic monosaccharide and/or oligosaccharide.

In some embodiments of the foregoing aspects, the preparation comprises at least one mammalian milk isolate.

In some embodiments of the foregoing aspects, the preparation comprises at least one lysate, slurry, powder, or derivative of partly milled grains and seeds, potato, banana, heat-treated starch products, barley, oats, rye, hulls of pea, soya bean meal, sugar-beet pulp, coconut cake, palm cake, apple, sugar-beet pulp, guar gum, rapeseed meal, Jerusalem artichokes, or mixtures thereof.

In some embodiments of the foregoing aspects, the preparation further comprises at least one polyethylene glycol. In some embodiments, the polyethylene glycol is polyethylene glycol 3350 Da.

In some embodiments of the foregoing aspects, at least one bacterial population is vegetative or in a vegetative state.

In some embodiments of the foregoing aspects, the preparation is encapsulated and optionally further comprising an enteric coating.

In some embodiments of the foregoing aspects, the preparation comprises a first prebiotic mixture capable of modulating at least one nucleic acid present in an isolated bacterial population. In some embodiments, the at least one nucleic acid is selected from the group consisting of any one of the sequences disclosed herein.

In some embodiments of the foregoing aspects, the preparation is suitable for oral or rectal administration.

In some embodiments of the foregoing aspects, at least 90% of at least one bacterial population are endospores or forespores, or a mixture thereof in any proportion, or wherein at least one bacterial population comprises at least $1 \times 10^4$ colony forming units (CFUs).

In some embodiments of the foregoing aspects, a first isolated bacterial population comprises at least $1 \times 10^4$ colony forming units (CFUs) and a second isolated bacterial population comprises at least $1 \times 10^4$ CFUs.

In some embodiments of the foregoing aspects, at least one isolated bacterial population comprises at least $1 \times 10^4$ CFUs of a bacterial entity comprising a 16S sequence disclosed herein.

In some embodiments of the foregoing aspects, the second isolated bacterial population comprises at least $1\times10^4$ CFUs of a bacterial entity comprising a 16S sequence selected disclosed herein.

In some embodiments of the foregoing aspects, at least about $1\times10^4$ CFUs vegetative organisms and a prebiotic mixture comprising two or more purified sugars.

In some embodiments of the foregoing aspects, the vegetative organism has an increased ability to form spores in the presence of the purified sugars than in the absence of the purified sugars.

In some embodiments of the foregoing aspects, at least one isolated bacterial population comprises bacteria that are non-pathogenic, attenuated, or a mixture thereof.

In some embodiments of the foregoing aspects, the preparation further comprises a non-bacterial therapeutic agent.

In some embodiments of the foregoing aspects, the therapeutic agent comprises a small molecule, nucleic acid, or polypeptide. In some embodiments, the therapeutic agent comprises a fungus, yeast, or archaea. In some embodiments, the therapeutic agent comprises a protein.

In some embodiments of the foregoing aspects, at least one bacterial population comprises an exogenous nucleic acid. In some embodiments, the exogenous nucleic acid comprises a sporulation-associated nucleic acid or a germination-associated amino acid.

In another aspect, the instant invention provides a pharmaceutical preparation comprising the pharmaceutical preparation of any of the foregoing aspects and embodiments thereof, further comprising a pharmaceutically acceptable excipient suitable for administration to a mammalian subject in need thereof.

In some embodiments of the foregoing aspects, the excipient is suitable for oral administration. In some embodiments of the foregoing aspects, the excipient is suitable for rectal administration.

In another aspect, the instant invention is directed to a method of treating, preventing, or reducing the severity of a disease, disorder, or condition in a mammalian subject, comprising the step of administering to the mammalian subject the preparation of any of the foregoing aspects and embodiments thereof.

In some embodiments of the foregoing aspects, the disease, disorder or condition is an autoimmune or inflammatory disease.

In another aspect, the instant invention provides a food product comprising the pharmaceutical preparation of any of the foregoing aspects and embodiments thereof.

In another aspect, the instant invention provides a medical food product comprising a preparation for the treatment of an autoimmune or inflammatory disease in a mammalian host in need thereof.

In some embodiments of the foregoing aspects, the food product is an infant formula. In some embodiments of the foregoing aspects, the food product is a yogurt. In some embodiments of the foregoing aspects, the food product is a chilled beverage.

In another aspect, the instant invention is directed to a method of increasing the titer of a spore-forming bacteria in the intestinal tract of a mammal, the method comprising administering to the mammal an effective amount of the pharmaceutical product of any of the foregoing aspects and embodiments thereof.

In some embodiments of the foregoing aspects, the pharmaceutical product is administered daily.

In some embodiments of the foregoing aspects, the pharmaceutical product is administered through the consumption of a food product comprising the pharmaceutical product.

In another aspect, the instant invention provides a method of increasing the titer of a desirable endogenous bacterial population in the intestinal tract of a mammal, the method comprising the administration to the mammal of an effective amount of the pharmaceutical preparation of any of the foregoing aspects and embodiments thereof.

In another aspect, the instant invention provides a method of decreasing the titer of an undesirable endogenous bacterial population in the intestinal tract of a mammal, the method comprising the administration to the mammal of an effective amount of the pharmaceutical preparation of any of the foregoing aspects and embodiments thereof.

In some embodiments of the foregoing aspects, the preparation acts by selectively enhancing the growth, division, or sporulation of a competitor strain to the undesirable endogenous bacterial population.

In another aspect, the instant invention provides a method of promoting the growth of beneficial microbiota in the gastrointestinal tract of an infant or toddler in need thereof, the method comprising the administration to the infant or toddler the preparation of any of the foregoing aspects and embodiments thereof.

In another aspect, the instant invention provides a method of enhancing or promoting the intestinal barrier integrity of an infant or toddler in need thereof, the method comprising the administration to the infant or toddler the preparation of any of the foregoing aspects and embodiments thereof.

In some embodiments of the foregoing aspects, the infant is a neonate delivered by Caesarian section.

In another aspect, the instant invention is directed to a method of stimulating enteric nerve cells in the gastrointestinal tract of an infant or toddler in need thereof, the method comprising the administration to the infant or toddler the preparation of any of the foregoing aspects and embodiments thereof.

In another aspect, the instant invention is directed to a method of treating obesity or facilitating weight loss in a mammalian host in need thereof, the method comprising administering to the mammalian host the preparation of any of the foregoing aspects and embodiments thereof.

In another aspect, the instant invention is directed to a method of treating or alleviating constipation in a mammalian host, the method comprising administering to the mammalian host the preparation of any of the foregoing aspects and embodiments thereof.

In another aspect, the instant invention is directed to a method of reconstituting, modulating, or creating a beneficial bacterial flora in the gastrointestinal tract of a mammalian host, the method comprising administering to the mammalian host the preparation of any of the foregoing aspects and embodiments thereof.

In another aspect, the instant invention is directed to a method of treating hepatic encephalopathy in a mammalian host, the method comprising administering to the mammalian host the preparation of any of the foregoing aspects and embodiments thereof.

In another aspect, the instant invention is directed to a method of preventing or treating one or more immune disorders in a mammalian host, the method comprising administering to the mammalian host the preparation of any of the foregoing aspects and embodiments thereof.

In some embodiments of the foregoing aspects, the immune disorder is an autoimmune disease. In some embodiments, the autoimmune disease is a disease of the gastrointestinal tract. In some embodiments, the autoimmune disease is Crohn's disease, ulcerative colitis, multiple sclerosis, rheumatoid arthritis, lupus, or primary sclerosing cholangitis.

In some embodiments of the foregoing aspects, the mammalian host is a human. In some embodiments, the human is an infant or a toddler.

In another aspect, the instant invention is directed to a method of preventing or treating one or more infections in a mammalian host, the method comprising administering to the mammalian host the preparation of any of the foregoing aspects and embodiments thereof.

In some embodiments of the foregoing aspects, the infection being prevented or treated is an infection of the upper respiratory tract.

In some embodiments of the foregoing aspects, the protective effect of the administered preparation stems in part from stimulation of an adaptive immune response.

In another aspect, the instant invention is directed to a method of treating irritable bowel syndrome in a mammalian host in need thereof, the method comprising administering to the mammalian host the preparation of any of the foregoing aspects and embodiments thereof.

In another aspect, the instant invention is directed to a method of restoring or repopulating the gastrointestinal bacterial population of a mammalian host following colonoscopy or endoscopic large bowel examination, the method comprising administering to the mammalian host the preparation of any of the foregoing aspects and embodiments thereof.

In another aspect, the instant invention is directed to a method of treating or preventing allergic disease in an mammalian host in need thereof, the method comprising administering to the mammalian host the preparation of any of the foregoing aspects and embodiments thereof.

In another aspect, the instant invention is directed to a method of treating or preventing lactose intolerance in an mammalian host in need thereof, the method comprising administering to the mammalian host the preparation of any of the foregoing aspects and embodiments thereof.

In another aspect, the instant invention is directed to a method of reducing the infiltration of at least one leukocyte cell population in an allergic legion on a mammalian host in need thereof, the method comprising administering to the mammalian host the preparation of any of the foregoing aspects and embodiments thereof.

In some embodiments of the foregoing aspects, the leukocyte cell population comprises eosinophils, neutrophils, or mononuclear cells.

In another aspect, the instant invention is directed to a method of inhibiting a Th2-type immune response, promoting a Th1-mediated immune response, or exerting both effects simultaneously, the method comprising administering to the mammalian host the preparation of any of the foregoing aspects and embodiments thereof.

In another aspect, the instant invention is directed to a method for improving the growth rate of a mammal, the method comprising administering to the mammal the preparation of any of the foregoing aspects and embodiments thereof.

In another aspect, the instant invention is directed to a method for improving the ability of the animal to extract nutrients from a feedstock, the method comprising administering to the mammal the preparation of any of the foregoing aspects and embodiments thereof.

In some embodiments of the foregoing aspects, the animal is an agricultural animal or a companion animal.

In some embodiments of the foregoing aspects, the mammal is a ruminant. In some embodiments, the mammal is a non-ruminant.

In another aspect, the instant invention is directed to a method of increasing the concentration of lactate, acetate, propionate, or butyrate in the gastrointestinal tract of a mammalian host, the method comprising administering to the mammalian host the preparation of any of the foregoing aspects and embodiments thereof.

In another aspect, the instant invention is directed to a method of increasing the biosynthesis or bioavailability of vitamin K in a mammalian host in need thereof, the method comprising administering to the mammalian host the preparation of any of the foregoing aspects and embodiments thereof.

In another aspect, the instant invention is directed to a method for improving the shelf life of a probiotic preparation, the method comprising combining the bacterial populations to be stored with a first isolated prebiotic mixture comprising at least one polymer or monomer, and at least one additional isolated prebiotic comprising at least one polymer or monomer.

In some embodiments of the foregoing aspects, a first isolated prebiotic mixture comprises at least one polymer or monomer selected from the group consisting of arabinoxylan, xylose, soluble fiber dextran, soluble corn fiber, polydextrose, lactose, N-acetyl-lactosamine, glucose, and mixtures thereof, and a second prebiotic mixture comprises at least one polymer or monomer selected from the group consisting of galactose, fructose, rhamnose, mannose, uronic acids, 3'-fucosyllactose, 3'sialylactose, 6'-sialyllactose, lacto-N-neotetraose, 2'-2'-fucosyllactose, and mixtures thereof.

In another aspect, the instant invention provides an assay comprising a detection means for measuring an immune product.

BRIEF DESCRIPTION OF THE TABLES

Table 1 provides a list of Operational Taxonomic Units (OTU) with taxonomic assignments made to Genus, Species, and Phylogenetic Clade. Clade membership of bacterial OTUs is based on 16S sequence data. Clades are defined based on the topology of a phylogenetic tree that is constructed from full-length 16S sequences using maximum likelihood methods familiar to individuals with ordinary skill in the art of phylogenetics. Clades are constructed to ensure that all OTUs in a given Clade are: (i) within a specified number of bootstrap supported nodes from one another, and (ii) within 5% genetic similarity. OTUs that are within the same Clade can be distinguished as genetically and phylogenetically distinct from OTUs in a different Clade based on 16S-V4 sequence data, while OTUs falling within the same Clade are closely related. OTUs falling within the same Clade are evolutionarily closely related and may or may not be distinguishable from one another using 16S-V4 sequence data. Members of the same Clade, due to their evolutionary relatedness, play similar functional roles in a microbial ecology such as that found in the human gut. Compositions substituting one species with another from the same Clade are likely to have conserved ecological function and therefore are useful in the present invention. All OTUs are denoted as to their putative capacity to form spores and whether they are a Pathogen or Pathobiont (see Definitions for description of "Pathobiont"). NAIAD Priority Pathogens are denoted as 'Category-A', 'Category-B', or 'Category-C', and Opportunistic Pathogens are denoted as 'OP'. OTUs that are not pathogenic or for which their ability to exist as a pathogen is unknown are denoted as 'N'. The 'SEQ ID Number' denotes the identifier of the OTU in the Sequence Listing File and 'Public DB Accession' denotes the identifier of the OTU in a public sequence repository. See, e.g., WO2014/121304.

Table 1A provides a list of exemplary bacteria useful in the present invention.

Table 1B provides a list of exemplary bacteria useful in the present invention.

Table 1C provides a list of exemplary bacteria useful in the present invention.

Table 1D provides a list of exemplary bacteria useful in the present invention.

Table 1E provides a list of exemplary bacteria useful in the present invention. These bacteria are preferably down-modulated in a subject.

Table 1F provides a list of exemplary bacteria that may be used in the invention. These bacteria are preferably up-modulated in a subject.

Table 2A lists species identified as "germinable" and "sporulatable" by colony picking approach.

Table 2B lists species identified as "germinable" using 16S colony picking approach.

Table 2C lists species identified as "sporulatable" using 16s-V4 NGS approach. See, e.g., WO2014/121304.

Table 3 provides criteria for stages of acute GVHD.

Table 4 provides representative examples of microbial enzymes that allow utilization of prebiotics.

Table 5 provides a list of species enriched in alive GVHD patients.

Table 6 lists anaerobic bacterial species tested for carbon source usage.

Table 7 provides exemplary prebiotics/carbon sources for use in the compositions and methods of the invention.

Table 8 provides bacterial species detected at low frequency in vaginal samples from vancomycin-treated mice (day 6) that were not present in untreated mice (day 0).

w) IL-8 concentration (pg/ml) after 48 hours. x) IL-8 concentration (pg/ml) after 72 hours.

FIG. 6 (a-d) is a panel of graphs showing the secreted levels of cytokines IFNγ (Ifng), IL-12p70, IL-1α (IL-1a), IL-6, IL-8, MCP1, MIP1α (MIP1a), MIP1β (MIP1b), TNFα (TNFa), IL-10, IL-13, IL-9, IL-4, IL-5, IL-17α (IL-17A) and IL-2 produced by PBMCs in the presence of a) *R. gnavus*, b) *B. wexlerae*, c) *E. rectale* and d) *B. luti*, alone or in combination with *E. faecalis* (Epv 8), relative to levels secreted following treatment with *E. faecalis* alone for 24 hours (*E. faecalis*=100%).

FIG. 7 (a-p) is a panel of graphs that show the effect of *R. gnavus* (Epv1) on cytokine concentration (pg/ml) either alone or in combination with Epv 8 (*E. faecalis*) on cytokine production by human PBMCs (pg/ml). a) IL-6, b) IFN-γ, c) IL-13, d) IL-10, e) IL-12p70, f) MCP-1, g) IL-8, h) IL17A, i) IL-α, j) IL-9, k) IL-2, l) IL-4, m) IL-5, n) MIP-1α, o) MIP-1β, p) TNF-α.

FIG. 8 (a-p) is a panel of graphs that show the effect of *E. rectale* (Epv2) on cytokine concentration (pg/ml) either alone or in combination with Epv 8 (*E. faecalis*) on cytokine production by human PBMCs (pg/ml). a) IL-6, b) IFN-γ, c) IL-13, d) IL-10, e) IL-12p70, f) MCP-1, g) IL-8, h) IL17A, i) IL-α, j) IL-9, k) IL-2, l) IL-4, m) IL-5, n) MIP-1α, o) MIP-1β, p) TNF-α.

FIG. 9 (a-p) is a panel of graphs that show the effect of *B. luti* (Epv3) on cytokine concentration (pg/ml) either alone or in combination with Epv 8 (*E. faecalis*) on cytokine production by human PBMCs (pg/ml). a) IL-6, b) IFN-γ, c) IL-13, d) IL-10, e) IL-12p70, f) MCP-1, g) IL-8, h) IL17α, i) IL-α, j) IL-9, k) IL-2, l) IL-4, m) IL-5, n) MIP-1α, o) MIP-1β, p) TNF-α.

FIG. 10 (a-p) is a panel of graphs that show the effect of *B. wexlarae*) on cytokine concentration (pg/ml) either alone or in combination with Epv 8 (*E. faecalis*) on cytokine production by human PBMCs (pg/ml). a) IL-6, b) IFN-γ, c) IL-13, d) IL-10, e) IL-12p70, f) MCP-1, g) IL-8, h) IL17α, i) IL-α, j) IL-9, k) IL-2, l) IL-4, m) IL-5, n) MIP-1α, o) MIP-1β, p) TNF-α.

Figure 11B:
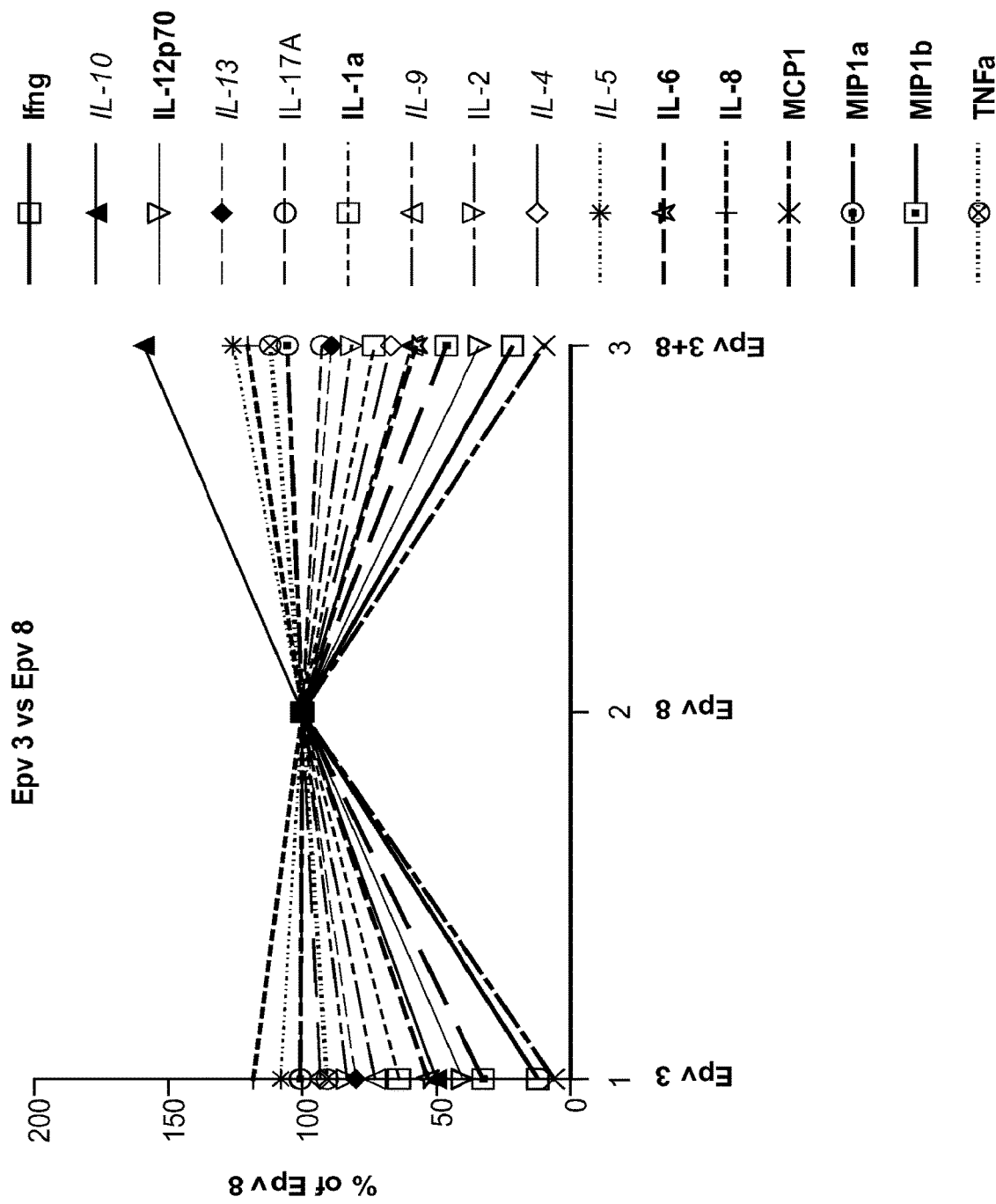
Figure 11C:
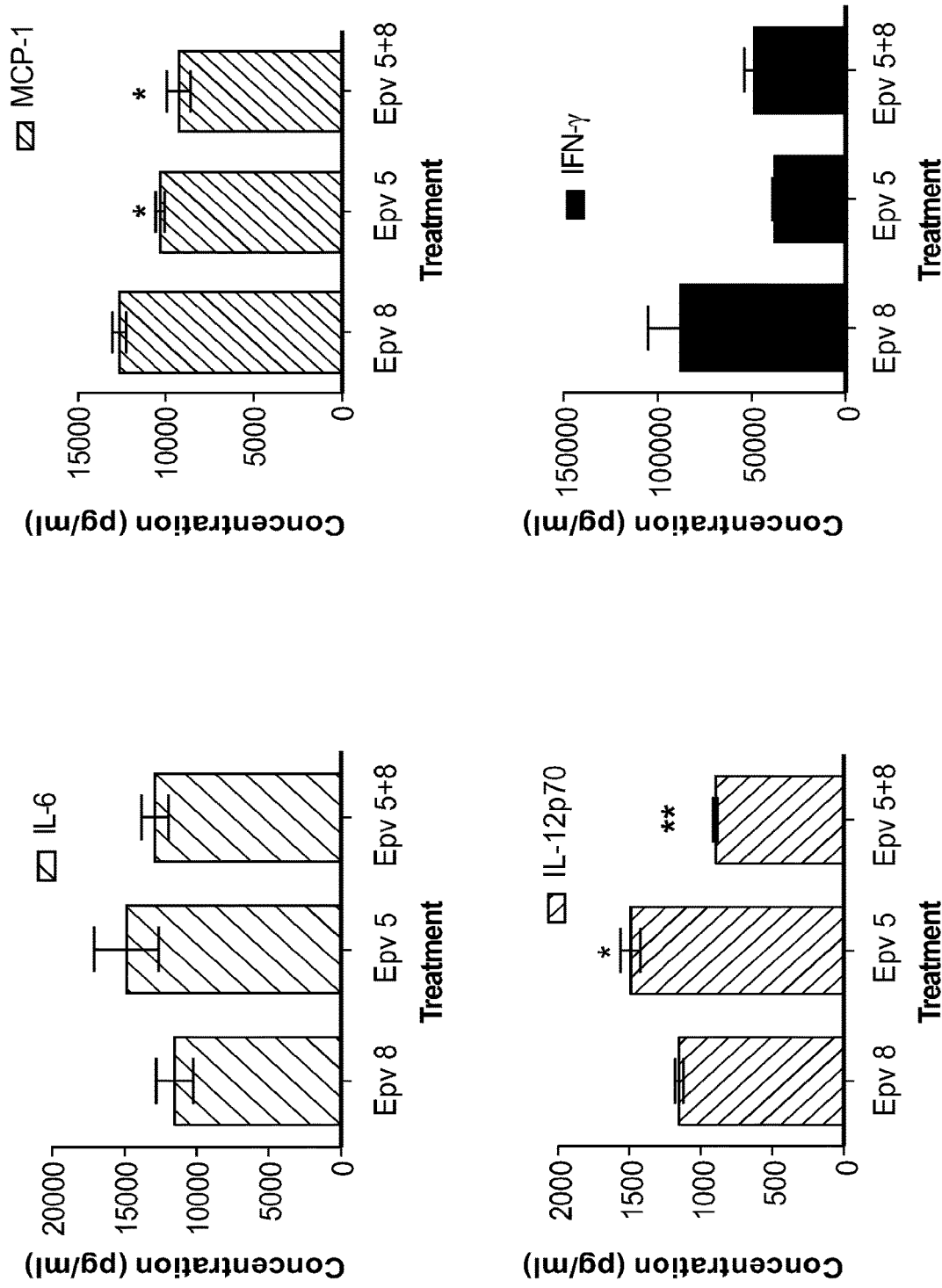
Figure 11D:
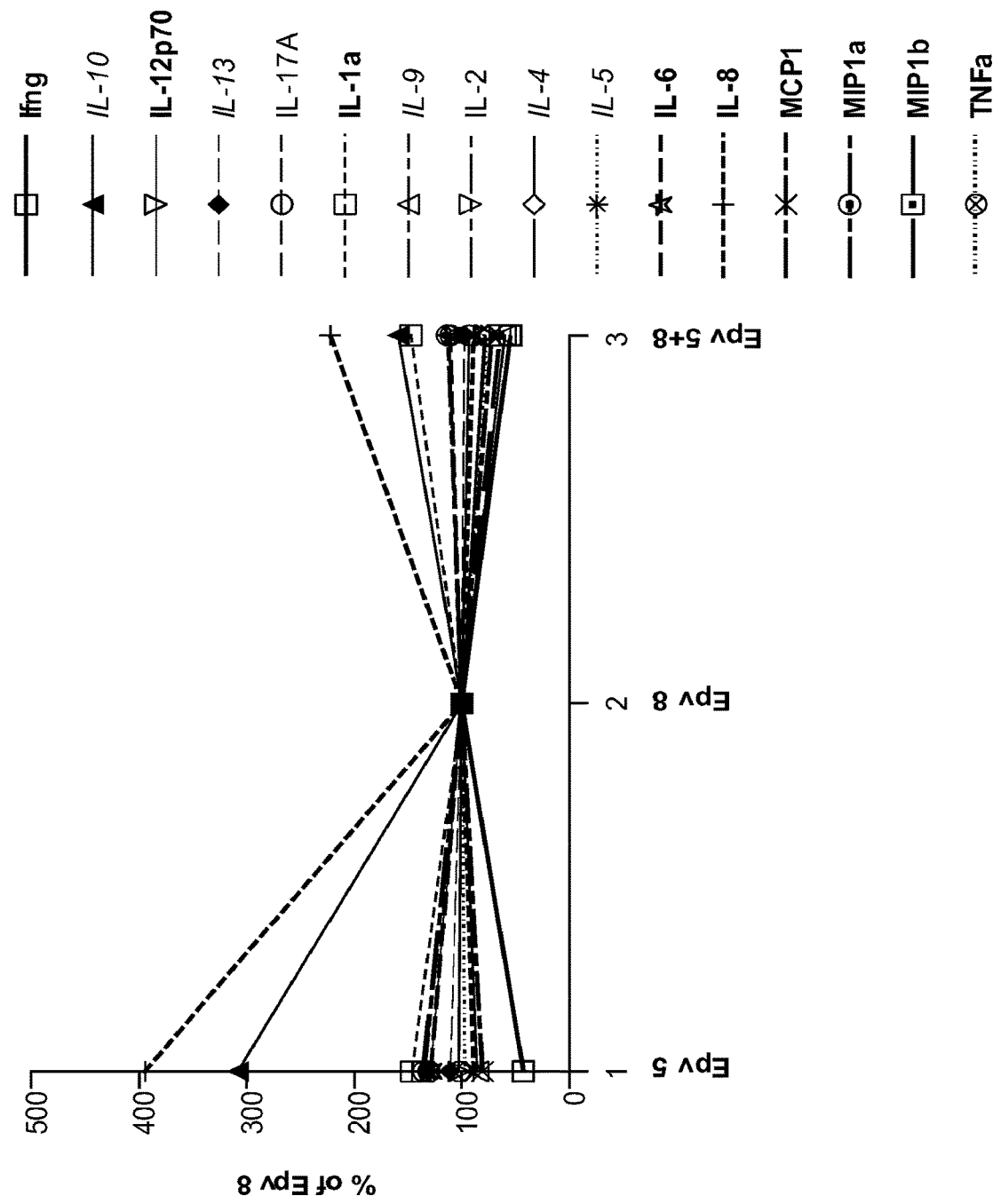

FIG. 11 (a-d) is a panel of graphs showing that (a-b) EPV3 is capable of inducing a desirable anti-inflammatory cytokine profile for treating or preventing GVHD and (c-d) EPV5 induces a suboptimal profile for GVHD.

Figure 12A:
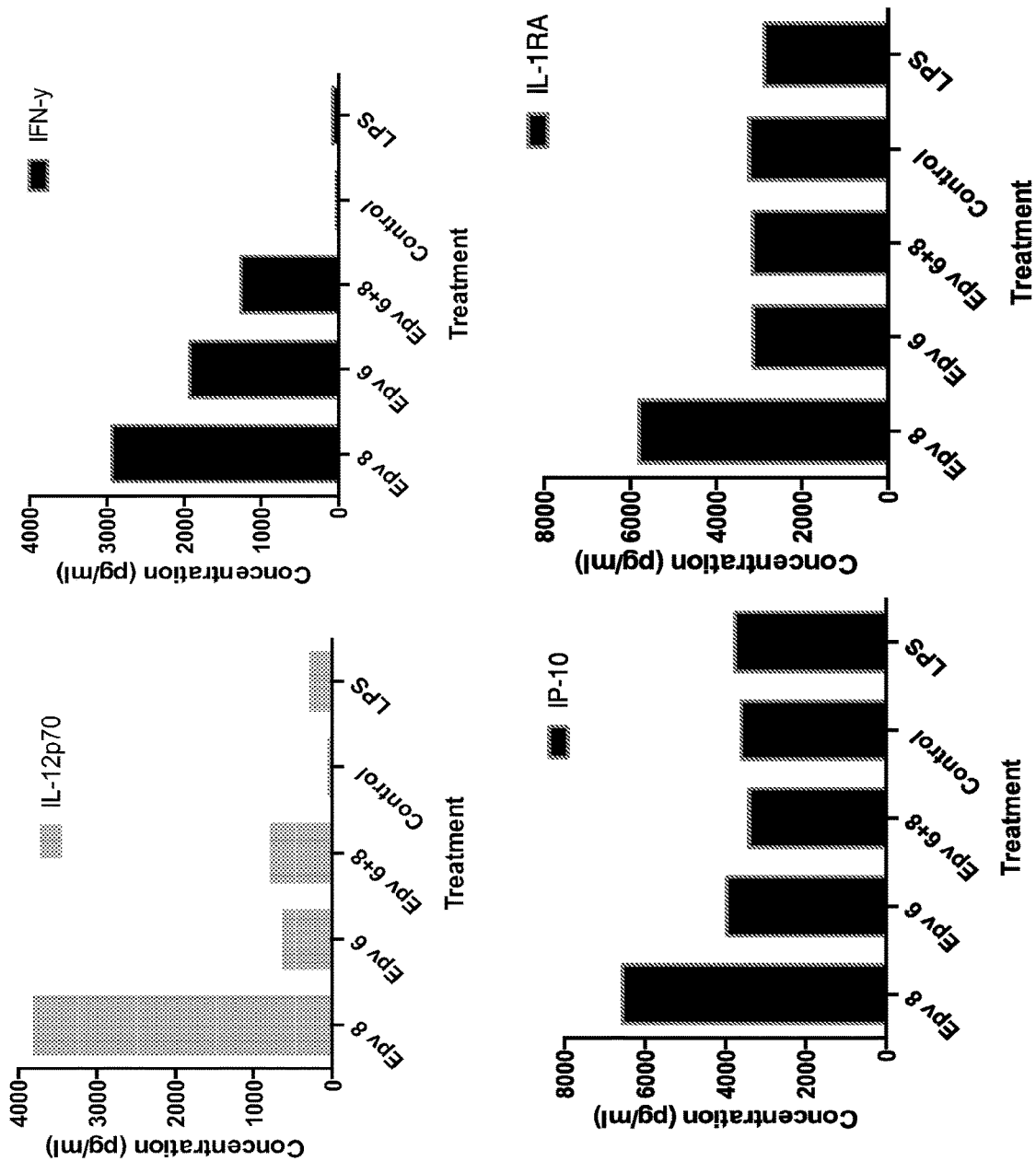
Figure 12B:
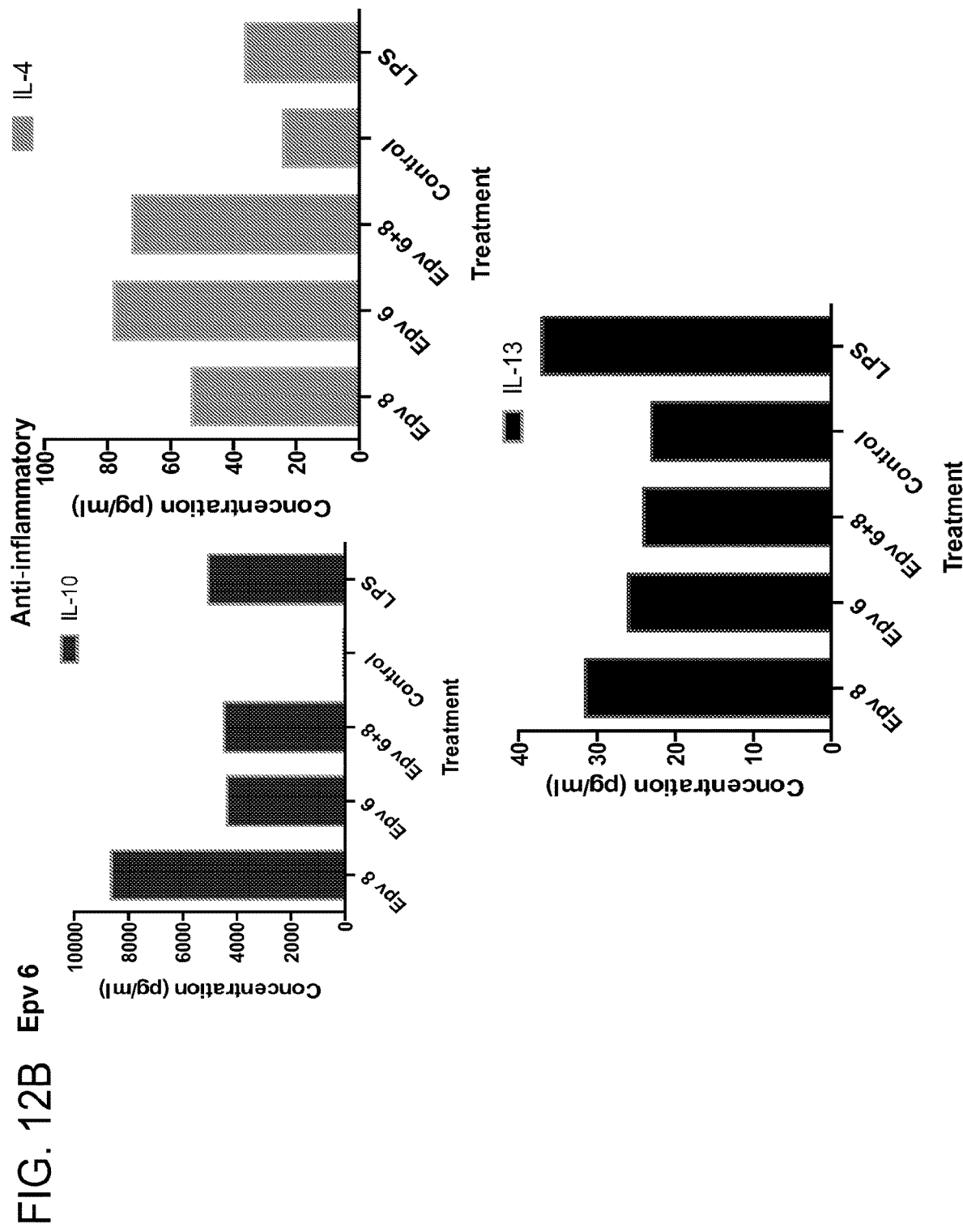

FIG. 12 (a-b) depicts the production of (a) pro-inflammatory (IL-12p70, IFN-γ, IP-10, IL-1RA) and (b) anti-inflammatory (IL-10, IL-4, IL-13) cytokines by human PBMCs following treatment with Epv6 (*Clostridium leptum*).

Figure 13A:
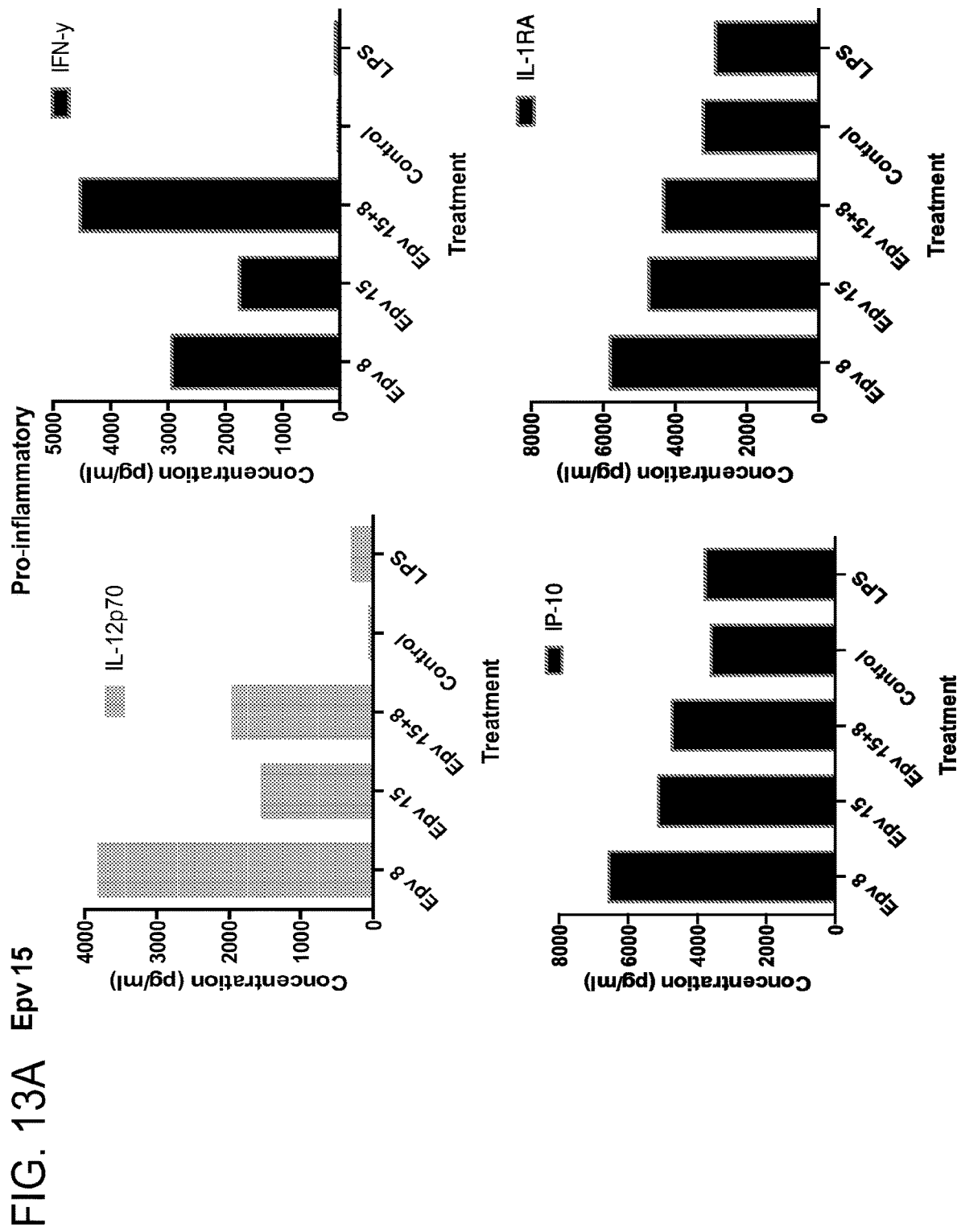
Figure 13B:
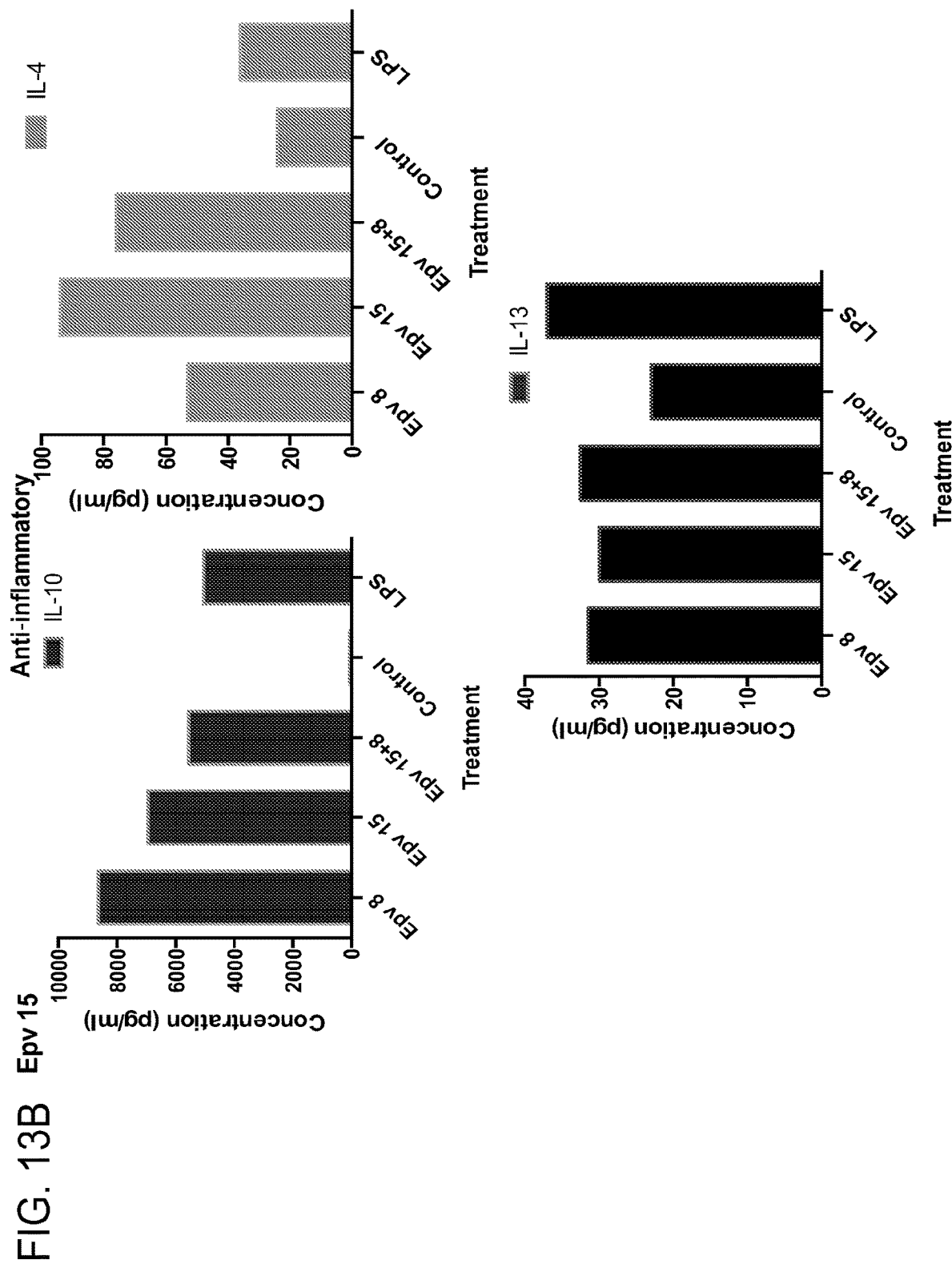

FIG. 13 (a-b) depicts the production of (a) pro-inflammatory (IL-12p70, IFN-γ, IP-10, IL-1RA) and (b) anti-inflammatory (IL-10, IL-4, IL-13) cytokines by human PBMCs following treatment with Epv15 (*Blautia faecis*).

Figure 14B:
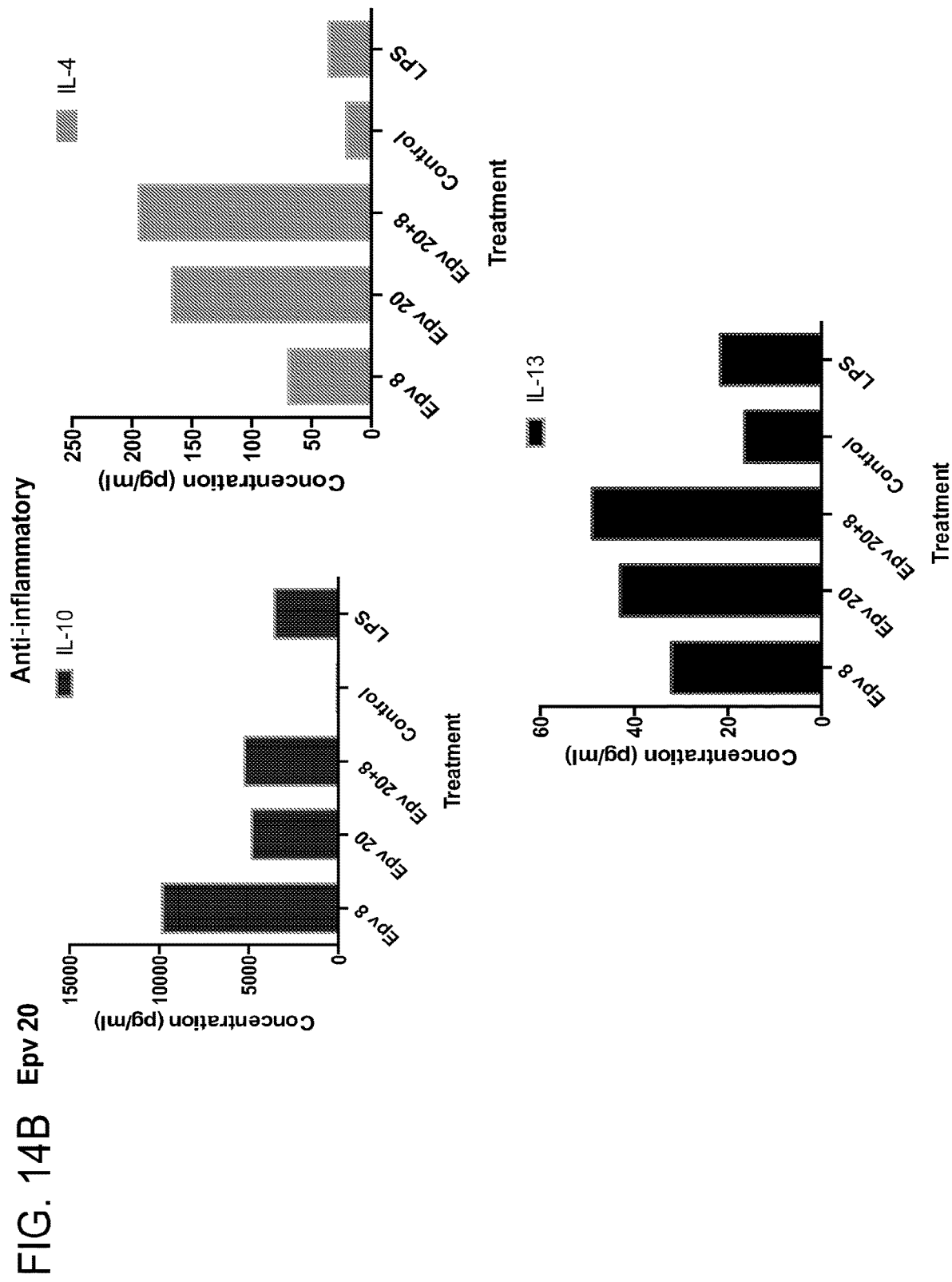

FIG. 14 (a-b) depicts the production of (a) pro-inflammatory (IL-12p70, IFN-γ, IP-10, IL-1RA) and (b) anti-inflammatory (IL-10, IL-4, IL-13) cytokines by human PBMCs following treatment with Epv20 (*Blautia/Ruminococcus obeum* ATCC 29174).

Figure 15A:
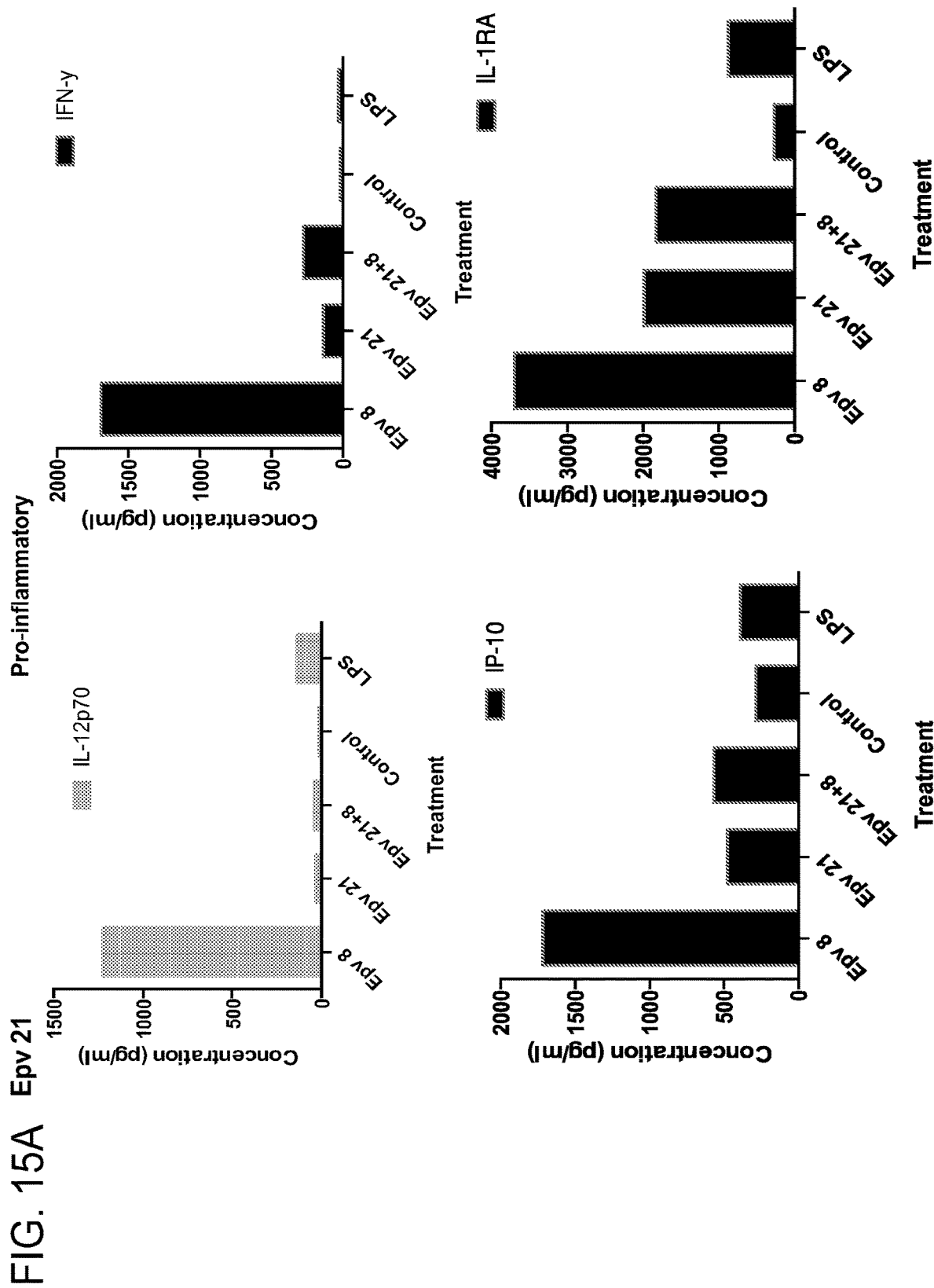

FIG. 15 (a-b) depicts the production of (a) pro-inflammatory (IL-12p70, IFN-γ, IP-10, IL-1RA) and (b) anti-inflammatory (IL-10, IL-4, IL-13) cytokines by human PBMCs following treatment with Epv21 (*Blautia producta* ATCC 27340).

Figure 16A:
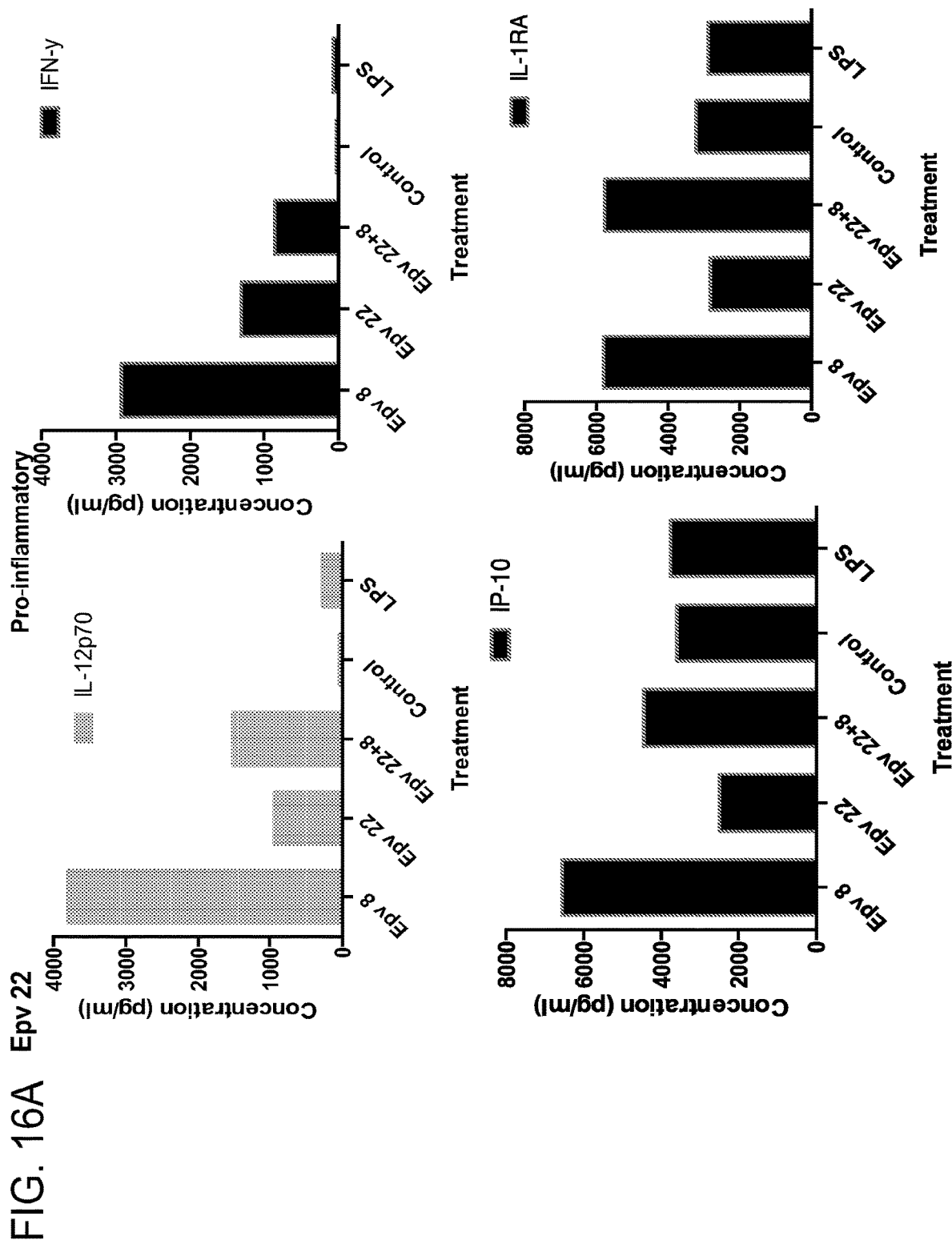

FIG. 16 (a-b) depicts the production of (a) pro-inflammatory (IL-12p70, IFN-γ, IP-10, IL-1RA) and (b) anti-inflammatory (IL-10, IL-4, IL-13) cytokines by human PBMCs following treatment with Epv22 (*Blautia coccoides* ATCC 29236).

Figure 17A:
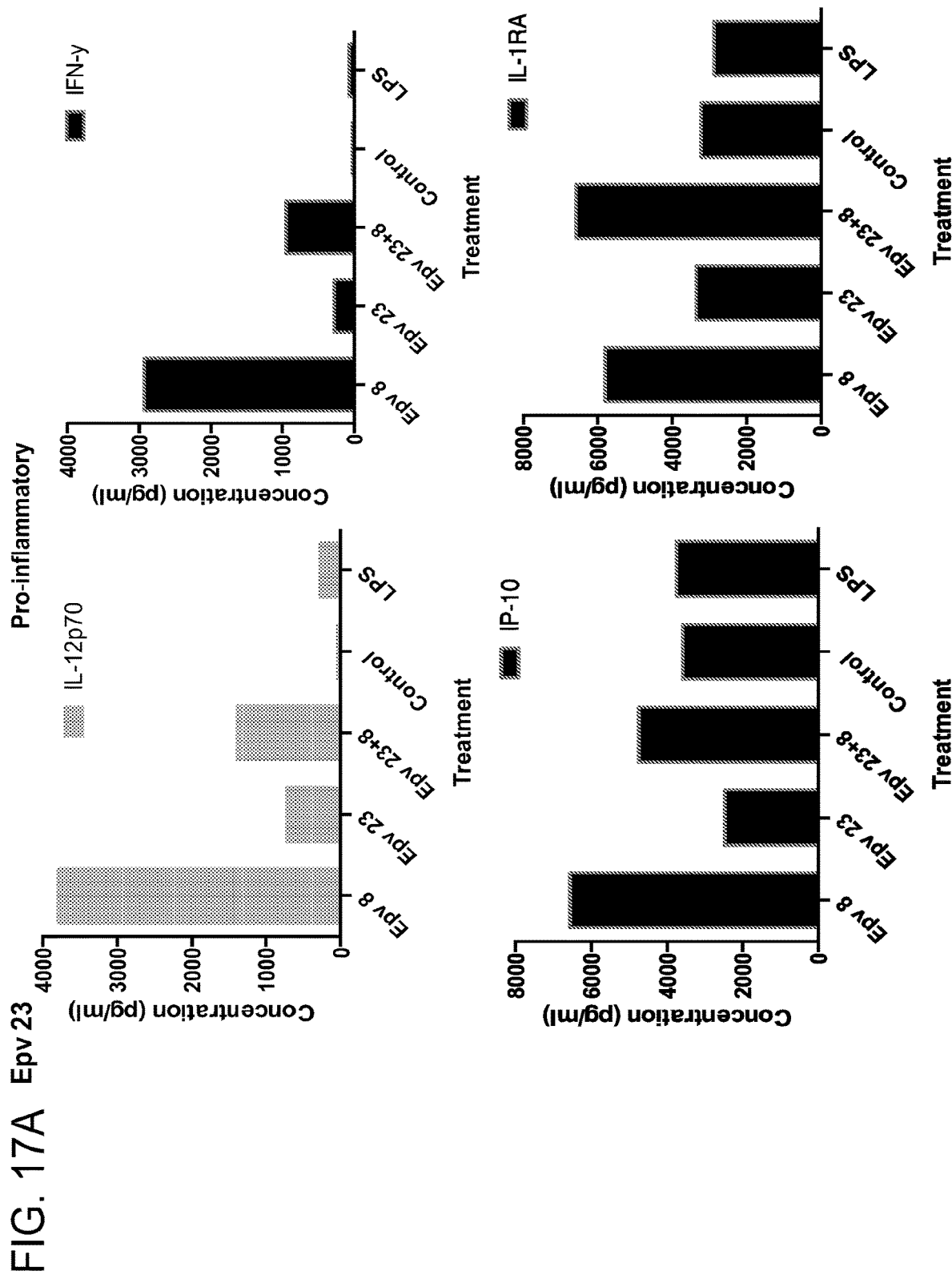

FIG. 17 (a-b) depicts the production of (a) pro-inflammatory (IL-12p70, IFN-γ, IP-10, IL-1RA) and (b) anti-inflammatory (IL-10, IL-4, IL-13) cytokines by human PBMCs following treatment with Epv23 (*Blautia hydrogenotrophica* ATCC BAA-2371).

Figure 18A:
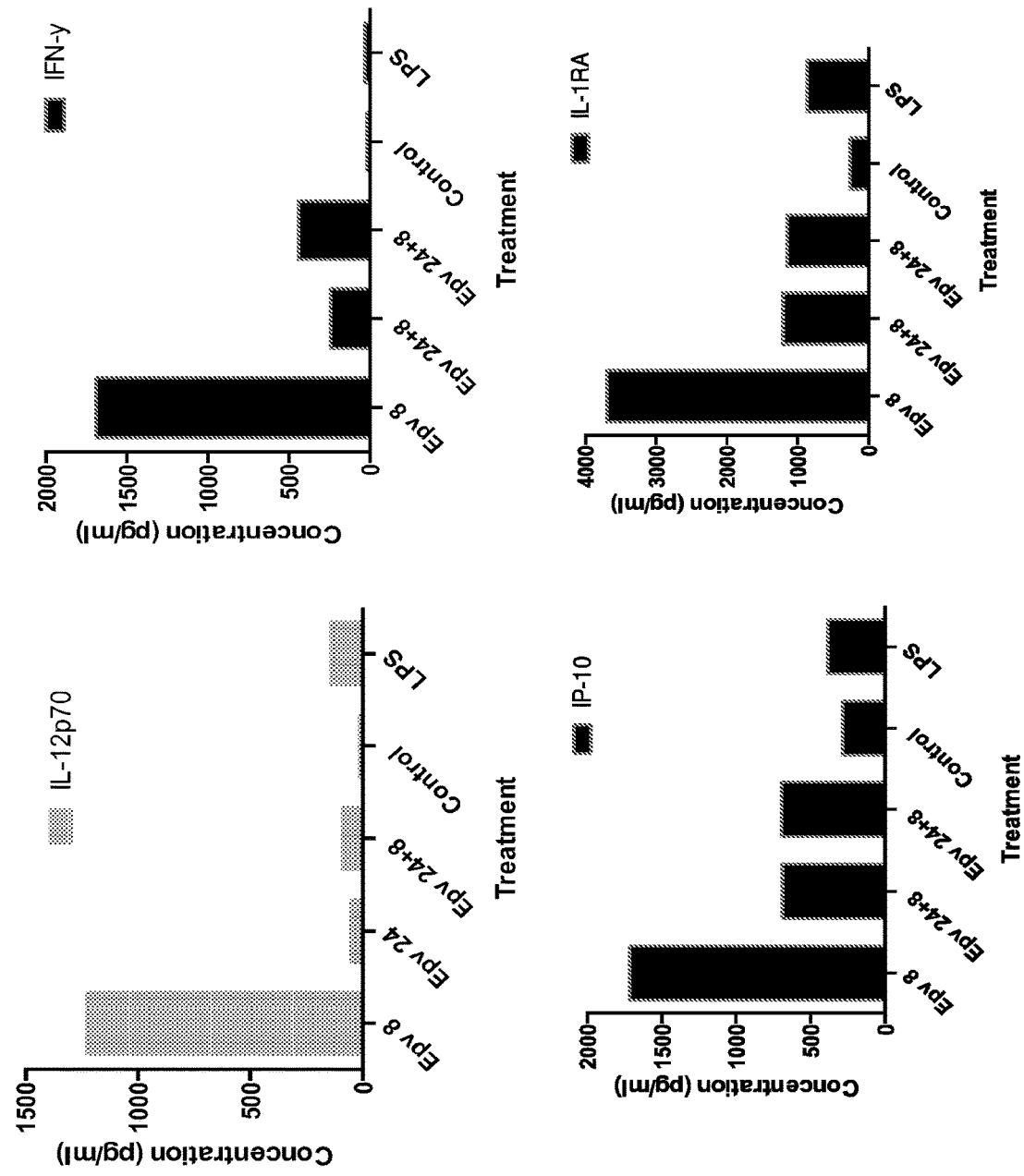
Figure 18B:
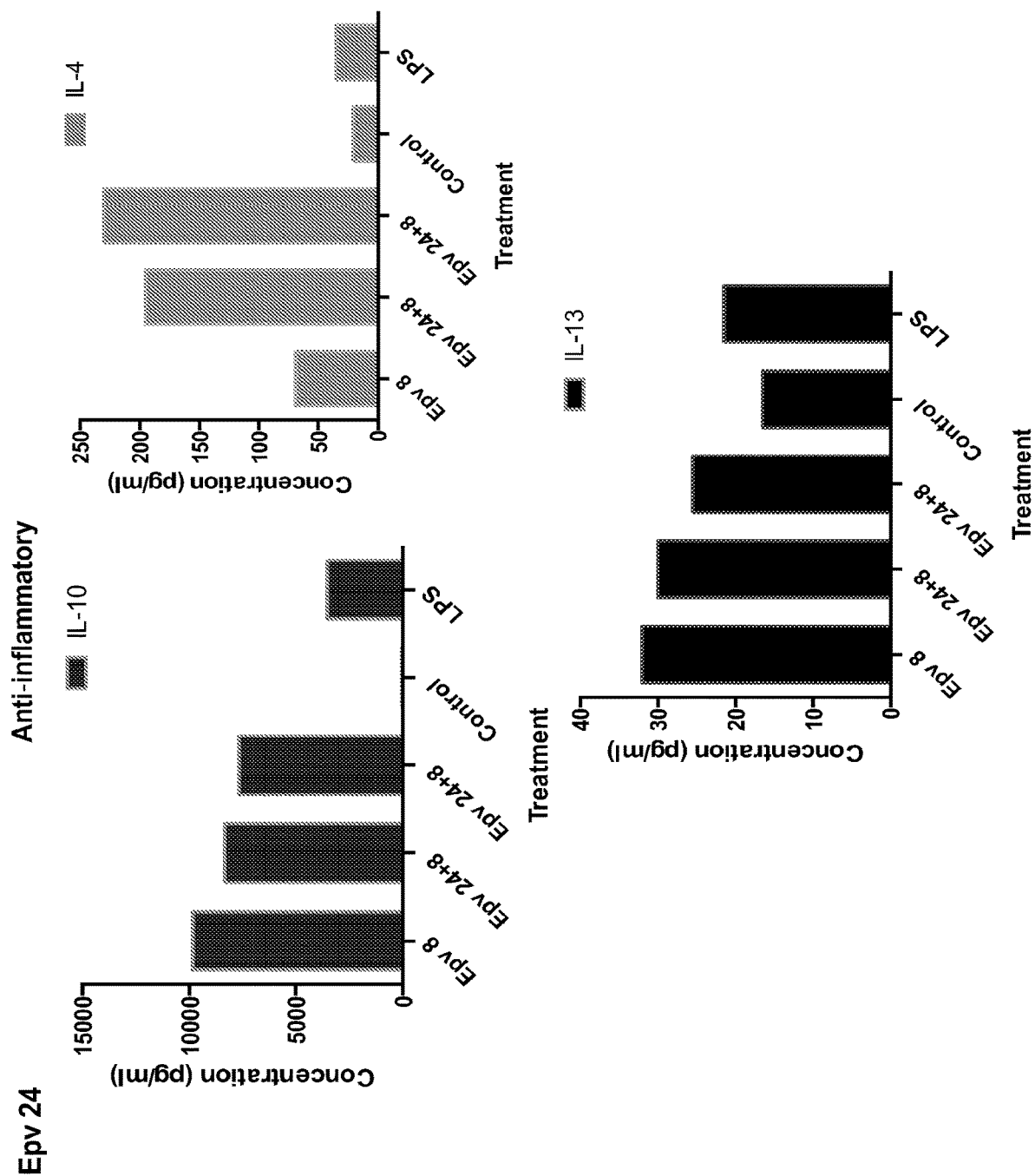

FIG. 18 (a-b) depicts the production of (a) pro-inflammatory (IL-12p70, IFN-γ, IP-10, IL-1RA) and (b) anti-inflammatory (IL-10, IL-4, IL-13) cytokines by human PBMCs following treatment with Epv24 (*Blautia Hansenii* ATCC27752).

Figure 19A:
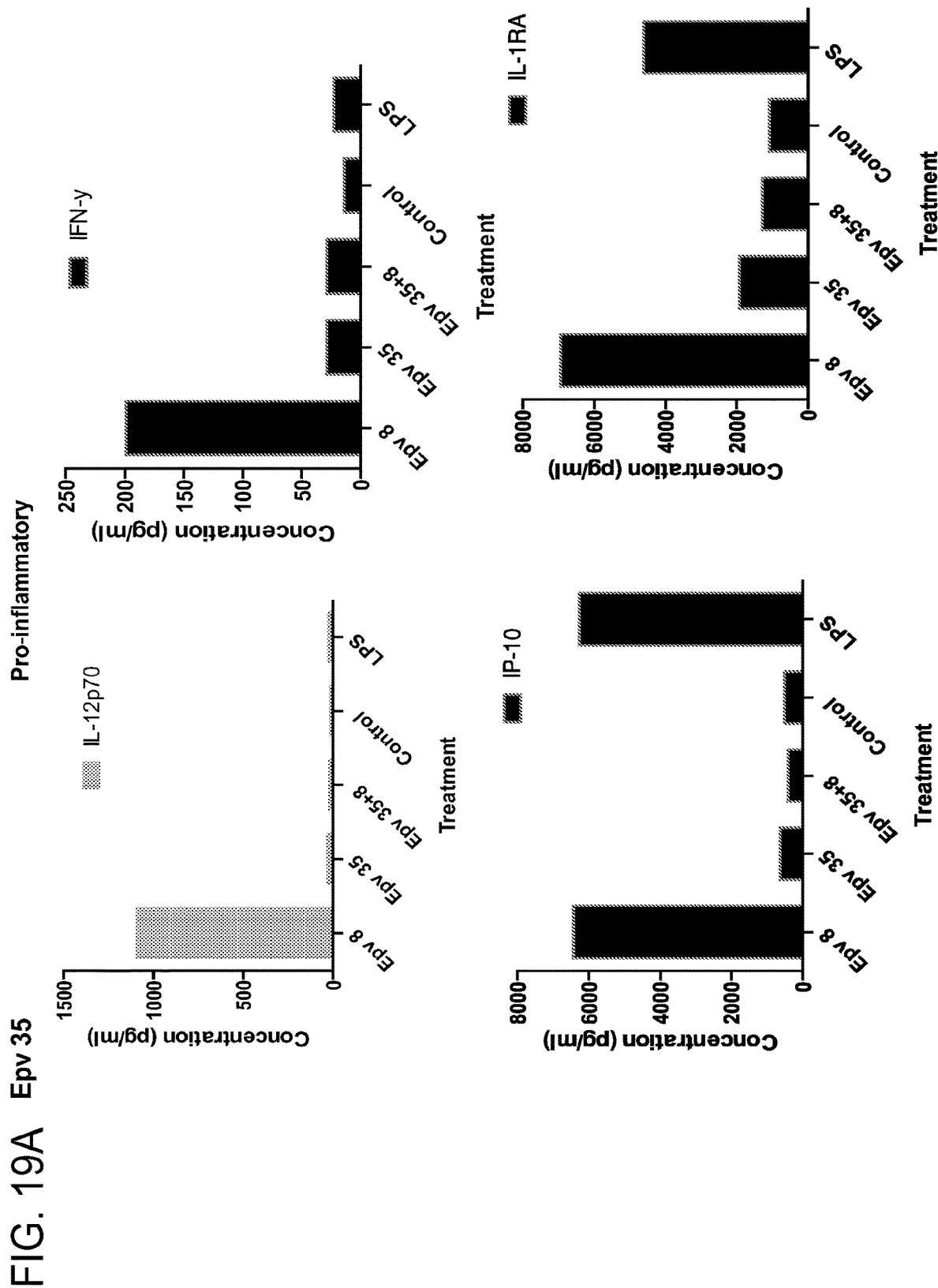

FIG. 19 (a-b) depicts the production of (a) pro-inflammatory (IL-12p70, IFN-γ, IP-10, IL-1RA) and (b) anti-inflammatory (IL-10, IL-4, IL-13) cytokines by human PBMCs following treatment with Epv35 (*Eubacterium rectale*).

FIG. 20 (a-b) depicts the production of (a) pro-inflammatory (IL-12p70, IFN-γ, IP-10, IL-1RA) and (b) anti-inflammatory (IL-10, IL-4, IL-13) cytokines by human PBMCs following treatment with Epv47 (previously uncultured *Blautia*, similar to GQ898099_s S1-5).

FIG. 21 (a-b) depicts the production of (a) pro-inflammatory (IL-12p70, IFN-γ, IP-10, IL-1RA) and (b) anti-inflammatory (IL-10, IL-4, IL-13) cytokines by human PBMCs following treatment with Epv51 (previously uncultured *Blautia*, similar to SJTU_C_14_16).

Figure 22A:
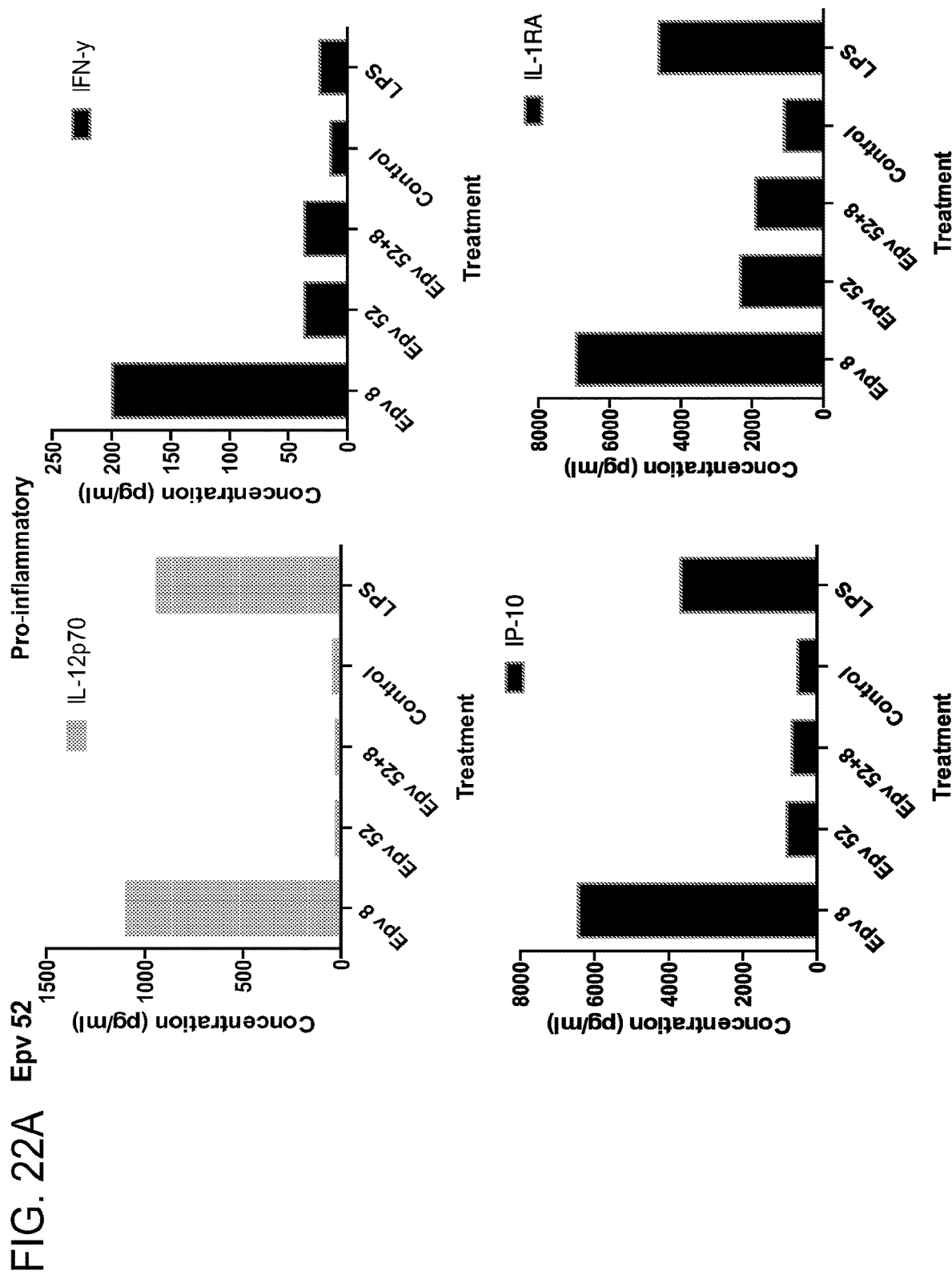

FIG. 22 (a-b) depicts the production of (a) pro-inflammatory (IL-12p70, IFN-γ, IP-10, IL-1RA) and (b) anti-inflammatory (IL-10, IL-4, IL-13) cytokines by human PBMCs following treatment with Epv52 (*Blautia wexlerae* (SJTU_B_09_77)).

FIG. 23 (a-b) depicts the production of (a) pro-inflammatory (IL-12p70, IFN-γ, IP-10, IL-1RA) and (b) anti-inflammatory (IL-10, IL-4, IL-13) cytokines by human PBMCs following treatment with Epv54 (*Blautia luti* ELU0087-T13-S-NI_000247).

Figure 24A:
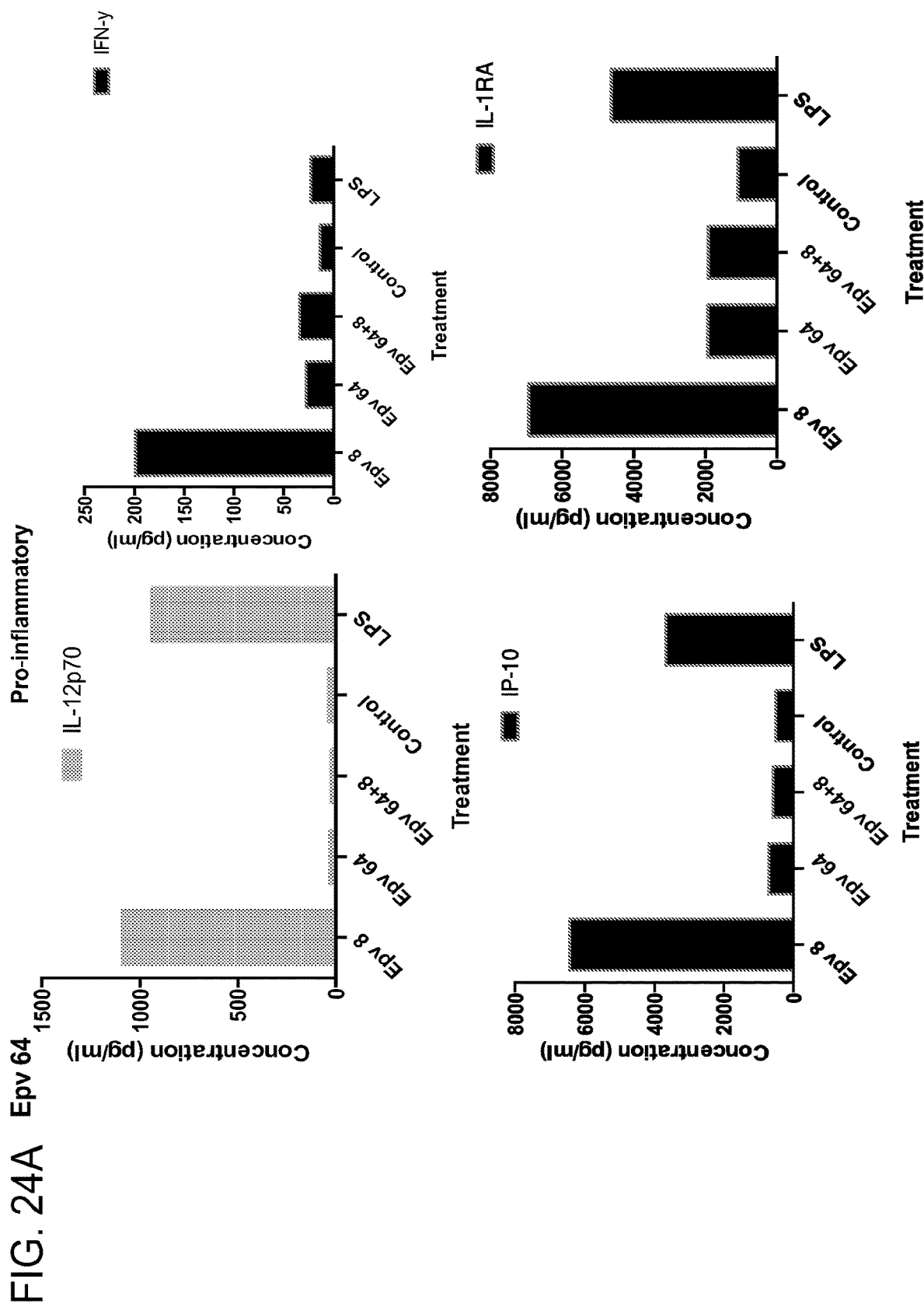
Figure 24B:
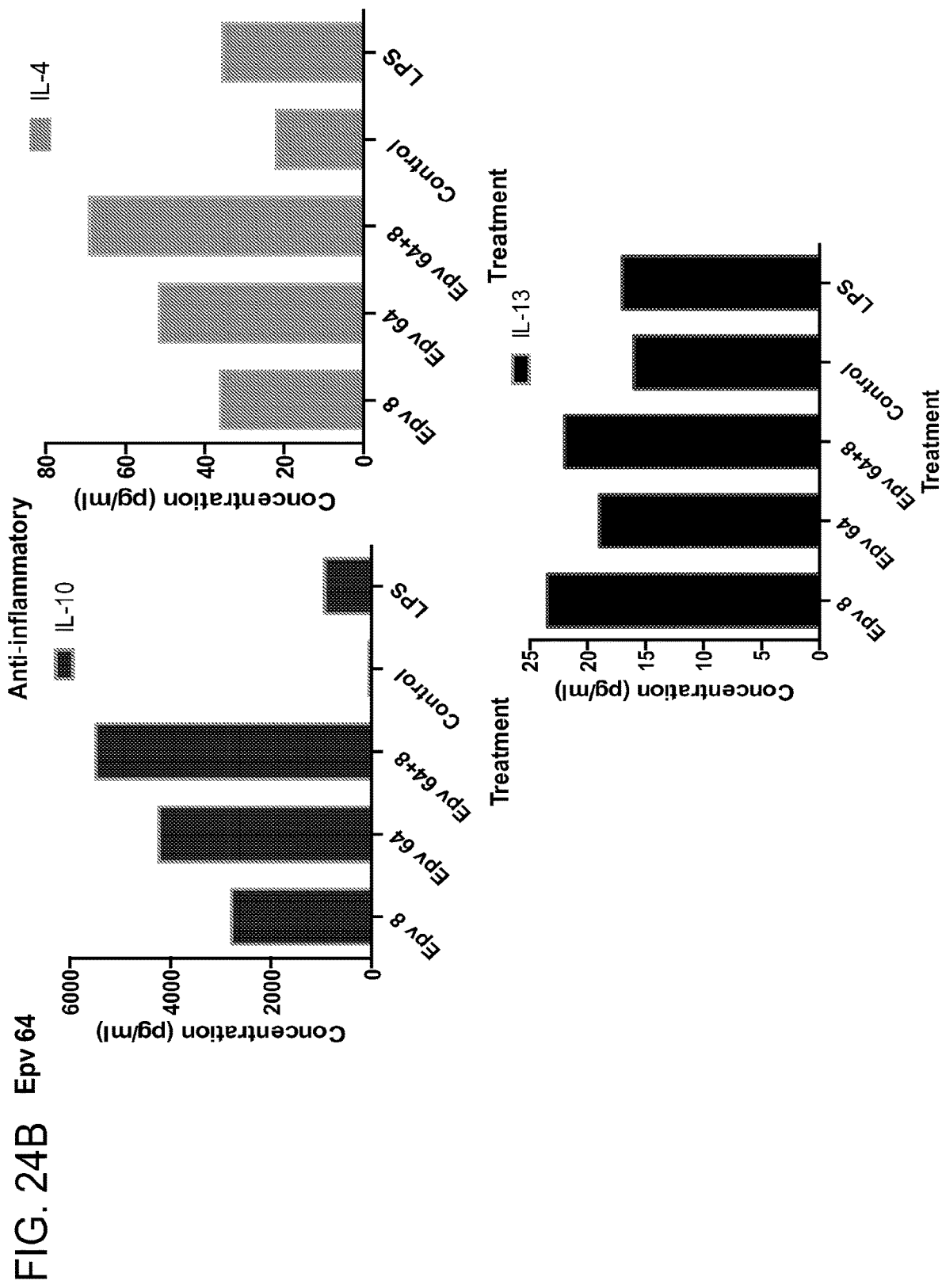

FIG. 24 (a-b) depicts the production of (a) pro-inflammatory (IL-12p70, IFN-γ, IP-10, IL-1RA) and (b) anti-inflammatory (IL-10, IL-4, IL-13) cytokines by human PBMCs following treatment with Epv64 (*Blautia wexlerae* WAL 14507).

Figure 25A:
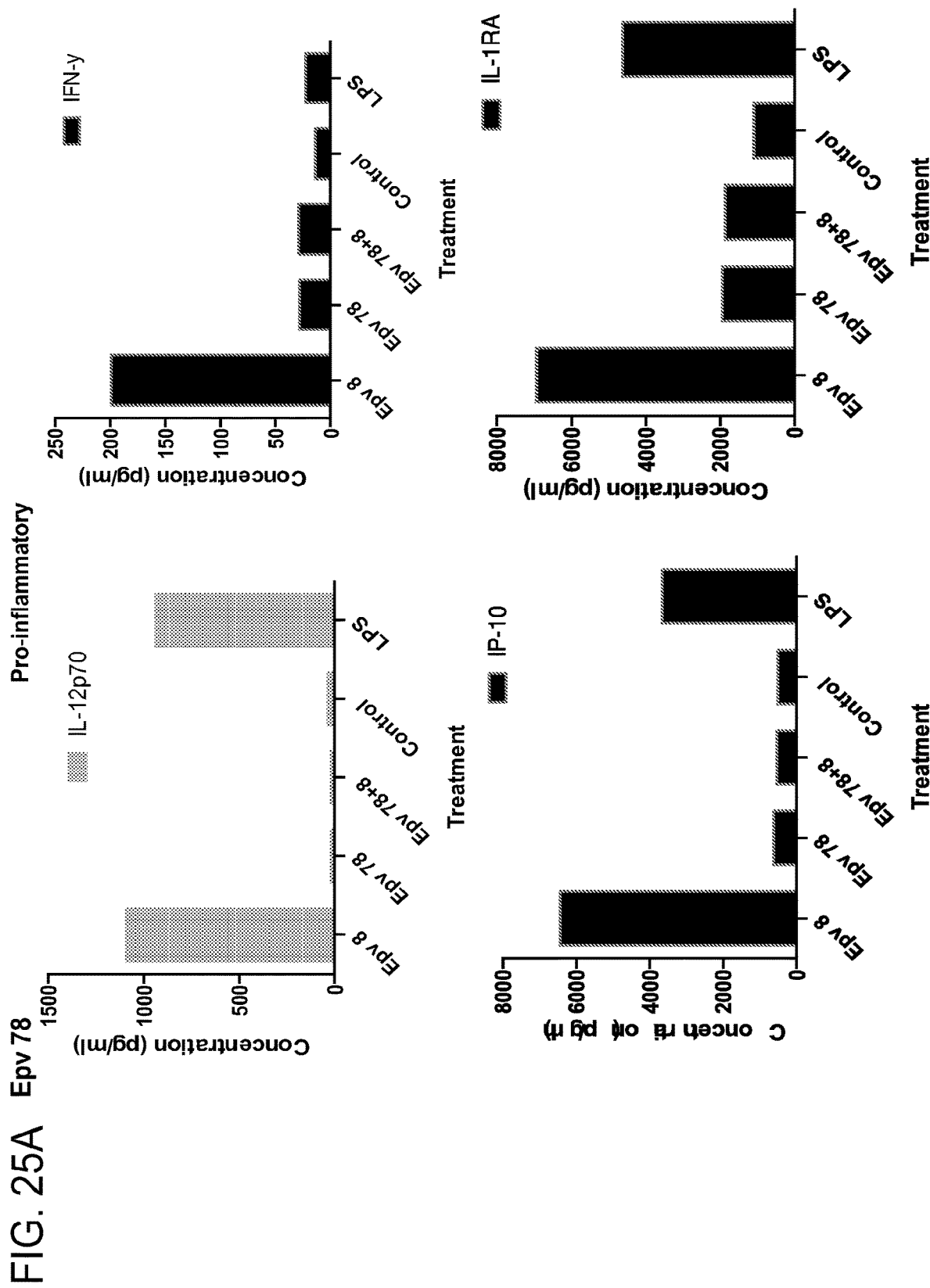
Figure 25B:
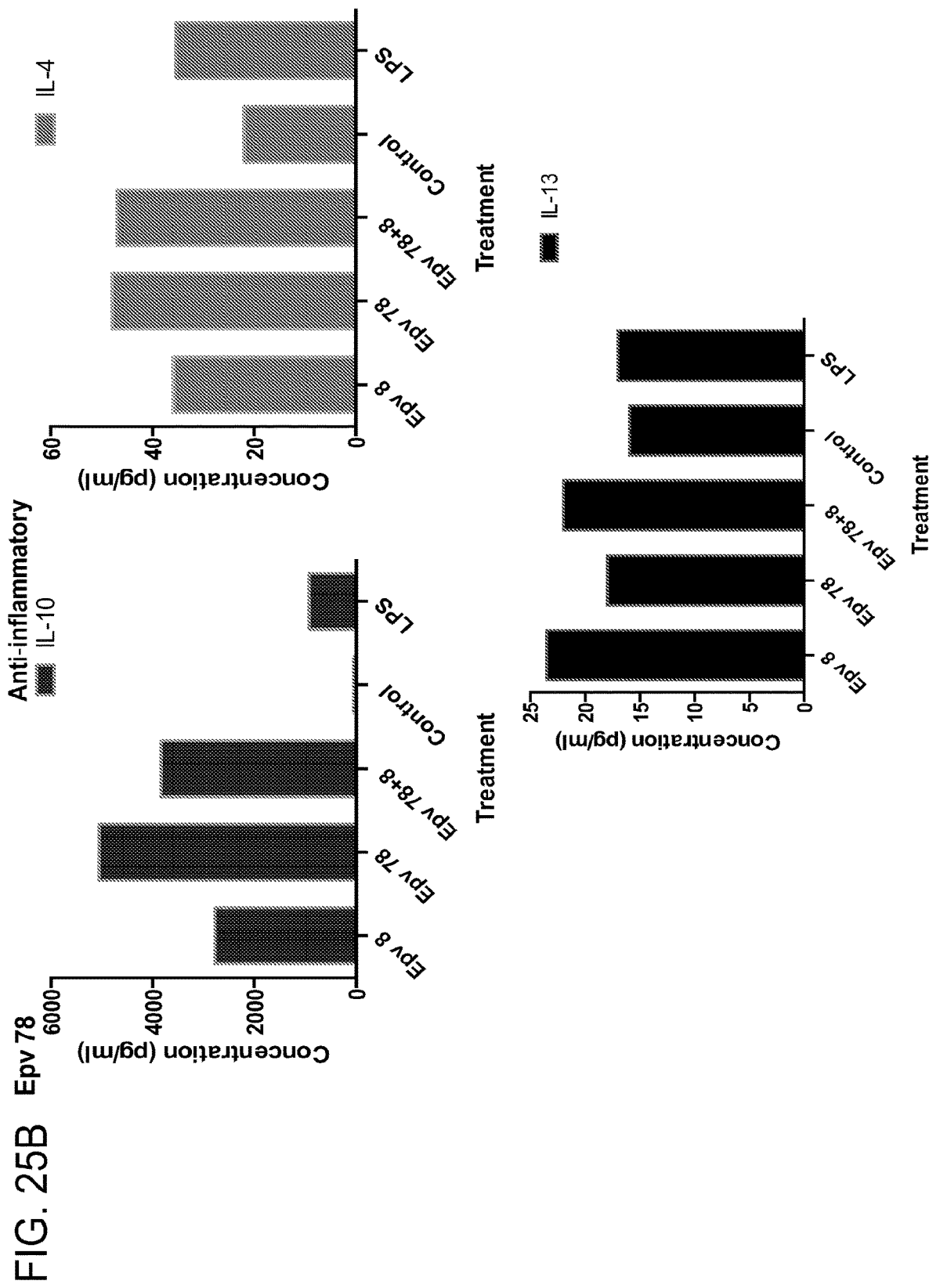

FIG. 25 (a-b) depicts the production of (a) pro-inflammatory (IL-12p70, IFN-γ, IP-10, IL-1RA) and (b) anti-inflammatory (IL-10, IL-4, IL-13) cytokines by human PBMCs following treatment with Epv78 (*Blautia obeum*).

Figure 26B:
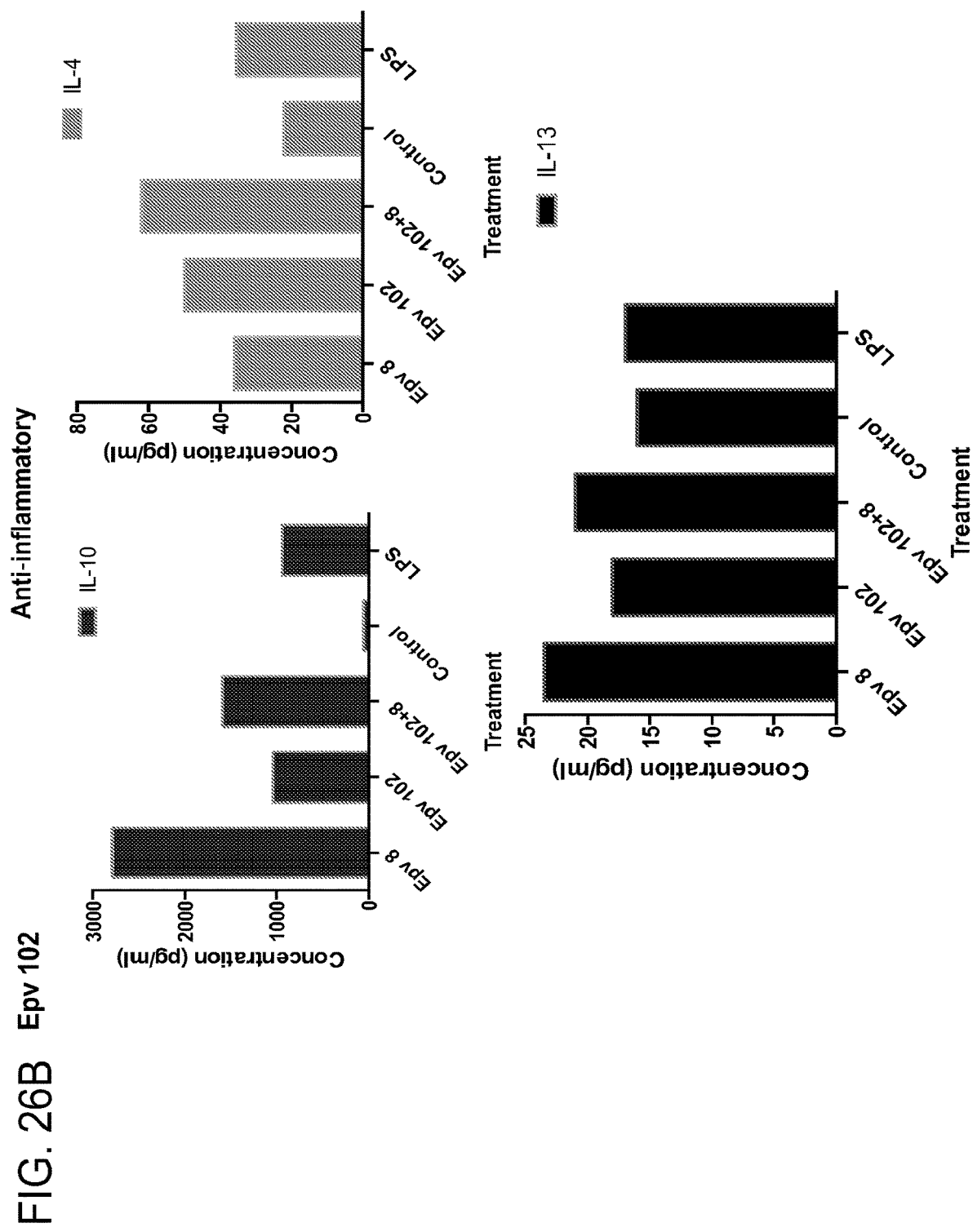
Figure 28A:
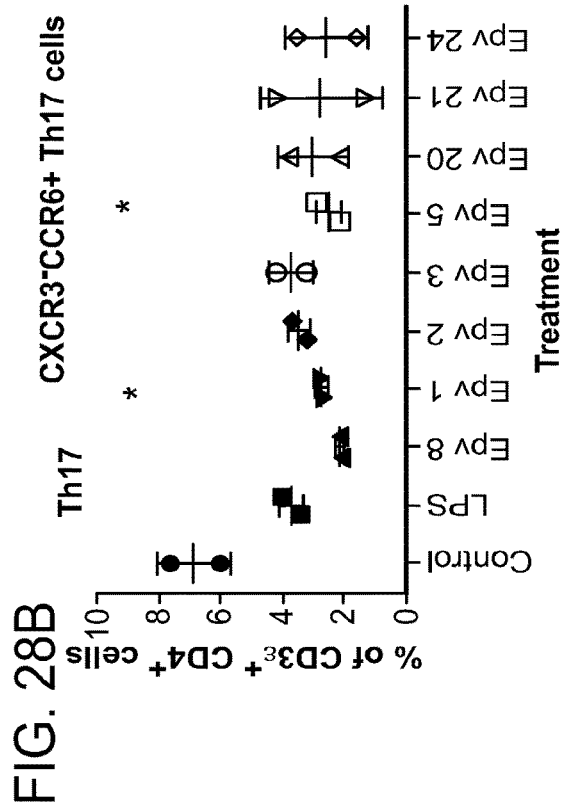
Figure 28B:
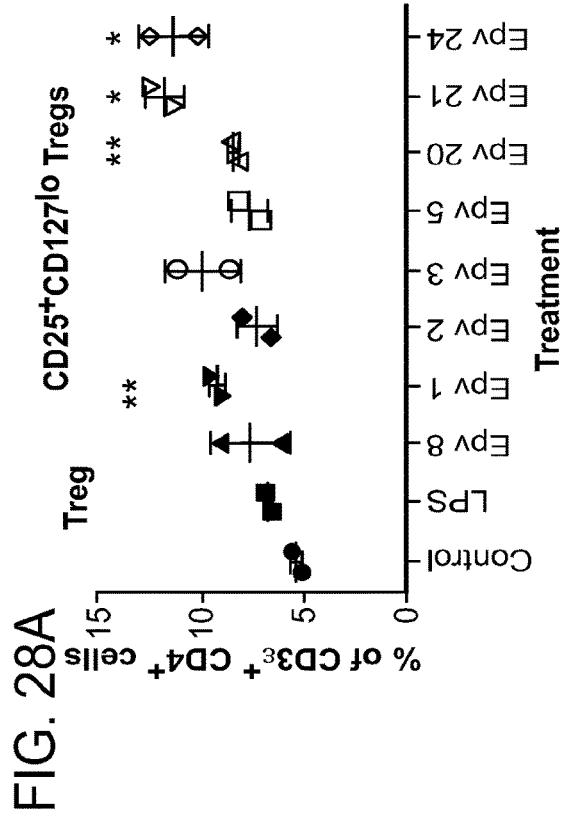
Figure 28C:
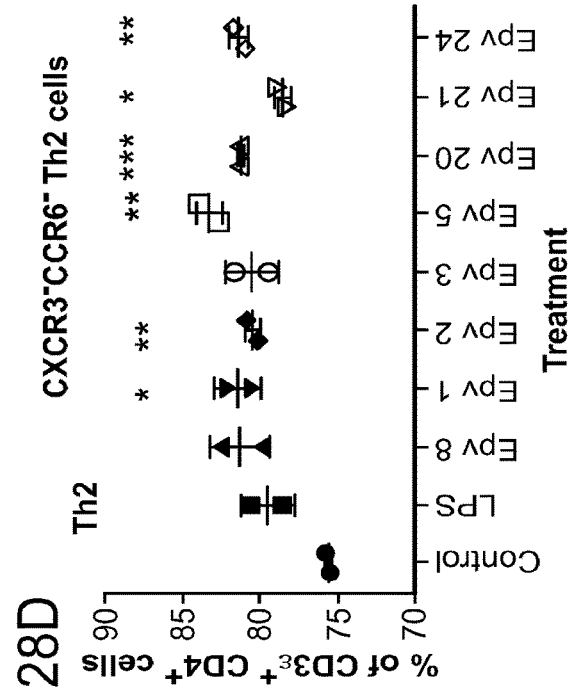
Figure 28D:
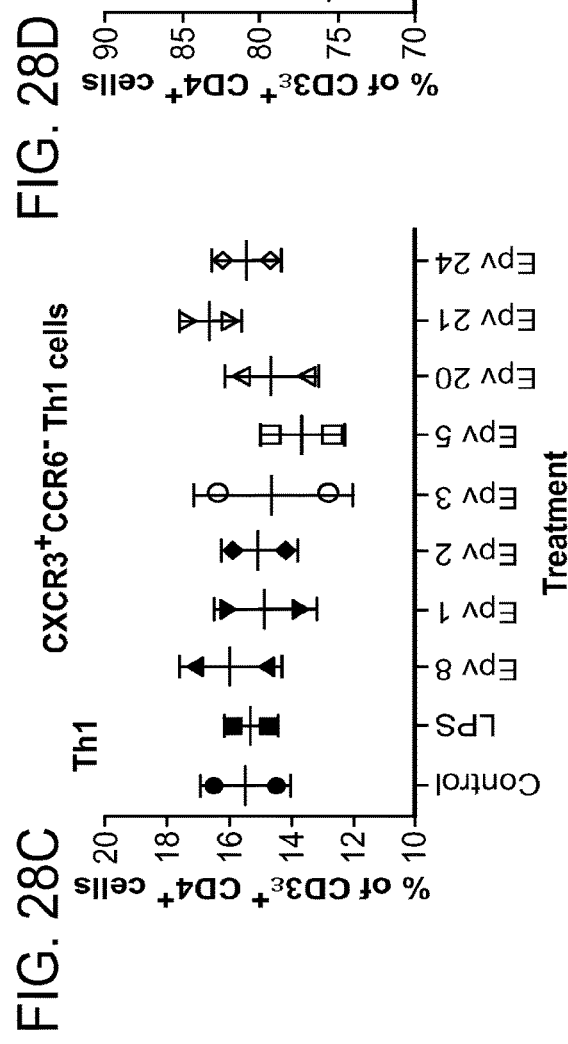

FIG. 26 (a-b) depicts the production of (a) pro-inflammatory (IL-12p70, IFN-γ, IP-10, IL-1RA) and (b) anti-inflammatory (IL-10, IL-4, IL-13) cytokines by human PBMCs following treatment with Epv102 (*Ruminococcus gnavus*).

FIG. 27 (a-b) depicts the production of (a) pro-inflammatory (IL-12p70, IFN-γ, IP-10, IL-1RA) and (b) anti-inflammatory (IL-10, IL-4, IL-13) cytokines by human PBMCs following treatment with Epv114 (*Blautia luti* (BlnIX)).

FIG. 28 (a-d) presents results from flow cytometry analysis of T cell populations in human PBMCs incubated in the presence of various commensal bacteria, determined using flow cytometry. A) Proportion of Treg cells(CD25$^+$ CD127$^{lo}$; B) Proportion of Th17 cells (CXCR3$^-$CCR6$^+$); C) Proportion of Th1 cells (CXCR3$^+$CCR6$^-$); D) Proportion of Th2 cells (CXCR3$^-$CCR6$^-$). Bacterial strains are as follows: Epv 1: *R. gnavus*; Epv 3: *B. luti*; Epv 2: *E. rectale*; Epv 5: *B. wexlerae*; Epv. 8: *E. faecalis*; Epv 20: *B. obeum*; Epv 21: *B. producta*; Epv 24: *B. hansenii*. The results are shown as percent (%) of CD3ε$^+$CD4$^+$ cells.

FIG. 29 (a-u) presents the preferred carbon sources utilized by various commensal bacteria. (a) *R. gnavus*; (b) *E.* rectale; (c) *C. leptum*; (d) *B. luti*; (e) *B. wexlerae*; (f) *B. faecis*; (g) *B. obeum*; (h) *B. producta*; (i) *B. coccoides*; (j) *B. hydrogenotrophica*; (k) *B. hansenii*; (l) *B. luti* Blnl X; (m) *B. luti* ELU; (n) *R. gnavus*; (o) *B. faecis*; (p) *R. torques*; (q) *B. wexlerae* WAL14507; (r) *B. wexlerae* SJTU; (s) SJTUI4I6; (t) GQ8980099; (u) *E. rectale*.

Figure 30:
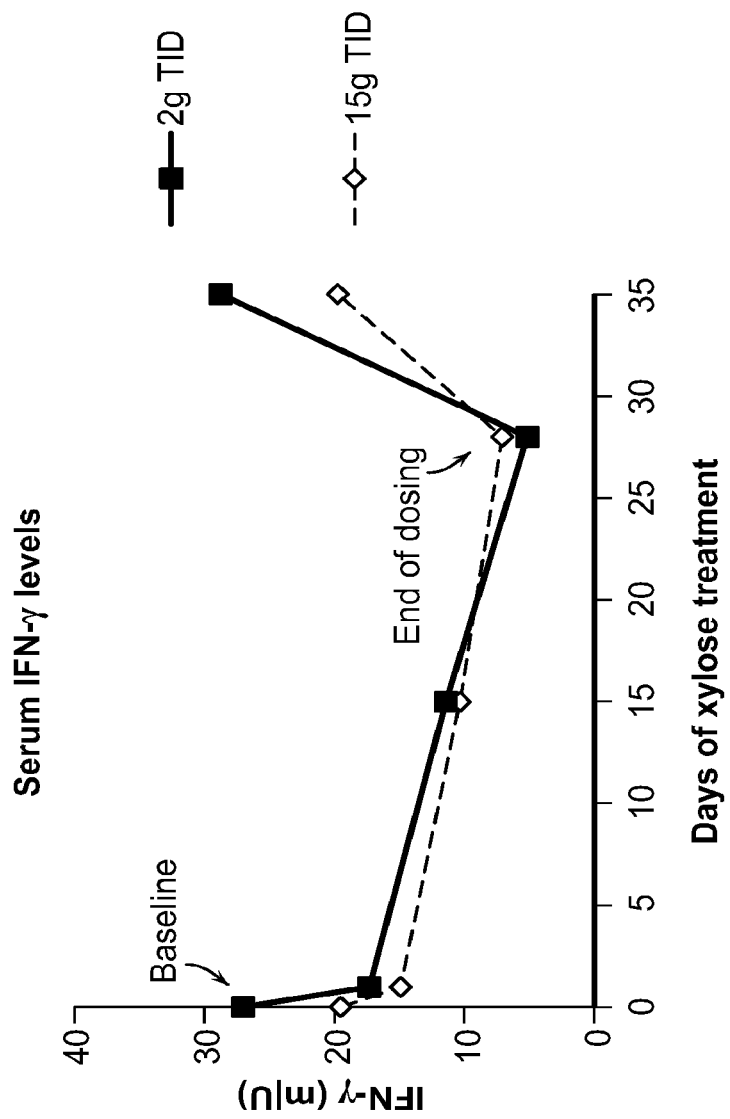

FIG. 30 graphically depicts levels of serum IFNγ before, during, and after treatment with a prebiotic formulation containing xylose.

Figure 31:
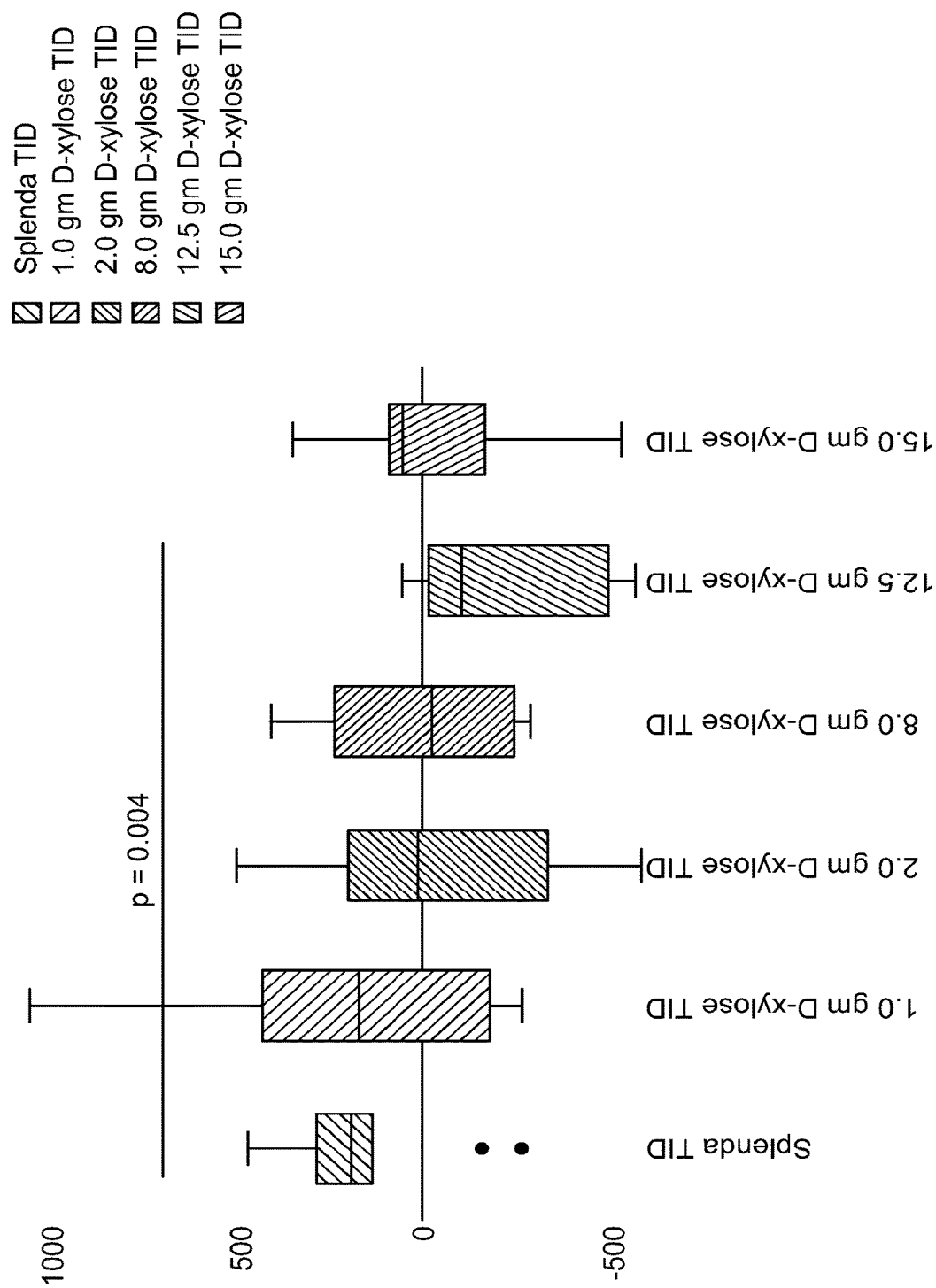

FIG. 31 is a graph that shows the change in Chao1 diversity (indicator of community richness) over time in subjects administered xylose three times per day (TID) at 1, 2, 8, 12.5 or 15 grams.

FIG. 32 depicts the impact of oral vancomycin on the microbiome of the gut and the vagina, by principal component analysis (PCA).

DETAILED DESCRIPTION

I. Overview

Disclosed herein are therapeutic compositions containing bacterial entities (e.g., non-pathogenic germination-competent bacterial entities), fungal entities, and/or prebiotics for the prevention, control, and treatment of immune and inflammatory diseases, disorders and conditions, and for general nutritional health. These compositions are advantageous in being suitable for safe administration to humans and other mammalian subjects and are efficacious in treating or preventing numerous immune and inflammatory diseases and gastrointestinal diseases, disorders and conditions associated with a dysbiosis.

While spore-based compositions are known, these are generally prepared according to various techniques such as lyophilization or spray-drying of liquid bacterial cultures, resulting in poor efficacy, instability, substantial variability and lack of adequate safety and efficacy.

It has now been found that populations of bacterial entities can be obtained from biological materials obtained from mammalian subjects, including humans. These populations are formulated into compositions as provided herein, and can be administered to mammalian subjects in accordance with the methods described herein.

The microbes that inhabit the human gastrointestinal tract, skin, lungs, vagina, and other niches are starting to be understood and appreciated for their roles in human health and disease (e.g. see Human Microbiome Project Consortium 2012, Structure, function, and diversity of the healthy human microbiome. Nature 486(7402):207-14). Aspects of the invention are based, in part, on the realization that, although autoimmune and inflammatory diseases are often attributed to genetic mutations, these conditions are also influenced by microbes. It is also appreciated that, because microbes not only interact with the host but with one another, the immunomodulatory behavior of microbes can depend on relationships between microbes. For example, a microbial network in a given niche may comprise diverse microbes that all accomplish one or more of the same functions, or may instead comprise diverse microbes that all individually contribute to accomplish one or more functions. In another example, microbes in a given niche may compete with one another for nutrients or space.

Microbes may influence the risk, progression, or treatment efficacy of an autoimmune or inflammatory disease. In certain aspects, microbes play a role in the prevention of an autoimmune or inflammatory disease or in the suppression of an innate or adaptive immune response. Conversely, in certain aspects, microbes may stimulate an inflammatory immune response and thereby contribute to, increase the risk of, or worsen the symptoms of an autoimmune or inflammatory disease. In certain aspects, some microbes may be associated with lower disease severity or mortality.

Accordingly, disclosed herein are compositions and methods for the prevention and/or treatment of disorders associated with disruptions of the systemic microbiome, e.g., autoimmune and inflammatory diseases, in human subjects.

II. Definitions

As used in the specification and the appended claims, the singular forms "a," "an," and "the" include plural referents unless the context clearly dictates otherwise. Thus, for example, "a compound" includes mixtures of compounds.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, jper the practice in the art. Alternatively, "about" can mean a range of up to 20%, or up to 10%, or up to 5%, or up to 1% of a given value. Alternatively, particularly with respect to biological systems or processes, the term can mean within an order of magnitude, or within 5-fold, or within 2-fold, of a value.

As used herein, the term "purified bacterial preparation" refers to a preparation that includes "isolated" bacteria or bacteria that have been separated from at least one associated substance found in a source material or any material associated with the bacteria in any process used to produce the preparation.

A "bacterial entity includes one or more bacteria. Generally, a first bacterial entity is distinguishable from a second bacterial entity.

As used herein, the term "formation" refers to synthesis or production.

As used herein, the term inducing" means increasing the amount or activity of a given material as dictated by context.

As used herein, the term "depletion" refers to reduction in amount of.

As used herein, a "prebiotic" refers to an ingredient that allows specific changes, both in the composition and/or activity in the gastrointestinal microbiota that may (or may not) confer benefits upon the host. In some embodiments, a prebiotic can be a comestible food or beverage or ingredient thereof. In some embodiments, a prebiotic may be a selectively fermented ingredient. Prebiotics may include complex carbohydrates, amino acids, peptides, minerals, or other essential nutritional components for the survival of the bacterial composition. Prebiotics include, but are not limited to, amino acids, biotin, fructooligosaccharide, galactooligosaccharides, hemicelluloses (e.g., arabinoxylan, xylan, xyloglucan, and glucomannan), inulin, chitin, lactulose, mannan oligosaccharides, oligofructose-enriched inulin, gums (e.g., guar gum, gum arabic and carregenaan), oligofructose, oligodextrose, tagatose, resistant maltodextrins (e.g., resistant starch), trans-galactooligosaccharide, pectins (e.g., xylogalactouronan, citrus pectin, apple pectin, and rhamnogalacturonan-I), dietary fibers (e.g., soy fiber, sugarbeet fiber, pea fiber, corn bran, and oat fiber) and xylooligosaccharides.

As used herein, "predetermined ratios" refer to ratios determined or selected in advance.

As used herein, "germinable bacterial spores" are spores capable of forming vegetative cells in response to a particular cue (e.g., an environmental condition or a small molecule).

As used herein, "detectably present" refers to presence in an amount that can be detected using assays provided herein or otherwise known the art that exist as of the filing date.

As used herein, "augmented" refers to an increase in amount and/or localization within to a point where it becomes detectably present.

As used herein, "fecal material" refers to a solid waste product of digested food and includes feces or bowel washes.

As used herein, the phrase "host cell response" refers to a response produced by a cell of a host organism.

As used herein, a "mammalian subject protein" refers to a protein produced by a mammalian subject and encoded by the mammalian subject genome. The term mammalian subject protein includes proteins that have been post-translationally processed and/or modified.

As used herein, the term "food-derived" refers to a protein or carbohydrate found in a consumed food.

As used herein, the term "biological material" refers to a material produced by a biological organism.

As used herein, the term "detection moiety" refers to an assay component that functions to detect an analyte.

As used herein, the term "incomplete network" refers to a partial network that lacks at least one of the entire set of components needed to carry out one or more network functions.

As used herein, the term "supplemental" refers to something that is additional and non-identical.

As used herein, a composition is "substantially free" of microbes when microbes are absent or undetectable as determined by the use of standard genomic and microbiological techniques. A composition is "substantially free" of a prebiotic or immunostimulatory carbohydrate when non-microbial carbohydrates are absent or undetectable as determined try the use of standard biochemical techniques, e.g., dye-based assays.

Microbial agents (individual or populations of microbes, microbial networks or parts of networks, or microbial metabolites) are considered to be "exogenous" to a subject (e.g., a human or non-human animal), a cell, tissue, organ or other environment of a human or non-human animal, if said subject, or said cell, tissue, organ or other environment of the subject, does not contain detectable levels of the microbial agent.

A microbial agent or population thereof is "heterologous" or "heterologously contained" on or in a host environment when, e.g., the microbial agent or population is administered or disposed on or in the host or host environment in a number, concentration, form or other modality that is not found in the host prior to administration of the microbial agent or population, or when the microbial agent or population contains an activity or structural component different from a host that does not naturally have the microbial agent within the target environment to which the microbe is administered or thereafter disposed.

As used herein, the term "antioxidant" is understood to include any one or more of various substances such as beta-carotene (a vitamin A precursor), vitamin C, vitamin E, and selenium) that inhibit oxidation or reactions promoted by Reactive Oxygen Species ("ROS") and other radical and non-radical species. Additionally, antioxidants are molecules capable of slowing or preventing the oxidation of other molecules. Non-limiting examples of antioxidants include astaxanthin, carotenoids, coenzyme Q10 ("CoQ10"), flavonoids, glutathione, Goji (wolfberry), hesperidin, lactowolfberry, lignan, lutein, lycopene, polyphenols, selenium, vitamin A, vitamin C, vitamin E, zeaxanthin, or combinations thereof.

"Backbone Network Ecology" or simply "Backbone Network" or "Backbone" are compositions of microbes that form a foundational composition that can be built upon or subtracted from to optimize a Network Ecology or Functional Network Ecology to have specific biological characteristics or to comprise desired functional properties, respectively. Microbiome therapeutics can be comprised of these "Backbone Networks Ecologies" in their entirety, or the "Backbone Networks" can be modified by the addition or subtraction of "R-Groups" to give the network ecology desired characteristics and properties. "R-Groups" can be defined in multiple terms including, but not limited to: individual OTUs, individual or multiple OTUs derived from a specific phylogenetic clade or a desired phenotype such as the ability to form spores, or functional bacterial compositions. "Backbone Networks" can comprise a computationally derived Network Ecology in its entirety or can comprise subsets of the computed network that represent key nodes in the network that contribute to efficacy such as but not limited to a composition of Keystone OTUs. The number of organisms in a human gastrointestinal tract, as well as the diversity between healthy individuals, is indicative of the functional redundancy of a healthy gut microbiome ecology. See The Human Microbiome Consortia. 2012. Structure, function and diversity of the healthy human microbiome. Nature 486: 207-214 This redundancy makes it highly likely that non-obvious subsets of OTUs or functional pathways (i.e. "Backbone Networks") are critical to maintaining states of health and/or catalyzing a shift from a dysbiotic state to one of health. One way of exploiting this redundancy is through the substitution of OM that share a given chide (see below) or by adding members of a clade not found in the Backbone Network.

"Bacterial Composition" refers to a a composition comprising bacteria, and/or bacterial spores. In some embodiments, a bacterial composition includes a consortium of microbes comprising two or more OTUs, Backbone Network Ecologies, Functional Network Ecologies, Network Classes, and Core Ecologies are all types of bacterial compositions. As used herein, Bacterial Composition includes a therapeutic microbial composition, a prophylactic microbial composition, a Spore Population, a Purified Spore Population, or an ethanol treated spore population.

"Bacterial translocation" refers to the passage of one or more bacteria across the epithelial layer of any organ of a human or non-human animal.

"Clade" refers to the OTUs or members of a phylogenetic tree that are downstream of a statistically valid node in a phylogenetic tree. The clade comprises a set of terminal leaves in the phylogenetic tree (i.e. tips of the tree) that are a distinct monophyletic evolutionary unit and that share some extent of sequence similarity. Clades are hierarchical, in one embodiment, the node in a phylogenetic tree that is selected to define a clade is dependent on the level of resolution suitable for the underlying data used to compute the tree topology.

The "colonization" of a host organism includes the non-transitory residence of a bacterium or other microscopic organism. As used herein, "reducing colonization" of a host subject's gastrointestinal tract or vagina (or any other microbiota niche) by a pathogenic or non-pathogenic bacterium includes a reduction in the residence time of the bacterium in the gastrointestinal tract or vagina as well as a reduction in the number (or concentration) of the bacterium in the gastrointestinal tract or vagina, or adhered to the luminal surface of the gastrointestinal tract. The reduction in colonization can be permanent or occur during a transient period of time. Measuring reductions of adherent pathogens can be demonstrated directly, e.g., by determining pathogenic burden in a biopsy sample, or reductions may be measured indirectly, e.g., by measuring the pathogenic burden in the stool of a mammalian host.

A "Combination" of two or more bacteria includes the physical co-existence of the two bacteria, either in the same material or product or in physically connected products, as well as the temporal co-administration or co-localization of the two bacteria.

"Cytotoxic" activity of a bacterium includes the ability to kill a cell, e.g., a bacterial cell, such as a pathogenic bacterial cell, or a host cell. A "cytostatic" activity of a bacterium includes the ability to inhibit (e.g., partially or fully) the growth, metabolism, and/or proliferation of a cell, e.g., a bacterial cell, such as a pathogenic bacterial cell. Cytotoxic activity may also apply to other cell types such as but not limited to eukaryotic cells, e.g., host cells.

The term "distal" generally is used in relation to the gastrointestinal tract, specifically the intestinal lumen, of a human or other mammal. Thus, a "distal dysbiosis" includes a dysbiosis outside of the lumen of the gastrointestinal tract, and a "distal microbiota" includes a microbiota outside of the lumen of the gastrointestinal tract. In specified instances, the term "distal" may be used in relation to the site of administration, engraftment, or colonization of a composition, e.g., a probiotic composition, of the invention. For example, if a probiotic composition is administered vaginally, a "distal" effect of the composition would occur outside the vagina.

"Dysbiosis" refers to a state of the microbiota or microbiome of the gut or other body area, including, e.g., mucosal or skin surfaces (or any other microbiota niche) in which the normal diversity and/or function of the ecological network is disrupted. Any disruption from the preferred (e.g., ideal) state of the microbiota can be considered a dysbiosis, even if such dysbiosis does not result in a detectable decrease in health. This state of dysbiosis may be unhealthy (e.g., result in a diseased state), or it may be unhealthy under only certain conditions, or it may prevent a subject from becoming healthier. Dysbiosis may be due to a decrease in diversity of the microbiota population composition, the overgrowth of one or more population of pathogens (e.g., a population of pathogenic bacteria) or pathobionts, the presence of and/or overgrowth of symbiotic organisms able to cause disease only when certain genetic and/or environmental conditions are present in a patient, or the shift to an ecological network that no longer provides a beneficial function to the host and therefore no longer promotes health. A "distal dysbiosis" includes, but is not limited to, a dysbiosis outside of the lumen of the gastrointestinal tract.

"Germinant" is a material or composition, or a physical-chemical process, capable of inducing the germination of vegetative bacterial cells from dormant spores, or the proliferation of vegetative bacterial cells, either directly or indirectly in a host organism and/or in vitro.

"Graft versus host disease" as used herein is an immunological disorder in which the immune cells of a transplant attack the tissues of a transplant recipient, potentially leading to organ dysfunction.

"Acute GVHD" as used herein is GVHD that presents within the first 100 days of transplant.

"Chronic GVHD" as used herein is GVHD that presents after the first 100 days of transplant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

"Inhibition" of a pathogen Or non-pathogen encompasses the inhibition of any desired function or activity of the pathogen or non-pathogen by the probiotic, e.g., bacterial, compositions of the present invention. Demonstrations of inhibition, such as a decrease in the growth of a pathogenic bacterial cell population or a reduction in the level of colonization of a pathogenic bacterial species are provided herein and otherwise recognized by one of ordinary skill in the art. Inhibition of a pathogenic or non-pathogenic bacterial population's "growth" may include inhibiting an increase in the size of a pathogenic or non-pathogenic bacterial cell population and/or inhibiting the proliferation (or multiplication) of a pathogenic or non-pathogenic bacterial cell population. Inhibition of colonization of a pathogenic or non-pathogenic bacterial species may be demonstrated by measuring and comparing the amount or burden of the bacterial species before and after a treatment. An "inhibition" or the act of "inhibiting" includes the total cessation and partial reduction of one or more activities of a pathogen, such as growth, proliferation, colonization, and function. As used herein, inhibition includes cytostatic and/or cytotoxic activities. Inhibition of function includes, for example, the inhibition of expression of a pathogenic gene product (e.g., the genes encoding a toxin and/or toxin biosynthetic pathway, or the genes encoding a structure required for intracellular invasion (e.g., an invasive pilus)) induced by the bacterial composition.

"Isolated" encompasses a bacterium or other entity or substance that has been (1) separated from at least some of the components with which it was associated when initially produced (whether in nature or in an experimental setting), and/or (2) produced, prepared, purified, and/or manufactured by the hand of man. Isolated bacteria includes, for example, those bacteria that are cultured, even if such cultures are not monocultures. Isolated bacteria may be separated from at least about 10%, about 20%, about 30%, about 40%, about 50%, about 60%, about 70%, about 80%, about 90%, or more of the other components with which they were initially associated. In some embodiments, isolated bacteria are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. The terms "purify," "purifying" and "purified" refer to a bacterium or other material that has been separated from at least some of the components with which it was associated either when initially produced or generated (e.g., whether in nature or in an experimental setting), or during any time after its initial production, A bacterium or a bacterial population may be considered purified if it is isolated at or after production, such as from a material or environment containing the bacterium or bacterial population, or by passage through culture, and a purified bacterium or bacterial population may contain other materials up to about 10%, about 20%, about 30%, about 40%, about 50%, about 60%, about 70%, about 80%, about 90%, or above about 90% o and still be considered "isolated." In some embodiments, purified bacteria and bacterial populations are more than about 80% o, about 85%, about 90%, about 91%, about 92%, about 93%, about 94%, about 95%, about 96%, about 97%, about 98%, about 99%, or more than about 99% pure. In the instance of bacterial compositions provided herein, the one or more bacterial types present in the composition can be independently purified from one or more other bacteria produced and/or present in the material or environment containing the bacterial type. In some embodiments, bacterial compositions and the bacterial components thereof are purified from residual habitat products. In other embodiments, bacterial compositions contain a defined mixture of isolated bacteria. For example, in some embodiments, the probiotic composition contains no more than 100 bacterial species. For example, in some embodiments, the probiotic composition contains no more than 75 bacterial species. In other embodiments, the probiotic composition contains no more than 50 bacterial species, e.g., no more than 40 bacterial species, no more than 30 bacterial species, no more than 25 bacterial species, no more than 20 bacterial species, no more than 15 bacterial species, no more than 10 bacterial species, etc. In other embodiments, the probiotic composition contains no more than 10 bacterial species, e.g., 10 bacterial species, 9 bacterial species, 8 bacterial species, 7 bacterial species, 6 bacterial species, 5 bacterial species, 4 bacterial species, 3 bacterial species, 2 bacterial species, 1 bacterial species. In some embodiments, the probiotic composition contains defined quantities of each bacterial species. In an exemplary embodiment, the probiotic composition contains isolated bacterial populations that are not isolated from fecal matter.

"Keystone OTU" or "Keystone Function" refers to one or more OTUs or Functional Pathways e KEGG or COG pathways) that are common to many network ecologies or functional network ecologies and are members of networks that occur in many subjects (i.e. "are pervasive). Due to the ubiquitous nature of Keystone OTUs and their associated Functions Pathways, they are central to the function of network ecologies in healthy subjects and are often missing or at reduced levels in subjects with disease. Keystone OTUs and their associated functions may exist in low, moderate, or high abundance in subjects. A "non-Keystone OTU" or "non-Keystone Function" refers to an OTU or Function that is observed in a Network Ecology or a Functional Network Ecology and is not a keystone OTU or Function.

"Metabolism" or "metabolic reaction" as used herein refers to any and all biomolecular catabolic or anabolic processes occurring or potentially occurring in mammalian cells or in microbes.

"Metabolite" as used herein refers to any and all molecular compounds, compositions, molecules, ions, co-factors, catalysts or nutrients used as substrates in any cellular or microbial metabolic reaction or resulting as product compounds, compositions, molecules, ions, co-factors, catalysts or nutrients from any cellular or microbial metabolic reaction.

"Microbiota" refers to the community of microorganisms that inhabit (sustainably or transiently) in and/or on a subject, (e.g., a mammal such as a human), including, but not limited to, eukaryotes (e.g., protozoa), archaea, bacteria, and viruses (including bacterial viruses, i.e., a phage).

"Microbiome" refers to the genetic content of the communities of microbes that live in and on the human body, both sustainably and transiently, including eukaryotes, archaea, bacteria, and viruses (including bacterial viruses (i.e., phage)), wherein "genetic content" includes genomic DNA, RNA such as ribosomal RNA, the epigenome, plasmids, and all other types of genetic information.

"Microbial Carriage" or simply "Carriage" refers to the population of microbes inhabiting a niche within or on a subject (e.g., a human subject). Carriage is often defined in terms of relative abundance. For example, OTU1 comprises 60% of the total microbial carriage, meaning that OTU1 has a relative abundance of 60% compared to the other OTUs in the sample from which the measurement is made. Carriage is most often based on genomic sequencing data where the relative abundance or carriage of a single OTU or group of OTUs is defined by the number of sequencing reads that are assigned to that OTU/s relative to the total number of sequencing reads for the sample.

"Microbial Augmentation" refers to the establishment or significant increase of a population of microbes that are (i) absent or undetectable (as determined by the use of standard genomic, biochemical and/or microbiological techniques) from the administered therapeutic microbial composition, and/or (ii) absent, undetectable, or present at low frequencies in the host niche (as an example: gastrointestinal tract, skin, anterior-nares, or vagina) before the delivery of the microbial composition; and (iii) are found, i.e, detectable, after the administration of the microbial composition or significantly increase, for instance increase in abundance by 2-fold, 5-fold, $1\times10^2$, $1\times10^3$, $1\times10^4$, $1\times10^5$, $1\times10^6$, $1\times10^7$, or greater than $1\times10^8$, in cases where they are present at low frequencies. The microbes that comprise an augmented ecology can be derived from exogenous sources such as food and the environment, or grow out from micro-niches within the host where they reside at low frequency.

The administration of the therapeutic composition can induce an environmental shift in the target niche that promotes favorable conditions for the growth of commensal microbes. In the absence of treatment with a therapeutic microbial composition, with or without one or more prebiotics, the host can be constantly exposed to these microbes; however, sustained growth and the positive health effects associated with the stable population of increased levels of the microbes comprising the augmented ecology are not observed.

"Microbial Engraftment" or simply "engraftment" refers to the establishment of OTUs comprised in a therapeutic microbial composition in a target niche. In one embodiment, the OTUs are absent in the treated host prior to treatment. The microbes that comprise the engrafted ecology are found in the therapeutic microbial composition and establish as constituents of the host microbial ecology upon treatment. Engrafted OTUs can establish for a transient period of time, or demonstrate long-term stability in the microbial ecology that populates the host post-treatment with a therapeutic microbial composition. The engrafted ecology can induce an environmental shift in the target niche that promotes favorable conditions for the growth of commensal microbes capable of catalyzing a shift from a dysbiotic ecology to one representative of a healthy state.

As used herein, the term "minerals" is understood to include boron, calcium, chromium, copper, iodine, iron, magnesium, manganese, molybdenum, nickel, phosphorus, potassium, selenium, silicon, tin, vanadium, zinc, or combinations thereof.

"Network Ecology" refers to a consortium of clades or OTUs that co-occur in some number of subjects. As used herein, a "network" is defined mathematically by a graph delineating how specific nodes (i.e. clades or OTUs) and edges (connections between specific chides or OTUs) relate to one another to define the structural ecology of a consortium of chides or OTUs. Any given Network Ecology will possess inherent phylogenetic diversity and functional properties.

A Network Ecology can also be defined in terms of its functional capabilities where for example the nodes would be comprised of elements such as, but not limited to, enzymes, clusters of orthologous groups (COGS; http://www.ncbi.nlm.nih.gov books/NBK21090/), or KEGG Orthology Pathways (www.genome.jp/kegg/); these networks are referred to as a "Functional Network Ecology". Functional Network Ecologies can be reduced to practice by defining the group of OTUs that together comprise the functions defined by the Functional Network Ecology.

The terms "Network Class", "Core Network" and "Network Class Ecology" refer to a group of network ecologies that in general are computationally determined to comprise ecologies with similar phylogenetic and/or functional characteristics. A Network Class therefore contains important biological features, defined either phylogenetically or functionally, of a group (i.e., a cluster) of related network ecologies. One representation of a Core Network Ecology is a designed consortium of microbes, typically non-pathogenic bacteria, that represents core features of a set of phylogenetically or functionally related network ecologies seen in many different subjects. In many occurrences, a Core Network, while designed as described herein, exists as a Network Ecology observed in one or more subjects. Core Network ecologies are useful for reversing or reducing a dysbiosis in subjects where the underlying, related Network Ecology has been disrupted.

"Ecological Niche" or simply "Niche" refers to the ecological space that an organism or group of organisms (e.g., a bacterial population) occupies. Niche describes how an organism or population or organisms responds to the distribution of resources, physical parameters (e.g., host tissue space) and competitors (e.g., by growing when resources are abundant, and/or when predators, parasites and pathogens are scarce) and how it in turn alters those same factors (e.g., limiting access to resources by other organisms, acting as a food source for predators and a consumer of prey).

To be free of "non-comestible products" means that a bacterial composition or other material provided herein does not have a substantial amount of a non-comestible product, e.g., a product or material that is inedible, harmful or otherwise undesired in a product suitable for administration, e.g., oral administration, to a human subject.

"Operational taxonomic units," "OTU" (or plural, "OTUs") refer to a terminal leaf in a phylogenetic tree and is defined by a nucleic acid sequence, e.g., the entire genome, or a specific genetic sequence, and all sequences that share sequence identity to this nucleic acid sequence at the level of species. In some embodiments the specific genetic sequence may be the 16S sequence or a portion of the 16S sequence. In other embodiments, the entire genomes of two entities are sequenced and compared. In another embodiment, select regions such as multilocus sequence tags (MLST), specific genes, or sets of genes may be genetically compared. In 16S embodiments, OTUs that share ≥97% average nucleotide identity across the entire 16S or some variable region of the 16S are considered the same OTU (see e.g. Claesson M J, Wang Q, O'Sullivan O, Greene-Diniz R, Cole J R, Ros R P, and O'Toole P W. 2010. Comparison of two next-generation sequencing technologies for resolving highly complex microbiota composition using tandem variable 16S rRNA gene regions. *Nucleic Acids Res* 38: e200. Konstantinidis K T, Ramette A, and Tiedje J M. 2006. The bacterial species definition in the genomic era. *Philos Trans R Soc Lond B Biol Sci* 361: 1929-1940). In embodiments involving the complete genome, MLSTs, specific genes, or sets of genes OTUs that share ≥95% average nucleotide identity are considered the same OTU (see e.g. Achtman M, and Wagner M. 2008. Microbial diversity and the genetic nature of microbial species. Nat. Rev. Microbiol. 6: 431-440. Konstantinidis K T, Ramette A, and Tiedje J M. 2006. The bacterial species definition in the genomic era. *Philos Trans R Soc Lond B Biol Sci* 361: 1929-1940). OTUs are frequently defined by comparing sequences between organisms. Generally, sequences with less than 95% sequence identity are not considered to form part of the same OTU. OTUs may also be characterized by any combination of nucleotide markers or genes, in particular highly conserved genes (e.g., "housekeeping" genes), or a combination thereof. Such characterization employs, e.g., WGS data or a whole genome sequence.

"Pathobionts" or "Opportunistic Pathogens" refers to symbiotic organisms able to cause disease only when certain genetic and/or environmental conditions are present in a subject.

The term "Phylogenetic Diversity" refers to the biodiversity present in a given Network Ecology, Core Network Ecology or Network Class Ecology based on the OTUs that comprise the network. Phylogenetic diversity is a relative term, meaning that a Network Ecology, Core Network or Network Class that is comparatively more phylogenetically diverse than another network contains a greater number of unique species, genera, and taxonomic families, Uniqueness of a species, genera, or taxonomic family is generally defined using a phylogenetic tree that represents the genetic diversity all species, genera, or taxonomic families relative to one another. In another embodiment phylogenetic diversity may be measured using the total branch length or average branch length of a phylogenetic tree.

Phylogenetic Diversity may be optimized in a bacterial composition by including a wide range of biodiversity.

"Phylogenetic tree" refers to a graphical representation of the evolutionary relationships of one genetic sequence to another that is generated using a defined set of phylogenetic reconstruction algorithms (e.g. parsimony, maximum likelihood, or Bayesian). Nodes in the tree represent distinct ancestral sequences and the confidence of any node is provided by a bootstrap or Bayesian posterior probability, which measures branch uncertainty.

As used herein "preventing" or "prevention" refers to any methodology where the disease state does not occur due to the actions of the methodology (such as, for example, administration of a probiotic and/or a prebiotic as described herein). In one aspect, it is understood that prevention can also mean that the disease is not established to the extent that occurs in untreated controls. For example, there can be a 5, 10, 15, 20, 25, 30, 35, 40, 50, 60, 70, 80, 90, or 100% reduction in the establishment of disease frequency relative to untreated controls. Accordingly, prevention of a disease encompasses a reduction in the likelihood that a subject will develop the disease, relative to an untreated subject (e.g. a subject who does not receive a probiotic and/or a prebiotic as described herein).

"rDNA", "rRNA", "16S-rDNA", "16S-rRNA", "16S", "16S sequencing", "16S-NGS", "18S", "18S-rRNA", "18S-rDNA", "18S sequencing", and "18S-NGS" refer to the nucleic acids that encode for the RNA subunits of the ribosome. rDNA refers to the gene that encodes the rRNA that comprises the RNA subunits. There are two RNA subunits in the ribosome termed the small subunit (SSU) and large subunit (LSU); the RNA genetic sequences (rRNA) of these subunits are related to the gene that encodes them (rDNA) by the genetic code. rDNA genes and their complementary RNA sequences are widely used for determination of the evolutionary relationships amount organisms as they are variable, yet sufficiently conserved to allow cross organism molecular comparisons.

Typically 16S rDNA sequence (approximately 1542 nucleotides in length) of the 30S SSU is used for molecular-based taxonomic assignments of Prokaryotes and the 18S rDNA sequence (approximately 1869 nucleotides in length) of 40S SSU is used for Eukaryotes. 16S sequences are used for phylogenetic reconstruction as they are in general highly conserved, but contain specific hypervariable regions that harbor sufficient nucleotide diversity to differentiate genera and species of most bacteria.

"Residual habitat products" refers to material derived from the habitat for microbiota within or on a human or animal. For example, microbiota live in feces in the gastrointestinal tract, on the skin itself, in saliva, mucus of the respiratory tract, or secretions of the genitourinary tract (i.e., biological matter associated with the microbial community). Substantially free of residual habitat products means that the bacterial composition no longer contains the biological matter associated with the microbial environment on or in the human or animal subject and is 100% free, 99% free, 98% free, 97% free, 96% free, or 95% free, 94% free, 93% free, 92% free, 91% free, 90% free, 85% free, 80% free, 75% free, 70% free, 65% free, or 60% free of any contaminating biological matter associated with the microbial community. Residual habitat products can include abiotic materials (including undigested food) or it can include unwanted microorganisms. Substantially free of residual habitat products may also mean that the bacterial composition contains no detectable cells from a human or animal and that only microbial cells are detectable. In one embodiment, substantially free of residual habitat products may also mean that the bacterial composition contains no detectable viral (including bacterial viruses (i.e., phage)), fungal, mycoplasmal contaminants. In another embodiment, it means that fewer than $1\times10^{-2}\%$, $1\times10^{-3}\%$, $1\times10^{-4}\%$, $1\times10^{-5}\%$, $1\times10^{-6}\%$, $1\times10^{-7}\%$, $1\times10^{-8}\%$ of the viable cells in the bacterial composition are human or animal, as compared to microbial cells. There are multiple ways to accomplish this degree of purity, none of which are limiting. Thus, contamination may be reduced by isolating desired constituents through multiple steps of streaking to single colonies on solid media until replicate (such as, but not limited to, two) streaks from serial single colonies have shown only a single colony morphology. Alternatively, reduction of contamination can be accomplished by multiple rounds of serial dilutions to single desired cells (e.g., a dilution of $10^{-8}$ or $10^{-9}$), such as through multiple 10-fold serial dilutions. This can further be confirmed by showing that multiple isolated colonies have similar cell shapes and Gram staining behavior. Other methods for confirming adequate purity include genetic analysis (e.g. PCR, DNA sequencing), serology and antigen analysis, enzymatic and metabolic analysis, and methods using instrumentation such as flow cytometry with reagents that distinguish desired constituents from contaminants.

In microbiology, "16S sequencing" or "16S-rRNA" or "16S" refers to sequence derived by characterizing the nucleotides that comprise the 16S ribosomal RNA gene(s). The bacterial 16S rDNA is approximately 1500 nucleotides in length and is used in reconstructing the evolutionary relationships and sequence similarity of one bacterial isolate to another using phylogenetic approaches. 16S sequences are used for phylogenetic reconstruction as they are in general highly conserved, but contain specific hypervariable regions that harbor sufficient nucleotide diversity to differentiate genera and species of most bacteria.

The "V1-V9 regions" of the 16S rRNA refers to the first through ninth hypervariable regions of the 16S rRNA gene that are used for genetic typing of bacterial samples. These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. Brosius et al., Complete nucleotide sequence of a 16S ribosomal RNA gene from *Escherichia coli*, PNAS 75(10):4801-4805 (1978). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU. A person of ordinary skill in the art can identify the specific hypervariable regions of a candidate 16S rRNA by comparing the candidate sequence in question to a reference sequence and identifying the hypervariable regions based on similarity to the reference hypervariable regions, or alternatively, one can employ Whole Genome Shotgun (WGS) sequence characterization of microbes or a microbial community.

The term "subject" refers to any organism or animal subject that is an object of a method or material, including mammals, e.g., humans, laboratory animals (e.g., primates, rats, mice, rabbits), livestock (e.g., cows, sheep, goats, pigs, turkeys, and chickens), household pets (e.g., dogs, cats, and rodents), horses, and transgenic non-human animals. The subject may be suffering from a dysbiosis, including, but not limited to, an infection due to a gastrointestinal pathogen or may be at risk of developing or transmitting to others an infection due to a gastrointestinal pathogen. Synonyms used herein include "patient" and "animal." In some embodiments, the subject or host may be suffering from a dysbiosis, that contributes to or causes a condition classified as an autoimmune or inflammatory disease, graft-versus-host disease, Crohn's disease, Celiac disease, inflammatory bowel disease, ulcerative colitis, multiple sclerosis, systemic lupus erythematosus, Sjogren's syndrome, or type 1 diabetes. In some embodiments, the host may be suffering from including but not limited to mechanisms such as metabolic endotoxemia, altered metabolism of primary bile acids, immune system activation, or an imbalance or reduced production of short chain fatty acids including butyrate, propionate, acetate, and branched chain fatty acids.

The term "phenotype" refers to a set of observable characteristics of an individual entity. As example an individual subject may have a phenotype of "health" or "disease". Phenotypes describe the state of an entity and all entities within a phenotype share the same set of characteristics that describe the phenotype. The phenotype of an individual results in part, or in whole, from the interaction of the entities genome and/or microbiome with the environment.

"Spore" or "endospore" refers to an entity, particularly a bacterial entity, which is in a dormant, non-vegetative and non-reproductive stage. Spores are generally resistant to environmental stress such as radiation, desiccation, enzymatic treatment, temperature variation, nutrient deprivation, and chemical disinfectants.

A "spore population" refers to a plurality of spores present in a composition. Synonymous terms used herein include spore composition, spore preparation, ethanol treated spore fraction and spore ecology. A spore population may be purified from a fecal donation, e.g. via ethanol or heat treatment, or a density gradient separation or any combination of methods described herein to increase the purity, potency and/or concentration of spores in a sample. Alternatively, a spore population may be derived through culture methods starting from isolated spore former species or spore former OTUs or from a mixture of such species, either in vegetative or spore form.

A "sporulation induction agent" is a material or physical-chemical process that is capable of inducing sporulation in a bacterium, either directly or indirectly, in a host organism and/or in vitro.

To increase production of bacterial entities includes an activity or a sporulation induction agent. Production includes conversion of vegetative bacterial cells into spores and augmentation of the rate of such conversion, as well as decreasing the germination of bacteria in spore form, decreasing the rate of spore decay in vivo, or ex vivo, or to increasing the total output of spores (e.g. via an increase in volumetric output of fecal material).

"Synergy" or "synergistic interactions" refers to the interaction or cooperation of two or more microbes to produce a combined effect greater than the sum of their separate effects. In one embodiment, "synergy" between two or more microbes can result in the inhibition of a pathogens ability to grow.

"Treatment," "treat," or "treating" means a method of reducing the effects of a disease or condition. Treatment can also refer to a method of reducing the disease or condition itself rather than just the symptoms. The treatment can be any reduction from pre-treatment levels and can be but is not limited to the complete ablation of the disease, condition, or the symptoms of the disease or condition. Therefore, in the disclosed methods, treatment" can refer to a 10%, 20%, 30%, 40%, 50%, 60%, 70%, 80%, 90%, or 100% reduction in the severity of an established disease or the disease progression. For example, a disclosed method for reducing the effects of GVHD is considered to be a treatment if there is a 10% reduction in one or more symptoms of the disease in a subject with GVHD when compared to pre-treatment levels in the same subject or control subjects. Thus, the reduction can be a 10, 20, 30, 40, 50, 60, 70, 80, 90, 100%, or any amount of reduction in between as compared to native or control levels. It is understood and herein contemplated that "treatment" does not necessarily refer to a cure of the disease or condition, but an improvement in the outlook of a disease or condition (e.g., GVHD).

As used herein the term "vitamin" is understood to include any of various fat-soluble or water-soluble organic substances (non-limiting examples include vitamin A, Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (folic acid), and Vitamin B12 (various cobalamins; commonly cyanocobalamin in vitamin supplements), vitamin C, vitamin D, vitamin E, vitamin K, K1 and K2 (i.e. MK-4, MK-7), folic acid and biotin) essential in minute amounts for normal growth and activity of the body and obtained naturally from plant and animal foods or synthetically made, pro-vitamins, derivatives, analogs. As used herein, the term "recipient" refers to the subject receives a bone marrow or a solid organ transplantation.

III. Probiotic Compositions of the Invention

Disclosed herein are bacterial, e.g., probiotic, compositions comprising a non-pathogenic bacterial or fungal population, e.g., an immunomodulatory bacterial population, such as an anti-inflammatory bacterial population, with or without one or more prebiotics, for the prevention, control, and treatment of inflammation, autoimmune and inflammatory disorders, dysbiosis, e.g., gastrointestinal or distal dysbiosis, disorders associated with dysbiosis, and for general nutritional health. These compositions are advantageous in being suitable for safe administration to humans and other mammalian subjects and are efficacious for the treatment, prevention, reduction and amelioration of inflammation, autoimmune and inflammatory disorders, dysbiosis, e.g., gastrointestinal or distal dysbiosis, disorders associated with dysbiosis, and for general nutritional health. While spore-based compositions are known, these are generally prepared according to various techniques such as lyophilization or spray-drying of liquid bacterial cultures, resulting in poor efficacy, instability, substantial variability and lack of adequate safety and efficacy.

It has now been found that bacterial and fungal populations can be obtained from biological materials obtained from mammalian subjects, including humans. These populations are formulated into compositions as provided herein, and administered to mammalian subjects using the methods as provided herein.

In one embodiment, therapeutic compositions are provided for the treatment, prevention, reduction of onset and amelioration of inflammation or one or more symptom of an autoimmune or inflammatory disorder, dysbiosis, e.g., gastrointestinal or distal dysbiosis, or a disorder associated with dysbiosis. As used herein, "therapeutic" compositions include compositions that function in a prophylactic (e.g., preventative) manner. Therapeutic compositions contain one or more populations of immunomodulatory bacteria and/or fungi, alone or in combination with one or more prebiotic. In one embodiment, the microbial entities are preferably produced by isolation and/or culture, using, for example, the following steps: a) providing fecal material and b) subjecting the material to a culture step and/or a treatment step resulting in purification of immunomodulatory bacteria and, optionally, c) formulating the purified population for administration, wherein the purified population is present in the composition in an amount effective to engraft and/or augment in the gastrointestinal tract in order to treat, prevent or reduce the severity of inflammation or one or more symptom of an autoimmune or inflammatory disorder, dysbiosis, e.g., gastrointestinal or distal dysbiosis, or a disorder associated with dysbiosis in a mammalian recipient subject to whom the therapeutic composition is administered. Generally, the population is provided in an amount effective to treat (including to prevent) a disease, disorder or condition associated with or characterized by inflammation, dysbiosis, e.g., gastrointestinal or distal dysbiosis, inflammation, or an autoimmune or inflammatory disorder. Such treatment may be effective to reduce the severity of at least one symptom of the dysbiosis, e.g., gastrointestinal or distal dysbiosis, or an autoimmune or inflammatory disorder. Such treatment may be effective to modulate the microbiota diversity present in the mammalian recipient.

In embodiments, the probiotic compositions contain immunomodulatory microbes, e.g., immunomodulatory bacteria, which are capable of altering the immune activity of a mammalian subject. In exemplary embodiments, the immunomodulatory bacteria are capable of reducing inflammation in a mammalian subject. Such immunomodulatory bacteria are referred to herein as anti-inflammatory bacteria. Immunomodulatory bacteria can act to alter the immune activity of a subject directly or indirectly. For example, immunomodulatory bacteria can act directly on immune cells through receptors for bacterial components (e.g. Toll-like receptors) or by producing metabolites such as immunomodulatory short chain fatty acids (SCFAs). SCFAs produced by immunomodulatory bacteria can include, e.g., butyrate, acetate, propionate, or valerate, or combinations thereof. Such SCFAs can have many positive impacts on the health of the subject, by, for example, reducing inflammation, or improving intestinal barrier integrity. In one embodiment, the improvement of gut epithelium barrier integrity results in reduced trafficking of bacteria, bacterial components and/or bacterial metabolites into the blood. In one embodiment, a probiotic composition is administered to a subject in an amount effective to increase short chain fatty acid production by one or more organisms in the gut of a mammalian host. Immunomodulatory bacteria can also impact the immune activity of a subject by producing glutathione or gamma-glutamylcysteine.

Probiotic compositions containing immunomodulatory bacteria can additionally or alternatively impact the immune activity of a subject indirectly by modulating the activity of immune cells in the subject. For example, immunomodulatory bacteria may alter cytokine expression by host immune cells (e.g., macrophages, B lymphocytes, T lymphocytes, mast cells, peripheral blood mononuclear cells (PBMCs), etc.) or other types of host cells capable of cytokine secretion (e.g., endothelia cells, fibroblasts, stromal cells, etc.). In an exemplary embodiment, probiotic compositions contain anti-inflammatory immunomodulatory bacteria that are capable of inducing secretion of anti-inflammatory cytokines by host cells. For example, anti-inflammatory bacteria can induce secretion of one or more anti-inflammatory cytokines such as but not limited to IL-10, IL-13, IL-9, IL-4, IL-5, TGFβ, and combinations thereof, by host cells (e.g., host immune cells). In another exemplary embodiment, probiotic compositions contain anti-inflammatory immunomodulatory bacteria that are capable of reducing secretion of one or more pro-inflammatory cytokines by host cells (e.g., host immune cells). For example, anti-inflammatory bacteria can reduce secretion of one or more pro-inflammatory cytokines such as but not limited to IFNγ, IL-12p70, IL-1α, IL-6, IL-8, MCP1, MIP1α, MIP1β, TNFα, and combinations thereof. Other cytokines that may be modulated by immunomodulatory bacteria include, for example, IL-17A, IL-2, and IL-9. In some embodiments, the induction and/or secretion of pro-inflammatory cytokines may be induced by (e.g., in response to, either directly or indirectly) a bacteria (e.g., *Enterococcus faecalis*).

In some embodiments, immunomodulatory bacteria are selected for inclusion in a probiotic composition of the invention based on the desired effect of the probiotic composition on cytokine secretion by host cells, e.g., host immune cells. For example, in one embodiment, a probiotic composition contains anti-inflammatory bacteria that increase secretion of an anti-inflammatory cytokine, for example, IL-10, IL-13, IL-9, IL-4, IL-5, TGFβ, and combinations thereof. In some embodiments, the anti-inflammatory bacteria increase secretion of two or more anti-inflammatory cytokines. In some embodiments, the anti-inflammatory bacteria increase secretion of three or more anti-inflammatory cytokines. In some embodiments, the anti-inflammatory bacteria increase secretion of four or more anti-inflammatory cytokines. In some embodiments, the anti-inflammatory bacteria increase secretion of five or more anti-inflammatory cytokines. In exemplary embodiments, the increase is an increase of at least 5%, 10%, 20%, 30%, 40%, 50%, 60%, 70%, 80%, 80%, 100%, 200%, 300%, 500% or more. In another embodiment, a probiotic composition contains anti-inflammatory bacteria that decrease secretion of a pro-inflammatory cytokine, for example, IFNγ, IL-12p70, IL-1α, IL-6, IL-8, MCP1, MIP1α, MIP1β, TNFα, and combinations thereof. In some embodiments, the anti-inflammatory bacteria decrease secretion of two or more pro-inflammatory cytokines. In some embodiments, the anti-inflammatory bacteria decrease secretion of three or more pro-inflammatory cytokines. In some embodiments, the anti-inflammatory bacteria decrease secretion of four or more pro-inflammatory cytokines. In some embodiments, the anti-inflammatory bacteria decrease secretion of five or more pro-inflammatory cytokines. In exemplary embodiments, the decrease is a decrease of at least 5%, 10%, 20%, 30%, 40%, 50%, 60%, 70%, 80%, 80%, 100%, 200%, 300%, 500% or more. In another embodiment, the probiotic composition contains anti-inflammatory bacteria that increase secretion of one or more anti-inflammatory cytokines and reduce secretion of one or more pro-inflammatory cytokines. Alterations in cytokine expression may occur locally, e.g., in the gastrointestinal tract of a subject, or at a site distal to the gastrointestinal tract.

In other embodiments, probiotics containing immunomodulatory bacteria impact the immune activity of a subject by promoting the differentiation and/or expansion of particular subpopulations of immune cells. For example, immunomodulatory bacteria can increase or decrease the proportion of Treg cells, Th17 cells, Th1 cells, or Th2 cells in a subject. The increase or decrease in the proportion of immune cell subpopulations may be systemic, or it may be localized to a site of action of the probiotic, e.g., in the gastrointestinal tract or at the site of a distal dysbiosis. In some embodiments, immunomodulatory bacteria are selected for inclusion in a probiotic composition of the invention based on the desired effect of the probiotic composition on the differentiation and/or expansion of subpopulations of immune cells in the subject.

In one embodiment, a probiotic composition contains immunomodulatory bacteria that increase the proportion of Treg cells in a subject. In another embodiment, a probiotic composition contains immunomodulatory bacteria that decrease the proportion of Treg cells in a subject. In one embodiment, a probiotic composition contains immunomodulatory bacteria that increase the proportion of Th17 cells in a subject (e.g., by inducing expansion of Th17 cells in the subject). In another embodiment, a probiotic composition contains immunomodulatory bacteria that decrease the proportion of Th17 cells in a subject. In one embodiment, a probiotic composition contains immunomodulatory bacteria that increase the proportion of Th1 cells in a subject (e.g., by inducing expansion of Th1 cells in the subject). In another embodiment, a probiotic composition contains immunomodulatory bacteria that decrease the proportion of Th1 cells in a subject. In one embodiment, a probiotic composition contains immunomodulatory bacteria that increase the proportion of Th2 cells in a subject (e.g., by inducing expansion of Th2 cells in the subject). In another embodiment, a probiotic composition contains immunomodulatory bacteria that decrease the proportion of Th2 cells in a subject. The increase or decrease in the proportion of immune cell subpopulations (e.g., Th17 cells, Th1 cells and Th2 cells) may be localized or systemic.

In one embodiment, a probiotic composition contains immunomodulatory bacteria capable of modulating the proportion of one or more populations of Treg cells, Th17 cells, Th1 cells, Th2 cells, and combinations thereof in a subject.

Certain immune cell profiles may be particularly desirable to treat or prevent particular disorders associated with a dysbiosis. For example, treatment or prevention of GVHD can be promoted by increased numbers of Treg cells and Th2 cells, and/or decreased numbers of Th17 cells and Th1 cells. Accordingly, probiotic compositions for the treatment or prevention of GVHD may contain probiotics capable of promoting Treg cells and Th2 cells, and reducing Th17 and Th1 cells.

In one embodiment, therapeutic probiotic compositions comprising a purified population of immunomodulatory microbes, e.g., bacteria, are provided, with or without one or more prebiotics, in an amount effective to i) treat or prevent dysbiosis, e.g., gastrointestinal or distal dysbiosis, inflammation, or an autoimmune or inflammatory disorder, and/or ii) augment at least one type of microbe, e.g., a bacterium, not present in the therapeutic composition in a mammalian recipient subject to whom the therapeutic composition is administered, and/or iii) engraft at least one type of microbe, e.g., a bacterium, present in the therapeutic composition but not present in a mammalian subject prior to treatment.

In another embodiment, therapeutic probiotic compositions comprising a purified population of immunomodulatory microbes are provided, in an amount effective to i) augment the microbiota diversity present in the mammalian recipient and/or ii) treat or prevent dysbiosis, e.g., gastrointestinal or distal dysbiosis, inflammation, or an autoimmune or inflammatory disorder in a mammalian recipient subject to whom the therapeutic composition is administered, wherein the purified population is obtained by separation of the population apart from at least one residual habitat product in a fecal material obtained from one or a plurality of mammalian donor subjects. In some embodiments, individual bacterial strains can be cultured from fecal material. These strains can then be purified or otherwise isolated and used singly or in combination. In one embodiment, the probiotic composition does not contain a fecal extract.

In one embodiment, the probiotic compositions described herein may be used to treat or correct a dysbiosis in a subject. The dysbiosis may be, for example, a local dysbiosis, or a distal dysbiosis. In another embodiment, the probiotic compositions described herein may be used to prevent a dysbiosis in a subject at risk for developing a dysbiosis.

In some embodiments, the purified population of immunomodulatory microbes described above is coadministered or formulated with one or more prebiotics, e.g., carbohydrates.

In some embodiments, the purified population of immunomodulatory microbes described above is administered before one or more prebiotics are administered to a subject. In some embodiments the purified population of immunomodulatory microbes is administered after one or more prebiotics have been administered to a subject. In some embodiments, the purified population of immunomodulatory microbes is administered concurrently with one or more prebiotics. In other embodiments, the purified population of immunomodulatory microbes is administered sequentially with one or more prebiotics. In some embodiments, the purified population of immunomodulatory microbes is administered in a composition formulated to contain one or more pharmaceutical excipients, and optionally one or more prebiotics.

Microbes involved in modulation of the host immune system i) may be human commensals; ii) may be part of an organ's healthy-state microbiome; ii) may be part of a distal organ's healthy-state microbiome; iv) may be exogenous microbes; v) may be innocuous; vi) may be pathobionts; vii) may be pathogens; viii) may be opportunistic pathogens; or ix) any combination thereof. In some aspects, microbes are not required to be actively proliferating (e.g., spores, dormant cells, cells with reduced metabolic rate, or heat-killed cells) to have an immunomodulatory effect. In certain aspects, microbial cell components, rather than whole microbial cells, may have immunomodulatory effects. Non-limiting examples of microbial components are lipids, carbohydrates, proteins, nucleic acids, and small molecules.

Microbial compositions are provided herein, optionally comprising prebiotics, non-microbial immunomodulatory carbohydrates, or microbial immunomodulatory cell components, that are effective for the prevention or treatment of an autoimmune or inflammatory disorder such as graft-versus-host disease (GVHD), an inflammatory bowel disease (IBD) including but not limited to ulterative colitis and Crohn's disease, multiple sclerosis (MS), systemic lupus erythematosus (SLE), type I diabetes, rheumatoid arthritis, Sjögren's syndrome, and celiac disease, or dysbiosis.

In certain embodiments, the compositions comprise at least one type of microbe and at least one type of carbohydrate (a prebiotic), and optionally further comprise microbial immunomodulatory cell components or substrates for the production of immunomodulatory metabolites, that are effective for the prevention or treatment of an autoimmune or inflammatory disorder. Methods for the prevention and/or treatment of autoimmune and inflammatory diseases in human subjects are also disclosed herein.

In some embodiments, the bacterial, e.g., probiotic, compositions of the invention comprise purified spore populations. As described herein, purified spore populations contain commensal bacteria of the human gut microbiota with the capacity to meaningfully provide one or more functions of a healthy microbiota when administered to a mammalian subject. Without being limited to a specific mechanism, it is thought that such compositions inhibit the growth of pathogens such as *C. difficile, Salmonella* spp., enteropathogenic *E. coli, Fusobacterium* spp., *Klebsiella* spp. and vancomycin-resistant *Enterococcus* spp., so that a healthy, diverse and protective microbiota can be maintained or, in the case of pathogenic bacterial infections, repopulate the intestinal lumen to reestablish ecological control over potential pathogens. In some embodiments, yeast spores and other fungal spores are also purified and selected for therapeutic use.

In one embodiment, the purified spore populations can engraft in the host and remain present for 1 day, 2 days, 3 days, 4 days, 5 days, 6 days, 7 days, 10 days, 14 days, 21 days, 25 days, 30 days, 60 days, 90 days, or longer than 90 days. Additionally, the purified spore populations can induce other healthy commensal bacteria found in a healthy gut to engraft in the host that are not present in the purified spore populations or present at lesser levels. Therefore, these species are considered to "augment" the delivered spore populations. In this manner, commensal species augmentation of the purified spore population in the recipient's gut leads to a more diverse population of gut microbiota than present initially.

In some embodiments, a probiotic composition of the invention contains a single species of bacteria. In other embodiments, the probiotic composition contains two or more species of bacteria, e.g., 2, 3, 4, 5, 6, 7, 8, 9, 10, 15, 20, 30, 40, 50, 60, 70, 80, 90, 100, 500, 1000 or more species of bacteria. In one embodiment, the probiotic composition contains no more than 20 species of bacteria, e.g., 20, 19, 18, 17, 16, 15, 14, 13, 12, 11, 10, 9, 8, 7, 6, 5, 4, 3, 2, or 1 species of bacteria. In exemplary embodiments, the probiotic composition contains 8 bacterial species. In other exemplary embodiments, the probiotic composition contains 9 bacterial species. In other embodiments, the probiotic composition contains or is administered in conjunction with a prebiotic, as described herein.

Preferred bacterial genera include *Acetanaerobacterium, Acetivibrio, Alicyclobacillus, Alkaliphilus, Anaerofustis, Anaerosporobacter, Anaerostipes, Anaerotruncus, Anoxybacillus, Bacillus, Bacteroides, Blautia, Brachyspira, Brevibacillus, Bryantella, Bulleidia, Butyricicoccus, Butyrivibrio, Catenibacterium, Chlamydiales, Clostridiaceae, Clostridiales, Clostridium, Collinsella, Coprobacillus, Coprococcus, Coxiella, Deferribacteres, Desulfitobacterium, Desulfotomaculum, Dorea, Eggerthella, Erysipelothrix, Erysipelotrichaceae, Ethanoligenens, Eubacterium, Faecalibacterium, Filifactor, Flavonifractor, Flexistipes, Fulvimonas, Fusobacterium, Gemmiger, Geobacillus, Gloeobacter, Holdemania, Hydrogenoanaerobacterium, Kocuria, Lachnobacterium, Lachnospira, Lachnospiraceae, Lactobacillus, Lactonifactor, Leptospira, Lutispora, Lysinibacillus, Mollicutes, Moorella, Nocardia, Oscillibacter, Oscillospira, Paenibacillus, Papillibacter, Pseudoflavonifractor, Robinsoniella, Roseburia, Ruminococcaceae, Ruminococcus, Saccharomonospora, Sarcina, Solobacterium, Sporobacter, Sporolactobacillus, Streptomyces, Subdoligranulum, Sutterella, Syntrophococcus, Thermoanaerobacter, Thermobifida,* and *Turicibacter.*

Preferred bacterial genera also include *Acetonema, Alkaliphilus, Amphibacillus, Ammonifex, Anaerobacter, Caldicellulosiruptor, Caloramator, Candidatus, Carboxydibrachium, Carboxydothermus, Cohnella, Dendrosporobacter Desulfitobacterium, Desulfosporosinus, Halobacteroides, Heliobacterium, Heliophilum, Heliorestis, Lachnoanaerobaculum, Lysinibacillus, Oceanobacillus, Orenia (S.), Oxalophagus, Oxobacter, Pelospora, Pelotomaculum, Propionispora, Sporohalobacter, Sporomusa, Sporosarcina, Sporotomaculum, Symbiobacterium, Syntrophobotulus, Syntrophospora, Terribacillus, Thermoanaerobacter,* and *Thermosinus.*

In another embodiment, a probiotic composition of the invention consists essentially of *Blautia.*

In one embodiment, a probiotic composition of the invention does not comprise *Blautia* alone.

As provided herein, therapeutic compositions comprise, or in the alternative, modulate, the colonization and/or engraftment, of the following exemplary bacterial entities: *Lactobacillus gasseri, Lactobacillus fermentum, Lactobacillus reuteri, Enterococcus faecalis, Enterococcus durans, Enterococcus villorum, Lactobacillus plantarum, Pediococcus acidilactici, Staphylococcus pasteuri, Staphylococcus cohnii, Streptococcus sanguinis, Streptococcus sinensis, Streptococcus mitis, Streptococcus* sp. SCA22, *Streptococcus* sp. CR-3145, *Streptococcus anginosus, Streptococcus mutans, Coprobacillus cateniformis, Clostridium saccharogumia, Eubacterium dolichum* DSM 3991, *Clostridium* sp. PPf35E6, *Clostridium sordelli* ATCC 9714, *Ruminococcus torques, Ruminococcus gnavus, Ruminococcus clostridioforme, Ruminococcus obeum, Blautia producta, Clostridium* sp. ID5, *Megasphaera micronuciformis, Veillonella parvula, Clostridium methylpentosum, Clostridium islandicum, Faecalibacterium prausnitzii, Bacteroides uniformmis, Bacteroides thetaiotaomicron, Bacteroides acidifaciens, Bacteroides ovatus, Bacteroides fragilis, Parabacteroides distasonis, Propinionibacteirum propionicum, Actinomycs hyovaginalis, Rothia mucilaginosa, Rothia aeria, Bifidobacterium breve, Scardovia inopinata* and *Eggerthella lenta.*

Preferred bacterial species are provided in Table 1, Table 1A, Table 1B, Table 1C, Table 1D, Table 1E, Table 1F, and Table 5. Optionally, in some embodiments, preferred bacterial species are spore formers. Where specific strains of a species are provided, one of skill in the art will recognize that other strains of the species can be substituted for the named strain.

In one embodiment, the bacterial entity, e.g., species or strain, useful in the compositions and methods of the invention is *Acidaminococcus intestine*. In one embodiment, the bacterial entity, e.g., species or strain, useful in the compositions and methods of the invention is *Acinetobacter baumannii*. In one embodiment, the bacterial entity, e.g., species or strain, useful in the compositions and methods of the invention is *Acinetobacter lwoffii*. In one embodiment, the bacterial entity, e.g., species or strain, useful in the compositions and methods of the invention is *Akkermansia muciniphila*. In one embodiment, the bacterial entity, e.g., species or strain, useful in the compositions and methods of the invention is *Alistipes putredinis*. In one embodiment, the bacterial entity, e.g., species or strain, useful in the compositions and methods of the invention is *Alistipes shahii*. In one embodiment, the bacterial entity, e.g., species or strain, useful in the compositions and methods of the invention is *Anaerostipes hadrus*. In one embodiment, the bacterial entity, e.g., species or strain, useful in the compositions and methods of the invention is *Anaerotruncus colihominis*. In one embodiment, the bacterial entity, e.g., species or strain, useful in the compositions and methods of the invention is *Bacteroides caccae*. In one embodiment, the bacterial entity, e.g., species or strain, useful in the compositions and methods of the invention is *Bacteroides cellulosilyticus*. In one embodiment, the bacterial entity, e.g., species or strain, useful in the compositions and methods of the invention is *Bacteroides dorei*. In one embodiment, the bacterial entity, e.g., species or strain, useful in the compositions and methods of the invention is *Bacteroides eggerthii*. In one embodiment, the bacterial entity, e.g., species or strain, useful in the compositions and methods of the invention is *Bacteroides finegoldii*. In one embodiment, the bacterial entity, e.g., species or strain, useful in the compositions and methods of the invention is *Bacteroides fragilis*. In one embodiment, the bacterial entity, e.g., species or strain, useful in the compositions and methods of the invention is *Bacteroides massiliensis*. In one embodiment, the bacterial entity, e.g., species or strain, useful in the compositions and methods of the invention is *Bacteroides ovatus*. In one embodiment, the bacterial entity, e.g., species or strain, useful in the compositions and methods of the invention is *Bacteroides salanitronis*. In one embodiment, the bacterial entity, e.g., species or strain, useful in the compositions and methods of the invention is *Bacteroides salyersiae*. In one embodiment, the bacterial entity, e.g., species or strain, useful in the compositions and methods of the invention is *Bacteroides* sp. 1_1_6. In one embodiment, the bacterial entity, e.g., species or strain, useful in the compositions and methods of the invention is *Bacteroides* sp. 3_1_23. In one embodiment, the bacterial entity, e.g., species or strain, useful in the compositions and methods of the invention is *Bacteroides* sp. D20. In one embodiment, the bacterial entity, e.g., species or strain, useful in the compositions and methods of the invention is *Bacteroides thetaiotaomicrond*. In one embodiment, the bacterial entity, e.g., species or strain, useful in the compositions and methods of the invention is *Bacteroides uniformis*. In one embodiment, the bacterial entity, e.g., species or strain, useful in the compositions and methods of the invention is *Bacteroides vulgatus*. In one embodiment, the bacterial entity, e.g., species or strain, useful in the compositions and methods of the invention is *Bifidobacterium adolescentis*. In one embodiment, the bacterial entity, e.g., species or strain, useful in the compositions and methods of the invention is *Bifidobacterium bifidum*. In one embodiment, the bacterial entity, e.g., species or strain, useful in the compositions and methods of the invention is *Bifidobacterium breve*. In one embodiment, the bacterial entity, e.g., species or strain, useful in the compositions and methods of the invention is *Bifidobacterium faecale*. In one embodiment, the bacterial entity, e.g., species or strain, useful in the compositions and methods of the invention is *Bifidobacterium kashiwanohense*. In one embodiment, the bacterial entity, e.g., species or strain, useful in the compositions and methods of the invention is *Bifidobacterium longum* subsp. *Longum*. In one embodiment, the bacterial entity, e.g., species or strain, useful in the compositions and methods of the invention is *Bifidobacterium pseudocatenulatum*. In one embodiment, the bacterial entity, e.g., species or strain, useful in the compositions and methods of the invention is *Bifidobacterium stercoris*. In one embodiment, the bacterial entity, e.g., species or strain, useful in the compositions and methods of the invention is *Blautia (Ruminococcus) coccoides*. In one embodiment, the bacterial entity, e.g., species or strain, useful in the compositions and methods of the invention is *Blautia faecis*. In one embodiment, the bacterial entity, e.g., species or strain, useful in the compositions and methods of the invention is *Blautia glucerasea*. In one embodiment, the bacterial entity, e.g., species or strain, useful in the compositions and methods of the invention is *Blautia (Ruminococcus) hansenii*. In one embodiment, the bacterial entity, e.g., species or strain, useful in the compositions and methods of the invention is *Blautia hydrogenotrophica (Ruminococcus hydrogenotrophicus)*. In one embodiment, the bacterial entity, e.g., species or strain, useful in the compositions and methods of the invention is *Blautia (Ruminococcus) luti*. In one embodiment, the bacterial entity, e.g., species or strain, useful in the compositions and methods of the invention is *Blautia (Ruminococcus) obeum*. In one embodiment, the bacterial entity, e.g., species or strain, useful in the compositions and methods of the invention is *Blautia producta (Ruminococcus productus)*. In one embodiment, the bacterial entity, e.g., species or strain, useful in the compositions and methods of the invention is *Blautia (Ruminococcus) schinkii*. In one embodiment, the bacterial entity, e.g., species or strain, useful in the compositions and methods of the invention is *Blautia stercoris*. In one embodiment, the bacterial entity, e.g., species or strain, useful in the compositions and methods of the invention is *Blautia* uncultured bacterium clone BKLE_a03_2 (GenBank: EU469501.1). In one embodiment, the bacterial entity, e.g., species or strain, useful in the compositions and methods of the invention is *Blautia* uncultured bacterium clone SJTU_B_14_30 (GenBank: EF402926.1). In one embodiment, the bacterial entity, e.g., species or strain, useful in the compositions and methods of the invention is *Blautia* uncultured bacterium clone SJTU_C_14_16 (GenBank: EF404657.1). In one embodiment, the bacterial entity, e.g., species or strain, useful in the compositions and methods of the invention is *Blautia* uncultured bacterium clone S1-5 (GenBank: GQ898099.1). In one embodiment, the bacterial entity, e.g., species or strain, useful in the compositions and methods of the invention is *Blautia* uncultured PAC000178_s (www.ezbiocloud.net/ez-taxon/hierarchy?m=browse&k=PAC000178&d=2). In one embodiment, the bacterial entity, e.g., species or strain, useful in the compositions and methods of the invention is *Blautia wexlerae*. In one embodiment, the bacterial entity, e.g., species or strain, useful in the compositions and methods of the invention is *Candidatus Arthromitus* sp. SFB-mouse-Yit. In one embodiment, the bacterial entity, e.g., species or strain, useful in the compositions and methods of the invention is *Catenibacterium mitsuokai*. In one embodiment, the bacterial entity, e.g., species or strain, useful in the compositions and methods of the invention is *Clostridiaceae* bacterium (*Dielma fastidiosa*) JC13. In one embodiment, the bacterial entity, e.g., species or strain, useful in the compositions and methods of the invention is *Clostridiales* bacterium 1_7_47FAA. In one embodiment, the bacterial entity, e.g., species or strain, useful in the compositions and methods of the invention is *Clostridium asparagiforme*. In one embodiment, the bacterial entity, e.g., species or strain, useful in the compositions and methods of the invention is *Clostridium bolteae*. In one embodiment, the bacterial entity, e.g., species or strain, useful in the compositions and methods of the invention is *Clostridium clostridioforme*. In one embodiment, the bacterial entity, e.g., species or strain, useful in the compositions and methods of the invention is *Clostridium glycyrrhizinilyticum*. In one embodiment, the bacterial entity, e.g., species or strain, useful in the compositions and methods of the invention is *Clostridium (Hungatella) hathewayi*. In one embodiment, the bacterial entity, e.g., species or strain, useful in the compositions and methods of the invention is *Clostridium histolyticum*. In one embodiment, the bacterial entity, e.g., species or strain, useful in the compositions and methods of the invention is *Clostridium indolis*. In one embodiment, the bacterial entity, e.g., species or strain, useful in the compositions and methods of the invention is *Clostridium leptum*. In one embodiment, the bacterial entity, e.g., species or strain, useful in the compositions and methods of the invention is *Clostridium (Tyzzerella) nexile*. In one embodiment, the bacterial entity, e.g., species or strain, useful in the compositions and methods of the invention is *Clostridium perfringens*. In one embodiment, the bacterial entity, e.g., species or strain, useful in the compositions and methods of the invention is *Clostridium (Erysipelatoclostridium) ramosum*. In one embodiment, the bacterial entity, e.g., species or strain, useful in the compositions and methods of the invention is *Clostridium scindens*. In one embodiment, the bacterial entity, e.g., species or strain, useful in the compositions and methods of the invention is *Clostridium septum*. In one embodiment, the bacterial entity, e.g., species or strain, useful in the compositions and methods of the invention is *Clostridium* sp. 14774. In one embodiment, the bacterial entity, e.g., species or strain, useful in the compositions and methods of the invention is *Clostridium* sp. 7_3_54FAA. In one embodiment, the bacterial entity, e.g., species or strain, useful in the compositions and methods of the invention is *Clostridium* sp. HGF2. In one embodiment, the bacterial entity, e.g., species or strain, useful in the compositions and methods of the invention is *Clostridium symbiosum*. In one embodiment, the bacterial entity, e.g., species or strain, useful in the compositions and methods of the invention is *Collinsella aerofaciens*. In one embodiment, the bacterial entity, e.g., species or strain, useful in the compositions and methods of the invention is *Collinsella intestinalis*. In one embodiment, the bacterial entity, e.g., species or strain, useful in the compositions and methods of the invention is *Coprobacillus* sp. D7. In one embodiment, the bacterial entity, e.g., species or strain, useful in the compositions and methods of the invention is *Coprococcus catus*. In one embodiment, the bacterial entity, e.g., species or strain, useful in the compositions and methods of the invention is

*Coprococcus comes*. In one embodiment, the bacterial entity, e.g., species or strain, useful in the compositions and methods of the invention is *Dorea formicigenerans*. In one embodiment, the bacterial entity, e.g., species or strain, useful in the compositions and methods of the invention is *Dorea longicatena*. In one embodiment, the bacterial entity, e.g., species or strain, useful in the compositions and methods of the invention is *Enterococcus faecalis*. In one embodiment, the bacterial entity, e.g., species or strain, useful in the compositions and methods of the invention is *Enterococcus faecium*. In one embodiment, the bacterial entity, e.g., species or strain, useful in the compositions and methods of the invention is Erysipelotrichaceae bacterium 3_1_53. In one embodiment, the bacterial entity, e.g., species or strain, useful in the compositions and methods of the invention is *Escherichia coli*. In one embodiment, the bacterial entity, e.g., species or strain, useful in the compositions and methods of the invention is *Escherichia coli* S88. In one embodiment, the bacterial entity, e.g., species or strain, useful in the compositions and methods of the invention is *Eubacterium eligens*. In one embodiment, the bacterial entity, e.g., species or strain, useful in the compositions and methods of the invention is *Eubacterium fissicatena*. In one embodiment, the bacterial entity, e.g., species or strain, useful in the compositions and methods of the invention is *Eubacterium ramulus*. In one embodiment, the bacterial entity, e.g., species or strain, useful in the compositions and methods of the invention is *Eubacterium rectale*. In one embodiment, the bacterial entity, e.g., species or strain, useful in the compositions and methods of the invention is *Faecalibacterium prausnitzii*. In one embodiment, the bacterial entity, e.g., species or strain, useful in the compositions and methods of the invention is *Flavonifractor plautii*. In one embodiment, the bacterial entity, e.g., species or strain, useful in the compositions and methods of the invention is *Fusobacterium mortiferum*. In one embodiment, the bacterial entity, e.g., species or strain, useful in the compositions and methods of the invention is *Fusobacterium nucleatum*. In one embodiment, the bacterial entity, e.g., species or strain, useful in the compositions and methods of the invention is *Holdemania filiformis*. In one embodiment, the bacterial entity, e.g., species or strain, useful in the compositions and methods of the invention is *Hydrogenoanaerobacterium saccharovorans*. In one embodiment, the bacterial entity, e.g., species or strain, useful in the compositions and methods of the invention is *Klebsiella oxytoca*. In one embodiment, the bacterial entity, e.g., species or strain, useful in the compositions and methods of the invention is Lachnospiraceae bacterium 3_1_57FAA_CT1. In one embodiment, the bacterial entity, e.g., species or strain, useful in the compositions and methods of the invention is Lachnospiraceae bacterium 7_1_58FAA. In one embodiment, the bacterial entity, e.g., species or strain, useful in the compositions and methods of the invention is Lachnospiraceae bacterium 5_1_57FAA. In one embodiment, the bacterial entity, e.g., species or strain, useful in the compositions and methods of the invention is *Lactobacillus casei*. In one embodiment, the bacterial entity, e.g., species or strain, useful in the compositions and methods of the invention is *Lactobacillus rhamnosus*. In one embodiment, the bacterial entity, e.g., species or strain, useful in the compositions and methods of the invention is *Lactobacillus ruminis*. In one embodiment, the bacterial entity, e.g., species or strain, useful in the compositions and methods of the invention is *Lactococcus casei*. In one embodiment, the bacterial entity, e.g., species or strain, useful in the compositions and methods of the invention is *Odoribacter splanchnicus*. In one embodiment, the bacterial entity, e.g., species or strain, useful in the compositions and methods of the invention is *Oscillibacter valericigenes*. In one embodiment, the bacterial entity, e.g., species or strain, useful in the compositions and methods of the invention is *Parabacteroides gordonii*. In one embodiment, the bacterial entity, e.g., species or strain, useful in the compositions and methods of the invention is *Parabacteroides johnsonii*. In one embodiment, the bacterial entity, e.g., species or strain, useful in the compositions and methods of the invention is *Parabacteroides merdae*. In one embodiment, the bacterial entity, e.g., species or strain, useful in the compositions and methods of the invention is *Pediococcus acidilactici*. In one embodiment, the bacterial entity, e.g., species or strain, useful in the compositions and methods of the invention is *Peptostreptococcus asaccharolyticus*. In one embodiment, the bacterial entity, e.g., species or strain, useful in the compositions and methods of the invention is *Propionibacterium granulosum*. In one embodiment, the bacterial entity, e.g., species or strain, useful in the compositions and methods of the invention is *Roseburia intestinalis*. In one embodiment, the bacterial entity, e.g., species or strain, useful in the compositions and methods of the invention is *Roseburia inulinivorans*. In one embodiment, the bacterial entity, e.g., species or strain, useful in the compositions and methods of the invention is *Ruminococcus faecis*. In one embodiment, the bacterial entity, e.g., species or strain, useful in the compositions and methods of the invention is *Ruminococcus gnavus*. In one embodiment, the bacterial entity, e.g., species or strain, useful in the compositions and methods of the invention is *Ruminococcus* sp. ID8. In one embodiment, the bacterial entity, e.g., species or strain, useful in the compositions and methods of the invention is *Ruminococcus torques*. In one embodiment, the bacterial entity, e.g., species or strain, useful in the compositions and methods of the invention is *Slackia piriformis*. In one embodiment, the bacterial entity, e.g., species or strain, useful in the compositions and methods of the invention is *Staphylococcus epidermidis*. In one embodiment, the bacterial entity, e.g., species or strain, useful in the compositions and methods of the invention is *Staphylococcus saprophyticus*. In one embodiment, the bacterial entity, e.g., species or strain, useful in the compositions and methods of the invention is *Streptococcus cristatus*. In one embodiment, the bacterial entity, e.g., species or strain, useful in the compositions and methods of the invention is *Streptococcus dysgalactiae* subsp. *Equisimilis*. In one embodiment, the bacterial entity, e.g., species or strain, useful in the compositions and methods of the invention is *Streptococcus infantis*. In one embodiment, the bacterial entity, e.g., species or strain, useful in the compositions and methods of the invention is *Streptococcus oralis*. In one embodiment, the bacterial entity, e.g., species or strain, useful in the compositions and methods of the invention is *Streptococcus sanguinis*. In one embodiment, the bacterial entity, e.g., species or strain, useful in the compositions and methods of the invention is *Streptococcus viridans*. In one embodiment, the bacterial entity, e.g., species or strain, useful in the compositions and methods of the invention is *Streptococcus thermophiles*. In one embodiment, the bacterial entity, e.g., species or strain, useful in the compositions and methods of the invention is *Veillonella dispar*.

In one embodiment, the bacterial population useful in the compositions and methods of the invention comprises *Acidaminococcus intestine*. In one embodiment, the bacterial population useful in the compositions and methods of the invention comprises *Acinetobacter baumannii*. In one embodiment, the bacterial population useful in the compositions and methods of the invention comprises *Acinetobacter lwoffii*. In one embodiment, the bacterial population useful in the compositions and methods of the invention comprises *Akkermansia muciniphila*. In one embodiment, the bacterial population useful in the compositions and methods of the invention comprises *Alistipes putredinis*. In one embodiment, the bacterial population useful in the compositions and methods of the invention comprises *Alistipes shahii*. In one embodiment, the bacterial population useful in the compositions and methods of the invention comprises *Anaerostipes hadrus*. In one embodiment, the bacterial population useful in the compositions and methods of the invention comprises *Anaerotruncus colihominis*. In one embodiment, the bacterial population useful in the compositions and methods of the invention comprises *Bacteroides caccae*. In one embodiment, the bacterial population useful in the compositions and methods of the invention comprises *Bacteroides cellulosilyticus*. In one embodiment, the bacterial population useful in the compositions and methods of the invention comprises *Bacteroides dorei*. In one embodiment, the bacterial population useful in the compositions and methods of the invention comprises *Bacteroides eggerthii*. In one embodiment, the bacterial population useful in the compositions and methods of the invention comprises *Bacteroides finegoldii*. In one embodiment, the bacterial population useful in the compositions and methods of the invention comprises *Bacteroides fragilis*. In one embodiment, the bacterial population useful in the compositions and methods of the invention comprises *Bacteroides massiliensis*. In one embodiment, the bacterial population useful in the compositions and methods of the invention comprises *Bacteroides ovatus*. In one embodiment, the bacterial population useful in the compositions and methods of the invention comprises *Bacteroides salanitronis*. In one embodiment, the bacterial population useful in the compositions and methods of the invention comprises *Bacteroides salyersiae*. In one embodiment, the bacterial population useful in the compositions and methods of the invention comprises *Bacteroides* sp. 1_1_6. In one embodiment, the bacterial population useful in the compositions and methods of the invention comprises *Bacteroides* sp. 3_1_23. In one embodiment, the bacterial population useful in the compositions and methods of the invention comprises *Bacteroides* sp. D20. In one embodiment, the bacterial population useful in the compositions and methods of the invention comprises *Bacteroides thetaiotaomicrond*. In one embodiment, the bacterial population useful in the compositions and methods of the invention comprises *Bacteroides uniformis*. In one embodiment, the bacterial population useful in the compositions and methods of the invention comprises *Bacteroides vulgatus*. In one embodiment, the bacterial population useful in the compositions and methods of the invention comprises *Bifidobacterium adolescentis*. In one embodiment, the bacterial population useful in the compositions and methods of the invention comprises *Bifidobacterium bifidum*. In one embodiment, the bacterial population useful in the compositions and methods of the invention comprises *Bifidobacterium breve*. In one embodiment, the bacterial population useful in the compositions and methods of the invention comprises *Bifidobacterium faecale*. In one embodiment, the bacterial population useful in the compositions and methods of the invention comprises *Bifidobacterium kashiwanohense*. In one embodiment, the bacterial population useful in the compositions and methods of the invention comprises *Bifidobacterium longum* subsp. *Longum*. In one embodiment, the bacterial population useful in the compositions and methods of the invention comprises *Bifidobacterium pseudocatenulatum*. In one embodiment, the bacterial population useful in the compositions and methods of the invention comprises *Bifidobacterium stercoris*. In one embodiment, the bacterial population useful in the compositions and methods of the invention comprises *Blautia* (*Ruminococcus*) *coccoides*. In one embodiment, the bacterial population useful in the compositions and methods of the invention comprises *Blautia faecis*. In one embodiment, the bacterial population useful in the compositions and methods of the invention comprises *Blautia glucerasea*. In one embodiment, the bacterial population useful in the compositions and methods of the invention comprises *Blautia* (*Ruminococcus*) *hansenii*. In one embodiment, the bacterial population useful in the compositions and methods of the invention comprises *Blautia hydrogenotrophica* (*Ruminococcus hydrogenotrophicus*). In one embodiment, the bacterial population useful in the compositions and methods of the invention comprises *Blautia* (*Ruminococcus*) *luti*. In one embodiment, the bacterial population useful in the compositions and methods of the invention comprises *Blautia* (*Ruminococcus*) *obeum*. In one embodiment, the bacterial population useful in the compositions and methods of the invention comprises *Blautia producta* (*Ruminococcus productus*). In one embodiment, the bacterial population useful in the compositions and methods of the invention comprises *Blautia* (*Ruminococcus*) *schinkii*. In one embodiment, the bacterial population useful in the compositions and methods of the invention comprises *Blautia stercoris*. In one embodiment, the bacterial population useful in the compositions and methods of the invention comprises *Blautia* uncultured bacterium clone BKLE_a03_2 (GenBank: EU469501.1). In one embodiment, the bacterial population useful in the compositions and methods of the invention comprises *Blautia* uncultured bacterium clone SJTU_B_14_30 (GenBank: EF402926.1). In one embodiment, the bacterial population useful in the compositions and methods of the invention comprises *Blautia* uncultured bacterium clone SJTU_C_14_16 (GenBank: EF404657.1). In one embodiment, the bacterial population useful in the compositions and methods of the invention comprises *Blautia* uncultured bacterium clone S1-5 (GenBank: GQ898099.1). In one embodiment, the bacterial population useful in the compositions and methods of the invention comprises *Blautia* uncultured PAC000178_s (www.ezbiocloud.net/eztaxon/hierarchy?m=browse&k=PAC000178&d=2). In one embodiment, the bacterial population useful in the compositions and methods of the invention comprises *Blautia wexlerae*. In one embodiment, the bacterial population useful in the compositions and methods of the invention comprises *Candidatus Arthromitus* sp. SFB-mouse-Yit. In one embodiment, the bacterial population useful in the compositions and methods of the invention comprises *Catenibacterium mitsuokai*. In one embodiment, the bacterial population useful in the compositions and methods of the invention comprises *Clostridiaceae* bacterium (*Dielma fastidiosa*) JC13. In one embodiment, the bacterial population useful in the compositions and methods of the invention comprises Clostridiales bacterium 1_7_47FAA. In one embodiment, the bacterial population useful in the compositions and methods of the invention comprises *Clostridium asparagiforme*. In one embodiment, the bacterial population useful in the compositions and methods of the invention comprises *Clostridium bolteae*. In one embodiment, the bacterial population useful in the compositions and methods of the invention comprises *Clostridium clostridioforme*. In one embodiment, the bacterial population useful in the compositions and methods of the invention comprises *Clostridium glycyrrhizinilyticum*. In one embodiment, the bacterial population useful in the compositions and methods of the invention comprises *Clostridium (Hungatella) hathewayi*. In one embodiment, the bacterial population useful in the compositions and methods of the invention comprises *Clostridium histolyticum*. In one embodiment, the bacterial population useful in the compositions and methods of the invention comprises *Clostridium indolis*. In one embodiment, the bacterial population useful in the compositions and methods of the invention comprises *Clostridium leptum*. In one embodiment, the bacterial population useful in the compositions and methods of the invention comprises *Clostridium (Tyzzerella) nexile*. In one embodiment, the bacterial population useful in the compositions and methods of the invention comprises *Clostridium perfringens*. In one embodiment, the bacterial population useful in the compositions and methods of the invention comprises *Clostridium (Erysipelatoclostridium) ramosum*. In one embodiment, the bacterial population useful in the compositions and methods of the invention comprises *Clostridium scindens*. In one embodiment, the bacterial entity, e.g., species or strain, useful in the compositions and methods of the invention is *Clostridium septum*. In one embodiment, the bacterial population useful in the compositions and methods of the invention comprises *Clostridium* sp. 14774. In one embodiment, the bacterial population useful in the compositions and methods of the invention comprises *Clostridium* sp. 7_3_54FAA. In one embodiment, the bacterial population useful in the compositions and methods of the invention comprises *Clostridium* sp. HGF2. In one embodiment, the bacterial population useful in the compositions and methods of the invention comprises *Clostridium symbiosum*. In one embodiment, the bacterial population useful in the compositions and methods of the invention comprises *Collinsella aerofaciens*. In one embodiment, the bacterial population useful in the compositions and methods of the invention comprises *Collinsella intestinalis*. In one embodiment, the bacterial population useful in the compositions and methods of the invention comprises *Coprobacillus* sp. D7. In one embodiment, the bacterial population useful in the compositions and methods of the invention comprises *Coprococcus catus*. In one embodiment, the bacterial population useful in the compositions and methods of the invention comprises *Coprococcus comes*. In one embodiment, the bacterial population useful in the compositions and methods of the invention comprises *Dorea formicigenerans*. In one embodiment, the bacterial population useful in the compositions and methods of the invention comprises *Dorea longicatena*. In one embodiment, the bacterial population useful in the compositions and methods of the invention comprises *Enterococcus faecalis*. In one embodiment, the bacterial population useful in the compositions and methods of the invention comprises *Enterococcus faecium*. In one embodiment, the bacterial population useful in the compositions and methods of the invention comprises Erysipelotrichaceae bacterium 3_1_53. In one embodiment, the bacterial population useful in the compositions and methods of the invention comprises *Escherichia coli*. In one embodiment, the bacterial population useful in the compositions and methods of the invention comprises *Escherichia coli* S88. In one embodiment, the bacterial population useful in the compositions and methods of the invention comprises *Eubacterium eligens*. In one embodiment, the bacterial population useful in the compositions and methods of the invention comprises *Eubacterium fissicatena*. In one embodiment, the bacterial population useful in the compositions and methods of the invention comprises *Eubacterium ramulus*. In one embodiment, the bacterial population useful in the compositions and methods of the invention comprises *Eubacterium rectale*. In one embodiment, the bacterial population useful in the compositions and methods of the invention comprises *Faecalibacterium prausnitzii*. In one embodiment, the bacterial population useful in the compositions and methods of the invention comprises *Flavonifractor plautii*. In one embodiment, the bacterial population useful in the compositions and methods of the invention comprises *Fusobacterium mortiferum*. In one embodiment, the bacterial population useful in the compositions and methods of the invention comprises *Fusobacterium nucleatum*. In one embodiment, the bacterial population useful in the compositions and methods of the invention comprises *Holdemania filiformis*. In one embodiment, the bacterial population useful in the compositions and methods of the invention comprises *Hydrogenoanaerobacterium saccharovorans*. In one embodiment, the bacterial population useful in the compositions and methods of the invention comprises *Klebsiella oxytoca*. In one embodiment, the bacterial population useful in the compositions and methods of the invention comprises Lachnospiraceae bacterium 3_1_57FAA_CT1. In one embodiment, the bacterial population useful in the compositions and methods of the invention comprises Lachnospiraceae bacterium 7_1_58FAA. In one embodiment, the bacterial population useful in the compositions and methods of the invention comprises Lachnospiraceae bacterium 5_1_57FAA. In one embodiment, the bacterial population useful in the compositions and methods of the invention comprises *Lactobacillus casei*. In one embodiment, the bacterial population useful in the compositions and methods of the invention comprises *Lactobacillus rhamnosus*. In one embodiment, the bacterial population useful in the compositions and methods of the invention comprises *Lactobacillus ruminis*. In one embodiment, the bacterial population useful in the compositions and methods of the invention comprises *Lactococcus casei*. In one embodiment, the bacterial population useful in the compositions and methods of the invention comprises *Odoribacter splanchnicus*. In one embodiment, the bacterial population useful in the compositions and methods of the invention comprises *Oscillibacter valericigenes*. In one embodiment, the bacterial population useful in the compositions and methods of the invention comprises *Parabacteroides gordonii*. In one embodiment, the bacterial population useful in the compositions and methods of the invention comprises *Parabacteroides johnsonii*. In one embodiment, the bacterial population useful in the compositions and methods of the invention comprises *Parabacteroides merdae*. In one embodiment, the bacterial population useful in the compositions and methods of the invention comprises *Pediococcus acidilactici*. In one embodiment, the bacterial population useful in the compositions and methods of the invention comprises *Peptostreptococcus asaccharolyticus*. In one embodiment, the bacterial population useful in the compositions and methods of the invention comprises *Propionibacterium granulosum*. In one embodiment, the bacterial population useful in the compositions and methods of the invention comprises *Roseburia intestinalis*. In one embodiment, the bacterial population useful in the compositions and methods of the invention comprises *Roseburia inulinivorans*. In one embodiment, the bacterial population useful in the compositions and methods of the invention comprises *Ruminococcus faecis*. In one embodiment, the bacterial population useful in the compositions and methods of the invention comprises *Ruminococcus gnavus*. In one embodiment, the bacterial population useful in the compositions and methods of the invention comprises *Ruminococcus* sp. ID8. In one embodiment, the bacterial population useful in the compositions and methods of the invention comprises *Ruminococcus torques*. In one embodiment, the bacterial population useful in the compositions and methods of the invention comprises *Slackia piriformis*. In one embodiment, the bacterial population useful in the compositions and methods of the invention comprises *Staphylococcus epidermidis*. In one embodiment, the bacterial population useful in the compositions and methods of the invention comprises *Staphylococcus saprophyticus*. In one embodiment, the bacterial population useful in the compositions and methods of the invention comprises *Streptococcus cristatus*. In one embodiment, the bacterial population useful in the compositions and methods of the invention comprises *Streptococcus dysgalactiae* subsp. *Equisimilis*. In one embodiment, the bacterial population useful in the compositions and methods of the invention comprises *Streptococcus infantis*. In one embodiment, the bacterial population useful in the compositions and methods of the invention comprises *Streptococcus oralis*. In one embodiment, the bacterial population useful in the compositions and methods of the invention comprises *Streptococcus sanguinis*. In one embodiment, the bacterial population useful in the compositions and methods of the invention comprises *Streptococcus viridans*. In one embodiment, the bacterial population useful in the compositions and methods of the invention comprises *Streptococcus thermophiles*. In one embodiment, the bacterial population useful in the compositions and methods of the invention comprises *Veillonella dispar*.

In some embodiments, the therapeutic composition comprises engineered microbes. For example, engineered microbes include microbes harboring i) one or more genetic changes, such change being an insertion, deletion, translocation, or substitution, or any combination thereof, of one or more nucleotides contained on the bacterial chromosome or on an endogenous plasmid, wherein the genetic change may result in the alteration, disruption, removal, or addition of one or more protein coding genes, non-protein-coding genes, gene regulatory regions, or any combination thereof, and wherein such change may be a fusion of two or more separate genomic regions or may be synthetically derived; ii) one or more foreign plasmids containing a mutant copy of an endogenous gene, such mutation being an insertion, deletion, or substitution, or any combination thereof, of one or more nucleotides; and iii) one or more foreign plasmids containing a mutant or non-mutant exogenous gene or a fusion of two or more endogenous, exogenous, or mixed genes. The engineered microbe(s) may be produced using techniques including but not limited to site-directed mutagenesis, transposon mutagenesis, knock-outs, knock-ins, polymerase chain reaction mutagenesis, chemical mutagenesis, ultraviolet light mutagenesis, transformation (chemically or by electroporation), phage transduction, or any combination thereof. Suitable microbes for engineering are known in the art. For example, as described in PCT Publications Nos. WO/93/18163, DELIVERY AND EXPRESSION OF A HYBRID SURFACE PROTEIN ON THE SURFACE OF GRAM POSITIVE BACTERIA; WO/03/06593, METHODS FOR TREATING CANCER BY ADMINISTERING TUMOR-TARGETED BACTERIA AND AN IMMUNOMODULATORY AGENT; and WO/2010/141143, ENGINEERED AVIRULENT BACTERIA STRAINS AND USE IN MEDICAL TREATMENTS.

In some embodiments, the engineered microbes are natural human commensals. In other embodiments, the engineered microbes are attenuated strains of pathogens, and may include, but are not limited to, *Pseudomonas aeruginosa, Salmonella species, Listeria monocytogenes, Mycoplasma hominis, Escherichia coli, Shigella species*, and *Streptococcus* species, see, e.g. PCT Publications No. WO/03/06593, METHODS FOR TREATING CANCER BY ADMINISTERING TUMOR-TARGETED BACTERIA AND AN IMMUNOMODULATORY AGENT. Attenuated strains of pathogens will lack all or parts of virulence operons, may lack immune-stimulatory surface moieties (e.g. lipopolysaccharide for Gram-negative bacteria), and may contain one or more nutrient auxotrophies. In specific embodiments, the engineered microbes are attenuated intracellular pathogens, such as a virulent strains of *Listeria monocytogenes*.

In some embodiments, the composition of the invention comprises one or more types of microbe capable of producing butyrate in a mammalian subject. Butyrate-producing microbes may be identified experimentally, such as by NMR or gas chromatography analyses of microbial products or colorimetric assays (Rose I A. 1955. Methods Enzymol. Acetate kinase of bacteria. 1: 591-5). Butyrate-producing microbes may also be identified computationally, such as by the identification of one or more enzymes involved in butyrate synthesis. Non-limiting examples of enzymes found in butyrate-producing microbes include butyrate kinase, phosphotransbutyrylase, and butyryl CoA:acetate CoA transferase (Louis P., et al. 2004. Restricted Distribution of the Butyrate Kinase Pathway among Butyrate-Producing Bacteria from the Human Colon. J Bact. 186(7): 2099-2106). Butyrate-producing strains include, but are not limited to, *Faecalibacterium prausnitzii, Eubacterium* spp., *Butyrivibrio fibrisolvens, Roseburia intestinalis, Clostridium* spp., *Anaerostipes caccae*, and *Ruminococcus* spp. In some embodiments, composition comprises two or more types of microbe, wherein at least two types of microbe are capable of producing butyrate in a mammalian subject. In other embodiments, the composition comprises two or more types of microbe, wherein two or more types of microbe cooperate (i.e., cross-feed) to produce an immunomodulatory SCFA (e.g., butyrate) in a mammalian subject. In a preferred embodiment, the composition comprises at least one type of microbe (e.g., *Bifidobacterium* spp.) capable of metabolizing a prebiotic, including but not limited to, inulin, inulin-type fructans, or oligofructose, such that the resulting metabolic product may be converted by a second type of microbe (e.g., a butyrate-producing microbe such as *Roseburia* spp.) to an immunomodulatory SCFA such as butyrate (Falony G., et al. 2006. Cross-Feeding between *Bifidobacterium longum* BB536 and Acetate-Converting, Butyrate-Producing Colon Bacteria during Grown on Oligofructose. Appl. Environ. Microbiol. 72(12): 7835-7841.) In other aspects, the composition comprises at least one acetate-producing microbe (e.g., *Bacteroides thetaiotaomicron*) and at least one acetate-consuming, butyrate-producing microbe (e.g., *Faecalibacterium prausnitzii*).

In some embodiments, the composition comprises one or more types of microbe capable of producing propionate in a mammalian subject, optionally further comprising a prebiotic or substrate appropriate for proprionate biosynthesis. Examples of prebiotics or substrates used for the production of propionate include, but are not limited to, L-rhamnose, D-tagalose, resistant starch, inulin, polydextrose, arabinoxylans, arabinoxylan oligosaccharides, mannooligosaccharides, and laminarans (Hosseini E., et al. 2011. Propionate as a health-promoting microbial metabolite in the human gut.

Nutrition Reviews. 69(5): 245-258). Propionate-producing microbes may be identified experimentally, such as by NMR or gas chromatography analyses of microbial products or colorimetric assays (Rose I A. 1955. Methods Enzymol. Acetate kinase of bacteria. 1: 591-5). Propionate-producing microbes may also be identified computationally, such as by the identification of one or more enzymes involved in propionate synthesis. Non-limiting examples of enzymes found in propionate-producing microbes include enzymes of the succinate pathway, including but not limited to phophoenylpyrvate carboxykinase, pyruvate kinase, pyruvate carboxylase, malate dehydrogenase, fumarate hydratase, succinate dehydrogenase, succinyl CoA synthetase, methylmalonyl Coa decarboxylase, and propionate CoA transferase, as well as enzymes of the acrylate pathway, including but not limited to L-lactate dehydrogenase, propionate CoA transferase, lactoyl CoA dehydratase, acyl CoA dehydrogenase, phosphate acetyltransferase, and propionate kinase. Non-limiting examples of microbes that utilize the succinate pathway are *Bacteroides fragilis* and other species (including *B. vulgatus*), *Propionibacterium* spp. (including *freudenrichii* and *acidipropionici*), *Veillonella* spp. (including *gazogenes*), *Micrococcus lactilyticus*, *Selenomonas ruminantium*, *Escherichia coli*, and *Prevotella ruminocola*. Non-limiting examples of microbes that utilize the acrylate pathway are *Clostridium neopropionicum* X4, and *Megasphaera elsdenii*.

In preferred embodiments, the combination of a microbe or microbial composition and a prebiotic is selected based on the fermentation or metabolic preferences of one or more microbes capable of producing immunomodulatory SCFAs (e.g., preference for complex versus simple sugar or preference for a fermentation product versus a prebiotic). For example, *M. eldsenii* prefers lactate fermentation to glucose fermentation, and maximization of propionate production by *M. eldsenii* in a mammalian subject may therefore be achieved by administering along with *M. eldsenii* a favored substrate (e.g., lactate) or one or more microbes capable of fermenting glucose into lactate (e.g., *Streptococcus bovis*) (Hosseini E., et al. 2011. Propionate as a health-promoting microbial metabolite in the human gut. Nutrition Reviews. 69(5): 245-258). Thus, in some embodiments, the composition comprises at least one type of SCFA-producing microbe and a sugar fermentation product (e.g., lactate). In other embodiments, the composition comprises at least one type of SCFA-producing microbe and at least one type of sugar-fermenting microbe, wherein the fermentation product of the second, sugar-fermenting microbe is the preferred substrate of the SCFA-producing microbe.

Immunomodulation can also be achieved by the microbial production of glutathione or gamma-glutamylcysteine. Thus, in certain embodiments, the pharmaceutical composition, dosage form, or kit comprises at least one type of microbe capable of producing glutathione and/or gamma-glutamylcysteine in a mammalian subject. In some aspects, the composition comprises one or more microbes selected for the presence of glutamate cysteine ligase (e.g., *Lactobacillus fermentum*) and/or L-proline biosynthesis enzymes (e.g., *E. coli*) (Peran et al., 2006. *Lactobacillus fermenum*, a probiotic capable to release glutathione, prevents colonic inflammation in the TNBS model of rat colitis. Int J Colorectal Dis. 21(8): 737-746; Veeravalli et al., 2011. Laboratory evolution of glutathione biosynthesis reveals naturally compensatory pathways. Nat Chem Bio. 7(2): 101-105). In a preferred embodiment, at least one microbe in the composition is *L. fermentum*.

para-cresol (p-cresol) is a microbial product, via the fermentation of tyrosine or phenylalanine. Sulfated in the liver or colon to p-cresyl sulfate, this molecule reduces Th1-mediated responses (Shiba T. et al. 2014. Effects of intestinal bacteria-derived p-cresyl sulfate on Th1-type immune response in vivo and in vitro. Tox and Applied Pharm. 274(2): 191-199). In some embodiments, the composition comprises at least one type of microbe capable of fermenting tyrosine and/or phenylalanine to p-cresol in a mammalian subject. Non-limiting examples of such microbes include *Bacteroides fragilis, Clostridium difficile*, and *Lactobacillus* sp. Strain #11198-11201 (Yokoyama M T and Carlson J R. 1981. Production of Skatole and para-Cresol by a Rumen *Lactobacillus* sp. Applied and Environmental Microbiology. 41(1): 71-76), and other microbes with p-hydroxylphenyl acetate decarboxylase activity.

IV. Methods of Making/Isolating Probiotic Compositions

In one embodiment, provided herein are therapeutic compositions containing a purified population of bacterial entities and/or fungal entities. The purified population can contain a single species, or multiple species. As used herein, the terms "purify", "purified" and "purifying" refer to the state of a population (e.g., a plurality of known or unknown amount and/or concentration) of desired bacterial entities and/or fungal entities, that have undergone one or more processes of purification, e.g., a selection or an enrichment of the desired bacterial, or alternatively a removal or reduction of residual habitat products as described herein. In some embodiments, a purified population has no detectable undesired activity or, alternatively, the level or amount of the undesired activity is at or below an acceptable level or amount. In other embodiments, a purified population has an amount and/or concentration of desired bacterial entities and/or fungal entities at or above an acceptable amount and/or concentration. In other embodiments, the ratio of desired-to-undesired activity (e.g., spores compared to vegetative bacteria), has changed by 2-, 5-, 10-, 30-, 100-, 300-, $1 \times 10^4$, $1 \times 10^5$, $1 \times 10^6$, $1 \times 10^7$, $1 \times 10^8$, or greater than $1 \times 10^8$. In other embodiments, the purified population of bacterial entities and/or fungal entities is enriched as compared to the starting material (e.g., a fecal material) from which the population is obtained. This enrichment may be by 10%, 20%, 30%, 40%, 50%, 60%, 70%, 80%, 90%, 95%, 96%, 97%, 98%, 99%, 99.9%, 99.99%, 99.999%, 99.9999%, 99.9999%, or greater than 99.999999% as compared to the starting material.

In certain embodiments, the purified populations of bacterial entities and/or fungal entities have reduced or undetectable levels of one or more pathogenic activities, such as toxicity, an ability to cause infection of the mammalian recipient subject, an undesired immunomodulatory activity, an autoimmune response, a metabolic response, or an inflammatory response or a neurological response. Such a reduction in a pathogenic activity may be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material. In other embodiments, the purified populations of bacterial entities and/or fungal entities have reduced sensory components as compared to fecal material, such as reduced odor, taste, appearance, and umami.

In another embodiment, the invention provides purified populations of bacterial entities and/or fungal entities that are substantially free of residual habitat products. In certain embodiments, this means that the bacterial composition no longer contains a substantial amount of the biological matter associated with the microbial community while living on or in the human or animal subject, and the purified population of spores may be 100% free, 99% free, 98% free, 97% free, 96% free, 95% free, 94% free, 93% free, 92% free, 91% free, 90% free, 85% free, 80% free, 75% free, 70% free, 60% free, or 50% free of any contamination of the biological matter associated with the microbial community. Substantially free of residual habitat products may also mean that the bacterial composition contains no detectable cells from a human or animal, and that only microbial cells are detectable, in particular, only desired microbial cells are detectable. In another embodiment, it means that fewer than $1\times10^{-2}\%$, $1\times10^{-3}\%$, $1\times10^{-4}\%$, $1\times10^{-5}\%$, $1\times10^{-6}\%$, $1\times10^{-7}\%$, $1\times10^{-8}\%$ of the cells in the bacterial composition are human or animal, as compared to microbial cells. In another embodiment, the residual habitat product present in the purified population is reduced at least a certain level from the fecal material obtained from the mammalian donor subject, e.g., reduced by at least about 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999%.

In one embodiment, substantially free of residual habitat products or substantially free of a detectable level of a pathogenic material means that the bacterial composition contains no detectable viral (including bacterial viruses (i.e., phage)), fungal, or mycoplasmal or toxoplasmal contaminants, or a eukaryotic parasite such as a helminth. Alternatively, the purified spore populations are substantially free of an acellular material, e.g., DNA, viral coat material, or non-viable bacterial material. Alternatively, the purified spore population may processed by a method that kills, inactivates, or removes one or more specific undesirable viruses, such as an enteric virus, including norovirus, poliovirus or hepatitis A virus.

As described herein, purified spore populations can be demonstrated by, for example, genetic analysis (e.g., PCR, DNA sequencing), serology and antigen analysis, microscopic analysis, microbial analysis including germination and culturing, or methods using instrumentation such as flow cytometry with reagents that distinguish desired bacterial entities and/or fungal entities from non-desired, contaminating materials.

In one embodiment, the spore preparation comprises spore-forming species wherein residual non-spore forming species have been inactivated by chemical or physical treatments including ethanol, detergent, heat, sonication, and the like; or wherein the non-spore forming species have been removed from the spore preparation by various separations steps including density gradients, centrifugation, filtration and/or chromatography; or wherein inactivation and separation methods are combined to make the spore preparation. In yet another embodiment, the spore preparation comprises spore-forming species that are enriched over viable non-spore formers or vegetative forms of spore formers. In this embodiment, spores are enriched by 2-fold, 5-fold, 10-fold, 50-fold, 100-fold, 1000-fold, 10,000-fold or greater than 10,000-fold compared to all vegetative forms of bacteria. In yet another embodiment, the spores in the spore preparation undergo partial germination during processing and formulation such that the final composition comprises spores and vegetative bacteria derived from spore forming species.

In another embodiment, provided herein are methods for production of a composition, e.g., a probiotic composition, comprising a bacterial population, e.g., an anti-inflammatory bacterial population, or a fungal population, with or without one or more prebiotic, suitable for therapeutic administration to a mammalian subject in need thereof. In one embodiment, the composition can be produced by generally following the steps of: (a) providing a fecal material obtained from a mammalian donor subject; and (b) subjecting the fecal material to at least one purification treatment or step under conditions such that a population of bacterial entities and/or fungal entities is produced from the fecal material.

Individual bacterial strains can also be isolated from stool samples using culture methods. For example, 5 mls of phosphate-buffered saline (PBS) is added to 1 mg of frozen stool sample and homogenized by vortexing in an anaerobic chamber for isolation of anaerobic bacteria. The suspension is then serially diluted ten-fold (e.g. $10^{-1}$ to $10^{-9}$ dilutions) and 100 μl aliquots of each dilution are spread evenly over the surface of agar plates containing different formulations e.g. anaerobic blood agar plates, *Bacteroides* bile esculin plates, laked kanamycin vancomycin plates, egg yolk agar plates and de Man Rogosa and Sharpe agar plates. Inverted plates are incubated in an anaerobic chamber for 48 hr+/−4 hours. Colonies with different morphologies are picked and replated on anaerobic blood agar plates for further testing, PCR analysis and 16 S sequencing. Selected bacterial strains can be grown for therapeutic use singly or in combination.

In one embodiment, a probiotic composition of the invention is not a fecal transplant. In some embodiments all or essentially all of the bacterial entities present in a purified population are originally obtained from a fecal material and subsequently, e.g., for production of pharmaceutical compositions, are grown in culture as described herein or otherwise known in the art. In one embodiment, the bacterial cells are cultured from a bacterial stock and purified as described herein. In one embodiment, each of the populations of bacterial cells are independently cultured and purified, e.g., each population is cultured separately and subsequently mixed together. In one embodiment, one or more of the populations of bacterial cells in the composition are co-cultured.

Donor Materials and Screening

Typically, bacteria and fungi are derived from biological samples, which may include one or more micriobiotal populations. Exemplary biological samples include fecal materials such as feces or materials isolated from the various segments of the small and large intestine. Fecal materials are obtained from a mammalian donor subject, or can be obtained from more than one donor subject, e.g., 2, 3, 4, 5, 6, 7, 8, 9, 10, 15, 20, 25, 30, 35, 40, 45, 50, 75, 100, 200, 300, 400, 500, 750, 1000 or from greater than 1000 donors, where such materials are then pooled prior to purification of the desired bacterial entities and/or fungal entities. In another embodiment, fecal materials can be obtained from a single donor subject over multiple times and pooled from multiple samples, e.g., 1, 2, 3, 4, 5, 6, 7, 8, 9, 10, 15, 20, 25, 30, 32, 35, 40, 45, 48, 50, 100 samples from a single donor.

In alternative embodiments, the desired bacterial entities and/or fungal entities are purified from a single fecal material sample obtained from a single donor, and after such purification are combined with purified spore populations from other purifications, either from the same donor at a different time, or from one or more different donors, or both.

In some embodiments, all or essentially all of the bacterial entities and/or fungal entities present in a purified population are obtained from a fecal material treated as described herein or otherwise known in the art. In some embodiments all or essentially all of the bacterial entities and/or fungal entities present in a purified population are obtained from a fecal material and subsequently are grown in culture as described herein or otherwise known in the art. In alternative embodiments, one or more than one bacterial entities and/or fungal entities or types of bacterial entities and/or fungal entities are generated in culture and combined to form a purified spore population. In other alternative embodiments, one or more of these culture-generated spore populations are combined with a fecal material-derived spore population to generate a hybrid spore population.

Preferably the biological sample includes a fecal material, such as obtained from a healthy mammalian donor subject or a plurality of mammalian donor subjects. In some embodiments, the biological material is not a fecal sample. Other appropriate biological samples include, but are not limited to, vaginal or cervical swabs, skin swabs, and bronchoalveolar lavage fluid (BALF).

In some embodiments, mammalian donor subjects are generally of good health and have microbiota consistent with such good health. In one embodiment, the donor subjects have not been administered antibiotic compounds within a certain period prior to the collection of the fecal material. In certain embodiments, the donor subjects are not obese or overweight, and may have body mass index (BMI) scores of below 25, such as between 18.5 and 24.9. In other embodiments, the donor subjects are not mentally ill or have no history or familial history of mental illness, such as anxiety disorder, depression, bipolar disorder, autism spectrum disorders, schizophrenia, panic disorders, attention deficit (hyperactivity) disorders, eating disorders or mood disorders. In other embodiments, the donor subjects do not have Irritable Bowel Disease (e.g., crohn's disease, ulcerative colitis), irritable bowel syndrome, celiac disease, colorectal cancer or a family history of these diseases. In other embodiments, donors have been screened for blood borne pathogens and fecal transmissible pathogens using standard techniques known to one in the art (e.g., nucleic acid testing, serological testing, antigen testing, culturing techniques, enzymatic assays, assays of cell free fecal filtrates looking for toxins on susceptible cell culture substrates).

In some embodiments, donors are also selected for the presence of certain genera and/or species that provide increased efficacy of therapeutic compositions containing these genera or species. In other embodiments, donors are preferred that produce relatively higher concentrations of spores in fecal material than other donors. In further embodiments, donors are preferred that provide fecal material from which spores having increased efficacy are purified; this increased efficacy is measured using in vitro or in animal studies as described below. In some embodiments, the donor may be subjected to one or more pre-donation treatments in order to reduce undesired material in the fecal material, and/or increase desired spore populations.

In one embodiment, it is advantageous to screen the health of the donor subject prior to and optionally, one or more times after, the collection of the fecal material. Such screening identifies donors carrying pathogenic materials such as viruses (HIV, hepatitis, polio) and pathogenic bacteria. Post-collection, donors are screened about one week, two weeks, three weeks, one month, two months, three months, six months, one year or more than one year, and the frequency of such screening may be daily, weekly, bi-weekly, monthly, bi-monthly, semi-yearly or yearly. Donors that are screened and do not test positive, either before or after donation or both, are considered "validated" donors.

Methods for Purifying Spores

In one embodiment, treatment of fecal sample includes heating the material, e.g., above 25 degrees Celsius for at least 30 seconds, and/or contacting the material with a solvent, and/or and or contacting a chemical or providing a physical manipulation of the material. Culture of fecal material includes replicating the purified population in a liquid suspension and/or a solid medium. Optionally, one removes at least a portion of an acellular component of the fecal material, thereby separating immunomodulatory bacteria from acellular material. The treatment step may also include depleting or inactivating a pathogenic material.

Solvent treatments. The bacteria and/or fungi may contain a purified population obtained from a miscible solvent treatment of the fecal material or a fraction or derivative thereof. In one embodiment, to purify the bacterial entities and/or fungal entities, the fecal material can be subjected to one or more solvent treatments. A solvent treatment is a miscible solvent treatment (either partially miscible or fully miscible) or an immiscible solvent treatment. Miscibility is the ability of two liquids to mix with each to form a homogeneous solution. Water and ethanol, for example, are fully miscible such that a mixture containing water and ethanol in any ratio will show only one phase. Miscibility is provided as a wt/wt %, or weight of one solvent in 100 g of final solution. If two solvents are fully miscible in all proportions, their miscibility is 100%. Provided as fully miscible solutions with water are alcohols, e.g., methanol, ethanol, isopropanol, butanol, propanediol, butanediol, etc. The alcohols can be provided already combined with water; e.g., a solution containing 10%, 20%, 25%, 30%, 35%, 40%, 45%, 50%, 55%, 60%, 65%, 70%, 75%, 89%, 85%, 90%, 95% or greater than 95% water. Other solvents are only partially miscible, meaning that only some portion will dissolve in water. Diethyl ether, for example, is partially miscible with water. Up to 7 grams of diethyl ether will dissolve in 93 grams of water to give a 7% (wt/wt %) solution. If more diethyl ether is added, a two-phase solution will result with a distinct diethyl ether layer above the water. Other partially miscible materials include ethers, propanoate, butanoate, chloroform, dimethoxyethane, or tetrahydrofuran. In contrast, an oil such as an alkane and water are immiscible and form two phases. Further, immiscible treatments are optionally combined with a detergent, either an ionic detergent or a non-ionic detergent. Exemplary detergents include Triton X-100, Tween 20, Tween 80, Nonidet P40, a pluronic, or a polyol.

In one embodiment, the solvent treatment steps reduces the viability of non-spore forming bacterial species by 10%, 20%, 30%, 40%, 50%, 60%, 70%, 80%, 85%, 90%, 95%, 99%, 99.9%, 99.99%, 99.999%, or 99.9999%, and it may optionally reduce the viability of contaminating protists, parasites and/or viruses.

Chromatography treatments. To purify spore populations, the fecal materials may be subjected to one or more chromatographic treatments, either sequentially or in parallel. In a chromatographic treatment, a solution containing the fecal material is contacted with a solid medium containing a hydrophobic interaction chromatographic (HIC) medium or an affinity chromatographic medium. In an alternative embodiment, a solid medium capable of absorbing a residual habitat product present in the fecal material is contacted with a solid medium that adsorbs a residual habitat product. In certain embodiments, the HIC medium contains sepharose or a derivatized sepharose such as butyl sepharose, octyl sepharose, phenyl sepharose, or butyl-s sepharose. In other embodiments, the affinity chromatographic medium contains material derivatized with mucin type I, II, III, IV, V, or VI, or oligosaccharides derived from or similar to those of mucins type I, II, III, IV, V, or VI. Alternatively, the affinity chromatographic medium contains material derivatized with antibodies that recognize immunomodulatory bacteria.

Mechanical treatments. In one embodiment, the fecal material can be physically disrupted, particularly by one or more mechanical treatment such as blending, mixing, shaking, vortexing, impact pulverization, and sonication. As provided herein, the mechanical disrupting treatment substantially disrupts a non-spore material present in the fecal material and does not substantially disrupt a spore present in the fecal material, or it may disrupt the spore material less than the non-spore material, e.g., 2-fold less, 5-, 10-, 30-, 100-, 300-, 1000- or greater than 1000-fold less. Furthermore, mechanical treatment homogenizes the material for subsequent sampling, testing, and processing. Mechanical treatments optionally include filtration treatments, where the desired spore populations are retained on a filter while the undesirable (non-spore) fecal components to pass through, and the spore fraction is then recovered from the filter medium. Alternatively, undesirable particulates and eukaryotic cells may be retained on a filter while bacterial cells including spores pass through. In some embodiments the spore fraction retained on the filter medium is subjected to a diafiltration step, wherein the retained spores are contacted with a wash liquid, typically a sterile saline-containing solution or other diluent such as a water compatible polymer including a low-molecular polyethylene glycol (PEG) solution, in order to further reduce or remove the undesirable fecal components.

Thermal treatments. In another embodiment, thermal disruption of the fecal material may be utilized. Generally, in one embodiment, the fecal material is mixed in a saline-containing solution such as phosphate-buffered saline (PBS) and subjected to a heated environment, such as a warm room, incubator, water-bath, or the like, such that efficient heat transfer occurs between the heated environment and the fecal material. Preferably the fecal material solution is mixed during the incubation to enhance thermal conductivity and disrupt particulate aggregates. Thermal treatments can be modulated by the temperature of the environment and/or the duration of the thermal treatment. For example, the fecal material or a liquid comprising the fecal material is subjected to a heated environment, e.g., a hot water bath of at least about 20, 25, 30, 35, 40, 45, 50, 55, 60, 65, 70, 75, 80, 85, 90, 95, 100 or greater than 100 degrees Celsius, for at least about 1, 5, 10, 15, 20, 30, 45 seconds, or 1, 2, 3, 4, 5, 6, 7, 8, 9, 10, 15, 20, 25, 30, 40, or 50 minutes, or 1, 2, 3, 4, 5, 6, 7, 8, 9, 10 or more than 10 hours. In certain embodiments the thermal treatment occurs at two different temperatures, such as 30 seconds in a 100 degree Celsius environment followed by 10 minutes in a 50 degree Celsius environment. In preferred embodiments the temperature and duration of the thermal treatment are sufficient to kill or remove pathogenic materials while not substantially damaging or reducing the germination-competency of the spores. In other preferred embodiments, the temperature and duration of the thermal treatment is short enough to reduce the germination of the spore population.

Irradiation treatments. In another embodiment, methods of treating the fecal material or separated contents of the fecal material with ionizing radiation, typically gamma irradiation, ultraviolet irradiation or electron beam irradiation provided at an energy level sufficient to kill pathogenic materials while not substantially damaging the desired spore populations may be used. For example, ultraviolet radiation at 254 nm provided at an energy level below about 22,000 microwatt seconds per $cm^2$ will not generally destroy desired spores.

Centrifugation and density separation treatments. In one embodiment, desired spore populations may be separated from the other components of the fecal material by centrifugation. For example, a solution containing the fecal material can be subjected to one or more centrifugation treatments, e.g., at about 200× g, 1000× g, 2000× g, 3000× g, 4000× g, 5000× g, 6000× g, 7000× g, 8000× g or greater than 8000× g. Differential centrifugation separates desired spores from undesired non-spore material; at low forces the spores are retained in solution, while at higher forces the spores are pelleted while smaller impurities (e.g., virus particles, phage, microscopic fibers, biological macromolecules such as free protein, nucleic acids and lipids) are retained in solution. For example, a first low force centrifugation pellets fibrous materials; a second, higher force centrifugation pellets undesired eukaryotic cells, and a third, still higher force centrifugation pellets the desired spores while smaller contaminants remain in suspension. In some embodiments density or mobility gradients or cushions (e.g., step cushions), such as CsCl, Percoll, Ficoll, Nycodenz, Histodenz or sucrose gradients, are used to separate desired spore populations from other materials in the fecal material.

Also provided herein are methods of producing spore populations that combine two or more of the treatments described herein in order to synergistically purify the desired spores while killing or removing undesired materials and/or activities from the spore population. It is generally desirable to retain the spore populations under non-germinating and non-growth promoting conditions and media, in order to minimize the growth of pathogenic bacteria present in the spore populations and to minimize the germination of spores into vegetative bacterial cells.

The bacteria and/or fungi may contain a spore population, e.g., spores and/or spore-formers, or a population containing vegetative cells.

Methods for Preparing a Bacterial Composition for Administration to a Subject.

In one embodiment, methods for producing bacterial compositions can include three main processing steps, combined with one or more mixing steps. For example, the steps can include organism banking, organism production, and preservation.

For banking, the strains included in the bacterial composition may be (1) isolated directly from a specimen or taken from a banked stock, (2) optionally cultured on a nutrient agar or broth that supports growth to generate viable biomass, and (3) the biomass optionally preserved in multiple aliquots in long-term storage.

In embodiments that use a culturing step, the agar or broth can contain nutrients that provide essential elements and specific factors that enable growth. An example includes a medium composed of 20 g/L glucose, 10 g/L yeast extract, 10 g/L soy peptone, 2 g/L citric acid, 1.5 g/L sodium phosphate monobasic, 100 mg/L ferric ammonium citrate, 80 mg/L magnesium sulfate, 10 mg/L hemin chloride, 2 mg/L calcium chloride, 1 mg/L menadione. A variety of microbiological media and variations are well known in the art (e.g. R. M. Atlas, *Handbook of Microbiological Media* (2010) CRC Press). Medium can be added to the culture at the start, may be added during the culture, or may be intermittently/continuously flowed through the culture. The strains in the bacterial composition may be cultivated alone, as a subset of the bacterial composition, or as an entire collection comprising the bacterial composition. As an example, a first strain may be cultivated together with a second strain in a mixed continuous culture, at a dilution rate lower than the maximum growth rate of either cell to prevent the culture from washing out of the cultivation.

The inoculated culture may be incubated under favorable conditions for a time sufficient to build biomass. For bacterial compositions for human use, this may be at 37° C., with pH, and other parameters having values similar to the normal human niche. The environment can be actively controlled, passively controlled (e.g., via buffers), or allowed to drift. For example, for anaerobic bacterial compositions (e.g., gut microbiota), an anoxic/reducing environment can be employed. This can be accomplished by addition of reducing agents such as cysteine to the broth, and/or stripping it of oxygen. As an example, a culture of a bacterial composition can be grown at 37° C., pH 7, in the medium above, pre-reduced with 1 g/L cysteine-HCl.

In one embodiment, when the culture has generated sufficient biomass, it can be preserved for banking. The organisms can be placed into a chemical milieu that protects from freezing (adding 'cryoprotectants'), drying ('lyoprotectants'), and/or osmotic shock ('osmoprotectants'), dispensing into multiple (optionally identical) containers to create a uniform bank, and then treating the culture for preservation. In one embodiment, containers can be generally impermeable and have closures that assure isolation from the environment. Cryopreservation treatment can be accomplished by freezing a liquid at ultra-low temperatures (e.g., at or below −80° C.). Dried preservation removes water from the culture by evaporation (in the case of spray drying or 'cool drying') or by sublimation (e.g., for freeze drying, spray freeze drying). Removal of water improves long-term bacterial composition storage stability at temperatures elevated above cryogenic. If the bacterial composition comprises spore forming species and results in the production of spores, the final composition can be purified by additional means, such as density gradient centrifugation preserved using the techniques described above. Bacterial composition banking can be done by culturing and preserving the strains individually, or by mixing the strains together to create a combined bank. As an example of cryopreservation, a bacterial composition culture can be harvested by centrifugation to pellet the cells from the culture medium, the supernate decanted and replaced with fresh culture broth containing 15% glycerol. The culture can then be aliquoted into 1 mL cryotubes, sealed, and placed at −80° C. for long-term viability retention. This procedure achieves acceptable viability upon recovery from frozen storage.

Organism production can be conducted using similar culture steps to banking, including medium composition and culture conditions. In one embodiment, it can be conducted at larger scales of operation, especially for clinical development or commercial production. At larger scales, there can be several subcultivations of the bacterial composition prior to the final cultivation. At the end of cultivation, the culture can be harvested to enable further formulation into a dosage form for administration. This can involve concentration, removal of undesirable medium components, and/or introduction into a chemical milieu that preserves the bacterial composition and renders it acceptable for administration via the chosen route. For example, a bacterial composition can be cultivated to a concentration of $10^{10}$ CFU/mL, then concentrated 20-fold by tangential flow microfiltration; the spent medium can be exchanged by diafiltering with a preservative medium consisting of s2% gelatin, 100 mM trehalose, and 10 mM sodium phosphate buffer. The suspension can then be freeze-dried to a powder and titrated.

In one embodiment, after drying, the powder can be blended to an appropriate potency, and mixed with other cultures and/or a filler such as microcrystalline cellulose for consistency and ease of handling, and the bacterial composition formulated as provided herein.

Methods of Characterization of Compositions

In certain embodiments, methods are provided for testing certain characteristics of compositions comprising microbes or microbes and prebiotics. For example, the sensitivity of bacterial compositions to certain environmental variables is determined, e.g., in order to select for particular desirable characteristics in a given composition, formulation and/or use. For example, the bacterial constituents of the composition can be tested for pH resistance, bile acid resistance, and/or antibiotic sensitivity, either individually on a constituent-by-constituent basis or collectively as a bacterial composition comprised of multiple bacterial constituents (collectively referred to in this section as bacterial composition).

pH sensitivity testing. If a microbial composition, with or without prebiotic, will be administered other than to the colon or rectum (i.e., for example, an oral route), optionally testing for pH resistance enhances the selection of microbes or therapeutic compositions that will survive at the highest yield possible through the varying pH environments of the distinct regions of the GI tract or vagina. Understanding how the bacterial compositions react to the pH of the GI tract or vagina also assists in formulation, so that the number of microbes in a dosage form can be increased if beneficial and/or so that the composition may be administered in an enteric-coated capsule or tablet or with a buffering or protective composition.

As the pH of the stomach can drop to a pH of 1 to 2 after a high-protein meal for a short time before physiological mechanisms adjust it to a pH of 3 to 4 and often resides at a resting pH of 4 to 5, and as the pH of the small intestine can range from a pH of 6 to 7.4, bacterial compositions can be prepared that survive these varying pH ranges (specifically wherein at least 1%, 5%, 10%, 15%, 20%, 25%, 30%, 40%, 50%, 60%, 70%, 80%, 90%, or as much as 100% of the bacteria can survive gut transit times through various pH ranges). This can be tested by exposing the bacterial composition to varying pH ranges for the expected gut transit times through those pH ranges. Therefore, as a nonlimiting example only, 18-hour cultures of compositions comprising one or more bacterial species or strains can be grown in standard media, such as gut microbiota medium ("GMM", see Goodman et al., Extensive personal human gut microbiota culture collections characterized and manipulated in gnotobiotic mice, PNAS 108(15):6252-6257 (2011)) or another animal-products-free medium, with the addition of pH adjusting agents for a pH of 1 to 2 for 30 minutes, a pH of 3 to 4 for 1 hour, a pH of 4 to 5 for 1 to 2 hours, and a pH of 6 to 7.4 for 2.5 to 3 hours. An alternative method for testing stability to acid is described in U.S. Pat. No. 4,839,281. Survival of bacteria may be determined by culturing the bacteria and counting colonies on appropriate selective or non-selective media.

Bile acid sensitivity testing. Additionally, in some embodiments, testing for bile-acid resistance enhances the selection of microbes or therapeutic compositions that will survive exposures to bile acid during transit through the GI tract or vagina. Bile acids are secreted into the small intestine and can, like pH, affect the survival of bacterial compositions. This can be tested by exposing the compositions to bile acids for the expected gut exposure time to bile acids. For example, bile acid solutions can be prepared at desired concentrations using 0.05 mM Tris at pH 9 as the solvent. After the bile acid is dissolved, the pH of the solution may be adjusted to 7.2 with 10% HCl. Bacterial components of the therapeutic compositions can be cultured in 2.2 ml of a bile acid composition mimicking the concentration and type of bile acids in the patient, 1.0 ml of 10% sterile-filtered feces media and 0.1 ml of an 18-hour culture of the given strain of bacteria. Incubations may be conducted for from 2.5 to 3 hours or longer. An alternative method for testing stability to bile acid is described in U.S. Pat. No. 4,839,281. Survival of bacteria may be determined by culturing the bacteria and counting colonies on appropriate selective or non-selective media.

Antibiotic sensitivity testing. As a further optional sensitivity test, the bacterial components of the microbial compositions, with or without prebiotics, can be tested for sensitivity to antibiotics. In one embodiment, the bacterial components can be chosen so that they are sensitive to antibiotics such that if necessary they can be eliminated or substantially reduced from the patient's gastrointestinal tract or vagina by at least one antibiotic targeting the bacterial composition.

Adherence to gastrointestinal cells. The compositions may optionally be tested for the ability to adhere to gastrointestinal cells. A method for testing adherence to gastrointestinal cells is described in U.S. Pat. No. 4,839,281.

Identification of immunomodulatory bacteria. In some embodiments, immunomodulatory bacteria are identified by the presence of nucleic acid sequences that modulate sporulation. In particular, signature sporulation genes are highly conserved across members of distantly related genera including *Clostridium* and *Bacillus*. Traditional approaches of forward genetics have identified many, if not all, genes that are essential for sporulation (spo). The developmental program of sporulation is governed in part by the successive action of four compartment-specific sigma factors (appearing in the order σF, σE, σG and σK), whose activities are confined to the forespore (σF and σG) or the mother cell (σE and σK). In other embodiments, immunomodulatory bacteria are identified by the biochemical activity of DPA producing enzymes or by analyzing DPA content of cultures. As part of the bacterial sporulation, large amounts of DPA are produced, and comprise 5-15% of the mass of a spore. Because not all viable spores germinate and grow under known media conditions, it is difficult to assess a total spore count in a population of bacteria. As such, a measurement of DPA content highly correlates with spore content and is an appropriate measure for characterizing total spore content in a bacterial population.

In other embodiments, immunomodulatory bacteria are identified by screening bacteria to determine whether the bacteria induce secretion of pro-inflammatory or anti-inflammatory cytokines by host cells. For example, human or mammalian cells capable of cytokine secretion, such as immune cells (e.g., PBMCs, macrophages, T cells, etc.) can be exposed to candidate immunomodulatory bacteria, or supernatants obtained from cultures of candidate immunomodulatory bacteria, and changes in cytokine expression or secretion can be measured using standard techniques, such as ELISA, immunoblot, Luminex, antibody array, quantitative PCR, microarray, etc. Bacteria can be selected for inclusion in a probiotic composition based on the ability to induce a desired cytokine profile in human or mammalian cells. For example, anti-inflammatory bacteria can be selected for inclusion in a probiotic composition based on the ability to induce secretion of one or more anti-inflammatory cytokines, and/or the ability to reduce secretion of one or more pro-inflammatory cytokines. Anti-inflammatory cytokines include, for example, IL-10, IL-13, IL-9, IL-4, IL-5, and combinations thereof. Other inflammatory cytokines include, for example, TGFβ. Pro-inflammatory cytokines include, for example, IFNγ, IL-12p70, IL-1α, IL-6, IL-8, MCP1, MIP1α, MIP1β, TNFα, and combinations thereof. In some embodiments, anti-inflammatory bacteria may be selected for inclusion in a probiotic composition based on the ability to modulate secretion of one or more anti-inflammatory cytokines and/or the ability to reduce secretion of one or more pro-inflammatory cytokines by a host cell induced by a bacteria of a different type (e.g., a bacteria from a different species or from a different strain of the same species).

In other embodiments, immunomodulatory bacteria are identified by screening bacteria to determine whether the bacteria impact the differentiation and/or expansion of particular subpopulations of immune cells. For example, candidate bacteria can be screened for the ability to promote differentiation and/or expansion of Treg cells, Th17 cells, Th1 cells and/or Th2 cells from precursor cells, e.g. naive T cells. By way of example, naïve T cells can be cultured in the presence of candidate bacteria or supernatants obtained from cultures of candidate bacteria, and numbers of Treg cells, Th17 cells, Th1 cells and/or Th2 cells can be determined using standard techniques, such as FACS analysis. Markers indicative of Treg cells include, for example, $CD25^+CD127^{lo}$. Markers indicative of Th17 cells include, for example, $CXCR3^-CCR6^+$. Markers indicative of Th1 cells include, for example, $CXCR3^+CCR6^-$. Markers indicative of Th2 cells include, for example, $CXCR3^-CCR6^-$. Other markers indicative of particular T cells subpopulations are known in the art, and may be used in the assays described herein, e.g., to identify populations of immune cells impacted by candidate immunomodulatory bacteria. Bacteria can be selected for inclusion in a probiotic composition based on the ability to promote differentiation and/or expansion of a desired immune cell subpopulation.

In other embodiments, immunomodulatory bacteria are identified by screening bacteria to determine whether the bacteria secrete short chain fatty acids (SCFA), such as, for example, butyrate, acetate, propionate, or valerate, or combinations thereof. For example, secretion of short chain fatty acids into bacterial supernatants can be measured using standard techniques. In one embodiment, bacterial supernatants can be screened to measure the level of one or more short chain fatty acids using NMR, mass spectrometry (e.g., GC-MS, tandem mass spectrometry, matrix-assisted laser desorption/ionization, etc.), ELISA, or immunoblot. Expression of bacterial genes responsible for production of short chain fatty acids can also be determined by standard techniques, such as Northern blot, microarray, or quantitative PCR.

V. Mixtures of Bacteria and Microbial Networks

In one embodiment, provided herein are spore populations containing more than one type of bacterium. As used herein, a "type" or more than one "types" of bacteria may be differentiated at the genus level, the species level, the sub-species level, the strain level or by any other taxonomic method, as described herein and otherwise known in the art.

In one embodiment, the microbial, e.g., probiotic, population comprises a single microbial preparation or a combination of microbial preparations, wherein each microbial preparation can be purified from a fecal material obtained from a single mammalian donor subject, or from two or more donor subjects.

In some embodiments, all or essentially all of the bacterial entities and/or fungal entities present in an isolated population are obtained from a fecal material treated as described herein or otherwise known in the art. In alternative embodiments, one or more than one bacterial entities and/or fungal entities or types of bacterial entities and/or fungal entities are generated in culture and combined to form a purified spore population. In other alternative embodiments, one or more of these culture-generated spore populations are combined with one or more fecal material-derived spore population to generate a hybrid spore population.

In a preferred embodiment, a bacterial, e.g., probiotic, composition may contain one or at least two types of preferred bacteria, including strains of the same species or of different species. For instance, a bacterial composition may comprise 1, at least 2, at least 3, or at least 4 types of bacteria. In another embodiment, a bacterial composition may comprise at least 5, at least 6, at least 7, at least 8, at least 9, at least 10, at least 11, at least 12, at least 13, at least 14, at least 15, at least 16, at least 17, at least 18, at least 19, or at least 20 or more than 20 types of bacteria, as defined by species or operational taxonomic unit (OTU) encompassing such species. In a preferred embodiment, a bacterial composition comprises from 2 to no more than 40, from 2 to no more than 30, from 2 to no more than 20, from 2 to no more than 15, from 2 to no more than 10, from 2 to no more than 5, types of bacteria. In another preferred embodiment, a bacterial composition comprises a single type of bacteria.

In one embodiment, bacterial compositions may comprise two types of bacteria (termed "binary combinations" or "binary pairs") or greater than two types of bacteria. Bacterial compositions that comprise three types of bacteria are termed "ternary combinations".

Microbial compositions can comprise two types of microbes or a large number of microbe types. As used herein, a "type" or more than one "types" of microbes may be differentiated at the genus level, the species, level, the sub-species level, the strain level or by any other taxonomic method, as described herein and otherwise known in the art. For instance, a microbial composition can comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21, 22, 23, 24, 25, 26, 27, 28, 29 30, 31, 32, 33, 34, 35, 36, 37, 38, 39, or at least 40, at least 50 or greater than 50 types of microbes, e.g. as defined by species or operational taxonomic unit (OTU), or otherwise as provided herein. In some embodiments, the microbial composition includes at least 60, 70, 80, 90, 100, 150, 200, 250, 300, 350, 400, 450, 500, 550, 600, or greater numbers of types of microbes.

Alternatively, the number of types of microbes present in a microbial composition is at or below a known value. For example, the microbial composition comprises 1000, 900, 800, 700, 600, 500, 400, 300, 200, 100, 50 or fewer types of microbes, such as 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 or fewer, or 9 or fewer types of microbes, 8 or fewer types of microbes, 7 or fewer types of microbes, 6 or fewer types of microbes, 5 or fewer types of microbes, 4 or fewer types of microbes, or 3 or fewer types of microbes. In a preferred embodiment, a bacterial composition comprises from 2 to no more than 40, from 2 to no more than 30, from 2 to no more than 20, from 2 to no more than 15, from 2 to no more than 10, from 2 to no more than 5, types of microbes. In another preferred embodiment, a bacterial composition comprises a single type of microbe.

In a preferred embodiment, the composition comprises about 20 or fewer isolated populations of bacterial cells. In another embodiment, the composition comprises about 15 or fewer isolated populations of bacterial cells. In another embodiment, the composition comprises about 10 or fewer isolated populations of bacterial cells. In another embodiment, the composition comprises about 5 or fewer isolated populations of bacterial cells. In another embodiment, the composition comprises about 4 or fewer isolated populations of bacterial cells. In another embodiment, the composition comprises about 3 or fewer isolated populations of bacterial cells. In another embodiment, the composition comprises about 2 isolated populations of bacterial cells. In another embodiment, the composition comprises between about 12 and 20 isolated populations of bacterial cells. In another embodiment, the composition comprises a single isolated population of bacterial cells. In another embodiment, the composition comprises at least two isolated populations of bacterial cells. In yet another embodiment, the composition comprises about 1, 2, 3, 4, 5, 6, 7, 8, 9, 10, 11, 12, 13, 14, 15, 16, 17, 18, 19, or 20 isolated populations of bacterial cells.

Aspects of the invention relate to microbial compositions that are reconstituted from purified strains. Provided are microbial compositions comprising at least one, at least two or at least three microbes that are not identical and that are capable of decreasing the risk and/or severity of an autoimmune or inflammatory disease, symptom, condition, or disorder, or dysbiosis. In an embodiment, the microbial composition comprises at least about 2, 3, 4, 5, 6, 7, 8, 9, or 10 types of isolated microbes. In one embodiment, the microbial composition comprises at least about 4 types of isolated microbes or at least about 5, 6, 7, 8, 9, 10, 11, 12, 13, 14, 15, 16, 17, 18, 19, 20, 21, 22, 23, 24, 25, 26, 27, 28, 29, 30 or more types of isolated microbes. In some embodiments, the above invention relates to microbial compositions further comprising one or more prebiotics.

Bacterial compositions can be described by operational taxonomic units (OTUs). Bacterial compositions may be prepared comprising one or at least two types of isolated bacteria, wherein a first type and a second type are independently chosen from the species or OTUs listed in Table 1. Certain embodiments of bacterial compositions with at least two types of isolated bacteria containing binary pairs are reflected herein. Additionally, a bacterial composition may be prepared comprising at least two types of isolated bacteria, wherein a first OTU and a second OTU are independently characterized by, i.e., at least 95%, 96%, 97%, 98%, 99% or including 100% sequence identity to, sequences listed.

Bacterial compositions may be prepared comprising one or at least two types of isolated bacteria, chosen from the species in Table 1, Table 1A, Table 1B, Table 1C, Table 1D, Table 1E, Table 1F, or Table 5. Generally, the first bacteria and the second bacteria are not the same. The sequences provided in the sequencing listing file for OTUs in Table 1 are full 16S sequences. Therefore, in one embodiment, the first and/or second OTUs may be characterized by the full 16S sequences of OTUs listed in Table 1. In another embodiment, the first and/or second OTUs may be characterized by one or more of the variable regions of the 16S sequence (V1-V9). These regions in bacteria are defined by nucleotides 69-99, 137-242, 433-497, 576-682, 822-879, 986-

1043, 1117-1173, 1243-1294 and 1435-1465 respectively using numbering based on the *E. coli* system of nomenclature. (See, e.g., Brosius et al., Complete nucleotide sequence of a 16S ribosomal RNA gene from *Escherichia coli*, PNAS 75(10):4801-4805 (1978)). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU.

OTUs may be defined either by full 16S sequencing of the rRNA gene, by sequencing of a specific hypervariable region of this gene (i.e., V1, V2, V3, V4, V5, V6, V7, V8, or V9), or by sequencing of any combination of hypervariable regions from this gene (e.g. V1-3 or V3-5). The bacterial 16S rDNA is approximately 1500 nucleotides in length and is used in reconstructing the evolutionary relationships and sequence similarity of one bacterial isolate to another using phylogenetic approaches. 16S sequences are used for phylogenetic reconstruction as they are in general highly conserved, but contain specific hypervariable regions that harbor sufficient nucleotide diversity to differentiate genera and species of most microbes.

Using well known techniques, in order to determine the full 16S sequence or the sequence of any hypervariable region of the 16S sequence, genomic DNA is extracted from a bacterial sample, the 16S rDNA (full region or specific hypervariable regions) amplified using polymerase chain reaction (PCR), the PCR products cleaned, and nucleotide sequences delineated to determine the genetic composition of 16S gene or subdomain of the gene. If full 16S sequencing is performed, the sequencing method used may be, but is not limited to, Sanger sequencing. If one or more hypervariable regions are used, such as the V4 region, the sequencing may be, but is not limited to being, performed using the Sanger method or using a next-generation sequencing method, such as an Illumina (sequencing by synthesis) method using barcoded primers allowing for multiplex reactions.

OTUs can be defined by a combination of nucleotide markers or genes, in particular highly conserved genes (e.g., "house-keeping" genes), or a combination thereof, full-genome sequence, or partial genome sequence generated using amplified genetic products, or whole genome sequence (WGS). Using well defined methods DNA extracted from a bacterial sample will have specific genomic regions amplified using PCR and sequenced to determine the nucleotide sequence of the amplified products. In the whole genome shotgun (WGS) method, extracted DNA will be directly sequenced without amplification. Sequence data can be generated using any sequencing technology including, but not limited to Sanger, Illumina, 454 Life Sciences, Ion Torrent, ABI, Pacific Biosciences, and/or Oxford Nanopore.

VI. Prebiotic Compositions

A prebiotic is a selectively fermented ingredient that allows specific changes, both in the composition and/or activity in the gastrointestinal microbiota, that confers benefits upon host well-being and health. Prebiotics can include complex carbohydrates, amino acids, peptides, or other nutritional components useful for the survival of the bacterial composition. Prebiotics include, but are not limited to, amino acids, biotin, fructooligosaccharide, galactooligosaccharides, inulin, lactulose, mannan oligosaccharides, oligofructose-enriched inulin, oligofructose, oligodextrose, tagatose, trans-galactooligosaccharide, and xylooligosaccharides.

Suitable prebiotics are usually plant-derived complex carbohydrates, oligosaccharides or polysaccharides. Generally, prebiotics are indigestible or poorly digested by humans and serve as a food source for bacteria. Prebiotics which can be used in the pharmaceutical dosage forms, pharmaceutical compositions, and kits provided herein include, without limitation, galactooligosaccharides (GOS), trans-galactooligosaccharides, fructooligosaccharides or oligofructose (FOS), inulin, oligofructose-enriched inulin, lactulose, arabinoxylan, xylooligosaccharides (XOS), mannooligosaccharides, gum guar, gum Arabic, tagatose, amylose, amylopectin, xylan, pectin, and the like and combinations of thereof. Prebiotics can be found in certain foods, e.g. chicory root, Jerusalem artichoke, Dandelion greens, garlic, leek, onion, asparagus, wheat bran, wheat flour, banana, milk, yogurt, sorghum, burdock, broccoli, Brussels sprouts, cabbage, cauliflower, collard greens, kale, radish and rutabaga, and miso. Alternatively, prebiotics can be purified or chemically or enzymatically synthesized.

Prebiotics of the Invention

In some embodiments, the composition comprises at least one prebiotic. In one embodiment, the prebiotic is a carbohydrate. In some embodiments, the composition of the present invention comprises a prebiotic mixture, which comprises at least one carbohydrate. A "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $(CH_2O)n$. A carbohydrate can be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates can contain modified saccharide units, such as 2'-deoxyribose wherein a hydroxyl group is removed, 2'-fluororibose wherein a hydroxyl group is replace with a fluorine, or N-acetylglucosamine, a nitrogen-containing form of glucose (e.g., 2'-fluororibose, deoxyribose, and hexose). Carbohydrates can exist in many different forms, for example, conformers, cyclic forms, acyclic forms, stereoisomers, tautomers, anomers, and isomers. Carbohydrates may be purified from natural (e.g., plant or microbial) sources (i.e., they are enzymatically synthetized), or they may be chemically synthesized or modified.

Suitable prebiotic carbohydrates can include one or more of a carbohydrate, carbohydrate monomer, carbohydrate oligomer, or carbohydrate polymer. In certain embodiments, the pharmaceutical composition, dosage form, or kit comprises at least one type of microbe and at least one type of non-digestible saccharide, which includes non-digestible monosaccharides, non-digestible oligosaccharides, or non-digestible polysaccharides. In one embodiment, the sugar units of an oligosaccharide or polysaccharide can be linked in a single straight chain or can be a chain with one or more side branches. The length of the oligosaccharide or polysaccharide can vary from source to source. In one embodiment, small amounts of glucose can also be contained in the chain. In another embodiment, the prebiotic composition can be partially hydrolyzed or contain individual sugar moieties that are components of the primary oligosaccharide (see U.S. Pat. No. 8,486,668, PREBIOTIC FORMULATIONS AND METHODS OF USE).

Prebiotic carbohydrates may include, but are not limited to monosaccharaides (e.g., trioses, tetroses, pentoses, aldopentoses, ketopentoses, hexoses, cyclic hemiacetals, ketohexoses, heptoses) and multimers thereof, as well as epimers, cyclic isomers, stereoisomers, and anomers thereof. Nonlimiting examples of monosaccharides include (in either the L- or D-conformation) glyceraldehyde, threose, ribose, altrose, glucose, mannose, talose, galactose, gulose, idose, lyxose, arabanose, xylose, allose, erythrose, erythrulose, tagalose, sorbose, ribulose, psicose, xylulose, fructose, dihydroxyacetone, and cyclic (alpha or beta) forms thereof. Multimers (disaccharides, trisaccharides, oligosaccharides, polysaccharides) thereof include but are not limited to sucrose, lactose, maltose, lactulose, trehalose, cellobiose, kojibiose, nigerose, isomaltose, sophorose, laminaribiose, gentioboise, turanose, maltulose, palatinose, gentiobiulose, mannobiose, melibiulose, rutinose, rutinulose, xylobiose, primeverose, amylose, amylopectin, starch (including resistant starch), chitin, cellulose, agar, agarose, xylan, glycogen, bacterial polysaccharides such as capsular polysaccharides, LPS, and peptodglycan, and biofilm exopolysaccharide (e.g., alginate, EPS), N-linked glycans, and O-linked glycans. Prebiotic sugars may be modified and carbohydrate derivatives include amino sugars (e.g., sialic acid, N-acetylglucosamine, galactosamine), deoxy sugars (e.g., rhamnose, fucose, deoxyribose), sugar phosphates, glycosylamines, sugar alcohols, and acidic sugars (e.g., glucuronic acid, ascorbic acid).

In one embodiment, the prebiotic carbohydrate component of the pharmaceutical composition, dosage form, or kit consists essentially of one or more non-digestible saccharides. In one embodiment, non-digestible oligosaccharides the non-digestible oligosaccharides are galactooligosaccharides (GOS). In another embodiment, the non-digestible oligosaccharides are fructooligosaccharides (FOS).

In one embodiment, the prebiotic carbohydrate component of the pharmaceutical composition, dosage form, or kit allows the commensal colonic microbiota, comprising microorganisms associated with a healthy-state microbiome or presenting a low risk of a patient developing an autoimmune or inflammatory condition, to be regularly maintained. In one embodiment, the prebiotic carbohydrate allows the co-administered or co-formulated microbe or microbes to engraft, grow, and/or be regularly maintained in a mammalian subject. In some embodiments, the mammalian subject is a human subject. In preferred embodiments, the mammalian subject suffers from or is at risk of developing an autoimmune or inflammatory disorder.

In some embodiments, the prebiotic favors the growth of an administered microbe, wherein the growth of the administered microbe and/or the fermentation of the administered prebiotic by the administered microbe slows or reduces the growth of a pathogen or pathobiont. For example, FOS, neosugar, or inulin promotes the growth of acid-forming bacteria in the colon such as bacteria belonging to the genera *Lactobacillus* or *Bifidobacterium* and *Lactobacillus acidophilus* and *Bifidobacterium bifidus* can play a role in reducing the number of pathogenic bacteria in the colon (see U.S. Pat. No. 8,486,668, PREBIOTIC FORMULATIONS AND METHODS OF USE). Other polymers, such as various galactans, lactulose, and carbohydrate based gums, such as psyllium, guar, carrageen, gellan, and konjac, are also known to improve gastrointestinal (GI) health.

In some embodiments, the prebiotic composition of the invention comprises one or more of GOS, lactulose, raffinose, stachyose, lactosucrose, FOS (i.e., oligofructose or oligofructan), inulin, isomalto-oligosaccharide, xylo-oligosaccharide, paratinose oligosaccharide, transgalactosylated oligosaccharides (i.e., transgalacto-oligosaccharides), transgalactosylate disaccharides, soybean oligosaccharides (i.e., soyoligosaccharides), gentiooligosaccharides, glucooligosaccharides, pecticoligosaccharides, palatinose polycondensates, difructose anhydride III, sorbitol, maltitol, lactitol, polyols, polydextrose, reduced paratinose, cellulose, β-glucose, β-galactose, β-fructose, verbascose, galactinol, and β-glucan, guar gum, pectin, high, sodium alginate, and lambda carrageenan, or mixtures thereof. The GOS may be a short-chain GOS, a long-chain GOS, or any combination thereof. The FOS may be a short-chain FOS, a long-chain FOS, or any combination thereof.

In some embodiments, the prebiotic composition comprises two carbohydrate species (nonlimiting examples being a GOS and FOS) in a mixture of at least 1:1, at least 2:1, at least 5:1, at least 9:1, at least 10:1, about 20:1, or at least 20:1.

In some embodiments, the prebiotic composition of the invention comprises a mixture of one or more non-digestible oligosaccharides, non-digestible polysaccharides, free monosaccharides, non-digestible saccharides, starch, or non-starch polysaccharides. In one embodiment, a prebiotic component of a prebiotic composition is a GOS composition. In one embodiment, a prebiotic composition is a pharmaceutical composition. In one embodiment, a pharmaceutical composition is a GOS composition.

Oligosaccharides are generally considered to have a reducing end and a non-reducing end, whether or not the saccharide at the reducing end is in fact a reducing sugar. Most oligosaccharides described herein are described with the name or abbreviation for the non-reducing saccharide (e.g., Gal or D-Gal), preceded or followed by the configuration of the glycosidic bond ($\alpha$ or $\beta$), the ring bond, the ring position of the reducing saccharide involved in the bond, and then the name or abbreviation of the reducing saccharide (e.g., Glc or D-Glc). The linkage (e.g., glycosidic linkage, galactosidic linkage, glucosidic linkage) between two sugar units can be expressed, for example, as 1,4, 1->4, or (1-4).

Both FOS and GOS are non-digestible saccharides. β glycosidic linkages of saccharides, such as those found in, but not limited to, FOS and GOS, make these prebiotics mainly non-digestible and unabsorbable in the stomach and small intestine α-linked GOS (α-GOS) is also not hydrolyzed by human salivary amylase, but can be used by *Bifidobacterium bifidum* and *Clostridium butyricum* (Yamashita A. et al., 2004. J. Appl. Glycosci. 51:115-122). FOS and GOS can pass through the small intestine and into the large intestine (colon) mostly intact, except where commensal microbes and microbes administered as part of a pharmaceutical composition are able to metabolize the oligosaccharides.

GOS (also known as galacto-oligosaccharides, galactooligosaccharides, trans-oligosaccharide (TOS), trans-galactooligosaccharide (TGOS), and trans-galactooligosaccharide) are oligomers or polymers of galactose molecules ending mainly with a glucose or sometimes ending with a galactose molecule and have varying degree of polymerization (generally the DP is between 2-20) and type of linkages. In one embodiment, GOS comprises galactose and glucose molecules. In another embodiment, GOS comprises only galactose molecules. In a further embodiment, GOS are galactose-containing oligosaccharides of the form of [β-D-Gal-(1-6)]$_n$-β-D-Gal-(1-4)-D-Glc wherein n is 2-20. In another embodiment, GOS are galactose-containing oligosaccharides of the form Glc α1-4-[β Gal 1-6)]$_n$ where n=2-20. In another embodiment, GOS are in the form of α-D-Glc (1-4)-[β-D-Gal-(1-6)-]$_n$ where n=2-20. Gal is a galactopyranose unit and Glc (or Glu) is a glucopyranose unit.

In one embodiment, a prebiotic composition comprises a GOS-related compound. A GOS-related compound can have the following properties: a) a "lactose" moiety; e.g., GOS with a gal-glu moiety and any polymerization value or type of linkage; or b) be stimulatory to "lactose fermenting" microbes in the human GI tract; for example, raffinose (gal-fru-glu) is a "related" GOS compound that is stimulatory to both lactobacilli and bifidobacteria.

In one embodiment, a prebiotic composition comprises GOS with a low degree of polymerization. In one embodiment a prebiotic composition comprising GOS with a low degree of polymerization increases growth of probiotic and select commensal bacteria to a greater extent than an equivalent amount of a prebiotic composition comprising GOS with a high degree of polymerization. In one embodiment, a prebiotic composition comprising a high percentage of GOS with a low degree of polymerization increases growth of probiotic and beneficial commensal bacteria to a greater extent than an equivalent amount of a prebiotic composition comprising a low percentage of GOS with a low degree of polymerization (DP). In one embodiment a prebiotic composition comprises GOS with a DP less than 20, such as less than 10, less than 9, less than 8, less than 7, less than 6, less than 5, less than 4, or less than 3. In another embodiment a prebiotic composition comprising GOS with a low DP increases growth of co-formulated or co-administered microbes and/or beneficial commensal microbes in the GI tract of a subject.

Linkages between the individual sugar units found in GOS and other oligosaccharides include β-(1-6), β-(1-4), β-(1-3) and β-(1-2) linkages. In one embodiment, the administered oligosaccharides (e.g., GOS) are branched saccharides. In another embodiment, the administered oligosacchardies (e.g, GOS) are linear saccharides.

In some embodiments, the GOS comprises a disaccharide Gal α (1-6) Gal, at least one trisaccharide selected from Gal β (1-6)-Gal β (1-4)-Glc and Gal β (1-3)-Gal β (1-4)-Glc, the tetrasaccharide Gal β(1-6)-Gal β (1-6)-Gal β (1-4)-Glc and the pentasaccharide Gal β (1-6)-Gal β (1-6)-Gal β (1-6)-Gal β (1-4)-Glc.

In one embodiment, a GOS composition is a mixture of 10 to 45% w/v disaccharide, 10 to 45% w/v trisaccharide, 10 to 45% w/v tetrasaccharide and 10 to 45% w/v pentasaccharide. In another embodiment, a GOS composition is a mixture of oligosaccharides comprising 20-28% by weight of β (1-3) linkages, 20-25% by weight of β (1-4) linkages, and 45-55% by weight of β (1-6) linkages. In one embodiment, a GOS composition is a mixture of oligosaccharides comprising 26% by weight of β (1-3) linkages, 23% by weight of β (1-4) linkages, and 51% by weight of β (1-6) linkages.

Alpha-GOS (also called alpha-bond GOS or alpha-linked GOS) are oligosaccharides having an alpha-galactopyranosyl group. Alpha-GOS comprises at least one alpha glycosidic linkage between the saccharide units. Alpha-GOS are generally represented by α-(Gal)$_n$ (n usually represents an integer of 2 to 10) or α-(Gal)$_n$ Glc (n usually represents an integer of 1 to 9). Examples include a mixture of α-galactosylglucose, α-galactobiose, α-galactotriose, α-galactotetraose, and higher oligosaccharides. Additional non-limiting examples include melibiose, manninootriose, raffinose, stachyose, and the like, which can be produced from beat, soybean oligosaccharide, and the like.

Commercially available and enzyme synthesized alpha-GOS products are also useful for the compositions described herein. Synthesis of alpha-GOS with an enzyme is conducted utilizing the dehydration condensation reaction of α-galactosidase with the use of galactose, galactose-containing substance, or glucose as a substrate. The galactose-containing substance includes hydrolysates of galactose-containing substances, for example, a mixture of galactose and glucose obtained by allowing beta-galactosidase to act on lactose, and the like. Glucose can be mixed separately with galactose and be used as a substrate with α-galactosidase (see e.g., WO 02/18614). Methods of preparing alpha-GOS have been described (see e.g., EPI 514551 and EP2027863).

In one embodiment, a GOS composition comprises a mixture of saccharides that are alpha-GOS and saccharides that are produced by transgalactosylation using β-galactosidase. In another embodiment, GOS comprises alpha-GOS. In another embodiment, alpha-GOS comprises α-(Gal)$_2$ from 10% to 100% by weight. In one embodiment, GOS comprises only saccharides that are produced by transgalactosylation using β-galactosidase.

In one embodiment, a GOS composition can comprise GOS with alpha linkages and beta linkages.

In one embodiment, the pharmaceutical composition, dosage form, or kit comprises, in addition to one or more microbes, an oligosaccharide composition that is a mixture of oligosaccharides comprising 1-20% by weight of di-saccharides, 1-20% by weight tri-saccharides, 1-20% by weight tetra-saccharides, and 1-20% by weight penta-saccharides. In another embodiment, an oligosaccharide composition is a mixture of oligosaccharides consisting essentially of 1-20% by weight of di-saccharides, 1-20% by weight tri-saccharides, 1-20% by weight tetra-saccharides, and 1-20% by weight penta-saccharides.

In one embodiment, a prebiotic composition is a mixture of oligosaccharides comprising 1-20% by weight of saccharides with a degree of polymerization (DP) of 1-3, 1-20% by weight of saccharides with DP of 4-6, 1-20% by weight of saccharides with DP of 7-9, and 1-20% by weight of saccharides with DP of 10-12, 1-20% by weight of saccharides with DP of 13-15.

In another embodiment, a prebiotic composition comprises a mixture of oligosaccharides comprising 50-55% by weight of di-saccharides, 20-30% by weight tri-saccharides, 10-20% by weight tetra-saccharide, and 1-10% by weight penta-saccharides. In one embodiment, a GOS composition is a mixture of oligosaccharides comprising 52% by weight of di-saccharides, 26% by weight tri-saccharides, 14% by weight tetra-saccharide, and 5% by weight penta-saccharides. In another embodiment, a prebiotic composition comprises a mixture of oligosaccharides comprising 45-55% by weight tri-saccharides, 15-25% by weight tetra-saccharides, 1-10% by weight penta-saccharides.

In certain embodiments, the composition according to the invention comprises a mixture of neutral and acid oligosaccharides as disclosed in WO 2005/039597 (N.V. Nutricia) and US Patent Application 20150004130, which are hereby incorporated by reference. In one embodiment, the acid oligosaccharide has a degree of polymerization (DP) between 1 and 5000. In another embodiment, the DP is between 1 and 1000. In another embodiment, the DP is between 2 and 250. If a mixture of acid oligosaccharides with different degrees of polymerization is used, the average DP of the acid oligosaccharide mixture is preferably between 2 and 1000. The acid oligosaccharide may be a homogeneous or heterogeneous carbohydrate. The acid oligosaccharides may be prepared from pectin, pectate, alginate, chondroitine, hyaluronic acids, heparin, heparane, bacterial carbohydrates, sialoglycans, fucoidan, fucooligosaccharides or carrageenan, and are preferably prepared from pectin or alginate. The acid oligosaccharides may be prepared by the methods described in WO 01/60378, which is hereby incorporated by reference. The acid oligosaccharide is preferably prepared from high methoxylated pectin, which is characterized by a degree of methoxylation above 50%. As used herein, "degree of methoxylation" (also referred to as DE or "degree of esterification") is intended to mean the extent to which free carboxylic acid groups contained in the polygalacturonic acid chain have been esterified (e.g. by methylation). In some embodiments, the acid oligosaccharides have a degree of methoxylation above about 10%, above about 20%, above about 50%, above about 70%. In some embodiments, the acid oligosaccharides have a degree of methylation above about 10%, above about 20%, above about 50%, above about 70%.

The term neutral oligosaccharides as used in the present invention refers to saccharides which have a degree of polymerization of monose units exceeding 2, exceeding 3, exceeding 4, or exceeding 10, which are not or only partially digested in the intestine by the action of acids or digestive enzymes present in the human upper digestive tract (small intestine and stomach) but which are fermented by the human intestinal flora and preferably lack acidic groups. The neutral oligosaccharide is structurally (chemically) different from the acid oligosaccharide. The term neutral oligosaccharides as used herein preferably refers to saccharides which have a degree of polymerization of the oligosaccharide below 60 monose units. The term monose units refers to units having a closed ring structure e.g., the pyranose or furanose forms. In come embodiments, the neutral oligosaccharide comprises at least 90% or at least 95% monose units selected from the group consisting of mannose, arabinose, fructose, fucose, rhamnose, galactose, -D-galactopyranose, ribose, glucose, xylose and derivatives thereof, calculated on the total number of monose units contained therein. Suitable neutral oligosaccharides are preferably fermented by the gut flora. Nonlimiting examples of suitable neutral oligosaccharides are cellobiose (4-O-β-D-glucopyranosyl-D-glucose), cellodextrins ((4-O-β-D-glucopyranosyl)n-D-glucose), B-cyclo-dextrins (Cyclic molecules of α-1-4-linked D-glucose; α-cyclodextrin-hexamer, β-cyclodextrin-heptamer and γ-cyclodextrin-octamer), indigestible dextrin, gentiooligosaccharides (mixture of β-1-6 linked glucose residues, some 1-4 linkages), glucooligosaccharides (mixture of α-D-glucose), isomaltooligosaccharides (linear α-1-6 linked glucose residues with some 1-4 linkages), isomaltose (6-O-α-D-glucopyranosyl-D-glucose); isomaltriose (6-O-α-D-glucopyranosyl-(1-6)-α-D-glucopyranosyl-D-glucose), panose (6-O-α-D-glucopyranosyl-(1-6)-α-D-glucopyranosyl-(1-4)-D-glucose), leucrose (5-O-α-D-glucopyranosyl-D-fructopyranoside), palatinose or isomaltulose (6-O-α-D-glucopyranosyl-D-fructose), theanderose (O-α-D-glucopyranosyl-(1-6)-O-α-D-glucopyranosyl-(1-2)-B-D-fructo furanoside), D-agatose, D-lyxo-hexylose, lactosucrose (O-β-D-galactopyranosyl-(1-4)-O-α-D-glucopyranosyl-(1-2)-β-D-fructofuranoside), α-galactooligosaccharides including raffinose, stachyose and other soy oligosaccharides (O-α-D-galactopyranosyl-(1-6)-α-D-glucopyranosyl-β-D-fructofuranoside), β-galactooligosaccharides or transgalacto-oligosaccharides (β-D-galactopyranosyl-(1-6)-[β-D-glucopyranosyl]n-(1-4) α-D glucose), lactulose (4-O-β-D-galactopyranosyl-D-fructose), 4'-galatosyllactose (O-D-galactopyranosyl-(1-4)-O-β-D-glucopyranosyl-(1-4)-D-glucopyranose), synthetic galactooligosaccharide (neogalactobiose, isogalactobiose, galsucrose, isolactose I, II and III), fructans-Levan-type (β-D-(2→6)-fructofuranosyl)n α-D-glucopyranoside), fructans-Inulin-type (β-D-((2→1)-fructofuranosyl)n α-D-glucopyranoside), 1 f-β-fructofuranosylnystose (β-D-((2→1)-fructofuranosyl)n B-D-fructofuranoside), xylooligo-saccharides (B-D-((1→4)-xylose)n, lafinose, lactosucrose and arabinooligosaccharides.

In some embodiments, the neutral oligosaccharide is selected from the group consisting of fructans, fructooligosaccharides, indigestible dextrins galactooligo-saccharides (including transgalactooligosaccharides), xylooligosaccharides, arabinooligo-saccharides, glucooligosaccharides, mannooligosaccharides, fucooligosaccharides and mixtures thereof.

Suitable oligosaccharides and their production methods are further described in Laere K. J. M. (Laere, K. J. M., Degradation of structurally different non-digestible oligosaccharides by intestinal bacteria: glycosylhydrolases of Bi. adolescentis. PhD-thesis (2000), Wageningen Agricultural University, Wageningen, The Netherlands), the entire content of which is hereby incorporated by reference. Transgalactooligosaccharides (TOS) are for example sold under the trademark Vivinal™ (Borculo Domo Ingredients, Netherlands). Indigestible dextrin, which may be produced by pyrolysis of corn starch, comprises α(1→4) and α(1→6) glucosidic bonds, as are present in the native starch, and contains 1→2 and 1→3 linkages and levoglucosan. Due to these structural characteristics, indigestible dextrin contains well-developed, branched particles that are partially hydrolysed by human digestive enzymes. Numerous other commercial sources of indigestible oligosaccharides are readily available and known to skilled persons in the art. For example, transgalactooligosaccharide is available from Yakult Honsha Co., Tokyo, Japan. Soybean oligosaccharide is available from Calpis Corporation distributed by Ajinomoto U.S.A. Inc., Teaneck, N.J.

In a further preferred embodiment, the prebiotic mixture of the pharmaceutical composition described herein comprises an acid oligosaccharide with a DP between 1 and 5000, prepared from pectin, alginate, and mixtures thereof; and a neutral oligosaccharide, selected from the group of fructans, fructooligosaccharides, indigestible dextrins, galactooligosaccharides including transgalacto-oligosaccharides, xylooligosaccharides, arabinooligosaccharides, glucooligosaccharides, manno-oligosaccharides, fucooligosaccharides, and mixtures thereof.

In certain embodiments, the prebiotic mixture comprises xylose. In other embodiments, the prebiotic mixture comprises a xylose polymer (i.e. xylan). In some embodiments, the prebiotic comprises xylose derivatives, such as xylitol, a sugar alcohol generated by reduction of xylose by catalytic hydrogenation of xylose, and also xylose oligomers (e.g., xylooligosaccharide). While xylose can be digested by humans, via xylosyltransferase activity, most xylose ingested by humans is excreted in urine. In contrast, some microorganisms are efficient at xylose metabolism or may be selected for enhanced xylose metabolism. Microbial xylose metabolism may occur by at least four pathways, including the isomerase pathway, the Weimburg pathway, the Dahms pathway, and, for eukaryotic microorganisms, the oxidoreductase pathway.

The xylose isomerase pathway involves the direct conversion of D-xylose into D-xylulose by xylose isomerase, after which D-xylulose is phosphorylated by xylulose kinase to yield D-xylolose-5-phosphate, an intermediate of the pentose phosphate pathway.

In the Weimberg pathway, D-xylose is oxidized to D-xylono-lactone by a D-xylose dehydrogenase. Then D-xylose dehydrogenase is hydrolyzed by a lactonase to yield D-xylonic acid, and xylonate dehydratase activity then yields 2-keto-3-deoxy-xylonate. The final steps of the Weimberg pathway are a dehydratase reaction to form 2-keto glutarate semialdehyde and an oxidizing reaction to form 2-ketoglutarate, an intermediate of the Krebs cycle.

The Dahms pathway follows the same mechanism as the Weimberg pathway but diverges once it has yielded 2-keto-3-deoxy-xylonate. In the Dahms pathway, an aldolase splits 2-keto-3-deoxy-xylonate into pyruvate and glycolaldehyde.

The xylose oxido-reductase pathway, also known as the xylose reductase-xylitol dehydrogenase pathway, begins by the reduction of D-xylose to xylitol by xylose reductase followed by the oxidation of xylitol to D-xylulose by xylitol dehydrogenase. As in the isomerase pathway, the next step in the oxido-reductase pathway is the phosphorylation of D-xylulose by xylulose kinase to yield D-xylolose-5-phosphate.

Xylose is present in foods like fruits and vegetables and other plants such as trees for wood and pulp production. Thus, xylose can be obtained in the extracts of such plants. Xylose can be obtained from various plant sources using known processes including acid hydrolysis followed by various types of chromatography. Examples of such methods to produce xylose include those described in Maurelli, L. et al. (2013), Appl. Biochem. Biotechnol. 170:1104-1118; Hooi H. T et al. (2013), Appl. Biochem. Biotechnol. 170: 1602-1613; Zhang H-J. et al. (2014), Bioprocess Biosyst. Eng. 37:2425-2436.

Preferably, the metabolism of xylose and/or the shift in microbiota due to the metabolism of the xylose provided in a pharmaceutical composition of the invention confers a benefit to a host, e.g. immunological tolerance. For example, in aspects in which the patient is at risk or suffering from GVHD, the immunological tolerance may reduce graft-versus-host activity while maintaining graft-versus-leukemia activity. In another example, in aspects in which the patient suffers from Celiac disease, the immunological tolerance prevents an inappropriate immune response to gluten. The xylose may be, e.g. i) cytotoxic for an autoimmune disease- and/or inflammatory disease-associated associated pathogen or pathobiont, ii) cytostatic for an autoimmune disease- and/or inflammatory disease-associated pathogen or pathobiont, iii) capable of decreasing the growth of autoimmune disease- and/or inflammatory disease-associated pathogen or pathobiont, iv) capable of inhibiting the growth of an autoimmune disease- and/or inflammatory disease-associated pathogen or pathobiont, v) capable of decreasing the colonization of an autoimmune disease- and/or inflammatory disease-associated pathogen or pathobiont, vi) capable of inhibiting the colonization of an autoimmune disease- and/or inflammatory disease-associated pathogen or pathobiont, vii) capable of eliciting an immunomodulatory response in the host that reduces the risk of an autoimmune and/or inflammatory disorder, viii), capable of eliciting an immunomodulatory response in the host that reduces the severity of an autoimmune and/or inflammatory disorder, ix) capable of promoting barrier integrity directly or indirectly through its impact on microbiota, or x) any combination of i)-ix).

In some embodiments, the pharmaceutical composition or dosage form comprises a bacterial population and xylose in an amount effective to promote the growth of select bacteria of the family Clostridiacea, including members of the genus *Clostridium, Ruminococcus*, or *Blautia* or relatives thereof in a host. In some embodiments, the pharmaceutical composition or dosage form is further effective to promote the proliferation of select bacteria of the family Clostridiacea, including members of the genus *Clostridium, Ruminococcus*, or *Blautia* or relatives thereof in a host. In certain embodiments, the pharmaceutical composition or dosage form comprises a bacterial population and xylose in an amount effective to promote the colonization and/or engraftment of select bacteria of the family Clostridiacea, including members of the genus *Clostridium, Ruminococcus*, or *Blautia* or relatives thereof in a host. In preferred embodiments, the pharmaceutical composition or dosage form is further capable of altering a dysbiotic state such that the growth, proliferation, colonization, and/or engraftment of a host by a pathogen, pathobiont, disease-associated microbe, or a combination thereof such that the population of at least one pathogen, pathobiont, or disease-associated microbe is decreased 2-fold, 5-fold, 10-fold, 50-fold, 100-fold, 200-fold, 500-fold, 1000-fold, 10000-fold, or over 10000-fold. In one embodiment, the pharmaceutical composition or dosage form is capable of locally or systemically eliminating at least one pathogen, pathobiont, or disease-associated microbe from a host.

In some embodiments, the prebiotic mixture comprises a carbohydrate monomer or polymer that has been modified i.e., substituted with other substituents (e.g., acetyl group, glucuronic acid residue, arabinose residue, or the like) (see US Patent Application 20090148573, hereby incorporated by reference). The term "modified", as used herein, refers to a molecule modified from a reference molecule, and includes not only artificially produced molecules but also naturally occurring molecules. In preferred embodiments, the modification occurs at one or more hydroxyl groups of the reference carbohydrate. In some embodiments, the modification occurs at carbon-2 (C2), the modification occurs at carbon-6 (C6), or a combination thereof.

In some embodiments, a carbohydrate (a monomer or, preferably, a polymer) is modified with one or more hydrophilic groups. Nonlimiting examples of the hydrophilic groups include an acetyl group, a 4-O-methyl-α-D-glucuronic acid residue, an L-arabinofuranose residue, an L-arabinose residue, and an α-D-glucuronic acid residue. In some embodiments, the modification is the replacement of one or more hydroxyl groups with —H, —CH$_2$OH, —CH$_3$, or —NH$_2$.

In some embodiments, the composition comprises at least one carbohydrate that elicits an immunomodulatory response. Exemplary immunomodulary carbohydrates include (but are not limited to) fructo-oligosaccharides, glycosaminoglycans (e.g., heparin sulfate, chondroitin sulfate A, hyaluronan), O-glycans, and carrageenan oligosaccharides, and galacto-oligosaccharides. Immunomodulatory carbohydrates may be purified from plants or microbes or may be synthetically derived. Immunomodulatory carbohydrates may be effective to, for example, prevent disease, suppress symptoms, treat disease, or any combination thereof.

In some embodiments, immunomodulatory carbohydrates are C-type lectin receptor ligands. In preferred embodiments, the C-type lectin receptor ligands are produced by one or more fungal species. In other embodiments, the immunomodulatory carbohydrates are bacterial exopolysaccharides, such as (but not limited to) the exopolysaccharides (EPS) produced by *Bacillus subtilis*, *Bifidobacterium breve*, or *Bacteroides fragilis*. In some aspects, immunomodulatory carbohydrates are zwitterionic polysaccharides. In some aspects, immunomodulatory carbohydrates modulate toll-like receptor 2 (TLR2) and/or toll-like receptor 4 (TLR4) responses in a host. For example, autoimmune or inflammatory diseases characterized by intestinal inflammation may be prevented by a TLR4 agonist such as but not limited to *B. subtilis* EPS (Jones S, Paynich M L, Kearns D B, Knight K L, 2014. Protection from Intestinal Inflammation by Bacterial Exopolysaccharides. The Journal of Immunology. 192:4813-4820). Immunomodulatory carbohydrates may also activate CD4+ T cells and/or lead to an upregulation of the anti-inflammatory cytokine interleukin-10 (Mazmanian S K, Kasper D L, 2006. The love-hate relationship between bacterial polysaccharides and the host immune system. Nat. Rev. Immunol. 6: 849-858). Immunomodulatory carbohydrates may be selected for administration to a patient based on the presence, abundance, distribution, modification and/or linkages of sugar residues. For example, immunomodulatory carbohydrates used in the prevention of intestinal disorders or autoimmune conditions that manifest in the gut (non-limiting examples being IBD and GVHD) may be selected based on i) a high abundance of mannose residues; ii) the presence of terminal mannopyranosyl (t-Man) residues and/or 2,6 linked mannopyranosyl residues (2,6-Man), iii) a ratio of mannose to glucose residues in the approximate range of 8:2 to 9:1, iv) the presence of galactose residues, v) areas of positive charge, or vi) a combination thereof.

Carbohydrates may be selected according to the fermentation or metabolic preferences of a microbe selected for administration to a mammalian subject. Selection criteria include but are not limited to sugar complexity (e.g., monosaccharides, including but not limited to glucose, versus oligosaccharides or starches) as well as by desired end-product. Non-limiting examples include the fermentation products ethanol and carbon dioxide ($CO_2$) (e.g., via ethanol fermentation by *Saccharomyces* sp. *Zymomonas* sp.), lactate (e.g., via homolactic acid fermentation by *Lactococcus* sp., *Streptococcus* sp., *Enterococcus* sp., *Pediococcus* sp. and some species *Lactobacillus*), lactate, ethanol, and $CO_2$ (e.g., via heterolactic acid fermentation (which includes the phosphoketolase pathway) by some species of *Lactobacillus* as well as *Leuconostoc* sp., *Oenococcus* sp., and *Weissella* sp.), butanol, acetone, $CO_2$ and $H_2$ (via acetone-butanol fermentation by some *Clostridium* sp.), and short chain fatty acids (with or without the production of other products) (Muller V, 2011. Bacterial Fermentation. Encyclopedia of Life Sciences). Examples of fermentation leading to short chain fatty acid production include homoacetic acid fermentation (e.g., by *Acetobacterium* sp., and resulting in acetate), propionic acid fermentation (e.g., by *Propionibacterium* sp., and resulting in propionate, acetate and $CO_2$) mixed acid fermentation (e.g., by *Escherichia* sp., and resulting in ethanol, lactate, acetate, succinate, formate, $CO_2$, and $H_2$), butyrate fermentation (e.g., by some *Clostridium* sp., resulting in butyrate, $CO_2$, and $H_2$), and 2,3-butanediol fermentation (e.g., by *Enterobacter* sp., resulting in ethanol, butanediol, lactate, formate, $CO_2$, and $H_2$). In some embodiments, selection of carbohydrates for co-formulation of co-administration with a type of microbe or types of microbe may be achieved by computational analysis of microbial enzymatic pathways, including but not limited to the presence of metabolic/fermentation pathway enzymes including but not limited to the enzymes provided in Table 4.

Other prebiotics include molecules capable of selective or semi-selective utilization by microbes of the composition contained herein. The ability of a microbe to utilize a metabolite of interest is determined by the genomic capacity of that microbe. Public databases have characterized many microbes and automate the annotation of the genome to allow a computational analysis of the metabolites a microbe is potentially able to utilize. Databases such as the Cluster of Orthologous Groups (COGs) database characterize genomes from a variety of species in this manner and are capable of characterizing newly sequenced genomes as well (e.g. see in this fashion (Tatusov et al 2000. Nucl Acid Res). Furthermore, pathway analysis classifies COGs into different categories with associated one letter codes including J, translation; L replication, recombination, and repair, K transcription; O molecular chaperones and related functions, M, cell wall structure and biogenesis and outer membrane, N secretion motility and chemotaxis; T signal Transduction; P inorganic ion transport and metabolism; C energy production and conversion; G, carbohydrate metabolism and transport; E amino acid metabolism and transport; F, nueclotide metabolism and transport; D cell Division and chromosome partitioning; R general functional prediction. In preferred embodiments, COGs of the categories, N, M, P, C, G, E, and F are selected as preferred COGs to both provide enhanced growth on specific substrates and modified behaviors relevant for anti-tumor properties. Other preferred embodiments, include COGs for C, G, E, and specific COG functions are listed in Table 4.

COGs are selected to be specific or semi enriched in the host or other microbes within a host by searching for specific functions present in the microbe of interest but absent from a large set of other competition organisms. Tissue specific analysis of the host for enzymes expressed within a tissue is performed to identify tissue specific enzymatic activities in the host. Specific functions are absent from at least 90%, at least 80%, at least 70%, at least 60%, at least 50%, at least 40%, at least 30% at least 20% or at least 10% of the other organisms selected from the group of the host, the host tissue, the disease-associated microbiota, the host gut microbiota, the host niche specific to the engraftment of the microbial composition (e.g. GI tract, skin).

Once these COGs are identified, databases like KEGG were used to link the enzymatic functions to identify the metabolites that are substrates for these selective COGs. Furthermore, the selective analysis to generate selective metabolites is repeated on the set of substrate of COGs to validate that the pathways and metabolites are selective to the desired microbial composition.

Also provided are co-formulations of microbial populations and carbohydrates or other materials that foster desired microbial growth while, optionally, inhibiting undesired microbial growth. For example, one or more bacterial entities are encapsulated in a carbohydrate layer or coating (exemplary formulations include xylose-PEG and or xylose-PEG-PLGA).

Selecting Prebiotics for Particular Probiotics

It is well known that organisms, including bacteria, show a preferential and hierarchical utilization of different carbohydrates. Some bacteria will not respond at all to a sugar, while some bacterial will use a sugar preferentially. The metabolic effects of a sugar on a bacteria reflect how the bacteria senses and responds to its environment. Providing a sugar to a bacteria that has preferential utilization can encourage its growth/selection. Conversely, providing a sugar to a bacteria that is not preferred may lead to its down selection. For example, a particular sugar may not be a preferred substrate for metabolism, and thus may be utilized to bias for or enhance the growth and/or proliferation of particular microbial (e.g., bacterial) species or strains. Further, a particular sugar or the metabolism thereof may act as a selector to promote the survival, colonization, and/or engraftment of a desired microbial population in a host. Alternatively or simultaneously, a particular sugar or the metabolism thereof may act as a selector to reduce or eliminate the survival, colonization, and/or engraftment of an undesired microbial population in host.

Carbohydrates may be selected according to the fermentation or metabolic preferences of a microbe selected for administration to a mammalian subject. Selection criteria include but are not limited to sugar complexity (e.g., monosaccharides, including but not limited to glucose, versus oligosaccharides or starches) as well as by desired end-product. Non-limiting examples include the fermentation products ethanol and carbon dioxide ($CO_2$) (e.g., via ethanol fermentation by *Saccharomyces* sp. *Zymomonas* sp.), lactate (e.g., via homolactic acid fermentation by *Lactococcus* sp., *Streptococcus* sp., *Enterococcus* sp., *Pediococcus* sp. and some species *Lactobacillus*), lactate, ethanol, and $CO_2$ (e.g., via heterolactic acid fermentation (which includes the phosphoketolase pathway) by some species of *Lactobacillus* as well as *Leuconostoc* sp., *Oenococcus* sp., and *Weissella* sp.), butanol, acetone, $CO_2$ and $H_2$ (via acetone-butanol fermentation by some *Clostridium* sp.), and short chain fatty acids (with or without the production of other products) (Muller V, 2011. Bacterial Fermentation. Encyclopedia of Life Sciences). Examples of fermentation leading to short chain fatty acid production include homoacetic acid fermentation (e.g., by *Acetobacterium* sp., and resulting in acetate), propionic acid fermentation (e.g., by *Propionibacterium* sp., and resulting in propionate, acetate and $CO_2$) mixed acid fermentation (e.g., by *Escherichia* sp., and resulting in ethanol, lactate, acetate, succinate, formate, $CO_2$, and $H_2$), butyrate fermentation (e.g., by some *Clostridium* sp., resulting in butyrate, $CO_2$, and $H_2$), and 2,3-butanediol fermentation (e.g., by *Enterobacter* sp., resulting in ethanol, butanediol, lactate, formate, $CO_2$, and $H_2$). In some embodiments, selection of carbohydrates for co-formulation or co-administration with a type of microbe or types of microbe may be achieved by computational analysis of microbial enzymatic pathways, including but not limited to the presence of metabolic/fermentation pathway enzymes including but not limited to the enzymes provided in Table 4.

In preferred embodiments, the combination of a type of microbe or microbial composition and type of prebiotic mixture is selected based on the fermentation or metabolic preferences of one or more microbes capable of producing immunomodulatory SCFAs (e.g., preference for complex versus simple sugar or preference for a fermentation product versus a prebiotic). For example, *M. eldsenii* prefers lactate fermentation to glucose fermentation, and maximization of propionate production by *M. eldsenii* in a mammalian subject may therefore be achieved by administering along with *M. eldsenii* a favored substrate (e.g., lactate) or one or more microbes capable of fermenting glucose into lactate (e.g., *Streptococcus bovis*) (Hosseini E., et al. 2011. Propionate as a health-promoting microbial metabolite in the human gut. Nutrition Reviews. 69(5): 245-258).

Immunomodulation can also be achieved by the microbial production of glutathione or gamma-glutamylcysteine. Thus, in certain embodiments, the pharmaceutical composition, dosage form, or kit comprises at least one type of microbe capable of producing glutathione and/or gamma-glutamylcysteine In some aspects, the composition, dosage form, or kit comprises one or more microbes selected for the presence of glutamate cysteine ligase (e.g., *Lactobacillus fermentum*) and/or L-proline biosynthesis enzymes (e.g., *E. coli*) (Peran et al., 2006. *Lactobacillus fermenum*, a probiotic capable to release glutathione, prevents colonic inflammation in the TNBS model of rat colitis. Int J Colorectal Dis. 21(8): 737-746; Veeravalli et al., 2011. Laboratory evolution of glutathione biosynthesis reveals naturally compensatory pathways. Nat Chem Bio. 7(2): 101-105). In a preferred embodiment, at least one microbe in the pharmaceutical composition, dosage form, or kit is *L. fermentum*.

VII. Methods of Altering the Microbiome Using Prebiotics and/or Probiotics

Disclosed herein are therapeutic compositions containing non-pathogenic, germination-competent bacterial entities and/or fungal entities, for the prevention, control, and treatment of immune and inflammatory diseases, disorders and conditions and for general nutritional health. These compositions are advantageous in being suitable for safe administration to humans and other mammalian subjects and are efficacious in numerous immune and inflammatory diseases, disorders and conditions and in general nutritional health. While spore-based compositions are known, these are generally prepared according to various techniques such as lyophilization or spray-drying of liquid bacterial cultures, resulting in poor efficacy, instability, substantial variability and lack of adequate safety.

It has now been found that populations of bacterial entities and/or fungal entities can be obtained from biological materials obtained from mammalian subjects, including humans. These populations are formulated into compositions as provided herein, and administered to mammalian subjects using the methods as provided herein.

Purified spore populations. In some embodiments, the bacterial compositions comprise purified spore populations. As described herein, purified spore populations contain combinations of commensal bacteria of the human gut microbiota with the capacity to meaningfully provide functions of a healthy microbiota when administered to a mammalian subject. Without being limited to a specific mechanism, it is thought that such compositions inhibit the growth of a pathogen such as *C. difficile, Salmonella* spp., enteropathogenic *E. coli, Fusobacterium* spp., *Klebsiella* spp. and vancomycin-resistant *Enterococcus* spp., so that a healthy, diverse and protective microbiota can be maintained or, in the case of pathogenic bacterial infections, repopulate the intestinal lumen to reestablish ecological control over potential pathogens. In one embodiment, the purified spore populations can engraft in the host and remain present for 1 day, 2 days, 3 days, 4 days, 5 days, 6 days, 7 days, 10 days, 14 days, 21 days, 25 days, 30 days, 60 days, 90 days, or longer than 90 days. Additionally, the purified spore populations can induce other healthy commensal bacteria found in a healthy gut to engraft in the host that are not present in the purified spore populations or present at lesser levels and therefore these species are considered to "augment" the delivered spore populations. In this manner, commensal species augmentation of the purified spore population in the recipient's gut leads to a more diverse population of gut microbiota then present initially.

Preferably, the one or more microbes provided in a therapeutic composition act additively, more preferably synergistically to confer a benefit to a host, e.g. immunological tolerance. For example, in aspects in which the patient is at risk or suffering from GVHD, the immunological tolerance may reduce graft-versus-host activity while maintaining graft-versus-leukemia activity. In another example, in aspects in which the patient suffers from Celiac disease, the immunological tolerance prevents an inappropriate immune response to gluten. The microbes may additively or synergistically be, e.g. i) cytotoxic for an autoimmune disease- and/or inflammatory disease-associated associated pathogen or pathobiont, ii) cytostatic for an autoimmune disease- and/or inflammatory disease-associated pathogen or pathobiont, iii) capable of decreasing the growth of autoimmune disease- and/or inflammatory disease-associated pathogen or pathobiont, iv) capable of inhibiting the growth of an autoimmune disease- and/or inflammatory disease-associated pathogen or pathobiont, v) capable of decreasing the colonization of an autoimmune disease- and/or inflammatory disease-associated pathogen or pathobiont, vi) capable of inhibiting the colonization of an autoimmune disease- and/or inflammatory disease-associated pathogen or pathobiont, vii) capable of eliciting an immunomodulatory response in the host that reduces the risk of an autoimmune and/or inflammatory disorder, viii), capable of eliciting an immunomodulatory response in the host that reduces the severity of an autoimmune and/or inflammatory disorder, or ix) any combination of i)-viii).

The microbes described herein may additively or synergistically reduce the number of types of autoimmune disease- or inflammatory disease-associated pathogens or pathobionts either distally—e.g., orally-administered microbes reduce the total microbial burden in an organ not in the gastrointestinal tract, or intravaginally-administered microbes reduce the total microbial burden in an organ that is not the vagina—or locally, e.g., the intestines or vagina, respectively. Distal sites include but are not limited to the liver, spleen, fallopian tubes and uterus.

Thus provided are compositions formulated for vaginal administration, such as bacterial populations. The bacterial populations are capable of translocating across vaginal tissue to distal sites, or relocation from the vaginal canal into the gastrointestinal tract.

Similarly, the microbes described herein may additively or synergistically elicit an immunomodulatory response either distally, e.g., in which enteral administration of microbes results in altering the immune response at the skin or liver, or locally, e.g. the enteral administration of microbes results in altering the immune response in the intestines.

In some situations, the recipient subject is immunocompromised or immunosuppressed, or is at risk of developing an immune or inflammatory disorder.

Methods for Administrating Bacterial Compositions to Treat a Subject.

Administration of microbial compositions, with or without prebiotics. The microbial compositions of the invention, with or without one or more prebiotics, are suitable for administration to mammals and non-mammalian animals in need thereof. In certain embodiments, the mammalian subject is a human subject who has one or more symptoms of a dysbiosis, including but not limited to overgrowth of an undesired pathobiont or pathogen, reduced representation of key bacterial taxa such as the Bacteroidetes or Firmicutes or genera or species thereof, or reduced diversity of microbial species compared to a healthy individual, or reduced overall abundance of anaerobic bacteria.

When the mammalian subject is suffering from a disease, disorder or condition characterized by an aberrant microbiota, the bacterial compositions described herein are suitable for treatment thereof. In some embodiments, the mammalian subject has not received antibiotics in advance of treatment with the bacterial compositions. For example, the mammalian subject has not been administered at least two doses of vancomycin, metronidazole and/or or similar antibiotic compound within one week prior to administration of the therapeutic composition. In other embodiments, the mammalian subject has not previously received an antibiotic compound in the one month prior to administration of the therapeutic composition. In other embodiments, the mammalian subject has received one or more treatments with one or more different antibiotic compounds and such treatment (s) resulted in no improvement or a worsening of symptoms. In some embodiments, the composition is administered following a successful course of antibiotics to prevent dysbiosis and enhance recovery of a diverse, healthy microbiota.

In some embodiments, the gastrointestinal disease, disorder or condition is a pathogen infection, ulcerative colitis, colitis, Crohn's disease, or irritable bowel disease.

In some embodiments, the therapeutic composition is administered only once prior to improvement of the disease, disorder or condition. In some embodiments the therapeutic composition is administered at intervals greater than two days, such as once every three, four, five or six days, or every week or less frequently than every week. Or the preparation may be administered intermittently according to a set schedule, e.g., once a day, once weekly, or once monthly, or when the subject relapses from the primary illness. In another embodiment, the preparation may be administered on a long-term basis to individuals who are at risk for infection with or who may be carriers of these pathogens, including individuals who will have an invasive medical procedure (such as surgery), who will be hospitalized, who live in a long-term care or rehabilitation facility, who are exposed to pathogens by virtue of their profession (livestock and animal processing workers), or who could be carriers of pathogens (including hospital workers such as physicians, nurses, and other healthcare professionals).

In embodiments where a subject is administered a probiotic composition and a prebiotic composition, the probiotic and prebiotic can be administered simultaneously. For example, the probiotic composition can contain a prebiotic, or can be administered at the same time as a prebiotic. In other embodiments, the probiotic and the prebiotic are dosed on different regimens. For example, the prebiotic can be dosed prior to or after administration of the probiotic. In other embodiments, the prebiotic can be dosed regularly, and the probiotic is dosed at intervals of reduced frequency compared to dosing of the prebiotic.

Also provided are methods of treating or preventing a mammalian subject suffering from or at risk of developing a metabolic disease, and disorder or condition selected from the group consisting of diabetes, metabolic syndrome, obesity, heart disease, autoimmune disease, liver disease, and autism using the therapeutic compositions provided herein.

In embodiments, the microbial composition is administered enterically, with or without prebiotics. This preferentially includes oral administration, or by an oral or nasal tube (including nasogastric, nasojejunal, oral gastric, or oral jejunal). In other embodiments, administration includes rectal administration (including enema, suppository, or colonoscopy). The microbial composition may be administered to at least one region of the gastrointestinal tract, including the mouth, esophagus, stomach, small intestine, large intestine, and rectum. In some embodiments, it is administered to all regions of the gastrointestinal tract. The microbial compositions may be administered orally in the form of medicaments such as powders, capsules, tablets, gels or liquids. The microbial compositions may also be administered in gel or liquid form by the oral route or through a nasogastric tube, or by the rectal route in a gel or liquid form, by enema or instillation through a colonoscope or by a suppository. In some embodiments, the microbial composition of the above invention is administered enterically with one ore more prebiotics.

If the composition is administered colonoscopically and, optionally, if the microbial composition, with or without one or more prebiotics, is administered by other rectal routes (such as an enema or suppository) or even if the subject has an oral administration, the subject may have a colonic-cleansing preparation. The colon-cleansing preparation can facilitate proper use of the colonoscope or other administration devices, but even when it does not serve a mechanical purpose it can also maximize the proportion of the bacterial composition relative to the other organisms previously residing in the gastrointestinal tract of the subject. Any ordinarily acceptable colonic-cleansing preparation may be used such as those typically provided when a subject undergoes a colonoscopy.

To evaluate the subject, symptoms of dysbiosis are evaluated post treatment ranging from 1 day to 6 months after administration of the purified bacterial population. Fecal material is collected during this period and the microbes present in the gastrointestinal tract can be assessed by 16S rDNA or metagenomic sequencing analysis or other analyses commonly used by the skilled artisan. Repopulation by species provided by the spore population as well as Augmentation by commensal microbes not present in the spore population will occur in this time as the spore population catalyzes a reshaping of the gut or vagina ecology to a state of healthy biosis.

Methods of treating a subject. In some embodiments, the compositions disclosed herein are administered to a patient or a user (sometimes collectively referred to as a "subject"). As used herein "administer" and "administration" encompasses embodiments in which one person directs another to consume a bacterial composition in a certain manner and/or for a certain purpose, and also situations in which a user uses a bacteria composition in a certain manner and/or for a certain purpose independently of or in variance to any instructions received from a second person. Non-limiting examples of embodiments in which one person directs another to consume a bacterial composition in a certain manner and/or for a certain purpose include when a physician prescribes a course of conduct and/or treatment to a patient, when a parent commands a minor user (such as a child) to consume a bacterial composition, when a trainer advises a user (such as an athlete) to follow a particular course of conduct and/or treatment, and when a manufacturer, distributer, or marketer recommends conditions of use to an end user, for example through advertisements or labeling on packaging or on other materials provided in association with the sale or marketing of a product.

The microbial compositions, with or without one or more prebiotics, offer a protective and/or therapeutic effect against infection by one or more GI pathogens of interest and can be administered after an acute case of infection has been resolved in order to prevent relapse, during an acute case of infection as a complement to antibiotic therapy if the bacterial composition is not sensitive to the same antibiotics as the GI pathogen, or to prevent infection or reduce transmission from disease carriers.

The present microbial compositions, with or without one or more prebiotics, can be useful in a variety of clinical situations. For example, the compositions can be administered as a complementary treatment to antibiotics when a patient is suffering from an acute infection, to reduce the risk of recurrence after an acute infection has subsided, or when a patient will be in close proximity to others with or at risk of serious gastrointestinal infections (physicians, nurses, hospital workers, family members of those who are ill or hospitalized).

The present microbial compositions, with or without one or more prebiotics, can be administered to animals, including humans, laboratory animals (e.g., primates, rats, mice), livestock (e.g., cows, sheep, goats, pigs, turkeys, chickens), and household pets (e.g., dogs, cats, rodents).

In the present method, the microbial composition, with or without one or more prebiotics, can be administered enterically, in other words, by a route of access to the gastrointestinal tract or vagina. This includes oral administration, rectal administration (including enema, suppository, or colonoscopy), by an oral or nasal tube (nasogastric, nasojejunal, oral gastric, or oral jejunal), as detailed more fully herein.

Pretreatment protocols. Prior to administration of the microbial composition, with or without one or more prebiotics, the patient can optionally have a pretreatment protocol to prepare the gastrointestinal tract or vagina to receive the bacterial composition. In certain embodiments, the pretreatment protocol is advisable, such as when a patient has an acute infection with a highly resilient pathogen. In other embodiments, the pretreatment protocol is entirely optional, such as when the pathogen causing the infection is not resilient, or the patient has had an acute infection that has been successfully treated but where the physician is concerned that the infection may recur. In these instances, the pretreatment protocol can enhance the ability of the bacterial composition to affect the patient's microbiome.

As one way of preparing the patient for administration of the microbial ecosystem, at least one antibiotic can be administered to alter the bacteria in the patient. As another way of preparing the patient for administration of the microbial ecosystem, a standard colon-cleansing preparation can be administered to the patient to substantially empty the contents of the colon, such as used to prepare a patient for a colonoscopy. By "substantially emptying the contents of the colon," this application means removing at least 75%, at least 80%, at least 90%, at least 95%, or about 100% of the contents of the ordinary volume of colon contents. Antibiotic treatment can precede the colon-cleansing protocol.

If a patient has received an antibiotic for treatment of an infection, or if a patient has received an antibiotic as part of a specific pretreatment protocol, in one embodiment, the antibiotic can be stopped in sufficient time to allow the antibiotic to be substantially reduced in concentration in the gut or vagina before the bacterial composition is administered. In one embodiment, the antibiotic can be discontinued 1, 2, or 3 days before the administration of the bacterial composition. In another embodiment, the antibiotic can be discontinued 3, 4, 5, 6, or 7 antibiotic half-lives before administration of the bacterial composition. In another embodiment, the antibiotic can be chosen so the constituents in the bacterial composition have an MIC50 that is higher than the concentration of the antibiotic in the gut or vagina.

MIC50 of a bacterial composition or the elements in the composition can be determined by methods well known in the art. Reller et al., Antimicrobial Susceptibility Testing: A Review of General Principles and Contemporary Practices, Clinical Infectious Diseases 49(11):1749-1755 (2009). In such an embodiment, the additional time between antibiotic administration and administration of the bacterial composition is not necessary. If the pretreatment protocol is part of treatment of an acute infection, the antibiotic can be chosen so that the infection is sensitive to the antibiotic, but the constituents in the bacterial composition are not sensitive to the antibiotic.

Routes of administration. As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. Compositions can be administered by any route suitable for the delivery of disclosed compositions for treating, inhibiting, or preventing a dysbiosis, or diseases and disorders associated with a dysbiosis, including, but are not limited to orally, sublingually, rectally, parentally (e.g., intravenous injection (i.v.), intracranial injection (i.e.); intramuscular injection (i.m.), intraperitoneal injection (i.p.), and subcutaneous injection (s.c.) and intraosseous infusion (i.o.)), transdermally (using any standard patch), extracorporeally, inhalation, topically or the like, including topical intranasal administration or administration by inhalant. The compositions and dosage forms described herein can be administered by e.g., intradermal, ophthalmic, (intra)nasally, local, non-oral, such as aerosol, inhalation, subcutaneous, intramuscular, buccal, sublingual, (trans)rectal, vaginal, intra-arterial, and intrathecal, transmucosal (e.g., sublingual, lingual, (trans)buccal, (trans)urethral, vaginal (e.g., trans- and perivaginally), intravesical, intrapulmonary, intraduodenal, intragastrical, intrabronchial, etc. In preferred embodiments, the pharmaceutical compositions and dosage forms described herein are administered by routes selected from oral, topical, (trans)dermal, (intra)nasal, and rectal. In certain embodiments, the (intra)nasal administration is achieved via aerosol or inhalation.

The compositions of the invention are suitable for administration to mammals and non-mammalian animals in need thereof. In certain embodiments, the mammalian subject is a human subject who has one or more symptoms of a dysbiosis.

In some embodiments, the subject is fed a meal within one hour of administration of the probiotic composition. In another embodiment, the subject is fed a meal concurrently with administration of the probiotic composition.

When a mammalian subject is suffering from a disease, disorder or condition characterized by an aberrant microbiota, the bacterial compositions described herein are suitable for treatment thereof. In some embodiments, the mammalian subject has not received antibiotics in advance of treatment with the bacterial compositions. For example, the mammalian subject has not been administered at least two doses of vancomycin, metronidazole and/or or similar antibiotic compound within one week prior to administration of the therapeutic composition. In other embodiments, the mammalian subject has not previously received an antibiotic compound in the one month prior to administration of the therapeutic composition. In other embodiments, the mammalian subject has received one or more treatments with one or more different antibiotic compounds and such treatment(s) resulted in no improvement or a worsening of symptoms.

In some embodiments, the gastrointestinal disease, disorder or condition is a pathogen infection, ulcerative colitis, colitis, Crohn's disease, or irritable bowel disease. Beneficially, the therapeutic composition is administered only once prior to improvement of the disease, disorder or condition. In some embodiments, the therapeutic composition is administered at intervals greater than two days, such as once every three, four, five or six days, or every week or less frequently than every week. In other embodiments, the preparation can be administered intermittently according to a set schedule, e.g., once a day, once weekly, or once monthly, or when the subject relapses from the primary illness. In another embodiment, the preparation may be administered on a long-term basis to subjects who are at risk for infection with or who may be carriers of these pathogens, including subjects who will have an invasive medical procedure (such as surgery), who will be hospitalized, who live in a long-term care or rehabilitation facility, who are exposed to pathogens by virtue of their profession (livestock and animal processing workers), or who could be carriers of pathogens (including hospital workers such as physicians, nurses, and other health care professionals).

In certain embodiments, the microbial composition is administered enterically. This preferentially includes oral administration, or by an oral or nasal tube (including nasogastric, nasojejunal, oral gastric, or oral jejunal). In other embodiments, administration includes rectal administration (including enema, suppository, or colonoscopy). The microbial composition can be administered to at least one region of the gastrointestinal tract, including the mouth, esophagus, stomach, small intestine, large intestine, and rectum. In some embodiments, it is administered to all regions of the gastrointestinal tract. The microbial compositions can be administered orally in the form of medicaments such as powders, capsules, tablets, gels or liquids. The bacterial compositions can also be administered in gel or liquid form by the oral route or through a nasogastric tube, or by the rectal route in a gel or liquid form, by enema or instillation through a colonoscope or by a suppository. In certain embodiments of the above invention, the microbial composition is administered enterically with one or more prebiotics.

If the composition is administered colonoscopically and, optionally, if the composition is administered by other rectal routes (such as an enema or suppository) or even if the subject has an oral administration, the subject can have a colon-cleansing preparation. The colon-cleansing preparation can facilitate proper use of the colonoscope or other administration devices, but even when it does not serve a mechanical purpose, it can also maximize the proportion of the bacterial composition relative to the other organisms previously residing in the gastrointestinal tract of the subject. For example, the colon cleansing preparation may maximize the amount of bacterial entities of the bacterial composition that reach and/or engraft in the gastrointestinal tract of the subject. Any ordinarily acceptable colon-cleansing preparation may be used such as those typically provided when a subject undergoes a colonoscopy.

Dosages and Schedule for Administration.

The dose administered to a subject should be sufficient to prevent a dysbiosis, partially reverse a dysbiosis, fully reverse a dysbiosis, or establish a healthy-state microbiome. In some aspects, the dose administered to a subject should be sufficient to prevent the onset of symptoms associated with an autoimmune, inflammatory, or barrier disorder, to reduces the symptoms associated with an autoimmune, inflammatory, or barrier disorder, to eliminate the symptoms associated with an autoimmune, inflammatory, or barrier disorder, or to prevent relapse or recurrence of an autoimmune, inflammatory, or barrier disorder.

One skilled in the art will recognize that dosage will depend upon a variety of factors including the strength of the particular active components employed, as well as the age, species, condition, and body weight of the subject. The size of the dose will also be determined by the route, timing, and frequency of administration as well as the existence, nature, and extent of any adverse side-effects that might accompany the administration of a particular composition and the desired physiological effect.

Suitable doses and dosage regimens can be determined by conventional range-finding techniques known to those of ordinary skill in the art. Generally, treatment is initiated with smaller dosages, which are less than the optimum dose of the active components. Thereafter, the dosage is increased by small increments until the optimum effect under the circumstances is reached. An effective dosage and treatment protocol can be determined by routine and conventional means, starting e.g. with a low dose in laboratory animals and then increasing the dosage while monitoring the effects, and systematically varying the dosage regimen as well. Animal studies are commonly used to determine the maximal tolerable dose ("MTD") of bioactive agent per kilogram weight. Those skilled in the art regularly extrapolate doses for efficacy, while avoiding toxicity, in other species, including humans.

Dosing may be in one or a combination of two or more administrations, e.g., daily, bi-daily, weekly, monthly, or otherwise in accordance with the judgment of the clinician or practitioner, taking into account factors such as age, weight, severity of the disease, and the dose administered in each administration.

In accordance with the above, in therapeutic applications, the dosages of the composition used in accordance with the invention vary depending on the form, depending on the age, weight, and clinical condition of the recipient patient, and depending on the experience and judgment of the clinician or practitioner administering the therapy, among other factors affecting the selected dosage. Generally, the dose should be sufficient to result in relieving, and preferably eliminating, a dysbiosis or disease-associated microbiome, most preferably causing complete recovery from the autoimmune, inflammatory, or barrier disorder. Relief or elimination of a dysbiosis or disease-associated microbiome may be measured by culturing and/or sequencing techniques, and well as by detection of microbial biomarkers in bodily fluids including but not limited to serum, urine, and feces, or by other techniques known in the art. Relief or elimination of an autoimmune, inflammatory, or barrier disease, condition, or disorder may be indicated by biopsy and subsequent analysis of immune cells, microbial cells, and/or TEER, by local or systemic measurement of cytokine levels, by detection of biomarkers for immune cells, by a lactulose/mannitol test, or by other techniques known in the art.

In some embodiments, the microbes, carbohydrates, and microbial and prebiotic compositions are provided in a dosage form. In certain embodiments, the dosage form is designed for administration of at least one OTU or combination thereof disclosed herein, wherein the total amount of bacterial composition administered is selected from 0.1 ng to 10 g, 10 ng to 1 g, 100 ng to 0.1 g, 0.1 mg to 500 mg, 1 mg to 100 mg, or from 10-15 mg. In other embodiments, the bacterial composition is consumed at a rate of from 0.1 ng to 10 g a day, 10 ng to 1 g a day, 100 ng to 0.1 g a day, 0.1 mg to 500 mg a day, 1 mg to 100 mg a day, or from 10-15 mg a day, or more.

In certain embodiments, the treatment period is at least 1 day, at least 2 days, at least 3 days, at least 4 days, at least 5 days, at least 6 days, at least 1 week, at least 2 weeks, at least 3 weeks, at least 4 weeks, at least 1 month, at least 2 months, at least 3 months, at least 4 months, at least 5 months, at least 6 months, or at least 1 year. In some embodiments the treatment period is from 1 day to 1 week, from 1 week to 4 weeks, from 1 month, to 3 months, from 3 months to 6 months, from 6 months to 1 year, or for over a year.

In one embodiment, between about $10^5$ and about $10^{12}$ microorganisms (e.g., CFUs) total can be administered to the patient in a given dosage form. In another embodiment, an effective amount can be provided in from 1 to 500 ml or from 1 to 500 grams of the bacterial composition having from $10^7$ to $10^{11}$ bacteria per ml or per gram, or a capsule, tablet or suppository having from 1 mg to 1000 mg lyophilized powder having from $10^7$ to $10^{11}$ bacteria. Those receiving acute treatment can receive higher doses than those who are receiving chronic administration (such as hospital workers or those admitted into long-term care facilities).

Any of the preparations described herein can be administered once on a single occasion or on multiple occasions, such as once a day for several days or more than once a day on the day of administration (including twice daily, three times daily, or up to five times daily). In another embodiment, the preparation can be administered intermittently according to a set schedule, e.g., once weekly, once monthly, or when the patient relapses from the primary illness. In one embodiment, the preparation can be administered on a long-term basis to individuals who are at risk for infection with or who may be carriers of these pathogens, including individuals who will have an invasive medical procedure (such as surgery), who will be hospitalized, who live in a long-term care or rehabilitation facility, who are exposed to pathogens by virtue of their profession (livestock and animal processing workers), or who could be carriers of pathogens (including hospital workers such as physicians, nurses, and other health care professionals).

Patient selection. Particular microbial compositions, with or without one or more prebiotic, can be selected for individual patients or for patients with particular profiles. For example, 16S sequencing can be performed for a given patient to identify the bacteria present in his or her microbiota. The sequencing can either profile the patient's entire microbiome using 16S sequencing (to the family, genera, or species level), a portion of the patient's microbiome using 16S sequencing, or it can be used to detect the presence or absence of specific candidate bacteria that are biomarkers for health or a particular disease state, such as markers of multi-drug resistant organisms or specific genera of concern such as *Escherichia*. Based on the biomarker data, a particular composition can be selected for administration to a patient to supplement or complement a patient's microbiota in order to restore health or treat or prevent disease. In another embodiment, patients can be screened to determine the composition of their microbiota to determine the likelihood of successful treatment.

In some embodiments, metabolite profiles of patient tissue samples or microbes cultures from patient tissue are used to identify risk factors for developing a gastrointestinal, autoimmune or inflammatory response, to diagnose a gastrointestinal, autoimmune or inflammatory disease, to evaluate the prognosis or severity of said disease, to evaluate the success of a treatment regimen, or any combination thereof. Exemplary metabolites for the purposes of diagnosis, prognostic risk assessment, or treatment assessment purposes include short chain fatty acids, bile acids, and lactate. In preferred embodiments, metabolite profiles are taken at different time points during a patient's disease and treatment in order to better evaluate the patient's disease state including recovery or relapse events. Such monitoring is also important to lower the risk of a patient developing a new autoimmune condition following immunomodulatory treatment. In some embodiments, metabolite profiles inform subsequent treatment, including but not limited to alterations in dosage of therapeutic compositions, formations of prebiotic, or the administration of a particular prebiotic or bacterial population, in order to promote the growth, proliferation, colonization, and/or engraftment of a desired microbial population in the host. In some embodiments, a patient has a deficiency of a desired microbial population which is enhanced by treatment. In some embodiments, a patient has a excess of a desired microbial population which is decreased by treatment.

Pharmaceutical Compositions and Formulations of the Invention

Formulations. Provided are formulations for administration to humans and other subjects in need thereof. Generally the microbial compositions are combined with additional active and/or inactive materials in order to produce a final product, which may be in single dosage unit or in a multi-dose format. In some embodiments of the invention, the microbial compositions are comprised of microbes. In some embodiments of the invention, the microbial compositions are comprised of microbes and one or more prebiotics.

As described herein, the composition comprises at least one prebiotic carbohydrate. A "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate can be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates can contain modified saccharide units, such as 2'-deoxyribose wherein a hydroxyl group is removed, 2'-fluororibose wherein a hydroxyl group is replace with a fluorine, or N-acetylglucosamine, a nitrogen-containing form of glucose (e.g., 2'-fluororibose, deoxyribose, and hexose). Carbohydrates can exist in many different forms, for example, conformers, cyclic forms, acyclic forms, stereoisomers, tautomers, anomers, and isomers.

In some embodiments, the composition comprises at least one lipid. As used herein, a "lipid" includes fats, oils, triglycerides, cholesterol, phospholipids, fatty acids in any form including free fatty acids. Fats, oils and fatty acids can be saturated, unsaturated (cis or trans) or partially unsaturated (cis or trans). In some embodiments, the lipid comprises at least one fatty acid selected from lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid (18:3), octadecatetraenoic acid (18:4), arachidic acid (20:0), eicosenoic acid (20:1), eicosadienoic acid (20:2), eicosatetraenoic acid (20:4), eicosapentaenoic acid (20:5) (EPA), docosanoic acid (22:0), docosenoic acid (22:1), docosapentaenoic acid (22:5), docosahexaenoic acid (22:6) (DHA), and tetracosanoic acid (24:0). In other embodiments, the composition comprises at least one modified lipid, for example, a lipid that has been modified by cooking.

In some embodiments, the composition comprises at least one supplemental mineral or mineral source. Examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In certain embodiments, the composition comprises at least one supplemental vitamin. The at least one vitamin can be fat-soluble or water soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

The composition(s) may include different types of carriers depending on whether it is to be administered in solid, liquid or aerosol form, and whether it needs to be sterile for such routes of administration such as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intlrapericardially, intraumbilically, intraocularally, orally, topically, locally, as an injection, infusion, continuous infusion, localized perfusion bathing target cells directly, via a catheter, via a lavage, in lipid compositions (e.g., liposomes), as an aerosol, or by other method or any combination of the foregoing as would be known to one of ordinary skill in the art (see, for example, Remington's Pharmaceutical Sciences, 18th Ed. Mack Printing Company, 1990, incorporated herein by reference).

In other embodiments, the composition comprises an excipient. Non-limiting examples of suitable excipients include a buffering agent, a preservative, a stabilizer, a binder, a compaction agent, a lubricant, a dispersion enhancer, a disintegration agent, a flavoring agent, a sweetener, and a coloring agent.

In another embodiment, the excipient is a buffering agent. Non-limiting examples of suitable buffering agents include sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In cases where a probiotic formulation contains anerobic bacterial strains, the pharmaceutical formulation and excipients can be selected to prevent exposure of the bacterial strains to oxygen.

In other embodiments, the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof.

In another embodiment, the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In other embodiments, the composition comprises a dispersion enhancer as an excipient. Non-limiting examples of suitable dispersants include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments, the composition comprises a disintegrant as an excipient. In other embodiments, the disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pectin, and tragacanth. In another embodiment, the disintegrant is an effervescent disintegrant. Non-limiting examples of suitable effervescent disintegrants include sodium bicarbonate in combination with citric acid, and sodium bicarbonate in combination with tartaric acid.

In another embodiment, the excipient comprises a flavoring agent. Flavoring agents can be chosen from synthetic flavor oils and flavoring aromatics; natural oils; extracts from plants, leaves, flowers, and fruits; and combinations thereof. In some embodiments the flavoring agent is selected from cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In other embodiments, the excipient comprises a sweetener. Non-limiting examples of suitable sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; and sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In yet other embodiments, the composition comprises a coloring agent. Non-limiting examples of suitable color agents include food, drug and cosmetic colors (FD&C), drug and cosmetic colors (D&C), and external drug and cosmetic colors (Ext. D&C). The coloring agents can be used as dyes or their corresponding lakes.

The weight fraction of the excipient or combination of excipients in the formulation is usually about 99% or less, such as about 95% or less, about 90% or less, about 85% or less, about 80% or less, about 75% or less, about 70% or less, about 65% or less, about 60% or less, about 55% or less, 50% or less, about 45% or less, about 40% or less, about 35% or less, about 30% or less, about 25% or less, about 20% or less, about 15% or less, about 10% or less, about 5% or less, about 2% or less, or about 1% or less of the total weight of the composition.

The compositions disclosed herein can be formulated into a variety of forms and administered by a number of different means. The compositions can be administered orally, rectally, or parenterally, in formulations containing conventionally acceptable carriers, adjuvants, and vehicles as desired. The term "parenteral" as used herein includes subcutaneous, intravenous, intramuscular, or intrasternal injection and infusion techniques. In an exemplary embodiment, the composition is administered orally.

Solid dosage forms for oral administration include capsules, tablets, caplets, pills, troches, lozenges, powders, and granules. A capsule typically comprises a core material comprising a bacterial composition and a shell wall that encapsulates the core material. In some embodiments, the core material comprises at least one of a solid, a liquid, and an emulsion. In other embodiments, the shell wall material comprises at least one of a soft gelatin, a hard gelatin, and a polymer. Suitable polymers include, but are not limited to: cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, such as those formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). In yet other embodiments, at least one polymer functions as taste-masking agents.

Tablets, pills, and the like can be compressed, multiply compressed, multiply layered, and/or coated. The coating can be single or multiple. In one embodiment, the coating material comprises at least one of a saccharide, a polysaccharide, and glycoproteins extracted from at least one of a plant, a fungus, and a microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In some embodiments the coating material comprises a protein. In another embodiment, the coating material comprises at least one of a fat and an oil. In other embodiments, the at least one of a fat and an oil is high temperature melting. In yet another embodiment, the at least one of a fat and an oil is hydrogenated or partially hydrogenated. In one embodiment, the at least one of a fat and an oil is derived from a plant. In other embodiments, the at least one of a fat and an oil comprises at least one of glycerides, free fatty acids, and fatty acid esters. In some embodiments, the coating material comprises at least one edible wax. The edible wax can be derived from animals, insects, or plants. Non-limiting examples include beeswax, lanolin, bayberry wax, carnauba wax, and rice bran wax. Tablets and pills can additionally be prepared with enteric coatings.

Alternatively, powders or granules embodying the bacterial compositions disclosed herein can be incorporated into a food product. In some embodiments, the food product is a drink for oral administration. Non-limiting examples of a suitable drink include fruit juice, a fruit drink, an artificially flavored drink, an artificially sweetened drink, a carbonated beverage, a sports drink, a liquid diary product, a shake, an alcoholic beverage, a caffeinated beverage, infant formula and so forth. Other suitable means for oral administration include aqueous and nonaqueous solutions, emulsions, suspensions and solutions and/or suspensions reconstituted from non-effervescent granules, containing at least one of suitable solvents, preservatives, emulsifying agents, suspending agents, diluents, sweeteners, coloring agents, and flavoring agents.

In some embodiments, the food product can be a solid foodstuff. Suitable examples of a solid foodstuff include without limitation a food bar, a snack bar, a cookie, a brownie, a muffin, a cracker, an ice cream bar, a frozen yogurt bar, and the like.

In other embodiments, the compositions disclosed herein are incorporated into a therapeutic food. In some embodiments, the therapeutic food is a ready-to-use food that optionally contains some or all essential macronutrients and micronutrients. In another embodiment, the compositions disclosed herein are incorporated into a supplementary food that is designed to be blended into an existing meal. In one embodiment, the supplemental food contains some or all essential macronutrients and micronutrients. In another embodiment, the bacterial compositions disclosed herein are blended with or added to an existing food to fortify the food's protein nutrition. Examples include food staples (grain, salt, sugar, cooking oil, margarine), beverages (coffee, tea, soda, beer, liquor, sports drinks), snacks, sweets and other foods.

In one embodiment, the formulations are filled into gelatin capsules for oral administration. An example of an appropriate capsule is a 250 mg gelatin capsule containing from 10 (up to 100 mg) of lyophilized powder ($10^8$ to $10^{11}$ bacteria), 160 mg microcrystalline cellulose, 77.5 mg gelatin, and 2.5 mg magnesium stearate. In an alternative embodiment, from $10^5$ to $10^{12}$ bacteria may be used, $10^5$ to $10^7$, $10^6$ to $10^7$, or $10^8$ to $10^{10}$, with attendant adjustments of the excipients if necessary. In an alternative embodiment, an enteric-coated capsule or tablet or with a buffering or protective composition can be used.

The microbial compositions, with or without one or more prebiotics, are generally formulated for oral or gastric administration, typically to a mammalian subject. In particular embodiments, the composition is formulated for oral administration as a solid, semi-solid, gel, or liquid form, such as in the form of a pill, tablet, capsule, or lozenge. In some embodiments, such formulations contain or are coated by an enteric coating to protect the bacteria through the stomach and small intestine, although spores are generally resistant to the stomach and small intestines. In other embodiments, the microbial compositions, with or without one or more prebiotics, may be formulated with a germinant to enhance engraftment, or efficacy. In yet other embodiments, the bacterial compositions may be co-formulated or co-administered with prebiotic substances, to enhance engraftment or efficacy. In some embodiments, bacterial compositions may be co-formulated or co-administered with prebiotic substances, to enhance engraftment or efficacy.

The microbial compositions, with or without one or more prebiotics, may be formulated to be effective in a given mammalian subject in a single administration or over multiple administrations. For example, a single administration is substantially effective to reduce inflammatory and immune response in a mammalian subject to whom the composition is administered. Substantially effective means that inflammatory and/or immune response in the subject is reduced by at least 10%, 20%, 30%, 40%, 50%, 60%, 70%, 80%, 90%, 95%, 98%, 99% or greater than 99% following administration of the composition. For example, a single administration is substantially effective to reduce *Cl. difficile* and/or *Cl. difficile* toxin content in a mammalian subject to whom the composition is administered. Substantially effective means that *Cl. difficile* and/or *Cl. difficile* toxin content in the subject is reduced by at least 10%, 20%, 30%, 40%, 50%, 60%, 70%, 80%, 90%, 95%, 98%, 99% or greater than 99% following administration of the composition. In some embodiments, microbial and prebiotic compositions may be formulated as described above.

The composition is formulated such that a single oral dose contains at least about $1 \times 10^4$ colony forming units of the bacterial entities and/or fungal entities, and a single oral dose will typically contain about $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, or greater than $1 \times 10^{15}$ CFUs of the bacterial entities and/or fungal entities. The presence and/or concentration of a given type of bacterial may be known or unknown in a given purified spore population. If known, for example the concentration of spores of a given strain, or the aggregate of all strains, is e.g., $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, or greater than $1 \times 10^{15}$ viable bacterial entities (e.g., CFUs) and/or fungal entities per gram of composition or per administered dose.

In some formulations, the composition contains at least about 0.5%, 1%, 2%, 5%, 10%, 20%, 30%, 40%, 50%, 60%, 70%, 80%, 90% or greater than 90% spores on a mass basis. In some formulations, the administered dose does not exceed 200, 300, 400, 500, 600, 700, 800, 900 milligrams or 1, 1.1, 1.2, 1.3, 1.4, 1.5, 1.6, 1.7, 1.8, or 1.9 grams in mass.

The bacteria and/or fungi may contain a purified population that includes a substantial enrichment of bacterial entities present in the fecal material, and wherein the composition optionally comprises a germinant, such as BHIS oxgall, CaDPA, one or more amino acids, a sugar, a nucleoside, a bile salt, a metal or a metal cation, a fatty acid, and a long-chain alkyl amine, or a combination thereof.

It has recently come to light that the DNA of commensal microbes, including many species of *Lactobacillus* protect against activation of lamina propia dendritic cells and sustain regulatory T cell conversion (Bouladoux N, Hall J A, Grainger J R, dos Santos L M, Kann M G, Nagarajan V, Verthelyi D, and Belkaid Y, 2012. Regulatory role of suppressive motifs from commensal DNA. Mucosal Immunol. 5: 623-634). Thus commensal DNA may protect against colitis, IBD, and/or other immunological intolerances in the gut. Furthermore, *Lactobacillus* species are prevalent in the healthy vaginal microbiome. Thus, DNA from *Lactobacillus* or other vaginal microbiome commensals may suppress immune responses in the vagina that could disrupt the normal healthy-state vaginal microbiome and lead to complications such as chronic HPV, infertility, miscarriages, or UTIs. As such, in certain embodiments, the microbial composition, pharmaceutical composition, dosage form, or kit additionally comprises DNA isolated from one or more host commensals.

Combination therapy. The microbial compositions, with or without one or more prebiotics, can be administered with other agents in a combination therapy mode, including anti-microbial agents. Administration can be sequential, over a period of hours or days, or simultaneous.

In one embodiment, the microbial compositions, with or without one or more prebiotics, are included in combination therapy with one or more anti-microbial agents, which include anti-bacterial agents, anti-fungal agents, anti-viral agents and anti-parasitic agents.

Anti-bacterial agents can include cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); and carbapenem antibiotics (ertapenem, doripenem, imipenem/cilastatin, and meropenem).

Anti-viral agents can include Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, Foscarnet, Fomivirsen, Ganciclovir, Indinavir, Idoxuridine, Lamivudine, Lopinavir Maraviroc, MK-2048, Nelfinavir, Nevirapine, Penciclovir, Raltegravir, Rilpivirine, Ritonavir, Saquinavir, Stavudine, Tenofovir Trifluridine, Valaciclovir, Valganciclovir, Vidarabine, Ibacitabine, Amantadine, Oseltamivir, Rimantidine, Tipranavir, Zalcitabine, Zanamivir and Zidovudine.

Examples of antifungal compounds include, but are not limited to polyene antifungals such as natamycin, rimocidin, filipin, nystatin, amphotericin B, candicin, and hamycin; imidazole antifungals such as miconazole, ketoconazole, clotrimazole, econazole, omoconazole, bifonazole, butoconazole, fenticonazole, isoconazole, oxiconazole, sertaconazole, sulconazole, and tioconazole; triazole antifungals such as fluconazole, itraconazole, isavuconazole, ravuconazole, posaconazole, voriconazole, terconazole, and albaconazole; thiazole antifungals such as abafungin; allylamine antifungals such as terbinafine, naftifine, and butenafine; and echinocandin antifungals such as anidulafungin, caspofungin, and micafungin. Other compounds that have antifungal properties include, but are not limited to polygodial, benzoic acid, ciclopirox, tolnaftate, undecylenic acid, flucytosine or 5-fluorocytosine, griseofulvin, and haloprogin.

In one embodiment, the bacterial compositions are included in combination therapy with one or more corticosteroids, mesalazine, mesalamine, sulfasalazine, sulfasalazine derivatives, immunosuppressive drugs, cyclosporin A, mercaptopurine, azathioprine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines, and combinations thereof.

In one embodiment, the bacterial compositions are included in a combination or adjuvant therapy with one or more additional treatments for GVHD. For example, the bacterial compositions can be administered to a transplant subject who has been or currently is being treated with an immunosuppressive treatment like cyclosporine, high dose steroids, methotrexate, or methylprednisolone.

A prebiotic is an ingredient that can allow specific changes in both the composition and/or activity in the gastrointestinal microbiota that confers benefits upon host well-being and health. Prebiotics can include complex carbohydrates, amino acids, peptides, or other essential nutritional components for the survival of the bacterial composition. Prebiotics include, but are not limited to, amino acids, biotin, fructooligosaccharide, galactooligosaccharides, inulin, lactulose, mannan oligosaccharides, oligofructose-enriched inulin, oligofructose, oligodextrose, tagatose, transgalactooligosaccharide, and xylooligosaccharides.

Methods for Testing Compositions for Populating Effect

In vivo assay for determining whether a composition populates a subject's gastrointestinal tract or vagina. In order to determine that the composition populates the gastrointestinal tract or vagina of a subject, an animal model, such as a mouse model, can be used. The model can begin by evaluating the microbiota of the mice. Qualitative assessments can be accomplished using 16S profiling of the microbial community in the feces of normal mice. It can also be accomplished by full genome sequencing, whole genome shotgun sequencing (WGS), or traditional microbiological techniques. Quantitative assessments can be conducted using quantitative PCR (qPCR), described below, or by using traditional microbiological techniques and counting colony formation.

Optionally, the mice can receive an antibiotic treatment to mimic the condition of dysbiosis. Antibiotic treatment can decrease the taxonomic richness, diversity, and evenness of the community, including a reduction of abundance of a significant number of bacterial taxa. Dethlefsen et al., The pervasive effects of an antibiotic on the human gut microbiota, as revealed by deep 16S rRNA sequencing, PLoS Biology 6(11):3280 (2008). At least one antibiotic can be used, and antibiotics are well known. Antibiotics can include aminoglycoside antibiotic (amikacin, arbekacin, gentamicin, kanamycin, neomycin, netilmicin, paromomycin, rhodostreptomycin, streptomycin, tobramycin, and apramycin), amoxicillin, ampicillin, Augmentin (an amoxicillin/clavulanate potassium combination), cephalosporin (cefaclor, defadroxil, cefazolin, cefixime, fefoxitin, cefprozil, ceftazimdime, cefuroxime, cephalexin), clavulanate potassium, clindamycin, colistin, gentamycin, kanamycin, metronidazole, or vancomycin. As an individual, nonlimiting specific example, the mice can be provided with drinking water containing a mixture of the antibiotics kanamycin, colistin, gentamycin, metronidazole and vancomycin at 40 mg/kg, 4.2 mg/kg, 3.5 mg/kg, 21.5 mg/kg, and 4.5 mg/kg (mg per average mouse body weight), respectively, for 7 days. Alternatively, mice can be administered ciprofloxacin at a dose of 15-20 mg/kg (mg per average mouse body weight), for 7 days.

If the mice are provided with an antibiotic, a wash out period of from one day to three days may be provided with no antibiotic treatment and no bacterial composition treatment.

Subsequently, the composition is administered to the mice by oral gavage. The composition may be administered in a volume of 0.2 ml containing $10^4$ CFUs of each type of bacteria in the therapeutic composition. Dose-response may be assessed by using a range of doses, including, but not limited to $10^2$, $10^3$, $10^4$, $10^5$, $10^6$, $10^7$, $10^8$, $10^9$, and/or $10^{10}$.

The mice can be evaluated using 16S sequencing, full genome sequencing, whole genome shotgun sequencing (WGS), or traditional microbiological techniques to determine whether administering the composition has resulted in the population by one or more administered bacteria in the gastrointestinal tract or vagina of the mice. For example only, one day, three days, one week, two weeks, and one month after administration of the bacterial composition to the mice, 16S profiling is conducted to determine whether administering the composition has resulted in population by one or more administered bacteria in the gastrointestinal tract or vagina of the mice. Quantitative assessments, including qPCR and traditional microbiological techniques such as colony counting, can additionally or alternatively be performed, at the same time intervals.

Furthermore, the number of sequence counts that correspond exactly to those in the composition over time can be assessed to determine specifically which components of the bacterial composition reside in the gastrointestinal tract or vagina over a particular period of time. In one embodiment, the bacterial strains of the composition persist for a desired period of time. In another embodiment, the bacterial strains of the composition persist for a desired period of time, while also increasing the ability of other microbes (such as those present in the environment, food, etc.) to populate the gastrointestinal tract or vagina, further increasing overall diversity, as discussed below.

Ability of compositions to populate different regions of the gastrointestinal tract or vagina. The present microbial compositions can also be assessed for their ability to populate different regions on the gastrointestinal tract or vagina. In one embodiment, a microbes of the therapeutic composition can be chosen for its ability to populate one or more than one region of the gastrointestinal tract, including, but not limited to the stomach, the small intestine (duodenum, jejunum, and ileum), the large intestine (the cecum, the colon (the ascending, transverse, descending, and sigmoid colon), and the rectum). In another embodiment, the bacterial composition can be chosen for its ability to populate one or more than one region of the vagina. In some embodiments of the above invention, the microbial compositions comprise microbes and one or more prebiotics.

An in vivo study can be conducted to determine which regions of the gastrointestinal tract or vagina a given bacterial composition will populate. A mouse model similar to the one described above can be conducted, except instead of assessing the feces produced by the mice, particular regions of the gastrointestinal tract or vagina can be removed and studied individually. For example, at least one particular region of the gastrointestinal tract or vagina can be removed and a qualitative or quantitative determination can be performed on the contents of that region of the gastrointestinal tract or vagina. In another embodiment, the contents can optionally be removed and the qualitative or quantitative determination may be conducted on the tissue removed from the mouse.

qPCR. As one quantitative method for determining whether a microbial composition, with or without one or more prebiotics, populates the gastrointestinal tract or vagina, quantitative PCR (qPCR) can be performed. Standard techniques can be followed to generate a standard curve for the bacterial composition of interest, either for all of the components of the bacterial composition collectively, individually, or in subsets (if applicable). Genomic DNA can be extracted from samples using commercially-available kits, such as the Mo Bio Powersoil®-htp 96 Well Soil DNA Isolation Kit (Mo Bio Laboratories, Carlsbad, Calif.), the Mo Bio Powersoil® DNA Isolation Kit (Mo Bio Laboratories, Carlsbad, Calif.), or the QIAamp DNA Stool Mini Kit (QIAGEN, Valencia, Calif.) according to the manufacturer's instructions.

In some embodiments, qPCR can be conducted using HotMasterMix (5PRIME, Gaithersburg, Md.) and primers specific for the bacterial composition of interest, and may be conducted on a MicroAmp® Fast Optical 96-well Reaction Plate with Barcode (0.1 mL) (Life Technologies, Grand Island, N.Y.) and performed on a BioRad C1000™ Thermal Cycler equipped with a CFX96™ Real-Time System (Bio-Rad, Hercules, Calif.), with fluorescent readings of the FAM and ROX channels. The Cq value for each well on the FAM channel is determined by the CFX Manager™ software version 2.1. The $\log_{10}$(cfu/ml) of each experimental sample is calculated by inputting a given sample's Cq value into linear regression model generated from the standard curve comparing the Cq values of the standard curve wells to the known $\log_{10}$(cfu/ml) of those samples. The skilled artisan may employ alternative qPCR modes.

VIII. Gastrointestinal Dysbiosis

"Dysbiosis" refers to a state of the microbiota of the gut or other body area in a subject, including mucosal or skin surfaces in which the normal diversity and/or function of the ecological network is disrupted. This unhealthy state can be due to a decrease in diversity, the overgrowth of one or more pathogens or pathobionts, symbiotic organisms able to cause disease only when certain genetic and/or environmental conditions are present in a subject, or the shift to an ecological microbial network that no longer provides an essential function to the host subject, and therefore no longer promotes health. Accordingly, a "gastrointestinal dysbiosis" refers to a state of the microbiota or microbiome of the gut in which the normal diversity and/or function of the ecological network or niche is disrupted. The term "gut" as used herein is meant to refer to the entire gastrointestinal or digestive tract (also referred to as the alimentary canal) and it refers to the system of organs within multi-cellular animals which takes in food, digests it to extract energy and nutrients, and expels the remaining waste. As used herein the term "gastrointestinal tract" refers to the entire digestive canal, from the oral cavity to the rectum. The term "gastrointestinal tract" includes, but is not limited to, the mouth and proceeds to the esophagus, stomach, small intestine, large intestine, rectum and, finally, the anus.

Any disruption from a preferred (e.g., ideal, normal, or beneficial) state of the microbiota can be considered a dysbiosis, even if such dysbiosis does not result in a detectable disease or disorder (e.g., a gastrointestinal disease, disorder or condition), or decrease in health. This state of dysbiosis may lead to a disease or disorder (e.g. a gastrointestinal disease, disorder or condition), or the state of dysbiosis may lead to a disease or disorder (e.g. a gastrointestinal disease, disorder or condition) only under certain conditions, or the state of dysbiosis may prevent a subject from responding to treatment or recovering from a disease or disorder (e.g. a gastrointestinal disease, disorder or condition).

In certain aspects, the present invention is directed to a method of reconstituting, modulating, or creating a beneficial bacterial flora in the gastrointestinal tract of a mammalian host in need thereof, comprising administering to the mammalian host a composition comprising at least one isolated bacterial population. In one embodiment, the at least one bacterial population is coadministered or coformulated with one or more prebiotic, e.g, at least one polymer or monomer. In one embodiment, the prebiotic is a carbohydrate, e.g., xylose. In one embodiment, the subject is suffering from a gastrointestinal disorder. In certain embodiments the gastrointestinal disease, disorder or condition is a disease or disorder associated with or characterized by reduced barrier intestinal integrity.

In certain other aspects, the present invention is directed to a method of treating or alleviating a gastrointestinal disorder in a subject in need thereof, the method comprising a administering to the subject at least one isolated bacterial population. In one embodiment, the at least one bacterial population is coadministered or coformulated with one or more prebiotic, e.g, at least one polymer or monomer. In one embodiment, the one or more prebiotic is a carbohydrate, e.g., xylose.

In some embodiments, a prebiotic comprises at least one polymer or monomer. For example, the prebiotic may be selected from the group consisting of arabinoxylan, xylose, soluble fiber dextran, soluble corn fiber, polydextrose, lactose, N-acetyl-lactosamine, glucose, and mixtures thereof. In some embodiments, the prebiotic comprises a sugar selected from the group consisting of arabinose, fructose, fucose, lactose, galactose, glucose, mannose, D-xylose, xylitol, ribose, xylobiose, sucrose, maltose, lactose, lactulose, trehalose, cellobiose, xylooligosaccharide, and combinations thereof.

In some embodiments, the composition comprises more than one prebiotic. For example, in one embodiment, the one or more additional prebiotic can comprise at least one polymer or monomer selected from the group consisting of galactose, fructose, rhamnose, mannose, uronic acids, 3'-fucosyllactose, 3' sialyllactose, 6'-sialyllactose, lacto-N-neotetraose, 2'-2'-fucosyllactose, and mixtures thereof.

In one embodiment, the bacterial cells and prebiotic are capable of functionally interacting. In another embodiment, the bacterial cells and prebiotic are formulated to functionally interact when co-localized in the gastrointestinal tract of a human subject.

In one embodiment, the compositions used in the methods of the invention can further comprise a non-bacterial therapeutic agent. For example, the non-bacterial therapeutic agent can comprise a small molecule, nucleic acid, or polypeptide. The non-bacterial therapeutic agent can also comprise, for example, a fungus, yeast, or Archea.

In one embodiment of these aspects, the subject is an adult subject. In another embodiment, the subject is an infant or toddler. In another embodiment, the subject is a child or an adolescent. In another embodiment, the subject has undergone a colonoscopy or endoscopic large bowel examination. The compositions of the present invention can be administered by any method known to one of skill in the art. For example, in one embodiment, the compositions of the invention can be administered orally or rectally.

As used herein the term "gastrointestinal disease, disorder or condition" includes any acute or chronic disease, disorder and condition that is related to or has an affect on the gut or gastrointestinal tract, including, but not limited to inflammatory gastrointestinal diseases, disorders and conditions, autoimmune diseases, disorders, and conditions, and gastrointestinal diseases, disorders and conditions related to or caused by dysbiosis or infection or colonization with a microbe, e.g., a bacterial or fungal infection. In some embodiments, the gastrointestinal disease, disorder or condition is selected from the group consisting of antibiotic associated diarrhea, *Clostridium difficile*-induced diarrhea, constipation, inflammatory Bowel Disease (IBD), including Crohn's Disease and celiac disease, irritable bowel syndrome (IBS), colonization with a pathogen or pathobiont, infection with a drug-resistant pathogen or pathobiont, and colitis. In one embodiment, the gastrointestinal disease, disorder or condition is antibiotic associated diarrhea. In one embodiment, the gastrointestinal disease, disorder or condition is *Clostridium difficile*-induced diarrhea. In one embodiment, the gastrointestinal disease, disorder or condition is constipation. In one embodiment, the gastrointestinal disease, disorder or condition is IBD. In one embodiment, the gastrointestinal disease, disorder or condition is Crohn's Disease. In one embodiment, the gastrointestinal disease, disorder or condition is celiac disease. In one embodiment, the gastrointestinal disease, disorder or condition is IBS. In one embodiment, the gastrointestinal disease, disorder or condition is colonization with a pathogen or pathobiont. In one embodiment, the gastrointestinal disease, disorder or condition is infection with a drug-resistant pathogen or pathobiont. In one embodiment, the gastrointestinal disease, disorder or condition is colitis.

In one embodiment, the gastrointestinal disease, disorder or condition is a chronic disease, disorder or condition. For example, a chronic gastrointestinal disease includes, but is not limited to, *Clostridium difficile*-induced diarrhea, constipation, inflammatory bowel disease (IBD), including Crohn's Disease and celiac disease, irritable bowel syndrome (IBS), GI complications of chronic graft versus host disease (GVHD), gastritis, gastric ulcers, congenital sucrase-somaltase deficiency (CSID), diverticulosis and diverticulitis.

In another embodiment, the gastrointestinal disease, disorder or condition is an acute gastrointestinal disease, disorder or condition. For example, an acute gastrointestinal disease includes, but is not limited to, acute diarrhea, acute constipation, or acute bacterial infections, and related symptoms thereof. In certain embodiments, an acute gastrointestinal disease includes, but is not limited to, GI complications of acute graft versus host disease (GVHD), infectious colitis, esophagitis, acute diarrhea, and gastroenteritis.

In certain aspects of the invention, one or more bacterial populations administered to the subject or host are capable of engraftment in the subject or host. In one embodiment, each of the bacterial populations or species administered to the subject or host are capable of engraftment in the subject or host. In another embodiment, a subset of the bacterial populations or species administered to the subject or mammalian host are capable of engraftment in the subject or host. In one embodiment, engraftment of the one or more bacterial populations in the host is beneficial for the treatment of an acute gastrointestinal disease, disorder or condition in that engraftment provides long-term, sustained alleviation of the disease, disorder or condition. In a preferred embodiment, engraftment of the one or more bacterial populations in the host is beneficial for the treatment of a chronic gastrointestinal disease, disorder or condition in that engraftment provides long-term, sustained alleviation of the disease, disorder or condition.

In one embodiment, at least one of the bacterial populations or species useful in the compositions and methods of the invention is capable of forming spores. In one embodiment, at least 10%, 20%, 30%, 40%, 50%, 60%, 70%, 80%, 90%, 95% or more of the bacterial populations or species useful in the compositions and methods of the invention are capable of forming spores. In one embodiment, each of the bacterial populations or species useful in the compositions and methods of the invention are capable of forming spores. In another embodiment, at least one of the bacterial populations or species useful in the compositions and methods of the invention is incapable of forming spores. In one embodiment, at least 10%, 20%, 30%, 40%, 50%, 60%, 70%, 80%, 90%, 95% or more of the bacterial populations or species useful in the compositions and methods of the invention are incapable of forming spores. In one embodiment, each of the bacterial populations or species useful in the compositions and methods of the invention are incapable of forming spores.

In one embodiment, a composition comprising about 20 or fewer isolated populations of bacterial cells is administered to the subject or host. In another embodiment, a composition comprising about 15 or fewer isolated populations of bacterial cells is administered to the subject or host. In another embodiment, a composition comprising about 10 or fewer isolated populations of bacterial cells is administered to the subject or host. In another embodiment, a composition comprising about 5 or fewer isolated populations of bacterial cells is administered to the subject or host. In another embodiment, a composition comprising about 4 or fewer isolated populations of bacterial cells is administered to the subject or host. In another embodiment, a composition comprising about 3 or fewer isolated populations of bacterial cells is administered to the subject or host. In another embodiment, a composition comprising 2 isolated populations of bacterial cells is administered to the subject or host. In another embodiment, a composition comprising between about 12 and 20 isolated populations of bacterial cells is administered to the subject or host. In another embodiment, a composition comprising a single isolated population of bacterial cells is administered to the subject or host. In another embodiment, a composition comprising at least two isolated populations of bacterial cells is administered to the subject or host. In yet another embodiment, 1, 2, 3, 4, 5, 6, 7, 8, 9, 10, 11, 12, 13, 14, 15, 16, 17, 18, 19, or 20 isolated populations of bacterial cells is administered to the subject or host.

In one embodiment, the population of bacterial cells comprise anti-inflammatory bacterial cells. In some embodiments of the invention, the anti-inflammatory bacterial cells decrease secretion of a pro-inflammatory cytokine and/or increase secretion of an anti-inflammatory cytokine by a population of human peripheral blood mononuclear cells (PBMCs). In some embodiments of the invention, the anti-inflammatory bacterial cells decrease secretion of a pro-inflammatory cytokine selected from the group consisting of IFNγ, IL-12p70, IL-1α, IL-6, IL-8, MCP1, MIP1α, MIP1β, TNFα, and combinations thereof. In other embodiments, the anti-inflammatory bacterial cells increase secretion of an anti-inflammatory cytokine selected from the group consisting of IL-10, IL-13, IL-4, IL-5, and combinations thereof.

In some embodiments of the foregoing aspects, the bacterial cells used in the methods of the invention comprise a bacterial cell of the order Clostridiales. In some embodiments of the foregoing aspects, the bacterial cells used in the methods of the invention are of the genus *Blautia*, *Clostridium*, or *Ruminococcus*.

In some embodiments, the bacterial cells used in the methods of the invention belong to bacterial strain or species set forth in Table 1. In some embodiments, the bacterial cells used in the methods of the invention belong to a single bacterial strain or species set forth in Table 1A, Table 1B, Table 1C, Table 1D, Table 1E, or Table 1F.

In one embodiment, the bacterial entity, e.g., species or strain, useful in the compositions and methods of the invention relating to gastrointestinal disorders is *Acidaminococcus intestine*. In one embodiment, the bacterial entity, e.g., species or strain, useful in the compositions and methods of the invention is *Acinetobacter baumannii*. In one embodiment, the bacterial entity, e.g., species or strain, useful in the compositions and methods of the invention is *Acinetobacter lwoffii*. In one embodiment, the bacterial entity, e.g., species or strain, useful in the compositions and methods of the invention is *Akkermansia muciniphila*. In one embodiment, the bacterial entity, e.g., species or strain, useful in the compositions and methods of the invention is *Alistipes putredinis*. In one embodiment, the bacterial entity, e.g., species or strain, useful in the compositions and methods of the invention is *Alistipes shahii*. In one embodiment, the bacterial entity, e.g., species or strain, useful in the compositions and methods of the invention is *Anaerostipes hadrus*. In one embodiment, the bacterial entity, e.g., species or strain, useful in the compositions and methods of the invention is *Anaerotruncus colihominis*. In one embodiment, the bacterial entity, e.g., species or strain, useful in the compositions and methods of the invention is *Bacteroides caccae*. In one embodiment, the bacterial entity, e.g., species or strain, useful in the compositions and methods of the invention is *Bacteroides cellulosilyticus*. In one embodiment, the bacterial entity, e.g., species or strain, useful in the compositions and methods of the invention is *Bacteroides dorei*. In one embodiment, the bacterial entity, e.g., species or strain, useful in the compositions and methods of the invention is *Bacteroides eggerthii*. In one embodiment, the bacterial entity, e.g., species or strain, useful in the compositions and methods of the invention is *Bacteroides finegoldii*. In one embodiment, the bacterial entity, e.g., species or strain, useful in the compositions and methods of the invention is *Bacteroides fragilis*. In one embodiment, the bacterial entity, e.g., species or strain, useful in the compositions and methods of the invention is *Bacteroides massiliensis*. In one embodiment, the bacterial entity, e.g., species or strain, useful in the compositions and methods of the invention is *Bacteroides ovatus*. In one embodiment, the bacterial entity, e.g., species or strain, useful in the compositions and methods of the invention is *Bacteroides salanitronis*. In one embodiment, the bacterial entity, e.g., species or strain, useful in the compositions and methods of the invention is *Bacteroides salyersiae*. In one embodiment, the bacterial entity, e.g., species or strain, useful in the compositions and methods of the invention is *Bacteroides* sp. 1_1_6. In one embodiment, the bacterial entity, e.g., species or strain, useful in the compositions and methods of the invention is *Bacteroides* sp. 3_1_23. In one embodiment, the bacterial entity, e.g., species or strain, useful in the compositions and methods of the invention is *Bacteroides* sp. D20. In one embodiment, the bacterial entity, e.g., species or strain, useful in the compositions and methods of the invention is *Bacteroides thetaiotaomicrond*. In one embodiment, the bacterial entity, e.g., species or strain, useful in the compositions and methods of the invention is *Bacteroides uniformis*. In one embodiment, the bacterial entity, e.g., species or strain, useful in the compositions and methods of the invention is *Bacteroides vulgatus*. In one embodiment, the bacterial entity, e.g., species or strain, useful in the compositions and methods of the invention is *Bifidobacterium adolescentis*. In one embodiment, the bacterial entity, e.g., species or strain, useful in the compositions and methods of the invention is *Bifidobacterium bifidum*. In one embodiment, the bacterial entity, e.g., species or strain, useful in the compositions and methods of the invention is *Bifidobacterium breve*. In one embodiment, the bacterial entity, e.g., species or strain, useful in the compositions and methods of the invention is *Bifidobacterium faecale*. In one embodiment, the bacterial entity, e.g., species or strain, useful in the compositions and methods of the invention is *Bifidobacterium kashiwanohense*. In one embodiment, the bacterial entity, e.g., species or strain, useful in the compositions and methods of the invention is *Bifidobacterium longum* subsp. *Longum*. In one embodiment, the bacterial entity, e.g., species or strain, useful in the compositions and methods of the invention is *Bifidobacterium pseudocatenulatum*. In one embodiment, the bacterial entity, e.g., species or strain, useful in the compositions and methods of the invention is *Bifidobacterium stercoris*. In one embodiment, the bacterial entity, e.g., species or strain, useful in the compositions and methods of the invention is *Blautia (Ruminococcus) coccoides*. In one embodiment, the bacterial entity, e.g., species or strain, useful in the compositions and methods of the invention is *Blautia faecis*. In one embodiment, the bacterial entity, e.g., species or strain, useful in the compositions and methods of the invention is *Blautia glucerasea*. In one embodiment, the bacterial entity, e.g., species or strain, useful in the compositions and methods of the invention is *Blautia (Ruminococcus) hansenii*. In one embodiment, the bacterial entity, e.g., species or strain, useful in the compositions and methods of the invention is *Blautia hydrogenotrophica (Ruminococcus hydrogenotrophicus)*. In one embodiment, the bacterial entity, e.g., species or strain, useful in the compositions and methods of the invention is *Blautia (Ruminococcus) luti*. In one embodiment, the bacterial entity, e.g., species or strain, useful in the compositions and methods of the invention is *Blautia (Ruminococcus) obeum*. In one embodiment, the bacterial entity, e.g., species or strain, useful in the compositions and methods of the invention is *Blautia producta (Ruminococcus productus)*. In one embodiment, the bacterial entity, e.g., species or strain, useful in the compositions and methods of the invention is *Blautia (Ruminococcus) schinkii*. In one embodiment, the bacterial entity, e.g., species or strain, useful in the compositions and methods of the invention is *Blautia stercoris*. In one embodiment, the bacterial entity, e.g., species or strain, useful in the compositions and methods of the invention is *Blautia* uncultured bacterium clone BKLE_a03_2 (GenBank: EU469501.1). In one embodiment, the bacterial entity, e.g., species or strain, useful in the compositions and methods of the invention is *Blautia* uncultured bacterium clone SJTU_B_14_30 (GenBank: EF402926.1). In one embodiment, the bacterial entity, e.g., species or strain, useful in the compositions and methods of the invention is *Blautia* uncultured bacterium clone SJTU_C_14_16 (GenBank: EF404657.1). In one embodiment, the bacterial entity, e.g., species or strain, useful in the compositions and methods of the invention is *Blautia* uncultured bacterium clone S1-5 (GenBank: GQ898099.1). In one embodiment, the bacterial entity, e.g., species or strain, useful in the compositions and methods of the invention is *Blautia* uncultured PAC000178_s (www.ezbiocloud.net/eztaxon/hierarchy?m=browse&k=PAC000178&d=2). In one embodiment, the bacterial entity, e.g., species or strain, useful in the compositions and methods of the invention is *Blautia wexlerae*. In one embodiment, the bacterial entity, e.g., species or strain, useful in the compositions and methods of the invention is *Candidatus Arthromitus* sp. SFB-mouse-Yit. In one embodiment, the bacterial entity, e.g., species or strain, useful in the compositions and methods of the invention is *Catenibacterium mitsuokai*. In one embodiment, the bacterial entity, e.g., species or strain, useful in the compositions and methods of the invention is *Clostridiaceae* bacterium (*Dielma fastidiosa*) JC13. In one embodiment, the bacterial entity, e.g., species or strain, useful in the compositions and methods of the invention is Clostridiales bacterium 1_7_47FAA. In one embodiment, the bacterial entity, e.g., species or strain, useful in the compositions and methods of the invention is *Clostridium asparagiforme*. In one embodiment, the bacterial entity, e.g., species or strain, useful in the compositions and methods of the invention is *Clostridium bolteae*. In one embodiment, the bacterial entity, e.g., species or strain, useful in the compositions and methods of the invention is *Clostridium clostridioforme*. In one embodiment, the bacterial entity, e.g., species or strain, useful in the compositions and methods of the invention is *Clostridium glycyrrhizinilyticum*. In one embodiment, the bacterial entity, e.g., species or strain, useful in the compositions and methods of the invention is *Clostridium (Hungatella) hathewayi*. In one embodiment, the bacterial entity, e.g., species or strain, useful in the compositions and methods of the invention is *Clostridium histolyticum*. In one embodiment, the bacterial entity, e.g., species or strain, useful in the compositions and methods of the invention is *Clostridium indolis*. In one embodiment, the bacterial entity, e.g., species or strain, useful in the compositions and methods of the invention is *Clostridium leptum*. In one embodiment, the bacterial entity, e.g., species or strain, useful in the compositions and methods of the invention is *Clostridium (Tyzzerella) nexile*. In one embodiment, the bacterial entity, e.g., species or strain, useful in the compositions and methods of the invention is *Clostridium perfringens*. In one embodiment, the bacterial entity, e.g., species or strain, useful in the compositions and methods of the invention is *Clostridium (Erysipelatoclostridium) ramosum*. In one embodiment, the bacterial entity, e.g., species or strain, useful in the compositions and methods of the invention is *Clostridium scindens*. In one embodiment, the bacterial entity, e.g., species or strain, useful in the compositions and methods of the invention is *Clostridium septum*. In one embodiment, the bacterial entity, e.g., species or strain, useful in the compositions and methods of the invention is *Clostridium* sp. 14774. In one embodiment, the bacterial entity, e.g., species or strain, useful in the compositions and methods of the invention is *Clostridium* sp. 7_3_54FAA. In one embodiment, the bacterial entity, e.g., species or strain, useful in the compositions and methods of the invention is *Clostridium* sp. HGF2. In one embodiment, the bacterial entity, e.g., species or strain, useful in the compositions and methods of the invention is *Clostridium symbiosum*. In one embodiment, the bacterial entity, e.g., species or strain, useful in the compositions and methods of the invention is *Collinsella aerofaciens*. In one embodiment, the bacterial entity, e.g., species or strain, useful in the compositions and methods of the invention is *Collinsella intestinalis*. In one embodiment, the bacterial entity, e.g., species or strain, useful in the compositions and methods of the invention is *Coprobacillus* sp. D7. In one embodiment, the bacterial entity, e.g., species or strain, useful in the compositions and methods of the invention is *Coprococcus catus*. In one embodiment, the bacterial entity, e.g., species or strain, useful in the compositions and methods of the invention is *Coprococcus comes*. In one embodiment, the bacterial entity, e.g., species or strain, useful in the compositions and methods of the invention is *Dorea formicigenerans*. In one embodiment, the bacterial entity, e.g., species or strain, useful in the compositions and methods of the invention is *Dorea longicatena*. In one embodiment, the bacterial entity, e.g., species or strain, useful in the compositions and methods of the invention is *Enterococcus faecalis*. In one embodiment, the bacterial entity, e.g., species or strain, useful in the compositions and methods of the invention is *Enterococcus faecium*. In one embodiment, the bacterial entity, e.g., species or strain, useful in the compositions and methods of the invention is Erysipelotrichaceae bacterium 3_1_53. In one embodiment, the bacterial entity, e.g., species or strain, useful in the compositions and methods of the invention is *Escherichia coli*. In one embodiment, the bacterial entity, e.g., species or strain, useful in the compositions and methods of the invention is *Escherichia coli* S88. In one embodiment, the bacterial entity, e.g., species or strain, useful in the compositions and methods of the invention is *Eubacterium eligens*. In one embodiment, the bacterial entity, e.g., species or strain, useful in the compositions and methods of the invention is *Eubacterium fissicatena*. In one embodiment, the bacterial entity, e.g., species or strain, useful in the compositions and methods of the invention is *Eubacterium ramulus*. In one embodiment, the bacterial entity, e.g., species or strain, useful in the compositions and methods of the invention is *Eubacterium rectale*. In one embodiment, the bacterial entity, e.g., species or strain, useful in the compositions and methods of the invention is *Faecalibacterium prausnitzii*. In one embodiment, the bacterial entity, e.g., species or strain, useful in the compositions and methods of the invention is *Flavonifractor plautii*. In one embodiment, the bacterial entity, e.g., species or strain, useful in the compositions and methods of the invention is *Fusobacterium mortiferum*. In one embodiment, the bacterial entity, e.g., species or strain, useful in the compositions and methods of the invention is *Fusobacterium nucleatum*. In one embodiment, the bacterial entity, e.g., species or strain, useful in the compositions and methods of the invention is *Holdemania filiformis*. In one embodiment, the bacterial entity, e.g., species or strain, useful in the compositions and methods of the invention is *Hydrogenoanaerobacterium saccharovorans*. In one embodiment, the bacterial entity, e.g., species or strain, useful in the compositions and methods of the invention is *Klebsiella oxytoca*. In one embodiment, the bacterial entity, e.g., species or strain, useful in the compositions and methods of the invention is Lachnospiraceae bacterium 3_1_57FAA_CT1. In one embodiment, the bacterial entity, e.g., species or strain, useful in the compositions and methods of the invention is Lachnospiraceae bacterium 7_1_58FAA. In one embodiment, the bacterial entity, e.g., species or strain, useful in the compositions and methods of the invention is Lachnospiraceae bacterium 5_1_57FAA. In one embodiment, the bacterial entity, e.g., species or strain, useful in the compositions and methods of the invention is *Lactobacillus casei*. In one embodiment, the bacterial entity, e.g., species or strain, useful in the compositions and methods of the invention is *Lactobacillus rhamnosus*. In one embodiment, the bacterial entity, e.g., species or strain, useful in the compositions and methods of the invention is *Lactobacillus ruminis*. In one embodiment, the bacterial entity, e.g., species or strain, useful in the compositions and methods of the invention is *Lactococcus casei*. In one embodiment, the bacterial entity, e.g., species or strain, useful in the compositions and methods of the invention is *Odoribacter splanchnicus*. In one embodiment, the bacterial entity, e.g., species or strain, useful in the compositions and methods of the invention is *Oscillibacter valericigenes*. In one embodiment, the bacterial entity, e.g., species or strain, useful in the compositions and methods of the invention is *Parabacteroides gordonii*. In one embodiment, the bacterial entity, e.g., species or strain, useful in the compositions and methods of the invention is *Parabacteroides johnsonii*. In one embodiment, the bacterial entity, e.g., species or strain, useful in the compositions and methods of the invention is *Parabacteroides merdae*. In one embodiment, the bacterial entity, e.g., species or strain, useful in the compositions and methods of the invention is *Pediococcus acidilactici*. In one embodiment, the bacterial entity, e.g., species or strain, useful in the compositions and methods of the invention is *Peptostreptococcus asaccharolyticus*. In one embodiment, the bacterial entity, e.g., species or strain, useful in the compositions and methods of the invention is *Propionibacterium granulosum*. In one embodiment, the bacterial entity, e.g., species or strain, useful in the compositions and methods of the invention is *Roseburia intestinalis*. In one embodiment, the bacterial entity, e.g., species or strain, useful in the compositions and methods of the invention is *Roseburia inulinivorans*. In one embodiment, the bacterial entity, e.g., species or strain, useful in the compositions and methods of the invention is *Ruminococcus faecis*. In one embodiment, the bacterial entity, e.g., species or strain, useful in the compositions and methods of the invention is *Ruminococcus gnavus*. In one embodiment, the bacterial entity, e.g., species or strain, useful in the compositions and methods of the invention is *Ruminococcus* sp. ID8. In one embodiment, the bacterial entity, e.g., species or strain, useful in the compositions and methods of the invention is *Ruminococcus torques*. In one embodiment, the bacterial entity, e.g., species or strain, useful in the compositions and methods of the invention is *Slackia piriformis*. In one embodiment, the bacterial entity, e.g., species or strain, useful in the compositions and methods of the invention is *Staphylococcus epidermidis*. In one embodiment, the bacterial entity, e.g., species or strain, useful in the compositions and methods of the invention is *Staphylococcus saprophyticus*. In one embodiment, the bacterial entity, e.g., species or strain, useful in the compositions and methods of the invention is *Streptococcus cristatus*. In one embodiment, the bacterial entity, e.g., species or strain, useful in the compositions and methods of the invention is *Streptococcus dysgalactiae* subsp. *Equisimilis*. In one embodiment, the bacterial entity, e.g., species or strain, useful in the compositions and methods of the invention is *Streptococcus infantis*. In one embodiment, the bacterial entity, e.g., species or strain, useful in the compositions and methods of the invention is *Streptococcus oralis*. In one embodiment, the bacterial entity, e.g., species or strain, useful in the compositions and methods of the invention is *Streptococcus sanguinis*. In one embodiment, the bacterial entity, e.g., species or strain, useful in the compositions and methods of the invention is *Streptococcus viridans*. In one embodiment, the bacterial entity, e.g., species or strain, useful in the compositions and methods of the invention is *Streptococcus thermophiles*. In one embodiment, the bacterial entity, e.g., species or strain, useful in the compositions and methods of the invention is *Veillonella dispar.*

In one embodiment, the bacterial population useful in the compositions and methods of the invention relating to gastrointestinal disorders comprises *Acidaminococcus intestine*. In one embodiment, the bacterial population useful in the compositions and methods of the invention comprises *Acinetobacter baumannii*. In one embodiment, the bacterial population useful in the compositions and methods of the invention comprises *Acinetobacter lwoffii*. In one embodiment, the bacterial population useful in the compositions and methods of the invention comprises *Akkermansia muciniphila*. In one embodiment, the bacterial population useful in the compositions and methods of the invention comprises *Alistipes putredinis*. In one embodiment, the bacterial population useful in the compositions and methods of the invention comprises *Alistipes shahii*. In one embodiment, the bacterial population useful in the compositions and methods of the invention comprises *Anaerostipes hadrus*. In one embodiment, the bacterial population useful in the compositions and methods of the invention comprises *Anaerotruncus colihominis*. In one embodiment, the bacterial population useful in the compositions and methods of the invention comprises *Bacteroides caccae*. In one embodiment, the bacterial population useful in the compositions and methods of the invention comprises *Bacteroides cellulosilyticus*. In one embodiment, the bacterial population useful in the compositions and methods of the invention comprises *Bacteroides dorei*. In one embodiment, the bacterial population useful in the compositions and methods of the invention comprises *Bacteroides eggerthii*. In one embodiment, the bacterial population useful in the compositions and methods of the invention comprises *Bacteroides finegoldii*. In one embodiment, the bacterial population useful in the compositions and methods of the invention comprises *Bacteroides fragilis*. In one embodiment, the bacterial population useful in the compositions and methods of the invention comprises *Bacteroides massiliensis*. In one embodiment, the bacterial population useful in the compositions and methods of the invention comprises *Bacteroides ovatus*. In one embodiment, the bacterial population useful in the compositions and methods of the invention comprises *Bacteroides salanitronis*. In one embodiment, the bacterial population useful in the compositions and methods of the invention comprises *Bacteroides salyersiae*. In one embodiment, the bacterial population useful in the compositions and methods of the invention comprises *Bacteroides* sp. 1_1_6. In one embodiment, the bacterial population useful in the compositions and methods of the invention comprises *Bacteroides* sp. 3_1_23. In one embodiment, the bacterial population useful in the compositions and methods of the invention comprises *Bacteroides* sp. D20. In one embodiment, the bacterial population useful in the compositions and methods of the invention comprises *Bacteroides thetaiotaomicrond*. In one embodiment, the bacterial population useful in the compositions and methods of the invention comprises *Bacteroides uniformis*. In one embodiment, the bacterial population useful in the compositions and methods of the invention comprises *Bacteroides vulgatus*. In one embodiment, the bacterial population useful in the compositions and methods of the invention comprises *Bifidobacterium adolescentis*. In one embodiment, the bacterial population useful in the compositions and methods of the invention comprises *Bifidobacterium bifidum*. In one embodiment, the bacterial population useful in the compositions and methods of the invention comprises *Bifidobacterium breve*. In one embodiment, the bacterial population useful in the compositions and methods of the invention comprises *Bifidobacterium faecale*. In one embodiment, the bacterial population useful in the compositions and methods of the invention comprises *Bifidobacterium kashiwanohense*. In one embodiment, the bacterial population useful in the compositions and methods of the invention comprises *Bifidobacterium longum* subsp. *Longum*. In one embodiment, the bacterial population useful in the compositions and methods of the invention comprises *Bifidobacterium pseudocatenulatum*. In one embodiment, the bacterial population useful in the compositions and methods of the invention comprises *Bifidobacterium stercoris*. In one embodiment, the bacterial population useful in the compositions and methods of the invention comprises *Blautia (Ruminococcus) coccoides*. In one embodiment, the bacterial population useful in the compositions and methods of the invention comprises *Blautia faecis*. In one embodiment, the bacterial population useful in the compositions and methods of the invention comprises *Blautia glucerasea*. In one embodiment, the bacterial population useful in the compositions and methods of the invention comprises *Blautia (Ruminococcus) hansenii*. In one embodiment, the bacterial population useful in the compositions and methods of the invention comprises *Blautia hydrogenotrophica (Ruminococcus hydrogenotrophicus)*. In one embodiment, the bacterial population useful in the compositions and methods of the invention comprises *Blautia (Ruminococcus) luti*. In one embodiment, the bacterial population useful in the compositions and methods of the invention comprises *Blautia (Ruminococcus) obeum*. In one embodiment, the bacterial population useful in the compositions and methods of the invention comprises *Blautia producta (Ruminococcus productus)*. In one embodiment, the bacterial population useful in the compositions and methods of the invention comprises *Blautia (Ruminococcus) schinkii*. In one embodiment, the bacterial population useful in the compositions and methods of the invention comprises *Blautia stercoris*. In one embodiment, the bacterial population useful in the compositions and methods of the invention comprises *Blautia* uncultured bacterium clone BKLE_a03_2 (GenBank: EU469501.1). In one embodiment, the bacterial population useful in the compositions and methods of the invention comprises *Blautia* uncultured bacterium clone SJTU_B_14_30 (GenBank: EF402926.1). In one embodiment, the bacterial population useful in the compositions and methods of the invention comprises *Blautia* uncultured bacterium clone SJTU_C_14_16 (GenBank: EF404657.1). In one embodiment, the bacterial population useful in the compositions and methods of the invention comprises *Blautia* uncultured bacterium clone S1-5 (GenBank: GQ898099.1). In one embodiment, the bacterial population useful in the compositions and methods of the invention comprises *Blautia* uncultured PAC000178_s (www.ezbiocloud.net/eztaxon/hierarchy?m=browse&k=PAC000178&d=2). In one embodiment, the bacterial population useful in the compositions and methods of the invention comprises *Blautia wexlerae*. In one embodiment, the bacterial population useful in the compositions and methods of the invention comprises *Candidatus Arthromitus* sp. SFB-mouse-Yit. In one embodiment, the bacterial population useful in the compositions and methods of the invention comprises *Catenibacterium mitsuokai*. In one embodiment, the bacterial population useful in the compositions and methods of the invention comprises *Clostridiaceae* bacterium (*Dielma fastidiosa*) JC13. In one embodiment, the bacterial population useful in the compositions and methods of the invention comprises *Clostridiales* bacterium 1_7_47FAA. In one embodiment, the bacterial population useful in the compositions and methods of the invention comprises *Clostridium asparagiforme*. In one embodiment, the bacterial population useful in the compositions and methods of the invention comprises *Clostridium bolteae*. In one embodiment, the bacterial population useful in the compositions and methods of the invention comprises *Clostridium clostridioforme*. In one embodiment, the bacterial population useful in the compositions and methods of the invention comprises *Clostridium glycyrrhizinilyticum*. In one embodiment, the bacterial population useful in the compositions and methods of the invention comprises *Clostridium (Hungatella) hathewayi*. In one embodiment, the bacterial population useful in the compositions and methods of the invention comprises *Clostridium histolyticum*. In one embodiment, the bacterial population useful in the compositions and methods of the invention comprises *Clostridium indolis*. In one embodiment, the bacterial population useful in the compositions and methods of the invention comprises *Clostridium leptum*. In one embodiment, the bacterial population useful in the compositions and methods of the invention comprises *Clostridium (Tyzzerella) nexile*. In one embodiment, the bacterial population useful in the compositions and methods of the invention comprises *Clostridium perfringens*. In one embodiment, the bacterial population useful in the compositions and methods of the invention comprises *Clostridium (Erysipelatoclostridium) ramosum*. In one embodiment, the bacterial population useful in the compositions and methods of the invention comprises *Clostridium scindens*. In one embodiment, the bacterial entity, e.g., species or strain, useful in the compositions and methods of the invention is *Clostridium septum*. In one embodiment, the bacterial population useful in the compositions and methods of the invention comprises *Clostridium* sp. 14774. In one embodiment, the bacterial population useful in the compositions and methods of the invention comprises *Clostridium* sp. 7_3_54FAA. In one embodiment, the bacterial population useful in the compositions and methods of the invention comprises *Clostridium* sp. HGF2. In one embodiment, the bacterial population useful in the compositions and methods of the invention comprises *Clostridium symbiosum*. In one embodiment, the bacterial population useful in the compositions and methods of the invention comprises *Collinsella aerofaciens*. In one embodiment, the bacterial population useful in the compositions and methods of the invention comprises *Collinsella intestinalis*. In one embodiment, the bacterial population useful in the compositions and methods of the invention comprises *Coprobacillus* sp. D7. In one embodiment, the bacterial population useful in the compositions and methods of the invention comprises *Coprococcus catus*. In one embodiment, the bacterial population useful in the compositions and methods of the invention comprises *Coprococcus comes*. In one embodiment, the bacterial population useful in the compositions and methods of the invention comprises *Dorea formicigenerans*. In one embodiment, the bacterial population useful in the compositions and methods of the invention comprises *Dorea longicatena*. In one embodiment, the bacterial population useful in the compositions and methods of the invention comprises *Enterococcus faecalis*. In one embodiment, the bacterial population useful in the compositions and methods of the invention comprises *Enterococcus faecium*. In one embodiment, the bacterial population useful in the compositions and methods of the invention comprises Erysipelotrichaceae bacterium 3_1_53. In one embodiment, the bacterial population useful in the compositions and methods of the invention comprises *Escherichia coli*. In one embodiment, the bacterial population useful in the compositions and methods of the invention comprises *Escherichia coli* S88. In one embodiment, the bacterial population useful in the compositions and methods of the invention comprises *Eubacterium eligens*. In one embodiment, the bacterial population useful in the compositions and methods of the invention comprises *Eubacterium fissicatena*. In one embodiment, the bacterial population useful in the compositions and methods of the invention comprises *Eubacterium ramulus*. In one embodiment, the bacterial population useful in the compositions and methods of the invention comprises *Eubacterium rectale*. In one embodiment, the bacterial population useful in the compositions and methods of the invention comprises *Faecalibacterium prausnitzii*. In one embodiment, the bacterial population useful in the compositions and methods of the invention comprises *Flavonifractor plautii*. In one embodiment, the bacterial population useful in the compositions and methods of the invention comprises *Fusobacterium mortiferum*. In one embodiment, the bacterial population useful in the compositions and methods of the invention comprises *Fusobacterium nucleatum*. In one embodiment, the bacterial population useful in the compositions and methods of the invention comprises *Holdemania filiformis*. In one embodiment, the bacterial population useful in the compositions and methods of the invention comprises *Hydrogenoanaerobacterium saccharovorans*. In one embodiment, the bacterial population useful in the compositions and methods of the invention comprises *Klebsiella oxytoca*. In one embodiment, the bacterial population useful in the compositions and methods of the invention comprises Lachnospiraceae bacterium 3_1_57FAA_CT1. In one embodiment, the bacterial population useful in the compositions and methods of the invention comprises Lachnospiraceae bacterium 7_1_58FAA. In one embodiment, the bacterial population useful in the compositions and methods of the invention comprises Lachnospiraceae bacterium 5_1_57FAA. In one embodiment, the bacterial population useful in the compositions and methods of the invention comprises *Lactobacillus casei*. In one embodiment, the bacterial population useful in the compositions and methods of the invention comprises *Lactobacillus rhamnosus*. In one embodiment, the bacterial population useful in the compositions and methods of the invention comprises *Lactobacillus ruminis*. In one embodiment, the bacterial population useful in the compositions and methods of the invention comprises *Lactococcus casei*. In one embodiment, the bacterial population useful in the compositions and methods of the invention comprises *Odoribacter splanchnicus*. In one embodiment, the bacterial population useful in the compositions and methods of the invention comprises *Oscillibacter valericigenes*. In one embodiment, the bacterial population useful in the compositions and methods of the invention comprises *Parabacteroides gordonii*. In one embodiment, the bacterial population useful in the compositions and methods of the invention comprises *Parabacteroides johnsonii*. In one embodiment, the bacterial population useful in the compositions and methods of the invention comprises *Parabacteroides merdae*. In one embodiment, the bacterial population useful in the compositions and methods of the invention comprises *Pediococcus acidilactici*. In one embodiment, the bacterial population useful in the compositions and methods of the invention comprises *Peptostreptococcus asaccharolyticus*. In one embodiment, the bacterial population useful in the compositions and methods of the invention comprises *Propionibacterium granulosum*. In one embodiment, the bacterial population useful in the compositions and methods of the invention comprises *Roseburia intestinalis*. In one embodiment, the bacterial population useful in the compositions and methods of the invention comprises *Roseburia inulinivorans*. In one embodiment, the bacterial population useful in the compositions and methods of the invention comprises *Ruminococcus faecis*. In one embodiment, the bacterial population useful in the compositions and methods of the invention comprises *Ruminococcus gnavus*. In one embodiment, the bacterial population useful in the compositions and methods of the invention comprises *Ruminococcus* sp. ID8. In one embodiment, the bacterial population useful in the compositions and methods of the invention comprises *Ruminococcus torques*. In one embodiment, the bacterial population useful in the compositions and methods of the invention comprises *Slackia piriformis*. In one embodiment, the bacterial population useful in the compositions and methods of the invention comprises *Staphylococcus epidermidis*. In one embodiment, the bacterial population useful in the compositions and methods of the invention comprises *Staphylococcus saprophyticus*. In one embodiment, the bacterial population useful in the compositions and methods of the invention comprises *Streptococcus cristatus*. In one embodiment, the bacterial population useful in the compositions and methods of the invention comprises *Streptococcus dysgalactiae* subsp. *Equisimilis*. In one embodiment, the bacterial population useful in the compositions and methods of the invention comprises *Streptococcus infantis*. In one embodiment, the bacterial population useful in the compositions and methods of the invention comprises *Streptococcus oralis*. In one embodiment, the bacterial population useful in the compositions and methods of the invention comprises *Streptococcus sanguinis*. In one embodiment, the bacterial population useful in the compositions and methods of the invention comprises *Streptococcus viridans*. In one embodiment, the bacterial population useful in the compositions and methods of the invention comprises *Streptococcus thermophiles*. In one embodiment, the bacterial population useful in the compositions and methods of the invention comprises *Veillonella dispar*.

In one embodiment, at least one or more of the populations of bacterial cells used in the methods of the invention comprise a bacterial cell in vegetative form. In one embodiment, all of the populations of bacterial cells in the composition are in vegetative form.

The populations of bacterial cells used in the methods of the invention can be isolated by any methods known to one of ordinary skill in the art. For example, the bacterial cells can be purified from fecal matter. In another embodiment, the bacterial cells are cultured from a bacterial stock and purified as described herein. In one embodiment, each of the populations of bacterial cells are independently cultured and purified, e.g., each population is cultured separately and subsequently mixed together. In one embodiment, one or more of the populations of bacterial cells in the composition are co-cultured.

In some embodiments, at least one population of bacterial cells comprises at least $1 \times 10^4$ colony forming units (CFUs). In some embodiments, a first population of bacterial cells comprises at least $1 \times 10^4$ colony forming units (CFUs) and a second population of bacterial cells comprises at least $1 \times 10^4$ CFUs. In some embodiments, at least one population of bacterial cells comprises at least $1 \times 10^4$ CFUs of an OTU comprising a 16S sequence selected from the group consisting of SEQ ID NO 1-2032. In some embodiments, a first and second isolated population of bacterial cells independently comprise at least $1 \times 10^4$ CFUs of an OTU comprising a 16S sequence selected from the group consisting of SEQ ID NO 1-2032.

Irritable Bowel Syndrome (IBS)

In certain embodiments, the present invention provides methods of treating or alleviating Irritable bowel syndrome (IBS), comprising administering to the subject a composition of the invention, e.g., a composition comprising at least one isolated bacterial population and, optionally, one or more prebiotic. IBS is a common functional disorder of the bowel that has a pronounced effect on quality of life. A defining characteristic of IBS is abdominal discomfort or pain. The Rome III Diagnostic Criteria (a system for diagnosing functional gastrointestinal disorders based on symptoms) for IBS are the accepted current standard for diagnosing IBS in the clinical setting and are consistent with FDA guidance.

Other symptoms that support the diagnosis of IBS include pain; abnormal stool passage (straining, urgency, or feeling of incomplete evacuation); passage of mucus; and bloating or feeling of abdominal distension. Patients can be subdivided by their underlying bowel habits: (i) diarrhea-predominant IBS, (ii) constipation-predominant IBS, and (ii) constipation alternating with diarrhea (alternating IBS).

Inflammatory Bowel Disease (IBD)

In certain embodiments, the present invention provides methods of treating or alleviating inflammatory bowel disease (IBD) comprising administering to the subject a composition of the invention, e.g., a composition comprising at least one isolated bacterial population and, optionally, one or more prebiotic. IBD is characterized by inflammation or ulcerations in the small and/or large intestine. In some embodiments, IBD is characterized as including ulcerative colitis or Crohn disease. In one embodiment, IBD also includes forms of microscopic colitis, e.g., histologic evidence of mucosal inflammation without macroscopic abnormalities. IBD is characterized by a constellation of patient-reported history and endoscopic, histopathologic, and radiologic findings, often with serologic correlates. Exemplary signs that reflect the inflammatory process within the gastrointestinal tract are rectal bleeding, diarrhea, fever, and weight loss, occasionally associated with extraintestinal manifestations.

While Crohn's disease and ulcerative colitis share elements of their characteristic immune responses (e.g., high TNF-α, which can be detected in a patient's feces), their associated immune responses can also have distinguishing markers. For example, interleukin-16 (IL-16) levels are high and T-bet is overexpressed the lamina propia T cell nucleus in patients with Crohn's disease, but not in those suffering from ulcerative colitis. Notably T-bets produce the pro-inflammatory cytokine IFN-γ. One similarity among IBDs is high IFN-γ (by about 4-fold), caused in part due to high TL1A and TNF-α. Moreover, the levels of these cytokines correlate with the severity of the IBD.

Early Crohn's disease has a different immunological signature than does chronic Crohn's disease. In aspects in which a patient presents with early lesions, the microbial composition may be selected, with or without one or more prebiotics, to counteract a T helper cell 2-mediated response. For example, the microbial composition, optionally combined with immunomodulatory molecules such as nucleotides or carbohydrates, may decrease interleukin-4 (IL-4) levels or increase IFN-γ. In aspects in which a patient presents with chronic lesions, the microbial composition may be selected to counteract a T helper cell 1-mediated response. For example, the microbial composition, optionally combined with immunomodulatory molecules such as nucleotides or carbohydrates, may decrease IL-2, IFN-γ, TNF-α, TL1A, IL-12, and/or IL-18. In some embodiments, in which a patient suffers from an IBD including but not limited to Crohn's disease, a probiotic microbial composition, with or without one or more prebiotics, is administered to the patient such that it is effective to reduce TNF-α levels, as detectable in feces samples, by approximately 5-fold, 10-fold, 25-fold, 50-fold, or 100-fold. Crohn's disease patients tend to present with low plasma levels of vitamins or minerals including but not limited to vitamin A, vitamin E, vitamin C, lycopene, carotenoids, and/or selenium. Patients eligible for immunomodulatory treatment may thus be administered an immunomodulatory microbe, molecule, and/or microbial component optionally combined with an appropriate vitamin or mineral supplement, as determined by plasma deficiency.

Celiac Disease

In certain embodiments, the present invention provides methods of treating or alleviating celiac disease comprising administering to the subject a composition of the invention, e.g., a composition comprising at least one isolated bacterial population and, optionally, one or more prebiotic. The methods of the present invention increase intestinal barrier integrity (i.e., reduce the passage of dietary and microbial antigens, particularly food allergens, from the intestinal lumen into the mucosa or systemic circulation), and hence can be advantageously used for the treatment or prevention of celiac disease, by preventing the food allergen from entering the mucosa or systemic circulation. Celiac disease is an autoimmune disorder wherein ingestion of gluten elicits an immune response that results in damage to the small intestine.

Antibiotic Associated Diarrhea

Antibiotic-associated diarrhea includes frequent, watery bowel movements (diarrhea) that occur in response to medications used to treat bacterial infections (antibiotics). Antibiotic-associated diarrhea results from an imbalance in the colonic microbiota caused by antibiotic therapy and can be either mild or severe. Often, antibiotic-associated diarrhea is resolved shortly after the antibiotic is discontinued. However, in some cases, antibiotic-associated diarrhea leads to colitis, an inflammation of the colon, or a more serious form of colitis referred to as pseudomembranous colitis. Both can cause abdominal pain, fever and bloody diarrhea. Risk factors for antibiotic-associated diarrhea include compromised immune status, advanced age, abdominal surgery, comorbidity, types and prolonged use of antibiotics, reduced gastric acid, and the length of hospitalization.

Inhibition and Reduction of Colonization with a Pathogen or Pathobiont and/or Pathogen or Pathobiont Infection In certain embodiments, the present invention provides methods of treating or alleviating colonization with a pathogen or pathobiont or infection with a drug-resistant pathogen or pathobiont comprising administering to the subject a composition of the invention, e.g., a composition comprising at least one isolated bacterial population and, optionally, a one or more prebiotic. Provided are bacteria and combinations of bacteria of the human gut microbiota with the capacity to meaningfully provide the functions of a healthy microbiota when administered to mammalian hosts. Without being limited to a specific mechanism, it is thought that such compositions inhibit the growth, proliferation, and/or colonization of one or a plurality of pathogenic bacteria in the dysbiotic microbiotal niche, so that a healthy, diverse and protective microbiota colonizes and populates the intestinal lumen (and microbiotal niches distal to the intestinal lumen) to establish or reestablish ecological control over pathogens or potential pathogens (e.g., some bacteria are pathogenic bacteria only when present in a dysbiotic environment). Inhibition of pathogens includes those pathogens such as *C. difficile*, *Salmonella* spp., enteropathogenic *E. coli*, multi-drug resistant bacteria such as *Klebsiella*, and *E. coli*, Carbapenem-resistant Enterobacteriaceae (CRE), extended spectrum beta-lactam resistant Enterococci (ESBL), and vancomycin-resistant Enterococci (VRE).

In some embodiments, the methods of the invention include the administration of a composition comprising a prebiotic, e.g., a carbohydrate, such as xylose, and a bacterial population. In some embodiments, the bacterial compositions comprise purified spore populations. Purified spore populations contain combinations of commensal bacteria of the human gut microbiota with the capacity to meaningfully provide functions of a healthy microbiota when administered to a mammalian subject. Without being limited to a specific mechanism, it is thought that such compositions inhibit the growth of a pathogen such as *C. difficile*, *Salmonella* spp., enteropathogenic *E. coli*, and vancomycin-resistant *Enterococcus* spp., so that a healthy, diverse and protective microbiota can be maintained or, in the case of pathogenic bacterial infections, repopulate the intestinal lumen to reestablish ecological control over potential pathogens. In some embodiments, yeast spores and other fungal spores are also purified and selected for therapeutic use. In other embodiments, the bacterial compositions used in the methods of the invention comprise purified non-spore forming populations.

In some embodiments, the bacterial composition provides a protective or therapeutic effect against infection by one or more GI pathogens of interest.

In some embodiments, the pathogenic bacterium is selected from the group consisting of *Yersinia*, *Vibrio*, *Treponema*, *Streptococcus*, *Staphylococcus*, *Shigella*, *Salmonella*, *Rickettsia*, *Orientia*, *Pseudomonas*, *Neisseria*, *Mycoplasma*, *Mycobacterium*, *Listeria*, *Leptospira*, *Legionella*, *Klebsiella*, *Helicobacter*, *Haemophilus*, *Francisella*, *Escherichia*, *Ehrlichia*, *Enterococcus*, *Coxiella*, *Corynebacterium*, *Clostridium*, *Chlamydia*, *Chlamydophila*, *Campylobacter*, *Burkholderia*, *Brucella*, *Borrelia*, *Bordetella*, *Bifidobacterium*, *Bacillus*, multi-drug resistant bacteria, extended spectrum beta-lactam resistant Enterococci (ESBL), Carbapenem-resistant Enterobacteriaceae (CRE), and vancomycin-resistant Enterococci (VRE).

In some embodiments, these pathogens include, but are not limited to, *Aeromonas hydrophila*, *Campylobacter fetus*, *Plesiomonas shigelloides*, *Bacillus cereus*, *Campylobacter jejuni*, *Clostridium botulinum*, *Clostridium difficile*, *Clostridium perfringens*, enteroaggregative *Escherichia coli*, enterohemorrhagic *Escherichia coli*, enteroinvasive *Escherichia coli*, enterotoxigenic *Escherichia coli* (such as, but not limited to, LT and/or ST), *Escherichia coli* O157:H7, *Helicobacter pylori*, *Klebsiella* pneumonia, Lysteria *monocytogenes*, *Plesiomonas shigelloides*, *Salmonella* spp., *Salmonella typhi*, *Salmonella paratyphi*, *Shigella* spp., *Staphylococcus* spp., *Staphylococcus aureus*, vancomycin-resistant *enterococcus* spp., *Vibrio* spp., *Vibrio cholerae*, *Vibrio parahaemolyticus*, *Vibrio vulnificus*, and *Yersinia enterocolitica*.

In one embodiment, the pathogen of interest is at least one pathogen chosen from *Clostridium difficile*, *Salmonella* spp., pathogenic *Escherichia coli*, vancomycin-resistant *Enterococcus* spp., and extended spectrum beta-lactam resistant Enterococci (ESBL).

The bacterial compositions provided herein are produced and the efficacy thereof in inhibiting pathogenic bacteria is demonstrated as provided in further detail herein.

In particular, in order to characterize those antagonistic relationships between gut commensals that are relevant to the dynamics of the mammalian gut habitat, provided are assays that demonstrate the efficacy of those bacterial compositions, including the ability to inhibit (or antagonize) the growth of a bacterial pathogen or pathobiont, typically a gastrointestinal microorganism. These methods provide novel combinations of gut microbiota species and OTUs that are able to restore or enhance ecological control over important pathogens or pathobionts in vivo.

In some embodiments, bacterial compositions are provided with the ability to exclude, reduce or downmodulate pathogenic bacteria. Exemplary bacterial compositions are demonstrated to reduce or downmodulate the growth rate of a pathogen or pathobiont, as provided herein, wherein the ability of the bacterial compositions is demonstrated by assessing the antagonism activity of a combination of OTUs or strains towards a given pathogen using in vitro assays.

In some embodiments, bacterial compositions with the capacity to durably exclude a pathogen or pathobiont, are developed using a methodology for estimating an Ecological Control Factor (ECF) for constituents within the human microbiota. The ECF is determined by assessing the antagonistic activity of a given commensal strain or combination of strains towards a given pathogen using an in vitro assay, resulting in observed levels of ecological control at various concentrations of the added commensal strains. The ECF for a commensal strain or combination of strains is somewhat analogous to the longstanding minimal inhibitory concentration (MIC) assessment that is employed in the assessment of antibiotics. The ECF allows for the assessment and ranking of relative potencies of commensal strains and combinations of strains for their ability to antagonize gastrointestinal pathogens. The ECF of a commensal strain or combination of strains may be calculated by assessing the concentration of that composition that is able to mediate a given percentage of inhibition (e.g., at least 10%, 20%, 30%, 40%, 50%, 70%, 75%, 80%, 85%, 90%, 95%, or 100%) of a target pathogen in the in vitro assay. Provided herein are combinations of strains or OTUs within the human microbiota that are able to significantly reduce the rate of gastrointestinal pathogen replication within the in vitro assay. These compositions are capable of providing a safe and effective means by which to affect the growth, replication, and disease severity of such bacterial pathogens.

In one embodiment, the prebiotic carbohydrate component (e.g. xylose) of the pharmaceutical composition, dosage form, or kit allows the commensal colonic microbiota, comprising microorganisms associated with a healthy-state microbiome or presenting a low risk of a patient developing dysbiosis, e.g., gastrointestinal dysbiosis, or a gastrointestinal disease, disorder or condition selected from the group consisting of antibiotic associated diarrhea, *Clostridium difficile*-induced diarrhea, constipation, inflammatory Bowel Disease (IBD), including Crohn's Disease and celiac disease, irritable bowel syndrome (IBS), colonization with a pathogen or pathobiont, infection with a drug-resistant pathogen or pathobiont, or colitis, to be regularly maintained. In one embodiment, the prebiotic carbohydrate component of the pharmaceutical composition, dosage form, or kit allows the co-administered or co-formulated microbe or microbes to survive, engraft, grow, and/or be regularly maintained in a mammalian subject. In some embodiments, the mammalian subject is a human subject. In preferred embodiments, the mammalian subject suffers from or is at risk of developing dysbiosis, e.g., gastrointestinal dysbiosis, or a gastrointestinal disease, disorder or condition. In some embodiments, the prebiotic component of the invention favors the growth of an administered or endogenous microbe, wherein the growth of the administered or endogenous microbe and/or the fermentation of the administered prebiotic by the administered or endogenous microbe slows or reduces the growth of a pathogen or pathobiont. For example, FOS, neosugar, or inuliri promotes the growth of acid-forming bacteria in the colon such as bacteria belonging to the genera *Lactobacillus* or *Bifidobacterium* and *Lactobacillus acidophilus* and *Bifidobacterium bifidus* can play a role in reducing the number of pathogenic bacteria in the colon (U.S. Pat. No. 8,486,668 PREBIOTIC FORMULATIONS AND METHODS OF USE). Other polymers, such as various galactans, lactulose, and carbohydrate based gums, such as psyllium, guar, carrageen, gellan, and konjac, are also known to improve gastrointestinal (GI) health.

As provided herein, therapeutic compositions comprise, or in the alternative modulate the colonization and/or engraftment, of the following exemplary bacterial entities: *Lactobacillus gasseri, Lactobacillus fermentum, Lactobacillus reuteri, Enterococcus* faecalis, *Enterococcus* durans, *Enterococcus villorum, Lactobacillus plantarum, Pediococcus acidilactici, Staphylococcus pasteuri, Staphylococcus cohnii, Streptococcus sanguinis, Streptococcus sinensis, Streptococcus mitis, Streptococcus* sp. SCA22, *Streptococcus* sp. CR-3145, *Streptococcus anginosus, Streptococcus mutans, Coprobacillus cateniformis, Clostridium saccharogumia, Eubacterium dolichum* DSM 3991, *Clostridium* sp. PPf35E6, *Clostridium sordelli* ATCC 9714, *Ruminococcus torques, Ruminococcus gnavus, Clostridium clostridioforme, Ruminococcus obeum, Blautia producta, Clostridium* sp. ID5, *Megasphaera micronuciformis, Veillonella parvula, Clostridium methylpentosum, Clostridium islandicum, Faecalibacterium prausnitzii, Bacteroides uniformmis, Bacteroides thetaiotaomicron, Bacteroides acidifaciens, Bacteroides ovatus, Bacteroides fragilis, Parabacteroides distasonis, Propinionibacteirum propionicum, Actinomycs hyovaginalis, Rothia mucilaginosa, Rothia aeria, Bifidobacterium breve, Scardovia inopinata* and *Eggerthella lenta*.

In vitro assays substantiating protective effect of bacterial compositions.

In one embodiment, provided is an in vitro assay utilizing competition between the bacterial compositions or subsets thereof and a pathogen or pathobiont. Exemplary embodiments of this assay are provided herein and in the Examples.

In another embodiment, provided is an in vitro assay utilizing 10% (wt/vol) Sterile-Filtered Stool. Provided is an in vitro assay to test for the protective effect of the bacterial compositions and to screen in vitro for combinations of microbes that inhibit the growth of a pathogen. The assay can operate in automated high-throughput or manual modes. Under either system, human or animal stool may be re-suspended in an anaerobic buffer solution, such as pre-reduced PBS or other suitable buffer, the particulate removed by centrifugation, and filter sterilized. This 10% sterile-filtered stool material serves as the base media for the in vitro assay. To test a bacterial composition, an investigator may add it to the sterile-filtered stool material for a first incubation period and then may inoculate the incubated microbial solution with the pathogen of interest for a second incubation period. The resulting titer of the pathogen may be quantified by any number of methods such as those described below, and the change in the amount of pathogen is compared to standard controls including the pathogen cultivated in the absence of the bacterial composition. The assay is conducted using at least one control. Stool from a healthy subject may be used as a positive control. As a negative control, antibiotic-treated stool or heat-treated stool may be used. Various bacterial compositions may be tested in this material and the bacterial compositions optionally compared to the positive and/or negative controls. The ability to inhibit the growth of the pathogen may be measured by plating the incubated material on *C. difficile* selective media and counting colonies. After competition between the bacterial composition and *C. difficile*, each well of the in vitro assay plate is serially diluted ten-fold six times, and plated on selective media, such as but not limited to cycloserine cefoxitin mannitol agar (CCMA) or cycloserine cefoxitin fructose agar (CCFA), and incubated. Colonies of *C. difficile* are then counted to calculate the concentration of viable cells in each well at the end of the competition. Colonies of pathogen or pathobiont are confirmed by their characteristic diffuse colony edge morphology as well as fluorescence under UV light.

In another embodiment, the in vitro assay utilizes Antibiotic-Treated Stool. In an alternative embodiment, and instead of using 10% sterile-filtered stool, human or animal stool may be re-suspended in an anaerobic buffer solution, such as pre-reduced PBS or other suitable buffer. The resuspended stool is treated with an antibiotic, such as clindamycin, or a cocktail of several antibiotics in order to reduce the ability of stool from a healthy subject to inhibit the growth of pathogen or pathobiont; this material is termed the antibiotic-treated matrix. While not being bound by any mechanism, it is believed that beneficial bacteria in healthy subjects protect them from infection by competing out pathogen or pathobiont Treating stool with antibiotics kills or reduces the population of those beneficial bacteria, allowing pathogen or pathobiont to grow in this assay matrix. Antibiotics in addition to clindamycin that inhibit the normal flora include ceftriaxone and piperacillin-tazobactam and may be substituted for the clindamycin. The antibiotic-treated matrix is centrifuged, the supernatant removed, and the pelleted material resuspended in filter-sterilized, diluted stool in order to remove any residual antibiotic. This washed antibiotic-treated matrix may be used in the in vitro assay described above in lieu of the 10% sterile-filtered stool.

Also provided is an in vitro assay utilizing competition between the bacterial compositions or subsets thereof and vancomycin-resistant *Enterococcus faecium*. Exemplary embodiments of this assay are provided herein and in the Examples.

Also provided is an in vitro assay utilizing competition between the bacterial compositions or subsets thereof and *Morganella morganii*. Exemplary embodiments of this assay are provided herein and in the Examples.

Also provided is an in vitro assay utilizing competition between the bacterial compositions or subsets thereof and *Klebsiella pneumoniae*. Exemplary embodiments of this assay are provided herein and in the Examples.

Alternatively, the ability to inhibit the growth of the pathogen may be measured by quantitative PCR (qPCR). Standard techniques may be followed to generate a standard curve for the pathogen of interest. Genomic DNA may be extracted from samples using commercially-available kits, such as the Mo Bio Powersoil®-htp 96 Well Soil DNA Isolation Kit (Mo Bio Laboratories, Carlsbad, Calif.), the Mo Bio Powersoil® DNA Isolation Kit (Mo Bio Laboratories, Carlsbad, Calif.), or the QIAamp DNA Stool Mini Kit (QIAGEN, Valencia, Calif.) according to the manufacturer's instructions. The qPCR may be conducted using HotMasterMix (5PRIME, Gaithersburg, Md.) and primers specific for the pathogen of interest, and may be conducted on a MicroAmp® Fast Optical 96-well Reaction Plate with Barcode (0.1 mL) (Life Technologies, Grand Island, N.Y.) and performed on a BioRad C1000™ Thermal Cycler equipped with a CFX96™ Real-Time System (BioRad, Hercules, Calif.), with fluorescent readings of the FAM and ROX channels.

*C. difficile* Infection and *C. difficile*-Induced Diarrhea

In certain embodiments, the present invention provides methods of treating or alleviating *Clostridium difficile*-induced diarrhea resulting from infection by *Clostridium difficile*, in a subject in need thereof, the method comprising administering to the subject a composition of the invention, e.g., a composition comprising at least one isolated bacterial population. In one embodiment, the at least one bacterial population is coadministered or coformulated with one or more prebiotic, e.g, at least one polymer or monomer. In one embodiment, the prebiotic is a carbohydrate, e.g., xylose.

Often called *C. difficile* or *C. diff, Clostridium. difficile* is a gram positive, anaerobic organism found naturally in the human colon. *C. difficile* infection can cause symptoms ranging from diarrhea to life-threatening inflammation of the colon. Illness from *C. difficile* most commonly affects older adults in hospitals or in long-term care facilities and typically occurs after use of antibiotic medications. Hospital-acquired *Clostridium difficile*-associated diarrhea (CDAD) is becoming a major public health problem worldwide.

A mouse model of CDAD has been provided by Chen et al. (2008. Gastroenterology 135:1984-1992, the entire content of which is hereby expressly incorporated by reference). They describe a model that is reported to closely represent human disease and as such is useful for testing the in vivo efficacy of the compositions of the invention. Another model is provided in mice as described by Kaur et al. (2010. J. Gastroenterol. Hepatol. 25:832-838). In such models, the compositions of the invention can be tested for a protective effect against infections where the infection established is from inoculation of the animal with *C. difficile*.

Using these models, bacterial compositions may be given either before (prophylactic treatment) or after (therapeutic treatment) *C. difficile* gavage. Further, bacterial compositions may be given after (optional) vancomycin treatment (see below) to assess their ability to prevent recurrence and thus suppress the pathogen in vivo. The outcomes assessed are weight, clinical signs, mortality and shedding of *C. difficile* in the stool. Weight loss, clinical signs of disease, and *C. difficile* shedding are typically observed without treatment.

For example, in an exemplary experiment, mice are made susceptible to *C. difficile* by a 7 day treatment (days −12 to −5 of experiment) with 5 to 7 antibiotics (including kanamycin, colistin, gentamycin, metronidazole and vancomycin and optionally including ampicillin and ciprofloxacin) delivered via their drinking water, followed by a single dose with Clindamycin on day −3, then challenged three days later on day 0 with $10^4$ spores of *C. difficile* via oral gavage (i.e., oro-gastric lavage). Bacterial compositions may be given either before (prophylactic treatment) or after (therapeutic treatment) *C. difficile* gavage. Further, bacterial compositions may be given after (optional) vancomycin treatment (see below) to assess their ability to prevent recurrence and thus suppress the pathogen in vivo. The outcomes assessed each day from day −1 to day 6 (or beyond, for prevention of recurrence) are weight, clinical signs, mortality and shedding of *C. difficile* in the stool. Weight loss, clinical signs of disease, and *C. difficile* shedding are typically observed without treatment. Vancomycin provided by oral gavage on days −1 to 4 protects against these outcomes and serves as a positive control. Clinical signs are subjective, and scored each day by the same experienced observer. Animals that lose greater than or equal to 25% of their body weight are euthanized and counted as infection-related mortalities. Stool are gathered from mouse cages (5 mice per cage) each day, and the shedding of *C. difficile* spores is detected in the stool using a selective plating assay as described for the in vitro assay above.

Constipation

In certain embodiments, the present invention provides methods of treating or alleviating constipation in a subject in need thereof, the method comprising a administering to the subject at least one isolated bacterial population. In one embodiment, the at least one bacterial population is coadministered or coformulated with one or more prebiotic, e.g, at least one polymer or monomer. In one embodiment, the prebiotic is a carbohydrate, e.g., xylose.

Constipation is generally described as having fewer than three bowel movements a week. Chronic constipation is infrequent bowel movements or difficult passage of stools that persists for several weeks or longer. The present invention also provides methods for the treatment, prevention or alleviation of diseases and disorders exhibiting constipation as a symptom.

Subjects and Subject Selection

The present composition can be advantageously used in a method for improving intestinal barrier integrity in mammals, particularly humans. The present composition can also be advantageously used in a method for the treatment or prevention of diseases associated with reduced intestinal barrier integrity, said method comprising administering to a mammal the present compositions.

In certain embodiments, the methods of the present invention are advantageously carried out in a infant or baby (between 0 and 2 years old), and may be combined with complete nutrition, including protein, carbohydrate and fat. Since the intestinal barrier function of newborns has not been fully developed, the present composition can be advantageously administered to young infants, i.e. infants with the age between 0 and 6 months. The composition may be administered to the infant in the form of an infant formula without human milk or admixed with human milk. Hence the present invention also provides for a formula feed comprising human milk and the present composition. In certain embodiments, the present methods are carried our in a premature infant (an infant born before 37 weeks gestation). In further embodiments, the invention can also be used to treat or prevent infant diarrhea.

Furthermore, the methods of the present invention can be used in subjects which have undergone or are undergoing abdominal surgery and subjects that experience postoperative dysfunction of the gut and/or malnourished subjects. The methods of the present invention can also be used in a subject following colonoscopy or endoscopic large bowel examination. Accordingly, the methods can be carried out in a subject prior to or after a medical treatment, which may cause intestinal damage. Such medical treatment may for example be surgery or enteral medicine treatment (e.g. antibiotic, analgesic, NSAID, chemotherapeutic agents etc).

In other particular embodiments, the methods of the invention may be carried out on a subject or subjects with particular profiles. For example, 16S sequencing may be performed for a given subject to identify the bacteria present in his or her microbiota. The sequencing may either profile the subject's entire microbiome using 16S sequencing (to the family, genera, or species level), a portion of the subject's microbiome using 16S sequencing, or it may be used to detect the presence or absence of specific candidate bacteria that are biomarkers for health or a particular disease state, such as markers of multi-drug resistant organisms or specific genera of concern such as *Escherichia*. Based on the biomarker data, the subject may be selected for treatment with the methods of the present invention to supplement or complement a subject's microbiota in order to restore health or treat or prevent disease. In another embodiment, subjects may be screened to determine the composition of their microbiota to determine the likelihood of successful treatment.

Combination Treatment

The compositions of the invention may be administered with other agents in combination therapy. Accordingly, in certain embodiments the methods of the invention further include administration of one or more other agents. Administration may be sequential, over a period of hours or days, or simultaneous. In one embodiment, the compositions are included in combination therapy with one or more antimicrobial agents, which include anti-bacterial agents, anti-fungal agents, anti-viral agents, anti-parasitic agents.

Anti-bacterial agents include cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); and carbapenem antibiotics (ertapenem, doripenem, imipenem/cilastatin, and meropenem).

Anti-viral agents include Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, Foscarnet, Fomivirsen, Ganciclovir, Indinavir, Idoxuridine, Lamivudine, Lopinavir Maraviroc, MK-2048, Nelfinavir, Nevirapine, Penciclovir, Raltegravir, Rilpivirine, Ritonavir, Saquinavir, Stavudine, Tenofovir Trifluridine, Valaciclovir, Valganciclovir, Vidarabine, Ibacitabine, Amantadine, Oseltamivir, Rimantidine, Tipranavir, Zalcitabine, Zanamivir and Zidovudine.

Examples of antifungal compounds include, but are not limited to polyene antifungals such as natamycin, rimocidin, filipin, nystatin, amphotericin B, candicin, and hamycin; imidazole antifungals such as miconazole, ketoconazole, clotrimazole, econazole, omoconazole, bifonazole, butoconazole, fenticonazole, isoconazole, oxiconazole, sertaconazole, sulconazole, and tioconazole; triazole antifungals such as fluconazole, itraconazole, isavuconazole, ravuconazole, posaconazole, voriconazole, terconazole, and albaconazole; thiazole antifungals such as abafungin; allylamine antifungals such as terbinafine, naftifine, and butenafine; and echinocandin antifungals such as anidulafungin, caspofungin, and micafungin. Other compounds that have antifungal properties include, but are not limited to polygodial, benzoic acid, ciclopirox, tolnaftate, undecylenic acid, flucytosine or 5-fluorocytosine, griseofulvin, and haloprogin.

In one embodiment, the compositions are included in combination therapy with one or more corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines, and combinations thereof.

IX. Distal Dysbiosis

The probiotic compositions described herein have beneficial effects for the subject locally, at the site of administration (e.g., in the gastrointestinal tract for compositions administered orally, or in the vagina for compositions administered vaginally), as previously described. Surprisingly, the probiotic compositions described herein may also be used to correct or prevent a dysbiosis at a site distal to the site of administration.

The term "distal" generally is used in relation to the gastrointestinal tract, specifically the intestinal lumen, of a human or other mammal, which represent the intended sites of engraftment or colonization for probiotics administered orally. Thus, in relation to probiotics administered to the gastrointestinal tract, a "distal dysbiosis" includes a dysbiosis outside of the lumen of the gastrointestinal tract. In other instances, the term "distal" may be used in relation to the site of administration, intended engraftment, or intended colonization of a composition, e.g., a probiotic composition, of the invention. For example, if a probiotic composition is administered vaginally, a distal effect of the composition would occur outside the vagina. Similarly, if a probiotic composition is administered to the skin, e.g., through a skin patch, transdermal lotion, etc., a distal effect of the composition would occur in a niche other than the skin. If a probiotic composition is administered to the lungs, e.g., in an inhalable formulation, a distal effect of the composition would occur outside the lungs. If a probiotic composition is administered to the ear, eye, nose, etc., a distal effect of the composition would occur at a site other than the site of administration, engraftment, or colonization of the composition (i.e., distal to the ear, distal to the eye, distal to the nose, etc.).

Distal sites include but are not limited to the liver, spleen, fallopian tubes and uterus. Other distal sites include skin, blood and lymph nodes. In other embodiments, the distal site is placenta, spleen, liver, uterus, blood, eyes, ears, lungs, liver, pancreas, brain, embryonic sac, or vagina. In another embodiment, the distal site is vagina, skin, lungs, brain, nose, ear, eyes/conjunctiva, mouth, circulatory system, e.g., blood, placenta, reproductive tract, cardiovascular system, and/or nervous system. A probiotic composition may have an effect on the microbiota of more than one distal site in a subject. For example, in some embodiments, a probiotic composition modulates the microbiota of one or more sites distal to the site of administration, engraftment, or colonization, e.g., one or more of placenta, spleen, liver, uterus, blood, eyes, ears, lungs, liver, pancreas, brain, embryonic sac, vagina, skin, brain, nose, mouth, reproductive tract, cardiovascular system, and/or nervous system.

Provided are compositions and methods to provide modulation, engraftment and/or augmentation of one or more bacterial and/or fungal entities to a distal site. In order to characterize the alteration of a target niche, such as by engraftment and/or augmentation of a bacteria within the niche, provided are methods of detecting, quantifying and characterizing 16S, 18S and ITS signatures in skin, vagina, etc. Moreover, provided are methods of detecting bacterial and fungal components typically associated with one microbiota in a distal site, often associating with (in a physiological or manner) with the microbiota of that distal site. For example, following administration of a composition, bacteria detectably present in the GI tract or vagina prior to administration are detected in distal sites, for example, the blood, or another niche outside the GI lumen. For example, changes in the microbiome at a given site (e.g. GI tract) lead to changes in the microbiome at a distal site (e.g. vagina).

Accordingly, detecting and quantifying 16S, 18S and ITS signatures of the microbial network at a distal site can be used to characterize the components of the microbiome at the distal site under normal, healthy conditions, and can also be used to detect a dysbiosis at the distal site, when the components of the microbiome at the distal site are disrupted.

In order to characterize a distal dysbiosis, provided are methods of detecting, quantifying and characterizing 16S, 18S and ITS signatures in immune organs, such as the lymph nodes, spleen, etc. Moreover, provided are methods of detecting bacterial and fungal components typically associated with one microbiota in a distal site, often associating (in a physiological or pathological manner) with the microbiota of that distal site. For example, bacteria normally detected in the GI tract or vagina are detected in distal sites, for example, the blood.

A distal dysbiosis includes disruptions in the normal diversity and/or function of the microbial network in a subject at a site other than the gastrointestinal tract, which is generally the site of administration of probiotics provided orally. In cases where a probiotic composition is administered to a site other than the gastrointestinal tract, a distal dysbiosis can include disruptions in the normal diversity and/or function of the microbial network in a subject at a site other than the site of administration, colonization or engraftment.

Probiotic compositions described herein can correct or treat a distal dysbiosis by correcting the imbalance in microbial diversity that is present at the distal site. Bacteria contained in the probiotic composition can correct the distal dysbiosis directly, by translocating to the distal site. Bacteria contained in the probiotic composition can also correct the distal dysbiosis indirectly, by promoting translocation of other gut commensals to the distal site, or by modifying the microenvironment of the distal site to create conditions that restore a healthy microbiome, e.g., by reducing inflammation.

Without wishing to be bound by theory, the probiotic compositions of the invention may impact distal sites in several ways.

In one embodiment, a bacterial strain present in the probiotic composition engrafts in the gastrointestinal tract of a subject, and translocates to a distal site, thereby augmenting the bacterial strain present in the probiotic composition at the distal site. In one embodiment, the bacterial strain present in the probiotic composition is not detectably present at the distal site prior to administration of the probiotic.

In another embodiment, a bacterial strain present in the probiotic composition is augmented in the gastrointestinal tract of a subject without engraftment, and translocates to a distal site, thereby augmenting the bacterial strain present in the probiotic composition at the distal site. In one embodiment, the bacterial strain present in the probiotic composition is not detectably present at the distal site prior to administration of the probiotic.

In another embodiment, a bacterial strain present in the probiotic composition modulates the microenvironment of the gut, augmenting a second bacterial strain present within the gut microbiota. The second bacterial strain augmented in the gut translocates to a distal site, thereby augmenting the second bacterial strain at the distal site. In embodiments, the second bacterial strain is not present in the probiotic composition. In some embodiments, the bacterial strain present in the probiotic composition is an immunomodulatory bacteria, e.g., an anti-inflammatory bacteria. Modulation of the microenvironment of the gut may include, for example, alteration of cytokines secreted by host cells in and around the gut, reducing inflammation in the gut, increasing secretion of short chain fatty acids in the gut, or altering the proportion of immune cell subpopulations in the gut, each of which impacts the gut microbiome. Modulation of the microenvironment of the gut can include increasing or decreasing overall microbial diversity.

In another embodiment, a bacterial strain present in the probiotic composition modulates the microenvironment at a distal site in a subject, thereby augmenting a second bacterial strain at the distal site. In embodiments, the second bacterial strain is not present in the probiotic composition. In some embodiments, the bacterial strain present in the probiotic composition is an immunomodulatory bacteria, e.g., an anti-inflammatory bacteria. Immunomodulatory bacteria can modulate the microenvironment at a site distal to the gastrointestinal tract in a subject by, for example, reducing systemic inflammation. This can be achieved by altering the profile of cytokine expression by immune cells, or altering the proportion of immune cell subpopulations. Bacterial strains present in the probiotic composition can also modulate intestinal permeability, e.g., by secretion of short chain fatty acids, which impacts the microenvironment of distal sites. In addition or alternatively, bacterial strains present in the probiotic composition can increase or decrease overall microbial diversity.

Accordingly, the probiotic compositions described herein may additively or synergistically elicit an immunomodulatory response either distally, e.g., in which enteral administration of microbes results in altering the immune response at a site outside the gastrointestinal tract such as the skin or liver, or locally, e.g. the enteral administration of microbes results in altering the immune response in the gastrointestinal tract, e.g., in the intestines.

The immune system of a subject and the microbiome of the subject are closely linked, and interact systemically. Disruptions to the microbiome, both in the gastrointestinal tract and at distal sites, can have profound effects throughout the body of the subject. In particular, disruptions to the microbiome increase systemic inflammation and intestinal barrier dysfunction in a subject. Increased inflammation and intestinal barrier dysfunction negatively impact the health of the subject in many ways, by contributing to a wide range of inflammatory and autoimmune conditions distal to the gastrointestinal tract. Conversely, increased inflammation in a subject leads to disruptions in the subject's microbiome, and disruptions to the microbiome lead in turn to further increases in inflammation. Administration of a probiotic composition containing immunomodulatory bacteria can reduce inflammation in the gastrointestinal tract and restore intestinal barrier integrity, resulting in a reduction in inflammation at sites distal to the gastrointestinal tract, and improvement in the symptoms of autoimmune or inflammatory disorders associated with systemic inflammation. Administration of a probiotic composition containing bacterial strains that secrete short chain fatty acids are also capable of reducing inflammation restoring intestinal barrier integrity.

In other embodiments, the probiotic compositions of the invention improve blood/brain barrier integrity. In other embodiments, the probiotic compositions of the invention improve lung epithelium integrity.

The probiotic compositions and methods described herein can prevent or treat the loss or reduction of barrier function recognized to occur during dysbiosis or in the shift in one or more microbiotal populations that give rise to the dysbiosis. The loss of barrier function results in systemic seeding of bacterial populations resulting in dysbiotic activity, and in some events, the loss of barrier function results in a local reseeding of the bacterial populations. In both situations, the resulting immune activation leads to pathogenic inflammatory and immune responses. In response, provided are compositions that are capable of restoring barrier function, restoring the normal microbiotal components, and reducing (e.g., suppressing) immune/inflammatory response. In one embodiment, the improvement of gut epithelium barrier integrity results in reduced trafficking of bacteria, bacterial components and/or bacterial metabolites into the blood. In some compositions, provided are antibiotic agents that remove the existing microflora in a target niche, while newly administered or recruited bacteria and fungi populate (or re-populate) the target niche. The combination with carbohydrates (e.g., by co-administration or co-formulation) may synergistically affect this population/repopulation technique.

Disorders associated with a dysbiosis, i.e., a gastrointestinal dysbiosis or a distal dysbiosis, which increases systemic inflammation and/or reduces intestinal barrier integrity include, for example, autoimmune or inflammatory disorders, Crohn's Disease, vaginal dysbiosis, and transplant disorders such as graft-versus-host disease. These disorders can be treated by administration (e.g., oral administration) of probiotic compositions containing immunomodulatory (e.g., anti-inflammatory) bacterial strains.

In some embodiments, the probiotic compositions described herein may additively or synergistically reduce the number of types of autoimmune disease- or inflammatory disease-associated pathogens or pathobionts either distally—e.g., orally-administered microbes reduce the total microbial burden in an organ not in the gastrointestinal tract, or intravaginally-administered microbes reduce the total microbial burden in an organ that is not the vagina—or locally, e.g., the intestines or vagina, respectively.

Accordingly, in one aspect, the invention provides a method of reducing inflammation in a subject, comprising administering to the subject a probiotic composition comprising an isolated, anti-inflammatory bacterial population, such that inflammation in the subject is reduced. A systemic reduction in inflammation can modulate the microbiome of niches distal to the site of administration, intended engraftment, or intended colonization of the bacterial population. The probiotic composition can contain an excipient useful for formulation as a pharmaceutical composition. In instances where the bacterial population includes anaerobic bacteria, the excipient can, in one embodiment, reduce exposure of the bacterial population to oxygen.

In a preferred embodiment, administration of the probiotic composition can reduce inflammation at a site distal to the site of administration, engraftment, or colonization, such as, for example, vagina, skin, lungs, brain, nose, ear, eyes/conjunctiva, mouth, circulatory system, e.g., blood, placenta, embryonic sac, reproductive tract, cardiovascular system, and/or nervous system. In one embodiment, administration of the probiotic composition can reduce inflammation at a site selected from blood, skin, vagina, liver, spleen, fallopian tubes, uterus, or a combination thereof. In one embodiment, administration of the probiotic composition modulates the microbiome at a distal site.

The anti-inflammatory bacterial population can induce a decrease in secretion of pro-inflammatory cytokines and/or an increase in secretion of anti-inflammatory cytokines by host cells. The anti-inflammatory properties of the bacterial population can be determined by methods described herein or known in the art, for example, by measuring alterations in cytokine secretion by peripheral blood mononuclear cells (PBMCs) exposed to the bacterial population. Anti-inflammatory bacteria can be selected for inclusion in the probiotic formulation based on modulation of particular cytokines of interest. For example, anti-inflammatory bacteria can be selected based on the ability to decrease secretion of one or more pro-inflammatory cytokines, e.g., IFNγ, IL-12p70, IL-1α, IL-6, IL-8, MCP1, MIP1a, MIP1β, TNFα, and combinations thereof, and/or the ability to increase secretion of one or more anti-inflammatory cytokines, e.g., IL-10, IL-13, IL-4, IL-5, and combinations thereof.

In another aspect, the invention provides methods of treating or preventing a distal dysbiosis in a subject, by administering to the subject a probiotic composition comprising an isolated bacterial population in an amount sufficient to alter the microbiome at a site distal to the site of administration, engraftment, or colonization of the bacterial population, such that the distal dysbiosis is treated. For example, administration of the probiotic composition may modulate a first microbiome at the site of administration, engraftment or colonization of the bacterial population, causing subsequent modulation of a second microbiome at a site that is distinct from the first microbiome, e.g., a distal site.

In one embodiment, the invention provides methods of treating or preventing a distal dysbiosis, by orally administering a probiotic composition which alters the microbiome at a site distal to the gastrointestinal tract.

In another aspect, the invention provides a method of treating or preventing a disorder associated with a distal dysbiosis in a subject in need thereof, comprising administering to the subject a probiotic composition comprising an isolated bacterial population in an amount sufficient to alter the microbiome at a site of the distal dysbiosis, such that the disorder associated with the distal dysbiosis is treated. Disorders associated with distal dysbiosis, including disruptions to the systemic microbiome, are described herein and include, for example, autoimmune or inflammatory disorders such as graft-versus-host disease (GVHD), an inflammatory bowel disease (IBD), ulterative colitis, Crohn's disease, multiple sclerosis (MS), systemic lupus erythematosus (SLE), type I diabetes, rheumatoid arthritis, Sjögren's syndrome, and Celiac disease; transplant disorders such as graft-versus-host disease; and vaginal dysbiosis. In one embodiment, the disorder associated with distal dysbiosis occurs in the respiratory tract (e.g., lung), including but not limited to Cystic Fibrosis and chronic obstructive pulmonary disorder (COPD).

In one embodiment, the probiotic composition contains a species of bacteria that is deficient at the site of the distal dysbiosis. Administration of the probiotic composition can increase the quantity of the deficient species in the distal microbiome. In one embodiment, the deficient species is not detectably present at the site of the distal dysbiosis prior to administration of the probiotic composition. In one embodiment, the species of bacteria in the probiotic composition translocates to the site of the distal dysbiosis.

In another embodiment, the probiotic composition results in augmentation of a species of bacteria not present in the probiotic composition at a distal site. This augmentation can result from, for example, translocation of a species of bacteria not present in the probiotic composition to the distal site, and/or modulation of the microenvironment of the distal site in a manner that alters the microbiome.

In preferred embodiments, the probiotic composition contains immunomodulatory bacteria, e.g., anti-inflammatory bacteria.

In another aspect, the invention provides a method of reducing intestinal permeability in a subject, by administering a probiotic composition comprising an isolated bacterial population, wherein administration of the probiotic composition augments a species of bacteria that produces short chain fatty acids, such that the intestinal permeability of the subject is reduced. In other embodiments, intestinal permeability and disorders associated therewith is improved by administering a probiotic composition containing mucin-containing bacteria, and/or anti-inflammatory bacteria.

Probiotic compositions useful for correcting or treating a distal dysbiosis, or for treating a disorder distal to the gastrointestinal tract associated with a dysbiosis, can include any of the probiotic compositions described herein. In exemplary embodiments, a probiotic composition useful for correcting or treating a distal dysbiosis includes one or more bacterial strains from Table 1. In other embodiments, the probiotic composition useful for correcting or treating a distal dysbiosis includes one or more bacterial strains from Table 1A. In other embodiments, the probiotic composition useful for correcting or treating a distal dysbiosis includes one or more bacterial strains from Table 1B. In other embodiments, the probiotic composition useful for correcting or treating a distal dysbiosis includes one or more bacterial strains from Table 1C. In other embodiments, the probiotic composition useful for correcting or treating a distal dysbiosis includes one or more bacterial strains from Table 1D. In other embodiments, the probiotic composition useful for correcting or treating a distal dysbiosis includes one or more bacterial strains from Table 1E. In other embodiments, the probiotic composition useful for correcting or treating a distal dysbiosis includes one or more bacterial strains from Table 1F. In some embodiments, the probiotic composition contains a single strain of bacteria. In other embodiments, the probiotic composition contains two or more strains of bacteria, e.g., 2, 3, 4, 5, 6, 7, 8, 9, 10, 15, 20, 30, 40, 50, 60, 70, 80, 90, 100, 500, 1000 or more strains of bacteria. In other embodiments, the probiotic composition contains or is administered in conjunction with a prebiotic, as described herein.

Preferred bacterial genera include *Acetanaerobacterium, Acetivibrio, Alicyclobacillus, Alkaliphilus, Anaerofustis, Anaerosporobacter, Anaerostipes, Anaerotruncus, Anoxybacillus, Bacillus, Bacteroides, Blautia, Brachyspira, Brevibacillus, Bryantella, Bulleidia, Butyricicoccus, Butyrivibrio, Catenibacterium, Chlamydiales, Clostridiaceae, Clostridiales, Clostridium, Collinsella, Coprobacillus, Coprococcus, Coxiella, Deferribacteres, Desulfitobacterium, Desulfotomaculum, Dorea, Eggerthella, Erysipelothrix, Erysipelotrichaceae, Ethanoligenens, Eubacterium, Faecalibacterium, Filifactor, Flavonifractor, Flexistipes, Fulvimonas, Fusobacterium, Gemmiger, Geobacillus, Gloeobacter, Holdemania, Hydrogenoanaerobacterium, Kocuria, Lachnobacterium, Lachnospira, Lachnospiraceae, Lactobacillus, Lactonifactor, Leptospira, Lutispora, Lysinibacillus, Mollicutes, Moorella, Nocardia, Oscillibacter, Oscillospira, Paenibacillus, Papillibacter, Pseudoflavonifractor, Robinsoniella, Roseburia, Ruminococcaceae, Ruminococcus, Saccharomonospora, Sarcina, Solobacterium, Sporobacter, Sporolactobacillus, Streptomyces, Subdoligranulum, Sutterella, Syntrophococcus, Thermoanaerobacter, Thermobifida,* and *Turicibacter.*

Preferred bacterial genera also include *Acetonema, Alkaliphilus, Amphibacillus, Ammonifex, Anaerobacter, Caldicellulosiruptor, Caloramator, Candidatus, Carboxydibrachium, Carboxydothermus, Cohnella, Dendrosporobacter Desulfitobacterium, Desulfosporosinus, Halobacteroides, Heliobacterium, Heliophilum, Heliorestis, Lachnoanaerobaculum, Lysinibacillus, Oceanobacillus, Orenia (S.), Oxalophagus, Oxobacter, Pelospora, Pelotomaculum, Propionispora, Sporohalobacter, Sporomusa, Sporosarcina, Sporotomaculum, Symbiobacterium, Syntrophobotulus, Syntrophospora, Terribacillus, Thermoanaerobacter, Thermosinus* and *Heliobacillus.*

As provided herein, therapeutic compositions comprise, or in the alternative, modulate, the colonization and/or engraftment, of the following exemplary bacterial entities: *Lactobacillus gasseri, Lactobacillus fermentum, Lactobacillus reuteri, Enterococcus faecalis, Enterococcus durans, Enterococcus villorum, Lactobacillus plantarum, Pediococcus acidilactici, Staphylococcus pasteuri, Staphylococcus cohnii, Streptococcus sanguinis, Streptococcus sinensis, Streptococcus mitis, Streptococcus* sp. SCA22, *Streptococcus* sp. CR-3145, *Streptococcus anginosus, Streptococcus mutans, Coprobacillus cateniformis, Clostridium saccharogumia, Eubacterium dolichum* DSM 3991, *Clostridium* sp. PPf35E6, *Clostridium sordelli* ATCC 9714, *Ruminococcus torques, Ruminococcus gnavus, Clostridium clostridio-*

*forme, Ruminococcus obeum, Blautia producta, Clostridium* sp. ID5, *Megasphaera micronuciformis, Veillonella parvula, Clostridium methylpentosum, Clostridium islandicum, Faecalibacterium prausnitzii, Bacteroides uniformmis, Bacteroides thetaiotaomicron, Bacteroides acidifaciens, Bacteroides ovatus, Bacteroides fragilis, Parabacteroides distasonis, Propinionibacteirum propionicum, Actinomycs hyovaginalis, Rothia mucilaginosa, Rothia aeria, Bifidobacterium breve, Scardovia inopinata* and *Eggerthella lenta*.

Preferred bacterial species are provided in Table 1, Table 1A, Table 1B, Table 1C, Table 1D, Table 1E, Table 1F, and Table 5. Optionally, in some embodiments, preferred bacterial species are spore formers. The bacterial species may be used in vegetative form and/or in spore form. Thus, in some embodiments, the bacteria present in a composition are solely in spore form. In some embodiments, the bacteria present in a composition are solely in vegetative form. In some embodiments, the bacteria present in a composition are in a combination of vegetative form and spore form. Where specific strains of a species are provided, one of skill in the art will recognize that other strains of the species can be substituted for the named strain.

In one embodiment, the bacterial entity, e.g., species or strain, useful in the compositions and methods of the invention is *Acidaminococcus intestine*. In one embodiment, the bacterial entity, e.g., species or strain, useful in the compositions and methods of the invention is *Acinetobacter baumannii*. In one embodiment, the bacterial entity, e.g., species or strain, useful in the compositions and methods of the invention is *Acinetobacter lwoffii*. In one embodiment, the bacterial entity, e.g., species or strain, useful in the compositions and methods of the invention is *Akkermansia muciniphila*. In one embodiment, the bacterial entity, e.g., species or strain, useful in the compositions and methods of the invention is *Alistipes putredinis*. In one embodiment, the bacterial entity, e.g., species or strain, useful in the compositions and methods of the invention is *Alistipes shahii*. In one embodiment, the bacterial entity, e.g., species or strain, useful in the compositions and methods of the invention is *Anaerostipes hadrus*. In one embodiment, the bacterial entity, e.g., species or strain, useful in the compositions and methods of the invention is *Anaerotruncus colihominis*. In one embodiment, the bacterial entity, e.g., species or strain, useful in the compositions and methods of the invention is *Bacteroides caccae*. In one embodiment, the bacterial entity, e.g., species or strain, useful in the compositions and methods of the invention is *Bacteroides cellulosilyticus*. In one embodiment, the bacterial entity, e.g., species or strain, useful in the compositions and methods of the invention is *Bacteroides dorei*. In one embodiment, the bacterial entity, e.g., species or strain, useful in the compositions and methods of the invention is *Bacteroides eggerthii*. In one embodiment, the bacterial entity, e.g., species or strain, useful in the compositions and methods of the invention is *Bacteroides finegoldii*. In one embodiment, the bacterial entity, e.g., species or strain, useful in the compositions and methods of the invention is *Bacteroides fragilis*. In one embodiment, the bacterial entity, e.g., species or strain, useful in the compositions and methods of the invention is *Bacteroides massiliensis*. In one embodiment, the bacterial entity, e.g., species or strain, useful in the compositions and methods of the invention is *Bacteroides ovatus*. In one embodiment, the bacterial entity, e.g., species or strain, useful in the compositions and methods of the invention is *Bacteroides salanitronis*. In one embodiment, the bacterial entity, e.g., species or strain, useful in the compositions and methods of the invention is *Bacteroides salyersiae*. In one embodiment, the bacterial entity, e.g., species or strain, useful in the compositions and methods of the invention is *Bacteroides* sp. 1_1_6. In one embodiment, the bacterial entity, e.g., species or strain, useful in the compositions and methods of the invention is *Bacteroides* sp. 3_1_23. In one embodiment, the bacterial entity, e.g., species or strain, useful in the compositions and methods of the invention is *Bacteroides* sp. D20. In one embodiment, the bacterial entity, e.g., species or strain, useful in the compositions and methods of the invention is *Bacteroides thetaiotaomicrond*. In one embodiment, the bacterial entity, e.g., species or strain, useful in the compositions and methods of the invention is *Bacteroides uniformis*. In one embodiment, the bacterial entity, e.g., species or strain, useful in the compositions and methods of the invention is *Bacteroides vulgatus*. In one embodiment, the bacterial entity, e.g., species or strain, useful in the compositions and methods of the invention is *Bifidobacterium adolescentis*. In one embodiment, the bacterial entity, e.g., species or strain, useful in the compositions and methods of the invention is *Bifidobacterium bifidum*. In one embodiment, the bacterial entity, e.g., species or strain, useful in the compositions and methods of the invention is *Bifidobacterium breve*. In one embodiment, the bacterial entity, e.g., species or strain, useful in the compositions and methods of the invention is *Bifidobacterium faecale*. In one embodiment, the bacterial entity, e.g., species or strain, useful in the compositions and methods of the invention is *Bifidobacterium kashiwanohense*. In one embodiment, the bacterial entity, e.g., species or strain, useful in the compositions and methods of the invention is *Bifidobacterium longum* subsp. *Longum*. In one embodiment, the bacterial entity, e.g., species or strain, useful in the compositions and methods of the invention is *Bifidobacterium pseudocatenulatum*. In one embodiment, the bacterial entity, e.g., species or strain, useful in the compositions and methods of the invention is *Bifidobacterium stercoris*. In one embodiment, the bacterial entity, e.g., species or strain, useful in the compositions and methods of the invention is *Blautia (Ruminococcus) coccoides*. In one embodiment, the bacterial entity, e.g., species or strain, useful in the compositions and methods of the invention is *Blautia faecis*. In one embodiment, the bacterial entity, e.g., species or strain, useful in the compositions and methods of the invention is *Blautia glucerasea*. In one embodiment, the bacterial entity, e.g., species or strain, useful in the compositions and methods of the invention is *Blautia (Ruminococcus) hansenii*. In one embodiment, the bacterial entity, e.g., species or strain, useful in the compositions and methods of the invention is *Blautia hydrogenotrophica (Ruminococcus hydrogenotrophicus)*. In one embodiment, the bacterial entity, e.g., species or strain, useful in the compositions and methods of the invention is *Blautia (Ruminococcus) luti*. In one embodiment, the bacterial entity, e.g., species or strain, useful in the compositions and methods of the invention is *Blautia (Ruminococcus) obeum*. In one embodiment, the bacterial entity, e.g., species or strain, useful in the compositions and methods of the invention is *Blautia producta (Ruminococcus productus)*. In one embodiment, the bacterial entity, e.g., species or strain, useful in the compositions and methods of the invention is *Blautia (Ruminococcus) schinkii*. In one embodiment, the bacterial entity, e.g., species or strain, useful in the compositions and methods of the invention is *Blautia stercoris*. In one embodiment, the bacterial entity, e.g., species or strain, useful in the compositions and methods of the invention is *Blautia* uncultured bacterium clone BKLE_a03_2 (GenBank: EU469501.1). In one embodiment, the bacterial entity, e.g., species or strain, useful in the compositions and methods of the invention is *Blautia* uncultured bacterium clone SJTU_B_14_30 (GenBank: EF402926.1). In one embodiment, the bacterial entity, e.g., species or strain, useful in the compositions and methods of the invention is *Blautia* uncultured bacterium clone SJTU_C_14_16 (GenBank: EF404657.1). In one embodiment, the bacterial entity, e.g., species or strain, useful in the compositions and methods of the invention is *Blautia* uncultured bacterium clone S1-5 (GenBank: GQ898099.1). In one embodiment, the bacterial entity, e.g., species or strain, useful in the compositions and methods of the invention is *Blautia* uncultured PAC000178_s (www.ezbiocloud.net/ez-taxon/hierarchy?m=browse&k=PAC000178&d=2). In one embodiment, the bacterial entity, e.g., species or strain, useful in the compositions and methods of the invention is *Blautia wexlerae*. In one embodiment, the bacterial entity, e.g., species or strain, useful in the compositions and methods of the invention is *Candidatus Arthromitus* sp. SFB-mouse-Yit. In one embodiment, the bacterial entity, e.g., species or strain, useful in the compositions and methods of the invention is *Catenibacterium mitsuokai*. In one embodiment, the bacterial entity, e.g., species or strain, useful in the compositions and methods of the invention is *Clostridiaceae* bacterium (*Dielma fastidiosa*) JC13. In one embodiment, the bacterial entity, e.g., species or strain, useful in the compositions and methods of the invention is Clostridiales bacterium 1_7_47FAA. In one embodiment, the bacterial entity, e.g., species or strain, useful in the compositions and methods of the invention is *Clostridium asparagiforme*. In one embodiment, the bacterial entity, e.g., species or strain, useful in the compositions and methods of the invention is *Clostridium bolteae*. In one embodiment, the bacterial entity, e.g., species or strain, useful in the compositions and methods of the invention is *Clostridium clostridioforme*. In one embodiment, the bacterial entity, e.g., species or strain, useful in the compositions and methods of the invention is *Clostridium glycyrrhizinilyticum*. In one embodiment, the bacterial entity, e.g., species or strain, useful in the compositions and methods of the invention is *Clostridium (Hungatella) hathewayi*. In one embodiment, the bacterial entity, e.g., species or strain, useful in the compositions and methods of the invention is *Clostridium histolyticum*. In one embodiment, the bacterial entity, e.g., species or strain, useful in the compositions and methods of the invention is *Clostridium indolis*. In one embodiment, the bacterial entity, e.g., species or strain, useful in the compositions and methods of the invention is *Clostridium leptum*. In one embodiment, the bacterial entity, e.g., species or strain, useful in the compositions and methods of the invention is *Clostridium (Tyzzerella) nexile*. In one embodiment, the bacterial entity, e.g., species or strain, useful in the compositions and methods of the invention is *Clostridium perfringens*. In one embodiment, the bacterial entity, e.g., species or strain, useful in the compositions and methods of the invention is *Clostridium (Erysipelatoclostridium) ramosum*. In one embodiment, the bacterial entity, e.g., species or strain, useful in the compositions and methods of the invention is *Clostridium scindens*. In one embodiment, the bacterial entity, e.g., species or strain, useful in the compositions and methods of the invention is *Clostridium septum*. In one embodiment, the bacterial entity, e.g., species or strain, useful in the compositions and methods of the invention is *Clostridium* sp. 14774. In one embodiment, the bacterial entity, e.g., species or strain, useful in the compositions and methods of the invention is *Clostridium* sp. 7_3_54FAA. In one embodiment, the bacterial entity, e.g., species or strain, useful in the compositions and methods of the invention is *Clostridium* sp. HGF2. In one embodiment, the bacterial entity, e.g., species or strain, useful in the compositions and methods of the invention is *Clostridium symbiosum*. In one embodiment, the bacterial entity, e.g., species or strain, useful in the compositions and methods of the invention is *Collinsella aerofaciens*. In one embodiment, the bacterial entity, e.g., species or strain, useful in the compositions and methods of the invention is *Collinsella intestinalis*. In one embodiment, the bacterial entity, e.g., species or strain, useful in the compositions and methods of the invention is *Coprobacillus* sp. D7. In one embodiment, the bacterial entity, e.g., species or strain, useful in the compositions and methods of the invention is *Coprococcus catus*. In one embodiment, the bacterial entity, e.g., species or strain, useful in the compositions and methods of the invention is *Coprococcus comes*. In one embodiment, the bacterial entity, e.g., species or strain, useful in the compositions and methods of the invention is *Dorea formicigenerans*. In one embodiment, the bacterial entity, e.g., species or strain, useful in the compositions and methods of the invention is *Dorea longicatena*. In one embodiment, the bacterial entity, e.g., species or strain, useful in the compositions and methods of the invention is *Enterococcus faecalis*. In one embodiment, the bacterial entity, e.g., species or strain, useful in the compositions and methods of the invention is *Enterococcus faecium*. In one embodiment, the bacterial entity, e.g., species or strain, useful in the compositions and methods of the invention is Erysipelotrichaceae bacterium 3_1_53. In one embodiment, the bacterial entity, e.g., species or strain, useful in the compositions and methods of the invention is *Escherichia coli*. In one embodiment, the bacterial entity, e.g., species or strain, useful in the compositions and methods of the invention is *Escherichia coli* S88. In one embodiment, the bacterial entity, e.g., species or strain, useful in the compositions and methods of the invention is *Eubacterium eligens*. In one embodiment, the bacterial entity, e.g., species or strain, useful in the compositions and methods of the invention is *Eubacterium fissicatena*. In one embodiment, the bacterial entity, e.g., species or strain, useful in the compositions and methods of the invention is *Eubacterium ramulus*. In one embodiment, the bacterial entity, e.g., species or strain, useful in the compositions and methods of the invention is *Eubacterium rectale*. In one embodiment, the bacterial entity, e.g., species or strain, useful in the compositions and methods of the invention is *Faecalibacterium prausnitzii*. In one embodiment, the bacterial entity, e.g., species or strain, useful in the compositions and methods of the invention is *Flavonifractor plautii*. In one embodiment, the bacterial entity, e.g., species or strain, useful in the compositions and methods of the invention is *Fusobacterium mortiferum*. In one embodiment, the bacterial entity, e.g., species or strain, useful in the compositions and methods of the invention is *Fusobacterium nucleatum*. In one embodiment, the bacterial entity, e.g., species or strain, useful in the compositions and methods of the invention is *Holdemania filiformis*. In one embodiment, the bacterial entity, e.g., species or strain, useful in the compositions and methods of the invention is *Hydrogenoanaerobacterium saccharovorans*. In one embodiment, the bacterial entity, e.g., species or strain, useful in the compositions and methods of the invention is *Klebsiella oxytoca*. In one embodiment, the bacterial entity, e.g., species or strain, useful in the compositions and methods of the invention is Lachnospiraceae bacterium 3_1_7FAA_CT1. In one embodiment, the bacterial entity, e.g., species or strain, useful in the compositions and methods of the invention is Lachnospiraceae bacterium 7_1_58FAA. In one embodiment, the bacterial entity, e.g., species or strain, useful in the compositions and methods of the invention is Lachnospiraceae bacterium 5_1_57FAA. In one embodiment, the bacterial entity, e.g., species or strain, useful in the compositions and methods of the invention is *Lactobacillus casei*. In one embodiment, the bacterial entity, e.g., species or strain, useful in the compositions and methods of the invention is *Lactobacillus rhamnosus*. In one embodiment, the bacterial entity, e.g., species or strain, useful in the compositions and methods of the invention is *Lactobacillus ruminis*. In one embodiment, the bacterial entity, e.g., species or strain, useful in the compositions and methods of the invention is *Lactococcus casei*. In one embodiment, the bacterial entity, e.g., species or strain, useful in the compositions and methods of the invention is *Odoribacter splanchnicus*. In one embodiment, the bacterial entity, e.g., species or strain, useful in the compositions and methods of the invention is *Oscillibacter valericigenes*. In one embodiment, the bacterial entity, e.g., species or strain, useful in the compositions and methods of the invention is *Parabacteroides gordonii*. In one embodiment, the bacterial entity, e.g., species or strain, useful in the compositions and methods of the invention is *Parabacteroides johnsonii*. In one embodiment, the bacterial entity, e.g., species or strain, useful in the compositions and methods of the invention is *Parabacteroides merdae*. In one embodiment, the bacterial entity, e.g., species or strain, useful in the compositions and methods of the invention is *Pediococcus acidilactici*. In one embodiment, the bacterial entity, e.g., species or strain, useful in the compositions and methods of the invention is *Peptostreptococcus asaccharolyticus*. In one embodiment, the bacterial entity, e.g., species or strain, useful in the compositions and methods of the invention is *Propionibacterium granulosum*. In one embodiment, the bacterial entity, e.g., species or strain, useful in the compositions and methods of the invention is *Roseburia intestinalis*. In one embodiment, the bacterial entity, e.g., species or strain, useful in the compositions and methods of the invention is *Roseburia inulinivorans*. In one embodiment, the bacterial entity, e.g., species or strain, useful in the compositions and methods of the invention is *Ruminococcus faecis*. In one embodiment, the bacterial entity, e.g., species or strain, useful in the compositions and methods of the invention is *Ruminococcus gnavus*. In one embodiment, the bacterial entity, e.g., species or strain, useful in the compositions and methods of the invention is *Ruminococcus* sp. ID8. In one embodiment, the bacterial entity, e.g., species or strain, useful in the compositions and methods of the invention is *Ruminococcus torques*. In one embodiment, the bacterial entity, e.g., species or strain, useful in the compositions and methods of the invention is *Slackia piriformis*. In one embodiment, the bacterial entity, e.g., species or strain, useful in the compositions and methods of the invention is *Staphylococcus epidermidis*. In one embodiment, the bacterial entity, e.g., species or strain, useful in the compositions and methods of the invention is *Staphylococcus saprophyticus*. In one embodiment, the bacterial entity, e.g., species or strain, useful in the compositions and methods of the invention is *Streptococcus cristatus*. In one embodiment, the bacterial entity, e.g., species or strain, useful in the compositions and methods of the invention is *Streptococcus dysgalactiae* subsp. *Equisimilis*. In one embodiment, the bacterial entity, e.g., species or strain, useful in the compositions and methods of the invention is *Streptococcus infantis*. In one embodiment, the bacterial entity, e.g., species or strain, useful in the compositions and methods of the invention is *Streptococcus oralis*. In one embodiment, the bacterial entity, e.g., species or strain, useful in the compositions and methods of the invention is *Streptococcus sanguinis*. In one embodiment, the bacterial entity, e.g., species or strain, useful in the compositions and methods of the invention is *Streptococcus viridans*. In one embodiment, the bacterial entity, e.g., species or strain, useful in the compositions and methods of the invention is *Streptococcus thermophiles*. In one embodiment, the bacterial entity, e.g., species or strain, useful in the compositions and methods of the invention is *Veillonella dispar*.

In one embodiment, the bacterial population useful in the compositions and methods of the invention comprises *Acidaminococcus intestine*. In one embodiment, the bacterial population useful in the compositions and methods of the invention comprises *Acinetobacter baumannii*. In one embodiment, the bacterial population useful in the compositions and methods of the invention comprises *Acinetobacter lwoffii*. In one embodiment, the bacterial population useful in the compositions and methods of the invention comprises *Akkermansia muciniphila*. In one embodiment, the bacterial population useful in the compositions and methods of the invention comprises *Alistipes putredinis*. In one embodiment, the bacterial population useful in the compositions and methods of the invention comprises *Alistipes shahii*. In one embodiment, the bacterial population useful in the compositions and methods of the invention comprises *Anaerostipes hadrus*. In one embodiment, the bacterial population useful in the compositions and methods of the invention comprises *Anaerotruncus colihominis*. In one embodiment, the bacterial population useful in the compositions and methods of the invention comprises *Bacteroides caccae*. In one embodiment, the bacterial population useful in the compositions and methods of the invention comprises *Bacteroides cellulosilyticus*. In one embodiment, the bacterial population useful in the compositions and methods of the invention comprises *Bacteroides dorei*. In one embodiment, the bacterial population useful in the compositions and methods of the invention comprises *Bacteroides eggerthii*. In one embodiment, the bacterial population useful in the compositions and methods of the invention comprises *Bacteroides finegoldii*. In one embodiment, the bacterial population useful in the compositions and methods of the invention comprises *Bacteroides fragilis*. In one embodiment, the bacterial population useful in the compositions and methods of the invention comprises *Bacteroides massiliensis*. In one embodiment, the bacterial population useful in the compositions and methods of the invention comprises *Bacteroides ovatus*. In one embodiment, the bacterial population useful in the compositions and methods of the invention comprises *Bacteroides salanitronis*. In one embodiment, the bacterial population useful in the compositions and methods of the invention comprises *Bacteroides salyersiae*. In one embodiment, the bacterial population useful in the compositions and methods of the invention comprises *Bacteroides* sp. 1_1_6. In one embodiment, the bacterial population useful in the compositions and methods of the invention comprises *Bacteroides* sp. 3_1_23. In one embodiment, the bacterial population useful in the compositions and methods of the invention comprises *Bacteroides* sp. D20. In one embodiment, the bacterial population useful in the compositions and methods of the invention comprises *Bacteroides thetaiotaomicrond*. In one embodiment, the bacterial population useful in the compositions and methods of the invention comprises *Bacteroides uniformis*. In one embodiment, the bacterial population useful in the compositions and methods of the invention comprises *Bacteroides vulgatus*. In one embodiment, the bacterial population useful in the compositions and methods of the invention comprises *Bifidobacterium adolescentis*. In one embodiment, the bacterial population useful in the compositions and methods of the invention comprises *Bifidobacterium bifidum*. In one embodiment, the bacterial population useful in the compositions and methods of the invention comprises *Bifidobacterium breve*. In one embodiment, the bacterial population useful in the compositions and methods of the invention comprises *Bifidobacterium faecale*. In one embodiment, the bacterial population useful in the compositions and methods of the invention comprises *Bifidobacterium kashiwanohense*. In one embodiment, the bacterial population useful in the compositions and methods of the invention comprises *Bifidobacterium longum* subsp. *Longum*. In one embodiment, the bacterial population useful in the compositions and methods of the invention comprises *Bifidobacterium pseudocatenulatum*. In one embodiment, the bacterial population useful in the compositions and methods of the invention comprises *Bifidobacterium stercoris*. In one embodiment, the bacterial population useful in the compositions and methods of the invention comprises *Blautia (Ruminococcus) coccoides*. In one embodiment, the bacterial population useful in the compositions and methods of the invention comprises *Blautia faecis*. In one embodiment, the bacterial population useful in the compositions and methods of the invention comprises *Blautia glucerasea*. In one embodiment, the bacterial population useful in the compositions and methods of the invention comprises *Blautia (Ruminococcus) hansenii*. In one embodiment, the bacterial population useful in the compositions and methods of the invention comprises *Blautia hydrogenotrophica (Ruminococcus hydrogenotrophicus)*. In one embodiment, the bacterial population useful in the compositions and methods of the invention comprises *Blautia (Ruminococcus) luti*. In one embodiment, the bacterial population useful in the compositions and methods of the invention comprises *Blautia (Ruminococcus) obeum*. In one embodiment, the bacterial population useful in the compositions and methods of the invention comprises *Blautia producta (Ruminococcus productus)*. In one embodiment, the bacterial population useful in the compositions and methods of the invention comprises *Blautia (Ruminococcus) schinkii*. In one embodiment, the bacterial population useful in the compositions and methods of the invention comprises *Blautia stercoris*. In one embodiment, the bacterial population useful in the compositions and methods of the invention comprises *Blautia* uncultured bacterium clone BKLE_a03_2 (GenBank: EU469501.1). In one embodiment, the bacterial population useful in the compositions and methods of the invention comprises *Blautia* uncultured bacterium clone SJTU_B_14_30 (GenBank: EF402926.1). In one embodiment, the bacterial population useful in the compositions and methods of the invention comprises *Blautia* uncultured bacterium clone SJTU_C_14_16 (GenBank: EF404657.1). In one embodiment, the bacterial population useful in the compositions and methods of the invention comprises *Blautia* uncultured bacterium clone S1-5 (GenBank: GQ898099.1). In one embodiment, the bacterial population useful in the compositions and methods of the invention comprises *Blautia* uncultured PAC000178_s (www.ezbiocloud.net/eztaxon/hierarchy?m=browse&k=PAC000178&d=2). In one embodiment, the bacterial population useful in the compositions and methods of the invention comprises *Blautia wexlerae*. In one embodiment, the bacterial population useful in the compositions and methods of the invention comprises *Candidatus Arthromitus* sp. SFB-mouse-Yit. In one embodiment, the bacterial population useful in the compositions and methods of the invention comprises *Catenibacterium mitsuokai*. In one embodiment, the bacterial population useful in the compositions and methods of the invention comprises *Clostridiaceae* bacterium (*Dielma fastidiosa*) JC13. In one embodiment, the bacterial population useful in the compositions and methods of the invention comprises Clostridiales bacterium 1_7_47FAA. In one embodiment, the bacterial population useful in the compositions and methods of the invention comprises *Clostridium asparagiforme*. In one embodiment, the bacterial population useful in the compositions and methods of the invention comprises *Clostridium bolteae*. In one embodiment, the bacterial population useful in the compositions and methods of the invention comprises *Clostridium clostridioforme*. In one embodiment, the bacterial population useful in the compositions and methods of the invention comprises *Clostridium glycyrrhizinilyticum*. In one embodiment, the bacterial population useful in the compositions and methods of the invention comprises *Clostridium (Hungatella) hathewayi*. In one embodiment, the bacterial population useful in the compositions and methods of the invention comprises *Clostridium histolyticum*. In one embodiment, the bacterial population useful in the compositions and methods of the invention comprises *Clostridium indolis*. In one embodiment, the bacterial population useful in the compositions and methods of the invention comprises *Clostridium leptum*. In one embodiment, the bacterial population useful in the compositions and methods of the invention comprises *Clostridium (Tyzzerella) nexile*. In one embodiment, the bacterial population useful in the compositions and methods of the invention comprises *Clostridium perfringens*. In one embodiment, the bacterial population useful in the compositions and methods of the invention comprises *Clostridium (Erysipelatoclostridium) ramosum*. In one embodiment, the bacterial population useful in the compositions and methods of the invention comprises *Clostridium scindens*. In one embodiment, the bacterial entity, e.g., species or strain, useful in the compositions and methods of the invention is *Clostridium septum*. In one embodiment, the bacterial population useful in the compositions and methods of the invention comprises *Clostridium* sp. 14774. In one embodiment, the bacterial population useful in the compositions and methods of the invention comprises *Clostridium* sp. 7_3_54FAA. In one embodiment, the bacterial population useful in the compositions and methods of the invention comprises *Clostridium* sp. HGF2. In one embodiment, the bacterial population useful in the compositions and methods of the invention comprises *Clostridium symbiosum*. In one embodiment, the bacterial population useful in the compositions and methods of the invention comprises *Collinsella aerofaciens*. In one embodiment, the bacterial population useful in the compositions and methods of the invention comprises *Collinsella intestinalis*. In one embodiment, the bacterial population useful in the compositions and methods of the invention comprises *Coprobacillus* sp. D7. In one embodiment, the bacterial population useful in the compositions and methods of the invention comprises *Coprococcus catus*. In one embodiment, the bacterial population useful in the compositions and methods of the invention comprises *Coprococcus comes*. In one embodiment, the bacterial population useful in the compositions and methods of the invention comprises *Dorea formicigenerans*. In one embodiment, the bacterial population useful in the compositions and methods of the invention comprises *Dorea longicatena*. In one embodiment, the bacterial population useful in the compositions and methods of the invention comprises *Enterococcus faecalis*. In one embodiment, the bacterial population useful in the compositions and methods of the invention comprises *Enterococcus faecium*. In one embodiment, the bacterial population useful in the compositions and methods of the invention comprises Erysipelotrichaceae bacterium 3_1_53. In one embodiment, the bacterial population useful in the compositions and methods of the invention comprises *Escherichia coli*. In one embodiment, the bacterial population useful in the compositions and methods of the invention comprises *Escherichia coli* S88. In one embodiment, the bacterial population useful in the compositions and methods of the invention comprises *Eubacterium eligens*. In one embodiment, the bacterial population useful in the compositions and methods of the invention comprises *Eubacterium fissicatena*. In one embodiment, the bacterial population useful in the compositions and methods of the invention comprises *Eubacterium ramulus*. In one embodiment, the bacterial population useful in the compositions and methods of the invention comprises *Eubacterium rectale*. In one embodiment, the bacterial population useful in the compositions and methods of the invention comprises *Faecalibacterium prausnitzii*. In one embodiment, the bacterial population useful in the compositions and methods of the invention comprises *Flavonifractor plautii*. In one embodiment, the bacterial population useful in the compositions and methods of the invention comprises *Fusobacterium mortiferum*. In one embodiment, the bacterial population useful in the compositions and methods of the invention comprises *Fusobacterium nucleatum*. In one embodiment, the bacterial population useful in the compositions and methods of the invention comprises *Holdemania filiformis*. In one embodiment, the bacterial population useful in the compositions and methods of the invention comprises *Hydrogenoanaerobacterium saccharovorans*. In one embodiment, the bacterial population useful in the compositions and methods of the invention comprises *Klebsiella oxytoca*. In one embodiment, the bacterial population useful in the compositions and methods of the invention comprises Lachnospiraceae bacterium 3_1_7FAA_CT1. In one embodiment, the bacterial population useful in the compositions and methods of the invention comprises Lachnospiraceae bacterium 7_1_58FAA. In one embodiment, the bacterial population useful in the compositions and methods of the invention comprises Lachnospiraceae bacterium 5_1_57FAA. In one embodiment, the bacterial population useful in the compositions and methods of the invention comprises *Lactobacillus casei*. In one embodiment, the bacterial population useful in the compositions and methods of the invention comprises *Lactobacillus rhamnosus*. In one embodiment, the bacterial population useful in the compositions and methods of the invention comprises *Lactobacillus ruminis*. In one embodiment, the bacterial population useful in the compositions and methods of the invention comprises *Lactococcus casei*. In one embodiment, the bacterial population useful in the compositions and methods of the invention comprises *Odoribacter splanchnicus*. In one embodiment, the bacterial population useful in the compositions and methods of the invention comprises *Oscillibacter valericigenes*. In one embodiment, the bacterial population useful in the compositions and methods of the invention comprises *Parabacteroides gordonii*. In one embodiment, the bacterial population useful in the compositions and methods of the invention comprises *Parabacteroides johnsonii*. In one embodiment, the bacterial population useful in the compositions and methods of the invention comprises *Parabacteroides merdae*. In one embodiment, the bacterial population useful in the compositions and methods of the invention comprises *Pediococcus acidilactici*. In one embodiment, the bacterial population useful in the compositions and methods of the invention comprises *Peptostreptococcus asaccharolyticus*. In one embodiment, the bacterial population useful in the compositions and methods of the invention comprises *Propionibacterium granulosum*. In one embodiment, the bacterial population useful in the compositions and methods of the invention comprises *Roseburia intestinalis*. In one embodiment, the bacterial population useful in the compositions and methods of the invention comprises *Roseburia inulinivorans*. In one embodiment, the bacterial population useful in the compositions and methods of the invention comprises *Ruminococcus faecis*. In one embodiment, the bacterial population useful in the compositions and methods of the invention comprises *Ruminococcus gnavus*. In one embodiment, the bacterial population useful in the compositions and methods of the invention comprises *Ruminococcus* sp. ID8. In one embodiment, the bacterial population useful in the compositions and methods of the invention comprises *Ruminococcus torques*. In one embodiment, the bacterial population useful in the compositions and methods of the invention comprises *Slackia piriformis*. In one embodiment, the bacterial population useful in the compositions and methods of the invention comprises *Staphylococcus epidermidis*. In one embodiment, the bacterial population useful in the compositions and methods of the invention comprises *Staphylococcus saprophyticus*. In one embodiment, the bacterial population useful in the compositions and methods of the invention comprises *Streptococcus cristatus*. In one embodiment, the bacterial population useful in the compositions and methods of the invention comprises *Streptococcus dysgalactiae* subsp. *Equisimilis*. In one embodiment, the bacterial population useful in the compositions and methods of the invention comprises *Streptococcus infantis*. In one embodiment, the bacterial population useful in the compositions and methods of the invention comprises *Streptococcus oralis*. In one embodiment, the bacterial population useful in the compositions and methods of the invention comprises *Streptococcus sanguinis*. In one embodiment, the bacterial population useful in the compositions and methods of the invention comprises *Streptococcus viridans*. In one embodiment, the bacterial population useful in the compositions and methods of the invention comprises *Streptococcus thermophiles*. In one embodiment, the bacterial population useful in the compositions and methods of the invention comprises *Veillonella dispar*.

Exemplary probiotic compositions useful for treatment of disorders associated with a distal dysbiosis contain bacterial strains capable of reducing inflammation in a subject. As described herein, such immunomodulatory (anti-inflammatory) bacteria can modulate cytokine expression by host immune cells, resulting in an overall increase in secretion of anti-inflammatory cytokines and/or an overall decrease in secretion of pro-inflammatory cytokines, systemically reducing inflammation in the subject. In exemplary embodiments, probiotic compositions useful for treatment of disorders associated with a distal dysbiosis stimulate secretion of one or more anti-inflammatory cytokines by host immune cells, such as PBMCs. Anti-inflammatory cytokines include, but are not limited to, IL-10, IL-13, IL-9, IL-4, IL-5, TGFβ, and combinations thereof. In other exemplary embodiments, probiotic compositions useful for treatment of disorders associated with a distal dysbiosis inhibit secretion of one or more pro-inflammatory cytokines by host immune cells, such as PBMCs. Pro-inflammatory cytokines include, but are not limited to, IFNγ, IL-12p70, IL-1α, IL-6, IL-8, MCP1, MIP1α, MIP1β, TNFα, and combinations thereof.

Other exemplary cytokines are known in the art and are described herein. Probiotic compositions containing anti-inflammatory bacteria reduce inflammation at the site of administration, e.g., in the gastrointestinal tract, as well as at distal sites throughout the body of the subject.

Other exemplary probiotic compositions useful for treatment of disorders associated with a dysbiosis distal to the gastrointestinal tract contain bacterial strains capable of altering the proportion of immune subpopulations, e.g., T cell subpopulations, in the subject.

For example, immunomodulatory bacteria can increase or decrease the proportion of Treg cells, Th17 cells, Th1 cells, or Th2 cells in a subject. The increase or decrease in the proportion of immune cell subpopulations may be systemic, or it may be localized to a site of action of the probiotic, e.g., in the gastrointestinal tract or at the site of a distal dysbiosis. In some embodiments, a probiotic composition comprising immunomodulatory bacteria is used for treatment of disorders associated with a dysbiosis distal to the gastrointestinal tract based on the desired effect of the probiotic composition on the differentiation and/or expansion of subpopulations of immune cells in the subject.

In one embodiment, a probiotic composition contains immunomodulatory bacteria that increase the proportion of Treg cells in a subject. In another embodiment, a probiotic composition contains immunomodulatory bacteria that decrease the proportion of Treg cells in a subject. In one embodiment, a probiotic composition contains immunomodulatory bacteria that increase the proportion of Th17 cells in a subject. In another embodiment, a probiotic composition contains immunomodulatory bacteria that decrease the proportion of Th17 cells in a subject. In one embodiment, a probiotic composition contains immunomodulatory bacteria that increase the proportion of Th1 cells in a subject. In another embodiment, a probiotic composition contains immunomodulatory bacteria that decrease the proportion of Th1 cells in a subject. In one embodiment, a probiotic composition contains immunomodulatory bacteria that increase the proportion of Th2 cells in a subject. In another embodiment, a probiotic composition contains immunomodulatory bacteria that decrease the proportion of Th2 cells in a subject.

In one embodiment, a probiotic composition contains immunomodulatory bacteria capable of modulating the proportion of one or more of Treg cells, Th17 cells, Th1 cells, and combinations thereof in a subject. Certain immune cell profiles may be particularly desirable to treat or prevent particular disorders associated with a dysbiosis. For example, treatment or prevention of autoimmune or inflammatory disorders can be promoted by increasing numbers of Treg cells and Th2 cells, and decreasing numbers of Th17 cells and Th1 cells. Accordingly, probiotic compositions for the treatment or prevention of autoimmune or inflammatory disorders may contain probiotics capable of promoting Treg cells and Th2 cells, and reducing Th17 and Th1 cells.

Short chain fatty acids (SCFAs) can have immunomodulatory (i.e., immunosuppressive) effects and therefore their production (i.e., biosynthesis or conversion by fermentation) is advantageous for the prevention, control, mitigation, and treatment of autoimmune and/or inflammatory disorders (Lara-Villoslada F. et al., 2006. Short-chain fructooligosaccharides, in spite of being fermented in the upper part of the large intestine, have anti-inflammatory activity in the TNBS model of colitis. Eur J Nutr. 45(7): 418-425). In germ-free mice and vancomycin-treated conventional mice, administration of SCFA (acetate, propionate, or butyrate) restored normal numbers of Tregs in the large intestine (Smith P M, et al. Science. 2013; 569-573). Short-chain fatty acids (SCFA) are produced by some bacteria as a byproduct of xylose fermentation. SCFA are one of the most abundant metabolites produced by the gut microbiome, particularly the family Clostridiacea, including members of the genus *Clostridium, Ruminococcus*, or *Blautia*. In some aspects, the pharmaceutical composition, dosage form, or kit comprises at least one type of microbe (e.g., one or more microbial species, such as a bacterial species, or more than one strain of a particular microbial species) and at least one type of prebiotic such that the composition, dosage form, or kit is capable of increasing the level of one or more immunomodulatory SCFA (e.g., acetate, propionate, butyrate, or valerate) in a mammalian subject. Optionally, the pharmaceutical composition, dosage form, or kit further comprises one or more substrates of one or more SCFA-producing fermentation and/or biosynthesis pathways. In certain embodiments, the administration of the composition, dosage form, or kit to a mammalian subject results in the increase of one or more SCFAs in the mammalian subject by approximately 1.5-fold, 2-fold, 5-fold, 10-fold, 20-fold, 50-fold, 100-fold, or greater than 100-fold. In some embodiments, the dysbiosis is caused by a deficiency in microbes that produce short chain fatty acids. Accordingly, in some embodiments, the probiotic composition can contain a species of bacteria that produce short chain fatty acids.

Aspects of this invention also include medium chain triglycerides (MCTs). MCTs passively diffuse from the GI tract to the portal system (longer fatty acids are absorbed into the lymphatic system) without requirement for modification like long-chain fatty acids or very-long-chain fatty acids. In addition, MCTs do not require bile salts for digestion. Patients who have malnutrition or malabsorption syndromes are treated with MCTs because they do not require energy for absorption, use, or storage. Medium-chain triglycerides are generally considered a good biologically inert source of energy that the human body finds reasonably easy to metabolize. They have potentially beneficial attributes in protein metabolism, but may be contraindicated in some situations due to their tendency to induce ketogenesis and metabolic acidosis. Due to their ability to be absorbed rapidly by the body, medium-chain triglycerides have found use in the treatment of a variety of malabsorption ailments. MCT supplementation with a low-fat diet has been described as the cornerstone of treatment for primary intestinal lymphangiectasia (Waldmann's disease). MCTs are an ingredient in parenteral nutritional emulsions. Accordingly, in some embodiments, the xylose compositions are capable of increasing the level of one or more medium chain triglycerides in a mammalian subject. In certain embodiments, the administration of the xylose composition to a mammalian subject results in the increase of one or more medium chain triglycerides in the mammalian subject by approximately 1.5-fold, 2-fold, 5-fold, 10-fold, 20-fold, 50-fold, 100-fold, or greater than 100-fold.

Distal disorders associated with loss of intestinal barrier function can be treated or improved by administration of probiotic compositions containing bacterial strains that produce short chain fatty acids (SCFAs), such as, for example, butyrate, acetate, propionate, or valerate, or combinations thereof. Distal disorders associated with loss of intestinal barrier function can be treated or improved by administration of probiotic compositions containing bacterial strains that reduce inflammation, as described herein.

In other embodiments, the distal dysbiosis is caused by a deficiency in microbes that produce lactic acid. Accordingly, in one embodiment, the probiotic composition can contain a species of bacteria that produce lactic acid.

Probiotic compositions for modulating a distal microbiome may optionally be administered in conjunction with a prebiotic. For example, a prebiotic can be selected which augments the growth of the anti-inflammatory bacterial population present in the probiotic composition. Exemplary prebiotics are provided in Table 7. Exemplary prebiotics which may augment the growth of exemplary bacterial species are provided in FIG. 29. In one embodiment, the prebiotic can be a monomer or polymer selected from the group consisting of arabinoxylan, xylose, soluble fiber dextran, soluble corn fiber, polydextrose, lactose, N-acetyl-lactosamine, glucose, or combinations thereof. In another embodiment, the prebiotic can be a monomer or polymer, such as galactose, fructose, rhamnose, mannose, uronic acids, 3'-fucosyllactose, 3' sialyllactose, 6'-sialyllactose, lacto-N-neotetraose, 2'-2'-fucosyllactose, or combinations thereof. In one embodiment, the prebiotic can include a monosaccharide selected from the group consisting of arabinose, fructose, fucose, lactose, galactose, glucose, mannose, D-xylose, xylitol, ribose, and combinations thereof. In another embodiment, the prebiotic can include a disaccharide selected from the group consisting of xylobiose, sucrose, maltose, lactose, lactulose, trehalose, cellobiose, or a combination thereof. In another embodiment, the prebiotic comprises a polysaccharide, for example, a xylooligosaccharide. Exemplary prebiotics include sugars such as arabinose, fructose, fucose, lactose, galactose, glucose, mannose, D-xylose, xylitol, ribose, xylobiose, sucrose, maltose, lactose, lactulose, trehalose, cellobiose, and xylooligosaccharide, or combinations thereof.

The foregoing probiotic compositions (and optional prebiotic compositions) can be used for treatment of the following disorders associated with dysbiosis of the microbiome at particular niches within the subject, or with disorders of the systemic microbiome.

X. Autoimmune/Inflammatory Diseases

Herein, we disclose probiotic microbial compositions, optionally comprising prebiotics, non-microbial immunomodulatory carbohydrates, or microbial immunomodulatory cell components, that are effective for the prevention or treatment of disorders associated with systemic inflammation and/or loss of intestinal barrier function, such as autoimmune or inflammatory disorders, e.g., graft-versus-host disease (GVHD), an inflammatory bowel disease (IBD) including but not limited to ulterative colitis and Crohn's disease, multiple sclerosis (MS), systemic lupus erythematosus (SLE), type I diabetes, rheumatoid arthritis, Sjögren's syndrome, and Celiac disease. In certain embodiments, the compositions comprise at least one type of microbe and at least one type of carbohydrate (a prebiotic), and optionally further comprising microbial immunomodulatory cell components or substrates for the production of immunomodulatory metabolites, that are effective for the prevention or treatment of an autoimmune or inflammatory disorder. We also disclose herein methods for the prevention and/or treatment of autoimmune and inflammatory diseases in human subjects.

Autoimmune and inflammatory diseases include, but are not limited to: Acute Disseminated Encephalomyelitis, Acute necrotizing hemorrhagic leukoencephalitis, Addison's disease, adhesive capsulitis, Agammaglobulinemia, Alopecia areata, Amyloidosis, Ankylosing spondylitis, Anti-GBM nephritis, Anti-TBM nephritis, Antiphospholipid syndrome, arthofibrosis, atrial fibrosis, autoimmune angioedema, autoimmune aplastic anemia, autoimmune dusautonomia, autoimmune hepatitis, autoimmune hyperlipidemia, autoimmune immunodeficiency, autoimmune inner ear disease, autoimmune myocarditis, autoimmune oophoritis, autoimmune pancreatitis, autoimmune retinopathy, autoimmune thrombocytopenic purpura, autoimmune thyroid disease, autoimmune urticaria, axonal and neuronal neuropathies, Balo disease, Behçet's disease, benign mucosal pemphigold, Bullous pemphigold, cardiomyopathy, Castleman disease, Celiac Disease, Chagas disease, chronic fatigue syndrome, chronic inflammatory demyelinating polyneuropathy, chronic Lyme disease, chronic recurrent multifocal osteomyelitis, Churg-Strauss syndrome, cicatricial pemphigold, cirrhosis, Cogans syndrome, cold agglutinin disease, congenital heart block, Coxsackle myocarditis, CREST disease, Crohn's disease, Cystic Fibrosis, essential mixed cryoglobulinemia, deficiency of the interleukin-1 receptor antagonist, demyelinating neuropathies, dermatitis herpetiformis, dermatomyosis, Devic's disease, discoid lupus, Dressler's syndrome, Dupuytren's contracture, endometriosis, endomyocardial fibrosis, eosinophilic esophagitis, eosinophilic facsciitis, erythema nodosum, experimental allergic encephalomyelitis, Evans syndrome, Familial Mediterranean Fever, fibromyalgia, fibrosing alveolitis, giant cell arteritis, giant cell myocarditis, glomerulonephritis, Goodpasture's syndrome, Graft-versus-host disease (GVHD), granulomatosus with polyanglitis, Graves' disease, Guillain-Bare syndrome, Hashimoto's encephalitis, Hashimoto's thyroiditis, hemolytic anemia, Henoch-Schonlein purpura, hepatitis, herpes gestationis, hypogammaglobulinemia, idiopathic thrombocytopenic purpura, IgA nephropathy, IgG4-related sclerosing disease, immunoregulatory lipoproteins, inclusion body myositis, inflammatory bowel disorders, interstitial cystitis, juvenile arthritis, juvenile myositis, Kawasaki syndrome, keloid, Lambert-Eaton syndrome, leukocytoclastic vasculitis, lichen planus, lichen sclerosus, ligneous conjunctivitis, linear IgA disease, mediastinal fibrosis, Meniere's disease, microscopic polyanglitis, mixed connective tissue disease, Mooren's ulcer, Mucha-Hamermann disease, Multiple Sclerosis (MS), Myasthenia gravis, myelofibrosis, Myositis, narcolepsy, Neonatal Onset Multisystem Inflammatory Disease, nephrogenic systemic fibrosis, neutropenia, nonalcoholic fatty liver disease, nonalcoholic steatohepatitis (NASH), ocular-cicatricial pemphigold, optic neuritis, palindromic rheumatism, Pediatric Autoimmune Neuropsychiatric Disorders Associated with *Streptococcus* (PANDAS), paraneoplastic cerebellar degeneration, paroxysmal nocturnal nemoglobinuria, Parry Romberg syndrome, Parsonnage-Turner syndrome, Pars planitis, Pemphigus, Peripheral neuropathy, perivenous encephalomyelitis, pernicious anemia, Peyronie's disease, POEMS syndrome, polyarteritis nodosa, progressive massive fibrosis, Tumor Necrosis Factor Receptor-assoicated Periodic Syndrome, Type I autoimmune polyglandular syndrome, Type II autoimmune polyglandular syndrome, Type III autoimmune polyglandular syndrome, polymyalgia rhematica, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynauds phenomenon, reactic arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjögren's syndrome, sperm and testicular autoimmunity, stiff person syndrome, subacute bacterial endocarditis, Susac's syndrome, sympathetic ophthalmia, systemic lupus erythematosus (SLE), Takayasu's arthritis, temporal arteritis, thrombocytopenic purpura, Tolosa-Hunt syndrome, transverse myelitis, Type 1 diabetes, ulcerative colitis, undifferentiated connective tissue disease, uveitis, vasculitis, vesiculobullous dermatosis, and Vitiligo.

In some aspects, the administered microbes and/or carbohydrates modulate the release of immune stimulatory cytokines. In preferred embodiments, the administered microbes and/or carbohydrates inhibit or reduce the release of immune stimulatory cytokines. Non-limiting examples of immune modulating cytokines and ligands include B lymphocyte chemoattractant ("BLC"), C—C motif chemokine 11 ("Eotaxin-1"), Eosinophil chemotactic protein 2 ("Eotaxin-2"), Granulocyte colony-stimulating factor ("G-CSF"), Granulocyte macrophage colony-stimulating factor ("GM-CSF"), 1-309, Intercellular Adhesion Molecule 1 ("ICAM-1"), Interferon gamma ("IFN-γ"), Interlukin-1 alpha ("IL-1α"), Interlukin-1β ("IL-1β"), Interleukin 1 receptor antagonist ("IL-1 ra"), Interleukin-2 ("IL-2"), Interleukin-4 ("IL-4"), Interleukin-5 ("IL-5"), Interleukin-6 ("IL-6"), Interleukin-6 soluble receptor ("IL-6 sR"), Interleukin-7 ("IL-7"), Interleukin-8 ("IL-8"), Interleukin-10 ("IL-10"), Interleukin-11 ("IL-11"), Subunit β of Interleukin-12 ("IL-12 p40" or "IL-12 p70"), Interleukin-13 ("IL-13"), Interleukin-15 ("IL-15"), Interleukin-16 ("IL-16"), Interleukin-17 ("IL-17"), Chemokine (C—C motif) Ligand 2 ("MCP-1"), Macrophage colony-stimulating factor ("M-CSF"), Monokine induced by gamma interferon ("MIG"), Chemokine (C—C motif) ligand 2 ("MIP-1 alpha"), Chemokine (C—C motif) ligand 4 ("MIP-1β"), Macrophage inflammatory protein-1-δ ("MIP-1δ"), Platelet-derived growth factor subunit B ("PDGF-BB"), Chemokine (C—C motif) ligand 5, Regulated on Activation, Normal T cell Expressed and Secreted ("RANTES"), TIMP metallopeptidase inhibitor 1 ("TIMP-1"), TIMP metallopeptidase inhibitor 2 ("TIMP-2"), Tumor necrosis factor, lymphotoxin-α ("TNF-α"), Tumor necrosis factor, lymphotoxin-β ("TNF β"), Soluble TNF receptor type 1 ("sTNFRI"), sTNFRIIAR, Brain-derived neurotrophic factor ("BDNF"), Basic fibroblast growth factor ("bFGF"), Bone morphogenetic protein 4 ("BMP-4"), Bone morphogenetic protein 5 ("BMP-5"), Bone morphogenetic protein 7 ("BMP-7"), Nerve growth factor ("b-NGF"), Epidermal growth factor ("EGF"), Epidermal growth factor receptor ("EGFR"), Endocrine-gland-derived vascular endothelial growth factor ("EG-VEGF"), Fibroblast growth factor 4 ("FGF-4"), Keratinocyte growth factor ("FGF-7"), Growth differentiation factor 15 ("GDF-15"), Glial cell-derived neurotrophic factor ("GDNF"), Growth Hormone, Heparin-binding EGF-like growth factor ("HB-EGF"), Hepatocyte growth factor ("HGF"), Insulin-like growth factor binding protein 1 ("IGFBP-1"), Insulin-like growth factor binding protein 2 ("IGFBP-2"), Insulin-like growth factor binding protein 3 ("IGFBP-3"), Insulin-like growth factor binding protein 4 ("IGFBP-4"), Insulin-like growth factor binding protein 6 ("IGFBP-6"), Insulin-like growth factor 1 ("IGF-1"), Insulin, Macrophage colony-stimulating factor ("M-CSF R"), Nerve growth factor receptor ("NGF R"), Neurotrophin-3 ("NT-3"), Neurotrophin-4 ("NT-4"), Osteoclastogenesis inhibitory factor ("Osteoprotegerin"), Platelet-derived growth factor receptors ("PDGF-AA"), Phosphatidylinositol-glycan biosynthesis ("PIGF"), Skp, Cullin, F-box containing comples ("SCF"), Stem cell factor receptor ("SCF R"), Transforming growth factor α ("TGF-α"), Transforming growth factor β-1 ("TGF β1"), Transforming growth factor β-3 ("TGF β3"), Vascular endothelial growth factor ("VEGF"), Vascular endothelial growth factor receptor 2 ("VEGFR2"), Vascular endothelial growth factor receptor 3 ("VEGFR3"), VEGF-D 6Ckine, Tyrosine-protein kinase receptor UFO ("Axl"), Betacellulin ("BTC"), Mucosae-associated epithelial chemokine ("CCL28"), Chemokine (C—C motif) ligand 27 ("CTACK"), Chemokine (C—X—C motif) ligand 16 ("CXCL16"), C—X—C motif chemokine 5 ("ENA-78"), Chemokine (C—C motif) ligand 26 ("Eotaxin-3"), Granulocyte chemotactic protein 2 ("GCP-2"), GRO, Chemokine (C—C motif) ligand 14 ("HCC-1"), Chemokine (C—C motif) ligand 16 ("HCC-4"), Interleukin-9 ("IL-9"), Interleukin-17 F ("IL-17F"), Interleukin-18-binding protein ("IL-18 BPa"), Interleukin-28 A ("IL-28A"), Interleukin 29 ("IL-29"), Interleukin 31 ("IL-31"), C—X—C motif chemokine 10 ("IP-10"), Chemokine receptor CXCR3 ("I-TAC"), Leukemia inhibitory factor ("LIF"), Light, Chemokine (C motif) ligand ("Lymphotactin"), Monocyte chemoattractant protein 2 ("MCP-2"), Monocyte chemoattractant protein 3 ("MCP-3"), Monocyte chemoattractant protein 4 ("MCP-4"), Macrophage-derived chemokine ("MDC"), Macrophage migration inhibitory factor ("MIF"), Chemokine (C—C motif) ligand 20 ("MIP-3 α"), C—C motif chemokine 19 ("MIP-3 β"), Chemokine (C—C motif) ligand 23 ("MPIF-1"), Macrophage stimulating protein alpha chain ("MSP-α"), Nucleosome assembly protein 1-like 4 ("NAP-2"), Secreted phosphoprotein 1 ("Osteopontin"), Pulmonary and activation-regulated cytokine ("PARC"), Platelet factor 4 ("PF4"), Stroma cell-derived factor-1 α ("SDF-1 α"), Chemokine (C—C motif) ligand 17 ("TARC"), Thymus-expressed chemokine ("TECK"), Thymic stromal lymphopoietin ("TSLP 4-IBB"), CD 166 antigen ("ALCAM"), Cluster of Differentiation 80 ("B7-1"), Tumor necrosis factor receptor superfamily member 17 ("BCMA"), Cluster of Differentiation 14 ("CD14"), Cluster of Differentiation 30 ("CD30"), Cluster of Differentiation 40 ("CD40 Ligand"), Carcinoembryonic antigen-related cell adhesion molecule 1 (biliary glycoprotein) ("CEACAM-1"), Death Receptor 6 ("DR6"), Deoxythymidine kinase ("Dtk"), Type 1 membrane glycoprotein ("Endoglin"), Receptor tyrosine-protein kinase erbB-3 ("ErbB3"), Endothelial-leukocyte adhesion molecule 1 ("E-Selectin"), Apoptosis antigen 1 ("Fas"), Fms-like tyrosine kinase 3 ("Flt-3L"), Tumor necrosis factor receptor superfamily member 1 ("GITR"), Tumor necrosis factor receptor superfamily member 14 ("HVEM"), Intercellular adhesion molecule 3 ("ICAM-3"), IL-1 R4, IL-1 RI, IL-10 Rβ, IL-17R, IL-2Rγ, IL-21R, Lysosome membrane protein 2 ("LIMPII"), Neutrophil gelatinase-associated lipocalin ("Lipocalin-2"), CD62L ("L-Selectin"), Lymphatic endothelium ("LYVE-1"), MHC class I polypeptide-related sequence A ("MICA"), MHC class I polypeptide-related sequence B ("MICB"), NRG1-β1, Beta-type platelet-derived growth factor receptor ("PDGF Rβ"), Platelet endothelial cell adhesion molecule ("PECAM-1"), RAGE, Hepatitis A virus cellular receptor 1 ("TIM-1"), Tumor necrosis factor receptor superfamily member IOC ("TRAIL R3"), Trappin protein transglutaminase binding domain ("Trappin-2"), Urokinase receptor ("uPAR"), Vascular cell adhesion protein 1 ("VCAM-1"), XEDARActivin A, Agouti-related protein ("AgRP"), Ribonuclease 5 ("Angiogenin"), Angiopoietin 1, Angiostatin, Catheprin S, CD40, Cryptic family protein IB ("Cripto-1"), DAN, Dickkopf-related protein 1 ("DKK-1"), E-Cadherin, Epithelial cell adhesion molecule ("EpCAM"), Fas Ligand (FasL or CD95L), Fcg RIIB/C, FoUistatin, Galectin-7, Intercellular adhesion molecule 2 ("ICAM-2"), IL-13 R1, IL-13R2, IL-17B, IL-2 Ra, IL-2 Rb, IL-23, LAP, Neuronal cell adhesion molecule ("NrCAM"), Plasminogen activator inhibitor-1 ("PAI-1"), Platelet derived growth factor receptors ("PDGF-AB"), Resistin, stromal cell-derived factor 1 ("SDF-1 β"), sgp130, Secreted frizzled-related protein 2 ("ShhN"), Sialic acid-binding immunoglobulin-type lectins ("Siglec-5"), ST2, Transforming growth factor-β 2 ("TGF β 2"), Tie-2, Thrombopoietin ("TPO"), Tumor necrosis factor receptor superfamily member 10D ("TRAIL R4"), Triggering receptor expressed on myeloid cells 1 ("TREM-1"), Vascular endothelial growth factor C ("VEGF-C"), VEGFR1Adiponectin, Adipsin ("AND"), α-fetoprotein ("AFP"), Angiopoietin-like 4 ("ANGPTL4"), β-2-microglobulin ("B2M"), Basal cell adhesion molecule ("BCAM"), Carbohydrate antigen 125 ("CA125"), Cancer Antigen 15-3 ("CA15-3"), Carcinoembryonic antigen ("CEA"), cAMP receptor protein ("CRP"), Human Epidermal Growth Factor Receptor 2 ("ErbB2"), Follistatin, Follicle-stimulating hormone ("FSH"), Chemokine (C—X—C motif) ligand 1 ("GRO α"), human chorionic gonadotropin ("β HCG"), Insulin-like growth factor 1 receptor ("IGF-1 sR"), IL-1 sRII, IL-3, IL-18 Rb, IL-21, Leptin, Matrix metalloproteinase-1 ("MMP-1"), Matrix metalloproteinase-2 ("MMP-2"), Matrix metalloproteinase-3 ("MMP-3"), Matrix metalloproteinase-8 ("MMP-8"), Matrix metalloproteinase-9 ("MMP-9"), Matrix metalloproteinase-10 ("MMP-10"), Matrix metalloproteinase-13 ("MMP-13"), Neural Cell Adhesion Molecule ("NCAM-1"), Entactin ("Nidogen-1"), Neuron specific enolase ("NSE"), Oncostatin M ("OSM"), Procalcitonin, Prolactin, Prostate specific antigen ("PSA"), Sialic acid-binding Ig-like lectin 9 ("Siglec-9"), ADAM 17 endopeptidase ("TACE"), Thyroglobulin, Metalloproteinase inhibitor 4 ("TIMP-4"), TSH2B4, Disintegrin and metalloproteinase domain-containing protein 9 ("ADAM-9"), Angiopoietin 2, Tumor necrosis factor ligand superfamily member 13/Acidic leucine-rich nuclear phosphoprotein 32 family member B ("APRIL"), Bone morphogenetic protein 2 ("BMP-2"), Bone morphogenetic protein 9 ("BMP-9"), Complement component 5a ("C5a"), Cathepsin L, CD200, CD97, Chemerin, Tumor necrosis factor receptor superfamily member 6B ("DcR3"), Fatty acid-binding protein 2 ("FABP2"), Fibroblast activation protein, alpha ("FAP"), Fibroblast growth factor 19 ("FGF-19"), Galectin-3, Hepatocyte growth factor receptor ("HGF R"), IFN-γα/β R2, Insulin-like growth factor 2 ("IGF-2"), Insulin-like growth factor 2 receptor ("IGF-2 R"), Interleukin-1 receptor 6 ("IL-1R6"), Interleukin 24 ("IL-24"), Interleukin 33 ("IL-33", Kallikrein 14, Asparaginyl endopeptidase ("Legumain"), Oxidized low-density lipoprotein receptor 1 ("LOX-1"), Mannose-binding lectin ("MBL"), Neprilysin ("NEP"), Notch homolog 1, translocation-associated (Drosophila) ("Notch-1"), Nephroblastoma overexpressed ("NOV"), Osteoactivin, Programmed cell death protein 1 ("PD-1"), N-acetylmuramoyl-L-alanine amidase ("PGRP-5"), Serpin A4, Secreted frizzled related protein 3 ("sFRP-3"), Thrombomodulin, Toll-like receptor 2 ("TLR2"), Tumor necrosis factor receptor superfamily member 10A ("TRAIL R1"), Transferrin ("TRF"), WIF-1ACE-2, Albumin, AMICA, Angiopoietin 4, B-cell activating factor ("BAFF"), Carbohydrate antigen 19-9 ("CA19-9"), CD 163, Clusterin, CRT AM, Chemokine (C—X—C motif) ligand 14 ("CXCL14"), Cystatin C, Decorin ("DCN"), Dickkopf-related protein 3 ("Dkk-3"), Delta-like protein 1 ("DLL1"), Fetuin A, Heparin-binding growth factor 1 ("aFGF"), Folate receptor a ("FOLR1"), Furin, GPCR-associated sorting protein 1 ("GASP-1"), GPCR-associated sorting protein 2 ("GASP-2"), Granulocyte colony-stimulating factor receptor ("GCSF R"), Serine protease hepsin ("HAI-2"), Interleukin-17B Receptor ("IL-17B R"), Interleukin 27 ("IL-27"), Lymphocyte-activation gene 3 ("LAG-3"), Apolipoprotein A-V ("LDL R"), Pepsinogen I, Retinol binding protein 4 ("RBP4"), SOST, Heparan sulfate proteoglycan ("Syndecan-1"), Tumor necrosis factor receptor superfamily member 13B ("TACI"), Tissue factor pathway inhibitor ("TFPI"), TSP-1, Tumor necrosis factor receptor superfamily, member 10b ("TRAIL R2"), TRANCE, Troponin I, Urokinase Plasminogen Activator ("uPA"), Cadherin 5, type 2 or VE-cadherin (vascular endothelial) also known as CD144 ("VE-Cadherin"), WNT1-inducible-signaling pathway protein 1 ("WISP-1"), and Receptor Activator of Nuclear Factor κ B ("RANK").

Exemplary probiotic compositions useful for treatment or prevention of autoimmune or inflammatory disorders contain bacterial strains capable of reducing inflammation in a subject. Such immunomodulatory (anti-inflammatory) bacteria can modulate cytokine expression by host immune cells, resulting in an overall increase in secretion of anti-inflammatory cytokines and/or an overall decrease in secretion of pro-inflammatory cytokines, systemically reducing inflammation in the subject. In exemplary embodiments, probiotic compositions useful for treatment of immune or inflammatory disorders stimulate secretion of one or more anti-inflammatory cytokines by host immune cells, such as PBMCs. Anti-inflammatory cytokines include, but are not limited to, IL-10, IL-13, IL-9, IL-4, IL-5, TGFβ and combinations thereof. In other exemplary embodiments, probiotic compositions useful for treatment of autoimmune or inflammatory disorders inhibit secretion of one or more pro-inflammatory cytokines by host immune cells, such as PBMCs. Pro-inflammatory cytokines include, but are not limited to, IFNγ, IL-12p70, IL-1α, IL-6, IL-8, MCP1, MIP1α, MIP1β, TNFα, and combinations thereof. Other exemplary cytokines are known in the art and are described herein. Probiotic compositions containing anti-inflammatory bacteria reduce inflammation at the site of administration, e.g., in the gastrointestinal tract, as well as at distal sites throughout the body of the subject.

Other exemplary probiotic compositions useful for treatment of autoimmune or inflammatory disorders contain bacterial strains capable of altering the proportion of immune subpopulations, e.g., T cell subpopulations, in the subject.

For example, immunomodulatory bacteria can increase or decrease the proportion of Treg cells, Th17 cells, Th1 cells, or Th2 cells in a subject. The increase or decrease in the proportion of immune cell subpopulations may be systemic, or it may be localized to a site of action of the probiotic, e.g., in the gastrointestinal tract or at the site of a distal dysbiosis. In some embodiments, a probiotic composition comprising immunomodulatory bacteria is used for treatment of an autoimmune or inflammatory disorder based on the desired effect of the probiotic composition on the differentiation and/or expansion of subpopulations of immune cells in the subject.

In one embodiment, a probiotic composition contains immunomodulatory bacteria that increase the proportion of Treg cells in a subject. In another embodiment, a probiotic composition contains immunomodulatory bacteria that decrease the proportion of Treg cells in a subject. In one embodiment, a probiotic composition contains immunomodulatory bacteria that increase the proportion of Th17 cells in a subject. In another embodiment, a probiotic composition contains immunomodulatory bacteria that decrease the proportion of Th17 cells in a subject. In one embodiment, a probiotic composition contains immunomodulatory bacteria that increase the proportion of Th1 cells in a subject. In another embodiment, a probiotic composition contains immunomodulatory bacteria that decrease the proportion of Th1 cells in a subject. In one embodiment, a probiotic composition contains immunomodulatory bacteria that increase the proportion of Th2 cells in a subject. In another embodiment, a probiotic composition contains immunomodulatory bacteria that decrease the proportion of Th2 cells in a subject.

In one embodiment, a probiotic composition contains immunomodulatory bacteria capable of modulating the proportion of one or more of Treg cells, Th17 cells, Th1 cells, and combinations thereof in a subject. Certain immune cell profiles may be particularly desirable to treat or prevent autoimmune or inflammatory disorders. For example, in some embodiments, treatment or prevention of autoimmune or inflammatory disorders can be promoted by increasing numbers of Treg cells and Th2 cells, and decreasing numbers of Th17 cells and Th1 cells. Accordingly, probiotic compositions for the treatment or prevention of autoimmune or inflammatory disorders may contain probiotics capable of promoting Treg cells and Th2 cells, and reducing Th17 and Th1 cells.

Probiotic compositions useful for treating or preventing the autoimmune or inflammatory disorders described herein include, in exemplary embodiments, one or more bacterial strains from Table 1. In other embodiments, the probiotic composition includes one or more bacterial strains from Table 1A. In other embodiments, the probiotic composition includes one or more bacterial strains from Table 1B. In other embodiments, the probiotic composition includes one or more bacterial strains from Table 1C. In other embodiments, the probiotic composition includes one or more bacterial strains from Table 1D. In other embodiments, the probiotic composition includes one or more bacterial strains from Table 1E. In other embodiments, the probiotic composition includes one or more bacterial strains from Table 1F. In some embodiments, the probiotic composition contains a single strain of bacteria. In other embodiments, the probiotic composition contains two or more strains of bacteria, e.g., 2, 3, 4, 5, 6, 7, 8, 9, 10, 15, 20, 30, 40, 50, 60, 70, 80, 90, 100, 500, 1000 or more strains of bacteria. In other embodiments, the probiotic composition contains or is administered in conjunction with a prebiotic, as described herein.

Preferred bacterial genera include *Acetanaerobacterium, Acetivibrio, Alicyclobacillus, Alkaliphilus, Anaerofustis, Anaerosporobacter, Anaerostipes, Anaerotruncus, Anoxybacillus, Bacillus, Bacteroides, Blautia, Brachyspira, Brevibacillus, Bryantella, Bulleidia, Butyricicoccus, Butyrivibrio, Catenibacterium, Chlamydiales, Clostridiaceae, Clostridiales, Clostridium, Collinsella, Coprobacillus, Coprococcus, Coxiella, Deferribacteres, Desulfitobacterium, Desulfotomaculum, Dorea, Eggerthella, Erysipelothrix, Erysipelotrichaceae, Ethanoligenens, Eubacterium, Faecalibacterium, Filifactor, Flavonifractor, Flexistipes, Fulvimonas, Fusobacterium, Gemmiger, Geobacillus, Gloeobacter, Holdemania, Hydrogenoanaerobacterium, Kocuria, Lachnobacterium, Lachnospira, Lachnospiraceae, Lactobacillus, Lactonifactor, Leptospira, Lutispora, Lysinibacillus, Mollicutes, Moorella, Nocardia, Oscillibacter, Oscillospira, Paenibacillus, Papillibacter, Pseudoflavonifractor, Robinsoniella, Roseburia, Ruminococcaceae, Ruminococcus, Saccharomonospora, Sarcina, Solobacterium, Sporobacter, Sporolactobacillus, Streptomyces, Subdoligranulum, Sutterella, Syntrophococcus, Thermoanaerobacter, Thermobifida,* and *Turicibacter.*

Preferred bacterial genera also include *Acetonema, Alkaliphilus, Amphibacillus, Ammonifex, Anaerobacter, Caldicellulosiruptor, Caloramator, Candidatus, Carboxydibrachium, Carboxydothermus, Cohnella, Dendrosporobacter Desulfitobacterium, Desulfosporosinus, Halobacteroides, Heliobacterium, Heliophilum, Heliorestis, Lachnoanaerobaculum, Lysinibacillus, Oceanobacillus, Orenia (S.), Oxalophagus, Oxobacter, Pelospora, Pelotomaculum, Propionispora, Sporohalobacter, Sporomusa, Sporosarcina, Sporotomaculum, Symbiobacterium, Syntrophobotulus, Syntrophospora, Terribacillus, Thermoanaerobacter,* and *Thermosinus.*

As provided herein, therapeutic compositions comprise, or in the alternative, modulate, the colonization and/or engraftment, of the following exemplary bacterial entities: *Lactobacillus gasseri, Lactobacillus fermentum, Lactobacillus reuteri, Enterococcus faecalis, Enterococcus durans, Enterococcus villorum, Lactobacillus plantarum, Pediococcus acidilactici, Staphylococcus pasteuri, Staphylococcus cohnii, Streptococcus sanguinis, Streptococcus sinensis, Streptococcus mitis, Streptococcus* sp. SCA22, *Streptococcus* sp. CR-3145, *Streptococcus anginosus, Streptococcus mutans, Coprobacillus cateniformis, Clostridium saccharogumia, Eubacterium dolichum* DSM 3991, *Clostridium* sp. PPf35E6, *Clostridium sordelli* ATCC 9714, *Ruminococcus torques, Ruminococcus gnavus, Clostridium clostridioforme, Ruminococcus obeum, Blautia producta, Clostridium* sp. *ID5, Megasphaera micronuciformis, Veillonella parvula, Clostridium methylpentosum, Clostridium islandicum, Faecalibacterium prausnitzii, Bacteroides uniformmis, Bacteroides thetaiotaomicron, Bacteroides acidifaciens, Bacteroides ovatus, Bacteroides fragilis, Parabacteroides distasonis, Propinionibacteirum propionicum, Actinomycs hyovaginalis, Rothia mucilaginosa, Rothia aeria, Bifidobacterium breve, Scardovia inopinata* and *Eggerthella lenta.*

Preferred bacterial species are provided in Table 1, Table 1A, Table 1B, Table 1C, Table 1D, Table 1E, Table 1F, and Table 5. Optionally, in some embodiments, preferred bacterial species are spore formers. Where specific strains of a species are provided, one of skill in the art will recognize that other strains of the species can be substituted for the named strain.

In one embodiment, the bacterial entity, e.g., species or strain, useful in the compositions and methods of the invention is *Acidaminococcus intestine.* In one embodiment, the bacterial entity, e.g., species or strain, useful in the compositions and methods of the invention is *Acinetobacter baumannii.* In one embodiment, the bacterial entity, e.g., species or strain, useful in the compositions and methods of the invention is *Acinetobacter lwoffii.* In one embodiment, the bacterial entity, e.g., species or strain, useful in the compositions and methods of the invention is *Akkermansia muciniphila.* In one embodiment, the bacterial entity, e.g., species or strain, useful in the compositions and methods of the invention is *Alistipes putredinis.* In one embodiment, the bacterial entity, e.g., species or strain, useful in the compositions and methods of the invention is *Alistipes shahii.* In one embodiment, the bacterial entity, e.g., species or strain, useful in the compositions and methods of the invention is *Anaerostipes hadrus.* In one embodiment, the bacterial entity, e.g., species or strain, useful in the compositions and methods of the invention is *Anaerotruncus colihominis.* In one embodiment, the bacterial entity, e.g., species or strain, useful in the compositions and methods of the invention is *Bacteroides caccae.* In one embodiment, the bacterial entity, e.g., species or strain, useful in the compositions and methods of the invention is *Bacteroides cellulosilyticus.* In one embodiment, the bacterial entity, e.g., species or strain, useful in the compositions and methods of the invention is *Bacteroides dorei*. In one embodiment, the bacterial entity, e.g., species or strain, useful in the compositions and methods of the invention is *Bacteroides eggerthii*. In one embodiment, the bacterial entity, e.g., species or strain, useful in the compositions and methods of the invention is *Bacteroides finegoldii*. In one embodiment, the bacterial entity, e.g., species or strain, useful in the compositions and methods of the invention is *Bacteroides fragilis*. In one embodiment, the bacterial entity, e.g., species or strain, useful in the compositions and methods of the invention is *Bacteroides massiliensis*. In one embodiment, the bacterial entity, e.g., species or strain, useful in the compositions and methods of the invention is *Bacteroides ovatus*. In one embodiment, the bacterial entity, e.g., species or strain, useful in the compositions and methods of the invention is *Bacteroides salanitronis*. In one embodiment, the bacterial entity, e.g., species or strain, useful in the compositions and methods of the invention is *Bacteroides salyersiae*. In one embodiment, the bacterial entity, e.g., species or strain, useful in the compositions and methods of the invention is *Bacteroides* sp. 1_1_6. In one embodiment, the bacterial entity, e.g., species or strain, useful in the compositions and methods of the invention is *Bacteroides* sp. 3_1_23. In one embodiment, the bacterial entity, e.g., species or strain, useful in the compositions and methods of the invention is *Bacteroides* sp. D20. In one embodiment, the bacterial entity, e.g., species or strain, useful in the compositions and methods of the invention is *Bacteroides thetaiotaomicrond*. In one embodiment, the bacterial entity, e.g., species or strain, useful in the compositions and methods of the invention is *Bacteroides uniformis*. In one embodiment, the bacterial entity, e.g., species or strain, useful in the compositions and methods of the invention is *Bacteroides vulgatus*. In one embodiment, the bacterial entity, e.g., species or strain, useful in the compositions and methods of the invention is *Bifidobacterium adolescentis*. In one embodiment, the bacterial entity, e.g., species or strain, useful in the compositions and methods of the invention is *Bifidobacterium bifidum*. In one embodiment, the bacterial entity, e.g., species or strain, useful in the compositions and methods of the invention is *Bifidobacterium breve*. In one embodiment, the bacterial entity, e.g., species or strain, useful in the compositions and methods of the invention is *Bifidobacterium faecale*. In one embodiment, the bacterial entity, e.g., species or strain, useful in the compositions and methods of the invention is *Bifidobacterium kashiwanohense*. In one embodiment, the bacterial entity, e.g., species or strain, useful in the compositions and methods of the invention is *Bifidobacterium longum* subsp. *Longum*. In one embodiment, the bacterial entity, e.g., species or strain, useful in the compositions and methods of the invention is *Bifidobacterium pseudocatenulatum*. In one embodiment, the bacterial entity, e.g., species or strain, useful in the compositions and methods of the invention is *Bifidobacterium stercoris*. In one embodiment, the bacterial entity, e.g., species or strain, useful in the compositions and methods of the invention is *Blautia (Ruminococcus) coccoides*. In one embodiment, the bacterial entity, e.g., species or strain, useful in the compositions and methods of the invention is *Blautia faecis*. In one embodiment, the bacterial entity, e.g., species or strain, useful in the compositions and methods of the invention is *Blautia glucerasea*. In one embodiment, the bacterial entity, e.g., species or strain, useful in the compositions and methods of the invention is *Blautia (Ruminococcus) hansenii*. In one embodiment, the bacterial entity, e.g., species or strain, useful in the compositions and methods of the invention is *Blautia hydrogenotrophica (Ruminococcus hydrogenotrophicus)*. In one embodiment, the bacterial entity, e.g., species or strain, useful in the compositions and methods of the invention is *Blautia (Ruminococcus) luti*. In one embodiment, the bacterial entity, e.g., species or strain, useful in the compositions and methods of the invention is *Blautia (Ruminococcus) obeum*. In one embodiment, the bacterial entity, e.g., species or strain, useful in the compositions and methods of the invention is *Blautia producta (Ruminococcus productus)*. In one embodiment, the bacterial entity, e.g., species or strain, useful in the compositions and methods of the invention is *Blautia (Ruminococcus) schinkii*. In one embodiment, the bacterial entity, e.g., species or strain, useful in the compositions and methods of the invention is *Blautia stercoris*. In one embodiment, the bacterial entity, e.g., species or strain, useful in the compositions and methods of the invention is *Blautia* uncultured bacterium clone BKLE_a03_2 (GenBank: EU469501.1). In one embodiment, the bacterial entity, e.g., species or strain, useful in the compositions and methods of the invention is *Blautia* uncultured bacterium clone SJTU_B_14_30 (GenBank: EF402926.1). In one embodiment, the bacterial entity, e.g., species or strain, useful in the compositions and methods of the invention is *Blautia* uncultured bacterium clone SJTU_C_14_16 (GenBank: EF404657.1). In one embodiment, the bacterial entity, e.g., species or strain, useful in the compositions and methods of the invention is *Blautia* uncultured bacterium clone S1-5 (GenBank: GQ898099.1). In one embodiment, the bacterial entity, e.g., species or strain, useful in the compositions and methods of the invention is *Blautia* uncultured PAC000178_s (www.ezbiocloud.net/ez-taxon/hierarchy?m=browse&k=PAC000178&d=2). In one embodiment, the bacterial entity, e.g., species or strain, useful in the compositions and methods of the invention is *Blautia wexlerae*. In one embodiment, the bacterial entity, e.g., species or strain, useful in the compositions and methods of the invention is *Candidatus Arthromitus* sp. SFB-mouse-Yit. In one embodiment, the bacterial entity, e.g., species or strain, useful in the compositions and methods of the invention is *Catenibacterium mitsuokai*. In one embodiment, the bacterial entity, e.g., species or strain, useful in the compositions and methods of the invention is Clostridiaceae bacterium (*Dielma fastidiosa*) JC13. In one embodiment, the bacterial entity, e.g., species or strain, useful in the compositions and methods of the invention is Clostridiales bacterium 1_7_47FAA. In one embodiment, the bacterial entity, e.g., species or strain, useful in the compositions and methods of the invention is *Clostridium asparagiforme*. In one embodiment, the bacterial entity, e.g., species or strain, useful in the compositions and methods of the invention is *Clostridium bolteae*. In one embodiment, the bacterial entity, e.g., species or strain, useful in the compositions and methods of the invention is *Clostridium clostridioforme*. In one embodiment, the bacterial entity, e.g., species or strain, useful in the compositions and methods of the invention is *Clostridium glycyrrhizinilyticum*. In one embodiment, the bacterial entity, e.g., species or strain, useful in the compositions and methods of the invention is *Clostridium (Hungatella) hathewayi*. In one embodiment, the bacterial entity, e.g., species or strain, useful in the compositions and methods of the invention is *Clostridium histolyticum*. In one embodiment, the bacterial entity, e.g., species or strain, useful in the compositions and methods of the invention is *Clostridium indolis*. In one embodiment, the bacterial entity, e.g., species or strain, useful in the compositions and methods of the invention is *Clostridium leptum*. In one embodiment, the bacterial entity, e.g., species or strain, useful in the compositions and methods of the invention is *Clostridium (Tyzzerella) nexile*. In one embodiment, the bacterial entity, e.g., species or strain, useful in the compositions and methods of the invention is *Clostridium perfringens*. In one embodiment, the bacterial entity, e.g., species or strain, useful in the compositions and methods of the invention is *Clostridium (Erysipelatoclostridium) ramosum*. In one embodiment, the bacterial entity, e.g., species or strain, useful in the compositions and methods of the invention is *Clostridium scindens*. In one embodiment, the bacterial entity, e.g., species or strain, useful in the compositions and methods of the invention is *Clostridium septum*. In one embodiment, the bacterial entity, e.g., species or strain, useful in the compositions and methods of the invention is *Clostridium* sp. 14774. In one embodiment, the bacterial entity, e.g., species or strain, useful in the compositions and methods of the invention is *Clostridium* sp. 7_3_54FAA. In one embodiment, the bacterial entity, e.g., species or strain, useful in the compositions and methods of the invention is *Clostridium* sp. HGF2. In one embodiment, the bacterial entity, e.g., species or strain, useful in the compositions and methods of the invention is *Clostridium symbiosum*. In one embodiment, the bacterial entity, e.g., species or strain, useful in the compositions and methods of the invention is *Collinsella aerofaciens*. In one embodiment, the bacterial entity, e.g., species or strain, useful in the compositions and methods of the invention is *Collinsella intestinalis*. In one embodiment, the bacterial entity, e.g., species or strain, useful in the compositions and methods of the invention is *Coprobacillus* sp. D7. In one embodiment, the bacterial entity, e.g., species or strain, useful in the compositions and methods of the invention is *Coprococcus catus*. In one embodiment, the bacterial entity, e.g., species or strain, useful in the compositions and methods of the invention is *Coprococcus comes*. In one embodiment, the bacterial entity, e.g., species or strain, useful in the compositions and methods of the invention is *Dorea formicigenerans*. In one embodiment, the bacterial entity, e.g., species or strain, useful in the compositions and methods of the invention is *Dorea longicatena*. In one embodiment, the bacterial entity, e.g., species or strain, useful in the compositions and methods of the invention is *Enterococcus faecalis*. In one embodiment, the bacterial entity, e.g., species or strain, useful in the compositions and methods of the invention is *Enterococcus faecium*. In one embodiment, the bacterial entity, e.g., species or strain, useful in the compositions and methods of the invention is Erysipelotrichaceae bacterium 3_1_53. In one embodiment, the bacterial entity, e.g., species or strain, useful in the compositions and methods of the invention is *Escherichia coli*. In one embodiment, the bacterial entity, e.g., species or strain, useful in the compositions and methods of the invention is *Escherichia coli* S88. In one embodiment, the bacterial entity, e.g., species or strain, useful in the compositions and methods of the invention is *Eubacterium eligens*. In one embodiment, the bacterial entity, e.g., species or strain, useful in the compositions and methods of the invention is *Eubacterium fissicatena*. In one embodiment, the bacterial entity, e.g., species or strain, useful in the compositions and methods of the invention is *Eubacterium ramulus*. In one embodiment, the bacterial entity, e.g., species or strain, useful in the compositions and methods of the invention is *Eubacterium rectale*. In one embodiment, the bacterial entity, e.g., species or strain, useful in the compositions and methods of the invention is *Faecalibacterium prausnitzii*. In one embodiment, the bacterial entity, e.g., species or strain, useful in the compositions and methods of the invention is *Flavonifractor plautii*. In one embodiment, the bacterial entity, e.g., species or strain, useful in the compositions and methods of the invention is *Fusobacterium mortiferum*. In one embodiment, the bacterial entity, e.g., species or strain, useful in the compositions and methods of the invention is *Fusobacterium nucleatum*. In one embodiment, the bacterial entity, e.g., species or strain, useful in the compositions and methods of the invention is *Holdemania filiformis*. In one embodiment, the bacterial entity, e.g., species or strain, useful in the compositions and methods of the invention is *Hydrogenoanaerobacterium saccharovorans*. In one embodiment, the bacterial entity, e.g., species or strain, useful in the compositions and methods of the invention is *Klebsiella oxytoca*. In one embodiment, the bacterial entity, e.g., species or strain, useful in the compositions and methods of the invention is Lachnospiraceae bacterium 3_1_7FAA_CT1. In one embodiment, the bacterial entity, e.g., species or strain, useful in the compositions and methods of the invention is Lachnospiraceae bacterium 7_1_58FAA. In one embodiment, the bacterial entity, e.g., species or strain, useful in the compositions and methods of the invention is Lachnospiraceae bacterium 5_1_57FAA. In one embodiment, the bacterial entity, e.g., species or strain, useful in the compositions and methods of the invention is *Lactobacillus casei*. In one embodiment, the bacterial entity, e.g., species or strain, useful in the compositions and methods of the invention is *Lactobacillus rhamnosus*. In one embodiment, the bacterial entity, e.g., species or strain, useful in the compositions and methods of the invention is *Lactobacillus ruminis*. In one embodiment, the bacterial entity, e.g., species or strain, useful in the compositions and methods of the invention is *Lactococcus casei*. In one embodiment, the bacterial entity, e.g., species or strain, useful in the compositions and methods of the invention is *Odoribacter splanchnicus*. In one embodiment, the bacterial entity, e.g., species or strain, useful in the compositions and methods of the invention is *Oscillibacter valericigenes*. In one embodiment, the bacterial entity, e.g., species or strain, useful in the compositions and methods of the invention is *Parabacteroides gordonii*. In one embodiment, the bacterial entity, e.g., species or strain, useful in the compositions and methods of the invention is *Parabacteroides johnsonii*. In one embodiment, the bacterial entity, e.g., species or strain, useful in the compositions and methods of the invention is *Parabacteroides merdae*. In one embodiment, the bacterial entity, e.g., species or strain, useful in the compositions and methods of the invention is *Pediococcus acidilactici*. In one embodiment, the bacterial entity, e.g., species or strain, useful in the compositions and methods of the invention is *Peptostreptococcus asaccharolyticus*. In one embodiment, the bacterial entity, e.g., species or strain, useful in the compositions and methods of the invention is *Propionibacterium granulosum*. In one embodiment, the bacterial entity, e.g., species or strain, useful in the compositions and methods of the invention is *Roseburia intestinalis*. In one embodiment, the bacterial entity, e.g., species or strain, useful in the compositions and methods of the invention is *Roseburia inulinivorans*. In one embodiment, the bacterial entity, e.g., species or strain, useful in the compositions and methods of the invention is *Ruminococcus faecis*. In one embodiment, the bacterial entity, e.g., species or strain, useful in the compositions and methods of the invention is *Ruminococcus gnavus*. In one embodiment, the bacterial entity, e.g., species or strain, useful in the compositions and methods of the invention is *Ruminococcus* sp. ID8. In one embodiment, the bacterial entity, e.g., species or strain, useful in the compositions and methods of the invention is *Ruminococcus torques*. In one embodiment, the bacterial entity, e.g., species or strain, useful in the compositions and methods of the invention is *Slackia piriformis*. In one embodiment, the bacterial entity, e.g., species or strain, useful in the compositions and methods of the invention is *Staphylococcus epidermidis*. In one embodiment, the bacterial entity, e.g., species or strain, useful in the compositions and methods of the invention is *Staphylococcus saprophyticus*. In one embodiment, the bacterial entity, e.g., species or strain, useful in the compositions and methods of the invention is *Streptococcus cristatus*. In one embodiment, the bacterial entity, e.g., species or strain, useful in the compositions and methods of the invention is *Streptococcus dysgalactiae* subsp. *Equisimilis*. In one embodiment, the bacterial entity, e.g., species or strain, useful in the compositions and methods of the invention is *Streptococcus infantis*. In one embodiment, the bacterial entity, e.g., species or strain, useful in the compositions and methods of the invention is *Streptococcus oralis*. In one embodiment, the bacterial entity, e.g., species or strain, useful in the compositions and methods of the invention is *Streptococcus sanguinis*. In one embodiment, the bacterial entity, e.g., species or strain, useful in the compositions and methods of the invention is *Streptococcus viridans*. In one embodiment, the bacterial entity, e.g., species or strain, useful in the compositions and methods of the invention is *Streptococcus thermophiles*. In one embodiment, the bacterial entity, e.g., species or strain, useful in the compositions and methods of the invention is *Veillonella dispar*.

In one embodiment, the bacterial population useful in the compositions and methods of the invention comprises *Acidaminococcus intestine*. In one embodiment, the bacterial population useful in the compositions and methods of the invention comprises *Acinetobacter baumannii*. In one embodiment, the bacterial population useful in the compositions and methods of the invention comprises *Acinetobacter lwoffii*. In one embodiment, the bacterial population useful in the compositions and methods of the invention comprises *Akkermansia muciniphila*. In one embodiment, the bacterial population useful in the compositions and methods of the invention comprises *Alistipes putredinis*. In one embodiment, the bacterial population useful in the compositions and methods of the invention comprises *Alistipes shahii*. In one embodiment, the bacterial population useful in the compositions and methods of the invention comprises *Anaerostipes hadrus*. In one embodiment, the bacterial population useful in the compositions and methods of the invention comprises *Anaerotruncus colihominis*. In one embodiment, the bacterial population useful in the compositions and methods of the invention comprises *Bacteroides caccae*. In one embodiment, the bacterial population useful in the compositions and methods of the invention comprises *Bacteroides cellulosilyticus*. In one embodiment, the bacterial population useful in the compositions and methods of the invention comprises *Bacteroides dorei*. In one embodiment, the bacterial population useful in the compositions and methods of the invention comprises *Bacteroides eggerthii*. In one embodiment, the bacterial population useful in the compositions and methods of the invention comprises *Bacteroides finegoldii*. In one embodiment, the bacterial population useful in the compositions and methods of the invention comprises *Bacteroides fragilis*. In one embodiment, the bacterial population useful in the compositions and methods of the invention comprises *Bacteroides massiliensis*. In one embodiment, the bacterial population useful in the compositions and methods of the invention comprises *Bacteroides ovatus*. In one embodiment, the bacterial population useful in the compositions and methods of the invention comprises *Bacteroides salanitronis*. In one embodiment, the bacterial population useful in the compositions and methods of the invention comprises *Bacteroides salyersiae*. In one embodiment, the bacterial population useful in the compositions and methods of the invention comprises *Bacteroides* sp. 1_1_6. In one embodiment, the bacterial population useful in the compositions and methods of the invention comprises *Bacteroides* sp. 3_1_23. In one embodiment, the bacterial population useful in the compositions and methods of the invention comprises *Bacteroides* sp. D20. In one embodiment, the bacterial population useful in the compositions and methods of the invention comprises *Bacteroides thetaiotaomicrond*. In one embodiment, the bacterial population useful in the compositions and methods of the invention comprises *Bacteroides uniformis*. In one embodiment, the bacterial population useful in the compositions and methods of the invention comprises *Bacteroides vulgatus*. In one embodiment, the bacterial population useful in the compositions and methods of the invention comprises *Bifidobacterium adolescentis*. In one embodiment, the bacterial population useful in the compositions and methods of the invention comprises *Bifidobacterium bifidum*. In one embodiment, the bacterial population useful in the compositions and methods of the invention comprises *Bifidobacterium breve*. In one embodiment, the bacterial population useful in the compositions and methods of the invention comprises *Bifidobacterium faecale*. In one embodiment, the bacterial population useful in the compositions and methods of the invention comprises *Bifidobacterium kashiwanohense*. In one embodiment, the bacterial population useful in the compositions and methods of the invention comprises *Bifidobacterium longum* subsp. *Longum*. In one embodiment, the bacterial population useful in the compositions and methods of the invention comprises *Bifidobacterium pseudocatenulatum*. In one embodiment, the bacterial population useful in the compositions and methods of the invention comprises *Bifidobacterium stercoris*. In one embodiment, the bacterial population useful in the compositions and methods of the invention comprises *Blautia (Ruminococcus) coccoides*. In one embodiment, the bacterial population useful in the compositions and methods of the invention comprises *Blautia faecis*. In one embodiment, the bacterial population useful in the compositions and methods of the invention comprises *Blautia glucerasea*. In one embodiment, the bacterial population useful in the compositions and methods of the invention comprises *Blautia (Ruminococcus) hansenii*. In one embodiment, the bacterial population useful in the compositions and methods of the invention comprises *Blautia* hydrogenotrophica (*Ruminococcus hydrogenotrophicus*). In one embodiment, the bacterial population useful in the compositions and methods of the invention comprises *Blautia (Ruminococcus) luti*. In one embodiment, the bacterial population useful in the compositions and methods of the invention comprises *Blautia (Ruminococcus) obeum*. In one embodiment, the bacterial population useful in the compositions and methods of the invention comprises *Blautia producta (Ruminococcus productus)*. In one embodiment, the bacterial population useful in the compositions and methods of the invention comprises *Blautia (Ruminococcus) schinkii*. In one embodiment, the bacterial population useful in the compositions and methods of the invention comprises *Blautia stercoris*. In one embodiment, the bacterial population useful in the compositions and methods of the invention comprises *Blautia* uncultured bacterium clone BKLE_a03_2 (GenBank: EU469501.1). In one embodiment, the bacterial population useful in the compositions and methods of the invention comprises *Blautia* uncultured bacterium clone SJTU_B_14_30 (GenBank: EF402926.1). In one embodiment, the bacterial population useful in the compositions and methods of the invention comprises *Blautia* uncultured bacterium clone SJTU_C_14_16 (GenBank: EF404657.1). In one embodiment, the bacterial population useful in the compositions and methods of the invention comprises *Blautia* uncultured bacterium clone S1-5 (GenBank: GQ898099.1). In one embodiment, the bacterial population useful in the compositions and methods of the invention comprises *Blautia* uncultured PAC000178_s (www.ezbiocloud.net/eztaxon/hierarchy?m=browse&k=PAC000178&d=2). In one embodiment, the bacterial population useful in the compositions and methods of the invention comprises *Blautia wexlerae*. In one embodiment, the bacterial population useful in the compositions and methods of the invention comprises *Candidatus Arthromitus* sp. SFB-mouse-Yit. In one embodiment, the bacterial population useful in the compositions and methods of the invention comprises *Catenibacterium mitsuokai*. In one embodiment, the bacterial population useful in the compositions and methods of the invention comprises *Clostridiaceae* bacterium (*Dielma fastidiosa*) JC13. In one embodiment, the bacterial population useful in the compositions and methods of the invention comprises Clostridiales bacterium 1_7_47FAA. In one embodiment, the bacterial population useful in the compositions and methods of the invention comprises *Clostridium asparagiforme*. In one embodiment, the bacterial population useful in the compositions and methods of the invention comprises *Clostridium bolteae*. In one embodiment, the bacterial population useful in the compositions and methods of the invention comprises *Clostridium clostridioforme*. In one embodiment, the bacterial population useful in the compositions and methods of the invention comprises *Clostridium glycyrrhizinilyticum*. In one embodiment, the bacterial population useful in the compositions and methods of the invention comprises *Clostridium* (*Hungatella*) *hathewayi*. In one embodiment, the bacterial population useful in the compositions and methods of the invention comprises *Clostridium histolyticum*. In one embodiment, the bacterial population useful in the compositions and methods of the invention comprises *Clostridium indolis*. In one embodiment, the bacterial population useful in the compositions and methods of the invention comprises *Clostridium leptum*. In one embodiment, the bacterial population useful in the compositions and methods of the invention comprises *Clostridium* (*Tyzzerella*) *nexile*. In one embodiment, the bacterial population useful in the compositions and methods of the invention comprises *Clostridium perfringens*. In one embodiment, the bacterial population useful in the compositions and methods of the invention comprises *Clostridium* (*Erysipelatoclostridium*) *ramosum*. In one embodiment, the bacterial population useful in the compositions and methods of the invention comprises *Clostridium scindens*. In one embodiment, the bacterial entity, e.g., species or strain, useful in the compositions and methods of the invention is *Clostridium septum*. In one embodiment, the bacterial population useful in the compositions and methods of the invention comprises *Clostridium* sp. 14774. In one embodiment, the bacterial population useful in the compositions and methods of the invention comprises *Clostridium* sp. 7_3_54FAA. In one embodiment, the bacterial population useful in the compositions and methods of the invention comprises *Clostridium* sp. HGF2. In one embodiment, the bacterial population useful in the compositions and methods of the invention comprises *Clostridium symbiosum*. In one embodiment, the bacterial population useful in the compositions and methods of the invention comprises *Collinsella aerofaciens*. In one embodiment, the bacterial population useful in the compositions and methods of the invention comprises *Collinsella intestinalis*. In one embodiment, the bacterial population useful in the compositions and methods of the invention comprises *Coprobacillus* sp. D7. In one embodiment, the bacterial population useful in the compositions and methods of the invention comprises *Coprococcus catus*. In one embodiment, the bacterial population useful in the compositions and methods of the invention comprises *Coprococcus comes*. In one embodiment, the bacterial population useful in the compositions and methods of the invention comprises *Dorea formicigenerans*. In one embodiment, the bacterial population useful in the compositions and methods of the invention comprises *Dorea longicatena*. In one embodiment, the bacterial population useful in the compositions and methods of the invention comprises *Enterococcus faecalis*. In one embodiment, the bacterial population useful in the compositions and methods of the invention comprises *Enterococcus faecium*. In one embodiment, the bacterial population useful in the compositions and methods of the invention comprises Erysipelotrichaceae bacterium 3_1_53. In one embodiment, the bacterial population useful in the compositions and methods of the invention comprises *Escherichia coli*. In one embodiment, the bacterial population useful in the compositions and methods of the invention comprises *Escherichia coli* S88. In one embodiment, the bacterial population useful in the compositions and methods of the invention comprises *Eubacterium eligens*. In one embodiment, the bacterial population useful in the compositions and methods of the invention comprises *Eubacterium fissicatena*. In one embodiment, the bacterial population useful in the compositions and methods of the invention comprises *Eubacterium ramulus*. In one embodiment, the bacterial population useful in the compositions and methods of the invention comprises *Eubacterium rectale*. In one embodiment, the bacterial population useful in the compositions and methods of the invention comprises *Faecalibacterium prausnitzii*. In one embodiment, the bacterial population useful in the compositions and methods of the invention comprises *Flavonifractor plautii*. In one embodiment, the bacterial population useful in the compositions and methods of the invention comprises *Fusobacterium mortiferum*. In one embodiment, the bacterial population useful in the compositions and methods of the invention comprises *Fusobacterium nucleatum*. In one embodiment, the bacterial population useful in the compositions and methods of the invention comprises *Holdemania filiformis*. In one embodiment, the bacterial population useful in the compositions and methods of the invention comprises *Hydrogenoanaerobacterium saccharovorans*. In one embodiment, the bacterial population useful in the compositions and methods of the invention comprises *Klebsiella oxytoca*. In one embodiment, the bacterial population useful in the compositions and methods of the invention comprises Lachnospiraceae bacterium 3_1_7FAA_CT1. In one embodiment, the bacterial population useful in the compositions and methods of the invention comprises Lachnospiraceae bacterium 7_1_58FAA. In one embodiment, the bacterial population useful in the compositions and methods of the invention comprises Lachnospiraceae bacterium 5_1_57FAA. In one embodiment, the bacterial population useful in the compositions and methods of the invention comprises *Lactobacillus casei*. In one embodiment, the bacterial population useful in the compositions and methods of the invention comprises *Lactobacillus rhamnosus*. In one embodiment, the bacterial population useful in the compositions and methods of the invention comprises *Lactobacillus ruminis*. In one embodiment, the bacterial population useful in the compositions and methods of the invention comprises *Lactococcus casei*. In one embodiment, the bacterial population useful in the compositions and methods of the invention comprises *Odoribacter splanchnicus*. In one embodiment, the bacterial population useful in the compositions and methods of the invention comprises *Oscillibacter valericigenes*. In one embodiment, the bacterial population useful in the compositions and methods of the invention comprises *Parabacteroides gordonii*. In one embodiment, the bacterial population useful in the compositions and methods of the invention comprises *Parabacteroides johnsonii*. In one embodiment, the bacterial population useful in the compositions and methods of the invention comprises *Parabacteroides merdae*. In one embodiment, the bacterial population useful in the compositions and methods of the invention comprises *Pediococcus acidilactici*. In one embodiment, the bacterial population useful in the compositions and methods of the invention comprises *Peptostreptococcus asaccharolyticus*. In one embodiment, the bacterial population useful in the compositions and methods of the invention comprises *Propionibacterium granulosum*. In one embodiment, the bacterial population useful in the compositions and methods of the invention comprises *Roseburia intestinalis*. In one embodiment, the bacterial population useful in the compositions and methods of the invention comprises *Roseburia inulinivorans*. In one embodiment, the bacterial population useful in the compositions and methods of the invention comprises *Ruminococcus faecis*. In one embodiment, the bacterial population useful in the compositions and methods of the invention comprises *Ruminococcus gnavus*. In one embodiment, the bacterial population useful in the compositions and methods of the invention comprises *Ruminococcus* sp. ID8. In one embodiment, the bacterial population useful in the compositions and methods of the invention comprises *Ruminococcus torques*. In one embodiment, the bacterial population useful in the compositions and methods of the invention comprises *Slackia piriformis*. In one embodiment, the bacterial population useful in the compositions and methods of the invention comprises *Staphylococcus epidermidis*. In one embodiment, the bacterial population useful in the compositions and methods of the invention comprises *Staphylococcus saprophyticus*. In one embodiment, the bacterial population useful in the compositions and methods of the invention comprises *Streptococcus cristatus*. In one embodiment, the bacterial population useful in the compositions and methods of the invention comprises *Streptococcus dysgalactiae* subsp. *Equisimilis*. In one embodiment, the bacterial population useful in the compositions and methods of the invention comprises *Streptococcus infantis*. In one embodiment, the bacterial population useful in the compositions and methods of the invention comprises *Streptococcus oralis*. In one embodiment, the bacterial population useful in the compositions and methods of the invention comprises *Streptococcus sanguinis*. In one embodiment, the bacterial population useful in the compositions and methods of the invention comprises *Streptococcus viridans*. In one embodiment, the bacterial population useful in the compositions and methods of the invention comprises *Streptococcus thermophiles*. In one embodiment, the bacterial population useful in the compositions and methods of the invention comprises *Veillonella dispar*.

In one embodiment, the prebiotic carbohydrate component of the pharmaceutical composition, dosage form, or kit allows the commensal colonic microbiota, comprising microorganisms associated with a healthy-state microbiome or presenting a low risk of a patient developing an autoimmune or inflammatory condition, to be regularly maintained. In one embodiment, the prebiotic carbohydrate component of the pharmaceutical composition, dosage form, or kit allows the co-administered or co-formulated microbe or microbes to engraft, grow, and/or be regularly maintained in a mammalian subject. In some embodiments, the mammalian subject is a human subject. In preferred embodiments, the mammalian subject suffers from or is at risk of developing an autoimmune or inflammatory disorder. In some embodiments, the prebiotic component of the invention favors the growth of an administered microbe, wherein the growth of the administered microbe and/or the fermentation of the administered prebiotic by the administered microbe slows or reduces the growth of a pathogen or pathobiont. For example, FOS, neosugar, or inulin promotes the growth of acid-forming bacteria in the colon such as bacteria belonging to the genera *Lactobacillus* or *Bifidobacterium* and *Lactobacillus acidophilus* and *Bifidobacterium bifidus* can play a role in reducing the number of pathogenic bacteria in the colon (U.S. Pat. No. 8,486,668 PREBIOTIC FORMULATIONS AND METHODS OF USE). Other polymers, such as various galactans, lactulose, and carbohydrate based gums, such as *psyllium*, guar, carrageen, gellan, and konjac, are also known to improve gastrointestinal (GI) health.

Short chain fatty acids (SCFAs) can have immunomodulatory (i.e., immunosuppressive) effects and therefore their production (i.e., biosynthesis or conversion by fermentation) is advantageous for the prevention, control, mitigation, and treatment of autoimmune and/or inflammatory disorders (Lara-Villoslada F. et al., 2006. Short-chain fructooligosaccharides, in spite of being fermented in the upper part of the large intestine, have anti-inflammatory activity in the TNBS model of colitis. Eur J Nutr. 45(7): 418-425). In some aspects, the pharmaceutical composition, dosage form, or kit comprises at least one type of microbe and at least one type of prebiotic such that the composition, dosage form, or kit is capable of increasing the level of one or more immunomodulatory SCFA (e.g., acetate, propionate, butyrate, or valerate) in a mammalian subject. Optionally, the pharmaceutical composition, dosage form, or kit further comprises one or more substrates of one or more SCFA-producing fermentation and/or biosynthesis pathways. In certain embodiments, the administration of the composition, dosage form, or kit to a mammalian subject results in the increase of one or more SCFAs in the mammalian subject by approximately 1.5-fold, 2-fold, 5-fold, 10-fold, 20-fold, 50-fold, 100-fold, or greater than 100-fold.

In some embodiments, the prebiotic mixture is selected to favor the production of a particular immunomodulatory SCFA, including but not limited to butyrate, propionate, or acetate. In preferred embodiments, the fermentation product is butyrate or propionate. Non-limiting examples are resistant starch and carbohydrates with highly organized structures, such as high amylose maize starch, that are more likely to be fermented by microbes to produce butyrate than other SCFAs (Zhou Z et al. 2013. Starch structure modulates metabolic activity and gut microbiota profile. Anaerobe. 24:71-78). In some embodiments, one or more components of a prebiotic mixture is subjected to denaturation (e.g., thermal treatment) to favor the production of a SCFA (e.g., acetate) or a non-SCFA species including but not limited to lactate or succinate.

In some embodiments, the pharmaceutical composition, dosage form, or kit comprises one or more types of microbe capable of producing butyrate in a mammalian subject. Butyrate-producing microbes may be identified experimentally, such as by NMR or gas chromatography analyses of microbial products or colorimetric assays (Rose I A. 1955. Methods Enzymol. Acetate kinase of bacteria. 1: 591-5). Butyrate-producing microbes may also be identified computationally, such as by the identification of one or more enzymes involved in butyrate synthesis. Non-limiting examples of enzymes found in butyrate-producing microbes include butyrate kinase, phosphotransbutyrylase, and butyryl CoA:acetate CoA transferase (Louis P., et al. 2004. Restricted Distribution of the Butyrate Kinase Pathway among Butyrate-Producing Bacteria from the Human Colon. J Bact. 186(7): 2099-2106). Butyrate-producing strains include, but are not limited to, *Faecalibacterium prausnitzii, Eubacterium* spp., *Butyrivibrio fibrisolvens, Roseburia intestinalis, Clostridium* spp., *Anaerostipes caccae,* and *Ruminococcus* spp. In some embodiments, the pharmaceutical composition, dosage form, or kit comprises two or more types of microbe, wherein at least two types of microbe are capable of producing butyrate in a mammalian subject. In other embodiments, the pharmaceutical composition, dosage form, or kit comprises two or more types of microbe, wherein two or more types of microbe cooperate (i.e., cross-feed) to produce an immunomodulatory SCFA (e.g., butyrate) in a mammalian subject. In a preferred embodiment, the pharmaceutical composition, dosage form, or kit comprises at least one type of microbe (e.g., *Bifidobacterium* spp.) capable of metabolizing a prebiotic, including but not limited to, inulin, inulin-type fructans, or oligofructose, such that the resulting metabolic product may be converted by a second type of microbe (e.g, a butyrate-producing microbe such as *Roseburia* spp.) to an immunomodulatory SCFA such as butyrate (Falony G., et al. 2006. Cross-Feeding between *Bifidobacterium longum* BB536 and Acetate-Converting, Butyrate-Producing Colon Bacteria during Grown on Oligofructose. Appl. Environ. Microbiol. 72(12): 7835-7841.) In other aspects, the pharmaceutical composition, dosage form, or kit comprises at least one acetate-producing microbe (e.g., *Bacteroides thetaiotaomicron*) and at least one acetate-consuming, butyrate-producing microbe (e.g., *Faecalibacterium prausnitzii*).

In some embodiments, the pharmaceutical composition, dosage form, or kit comprises one or more types of microbe capable of producing propionate in a mammalian subject, optionally further comprising a prebiotic or substrate appropriate for proprionate biosynthesis. Examples of prebiotics or substrates used for the production of propionate include, but are not limited to, L-rhamnose, D-tagalose, resistant starch, inulin, polydextrose, arabinoxylans, arabinoxylan oligosaccharides, mannooligosaccharides, and laminarans (Hosseini E., et al. 2011. Propionate as a health-promoting microbial metabolite in the human gut. Nutrition Reviews. 69(5): 245-258). Propionate-producing microbes may be identified experimentally, such as by NMR or gas chromatography analyses of microbial products or colorimetric assays (Rose I A. 1955. Methods Enzymol. Acetate kinase of bacteria. 1: 591-5) Propionate-producing microbes may also be identified computationally, such as by the identification of one or more enzymes involved in propionate synthesis. Non-limiting examples of enzymes found in propionate-producing microbes include enzymes of the succinate pathway, including but not limited to phophoenylpyrvate carboxykinase, pyruvate kinase, pyruvate carboxylase, malate dehydrogenase, fumarate hydratase, succinate dehydrogenase, succinyl CoA synthetase, methylmalonyl Coa decarboxylase, and propionate CoA transferase, as well as enzymes of the acrylate pathway, including but not limited to L-lactate dehydrogenase, propionate CoA transferase, lactoyl CoA dehydratase, acyl CoA dehydrogenase, phosphate acetyltransferase, and propionate kinase. Non-limiting examples of microbes that utilize the succinate pathway are *Bacteroides fragilis* and other species (including *B. vulgatus*), *Propionibacterium* spp. (including *freudenrichii* and *acidipropionici*), *Veillonella* spp. (including *gazogenes*), *Micrococcus lactilyticus, Selenomonas ruminantium, Escherichia coli,* and *Prevotella ruminocola*. Non-limiting examples of microbes that utilize the acrylate pathway are *Clostridium neopropionicum* X4, and *Megasphaera elsdenii*. In preferred embodiments, the combination of a type of microbe or microbial composition and type of prebiotic mixture is selected based on the fermentation or metabolic preferences of one or more microbes capable of producing immunomodulatory SCFAs (e.g., preference for complex versus simple sugar or preference for a fermentation product versus a prebiotic). For example, *M. eldsenii* prefers lactate fermentation to glucose fermentation, and maximization of propionate production by *M. eldsenii* in a mammalian subject may therefore be achieved by administering along with *M. eldsenii* a favored substrate (e.g., lactate) or one or more microbes capable of fermenting glucose into lactate (e.g., *Streptococcus bovis*) (Hosseini E., et al. 2011. Propionate as a health-promoting microbial metabolite in the human gut. Nutrition Reviews. 69(5): 245-258). Thus, in some embodiments, the pharmaceutical composition, dosage form, or kit comprises at least one type of SCFA-producing microbe and a sugar fermentation product (e.g., lactate). In other embodiments, the pharmaceutical composition, dosage form, or kit comprises at least one type of SCFA-producing microbe and at least one type of sugar-fermenting microbe, wherein the fermentation product of the second, sugar-fermenting microbe is the preferred substrate of the SCFA-producing microbe.

In some embodiments, the pharmaceutical composition, dosage form, or kit comprises two or more types of microbe, wherein at least two types of microbe are capable of producing propionate in a mammalian subject. In other embodiments, the pharmaceutical composition, dosage form, or kit comprises two or more types of microbe, wherein two or more types of microbe cooperate (i.e., cross-feed) to produce an immunomodulatory SCFA (e.g., propionate) in a mammalian subject. In a preferred embodiment, the pharmaceutical composition, dosage form, or kit comprises at least one type of microbe (e.g., *Ruminococcus* spp. or *Bacteroides* spp.) capable of metabolizing a prebiotic into succinate, and a second type of microbe (e.g., *S. ruminantium*) capable of converting succinate (via the succinate pathway) into propionate in the mammalian subject.

Immunomodulation can also be achieved by the microbial production of glutathione or gamma-glutamylcysteine. Thus, in certain embodiments, the pharmaceutical composition, dosage form, or kit comprises at least one type of microbe capable of producing glutathione and/or gamma-glutamylcysteine in a mammalian subject. In some aspects, the composition, dosage form, or kit comprises one or more microbes selected for the presence of glutamate cysteine ligase (e.g., *Lactobacillus fermentum*) and/or L-proline biosynthesis enzymes (e.g., *E. coli*) (Peran et al., 2006. *Lactobacillus fermenum*, a probiotic capable to release glutathione, prevents colonic inflammation in the TNBS model of rat colitis. Int J Colorectal Dis. 21(8): 737-746; Veeravalli et al., 2011. Laboratory evolution of glutathione biosynthesis reveals naturally compensatory pathways. Nat Chem Bio. 7(2): 101-105). In a preferred embodiment, at least one microbe in the pharmaceutical composition, dosage form, or kit is L. fermentum.

para-cresol (p-cresol) is a microbial product, via the fermentation of tyrosine or phenylalanine. Sulfated in the liver or colon to p-cresyl sulfate, this molecule reduces Th1-mediated responses (Shiba T. et al. 2014. Effects of intestinal bacteria-derived p-cresyl sulfate on Th1-type immune response in vivo and in vitro. Tox and Applied Pharm. 274(2): 191-199). In some embodiments, the pharmaceutical composition, dosage form, or kit comprises at least one type of microbe capable of fermenting tyrosine and/or phenylalanine to p-cresol in a mammalian subject. Non-limiting examples of such microbes include Bacteroides fragilis, Clostridium difficile, and Lactobacillus sp. Strain #11198-11201 (Yokoyama M T and Carlson J R. 1981. Production of Skatole and para-Cresol by a Rumen Lactobacillus sp. Applied and Environmental Microbiology. 41(1): 71-76), and other microbes with p-hydroxylphenyl acetate decarboxylase activity.

It has recently come to light that the DNA of commensal microbes, including many species of Lactobacillus protect against activation of lamina propia dendritic cells and sustain regulatory T cell conversion (Bouladoux N, Hall J A, Grainger J R, dos Santos L M, Kann M G, Nagarajan V, Verthelyi D, and Belkaid Y, 2012. Regulatory role of suppressive motifs from commensal DNA. Mucosal Immunol. 5: 623-634). Thus commensal DNA may protect against colitis, IBD, and/or other immunological intolerances in the gut. Furthermore, Lactobacillus species are prevalent in the healthy vaginal microbiome. Thus, DNA from Lactobacillus or other vaginal microbiome commensals may suppress immune responses in the vagina that could disrupt the normal healthy-state vaginal microbiome and lead to complications such as chronic HPV, infertility, miscarriages, or UTIs. As such, in certain embodiments, the microbial composition, pharmaceutical composition, dosage form, or kit additionally comprises DNA isolated from one or more host commensals.

XI. Crohn's Disease

Crohn's disease and ulcerative colitis are types of IBDs. While both illness share elements of their characteristic immune responses (e.g., high TNF-α, which can be detected in a patient's feces), their associated immune responses can also have distinguishing markers. For example, interleukin-16 (IL-16) levels are high and T-bet is overexpressed the lamina propia T cell nucleus in patients with Crohn's disease, but not in those suffering from ulcerative colitis. Notably T-bets produce the pro-inflammatory cytokine IFN-γ. One similarity among IBDs is high IFN-γ (by about 4-fold), caused in part due to high TL1A and TNF-α. Moreover, the levels of these cytokines correlate with the severity of the IBD.

Early Crohn's disease has a different immunological signature than does chronic Crohn's disease. In aspects in which a patient presents with early lesions, the microbial composition may be selected, with or without one or more prebiotics, to counteract a T helper cell 2-mediated response. For example, the microbial composition, optionally combined with immunomodulatory molecules such as nucleotides or carbohydrates, may decrease interleukin-4 (IL-4) levels or increase IFN-γ. In aspects in which a patient presents with chronic lesions, the microbial composition may be selected to counteract a T helper cell 1-mediated response. For example, the microbial composition, optionally combined with immunomodulatory molecules such as nucleotides or carbohydrates, may decrease IL-2, IFN-γ, TNF-α, TL1A, IL-12, and/or IL-18. In some embodiments, in which a patient suffers from an IBD including but not limited to Crohn's disease, a probiotic microbial composition, with or without one or more prebiotics, is administered to the patient such that it is effective to reduce TNF-α levels, as detectable in feces samples, by approximately 5-fold, 10-fold, 25-fold, 50-fold, or 100-fold. Crohn's disease patients tend to present with low plasma levels of vitamins or minerals including but not limited to vitamin A, vitamin E, vitamin C, lycopene, carotenoids, and/or selenium. Patients eligible for immunomodulatory treatment may thus be administered an immunomodulatory microbe, molecule, and/or microbial component optionally combined with an appropriate vitamin or mineral supplement, as determined by plasma deficiency.

Probiotic compositions useful for treating or preventing Crohn's disease include, in exemplary embodiments, one or more bacterial strains from Table 1. In other embodiments, the probiotic composition includes one or more bacterial strains from Table 1A. In other embodiments, the probiotic composition includes one or more bacterial strains from Table 1B. In other embodiments, the probiotic composition includes one or more bacterial strains from Table 1C. In other embodiments, the probiotic composition includes one or more bacterial strains from Table 1D. In other embodiments, the probiotic composition includes one or more bacterial strains from Table 1E. In other embodiments, the probiotic composition includes one or more bacterial strains from Table 1F. In some embodiments, the probiotic composition contains a single strain of bacteria. In other embodiments, the probiotic composition contains two or more strains of bacteria, e.g., 2, 3, 4, 5, 6, 7, 8, 9, 10, 15, 20, 30, 40, 50, 60, 70, 80, 90, 100, 500, 1000 or more strains of bacteria. In other embodiments, the probiotic composition contains or is administered in conjunction with a prebiotic, as described herein.

Preferred bacterial genera include Acetanaerobacterium, Acetivibrio, Alicyclobacillus, Alkaliphilus, Anaerofustis, Anaerosporobacter, Anaerostipes, Anaerotruncus, Anoxybacillus, Bacillus, Bacteroides, Blautia, Brachyspira, Brevibacillus, Bryantella, Bulleidia, Butyricicoccus, Butyrivibrio, Catenibacterium, Chlamydiales, Clostridiaceae, Clostridiales, Clostridium, Collinsella, Coprobacillus, Coprococcus, Coxiella, Deferribacteres, Desulfitobacterium, Desulfotomaculum, Dorea, Eggerthella, Erysipelothrix, Erysipelotrichaceae, Ethanoligenens, Eubacterium, Faecalibacterium, Filifactor, Flavonifractor, Flexistipes, Fulvimonas, Fusobacterium, Gemmiger, Geobacillus, Gloeobacter, Holdemania, Hydrogenoanaerobacterium, Kocuria, Lachnobacterium, Lachnospira, Lachnospiraceae, Lactobacillus, Lactonifactor, Leptospira, Lutispora, Lysinibacillus, Mollicutes, Moorella, Nocardia, Oscillibacter, Oscillospira, Paenibacillus, Papillibacter, Pseudoflavonifractor, Robinsoniella, Roseburia, Ruminococcaceae, Ruminococcus, Saccharomonospora, Sarcina, Solobacterium, Sporobacter, Sporolactobacillus, Streptomyces, Subdoligranulum, Sutterella, Syntrophococcus, Thermoanaerobacter, Thermobifida, and Turicibacter.

Preferred bacterial genera also include Acetonema, Alkaliphilus, Amphibacillus, Ammonifex, Anaerobacter, Caldicellulosiruptor, Caloramator, Candidatus, Carboxydibrachium, Carboxydothermus, Cohnella, Dendrosporobacter Desulfitobacterium, Desulfosporosinus, Halobacteroides, Heliobacterium, Heliophilum, Heliorestis,

*Lachnoanaerobaculum, Lysinibacillus, Oceanobacillus, Orenia (S.), Oxalophagus, Oxobacter, Pelospora, Pelotomaculum, Propionispora, Sporohalobacter, Sporomusa, Sporosarcina, Sporotomaculum, Symbiobacterium, Syntrophobotulus, Syntrophospora, Terribacillus, Thermoanaerobacter,* and *Thermosinus*.

As provided herein, therapeutic compositions comprise, or in the alternative, modulate, the colonization and/or engraftment, of the following exemplary bacterial entities: *Lactobacillus gasseri, Lactobacillus fermentum, Lactobacillus reuteri, Enterococcus faecalis, Enterococcus durans, Enterococcus villorum, Lactobacillus plantarum, Pediococcus acidilactici, Staphylococcus pasteuri, Staphylococcus cohnii, Streptococcus sanguinis, Streptococcus sinensis, Streptococcus mitis, Streptococcus* sp. SCA22, *Streptococcus* sp. CR-3145, *Streptococcus anginosus, Streptococcus mutans, Coprobacillus cateniformis, Clostridium saccharogumia, Eubacterium dolichum* DSM 3991, *Clostridium* sp. PPf35E6, *Clostridium* sordelli ATCC 9714, *Ruminococcus torques, Ruminococcus gnavus, Clostridium clostridioforme, Ruminococcus obeum, Blautia producta, Clostridium* sp. ID5, *Megasphaera micronuciformis, Veillonella parvula, Clostridium methylpentosum, Clostridium islandicum, Faecalibacterium prausnitzii, Bacteroides uniformmis, Bacteroides thetaiotaomicron, Bacteroides acidifaciens, Bacteroides ovatus, Bacteroides fragilis, Parabacteroides distasonis, Propinionibacteirum propionicum, Actinomycs hyovaginalis, Rothia mucilaginosa, Rothia aeria, Bifidobacterium breve, Scardovia inopinata* and *Eggerthella lenta*.

Preferred bacterial species are provided in Table 1, Table 1A, Table 1B, Table 1C, Table 1D, Table 1E, Table 1F, and Table 5. Optionally, in some embodiments, preferred bacterial species are spore formers. Where specific strains of a species are provided, one of skill in the art will recognize that other strains of the species can be substituted for the named strain.

In one embodiment, the bacterial entity, e.g., species or strain, useful in the compositions and methods of the invention is *Acidaminococcus intestine*. In one embodiment, the bacterial entity, e.g., species or strain, useful in the compositions and methods of the invention is *Acinetobacter baumannii*. In one embodiment, the bacterial entity, e.g., species or strain, useful in the compositions and methods of the invention is *Acinetobacter lwoffii*. In one embodiment, the bacterial entity, e.g., species or strain, useful in the compositions and methods of the invention is *Akkermansia muciniphila*. In one embodiment, the bacterial entity, e.g., species or strain, useful in the compositions and methods of the invention is *Alistipes putredinis*. In one embodiment, the bacterial entity, e.g., species or strain, useful in the compositions and methods of the invention is *Alistipes shahii*. In one embodiment, the bacterial entity, e.g., species or strain, useful in the compositions and methods of the invention is *Anaerostipes hadrus*. In one embodiment, the bacterial entity, e.g., species or strain, useful in the compositions and methods of the invention is *Anaerotruncus colihominis*. In one embodiment, the bacterial entity, e.g., species or strain, useful in the compositions and methods of the invention is *Bacteroides caccae*. In one embodiment, the bacterial entity, e.g., species or strain, useful in the compositions and methods of the invention is *Bacteroides cellulosilyticus*. In one embodiment, the bacterial entity, e.g., species or strain, useful in the compositions and methods of the invention is *Bacteroides dorei*. In one embodiment, the bacterial entity, e.g., species or strain, useful in the compositions and methods of the invention is *Bacteroides eggerthii*. In one embodiment, the bacterial entity, e.g., species or strain, useful in the compositions and methods of the invention is *Bacteroides finegoldii*. In one embodiment, the bacterial entity, e.g., species or strain, useful in the compositions and methods of the invention is *Bacteroides fragilis*. In one embodiment, the bacterial entity, e.g., species or strain, useful in the compositions and methods of the invention is *Bacteroides massiliensis*. In one embodiment, the bacterial entity, e.g., species or strain, useful in the compositions and methods of the invention is *Bacteroides ovatus*. In one embodiment, the bacterial entity, e.g., species or strain, useful in the compositions and methods of the invention is *Bacteroides salanitronis*. In one embodiment, the bacterial entity, e.g., species or strain, useful in the compositions and methods of the invention is *Bacteroides salyersiae*. In one embodiment, the bacterial entity, e.g., species or strain, useful in the compositions and methods of the invention is *Bacteroides* sp. 1_1_6. In one embodiment, the bacterial entity, e.g., species or strain, useful in the compositions and methods of the invention is *Bacteroides* sp. 3_1_23. In one embodiment, the bacterial entity, e.g., species or strain, useful in the compositions and methods of the invention is *Bacteroides* sp. D20. In one embodiment, the bacterial entity, e.g., species or strain, useful in the compositions and methods of the invention is *Bacteroides thetaiotaomicrond*. In one embodiment, the bacterial entity, e.g., species or strain, useful in the compositions and methods of the invention is *Bacteroides uniformis*. In one embodiment, the bacterial entity, e.g., species or strain, useful in the compositions and methods of the invention is *Bacteroides vulgatus*. In one embodiment, the bacterial entity, e.g., species or strain, useful in the compositions and methods of the invention is *Bifidobacterium adolescentis*. In one embodiment, the bacterial entity, e.g., species or strain, useful in the compositions and methods of the invention is *Bifidobacterium bifidum*. In one embodiment, the bacterial entity, e.g., species or strain, useful in the compositions and methods of the invention is *Bifidobacterium breve*. In one embodiment, the bacterial entity, e.g., species or strain, useful in the compositions and methods of the invention is *Bifidobacterium faecale*. In one embodiment, the bacterial entity, e.g., species or strain, useful in the compositions and methods of the invention is *Bifidobacterium kashiwanohense*. In one embodiment, the bacterial entity, e.g., species or strain, useful in the compositions and methods of the invention is *Bifidobacterium longum* subsp. *Longum*. In one embodiment, the bacterial entity, e.g., species or strain, useful in the compositions and methods of the invention is *Bifidobacterium pseudocatenulatum*. In one embodiment, the bacterial entity, e.g., species or strain, useful in the compositions and methods of the invention is *Bifidobacterium stercoris*. In one embodiment, the bacterial entity, e.g., species or strain, useful in the compositions and methods of the invention is *Blautia (Ruminococcus) coccoides*. In one embodiment, the bacterial entity, e.g., species or strain, useful in the compositions and methods of the invention is *Blautia faecis*. In one embodiment, the bacterial entity, e.g., species or strain, useful in the compositions and methods of the invention is *Blautia glucerasea*. In one embodiment, the bacterial entity, e.g., species or strain, useful in the compositions and methods of the invention is *Blautia (Ruminococcus) hansenii*. In one embodiment, the bacterial entity, e.g., species or strain, useful in the compositions and methods of the invention is *Blautia hydrogenotrophica (Ruminococcus hydrogenotrophicus)*. In one embodiment, the bacterial entity, e.g., species or strain, useful in the compositions and methods of the invention is *Blautia (Ruminococcus) luti*. In one embodiment, the bacterial entity, e.g., species or strain, useful in the compositions and methods of the invention is *Blautia* (*Ruminococcus*) *obeum*. In one embodiment, the bacterial entity, e.g., species or strain, useful in the compositions and methods of the invention is *Blautia producta* (*Ruminococcus productus*). In one embodiment, the bacterial entity, e.g., species or strain, useful in the compositions and methods of the invention is *Blautia* (*Ruminococcus*) *schinkii*. In one embodiment, the bacterial entity, e.g., species or strain, useful in the compositions and methods of the invention is *Blautia stercoris*. In one embodiment, the bacterial entity, e.g., species or strain, useful in the compositions and methods of the invention is *Blautia* uncultured bacterium clone BKLE_a03_2 (GenBank: EU469501.1). In one embodiment, the bacterial entity, e.g., species or strain, useful in the compositions and methods of the invention is *Blautia* uncultured bacterium clone SJTU_B_14_30 (GenBank: EF402926.1). In one embodiment, the bacterial entity, e.g., species or strain, useful in the compositions and methods of the invention is *Blautia* uncultured bacterium clone SJTU_C_14_16 (GenBank: EF404657.1). In one embodiment, the bacterial entity, e.g., species or strain, useful in the compositions and methods of the invention is *Blautia* uncultured bacterium clone S1-5 (GenBank: GQ898099.1). In one embodiment, the bacterial entity, e.g., species or strain, useful in the compositions and methods of the invention is *Blautia* uncultured PAC000178_s (www.ezbiocloud.net/ez-taxon/hierarchy?m=browse&k=PAC000178&d=2). In one embodiment, the bacterial entity, e.g., species or strain, useful in the compositions and methods of the invention is *Blautia wexlerae*. In one embodiment, the bacterial entity, e.g., species or strain, useful in the compositions and methods of the invention is *Candidatus Arthromitus* sp. SFB-mouse-Yit. In one embodiment, the bacterial entity, e.g., species or strain, useful in the compositions and methods of the invention is *Catenibacterium mitsuokai*. In one embodiment, the bacterial entity, e.g., species or strain, useful in the compositions and methods of the invention is *Clostridiaceae* bacterium (*Dielma fastidiosa*) JC13. In one embodiment, the bacterial entity, e.g., species or strain, useful in the compositions and methods of the invention is Clostridiales bacterium 1_7_47FAA. In one embodiment, the bacterial entity, e.g., species or strain, useful in the compositions and methods of the invention is *Clostridium asparagiforme*. In one embodiment, the bacterial entity, e.g., species or strain, useful in the compositions and methods of the invention is *Clostridium bolteae*. In one embodiment, the bacterial entity, e.g., species or strain, useful in the compositions and methods of the invention is *Clostridium clostridioforme*. In one embodiment, the bacterial entity, e.g., species or strain, useful in the compositions and methods of the invention is *Clostridium glycyrrhizinilyticum*. In one embodiment, the bacterial entity, e.g., species or strain, useful in the compositions and methods of the invention is *Clostridium* (*Hungatella*) *hathewayi*. In one embodiment, the bacterial entity, e.g., species or strain, useful in the compositions and methods of the invention is *Clostridium histolyticum*. In one embodiment, the bacterial entity, e.g., species or strain, useful in the compositions and methods of the invention is *Clostridium indolis*. In one embodiment, the bacterial entity, e.g., species or strain, useful in the compositions and methods of the invention is *Clostridium leptum*. In one embodiment, the bacterial entity, e.g., species or strain, useful in the compositions and methods of the invention is *Clostridium* (*Tyzzerella*) *nexile*. In one embodiment, the bacterial entity, e.g., species or strain, useful in the compositions and methods of the invention is *Clostridium perfringens*. In one embodiment, the bacterial entity, e.g., species or strain, useful in the compositions and methods of the invention is *Clostridium* (*Erysipelatoclostridium*) *ramosum*. In one embodiment, the bacterial entity, e.g., species or strain, useful in the compositions and methods of the invention is *Clostridium scindens*. In one embodiment, the bacterial entity, e.g., species or strain, useful in the compositions and methods of the invention is *Clostridium septum*. In one embodiment, the bacterial entity, e.g., species or strain, useful in the compositions and methods of the invention is *Clostridium* sp. 14774. In one embodiment, the bacterial entity, e.g., species or strain, useful in the compositions and methods of the invention is *Clostridium* sp. 7_3_54FAA. In one embodiment, the bacterial entity, e.g., species or strain, useful in the compositions and methods of the invention is *Clostridium* sp. HGF2. In one embodiment, the bacterial entity, e.g., species or strain, useful in the compositions and methods of the invention is *Clostridium symbiosum*. In one embodiment, the bacterial entity, e.g., species or strain, useful in the compositions and methods of the invention is *Collinsella aerofaciens*. In one embodiment, the bacterial entity, e.g., species or strain, useful in the compositions and methods of the invention is *Collinsella intestinalis*. In one embodiment, the bacterial entity, e.g., species or strain, useful in the compositions and methods of the invention is *Coprobacillus* sp. D7. In one embodiment, the bacterial entity, e.g., species or strain, useful in the compositions and methods of the invention is *Coprococcus catus*. In one embodiment, the bacterial entity, e.g., species or strain, useful in the compositions and methods of the invention is *Coprococcus comes*. In one embodiment, the bacterial entity, e.g., species or strain, useful in the compositions and methods of the invention is *Dorea formicigenerans*. In one embodiment, the bacterial entity, e.g., species or strain, useful in the compositions and methods of the invention is *Dorea longicatena*. In one embodiment, the bacterial entity, e.g., species or strain, useful in the compositions and methods of the invention is *Enterococcus faecalis*. In one embodiment, the bacterial entity, e.g., species or strain, useful in the compositions and methods of the invention is *Enterococcus faecium*. In one embodiment, the bacterial entity, e.g., species or strain, useful in the compositions and methods of the invention is Erysipelotrichaceae bacterium 3_1_53. In one embodiment, the bacterial entity, e.g., species or strain, useful in the compositions and methods of the invention is *Escherichia coli*. In one embodiment, the bacterial entity, e.g., species or strain, useful in the compositions and methods of the invention is *Escherichia coli* S88. In one embodiment, the bacterial entity, e.g., species or strain, useful in the compositions and methods of the invention is *Eubacterium eligens*. In one embodiment, the bacterial entity, e.g., species or strain, useful in the compositions and methods of the invention is *Eubacterium fissicatena*. In one embodiment, the bacterial entity, e.g., species or strain, useful in the compositions and methods of the invention is *Eubacterium ramulus*. In one embodiment, the bacterial entity, e.g., species or strain, useful in the compositions and methods of the invention is *Eubacterium rectale*. In one embodiment, the bacterial entity, e.g., species or strain, useful in the compositions and methods of the invention is *Faecalibacterium prausnitzii*. In one embodiment, the bacterial entity, e.g., species or strain, useful in the compositions and methods of the invention is *Flavonifractor plautii*. In one embodiment, the bacterial entity, e.g., species or strain, useful in the compositions and methods of the invention is *Fusobacterium mortiferum*. In one embodiment, the bacterial entity, e.g., species or strain, useful in the compositions and methods of the invention is *Fusobacterium nucleatum*.

In one embodiment, the bacterial entity, e.g., species or strain, useful in the compositions and methods of the invention is *Holdemania filiformis*. In one embodiment, the bacterial entity, e.g., species or strain, useful in the compositions and methods of the invention is *Hydrogenoanaerobacterium saccharovorans*. In one embodiment, the bacterial entity, e.g., species or strain, useful in the compositions and methods of the invention is *Klebsiella oxytoca*. In one embodiment, the bacterial entity, e.g., species or strain, useful in the compositions and methods of the invention is Lachnospiraceae bacterium 3_1_7FAA_CT1. In one embodiment, the bacterial entity, e.g., species or strain, useful in the compositions and methods of the invention is Lachnospiraceae bacterium 7_1_58FAA. In one embodiment, the bacterial entity, e.g., species or strain, useful in the compositions and methods of the invention is Lachnospiraceae bacterium 5_1_57FAA. In one embodiment, the bacterial entity, e.g., species or strain, useful in the compositions and methods of the invention is *Lactobacillus casei*. In one embodiment, the bacterial entity, e.g., species or strain, useful in the compositions and methods of the invention is *Lactobacillus rhamnosus*. In one embodiment, the bacterial entity, e.g., species or strain, useful in the compositions and methods of the invention is *Lactobacillus ruminis*. In one embodiment, the bacterial entity, e.g., species or strain, useful in the compositions and methods of the invention is *Lactococcus casei*. In one embodiment, the bacterial entity, e.g., species or strain, useful in the compositions and methods of the invention is *Odoribacter splanchnicus*. In one embodiment, the bacterial entity, e.g., species or strain, useful in the compositions and methods of the invention is *Oscillibacter valericigenes*. In one embodiment, the bacterial entity, e.g., species or strain, useful in the compositions and methods of the invention is *Parabacteroides gordonii*. In one embodiment, the bacterial entity, e.g., species or strain, useful in the compositions and methods of the invention is *Parabacteroides johnsonii*. In one embodiment, the bacterial entity, e.g., species or strain, useful in the compositions and methods of the invention is *Parabacteroides merdae*. In one embodiment, the bacterial entity, e.g., species or strain, useful in the compositions and methods of the invention is *Pediococcus acidilactici*. In one embodiment, the bacterial entity, e.g., species or strain, useful in the compositions and methods of the invention is *Peptostreptococcus asaccharolyticus*. In one embodiment, the bacterial entity, e.g., species or strain, useful in the compositions and methods of the invention is *Propionibacterium granulosum*. In one embodiment, the bacterial entity, e.g., species or strain, useful in the compositions and methods of the invention is *Roseburia intestinalis*. In one embodiment, the bacterial entity, e.g., species or strain, useful in the compositions and methods of the invention is *Roseburia inulinivorans*. In one embodiment, the bacterial entity, e.g., species or strain, useful in the compositions and methods of the invention is *Ruminococcus faecis*. In one embodiment, the bacterial entity, e.g., species or strain, useful in the compositions and methods of the invention is *Ruminococcus gnavus*. In one embodiment, the bacterial entity, e.g., species or strain, useful in the compositions and methods of the invention is *Ruminococcus* sp. ID8. In one embodiment, the bacterial entity, e.g., species or strain, useful in the compositions and methods of the invention is *Ruminococcus torques*. In one embodiment, the bacterial entity, e.g., species or strain, useful in the compositions and methods of the invention is *Slackia piriformis*. In one embodiment, the bacterial entity, e.g., species or strain, useful in the compositions and methods of the invention is *Staphylococcus epidermidis*. In one embodiment, the bacterial entity, e.g., species or strain, useful in the compositions and methods of the invention is *Staphylococcus saprophyticus*. In one embodiment, the bacterial entity, e.g., species or strain, useful in the compositions and methods of the invention is *Streptococcus cristatus*. In one embodiment, the bacterial entity, e.g., species or strain, useful in the compositions and methods of the invention is *Streptococcus dysgalactiae* subsp. *Equisimilis*. In one embodiment, the bacterial entity, e.g., species or strain, useful in the compositions and methods of the invention is *Streptococcus infantis*. In one embodiment, the bacterial entity, e.g., species or strain, useful in the compositions and methods of the invention is *Streptococcus oralis*. In one embodiment, the bacterial entity, e.g., species or strain, useful in the compositions and methods of the invention is *Streptococcus sanguinis*. In one embodiment, the bacterial entity, e.g., species or strain, useful in the compositions and methods of the invention is *Streptococcus viridans*. In one embodiment, the bacterial entity, e.g., species or strain, useful in the compositions and methods of the invention is *Streptococcus thermophiles*. In one embodiment, the bacterial entity, e.g., species or strain, useful in the compositions and methods of the invention is *Veillonella dispar*.

In one embodiment, the bacterial population useful in the compositions and methods of the invention comprises *Acidaminococcus intestine*. In one embodiment, the bacterial population useful in the compositions and methods of the invention comprises *Acinetobacter baumannii*. In one embodiment, the bacterial population useful in the compositions and methods of the invention comprises *Acinetobacter lwoffii*. In one embodiment, the bacterial population useful in the compositions and methods of the invention comprises *Akkermansia muciniphila*. In one embodiment, the bacterial population useful in the compositions and methods of the invention comprises *Alistipes putredinis*. In one embodiment, the bacterial population useful in the compositions and methods of the invention comprises *Alistipes shahii*. In one embodiment, the bacterial population useful in the compositions and methods of the invention comprises *Anaerostipes hadrus*. In one embodiment, the bacterial population useful in the compositions and methods of the invention comprises *Anaerotruncus colihominis*. In one embodiment, the bacterial population useful in the compositions and methods of the invention comprises *Bacteroides caccae*. In one embodiment, the bacterial population useful in the compositions and methods of the invention comprises *Bacteroides cellulosilyticus*. In one embodiment, the bacterial population useful in the compositions and methods of the invention comprises *Bacteroides dorei*. In one embodiment, the bacterial population useful in the compositions and methods of the invention comprises *Bacteroides eggerthii*. In one embodiment, the bacterial population useful in the compositions and methods of the invention comprises *Bacteroides finegoldii*. In one embodiment, the bacterial population useful in the compositions and methods of the invention comprises *Bacteroides fragilis*. In one embodiment, the bacterial population useful in the compositions and methods of the invention comprises *Bacteroides massiliensis*. In one embodiment, the bacterial population useful in the compositions and methods of the invention comprises *Bacteroides ovatus*. In one embodiment, the bacterial population useful in the compositions and methods of the invention comprises *Bacteroides salanitronis*. In one embodiment, the bacterial population useful in the compositions and methods of the invention comprises *Bacteroides salyersiae*. In one embodiment, the bacterial population useful in the compositions and methods of the invention comprises *Bacteroides* sp. 1_1_6. In one embodiment, the bacterial population useful in the compositions and methods of the invention comprises *Bacteroides* sp. 3_1_23. In one embodiment, the bacterial population useful in the compositions and methods of the invention comprises *Bacteroides* sp. D20. In one embodiment, the bacterial population useful in the compositions and methods of the invention comprises *Bacteroides thetaiotaomicrond*. In one embodiment, the bacterial population useful in the compositions and methods of the invention comprises *Bacteroides uniformis*. In one embodiment, the bacterial population useful in the compositions and methods of the invention comprises *Bacteroides vulgatus*. In one embodiment, the bacterial population useful in the compositions and methods of the invention comprises *Bifidobacterium adolescentis*. In one embodiment, the bacterial population useful in the compositions and methods of the invention comprises *Bifidobacterium bifidum*. In one embodiment, the bacterial population useful in the compositions and methods of the invention comprises *Bifidobacterium breve*. In one embodiment, the bacterial population useful in the compositions and methods of the invention comprises *Bifidobacterium faecale*. In one embodiment, the bacterial population useful in the compositions and methods of the invention comprises *Bifidobacterium kashiwanohense*. In one embodiment, the bacterial population useful in the compositions and methods of the invention comprises *Bifidobacterium longum* subsp. *Longum*. In one embodiment, the bacterial population useful in the compositions and methods of the invention comprises *Bifidobacterium pseudocatenulatum*. In one embodiment, the bacterial population useful in the compositions and methods of the invention comprises *Bifidobacterium stercoris*. In one embodiment, the bacterial population useful in the compositions and methods of the invention comprises *Blautia (Ruminococcus) coccoides*. In one embodiment, the bacterial population useful in the compositions and methods of the invention comprises *Blautia faecis*. In one embodiment, the bacterial population useful in the compositions and methods of the invention comprises *Blautia glucerasea*. In one embodiment, the bacterial population useful in the compositions and methods of the invention comprises *Blautia (Ruminococcus) hansenii*. In one embodiment, the bacterial population useful in the compositions and methods of the invention comprises *Blautia hydrogenotrophica (Ruminococcus hydrogenotrophicus)*. In one embodiment, the bacterial population useful in the compositions and methods of the invention comprises *Blautia (Ruminococcus) luti*. In one embodiment, the bacterial population useful in the compositions and methods of the invention comprises *Blautia (Ruminococcus) obeum*. In one embodiment, the bacterial population useful in the compositions and methods of the invention comprises *Blautia producta (Ruminococcus productus)*. In one embodiment, the bacterial population useful in the compositions and methods of the invention comprises *Blautia (Ruminococcus) schinkii*. In one embodiment, the bacterial population useful in the compositions and methods of the invention comprises *Blautia stercoris*. In one embodiment, the bacterial population useful in the compositions and methods of the invention comprises *Blautia* uncultured bacterium clone BKLE_a03_2 (GenBank: EU469501.1). In one embodiment, the bacterial population useful in the compositions and methods of the invention comprises *Blautia* uncultured bacterium clone SJTU_B_14_30 (GenBank: EF402926.1). In one embodiment, the bacterial population useful in the compositions and methods of the invention comprises *Blautia* uncultured bacterium clone SJTU_C_14_16 (GenBank: EF404657.1).

In one embodiment, the bacterial population useful in the compositions and methods of the invention comprises *Blautia* uncultured bacterium clone S1-5 (GenBank: GQ898099.1). In one embodiment, the bacterial population useful in the compositions and methods of the invention comprises *Blautia* uncultured PAC000178_s (www.ezbiocloud.net/eztaxon/hierarchy?m=browse&k=PAC000178&d=2). In one embodiment, the bacterial population useful in the compositions and methods of the invention comprises *Blautia wexlerae*. In one embodiment, the bacterial population useful in the compositions and methods of the invention comprises *Candidatus Arthromitus* sp. SFB-mouse-Yit. In one embodiment, the bacterial population useful in the compositions and methods of the invention comprises *Catenibacterium mitsuokai*. In one embodiment, the bacterial population useful in the compositions and methods of the invention comprises *Clostridiaceae* bacterium (*Dielma fastidiosa*) JC13. In one embodiment, the bacterial population useful in the compositions and methods of the invention comprises Clostridiales bacterium 1_7_47FAA. In one embodiment, the bacterial population useful in the compositions and methods of the invention comprises *Clostridium asparagiforme*. In one embodiment, the bacterial population useful in the compositions and methods of the invention comprises *Clostridium bolteae*. In one embodiment, the bacterial population useful in the compositions and methods of the invention comprises *Clostridium clostridioforme*. In one embodiment, the bacterial population useful in the compositions and methods of the invention comprises *Clostridium glycyrrhizinilyticum*. In one embodiment, the bacterial population useful in the compositions and methods of the invention comprises *Clostridium (Hungatella) hathewayi*. In one embodiment, the bacterial population useful in the compositions and methods of the invention comprises *Clostridium histolyticum*. In one embodiment, the bacterial population useful in the compositions and methods of the invention comprises *Clostridium indolis*. In one embodiment, the bacterial population useful in the compositions and methods of the invention comprises *Clostridium leptum*. In one embodiment, the bacterial population useful in the compositions and methods of the invention comprises *Clostridium (Tyzzerella) nexile*. In one embodiment, the bacterial population useful in the compositions and methods of the invention comprises *Clostridium perfringens*. In one embodiment, the bacterial population useful in the compositions and methods of the invention comprises *Clostridium (Erysipelatoclostridium) ramosum*. In one embodiment, the bacterial population useful in the compositions and methods of the invention comprises *Clostridium scindens*. In one embodiment, the bacterial entity, e.g., species or strain, useful in the compositions and methods of the invention is *Clostridium septum*. In one embodiment, the bacterial population useful in the compositions and methods of the invention comprises *Clostridium* sp. 14774. In one embodiment, the bacterial population useful in the compositions and methods of the invention comprises *Clostridium* sp. 7_3_54FAA. In one embodiment, the bacterial population useful in the compositions and methods of the invention comprises *Clostridium* sp. HGF2. In one embodiment, the bacterial population useful in the compositions and methods of the invention comprises *Clostridium symbiosum*. In one embodiment, the bacterial population useful in the compositions and methods of the invention comprises *Collinsella aerofaciens*. In one embodiment, the bacterial population useful in the compositions and methods of the invention comprises *Collinsella intestinalis*. In one embodiment, the bacterial population useful in the compositions and methods of the invention comprises *Coprobacillus* sp. D7. In one embodiment, the bacterial population useful in the compositions and methods of the invention comprises *Coprococcus catus*. In one embodiment, the bacterial population useful in the compositions and methods of the invention comprises *Coprococcus comes*. In one embodiment, the bacterial population useful in the compositions and methods of the invention comprises *Dorea formicigenerans*. In one embodiment, the bacterial population useful in the compositions and methods of the invention comprises *Dorea longicatena*. In one embodiment, the bacterial population useful in the compositions and methods of the invention comprises *Enterococcus faecalis*. In one embodiment, the bacterial population useful in the compositions and methods of the invention comprises *Enterococcus faecium*. In one embodiment, the bacterial population useful in the compositions and methods of the invention comprises Erysipelotrichaceae bacterium 3_1_53. In one embodiment, the bacterial population useful in the compositions and methods of the invention comprises *Escherichia coli*. In one embodiment, the bacterial population useful in the compositions and methods of the invention comprises *Escherichia coli* S88. In one embodiment, the bacterial population useful in the compositions and methods of the invention comprises *Eubacterium eligens*. In one embodiment, the bacterial population useful in the compositions and methods of the invention comprises *Eubacterium fissicatena*. In one embodiment, the bacterial population useful in the compositions and methods of the invention comprises *Eubacterium ramulus*. In one embodiment, the bacterial population useful in the compositions and methods of the invention comprises *Eubacterium rectale*. In one embodiment, the bacterial population useful in the compositions and methods of the invention comprises *Faecalibacterium prausnitzii*. In one embodiment, the bacterial population useful in the compositions and methods of the invention comprises *Flavonifractor plautii*. In one embodiment, the bacterial population useful in the compositions and methods of the invention comprises *Fusobacterium mortiferum*. In one embodiment, the bacterial population useful in the compositions and methods of the invention comprises *Fusobacterium nucleatum*. In one embodiment, the bacterial population useful in the compositions and methods of the invention comprises *Holdemania filiformis*. In one embodiment, the bacterial population useful in the compositions and methods of the invention comprises *Hydrogenoanaerobacterium saccharovorans*. In one embodiment, the bacterial population useful in the compositions and methods of the invention comprises *Klebsiella oxytoca*. In one embodiment, the bacterial population useful in the compositions and methods of the invention comprises Lachnospiraceae bacterium 3_1_7FAA_CT1. In one embodiment, the bacterial population useful in the compositions and methods of the invention comprises Lachnospiraceae bacterium 7_1_58FAA. In one embodiment, the bacterial population useful in the compositions and methods of the invention comprises Lachnospiraceae bacterium 5_1_57FAA. In one embodiment, the bacterial population useful in the compositions and methods of the invention comprises *Lactobacillus casei*. In one embodiment, the bacterial population useful in the compositions and methods of the invention comprises *Lactobacillus rhamnosus*. In one embodiment, the bacterial population useful in the compositions and methods of the invention comprises *Lactobacillus ruminis*. In one embodiment, the bacterial population useful in the compositions and methods of the invention comprises *Lactococcus casei*. In one embodiment, the bacterial population useful in the compositions and methods of the invention comprises *Odoribacter splanchnicus*. In one embodiment, the bacterial population useful in the compositions and methods of the invention comprises *Oscillibacter valericigenes*. In one embodiment, the bacterial population useful in the compositions and methods of the invention comprises *Parabacteroides gordonii*. In one embodiment, the bacterial population useful in the compositions and methods of the invention comprises *Parabacteroides johnsonii*. In one embodiment, the bacterial population useful in the compositions and methods of the invention comprises *Parabacteroides merdae*. In one embodiment, the bacterial population useful in the compositions and methods of the invention comprises *Pediococcus acidilactici*. In one embodiment, the bacterial population useful in the compositions and methods of the invention comprises *Peptostreptococcus asaccharolyticus*. In one embodiment, the bacterial population useful in the compositions and methods of the invention comprises *Propionibacterium granulosum*. In one embodiment, the bacterial population useful in the compositions and methods of the invention comprises *Roseburia intestinalis*. In one embodiment, the bacterial population useful in the compositions and methods of the invention comprises *Roseburia inulinivorans*. In one embodiment, the bacterial population useful in the compositions and methods of the invention comprises *Ruminococcus faecis*. In one embodiment, the bacterial population useful in the compositions and methods of the invention comprises *Ruminococcus gnavus*. In one embodiment, the bacterial population useful in the compositions and methods of the invention comprises *Ruminococcus* sp. ID8. In one embodiment, the bacterial population useful in the compositions and methods of the invention comprises *Ruminococcus torques*. In one embodiment, the bacterial population useful in the compositions and methods of the invention comprises *Slackia piriformis*. In one embodiment, the bacterial population useful in the compositions and methods of the invention comprises *Staphylococcus epidermidis*. In one embodiment, the bacterial population useful in the compositions and methods of the invention comprises *Staphylococcus saprophyticus*. In one embodiment, the bacterial population useful in the compositions and methods of the invention comprises *Streptococcus cristatus*. In one embodiment, the bacterial population useful in the compositions and methods of the invention comprises *Streptococcus dysgalactiae* subsp. *Equisimilis*. In one embodiment, the bacterial population useful in the compositions and methods of the invention comprises *Streptococcus infantis*. In one embodiment, the bacterial population useful in the compositions and methods of the invention comprises *Streptococcus oralis*. In one embodiment, the bacterial population useful in the compositions and methods of the invention comprises *Streptococcus sanguinis*. In one embodiment, the bacterial population useful in the compositions and methods of the invention comprises *Streptococcus viridans*. In one embodiment, the bacterial population useful in the compositions and methods of the invention comprises *Streptococcus thermophiles*. In one embodiment, the bacterial population useful in the compositions and methods of the invention comprises *Veillonella dispar*.

XII. Vaginal Dysbiosis

The healthy human vagina is dominated by a variety of *Lactobacillus* species, which play an essential role in protecting women from urogenital infection. Lactobacilli have the ability to adhere to vaginal epithelia, to inhibit the adhesion and growth of pathogens, deplete nutrients otherwise available to pathogens, and modulate the host immune response and microenvironment [1,2]. Most importantly, Lactobacilli metabolize the glycogen contained in the cells of the vaginal vault, forming lactic acid as the final product. Thus, in a healthy vagina, pH-values of 4.0-4.5 are reached, a level at which many pathogens cannot flourish.

Because vaginal infection is an important mechanism of disease responsible for preterm birth [3], maintaining the natural, healthy balance of the *Lactobacillus flora* in the vagina is particularly important during pregnancy. A deficiency in Lactobacilli can upset the microbial balance in the vagina, frequently resulting in the syndrome of bacterial vaginosis, which may be associated with a quantitative and qualitative shift from normally occurring Lactobacilli to a mixed flora dominated by anaerobic bacteria [6]. According to some, bacterial vaginosis is characterized by a complete loss of Lactobacilli and a concomitant increase in Gram-variable and Gram-negative rods, primary among them *Gardnerella vaginalis* as well as *Bacteroides, Prevotella,* and *Mobiluncus* species. However, loss of vaginal Lactobacilli also leaves nonpregnant women susceptible to infection which may result in endometritis or even pelvic inflammatory disease. During menopause, involution of the female genital tract occurs, reflecting possibly a built-in biologic life expectancy interrelated with the neurohypophyseal endocrine axis. The major universal change is vaginal atrophy. Vaginal dryness, burning, itching and dyspareunia are frequent complaints along with dysuria, urinary frequency and recurrent infections. The genitourinary atrophy following menopause is associated with a decline in estrogen secretion accompanied by depletion of Lactobacilli and increased colonization by pathogenic microorganisms associated with bacterial vaginosis and urinary tract infections. In post-menopausal women, vaginal estriol therapy reduces *E. coli* colonization and increases the numbers of Lactobacilli, with the result that the incidence of recurrent urinary and genital tract infections drops significantly. Several species of *Lactobacillus* have been described to populate the vagina to varying degrees. For some time the flora of healthy women of childbearing age was believed to be dominated by *Lactobacillus acidophilus* and *Lactobacillus fermentum*, followed by *Lactobacillus brevis, Lactobacillus jensenii* and *Lactobacillus casei*. In their study on the vaginal *Lactobacillus flora*, Vasquez et al. found that the vaginal flora of most participants was dominated by a single *Lactobacillus* species, with the presence of other species showing wide individual variability. The most frequently occurring species were *L. crispatus, L. gasseri, L. iners,* and *L. jensenii*. In another study by Reid et al., the most commonly isolated *Lactobacillus* strains were *L. jensenii, L. acidophilus, L. casei,* and *L. gasseri*. In recent Austrian studies, the predominant *Lactobacillus* species identified by species-specific PCR, namely *L. crispatus, L. gasseri, L. jensenii,* and *L. rhamnosus* were used to generate DNA fingerprints. *L. crispatus, L. gasseri, L. jensenii* and *L. rhamnosus* can be regarded as the predominant species in the vagina. To remedy deficiencies in the *Lactobacillus flora* (and hence, in the protective capability of the vaginal flora), the administration of vaginal suppositories containing Lactobacilli is the most common way of Lactobacilli substitution. Some authors believe that the topical use of Lactobacilli is a safe and promising treatment for the prevention of vaginosis and recurrent urinary tract infections. While vaginal supplementation is a long-standing, widely accepted practice for Lactobacilli substitution, oral administration of a *Lactobacillus* preparation represents a new concept for the restitution of a normal vaginal flora. Recent results indicate that the probiotic strains *L. rhamnosus* GR-1 (ATCC 55826) and *L. reuteri* RC-14 (ATCC 55845) can be taken orally on a daily basis for two months without any side effects. The consumption then resulted in a significant improvement of the vaginal flora in terms of increased Lactobacilli presence and decreased yeast and coliforms. While one group of authors discussed the beneficial effects in terms of an alteration in mucosal immunity or of probiotic bacteria ascending to the vagina from the rectal area [18], another group recently demonstrated, by species-specific PCR-amplification, that *L. rhamnosus* GR-1 and *L. reuteri* RC-14 can be delivered to the vaginal environment when administered orally.

Thus provided are compositions formulated for vaginal administration, such as bacterial populations. The bacterial populations are capable of translocating across vaginal tissue to distal sites, or relocation from the vaginal canal into the gastrointestinal tract.

Also provided are methods of defining one or more normal vaginal microbial communities, the method comprising: obtaining a plurality of single vaginal samples, wherein each single sample comprises vaginal microorganisms obtained from a female without vaginal pathology; using analytical laboratory techniques to obtain a plurality of microbial profiles, wherein each microbial profile is obtained from the single sample of vaginal microorganisms obtained from a female without vaginal pathology; identifying a plurality of consensus profiles from among the plurality of microbial profiles, thereby defining a plurality of normal vaginal microbial communities; and providing the plurality of consensus profiles to a user.

Thus provided are compositions formulated for vaginal administration, such as bacterial populations. The bacterial populations are capable of translocating across vaginal tissue to distal sites, or relocation from the vaginal canal into the gastrointestinal tract.

It has recently come to light that the DNA of commensal microbes, including many species of *Lactobacillus* protect against activation of lamina propria dendritic cells and sustain regulatory T cell conversion (Bouladoux N, Hall J A, Grainger J R, dos Santos L M, Kann M G, Nagarajan V, Verthelyi D, and Belkaid Y, 2012. Regulatory role of suppressive motifs from commensal DNA. Mucosal Immunol. 5: 623-634). Thus commensal DNA may protect against colitis, IBD, and/or other immunological intolerances in the gut. Furthermore, *Lactobacillus* species are prevalent in the healthy vaginal microbiome. Thus, DNA from *Lactobacillus* or other vaginal microbiome commensals may suppress immune responses in the vagina that could disrupt the normal healthy-state vaginal microbiome and lead to complications such as chronic HPV, infertility, miscarriages, or UTIs. As such, in certain embodiments, the microbial composition, pharmaceutical composition, dosage form, or kit additionally comprises DNA isolated from one or more host commensals.

In another embodiment, patients experiencing bacterial vaginosis—which increases the risk that a woman will suffer from a sexually transmitted disease or experience fertility issues—often presents with abnormally low lactic acid levels. Thus, patients with low lactic acid production in the vagina may be administered a microbial composition comprising lactic acid producing microbes (e.g., *Lactobacillus* species) to restore a healthy microbiome state.

Immunomodulation can also be achieved by the microbial production of glutathione or gamma-glutamylcysteine. Thus, in certain embodiments, the pharmaceutical composition, dosage form, or kit comprises at least one type of microbe capable of producing glutathione and/or gamma-glutamylcysteine in a mammalian subject. In some aspects, the composition, dosage form, or kit comprises one or more microbes selected for the presence of glutamate cysteine ligase (e.g., *Lactobacillus fermentum*) and/or L-proline biosynthesis enzymes (e.g., *E. coli*) (Peran et al., 2006. *Lactobacillus fermenum*, a probiotic capable of releasing glutathione, prevents colonic inflammation in the TNBS model of rat colitis. Int J Colorectal Dis. 21(8): 737-746; Veeravalli et al., 2011. Laboratory evolution of glutathione biosynthesis reveals naturally compensatory pathways. Nat Chem Bio. 7(2): 101-105). In a preferred embodiment, at least one microbe in the pharmaceutical composition, dosage form, or kit is *L. fermentum*.

XIII. Transplant Disorders and Graft Versus Host Disease (GVHD)

Graft versus host disease (GVHD) is a common and devastating complication following an allogeneic tissue transplant and occurs in approximately 50% of transplant recipients. Acute GVHD is a major source of morbidity and mortality following allogeneic hematopoietic cell transplantation. Approximately 25,000 allogeneic hematopoietic cell transplants (bone marrow, peripheral blood stem cell [PBSC], or cord blood transplants) are performed annually worldwide. Over time, a continuous increase has occurred in the number of unrelated donors and in the number of allogeneic transplants for AML, ALL, MDS, and lymphomas and this trend continues. There is also an increase in the allogeneic transplantations for non-malignant diseases and in patients over 50 years of age. The global incidence of acute GVHD ranges from 26%-34% in recipients of fully matched, sibling donor grafts to 42%-52% in recipients of matched, unrelated donor grafts. Evidence from the US suggests that incidence ranges from 30% in recipients of fully histocompatible transplants to 60%-70% in recipients of mismatched hematopoietic cells or hematopoietic cells from an unrelated donor. There is no FDA approved treatment for either acute or chronic GVHD. Treatment strategies for acute GVHD aim to reduce the immune reaction of the donor T cells against host tissues and therefore includes immunosuppressive treatment like cyclosporine, high dose steroids, and methotrexate. The standard therapy for de novo acute GVHD is high dose methylprednisolone, with expected response rates of 18%-50%. For patients who develop steroid-refractory acute GVHD, there is no standard of care therapy, and expected survival is less than 30%. Therefore, novel therapies are urgently needed for this patient population.

Graft-versus-host disease (GVHD) is a common complication for patients who have received an allogeneic transplant (e.g., allogeneic bone marrow transplant or allogeneic stem cell transplant). GVHD may also develop in patients who have received a blood transfusion with blood products that had not been irradiated. Patients suffering from GVHD have elevated levels of pro-inflammatory cytokines, particularly interleukin-6 (IL-6), as well as others including tumor necrosis factor-alpha (TNF-α), interleukin-1 (IL-1), interleukin-12 (IL-12), interferon-gamma (IFN-γ), and interleukin-2 (IL-2). GVHD is also associated with low interleukin-22 (IL-22) and the loss of interleukin-23 (IL-23)-responsive or Lgr5+ innate lymphoid cells. Furthermore, GVHD patients have reduced numbers of intestinal stem cells, fewer or less active Paneth cells, and lower Foxp3 expression in T cells.

For over 40 years, it has been known that the bacteria inhabiting our intestines are important modulators of the biology of hematopoietic cell transplantation (HCT) and impact the development of graft versus host disease. Studies in mice have shown reduction of GVHD with gut-decontaminating antibiotics (van Bekkum et al., 1974) and transplantation in germ-free conditions (Jones et al., 1971). This led to clinical attempts to eliminate intestinal bacterial colonization in allogenic BMT patients with a combination of gut decontamination practices and maintenance of a near-sterile environment (Storb et al., 1983). Initial clinical studies employing strategies to suppress the intestinal microbiota showed considerable promise, but later reports failed to demonstrate a clear and consistent benefit.

The recent understanding of the microbiota that inhabit the human gastrointestinal tract, skin, lungs, vagina, and other niches is being appreciated in their role in health and disease of dysbiosis (e.g. see Human Microbiome Project Consortium 2012, Structure, function, and diversity of the healthy human microbiome. Nature 486(7402):207-14). Several groups have reported preliminary data on the significance of the gut microbiota in HCT patients and in the development of GVHD. Collectively these reports show, using murine and human studies, that there is a significant decreased in diversity of gut microbiome following HCT accompanied by marked changes in the population (Taur et al., 2012; Jenq et al., 2012; Taur et al., 2014). Most notably, we have found that as much as 90% of allo BMT patients demonstrate a loss of diversity and a corresponding expansion of a single type of bacteria that takes up much of the "space" within the intestinal flora compartment (Taur Y, et al. Clin Infect Dis. 2012).

Aspects of the invention are based, in part, on the realization that microbes play an important role in the prevention, initiation and development of graft versus host disease (GVHD). The presence of certain microbial populations correlate with the initiation and development of the disease. More importantly, the presence of some species correlates with reduced severity or mortality associated with the disease or protection from GVHD altogether.

Any disruption from a preferred (e.g., ideal, normal, or beneficial) state of the microbiota can be considered a dysbiosis, even if such dysbiosis does not result in a detectable disease or disorder, or decrease in health. This state of dysbiosis may lead to a disease or disorder (e.g. GVHD, transplant rejection, and related conditions), or the state of dysbiosis may lead to a disease or disorder (e.g. GVHD, transplant rejection, and related conditions) only under certain conditions, or the state of dysbiosis may prevent a subject from responding to treatment or recovering from a disease or disorder (e.g. GVHD, transplant rejection, and related conditions). In the case of GVHD, a gastrointestinal dysbiosis can contribute to the pathology of GVHD by increasing inflammation and/or reducing intestinal barrier integrity. A dysbiosis distal to the gastrointestinal tract can also contribute to GVHD pathology, for example, by increasing systemic inflammation in the subject. In one embodiment, the distal dysbiosis is at or near the site of the transplant. Accordingly, probiotic compositions of the invention that modulate the microbiome, e.g., to correct a dysbiosis, can be used to prevent or treat GVHD in a transplant recipient. In addition, probiotic compositions that reduce inflammation and/or increase intestinal barrier integrity can be used to prevent or treat GVHD in a transplant recipient.

In some aspects, the invention is a composition or method for the treatment of GVHD in patients suffering from chronic or acute GVHD. In certain embodiments, the pharmaceutical composition, dosage form, or kit comprises one or more microbes, with or without one or more prebiotics, capable of decreasing the expression or release of one or more of IL-6, IL-1, IL-12, IL-2, IFN-γ, and TNF-α. In some embodiments, the pharmaceutical composition, dosage form, or kit comprises one or more microbes capable of increasing the expression or release of IL-22. The microbial composition, with or without one or more prebiotics, may also be selected such that it is effective to stimulate or favor the survival of Paneth cells, intestinal stem cells, FoxP3+ Treg cells (e.g., CD4+ CD25+ FoxP3+ Treg cells), IL-23-responsive innate lymphoid cells, and/or Lgr5+ innate lymphoid cells. In some embodiments, the microbial composition, with or without one or more prebiotics, regulates expression of Foxp3 by modulating (de)methylation of the Foxp3 locus. In preferred embodiments, the immunological tolerance elicited by the microbial composition, with or without one or more prebiotics, does not reduce graft-vs-leukemia activity by the immune system.

In certain aspects, the invention provides probiotic microbial compositions, optionally comprising prebiotics, non-microbial immunomodulatory carbohydrates, or microbial immunomodulatory cell components, that are effective for the prevention or treatment of transplant disorders in a transplant recipient. Such disorders, e.g., GVHD, transplant rejection, sepsis, etc. are associated with systemic inflammation and/or loss of intestinal barrier function. In one embodiment, the transplant recipient has an autoimmune or inflammatory disorder. For example, a subject with an autoimmune or inflammatory disorder may receive a transplant, e.g., a hematopoietic stem cell transplant, for example, and autologous hematopoietic stem cell transplant, as a treatment modality for the autoimmune or inflammatory disorder. In this embodiment, administration of the probiotic (and optional prebiotic) compositions of the invention can be used to prevent or treat GVHD in the subject receiving the transplant, and can additionally or alternatively be used to treat the underlying autoimmune or inflammatory disorder. Exemplary autoimmune or inflammatory disorders include, for example, lupus, multiple sclerosis, systemic sclerosis, Crohn's disease, type I diabetes, or juvenile idiopathic arthritis. Additional autoimmune or inflammatory disorders include, for example, an inflammatory bowel disease (IBD) including but not limited to ulterative colitis and Crohn's disease, multiple sclerosis (MS), systemic lupus erythematosus (SLE), type I diabetes, rheumatoid arthritis, Sjögren's syndrome, and Celiac disease. In certain embodiments, the compositions comprise at least one type of microbe and at least one type of carbohydrate (a prebiotic), and optionally further comprise microbial immunomodulatory cell components or substrates for the production of immunomodulatory metabolites, that are effective for the prevention or treatment of an autoimmune or inflammatory disorder. We also disclose herein methods for the prevention and/or treatment of autoimmune and inflammatory diseases in human subjects, e.g., transplant recipients.

In one embodiment, the subject is receiving a hematopoietic stem cell transplant. In other embodiments, the subject is receiving a bone marrow transplant. In other embodiments, the subject is receiving a solid organ transplant, e.g., a kidney transplant, a heart transplant, a lung transplant, a skin transplant, a liver transplant, a pancreas transplant, an intestinal transplant, an endocrine gland transplant, a bladder transplant, and/or a skeletal muscle transplant.

In some aspects, the invention is a composition or method for the prevention of GVHD. Recent work has shown that small doses of IL-2 may be able to restore T cell homeostasis in patients at risk for GVHD (Kennedy-Nasser et al., 2014. Ultra low-dose IL-2 for GVHD prophylaxis after allogeneic hematopoietic stem cell transplantation mediates expansion of regulatory T cells without diminishing antiviral or anti-leukemic activity. Clin Cancer Res. 20:2215-2225). Thus in certain embodiments, the pharmaceutical composition, dosage form, or kit comprises one or more microbes capable of slightly increasing IL-2 levels in a patient such that the abundance of CD4+ CD25+ FoxP3+ Treg cells increases by 1.5-fold, 2-fold, or more than 5-fold. In a preferred embodiment, the IL-2-level enhancing treatment is administrated between one week and one month following the patient's transplant procedure.

Aspects of this invention are based at least in part on the discovery that presence of certain bacterial populations can protect from GVHD and that supplementation with such or similar bacterial compositions can prevent, treat or inhibit GVHD. Similarly, aspects of this invention also includes approaches used for augmentation of such bacterial compositions using various techniques including substrates for bacterial fermentation and propagation as well as delivery of key end products or metabolites of such bacteria which reconstitute needed functionality of a bacterial community can also be used to prevent, treat or inhibit GVHD. Other aspects of this invention include agents for targeting bacteria that increase GVHD mortality or exacerbate clinical GVHD.

Herein, we disclose methods for identifying bacterial subsets that increased or decreased GVHD related mortality in order to identify subsets that may modulate GVHD severity Stool specimen was collected from patients who underwent conventional (non-T cell depleted) allo BMT. Fecal samples were collected and stored weekly over the course of the transplant hospitalization this included prior to conditioning, as well as on days 0, 7, 14, 21, 30, 60, and 100. GVHD was diagnosed clinically, confirmed pathologically by biopsy whenever possible, and classified according to standard criteria. Patients who engrafted were evaluable for acute GVHD based on historical consensus criteria as described previously (see Rowlings P A, Przepiorka D, Klein J P, et al. IBMTR Severity Index for grading acute graft-versus-host disease: retrospective comparison with Glucksberg grade. *Br J Haematol.* 1997). These criteria were applied to GVHD with purely acute features that occurred after day 100. Cases of GVHD were further categorized by treatment with or without systemic steroids (prednisone or methylprednisolone, 0.5 mg/kg daily or higher). Cause of death was determined using a standard algorithm where outcomes were prioritized in the following order: 1) primary disease recurrence, 2) graft failure, 3) GVHD, 4) infection, and 5) organ failure; thus in patients without disease recurrence or graft failure, those who were being treated for GVHD at the time of death were considered to have succumbed to GVHD-related mortality, including those who died from infections. In some embodiments, the abundances of bacterial genera from patients who did or did not die from GVHD by linear discriminant analysis (LDA) effect size (LEfSe) was compared to identify bacterial subsets associated with either increased or decreased GVHD-related mortality.

Provided herein are probiotic compositions of bacteria that modulate GVHD severity and related mortality and thus can be used to prevent, treat or inhibit GVHD. In one embodiment, a probiotic composition is administered to a subject in an amount effective to increase short chain fatty acid production by one or more organisms in the gut of a mammalian host.

In certain aspects, the invention relates to microbial compositions. In certain embodiments, the microbial compositions can be used for the prevention, treatment or inhibition of GVHD. Aspects of the invention relate to microbial compositions that are being isolated from a subject's microbiota. In some embodiments, the subject is a healthy mammal. In other embodiments, the subject is the recipient of the transplant prior itself prior to inception of the conditioning regimen. In some embodiments, the microbial compositions comprise of bacteria that are enriched in alive GVHD patients. These bacteria are strongly predictive of improved overall survival following allo BMT and largely driven by reduced GVHD-related mortality.

In some embodiments, the microbial composition comprises bacteria that are associated with and can reduce clinical acute GVHD. In some embodiments, the microbial composition comprises of bacteria that can reduce acute GVHD grades 2-4. In some embodiments, the microbial composition comprises of bacteria that can reduce acute GVHD responsive to treatment with systemic corticosteroids. In some embodiments, the microbial composition comprises of bacteria that can reduce systemic corticosteroid treatment refractory acute GVHD. In some embodiments, the microbial composition comprises of bacteria that are associated with reduced lower gut GVHD. In some embodiments, the microbial composition comprises of bacteria that are associated with reduced liver GVHD. In some embodiments, the microbial composition comprises of bacteria that are associated with reduced skin GVHD.

In some embodiments, the microbial composition comprises bacteria that are associated with and can reduce clinical chronic GVHD in a subject. In some embodiments, the subject has chronic GVHD. The subject with chronic GVHD may be receiving an immunosuppressive treatment. The immunosuppressive treatment may be one or more of methotrexate, cyclosporine, a corticosteroid, and antithymocyte globulin. The corticosteroid may be methylprednisolone. In some embodiments, the subject requires or has required immunosuppressive treatment for a period of one or more years. In further embodiments, the subject has steroid-refractory GVHD. The subject may be receiving one or more of extracorporeal photophoresis, anti-TNF alpha antibody, mammalian target of rapamycin (mTOR) inhibitor, mycophenolate mofetil, interleukin-2 receptor antibody, alemtuzumab pentostatin, mesenchymal stem cells, and methotrexate.

Aspects of this intervention also includes identification of antimicrobial agents that increase GVHD incidence and severity by impacting bacteria that are protective against GVHD. Identification of such bacteria can be used as a guide to alter clinical practice to reduce GVHD incidence/severity. Antibiotics are used in BMT patients either for gut decontamination purposes or to treat neutropenic fever. In some embodiments, BMT patients were analyzed to identify if antibiotics they were administered such as piperacillin-tazobactam, imipenem-cilastatin, metronidazole, aztreonam and oral vancomycin lead to reduction in bacteria protective against GVHD including clostridiales such as *Blautia*. In some embodiments, BMT patients were analyzed to identify if antibiotics they were administered such as piperacillin-tazobactam, imipenem-cilastatin, metronidazole, aztreonam and oral vancomycin lead to increase in bacteria that exacerbate GVHD. In some embodiments, BMT patients were retroactively analyzed to see if exposure to antibiotics with or without anaerobic coverage could impact on GVHD. In some embodiments, the microbial composition comprises bacteria that are associated with GVHD-related mortality.

Aspects of this invention also includes agents that targets bacterial populations exacerbate clinical GVHD, increase incidence or severity of GVHD or increase GVHD related mortality.

Aspects of this invention also includes approaches used for augmentation of bacterial compositions that prevent or mitigate GVHD using various techniques including substrates for bacterial fermentation and propagation. It was noted that patients undergoing BMT can lose GVHD protective bacteria without any exposure to antibiotics. This phenomenon was also noted in murine models with experimental GVHD. In some embodiments, the composition of the invention comprises substrates that augment bacterial compositions that prevent or mitigate GVHD. Given diet and nutrition has a tremendous impact on gut microbiome composition and that oral nutrition intake is commonly reduced in allo BMT patients, the impact of nutrition on GVHD protective bacteria abundance was analyzed. In some embodiments, the effect of reduced oral caloric consumption, particularly below 500 kcal/day, on *Blautia* abundance was analyzed. A pilot experiment of daily nutritional and flora monitoring in five patients undergoing allo BMT showed that a reduction in oral caloric consumption, particularly below 500 kcal/day, was associated with a reduction in *Blautia* abundance. Given *Blautia*'s ability to mitigate GVHD, a nutrition method to augment *Blautia* levels in BMT patients would be a rationale strategy for mitigating GVHD. The ability of *Blautia* to ferment a variety of sugars was thus analyzed using pH and optical density to evaluate bacterial growth in media lacking glucose. In one embodiment, the growth of *Blautia* was analyzed. In another embodiment, bacteria that are potentially competing with *Blautia* such as *Lactobacillus johnsonii*. *Lactobacillus johnsonii* was evaluated. *Lactobacillus johnsonii* expands in the setting of calorie restriction at the expense of Clostridia (Jenq et al., 2012) and is thus presumably a direct competitor for nutrients in the murine intestine. Using such strategies, specific substrates or sugars were identified that are fermentable by *Blautia* but not *lactobacillus*. In one embodiment, the substrate that specifically augments *Blautia* but not *lactobacillus* was xylose. In another embodiment, the substrate that specifically augments *Blautia* but not *lactobacillus* was rhamnose. In another embodiment, the effect of administration of such substrates on *Blautia* level was investigated in experimental GVHD models. Administration of xylose in the drinking water of mice was found to lead to an expansion of *Blautia* in the intestinal flora de-spite the presence of GVHD on day 14 after BMT. In another embodiment, long term effect of xylose administration was evaluated to investigate effects on GVHD related survival. Long-term administration of xylose led to improved survival of mice with GVHD.

Aspects of this invention also include compositions of bacterial end products or metabolites that are responsible or can impart the functionality of a bacterial compositions that prevent or mitigate GVHD. Short-chain fatty acids (SCFA), which are produced by many bacteria as a byproduct of carbohydrate fermentation. SCFA are one of the most abundant metabolites produced by the gut microbiome, particularly the class clostridia. SCFA have been found to be important modulators of the immune system. In germ-free mice and vancomycin-treated conventional mice, administration of SCFA (acetate, propionate, or butyrate) restored normal numbers of Tregs in the large intestine (Smith P M, et al. Science. 2013; 569-573). In some embodiments, the SCFA levels of stool specimens from GVHD patients were analyzed for associations with *Blautia* abundance. Samples with reduced abundance of *Blautia* were also found to have reduced abundance of the SCFA butyrate and acetate. In some embodiments, SCFA will be administered post BMT to reduce incidence and severity of GVHD. In some embodiment, the SFCA administered is acetate. In some embodiment, the SFCA administered is butyrate while in other embodiments it is propionate. In some embodiments, SCFA will reduce GVHD without impacting graft versus tumor effects. In some embodiments, SCFA administration increases the number of peripheral tregs and leads to induction of Foxp3 expression. In some embodiments, SCFA administration reduces donor alloreactive T cells.

In some embodiments, metabolite profiles of patient tissue samples or microbes cultures from patient tissue are used to identify risk factors for developing an autoimmune or inflammatory response, to diagnose an autoimmune or inflammatory disease, to evaluate the prognosis or severity of said disease, to evaluate the success of a treatment regimen, or any combination thereof. Exemplary metabolites for the purposes of diagnosis, prognostic risk assessment, or treatment assessment purposes include short chain fatty acids, bile acids, and lactate. In preferred embodiments, metabolite profiles are taken at different time points during a patient's disease and treatment in order to better evaluate the patient's disease state including recovery or relapse events. Such monitoring is also important to lower the risk of a patient developing a new autoimmune condition following immunomodulatory treatment. In some embodiments, metabolite profiles inform subsequent treatment. For example, patients at risk for developing GVHD and presenting low levels of butyrate may be administered a microbial composition comprising microbes that produce butyrate (e.g., *Blautia* species) and excluding microbes capable of depleting butyrate (e.g. *Methanobacterium* species). Probiotic compositions that produce SCFA in the gut of a subject are particularly useful for the treatment of GVHD, because they improve intestinal barrier integrity, which is associated with improvement in overall survival in patients receiving a transplant.

In some embodiments, the administration is preventative or prophylactic in that the subject has not yet developed a detectable GVHD. In some embodiments, the preventative/prophylactic microbial composition will be administered prior after the completion of conditioning region but prior to the transplant. Typically, it takes 2-3 weeks for engraftment of the transplant to be completed. In some embodiments, the preventative/prophylactic microbial composition will be administered once prior to transplant and then again on day 17 after completion of antibiotics prescribed to prevent or treat neutropenic fever or other infections.

The classical definition of Graft versus host disease (GVHD) is that it is an immunological disorder in which the immune cells of a transplant attack the tissues of a transplant recipient and lead to organ dysfunction. In the case of allogeneic bone marrow (BM) transplantation, T-cells from the transplanted BM recognize the host (the bone marrow-transplanted patient i.e., the recipient) as non-self and attack its tissues and organs. The organs most commonly attacked are the gastrointestinal (GI) tract, skin, liver, and lungs. Historical data, however, says it is not only immune cells that are involved in disease pathogenesis and points to the importance of the resident host gut microbes in the development of GVHD.

GVHD can be mild, moderate, or severe, depending on the extent of damage inflicted to different organs. The disease is divided into acute and chronic GVHD according to clinical manifestations. Patients with acute GVHD typically suffer damage to the skin, GI tract, and liver. Skin damage ranges from redness to exfoliation. Insult to the GI tract can result in bloody diarrhea and blood loss. Liver manifestations, though usually cholestatic in nature, can include liver failure in rare cases.

Acute GVHD usually develops within the first 100 days after transplantation, but it can also occur later. The clinical manifestations of chronic GVHD include red and itchy skin, dry eyes, dry mouth, abnormal liver function with jaundice, and lung damage due to bronchiolitis obliterans. Chronic GVHD is the major cause of non-relapse mortality after allogeneic hematopoietic transplantations. Chronic GVHD usually develops more than 100 days after transplantation, but it can appear sooner.

Patients with chronic GVHD require prolonged immunosuppressive treatment, averaging two to three years in length. The mechanisms underlying chronic GVHD are considered to be somewhat distinct from those of acute GVHD. Thus, chronic GVHD is not simply an end-stage of acute GVHD.

Clinical Staging of Acute GVHD (aGVHD)—There are two systems for quantifying the severity of aGVHD, namely, the International Bone Marrow Transplant Registry (IBMTR) grading system and the Glucksberg grading system. For both systems, the stage of aGVHD is first determined separately in the three main target organs (skin, liver and gut). These grades are then used to determine an overall aGVHD grade, using either the International Bone Marrow Transplant Registry (IBMTR) or Glucksberg criteria.

For each grading system, the acute GVHD stage for each target organ is first determined according to certain clinical measures, as provided in Table 3.

The invention also provides, in one aspect, a method of increasing the duration of survival of a subject receiving a bone marrow transplant, by administering to the subject a probiotic composition comprising an isolated bacterial population, such that the duration of survival of the subject is increased. In a preferred embodiment, the bacterial population is a human-derived bacterial population. A human-derived bacterial population includes bacterial strains that natively inhabit a human host, as opposed to a non-human mammalian host. Administration of the probiotic composition can reduce the likelihood that the subject will develop sepsis following the bone marrow transplant. Administration of the probiotic composition can also reduce the likelihood that the subject will develop graft versus host disease (GVHD) following the bone marrow transplant. The probiotic composition can be administered to the subject prior to, after, or concurrently with receiving the bone marrow transplant.

In one embodiment, the probiotic composition reduces intestinal permeability in the subject. This can be achieved by, for example, administering a probiotic composition that contains bacteria which produce short chain fatty acids, which increase intestinal barrier integrity in a subject. In exemplary embodiments, the bacteria produce butyrate, acetate, propionate, or valerate, or combinations thereof. Also provided is a method of reducing intestinal permeability in a subject receiving a transplant, comprising administering to the subject a probiotic composition comprising an isolated bacterial population and a pharmaceutically acceptable excipient, such that the intestinal permeability of the subject of the subject receiving the transplant is reduced.

In another embodiment, the probiotic composition reduces inflammation in the subject, e.g., in the gastrointestinal tract, or in a distal location. The probiotic composition can contain anti-inflammatory bacteria. Anti-inflammatory bacteria are described herein. For example, anti-inflammatory bacteria included in the probiotic composition can decrease secretion of pro-inflammatory cytokines (e.g., IFNγ, IL-12p70, IL-1α, IL-6, IL-8, MCP1, MIP1α, MIP1β, TNFα, and combinations thereof) and/or increase secretion of anti-inflammatory cytokines (e.g., IL-10, IL-13, IL-4, IL-5, TGFβ, and combinations thereof) by human host cells, such as human epithelial cells or immune cells, e.g., peripheral blood mononuclear cells (PBMCs). Bacteria which produce short chain fatty acids also have anti-inflammatory properties.

In some embodiments, the subject has received or will receive a hematopoietic stem cell transplant. In some embodiments, the subject will receive a hematopoietic stem cell transplant that is T cell depleted.

In exemplary embodiments, the subject has a disorder such as a hematopoietic neoplastic disorder, leukemia, lymphoma, and multiple myeloma. In some embodiments, the subject has a hematopoietic neoplastic disorder. The subject may have leukemia. The leukemia may be chronic myelogenous leukemia or chronic lymphocytic leukemia. In some embodiments, the subject has lymphoma. The lymphoma may be Hodgkin's disease or non-Hodgkin's lymphoma. In some cases, the subject has multiple myeloma. The subject may receive or will receive a bone marrow, peripheral blood stem cell, or cord blood transplant. In some embodiments, the subject has received or will receive whole body irradiation. In further embodiments, the subject is female.

Due to the unique mechanism of action of probiotic compositions in the treatment or prevention of GVHD, probiotic compositions can be selected which minimize GVHD, but do not significantly reduce or eliminate the graft versus tumor (GVT) effect of the bone marrow transplant.

In other embodiments, the subject receiving the transplant has an autoimmune disorder, such as, for example, lupus, multiple sclerosis, systemic sclerosis, Crohn's disease, type I diabetes, and juvenile idiopathic arthritis. In another embodiment, the subject receiving the transplant has sickle cell disease or sickle cell anemia.

In an exemplary embodiment, the invention provides a method of increasing the duration of survival of a subject receiving a bone marrow transplant, comprising administering to the subject a probiotic composition comprising an isolated population of anti-inflammatory bacteria capable of decreasing secretion of pro-inflammatory cytokines and/or increasing secretion of anti-inflammatory cytokines by human peripheral blood mononuclear cells (PBMCs), and a pharmaceutically acceptable excipient, in an amount effective to reduce inflammation in the gastrointestinal tract of the subject, such that the duration of survival of the subject is increased.

In some embodiments, the subject has received or will receive a transplant from an HLA-matched related donor or an HLA-matched unrelated donor. The subject may also have received or may receive a transplant from an HLA-mismatched related or unrelated donor. In some embodiments, the subject will receive an autologous transplant. In some embodiments, the microbial composition will augment an autologous or allogeneic transplant. In some embodiments, the microbial composition will improve engraftment after an autologous or allogeneic transplant. In some embodiments, the microbial composition will improve neutropenic recovery after an autologous or allogeneic transplant. In some embodiments, the microbial composition will reduce complications after an allogeneic transplant. In some embodiments, the microbial composition will reduce complications after an autologous transplant. Complications after allogeneic transplant may include but are not limited to infections, organ failure, Veno-occlusive disease (VOD) of the liver, and/or Interstitial Pneumonia Syndrome (IPS).

In some embodiments, the subject will receive GVHD prophylaxis regimen that are standardly used in the clinic in addition to the microbial composition. This may include administering immunosuppressive treatment such as methotrexate, cyclosporine, corticosteroids, or anti-thymocyte globulin.

In some embodiments, the subject will receive GVHD treatment regimen that are standardly used in the clinic in addition to the microbial composition for management of graft versus host disease. The joint working group established by the Haemato-oncology subgroup of the British Committee for Standards in Haematology (BCSH) and the British Society for Bone Marrow Transplantation (BSBMT) reviewed the available literature and made recommendations in 2012 for the management of acute graft-versus-host disease. Their recommendations are as follows: (1) The management of grade I disease should include topical therapy and optimizing levels of calcineurin inhibitors without the need for additional systemic immunosuppression. (2) The use of systemic corticosteroids is recommended for first line therapy for grade II-IV GVHD. (3) The following agents are suggested for use in the second line treatment of steroid-refractory acute GVHD: extracorporeal photopheresis, anti-tumour necrosis factor a antibodies, mammalian target of rapamycin (mTOR) inhibitors, mycophenolate mofetil, interleukin-2 receptor antibodies. (4) The following agents are suggested as third line treatment options in acute steroid-refractory GVHD: alemtuzumab pentostatin, mesenchymal stem cells and methotrexate. In one aspect, disclosed herein are methods of treating, inhibiting, or preventing GVHD in a subject wherein the subject has acute steroid-refractory GVHD. In such methods, the method can further comprise administering to the subject extracorporeal photopheresis, anti-tumour necrosis factor a antibodies, mammalian target of rapamycin (mTOR) inhibitors, mycophenolate mofetil, interleukin-2 receptor antibodies, alemtuzumab pentostatin, mesenchymal stem cells, methotrexate, or any combination thereof.

In other embodiments, the subject is administered a prebiotic composition in conjunction with the probiotic composition. For example, in one aspect, the invention provides method of increasing the duration of survival of a subject receiving a bone marrow transplant, by administering to the subject a probiotic composition comprising an isolated bacterial population, wherein the probiotic composition reduces intestinal permeability in the subject, and administering a prebiotic that enhances the activity of the bacterial population, such that the duration of survival of the subject is increased. Prebiotic compositions of the invention are described herein. Exemplary prebiotics are provided in Table 7, and in FIG. 29.

The invention also provides, in certain aspects, method of preventing or treating graft versus host disease (GVHD) in a subject receiving a transplant, comprising administering to the subject a probiotic composition comprising an isolated bacterial population, such that GVHD is prevented or treated. The probiotic composition can increase the duration of survival of the transplant recipient, by preventing GVHD, and/or preventing the development of sepsis. Preferably the bacterial population is a human-derived bacterial population. As noted above, the subject may be receiving a hematopoietic stem cell transplant or a bone marrow transplant. In other embodiments, the subject is receiving a solid organ transplant.

GVHD commonly develops after an allogeneic bone marrow transplant (BMT) but it can also appear after solid organ transplantation. The exact incidence rate of GVHD after solid organ transplantation is unknown. Mild cases likely remain undiagnosed because the clinical features of fever, rash, and diarrhea can be misinterpreted as related to post-transplantation infections. The incidence rate of GVHD is highest after small bowel transplantation (about 5%), followed by liver transplantation. But in general, the incidence rate for solid organ transplantation is very small relative to bone marrow transplantation. In embodiments, the microbial composition is used to prevent or treat GVHD in solid organ transplant recipients.

In some embodiments, the microbial composition will be administered to subjects receiving solid organ transplantation. Transplanted solid organs may include a kidney, heart, skin, a lung, a liver, a pancreas, an intestine, an endocrine gland, a bladder, or a skeletal muscle. In some embodiments, microbial composition will be used to prevent graft rejection in a recipient of a transplanted solid organ. In some embodiments, microbial composition will be used to prevent other complications of solid organ transplantation such as infections.

In exemplary embodiments, the subject has a hematopoietic neoplastic disorder such as, for example, leukemia, lymphoma, or multiple myeloma, an autoimmune disorder such as, for example, lupus, multiple sclerosis, systemic sclerosis, Crohn's disease, type I diabetes, or juvenile idiopathic arthritis, or a sickle cell disorder such as, for example, sickle cell disease or sickle cell anemia.

Aspects of this invention also include an immune mechanism via which acute or chronic GVHD or solid organ transplant recipients are managed. In some embodiments, a test article inhibits the functionality of antigen presenting cells such as dendritic cells where the test article is the microbial composition, prebiotics, microbial composition plus prebiotics or microbial metabolites. In some embodiments, a test article inhibits maturation of antigen presenting cells such that levels of CD40, CD80, CD86, PD-L1 and PD-L2 are modulated. In some embodiments, test article inhibits activity of antigen presenting cells such that production of cytokines such as TGFβ, IL-10, IL-4, IL-12 are modulated. In some embodiments, test article inhibits activity of antigen presenting cells such as their endocytic/phagocytic capacity is hindered. In some embodiments, test article inhibits activity of antigen presenting cells such that their ability to activate naïve T cells is hindered.

In some embodiments, test article inhibits the functionality of T cells where the test article is the microbial composition, prebiotics, microbial composition plus prebiotics or microbial metabolites. In some embodiments, test article alters the functionality of CD4+ T cells such that their activation status is altered affecting surface levels of CD25. In some embodiments, test article alters the functionality of CD4+ T cells such that their proliferative capacity is inhibited. In some embodiments, test article increases the number and differentiation of peripheral regulatory T cells. In some embodiments, the test article affects production of cytokines by T cells such as but not limited to IL-6, TNF-alpha, IFN-γ, IL-10, IL-4. In some embodiments, the test article reduces the cytotoxic capacity of effector CD8+ cells.

As described herein, reducing systemic or local inflammation in a subject reduces the likelihood that a subject will develop GVHD. Accordingly, in another embodiment, the invention provides a method of reducing inflammation in the gastrointestinal tract of a subject receiving a transplant, by administering to the subject a probiotic composition comprising an isolated, anti-inflammatory bacterial population and a pharmaceutically acceptable excipient, such that inflammation in the gastrointestinal tract of the subject receiving the transplant is reduced. Probiotic compositions containing anti-inflammatory bacterial populations described herein are suitable for the practice of this embodiment.

Additional probiotic compositions useful for treatment or prevention of GVHD contain bacterial strains capable of reducing inflammation in a subject. Such immunomodulatory (anti-inflammatory) bacteria can modulate cytokine expression by host immune cells, resulting in an overall increase in secretion of anti-inflammatory cytokines and/or an overall decrease in secretion of pro-inflammatory cytokines, systemically reducing inflammation in the subject. In exemplary embodiments, probiotic compositions useful for treatment or prevention of GVHD stimulate secretion of one or more anti-inflammatory cytokines by host immune cells, such as PBMCs. Anti-inflammatory cytokines include, but are not limited to, IL-10, IL-13, IL-9, IL-4, IL-5, TGFβ, and combinations thereof. In other exemplary embodiments, probiotic compositions useful for treatment or prevention of GVHD inhibit secretion of one or more pro-inflammatory cytokines by host immune cells, such as PBMCs. Pro-inflammatory cytokines include, but are not limited to, IFNγ, IL-12p70, IL-1α, IL-6, IL-8, MCP1, MIP1α, MIP1β, TNFα, and combinations thereof. Other exemplary cytokines are known in the art and are described herein. Probiotic compositions containing anti-inflammatory bacteria reduce inflammation and restore barrier function at the site of administration, e.g., in the gastrointestinal tract, as well as at distal sites throughout the body of the subject.

Other exemplary probiotic compositions useful for treatment or prevention of GVHD contain bacterial strains capable of altering the proportion of immune subpopulations, e.g., T cell subpopulations, in the subject.

For example, immunomodulatory bacteria can increase or decrease the proportion of Treg cells, Th17 cells, Th1 cells, or Th2 cells in a subject. The increase or decrease in the proportion of immune cell subpopulations may be systemic, or it may be localized to a site of action of the probiotic, e.g., in the gastrointestinal tract or at the site of a distal dysbiosis. In some embodiments, a probiotic composition comprising immunomodulatory bacteria is used for treatment or prevention of GVHD based on the desired effect of the probiotic composition on the differentiation and/or expansion of sub-populations of immune cells in the subject.

In one embodiment, a probiotic composition contains immunomodulatory bacteria that increase the proportion of Treg cells in a subject. In another embodiment, a probiotic composition contains immunomodulatory bacteria that decrease the proportion of Treg cells in a subject. In one embodiment, a probiotic composition contains immunomodulatory bacteria that increase the proportion of Th17 cells in a subject. In another embodiment, a probiotic composition contains immunomodulatory bacteria that decrease the proportion of Th17 cells in a subject. In one embodiment, a probiotic composition contains immunomodulatory bacteria that increase the proportion of Th1 cells in a subject. In another embodiment, a probiotic composition contains immunomodulatory bacteria that decrease the proportion of Th1 cells in a subject. In one embodiment, a probiotic composition contains immunomodulatory bacteria that increase the proportion of Th2 cells in a subject. In another embodiment, a probiotic composition contains immunomodulatory bacteria that decrease the proportion of Th2 cells in a subject.

In one embodiment, a probiotic composition contains immunomodulatory bacteria capable of modulating the proportion of one or more of Treg cells, Th17 cells, Th1 cells, and combinations thereof in a subject. Certain immune cell profiles may be particularly desirable to treat or prevent GVHD. For example, in some embodiments, treatment or prevention of GVHD can be promoted by increasing numbers of Treg cells and Th2 cells, and decreasing numbers of Th17 cells and Th1 cells. Accordingly, probiotic compositions for the treatment or prevention of GVHD may contain probiotics capable of promoting Treg cells and Th2 cells, and reducing Th17 and Th1 cells.

Probiotic compositions useful for treating or preventing GVHD include, in exemplary embodiments, one or more bacterial species from Table 1. In other embodiments, the probiotic composition includes one or more bacterial species from Table 1A. In other embodiments, the probiotic composition includes one or more bacterial species from Table 1B. In other embodiments, the probiotic composition includes one or more bacterial species from Table 1C. In other embodiments, the probiotic composition includes one or more bacterial species from Table 1D. In other embodiments, the probiotic composition includes one or more bacterial species from Table 1E. In other embodiments, the probiotic composition includes one or more bacterial species from Table 1F. In other embodiments, the probiotic composition includes one or more bacterial species from Table 5. In some embodiments, the probiotic composition contains a single species of bacteria. In other embodiments, the probiotic composition contains two or more species of bacteria, e.g., 2, 3, 4, 5, 6, 7, 8, 9, 10, 15, 20, 30, 40, 50, 60, 70, 80, 90, 100, 500, 1000 or more species of bacteria. In one embodiment, the probiotic composition contains no more than 20 species of bacteria, e.g., 20, 19, 18, 17, 16, 15, 14, 13, 12, 11, 10, 9, 8, 7, 6, 5, 4, 3, 2, or 1 species of bacteria. In exemplary embodiments, the probiotic composition contains 8 bacterial species. In other exemplary embodiments, the probiotic composition contains 9 bacterial species. In other embodiments, the probiotic composition contains or is administered in conjunction with a prebiotic, as described herein.

Preferred bacterial genera include *Acetanaerobacterium, Acetivibrio, Alicyclobacillus, Alkaliphilus, Anaerofustis, Anaerosporobacter, Anaerostipes, Anaerotruncus, Anoxybacillus, Bacillus, Bacteroides, Blautia, Brachyspira, Brevibacillus, Bryantella, Bulleidia, Butyricicoccus, Butyrivibrio, Catenibacterium, Chlamydiales, Clostridiaceae, Clostridiales, Clostridium, Collinsella, Coprobacillus, Coprococcus, Coxiella, Deferribacteres, Desulfitobacterium, Desulfotomaculum, Dorea, Eggerthella, Erysipelothrix, Erysipelotrichaceae, Ethanoligenens, Eubacterium, Faecalibacterium, Filifactor, Flavonifractor, Flexistipes, Fulvimonas, Fusobacterium, Gemmiger, Geobacillus, Gloeobacter, Holdemania, Hydrogenoanaerobacterium, Kocuria, Lachnobacterium, Lachnospira, Lachnospiraceae, Lactobacillus, Lactonifactor, Leptospira, Lutispora, Lysinibacillus, Mollicutes, Moorella, Nocardia, Oscillibacter, Oscillospira, Paenibacillus, Papillibacter, Pseudoflavonifractor, Robinsoniella, Roseburia, Ruminococcaceae, Ruminococcus, Saccharomonospora, Sarcina, Solobacterium, Sporobacter, Sporolactobacillus, Streptomyces, Subdoligranulum, Sutterella, Syntrophococcus, Thermoanaerobacter, Thermobifida,* and *Turicibacter.*

Preferred bacterial genera also include *Acetonema, Alkaliphilus, Amphibacillus, Ammonifex, Anaerobacter, Caldicellulosiruptor, Caloramator, Candidatus, Carboxydibrachium, Carboxydothermus, Cohnella, Dendrosporobacter Desulfitobacterium, Desulfosporosinus, Halobacteroides, Heliobacterium, Heliophilum, Heliorestis, Lachnoanaerobaculum, Lysinibacillus, Oceanobacillus, Orenia (S.), Oxalophagus, Oxobacter, Pelospora, Pelotomaculum, Propionispora, Sporohalobacter, Sporomusa, Sporosarcina, Sporotomaculum, Symbiobacterium, Syntrophobotulus, Syntrophospora, Terribacillus, Thermoanaerobacter,* and *Thermosinus.*

In one embodiment, a probiotic composition for the treatment or prevention of GVHD consists essentially of *Blautia.*

In another embodiment, a probiotic composition for the treatment or prevention of GVHD does not contain *Blautia* alone.

As provided herein, therapeutic compositions comprise, or in the alternative, modulate, the colonization and/or engraftment, of the following exemplary bacterial entities: *Lactobacillus gasseri, Lactobacillus fermentum, Lactobacillus reuteri, Enterococcus* faecalis, *Enterococcus* durans, *Enterococcus villorum, Lactobacillus plantarum, Pediococcus acidilactici, Staphylococcus pasteuri, Staphylococcus cohnii, Streptococcus sanguinis, Streptococcus sinensis, Streptococcus mitis, Streptococcus* sp. SCA22, *Streptococcus* sp. CR-3145, *Streptococcus anginosus, Streptococcus mutans, Coprobacillus cateniformis, Clostridium saccharogumia, Eubacterium dolichum* DSM 3991, *Clostridium* sp. PPf35E6, *Clostridium sordelli* ATCC 9714, *Ruminococcus torques, Ruminococcus gnavus, Clostridium clostridioforme, Ruminococcus obeum, Blautia producta, Clostridium* sp. ID5, *Megasphaera micronuciformis, Veillonella parvula, Clostridium methylpentosum, Clostridium islandicum, Faecalibacterium prausnitzii, Bacteroides uniformmis, Bacteroides thetaiotaomicron, Bacteroides acidifaciens, Bacteroides ovatus, Bacteroides fragilis, Parabacteroides distasonis, Propinionibacteirum propionicum, Actinomycs hyovaginalis, Rothia mucilaginosa, Rothia aeria, Bifidobacterium breve, Scardovia inopinata* and *Eggerthella lenta.*

Preferred bacterial species are provided in Table 1, Table 1A, Table 1B, Table 1C, Table 1D, Table 1E, Table 1F, and Table 5. Optionally, in some embodiments, preferred bacterial species are spore formers. Where specific strains of a species are provided, one of skill in the art will recognize that other strains of the species can be substituted for the named strain.

In one embodiment, the bacterial entity, e.g., species or strain, useful in the compositions and methods of the invention is *Acidaminococcus intestine*. In one embodiment, the bacterial entity, e.g., species or strain, useful in the compositions and methods of the invention is *Acinetobacter baumannii*. In one embodiment, the bacterial entity, e.g., species or strain, useful in the compositions and methods of the invention is *Acinetobacter lwoffii*. In one embodiment, the bacterial entity, e.g., species or strain, useful in the compositions and methods of the invention is *Akkermansia muciniphila*. In one embodiment, the bacterial entity, e.g., species or strain, useful in the compositions and methods of the invention is *Alistipes putredinis*. In one embodiment, the bacterial entity, e.g., species or strain, useful in the compositions and methods of the invention is *Alistipes shahii*. In one embodiment, the bacterial entity, e.g., species or strain, useful in the compositions and methods of the invention is *Anaerostipes hadrus*. In one embodiment, the bacterial entity, e.g., species or strain, useful in the compositions and methods of the invention is *Anaerotruncus colihominis*. In one embodiment, the bacterial entity, e.g., species or strain, useful in the compositions and methods of the invention is *Bacteroides caccae*. In one embodiment, the bacterial entity, e.g., species or strain, useful in the compositions and methods of the invention is *Bacteroides cellulosilyticus*. In one embodiment, the bacterial entity, e.g., species or strain, useful in the compositions and methods of the invention is *Bacteroides dorei*. In one embodiment, the bacterial entity, e.g., species or strain, useful in the compositions and methods of the invention is *Bacteroides eggerthii*. In one embodiment, the bacterial entity, e.g., species or strain, useful in the compositions and methods of the invention is *Bacteroides finegoldii*. In one embodiment, the bacterial entity, e.g., species or strain, useful in the compositions and methods of the invention is *Bacteroides fragilis*. In one embodiment, the bacterial entity, e.g., species or strain, useful in the compositions and methods of the invention is *Bacteroides massiliensis*. In one embodiment, the bacterial entity, e.g., species or strain, useful in the compositions and methods of the invention is *Bacteroides ovatus*. In one embodiment, the bacterial entity, e.g., species or strain, useful in the compositions and methods of the invention is *Bacteroides salanitronis*. In one embodiment, the bacterial entity, e.g., species or strain, useful in the compositions and methods of the invention is *Bacteroides salyersiae*. In one embodiment, the bacterial entity, e.g., species or strain, useful in the compositions and methods of the invention is *Bacteroides* sp. 1_1_6. In one embodiment, the bacterial entity, e.g., species or strain, useful in the compositions and methods of the invention is *Bacteroides* sp. 3_1_23. In one embodiment, the bacterial entity, e.g., species or strain, useful in the compositions and methods of the invention is *Bacteroides* sp. D20. In one embodiment, the bacterial entity, e.g., species or strain, useful in the compositions and methods of the invention is *Bacteroides thetaiotaomicrond*. In one embodiment, the bacterial entity, e.g., species or strain, useful in the compositions and methods of the invention is *Bacteroides uniformis*. In one embodiment, the bacterial entity, e.g., species or strain, useful in the compositions and methods of the invention is *Bacteroides vulgatus*. In one embodiment, the bacterial entity, e.g., species or strain, useful in the compositions and methods of the invention is *Bifidobacterium adolescentis*. In one embodiment, the bacterial entity, e.g., species or strain, useful in the compositions and methods of the invention is *Bifidobacterium bifidum*. In one embodiment, the bacterial entity, e.g., species or strain, useful in the compositions and methods of the invention is *Bifidobacterium breve*. In one embodiment, the bacterial entity, e.g., species or strain, useful in the compositions and methods of the invention is *Bifidobacterium faecale*. In one embodiment, the bacterial entity, e.g., species or strain, useful in the compositions and methods of the invention is *Bifidobacterium kashiwanohense*. In one embodiment, the bacterial entity, e.g., species or strain, useful in the compositions and methods of the invention is *Bifidobacterium longum* subsp. *Longum*. In one embodiment, the bacterial entity, e.g., species or strain, useful in the compositions and methods of the invention is *Bifidobacterium pseudocatenulatum*. In one embodiment, the bacterial entity, e.g., species or strain, useful in the compositions and methods of the invention is *Bifidobacterium stercoris*. In one embodiment, the bacterial entity, e.g., species or strain, useful in the compositions and methods of the invention is *Blautia (Ruminococcus) coccoides*. In one embodiment, the bacterial entity, e.g., species or strain, useful in the compositions and methods of the invention is *Blautia faecis*. In one embodiment, the bacterial entity, e.g., species or strain, useful in the compositions and methods of the invention is *Blautia glucerasea*. In one embodiment, the bacterial entity, e.g., species or strain, useful in the compositions and methods of the invention is *Blautia (Ruminococcus) hansenii*. In one embodiment, the bacterial entity, e.g., species or strain, useful in the compositions and methods of the invention is *Blautia hydrogenotrophica (Ruminococcus hydrogenotrophicus)*. In one embodiment, the bacterial entity, e.g., species or strain, useful in the compositions and methods of the invention is *Blautia (Ruminococcus) luti*. In one embodiment, the bacterial entity, e.g., species or strain, useful in the compositions and methods of the invention is *Blautia (Ruminococcus) obeum*. In one embodiment, the bacterial entity, e.g., species or strain, useful in the compositions and methods of the invention is *Blautia producta (Ruminococcus productus)*. In one embodiment, the bacterial entity, e.g., species or strain, useful in the compositions and methods of the invention is *Blautia (Ruminococcus) schinkii*. In one embodiment, the bacterial entity, e.g., species or strain, useful in the compositions and methods of the invention is *Blautia stercoris*. In one embodiment, the bacterial entity, e.g., species or strain, useful in the compositions and methods of the invention is *Blautia* uncultured bacterium clone BKLE_a03_2 (GenBank: EU469501.1). In one embodiment, the bacterial entity, e.g., species or strain, useful in the compositions and methods of the invention is *Blautia* uncultured bacterium clone SJTU_B_14_30 (GenBank: EF402926.1). In one embodiment, the bacterial entity, e.g., species or strain, useful in the compositions and methods of the invention is *Blautia* uncultured bacterium clone SJTU_C_14_16 (GenBank: EF404657.1). In one embodiment, the bacterial entity, e.g., species or strain, useful in the compositions and methods of the invention is *Blautia* uncultured bacterium clone S1-5 (GenBank: GQ898099.1). In one embodiment, the bacterial entity, e.g., species or strain, useful in the compositions and methods of the invention is *Blautia* uncultured PAC000178_s (www.ezbiocloud.net/ez-taxon/hierarchy?m=browse&k=PAC000178&d=2). In one embodiment, the bacterial entity, e.g., species or strain, useful in the compositions and methods of the invention is *Blautia wexlerae*. In one embodiment, the bacterial entity, e.g., species or strain, useful in the compositions and methods of the invention is *Candidatus Arthromitus* sp. SFB-mouse-Yit. In one embodiment, the bacterial entity, e.g., species or strain, useful in the compositions and methods of the invention is *Catenibacterium mitsuokai*. In one embodiment, the bacterial entity, e.g., species or strain, useful in the compositions and methods of the invention is *Clostridiaceae* bacterium (*Dielma fastidiosa*) JC13. In one embodiment, the bacterial entity, e.g., species or strain, useful in the compositions and methods of the invention is Clostridiales bacterium 1_7_47FAA. In one embodiment, the bacterial entity, e.g., species or strain, useful in the compositions and methods of the invention is *Clostridium asparagiforme*. In one embodiment, the bacterial entity, e.g., species or strain, useful in the compositions and methods of the invention is *Clostridium bolteae*. In one embodiment, the bacterial entity, e.g., species or strain, useful in the compositions and methods of the invention is *Clostridium clostridioforme*. In one embodiment, the bacterial entity, e.g., species or strain, useful in the compositions and methods of the invention is *Clostridium glycyrrhizinilyticum*. In one embodiment, the bacterial entity, e.g., species or strain, useful in the compositions and methods of the invention is *Clostridium (Hungatella) hathewayi*. In one embodiment, the bacterial entity, e.g., species or strain, useful in the compositions and methods of the invention is *Clostridium histolyticum*. In one embodiment, the bacterial entity, e.g., species or strain, useful in the compositions and methods of the invention is *Clostridium indolis*. In one embodiment, the bacterial entity, e.g., species or strain, useful in the compositions and methods of the invention is *Clostridium leptum*. In one embodiment, the bacterial entity, e.g., species or strain, useful in the compositions and methods of the invention is *Clostridium (Tyzzerella) nexile*. In one embodiment, the bacterial entity, e.g., species or strain, useful in the compositions and methods of the invention is *Clostridium perfringens*. In one embodiment, the bacterial entity, e.g., species or strain, useful in the compositions and methods of the invention is *Clostridium (Erysipelatoclostridium) ramosum*. In one embodiment, the bacterial entity, e.g., species or strain, useful in the compositions and methods of the invention is *Clostridium scindens*. In one embodiment, the bacterial entity, e.g., species or strain, useful in the compositions and methods of the invention is *Clostridium septum*. In one embodiment, the bacterial entity, e.g., species or strain, useful in the compositions and methods of the invention is *Clostridium* sp. 14774. In one embodiment, the bacterial entity, e.g., species or strain, useful in the compositions and methods of the invention is *Clostridium* sp. 7_3_54FAA. In one embodiment, the bacterial entity, e.g., species or strain, useful in the compositions and methods of the invention is *Clostridium* sp. HGF2. In one embodiment, the bacterial entity, e.g., species or strain, useful in the compositions and methods of the invention is *Clostridium symbiosum*. In one embodiment, the bacterial entity, e.g., species or strain, useful in the compositions and methods of the invention is *Collinsella aerofaciens*. In one embodiment, the bacterial entity, e.g., species or strain, useful in the compositions and methods of the invention is *Collinsella intestinalis*. In one embodiment, the bacterial entity, e.g., species or strain, useful in the compositions and methods of the invention is *Coprobacillus* sp. D7. In one embodiment, the bacterial entity, e.g., species or strain, useful in the compositions and methods of the invention is *Coprococcus catus*. In one embodiment, the bacterial entity, e.g., species or strain, useful in the compositions and methods of the invention is *Coprococcus comes*. In one embodiment, the bacterial entity, e.g., species or strain, useful in the compositions and methods of the invention is *Dorea formicigenerans*. In one embodiment, the bacterial entity, e.g., species or strain, useful in the compositions and methods of the invention is *Dorea longicatena*. In one embodiment, the bacterial entity, e.g., species or strain, useful in the compositions and methods of the invention is *Enterococcus faecalis*. In one embodiment, the bacterial entity, e.g., species or strain, useful in the compositions and methods of the invention is *Enterococcus faecium*. In one embodiment, the bacterial entity, e.g., species or strain, useful in the compositions and methods of the invention is Erysipelotrichaceae bacterium 3_1_53. In one embodiment, the bacterial entity, e.g., species or strain, useful in the compositions and methods of the invention is *Escherichia coli*. In one embodiment, the bacterial entity, e.g., species or strain, useful in the compositions and methods of the invention is *Escherichia coli* S88. In one embodiment, the bacterial entity, e.g., species or strain, useful in the compositions and methods of the invention is *Eubacterium eligens*. In one embodiment, the bacterial entity, e.g., species or strain, useful in the compositions and methods of the invention is *Eubacterium fissicatena*. In one embodiment, the bacterial entity, e.g., species or strain, useful in the compositions and methods of the invention is *Eubacterium ramulus*. In one embodiment, the bacterial entity, e.g., species or strain, useful in the compositions and methods of the invention is *Eubacterium rectale*. In one embodiment, the bacterial entity, e.g., species or strain, useful in the compositions and methods of the invention is *Faecalibacterium prausnitzii*. In one embodiment, the bacterial entity, e.g., species or strain, useful in the compositions and methods of the invention is *Flavonifractor plautii*. In one embodiment, the bacterial entity, e.g., species or strain, useful in the compositions and methods of the invention is *Fusobacterium mortiferum*. In one embodiment, the bacterial entity, e.g., species or strain, useful in the compositions and methods of the invention is *Fusobacterium nucleatum*. In one embodiment, the bacterial entity, e.g., species or strain, useful in the compositions and methods of the invention is *Holdemania filiformis*. In one embodiment, the bacterial entity, e.g., species or strain, useful in the compositions and methods of the invention is *Hydrogenoanaerobacterium saccharovorans*. In one embodiment, the bacterial entity, e.g., species or strain, useful in the compositions and methods of the invention is *Klebsiella oxytoca*. In one embodiment, the bacterial entity, e.g., species or strain, useful in the compositions and methods of the invention is Lachnospiraceae bacterium 3_1_7FAA_CT1. In one embodiment, the bacterial entity, e.g., species or strain, useful in the compositions and methods of the invention is Lachnospiraceae bacterium 7_1_58FAA. In one embodiment, the bacterial entity, e.g., species or strain, useful in the compositions and methods of the invention is Lachnospiraceae bacterium 5_1_57FAA. In one embodiment, the bacterial entity, e.g., species or strain, useful in the compositions and methods of the invention is *Lactobacillus casei*. In one embodiment, the bacterial entity, e.g., species or strain, useful in the compositions and methods of the invention is *Lactobacillus rhamnosus*. In one embodiment, the bacterial entity, e.g., species or strain, useful in the compositions and methods of the invention is *Lactobacillus ruminis*. In one embodiment, the bacterial entity, e.g., species or strain, useful in the compositions and methods of the invention is *Lactococcus casei*. In one embodiment, the bacterial entity, e.g., species or strain, useful in the compositions and methods of the invention is *Odoribacter splanchnicus*. In one embodiment, the bacterial entity, e.g., species or strain, useful in the compositions and methods of the invention is *Oscillibacter valericigenes*. In one embodiment, the bacterial entity, e.g., species or strain, useful in the compositions and methods of the invention is *Parabacteroides gordonii*. In one embodiment, the bacterial entity, e.g., species or strain, useful in the compositions and methods of the invention is *Parabacteroides johnsonii*. In one embodiment, the bacterial entity, e.g., species or strain, useful in the compositions and methods of the invention is *Parabacteroides merdae*. In one embodiment, the bacterial entity, e.g., species or strain, useful in the compositions and methods of the invention is *Pediococcus acidilactici*. In one embodiment, the bacterial entity, e.g., species or strain, useful in the compositions and methods of the invention is *Peptostreptococcus asaccharolyticus*. In one embodiment, the bacterial entity, e.g., species or strain, useful in the compositions and methods of the invention is *Propionibacterium granulosum*. In one embodiment, the bacterial entity, e.g., species or strain, useful in the compositions and methods of the invention is *Roseburia intestinalis*. In one embodiment, the bacterial entity, e.g., species or strain, useful in the compositions and methods of the invention is *Roseburia inulinivorans*. In one embodiment, the bacterial entity, e.g., species or strain, useful in the compositions and methods of the invention is *Ruminococcus faecis*. In one embodiment, the bacterial entity, e.g., species or strain, useful in the compositions and methods of the invention is *Ruminococcus gnavus*. In one embodiment, the bacterial entity, e.g., species or strain, useful in the compositions and methods of the invention is

*Ruminococcus* sp. ID8. In one embodiment, the bacterial entity, e.g., species or strain, useful in the compositions and methods of the invention is *Ruminococcus torques*. In one embodiment, the bacterial entity, e.g., species or strain, useful in the compositions and methods of the invention is *Slackia piriformis*. In one embodiment, the bacterial entity, e.g., species or strain, useful in the compositions and methods of the invention is *Staphylococcus epidermidis*. In one embodiment, the bacterial entity, e.g., species or strain, useful in the compositions and methods of the invention is *Staphylococcus saprophyticus*. In one embodiment, the bacterial entity, e.g., species or strain, useful in the compositions and methods of the invention is *Streptococcus cristatus*. In one embodiment, the bacterial entity, e.g., species or strain, useful in the compositions and methods of the invention is *Streptococcus dysgalactiae* subsp. *Equisimilis*. In one embodiment, the bacterial entity, e.g., species or strain, useful in the compositions and methods of the invention is *Streptococcus infantis*. In one embodiment, the bacterial entity, e.g., species or strain, useful in the compositions and methods of the invention is *Streptococcus oralis*. In one embodiment, the bacterial entity, e.g., species or strain, useful in the compositions and methods of the invention is *Streptococcus sanguinis*. In one embodiment, the bacterial entity, e.g., species or strain, useful in the compositions and methods of the invention is *Streptococcus viridans*. In one embodiment, the bacterial entity, e.g., species or strain, useful in the compositions and methods of the invention is *Streptococcus thermophiles*. In one embodiment, the bacterial entity, e.g., species or strain, useful in the compositions and methods of the invention is *Veillonella dispar*.

In one embodiment, the bacterial population useful in the compositions and methods of the invention comprises *Acidaminococcus intestine*. In one embodiment, the bacterial population useful in the compositions and methods of the invention comprises *Acinetobacter baumannii*. In one embodiment, the bacterial population useful in the compositions and methods of the invention comprises *Acinetobacter lwoffii*. In one embodiment, the bacterial population useful in the compositions and methods of the invention comprises *Akkermansia muciniphila*. In one embodiment, the bacterial population useful in the compositions and methods of the invention comprises *Alistipes putredinis*. In one embodiment, the bacterial population useful in the compositions and methods of the invention comprises *Alistipes shahii*. In one embodiment, the bacterial population useful in the compositions and methods of the invention comprises *Anaerostipes hadrus*. In one embodiment, the bacterial population useful in the compositions and methods of the invention comprises *Anaerotruncus colihominis*. In one embodiment, the bacterial population useful in the compositions and methods of the invention comprises *Bacteroides caccae*. In one embodiment, the bacterial population useful in the compositions and methods of the invention comprises *Bacteroides cellulosilyticus*. In one embodiment, the bacterial population useful in the compositions and methods of the invention comprises *Bacteroides dorei*. In one embodiment, the bacterial population useful in the compositions and methods of the invention comprises *Bacteroides eggerthii*. In one embodiment, the bacterial population useful in the compositions and methods of the invention comprises *Bacteroides finegoldii*. In one embodiment, the bacterial population useful in the compositions and methods of the invention comprises *Bacteroides fragilis*. In one embodiment, the bacterial population useful in the compositions and methods of the invention comprises *Bacteroides massiliensis*. In one embodiment, the bacterial population useful in the compositions and methods of the invention comprises *Bacteroides ovatus*. In one embodiment, the bacterial population useful in the compositions and methods of the invention comprises *Bacteroides salanitronis*. In one embodiment, the bacterial population useful in the compositions and methods of the invention comprises *Bacteroides salyersiae*. In one embodiment, the bacterial population useful in the compositions and methods of the invention comprises *Bacteroides* sp. 1_1_6. In one embodiment, the bacterial population useful in the compositions and methods of the invention comprises *Bacteroides* sp. 3_1_23. In one embodiment, the bacterial population useful in the compositions and methods of the invention comprises *Bacteroides* sp. D20. In one embodiment, the bacterial population useful in the compositions and methods of the invention comprises *Bacteroides thetaiotaomicrond*. In one embodiment, the bacterial population useful in the compositions and methods of the invention comprises *Bacteroides uniformis*. In one embodiment, the bacterial population useful in the compositions and methods of the invention comprises *Bacteroides vulgatus*. In one embodiment, the bacterial population useful in the compositions and methods of the invention comprises *Bifidobacterium adolescentis*. In one embodiment, the bacterial population useful in the compositions and methods of the invention comprises *Bifidobacterium bifidum*. In one embodiment, the bacterial population useful in the compositions and methods of the invention comprises *Bifidobacterium breve*. In one embodiment, the bacterial population useful in the compositions and methods of the invention comprises *Bifidobacterium faecale*. In one embodiment, the bacterial population useful in the compositions and methods of the invention comprises *Bifidobacterium kashiwanohense*. In one embodiment, the bacterial population useful in the compositions and methods of the invention comprises *Bifidobacterium longum* subsp. *Longum*. In one embodiment, the bacterial population useful in the compositions and methods of the invention comprises *Bifidobacterium pseudocatenulatum*. In one embodiment, the bacterial population useful in the compositions and methods of the invention comprises *Bifidobacterium stercoris*. In one embodiment, the bacterial population useful in the compositions and methods of the invention comprises *Blautia (Ruminococcus) coccoides*. In one embodiment, the bacterial population useful in the compositions and methods of the invention comprises *Blautia faecis*. In one embodiment, the bacterial population useful in the compositions and methods of the invention comprises *Blautia glucerasea*. In one embodiment, the bacterial population useful in the compositions and methods of the invention comprises *Blautia (Ruminococcus) hansenii*. In one embodiment, the bacterial population useful in the compositions and methods of the invention comprises *Blautia hydrogenotrophica (Ruminococcus hydrogenotrophicus)*. In one embodiment, the bacterial population useful in the compositions and methods of the invention comprises *Blautia (Ruminococcus) luti*. In one embodiment, the bacterial population useful in the compositions and methods of the invention comprises *Blautia (Ruminococcus) obeum*. In one embodiment, the bacterial population useful in the compositions and methods of the invention comprises *Blautia producta (Ruminococcus productus)*. In one embodiment, the bacterial population useful in the compositions and methods of the invention comprises *Blautia (Ruminococcus) schinkii*. In one embodiment, the bacterial population useful in the compositions and methods of the invention comprises *Blautia stercoris*. In one embodiment, the bacterial population useful in the compositions and methods of the invention comprises *Blau-*

*tia* uncultured bacterium clone BKLE_a03_2 (GenBank: EU469501.1). In one embodiment, the bacterial population useful in the compositions and methods of the invention comprises *Blautia* uncultured bacterium clone SJTU_B_14_30 (GenBank: EF402926.1). In one embodiment, the bacterial population useful in the compositions and methods of the invention comprises *Blautia* uncultured bacterium clone SJTU_C_14_16 (GenBank: EF404657.1). In one embodiment, the bacterial population useful in the compositions and methods of the invention comprises *Blautia* uncultured bacterium clone S1-5 (GenBank: GQ898099.1). In one embodiment, the bacterial population useful in the compositions and methods of the invention comprises *Blautia* uncultured PAC000178_s (www.ezbiocloud.net/eztaxon/hierarchy?m=browse&k=PAC000178&d=2). In one embodiment, the bacterial population useful in the compositions and methods of the invention comprises *Blautia wexlerae*. In one embodiment, the bacterial population useful in the compositions and methods of the invention comprises *Candidatus Arthromitus* sp. SFB-mouse-Yit. In one embodiment, the bacterial population useful in the compositions and methods of the invention comprises *Catenibacterium mitsuokai*. In one embodiment, the bacterial population useful in the compositions and methods of the invention comprises *Clostridiaceae* bacterium (*Dielma fastidiosa*) JC13. In one embodiment, the bacterial population useful in the compositions and methods of the invention comprises Clostridiales bacterium 1_7_47FAA. In one embodiment, the bacterial population useful in the compositions and methods of the invention comprises *Clostridium asparagiforme*. In one embodiment, the bacterial population useful in the compositions and methods of the invention comprises *Clostridium bolteae*. In one embodiment, the bacterial population useful in the compositions and methods of the invention comprises *Clostridium clostridioforme*. In one embodiment, the bacterial population useful in the compositions and methods of the invention comprises *Clostridium glycyrrhizinilyticum*. In one embodiment, the bacterial population useful in the compositions and methods of the invention comprises *Clostridium* (*Hungatella*) *hathewayi*. In one embodiment, the bacterial population useful in the compositions and methods of the invention comprises *Clostridium histolyticum*. In one embodiment, the bacterial population useful in the compositions and methods of the invention comprises *Clostridium indolis*. In one embodiment, the bacterial population useful in the compositions and methods of the invention comprises *Clostridium leptum*. In one embodiment, the bacterial population useful in the compositions and methods of the invention comprises *Clostridium* (*Tyzzerella*) *nexile*. In one embodiment, the bacterial population useful in the compositions and methods of the invention comprises *Clostridium perfringens*. In one embodiment, the bacterial population useful in the compositions and methods of the invention comprises *Clostridium* (*Erysipelatoclostridium*) *ramosum*. In one embodiment, the bacterial population useful in the compositions and methods of the invention comprises *Clostridium scindens*. In one embodiment, the bacterial entity, e.g., species or strain, useful in the compositions and methods of the invention is *Clostridium septum*. In one embodiment, the bacterial population useful in the compositions and methods of the invention comprises *Clostridium* sp. 14774. In one embodiment, the bacterial population useful in the compositions and methods of the invention comprises *Clostridium* sp. 7_3_54FAA. In one embodiment, the bacterial population useful in the compositions and methods of the invention comprises *Clostridium* sp. HGF2. In one embodiment, the bacterial population useful in the compositions and methods of the invention comprises *Clostridium symbiosum*. In one embodiment, the bacterial population useful in the compositions and methods of the invention comprises *Collinsella aerofaciens*. In one embodiment, the bacterial population useful in the compositions and methods of the invention comprises *Collinsella intestinalis*. In one embodiment, the bacterial population useful in the compositions and methods of the invention comprises *Coprobacillus* sp. D7. In one embodiment, the bacterial population useful in the compositions and methods of the invention comprises *Coprococcus catus*. In one embodiment, the bacterial population useful in the compositions and methods of the invention comprises *Coprococcus comes*. In one embodiment, the bacterial population useful in the compositions and methods of the invention comprises *Dorea formicigenerans*. In one embodiment, the bacterial population useful in the compositions and methods of the invention comprises *Dorea longicatena*. In one embodiment, the bacterial population useful in the compositions and methods of the invention comprises *Enterococcus faecalis*. In one embodiment, the bacterial population useful in the compositions and methods of the invention comprises *Enterococcus faecium*. In one embodiment, the bacterial population useful in the compositions and methods of the invention comprises Erysipelotrichaceae bacterium 3_1_53. In one embodiment, the bacterial population useful in the compositions and methods of the invention comprises *Escherichia coli*. In one embodiment, the bacterial population useful in the compositions and methods of the invention comprises *Escherichia coli* S88. In one embodiment, the bacterial population useful in the compositions and methods of the invention comprises *Eubacterium eligens*. In one embodiment, the bacterial population useful in the compositions and methods of the invention comprises *Eubacterium fissicatena*. In one embodiment, the bacterial population useful in the compositions and methods of the invention comprises *Eubacterium ramulus*. In one embodiment, the bacterial population useful in the compositions and methods of the invention comprises *Eubacterium rectale*. In one embodiment, the bacterial population useful in the compositions and methods of the invention comprises *Faecalibacterium prausnitzii*. In one embodiment, the bacterial population useful in the compositions and methods of the invention comprises *Flavonifractor plautii*. In one embodiment, the bacterial population useful in the compositions and methods of the invention comprises *Fusobacterium mortiferum*. In one embodiment, the bacterial population useful in the compositions and methods of the invention comprises *Fusobacterium nucleatum*. In one embodiment, the bacterial population useful in the compositions and methods of the invention comprises *Holdemania filiformis*. In one embodiment, the bacterial population useful in the compositions and methods of the invention comprises *Hydrogenoanaerobacterium saccharovorans*. In one embodiment, the bacterial population useful in the compositions and methods of the invention comprises *Klebsiella oxytoca*. In one embodiment, the bacterial population useful in the compositions and methods of the invention comprises Lachnospiraceae bacterium 3_1_7FAA_CT1. In one embodiment, the bacterial population useful in the compositions and methods of the invention comprises Lachnospiraceae bacterium 7_1_58FAA. In one embodiment, the bacterial population useful in the compositions and methods of the invention comprises Lachnospiraceae bacterium 5_1_57FAA. In one embodiment, the bacterial population useful in the compositions and methods of the invention comprises *Lactobacillus casei*. In one embodiment, the bacterial population useful in the compositions and methods of the invention comprises *Lactobacillus rhamnosus*. In one embodiment, the bacterial population useful in the compositions and methods of the invention comprises *Lactobacillus ruminis*. In one embodiment, the bacterial population useful in the compositions and methods of the invention comprises *Lactococcus casei*. In one embodiment, the bacterial population useful in the compositions and methods of the invention comprises *Odoribacter splanchnicus*. In one embodiment, the bacterial population useful in the compositions and methods of the invention comprises *Oscillibacter valericigenes*. In one embodiment, the bacterial population useful in the compositions and methods of the invention comprises *Parabacteroides gordonii*. In one embodiment, the bacterial population useful in the compositions and methods of the invention comprises *Parabacteroides johnsonii*. In one embodiment, the bacterial population useful in the compositions and methods of the invention comprises *Parabacteroides merdae*. In one embodiment, the bacterial population useful in the compositions and methods of the invention comprises *Pediococcus acidilactici*. In one embodiment, the bacterial population useful in the compositions and methods of the invention comprises *Peptostreptococcus asaccharolyticus*. In one embodiment, the bacterial population useful in the compositions and methods of the invention comprises *Propionibacterium granulosum*. In one embodiment, the bacterial population useful in the compositions and methods of the invention comprises *Roseburia intestinalis*. In one embodiment, the bacterial population useful in the compositions and methods of the invention comprises *Roseburia inulinivorans*. In one embodiment, the bacterial population useful in the compositions and methods of the invention comprises *Ruminococcus faecis*. In one embodiment, the bacterial population useful in the compositions and methods of the invention comprises *Ruminococcus gnavus*. In one embodiment, the bacterial population useful in the compositions and methods of the invention comprises *Ruminococcus* sp. ID8. In one embodiment, the bacterial population useful in the compositions and methods of the invention comprises *Ruminococcus torques*. In one embodiment, the bacterial population useful in the compositions and methods of the invention comprises *Slackia piriformis*. In one embodiment, the bacterial population useful in the compositions and methods of the invention comprises *Staphylococcus epidermidis*. In one embodiment, the bacterial population useful in the compositions and methods of the invention comprises *Staphylococcus saprophyticus*. In one embodiment, the bacterial population useful in the compositions and methods of the invention comprises *Streptococcus cristatus*. In one embodiment, the bacterial population useful in the compositions and methods of the invention comprises *Streptococcus dysgalactiae* subsp. *Equisimilis*. In one embodiment, the bacterial population useful in the compositions and methods of the invention comprises *Streptococcus infantis*. In one embodiment, the bacterial population useful in the compositions and methods of the invention comprises *Streptococcus oralis*. In one embodiment, the bacterial population useful in the compositions and methods of the invention comprises *Streptococcus sanguinis*. In one embodiment, the bacterial population useful in the compositions and methods of the invention comprises *Streptococcus viridans*. In one embodiment, the bacterial population useful in the compositions and methods of the invention comprises *Streptococcus thermophiles*. In one embodiment, the bacterial population useful in the compositions and methods of the invention comprises *Veillonella dispar*.

XIV. Diagnostic Methods

In some embodiments, metabolite profiles of patient tissue samples or microbes cultures from patient tissue are used to identify risk factors for developing an autoimmune or inflammatory response, to diagnose an autoimmune or inflammatory disease, to evaluate the prognosis or severity of said disease, to evaluate the success of a treatment regimen, or any combination thereof. Exemplary metabolites for the purposes of diagnosis, prognostic risk assessment, or treatment assessment purposes include short chain fatty acids, bile acids, and lactate. In preferred embodiments, metabolite profiles are taken at different time points during a patient's disease and treatment in order to better evaluate the patient's disease state including recovery or relapse events. Such monitoring is also important to lower the risk of a patient developing a new autoimmune condition following immunomodulatory treatment. In some embodiments, metabolite profiles inform subsequent treatment. For example, patients at risk for developing GVHD and presenting low levels of butyrate may be administered a microbial composition comprising microbes that produce butyrate (e.g., *Blautia* species) and excluding microbes capable of depleting butyrate (e.g. *Methanobacterium* species). In another example, patients experiencing bacterial vaginosis—which increases the risk that a woman will suffer from a sexually transmitted disease or experience fertility issues—often presents with abnormally low lactic acid levels. Thus, patients with low lactic acid production in the vagina may be administered a microbial composition comprising lactic acid producing microbes (e.g., *Lactobacillus* species) to restore a healthy microbiome state.

Patient selection. Particular bacterial compositions can be selected for individual patients or for patients with particular profiles. For example, 16S sequencing can be performed for a given patient to identify the bacteria present in his or her microbiota. The sequencing can either profile the patient's entire microbiome using 16S sequencing (to the family, genera, or species level), a portion of the patient's microbiome using 16S sequencing, or it can be used to detect the presence or absence of specific candidate bacteria that are biomarkers for health or a particular disease state, such as markers of multi-drug resistant organisms or specific genera of concern such as *Escherichia*. Based on the biomarker data, a particular composition can be selected for administration to a patient to supplement or complement a patient's microbiota in order to restore health or treat or prevent disease. In another embodiment, patients can be screened to determine the composition of their microbiota to determine the likelihood of successful treatment.

XV. Kits

In certain aspects, the invention relates to kits for the treatment of an autoimmune disease and/or inflammatory disease. The kits may comprise a microbial composition and an immunomodulatory carbohydrate, a prebiotic, microbial DNA, a mucolytic agent or a combination thereof. Optionally, the microbial composition, the immunomodulatory carbohydrate, the prebiotic, microbial DNA, and/or the mucolytic agent are matched to exhibit a synergistic treatment effect in a subject when employing an appropriate treatment regimen or preventative measure for an autoimmune and/or inflammatory disease.

The kits provided may comprise one or more containers. The containers may comprise singly isolated microbial compositions comprising one or more microbes and/or singly isolated prebiotic compositions comprising one or more carbohydrates. The microbial compositions, with or without one or more prebiotics, in the different containers may be administered at the same time or at different times, and may be administered in a specific order.

The compositions may, optionally, additively, or synergistically provide immunomodulatory effects when administered to a subject. The microbial composition, with or without one or more prebiotics, may comprise live microbes, microbes that are lyophilized, freeze-dried, and/or substantially dehydrated, or the composition may comprise bacterial or fungal spores or virions. In some embodiments, the kit further comprises an effective amount of one or more immunomodulary carbohydrates in one or more containers. In some embodiments, the kit further comprises in one or more containers an effective amount of an anti-mucolytic agent. In some embodiments, the kit further comprises one or more containers an effective amount of a prebiotic. In some embodiments, the kit further comprises an effective amount of a pro-inflammatory or anti-inflammatory agent. In some embodiments, the kit further comprises a pharmaceutically acceptable excipient or diluent.

EXAMPLES

The invention is further illustrated by the following examples. The examples are offered for illustrative purposes only, and are not intended to limit the scope of the present invention in any way. The entire contents of all references, patents, and published patent applications cited throughout this application are hereby incorporated by reference in their entirety.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed.* (Plenum Press, Vols A and B, 1992). Enzyme Linked Immunosorbent Assays (ELISAs) and Western blots described below are performed using kits according to the manufacturers' (e.g., Life Technologies, Thermo Fisher Scientific, New York, USA) instructions.

Example 1. Assessment of Intestinal Permeability after Administration of Bacteria, Prebiotic or Combinations Thereof The main function of the gastrointestinal (GI) tract is to digest and absorb nutrients from food. The mucosa of the GI tract forms a selective barrier between the host and the environment of the gut lumen. The mucosa allows transport of nutrients while restricting passage of larger molecules and bacteria. Impaired barrier integrity is believed to contribute to the pathogenesis of many disorders including autoimmune diseases, including transplant disorders such as graft-versus-host-disease (GVHD), and neurological disorders. Disruption of the intestinal barrier due to toxins, dysbiosis, inflammation or other factors is believed to result in the passage and presentation of environmental antigens to the immune system leading to aberrant immune responses. Similarly, the leakage of bacterial endotoxin or other toxic metabolites into the circulation can lead to systemic inflammation promoting the development of autoimmunity and neuroinflammation.

Restoration of GI barrier integrity through the administration of selected prebiotics and/or probiotics represents an approach to correct a basic defect underlying multiple pathological conditions.

In a first set of experiments, intestinal permeability was assessed using serum endotoxin levels as a marker of gut permeability in mice treated with xylose and/or antibiotics. Basal levels of intestinal permeability can be measured under disease or normal conditions. Intestinal permeability can be induced in mice through administration of inflammatory stimuli such as cholera toxin (3 oral gavages of 10 µg cholera toxin, 5 days apart), Poly I:C (3 intraperitoneal injections of 1 mg/kg, 3 days apart) or dextran sulfate (3% dextran sulfate sodium salt in drinking water for 7 days). Quantitation of intestinal permeability was carried out by quantitatively measuring plasma levels of endotoxin originating from gut bacteria using a commercially available chromogenic assay (Lonza, Rockland, Me.). The results of these experiments are shown in FIG. 1.

Quantitation of intestinal permeability can also be conducted using a number of alternative methods (reviewed in Bischoff et al, 2014) for example, by quantifying leakage of fluorescently-labeled high molecular weight dextran (FITC-dextran) into the plasma following oral administration (oral gavage with 0.6 g/kg 4 kDa FITC-dextran, serum samples collected 4 hours later and read for fluorescence intensity at 521 nm; Hsiao et al, 2013). To study the effect of bacterial strains on intestinal permeability, mice are gavaged orally with $10^7$-$10^{10}$ bacterial cells for an average of 5 administrations, typically daily or 2 days apart. Bacteria can be administered as single strains or combinations of strains. The bacteria can be administered alone or in combination with a pre-biotic(s). The pre-biotic can be xylose or xylose-containing molecules as a preferred carbon source for anaerobic bacteria. Other prebiotics that can be used include, for example, those described in Table 7. After administration of bacteria +/− pre-biotic, intestinal permeability is assessed using the preferred method at the desired time point(s) starting on day 1 post-treatment.

Figure 1:
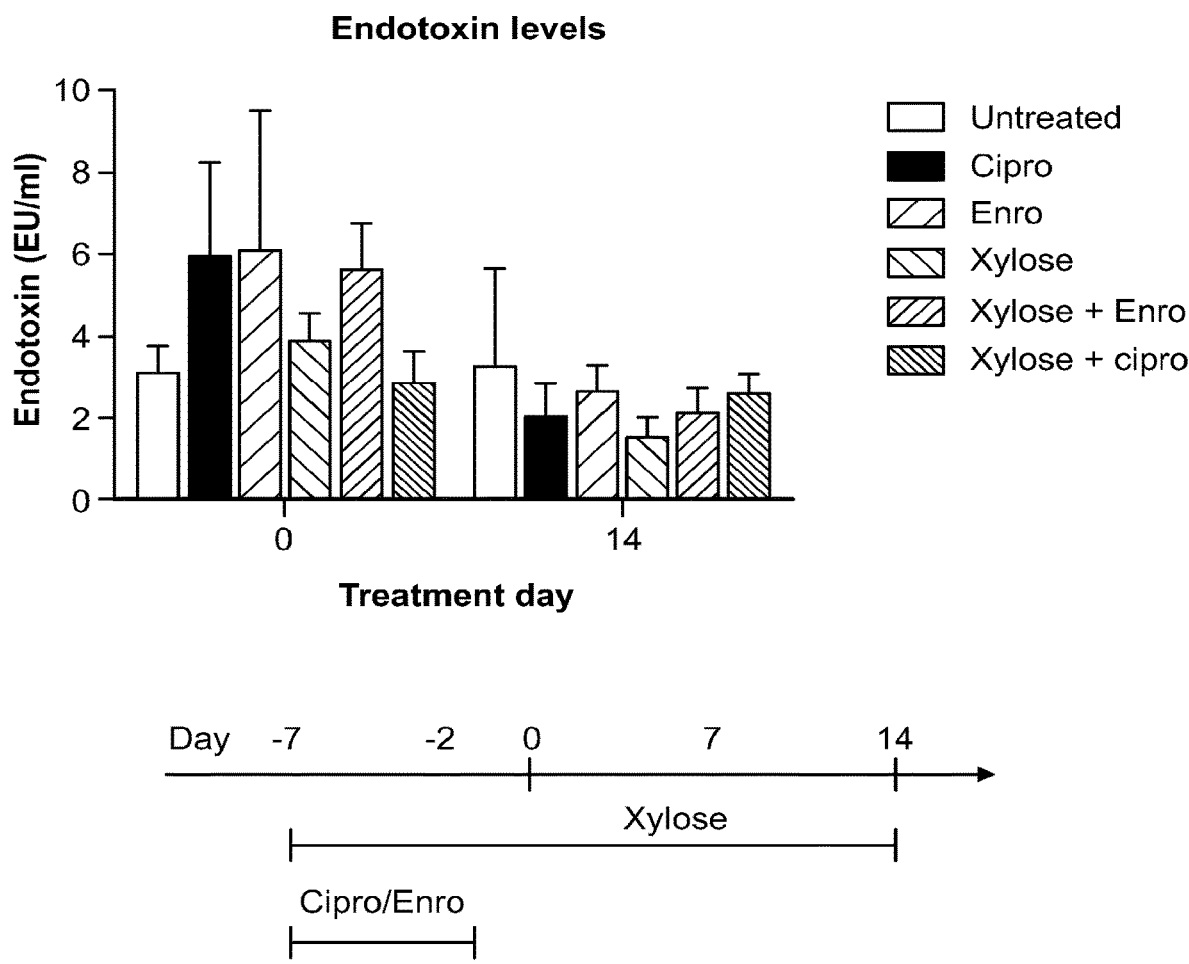
FIG. 1 is a graph depicting serum endotoxin levels (EU/ml) over time following treatment with xylose. Treatment of mice with xylose alone reduces basal levels of serum endotoxin (day 14 vs day 0). Antibiotic treatment (Ciprofloxacin (cipro) or enrofloxacin (enro)) leads to an increase in serum endotoxin levels (measured 2 days after a 5 day course, at day 0) with a return to baseline by day 14. Xylose counteracts the endotoxin increase caused by cipro but not enro antibiotic treatment.
Figure 2A:
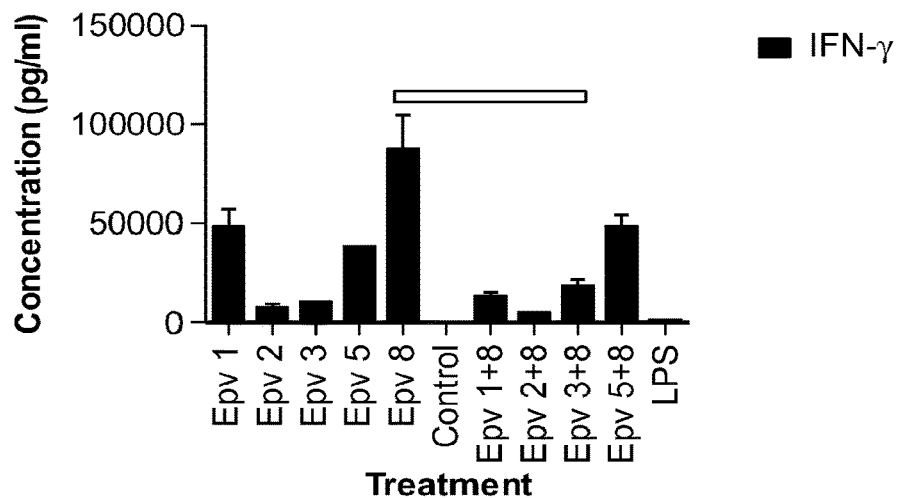
FIG. 2 (a-o) is a panel of graphs showing the time course of Th1 related cytokines that were released by human peripheral mononuclear cells (PBMCs) incubated with *Ruminococcus gnavus* (Epv 1), *Eubacterium rectale* (Epv 2), *Blautia luti* (Epv 3), *Blautia wexlerae* (Epv 5) and *Enterococcus faecalis* (Epv 8), or combinations of each bacterium with *E. faecalis*. Amounts of interferon gamma (IFN-γ), IL-12p70, IL-6, IL-2 and TNFα that were released in culture supernatants by PBMCs were measured after 24, 48 and 72 hours. a) IFN-γ concentration (pg/ml) after 24 hours. b) IFN-γ concentration (pg/ml) after 48 hours. c) IFN-γ concentration (pg/ml) after 72 hours. d) IL-12p'70 concentration (pg/ml) after 24 hours. e) IL-12p'70 concentration (pg/ml) after 48 hours. f) IL-12p70 concentration (pg/ml) after 72 hours. g) IL-6 concentration (pg/ml) after 24 hours. h) IL-6 concentration (pg/ml) after 48 hours. i) IL-6 concentration (pg/ml) after 72 hours. j) IL-2 concentration (pg/ml) after 24 hours. k) IL-2 concentration (pg/ml) after 48 hours. l) IL-2 concentration (pg/ml) after 72 hours. m) TNFα concentration (pg/ml) after 24 hours. n) TNFα concentration (pg/ml) after 48 hours. o) TNFα concentration (pg/ml) after 72 hours.
Figure 2B:
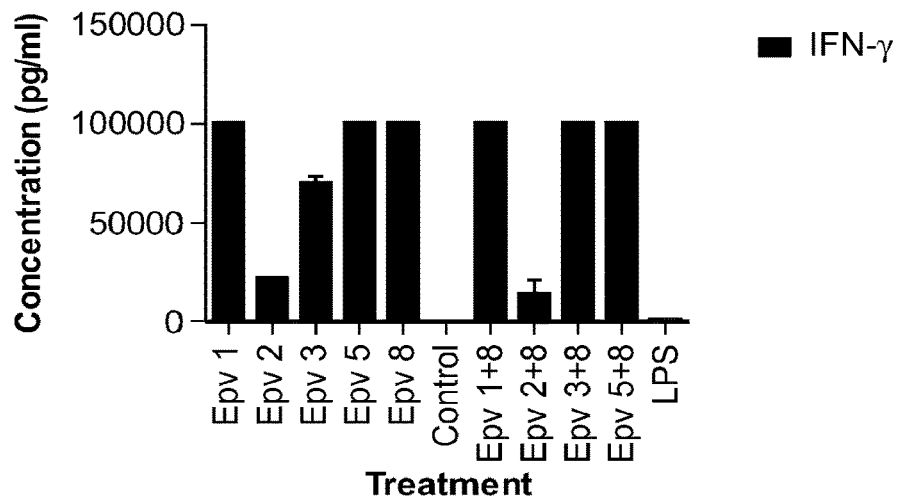
Figure 2C:
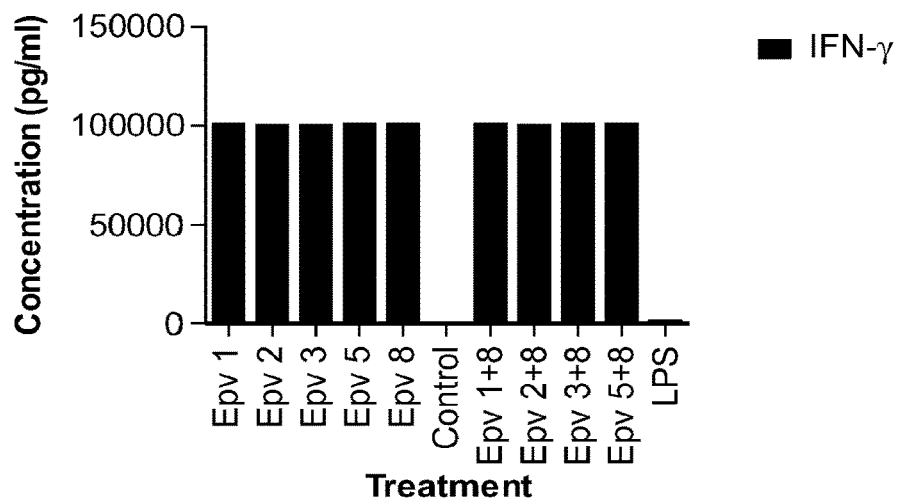
Figure 2D:
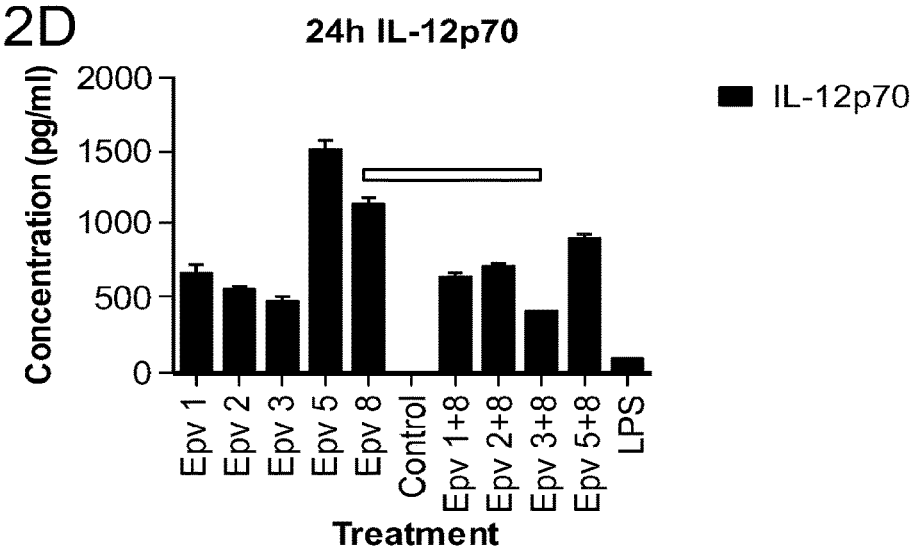
Figure 2E:
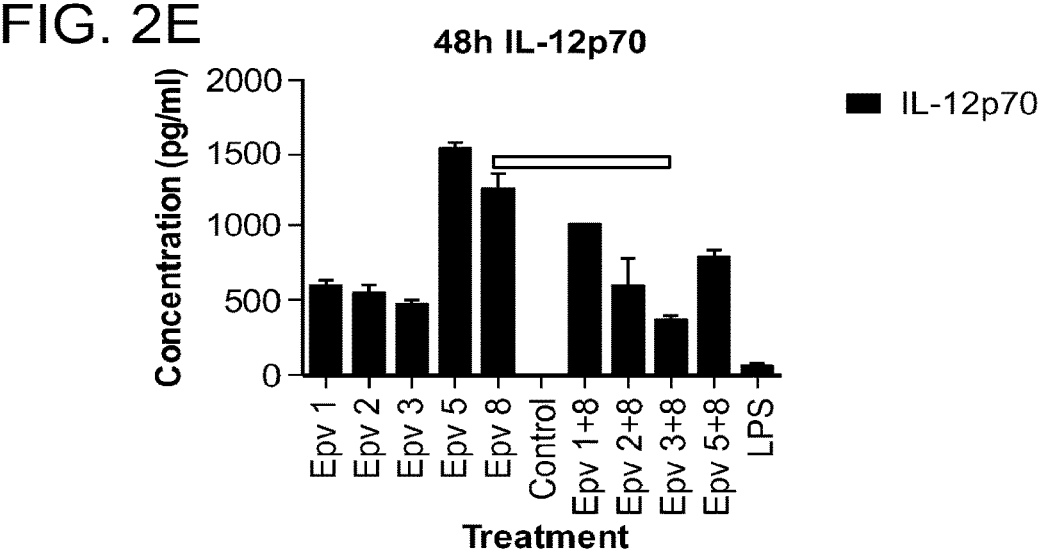
Figure 2F:
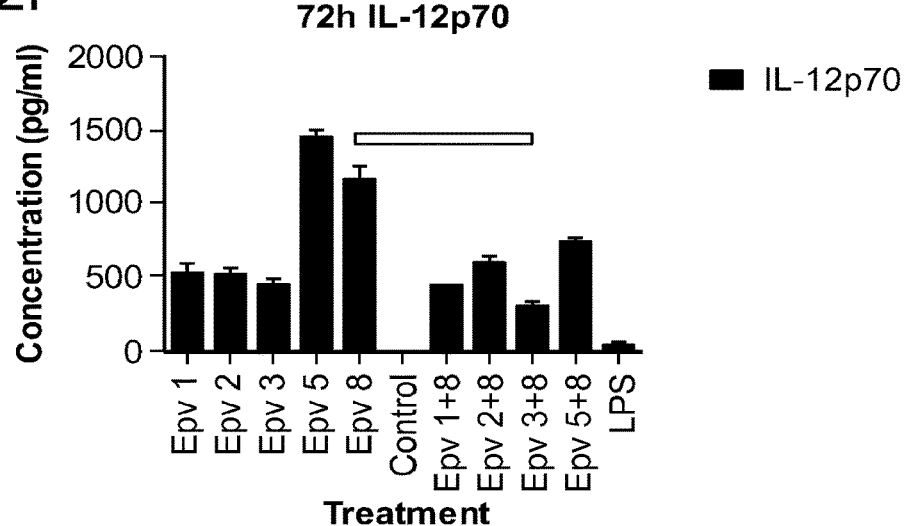
Figure 2G:
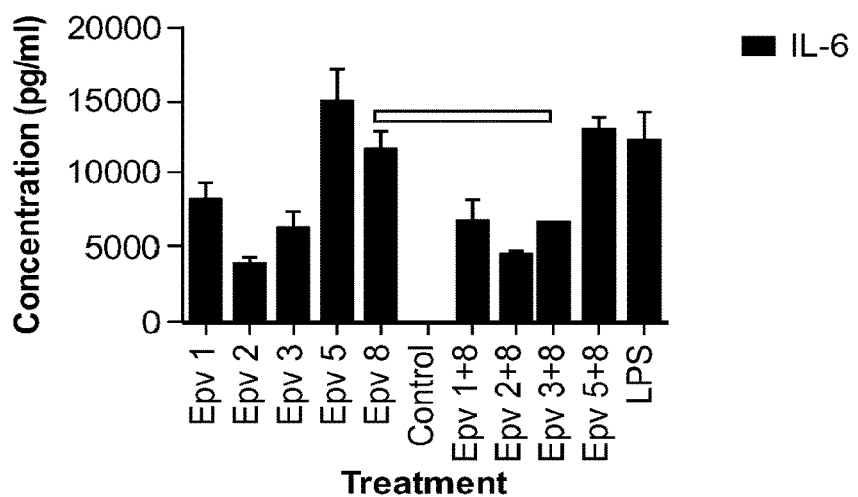
Figure 2H:
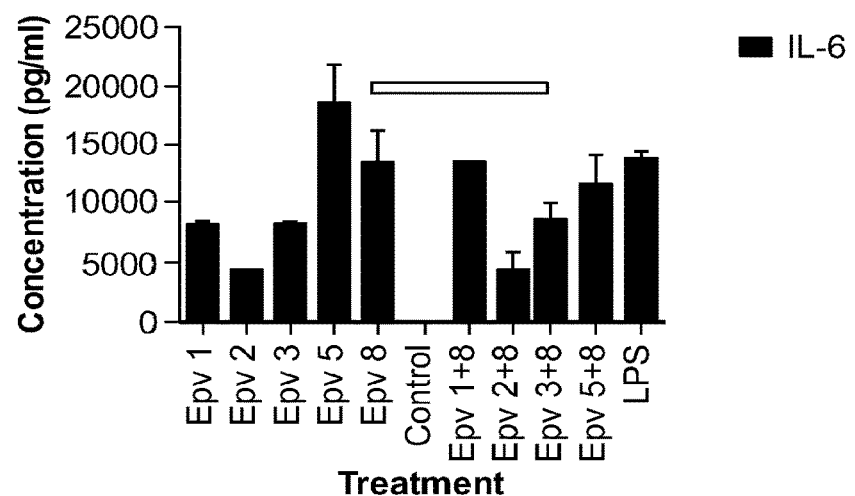
Figure 2I:
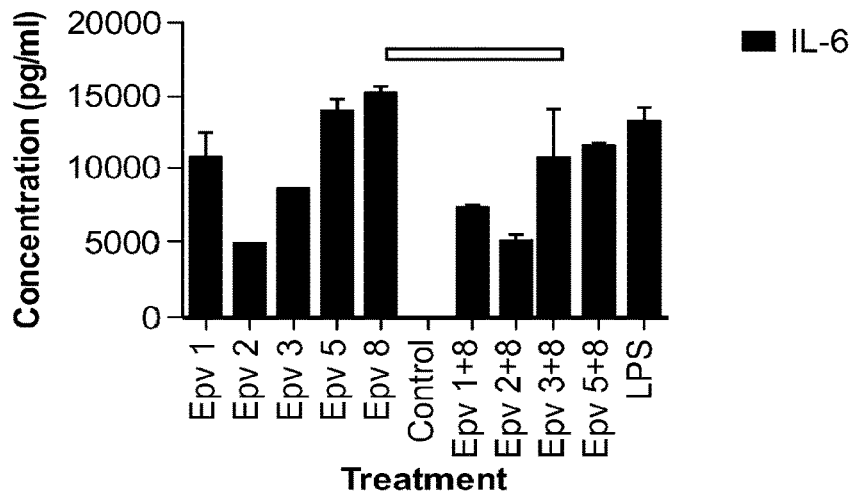
Figure 2J:
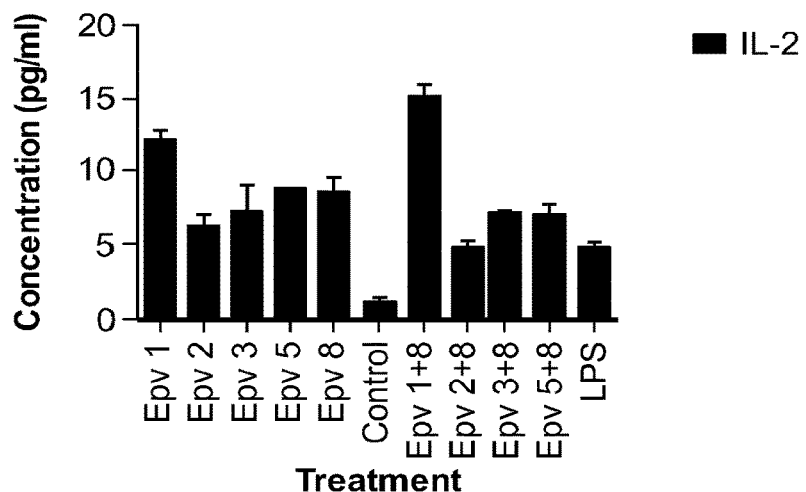
Figure 2K:
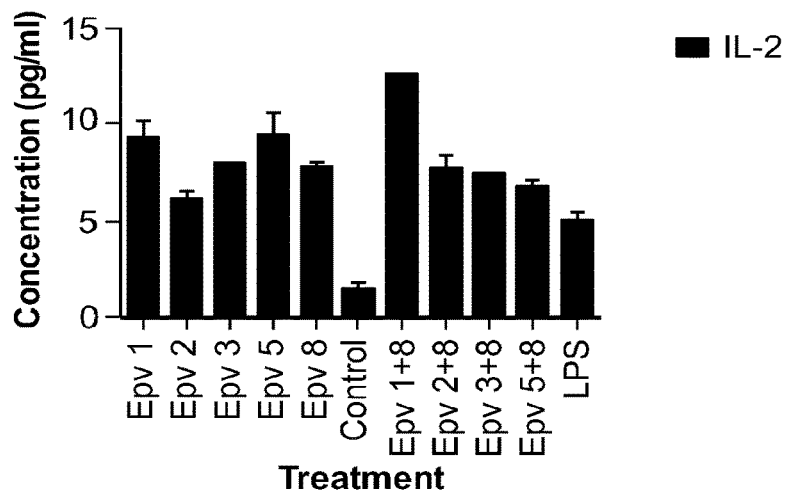
Figure 2L:
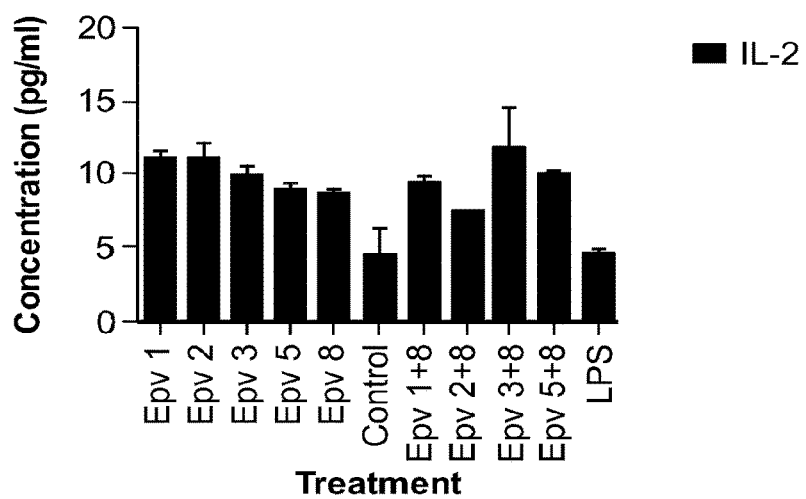
Figure 2M:
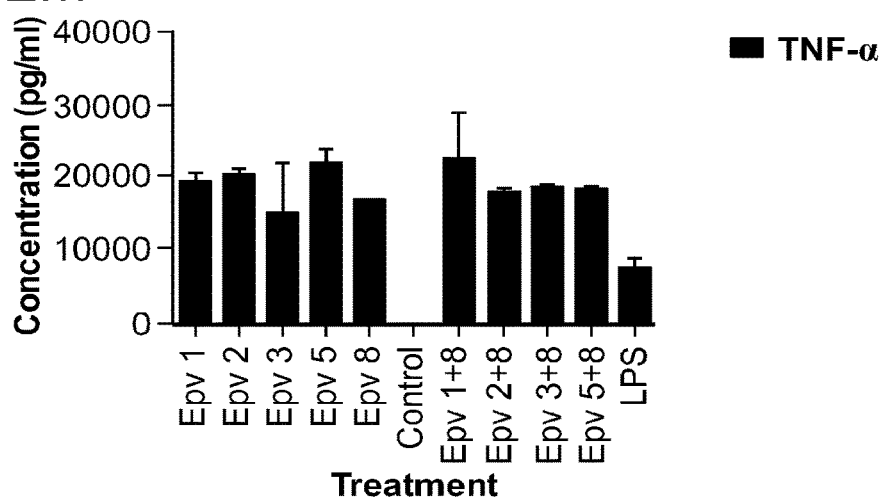
Figure 2N:
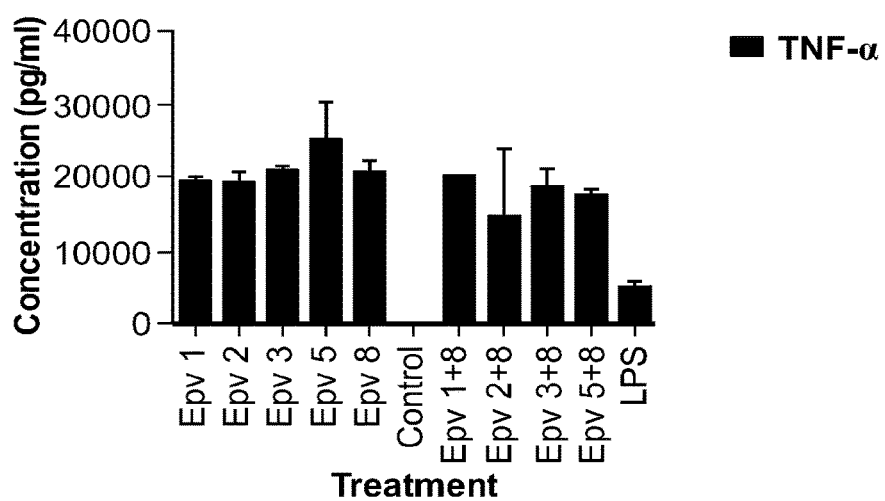
Figure 2O:
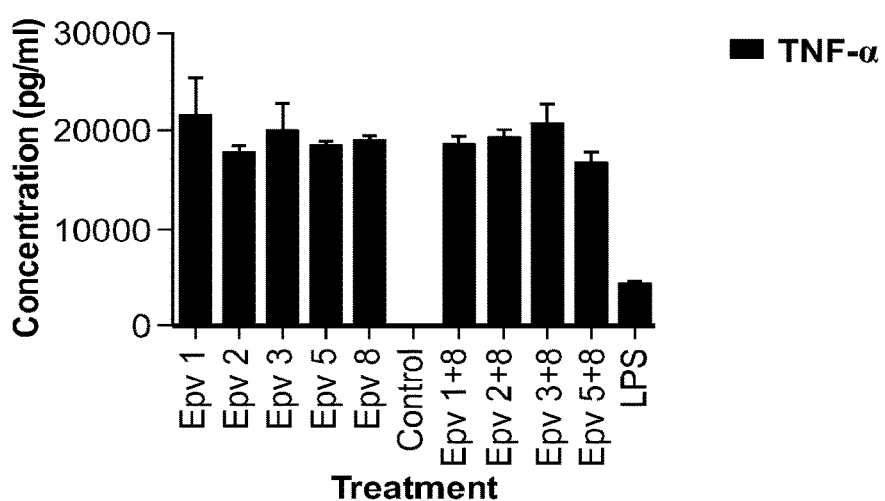
Figure 3A:
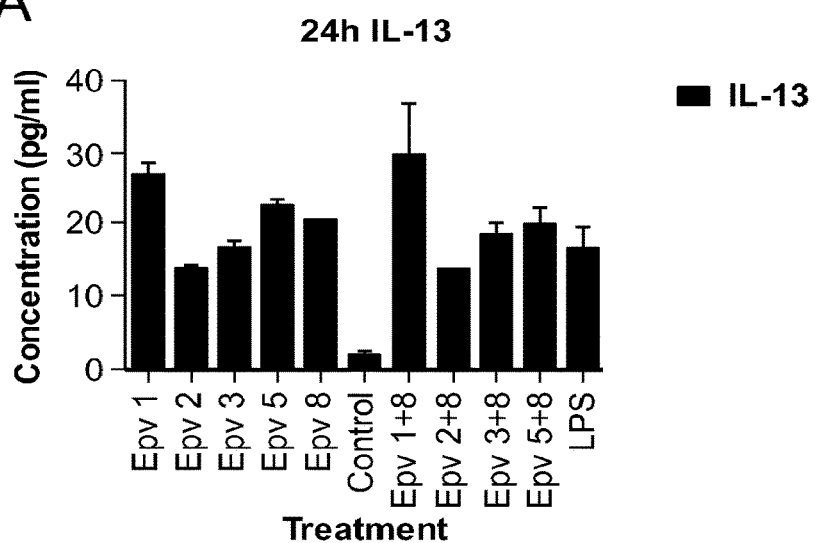
FIG. 3 (a-i) is a panel of graphs showing the time course of Th2 related cytokines that were released by human PBMCs incubated with *R. gnavus* (Epv 1), *E. rectale* (Epv 2), *B. luti* (Epv 3), *B. wexlerae* (Epv 5) and *E. faecalis* (Epv 8), or combinations of each bacterium with *E. faecalis*. Amounts of IL-13, IL-4 and IL-5 that were released in culture supernatants by PBMCs were measured after 24, 48 and 72 hours. a) IL-13 concentration (pg/ml) after 24 hours. b) IL-13 concentration (pg/ml) after 48 hours. c) IL-13 concentration (pg/ml) after 72 hours. d) IL-4 concentration (pg/ml) after 24 hours. e) IL-4 concentration (pg/ml) after 48 hours. f) IL-4 concentration (pg/ml) after 72 hours. g) IL-5 concentration (pg/ml) after 24 hours. h) IL-5 concentration (pg/ml) after 48 hours. i) IL-5 concentration (pg/ml) after 72 hours.
Figure 3B:
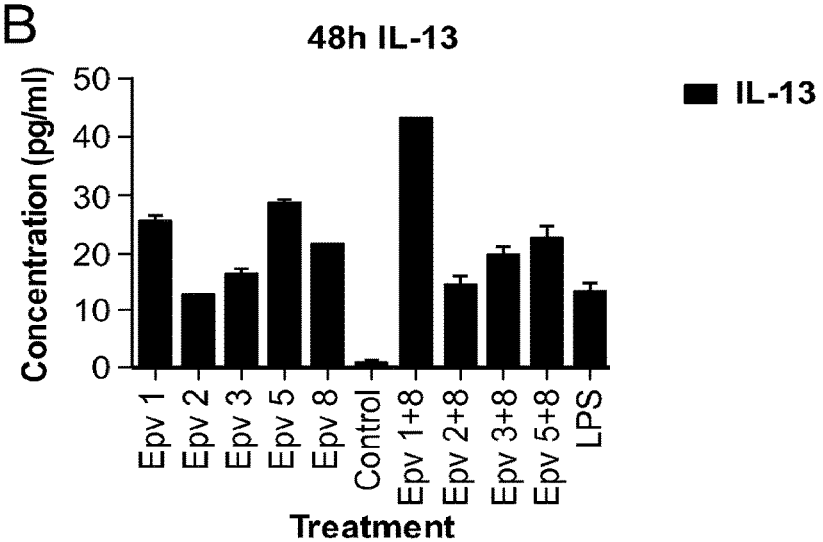
Figure 3C:
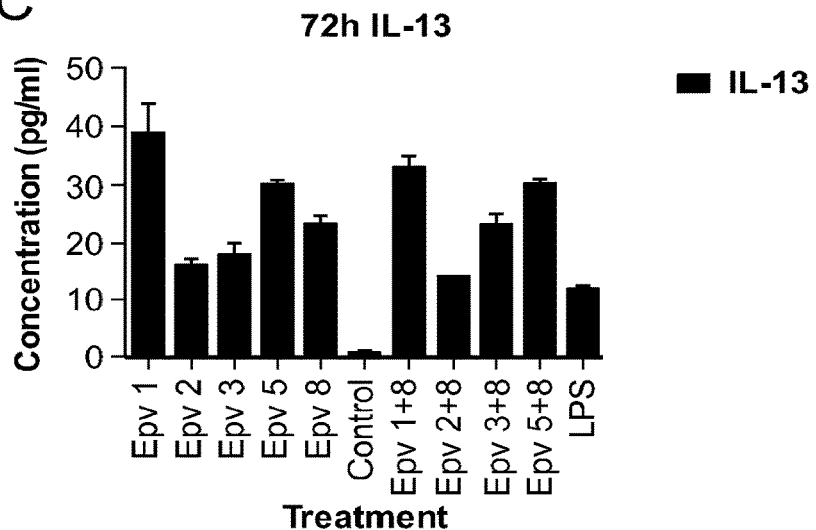
Figure 3D:
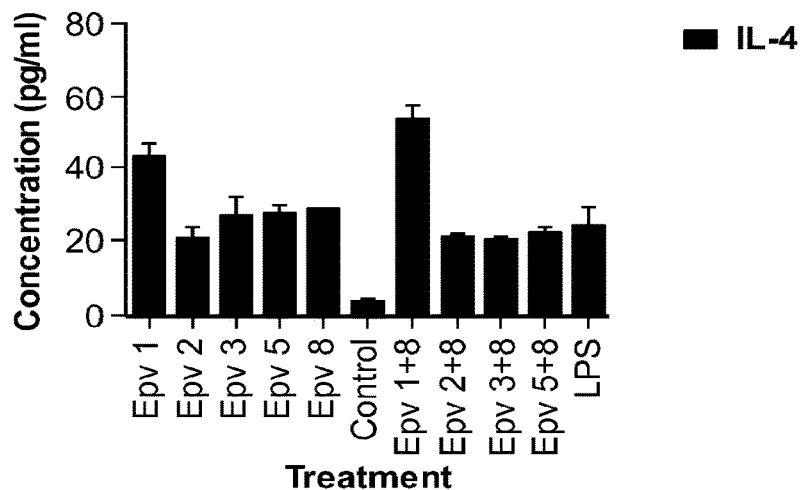
Figure 3E:
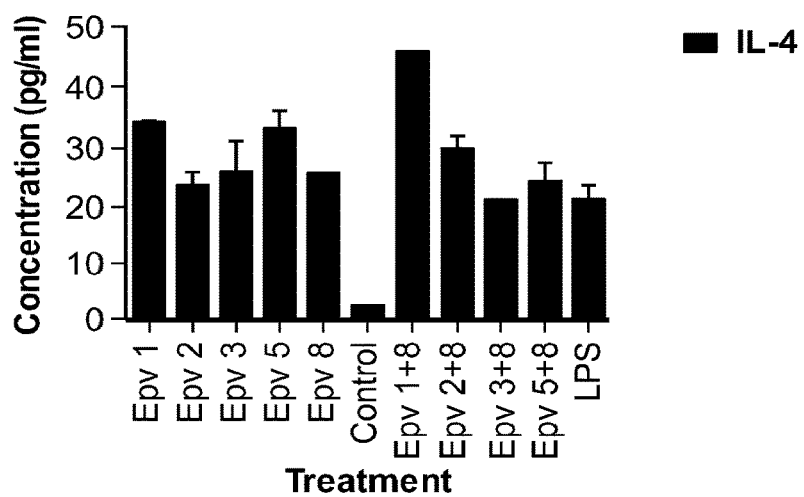
Figure 3F:
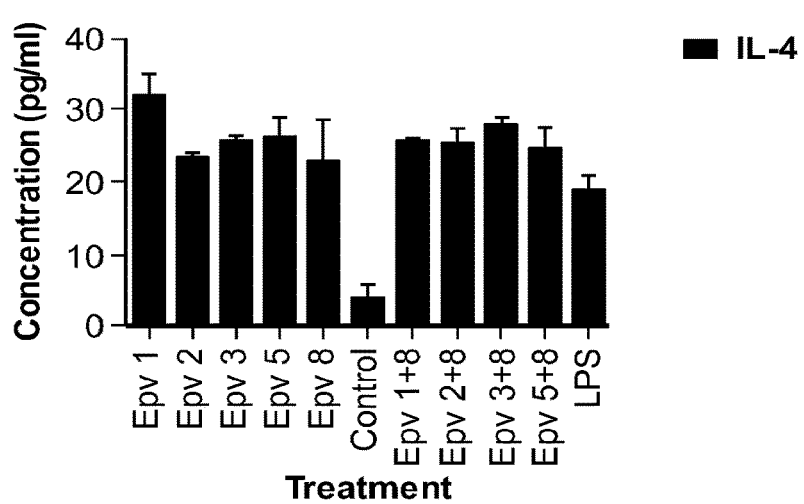
Figure 3G:
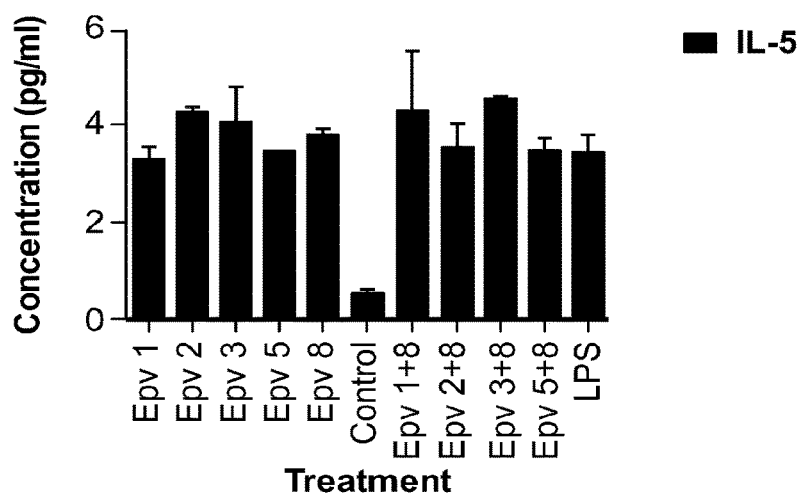
Figure 3H:
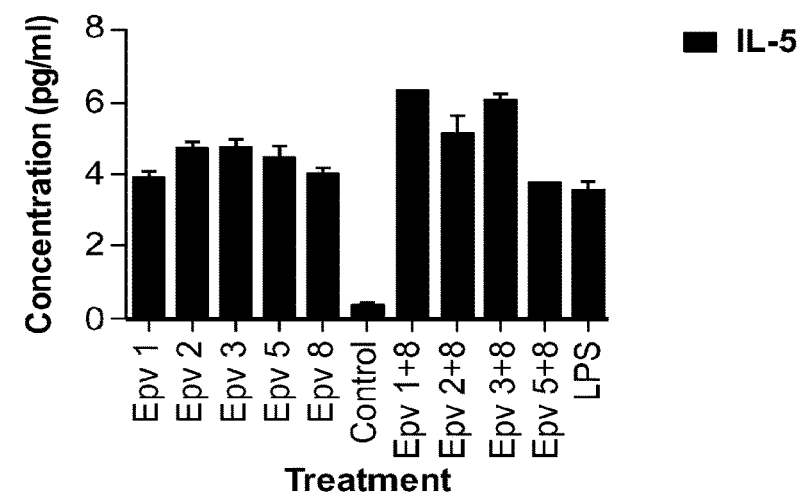
Figure 3I:
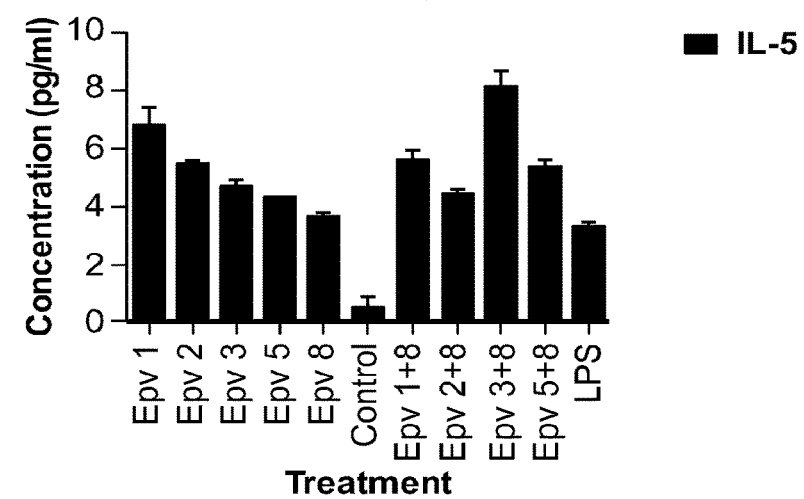
Figure 4A:
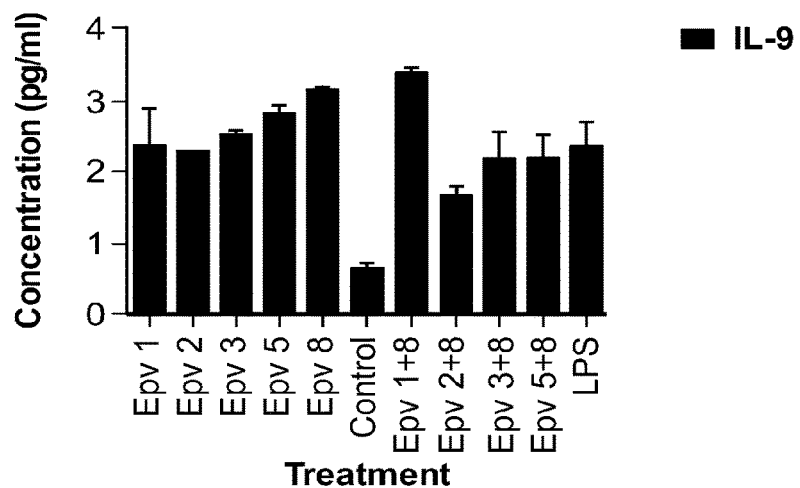
FIG. 4 (a-i) is a panel of graphs showing the time course of Th9, Th17 and Treg cytokines that were released by human PBMCs incubated with *R. gnavus* (Epv 1), *E. rectale* (Epv 2), *B. luti* (Epv 3), *B. wexlerae* (Epv 5) and *E. faecalis* (Epv 8), or combinations of each bacterium with *E. faecalis*. Amounts of IL-9, IL-17 and IL-10 that were released in culture supernatants by PBMCs were measured after 24, 48 and 72 hours. a) IL-9 concentration (pg/ml) after 24 hours. b) IL-9 concentration (pg/ml) after 48 hours. c) IL-9 concentration (pg/ml) after 72 hours. d) IL-17 concentration (pg/ml) after 24 hours. e) IL-17 concentration (pg/ml) after 48 hours. f) IL-17 concentration (pg/ml) after 72 hours. g) IL-10 concentration (pg/ml) after 24 hours. h) IL-10 concentration (pg/ml) after 48 hours. i) IL-10 concentration (pg/ml) after 72 hours.
Figure 4B:
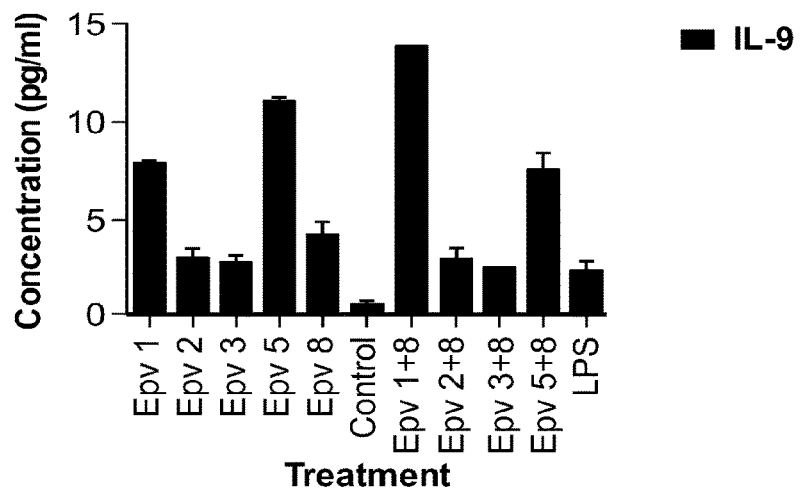
Figure 4C:
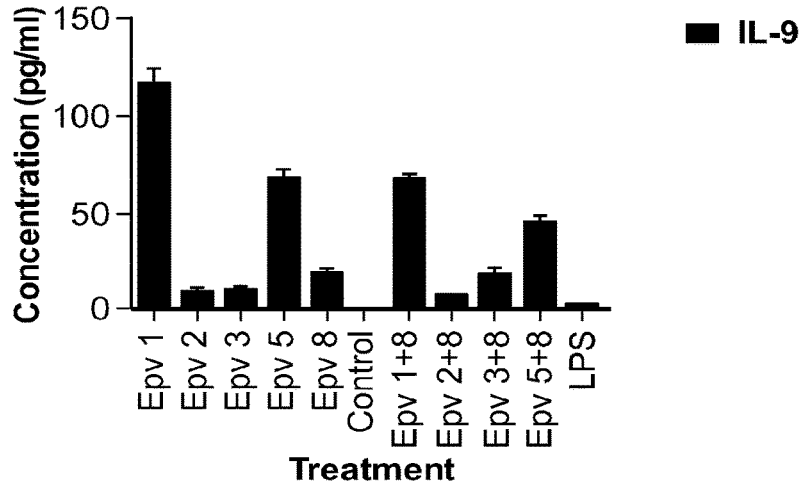
Figure 4D:
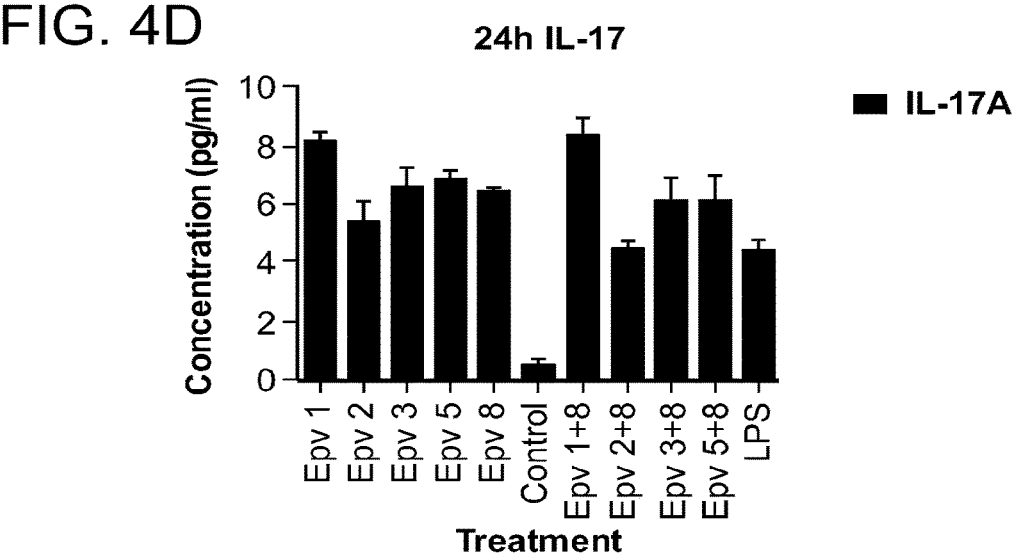
Figure 4E:
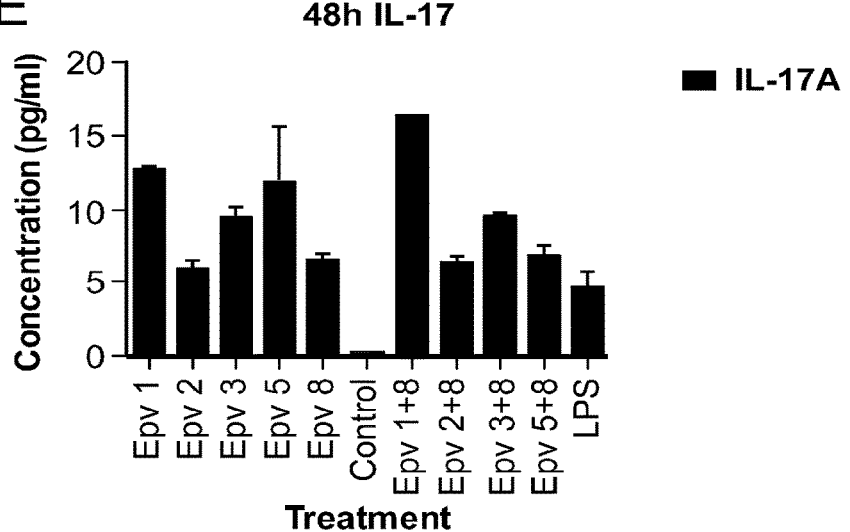
Figure 4F:
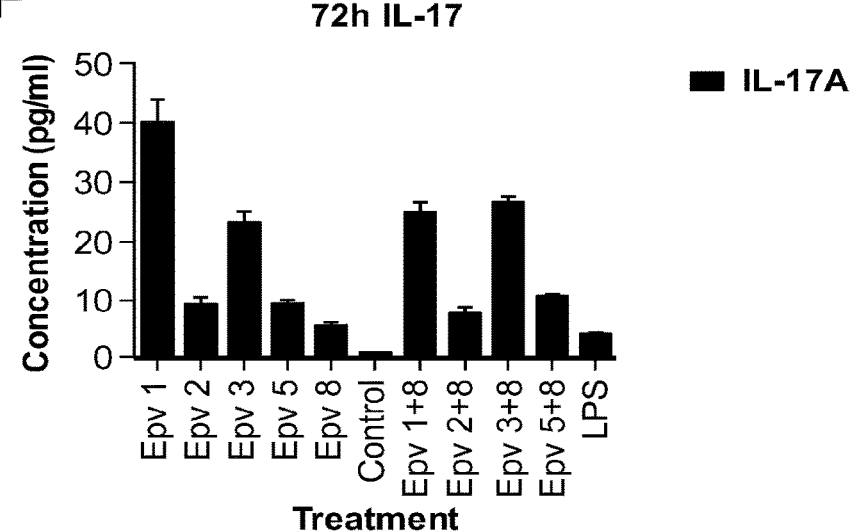
Figure 4G:
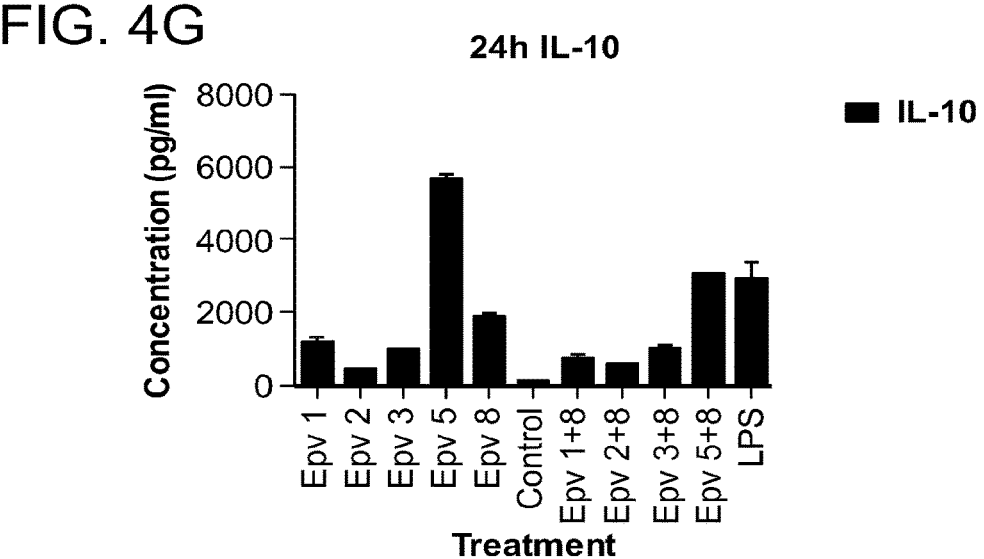
Figure 4H:
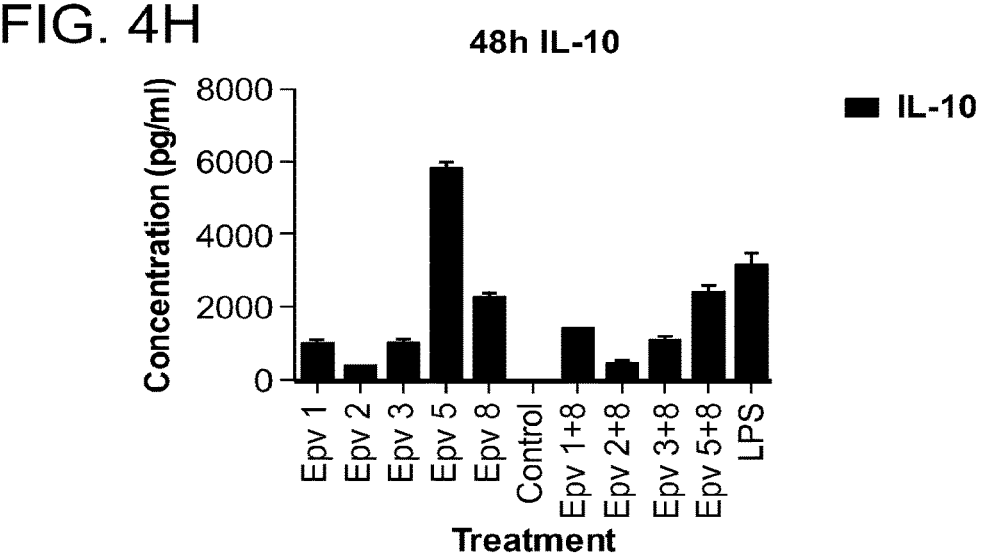
Figure 4I:
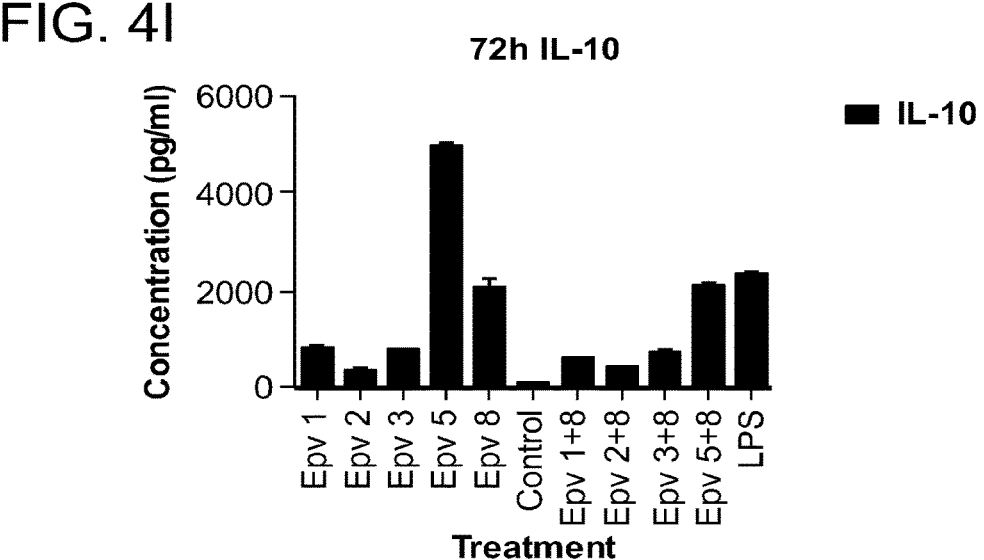
Figure 5A:
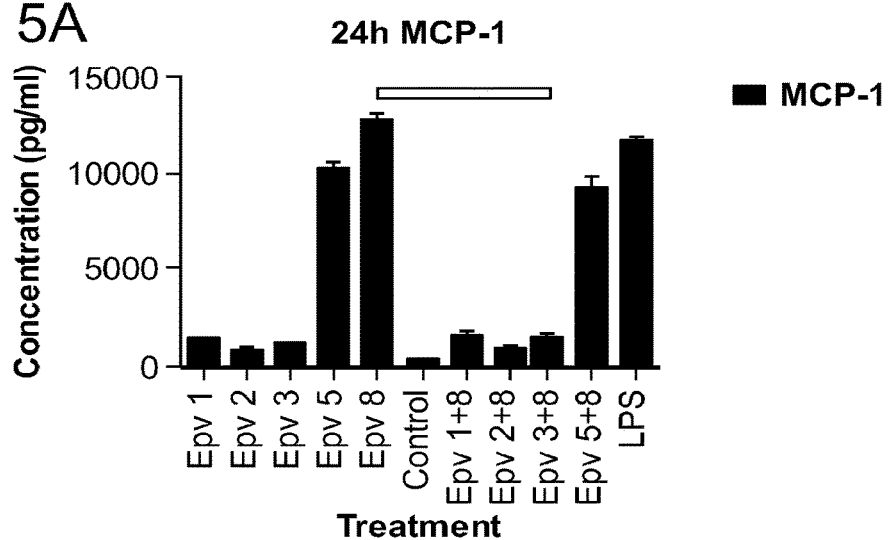
FIG. 5 (a-x) is a panel of graphs showing the time course of monocyte, macrophage and neutrophil-derived inflammatory cytokines that were released by human PBMCs incubated with *R. gnavus* (Epv 1), *E. rectale* (Epv 2), *B. luti* (Epv 3), *B. wexlerae* (Epv 5) and *E. faecalis* (Epv 8), or combinations of each bacterium with *E. faecalis*. Amounts of monocyte chemotactic protein 1 (MCP-1), macrophage inflammatory protein 1β (MIP1β), macrophage inflammatory protein 1α (MIP1α), regulated on activation, normal T expressed and secreted protein (RANTES), interleukin-1α (IL-1α), interleukin-1β (IL1β), interferon α2 (IFN-α2) and interleukin-8 (IL-8) that were released in culture supernatants by PBMCs were measured after 24, 48 and 72 hours. a) MCP-1 concentration (pg/ml) after 24 hours. b) MCP-1 concentration (pg/ml) after 48 hours. c) MCP-1 concentration (pg/ml) after 72 hours. d) MIP1β concentration (pg/ml) after 24 hours. e) MIP1β concentration (pg/ml) after 48 hours. f) MIP1β concentration (pg/ml) after 72 hours. g) MIP1α concentration (pg/ml) after 24 hours. h) MIP1α concentration (pg/ml) after 48 hours. i) MIP1α concentration (pg/ml) after 72 hours. j) RANTES concentration (pg/ml) after 24 hours. k) RANTES concentration (pg/ml) after 48 hours. l) RANTES concentration (pg/ml) after 72 hours. m) IL-1α concentration (pg/ml) after 24 hours. n) IL-1α concentration (pg/ml) after 48 hours. o) IL-1α concentration (pg/ml) after 72 hours. p) IL1β concentration (pg/ml) after 24 hours. q) IL1β concentration (pg/ml) after 48 hours. r) IL1β concentration (pg/ml) after 72 hours. s) IFN-α2 concentration (pg/ml) after 24 hours. t) IFN-α2 concentration (pg/ml) after 48 hours. u) IFN-α2 concentration (pg/ml) after 72 hours. v) IL-8 concentration (pg/ml) after 24 hours.
Figure 5B:
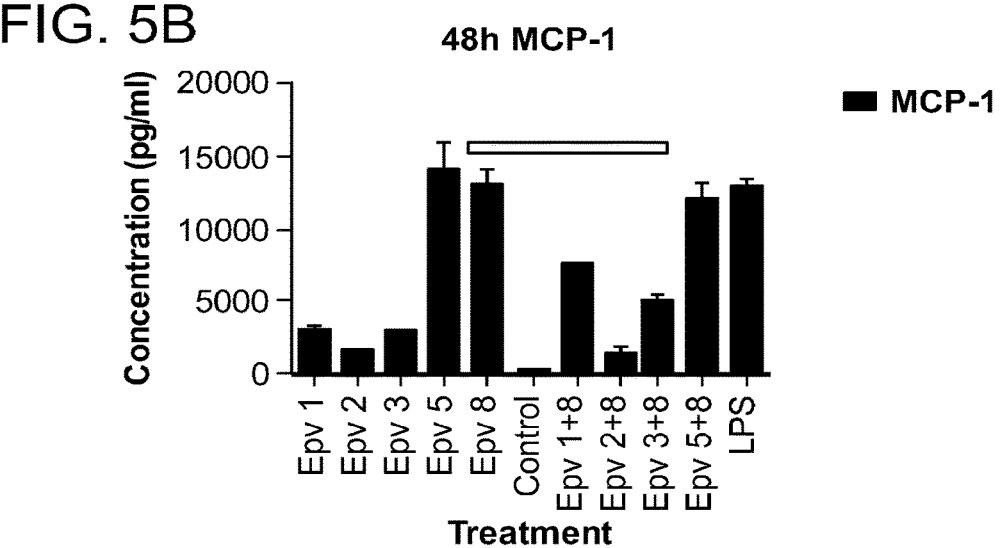
Figure 5C:
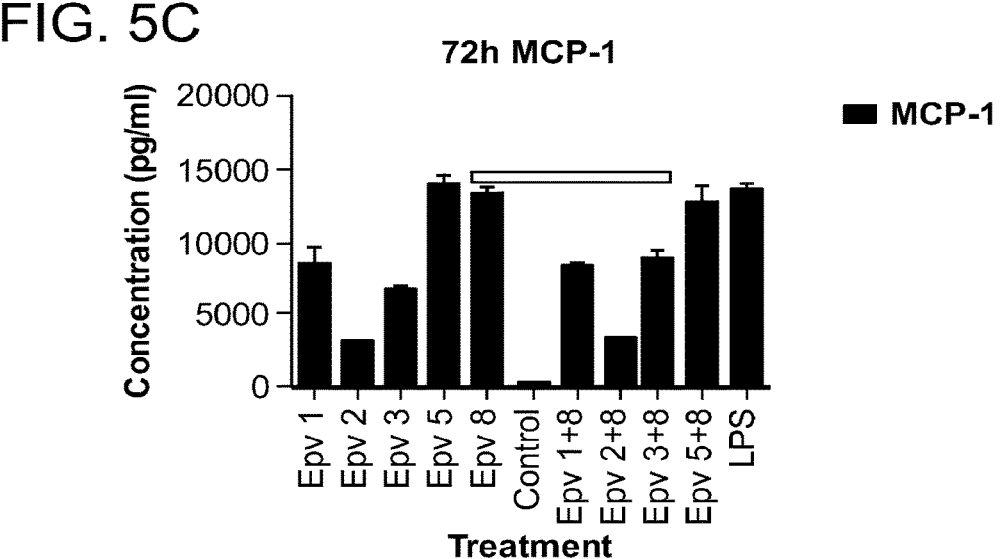
Figure 5D:
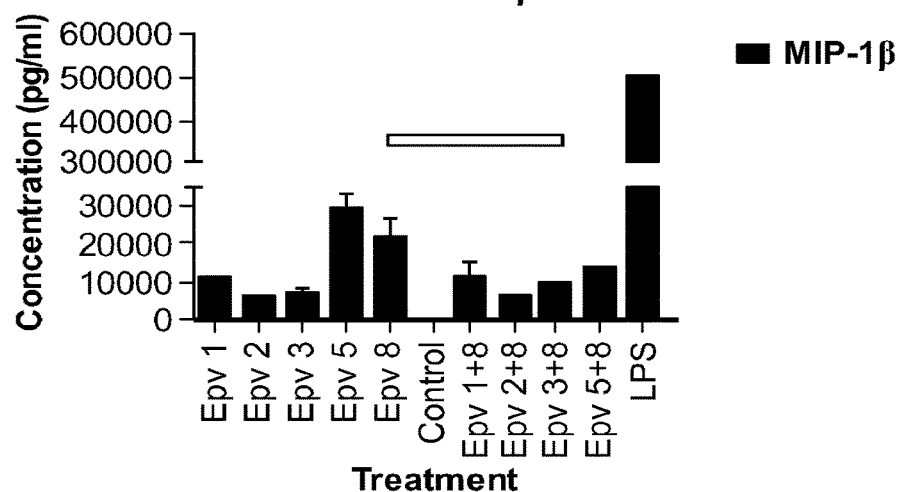
Figure 5E:
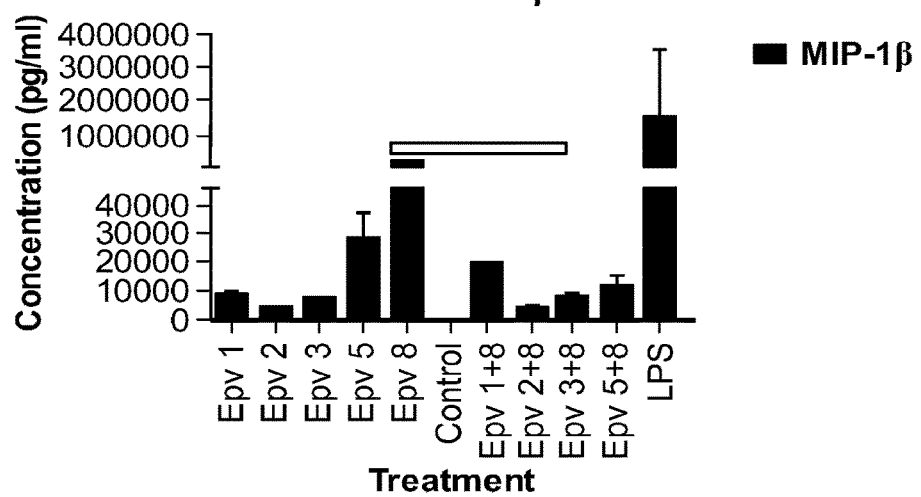
Figure 5F:
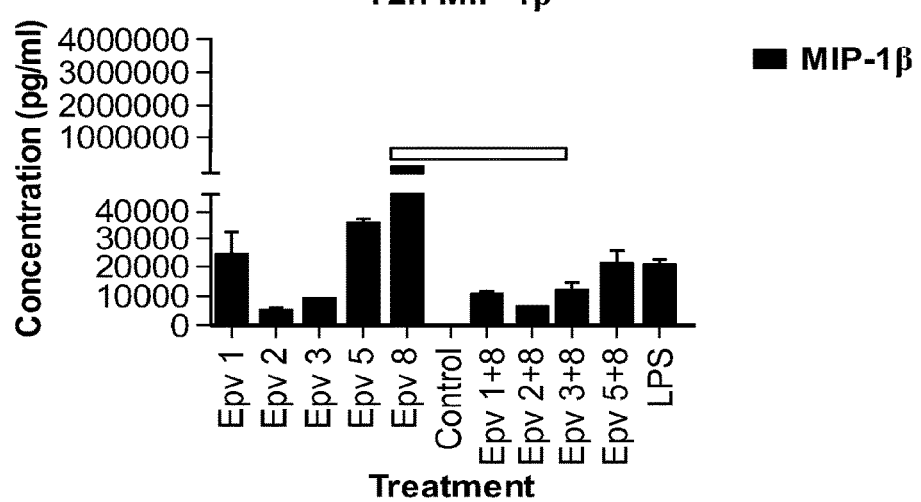
Figure 5G:
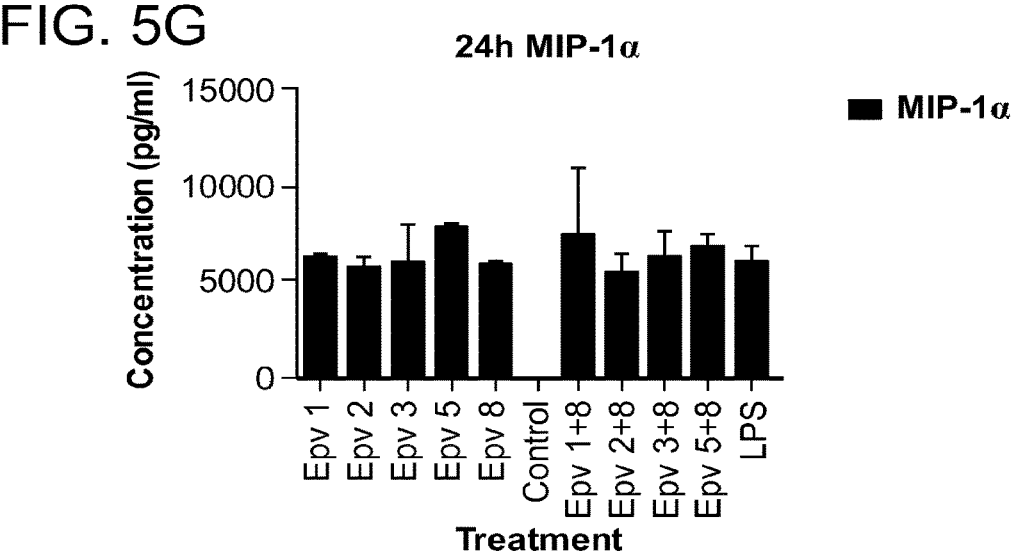
Figure 5H:
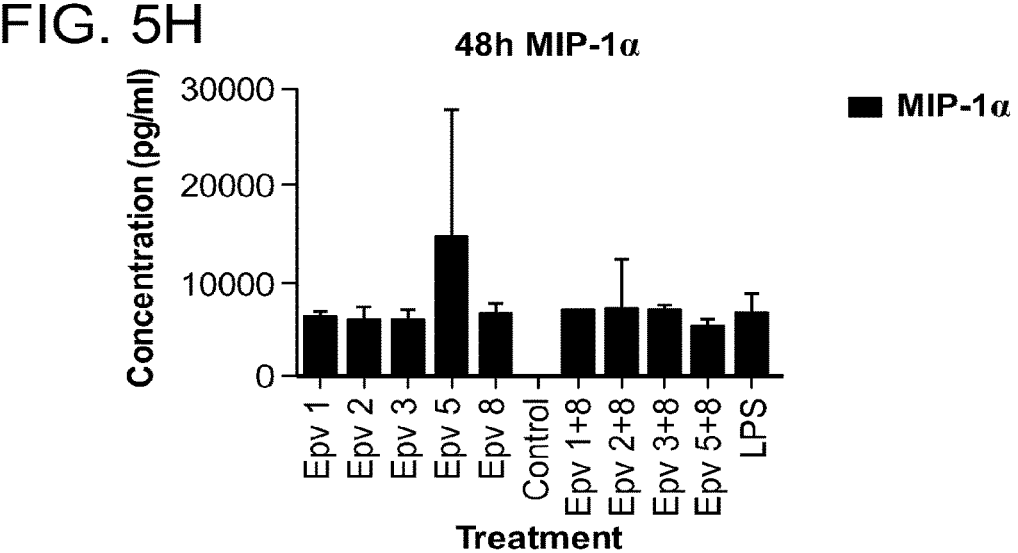
Figure 5I:
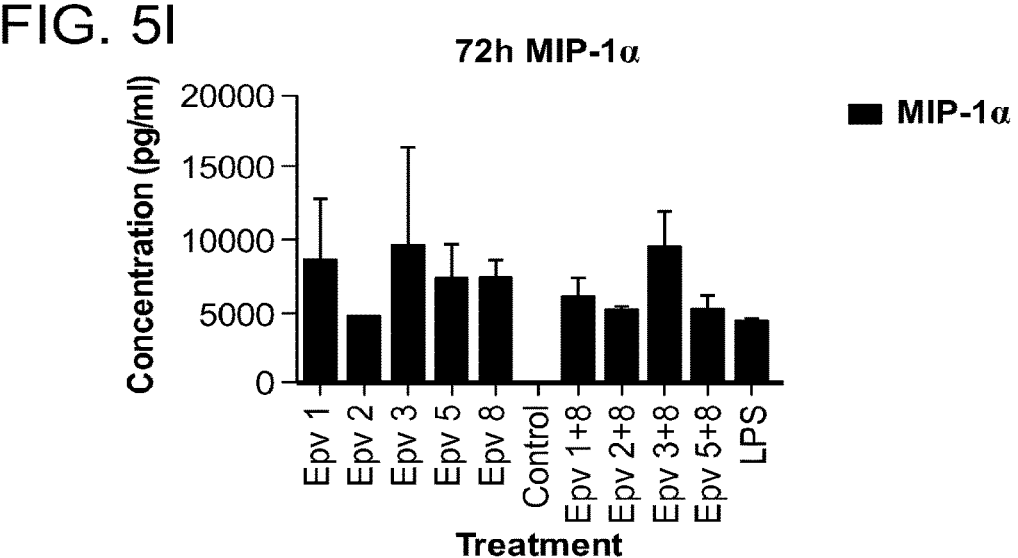
Figure 5J:
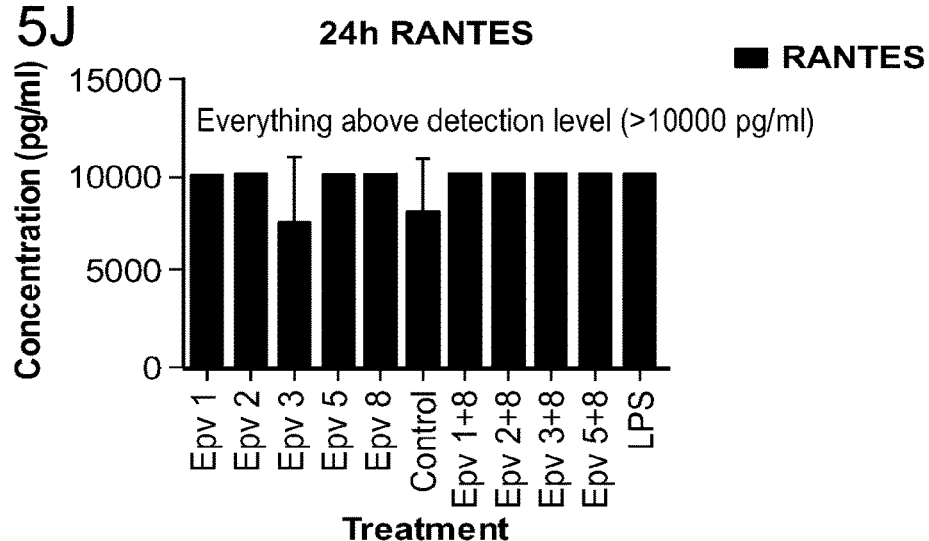
Figure 5K:
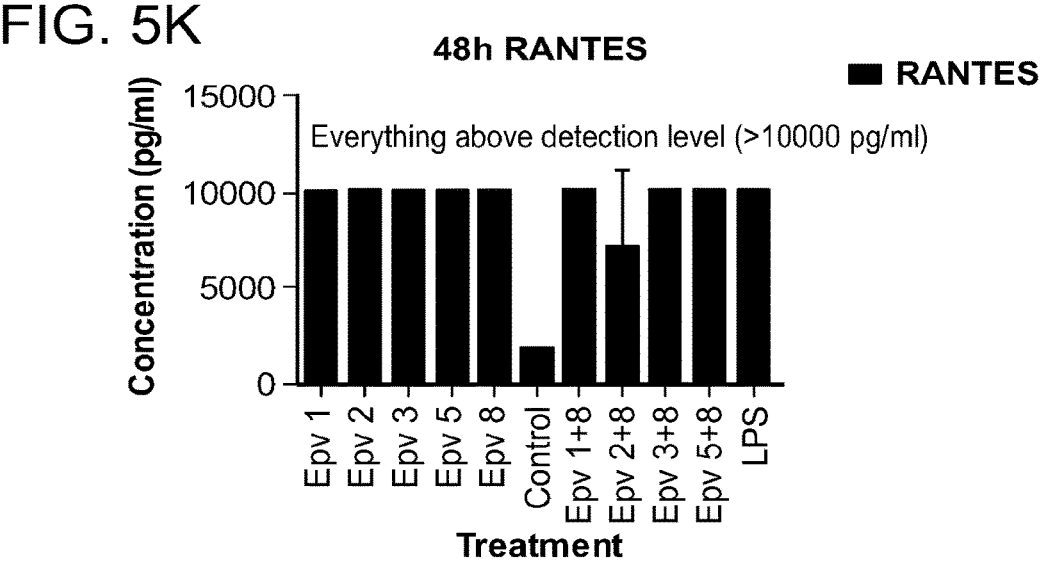
Figure 5L:
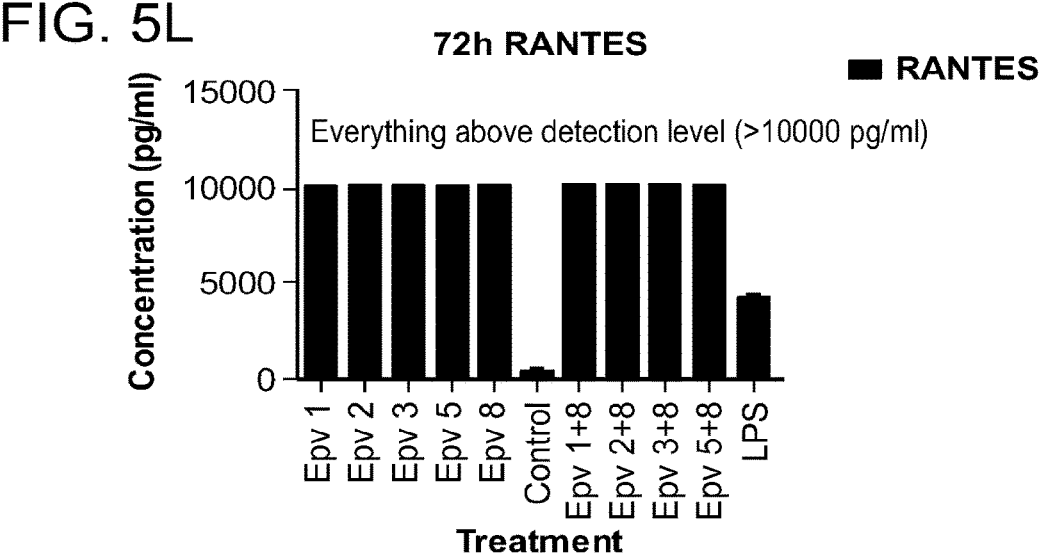
Figure 5M:
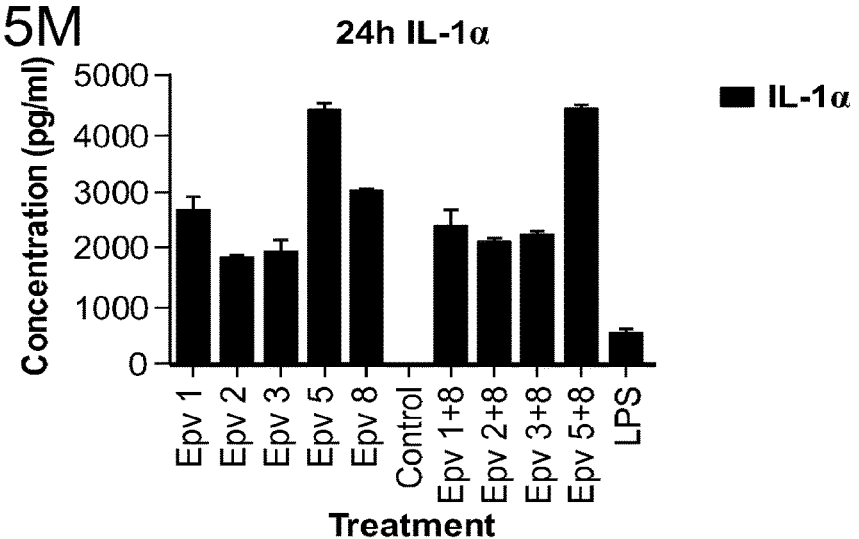
Figure 5N:
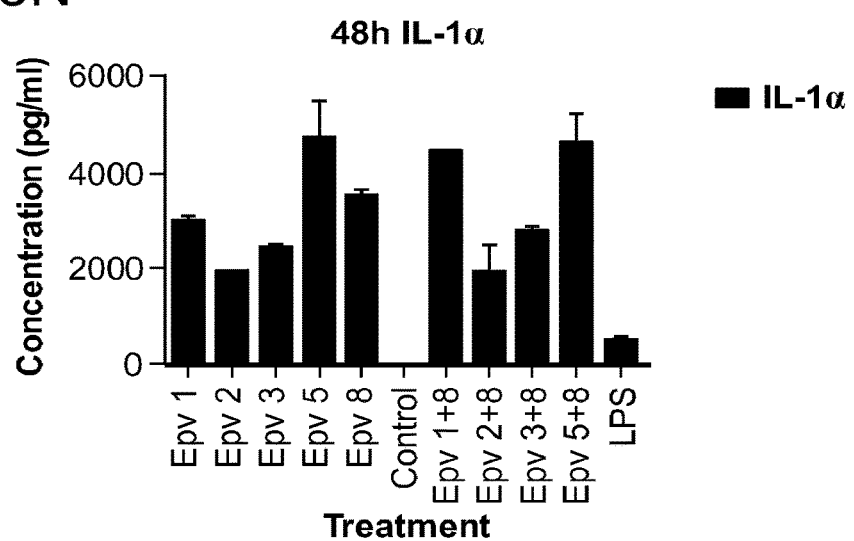
Figure 5O:
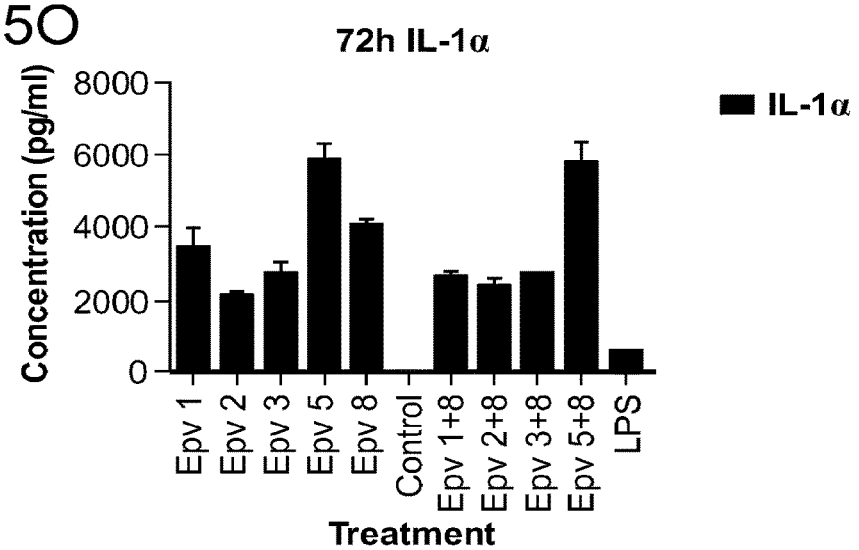
Figure 5P:
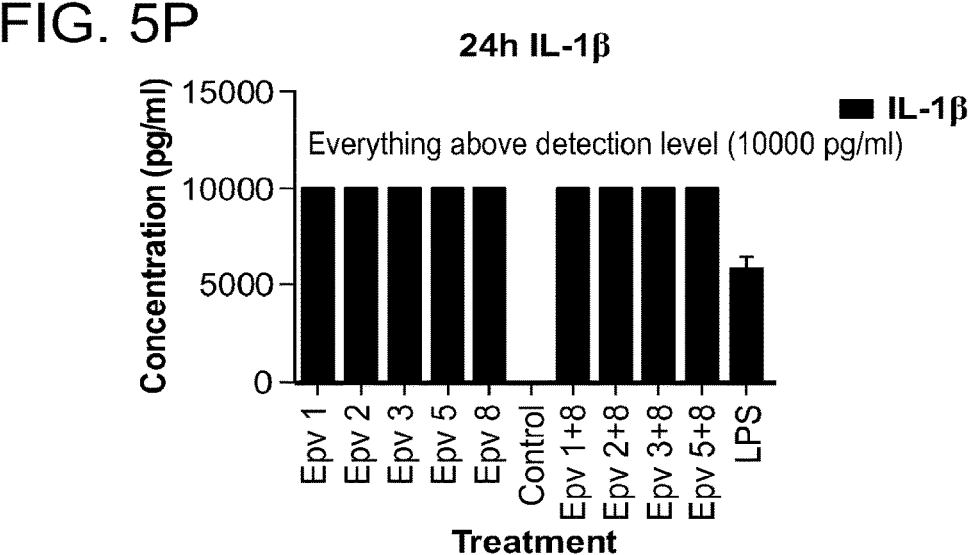
Figure 5Q:
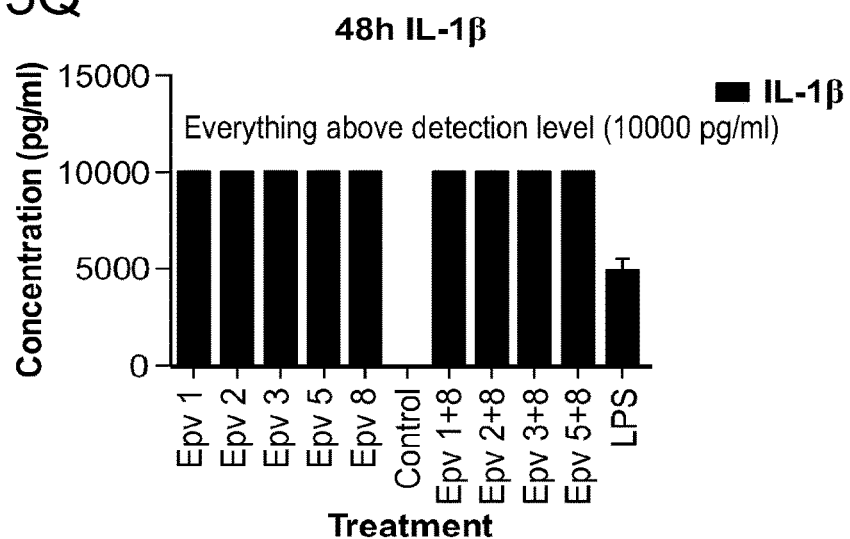
Figure 5R:
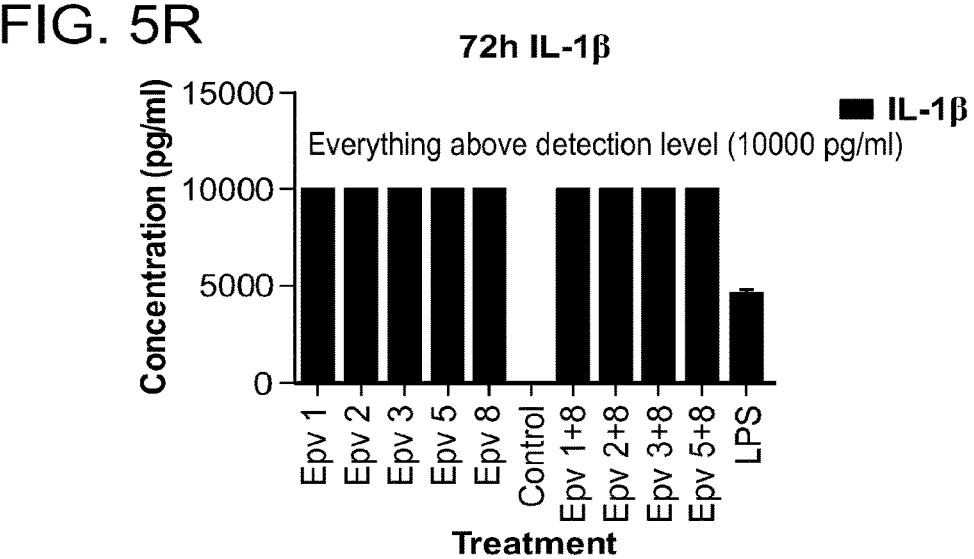
Figure 5S:
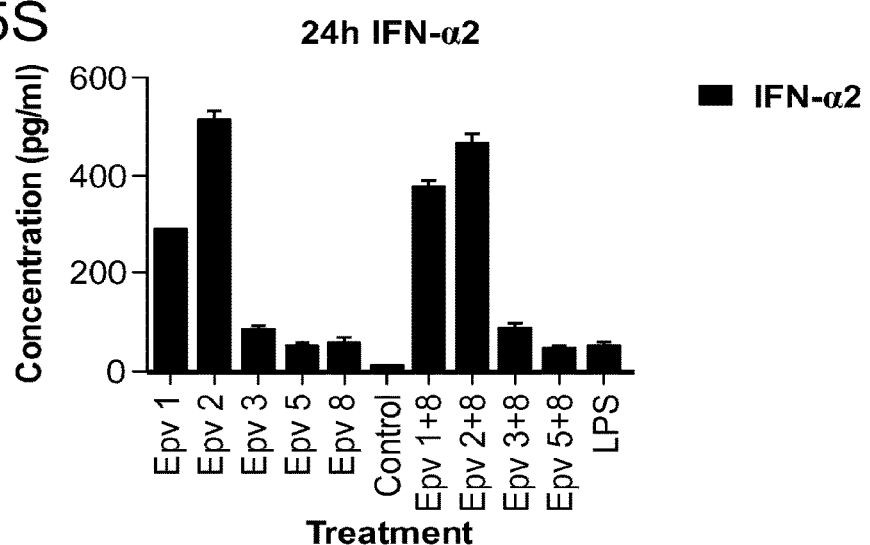
Figure 5T:
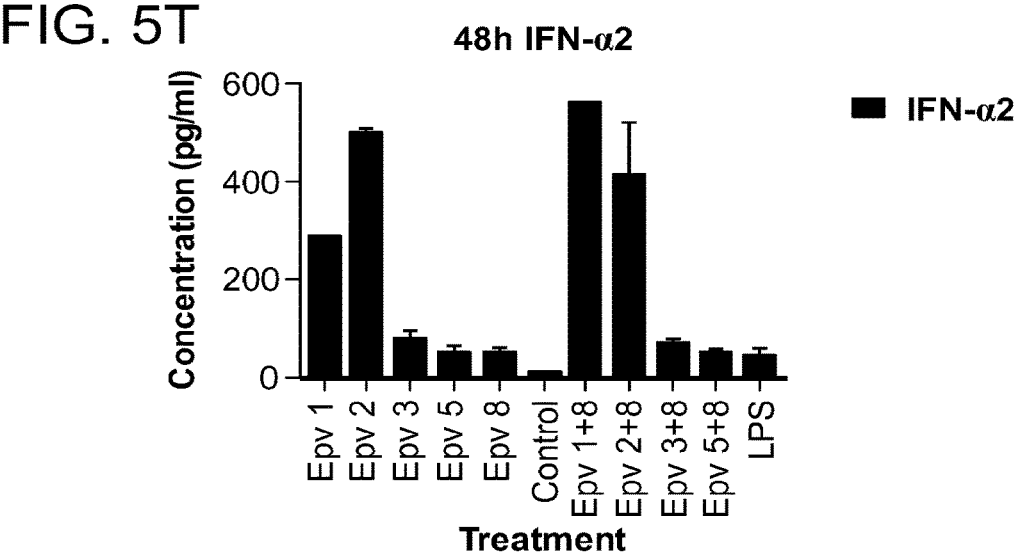
Figure 5U:
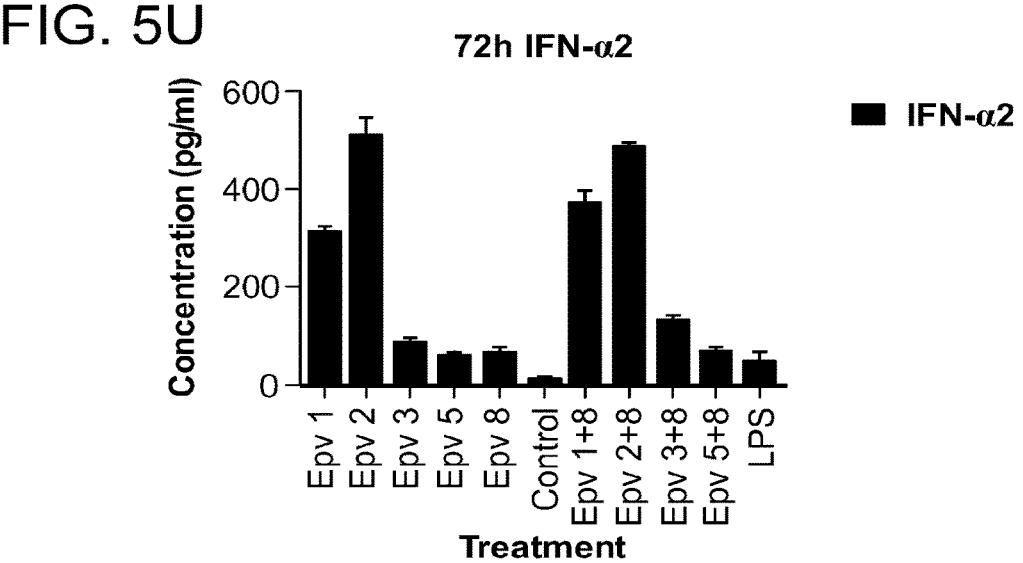
Figure 5V:
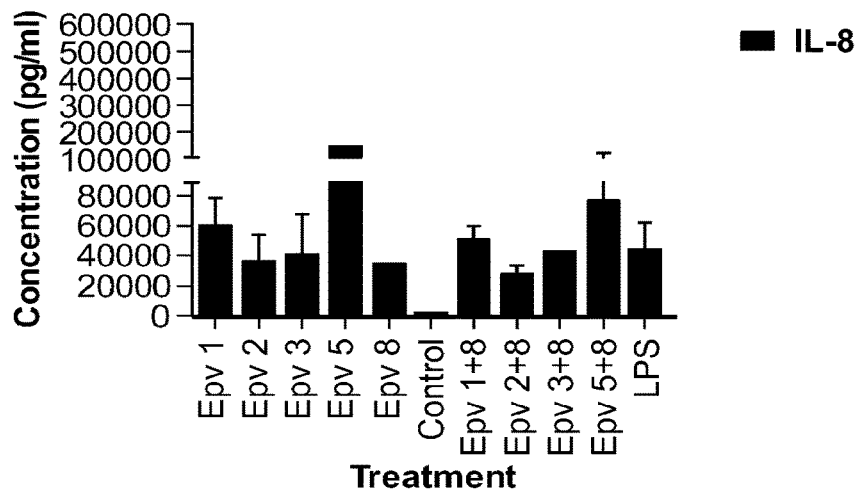
Figure 5W:
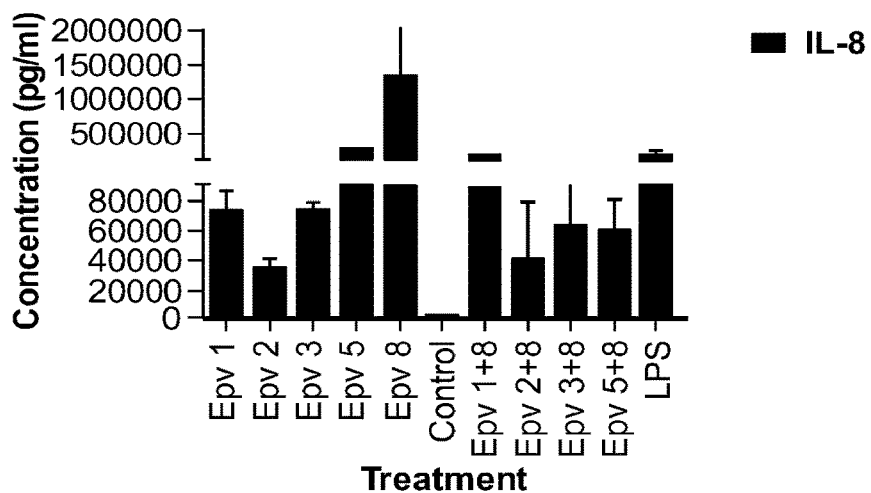
Figure 5X:
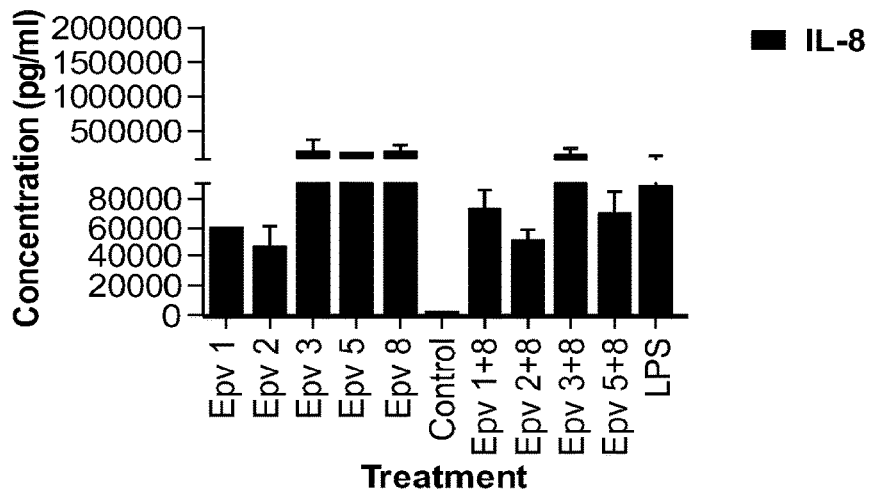
Figure 6A:
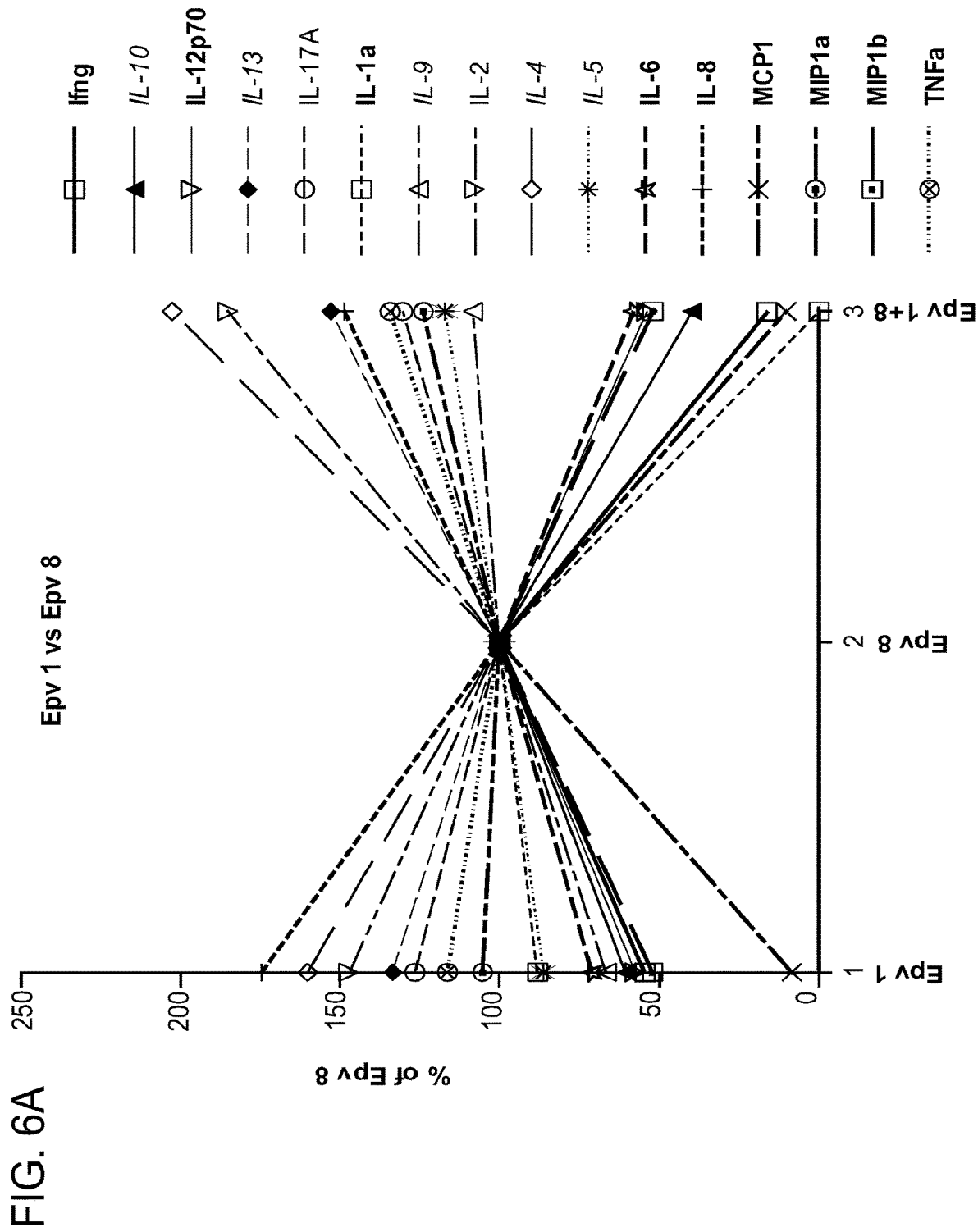
Figure 6B:
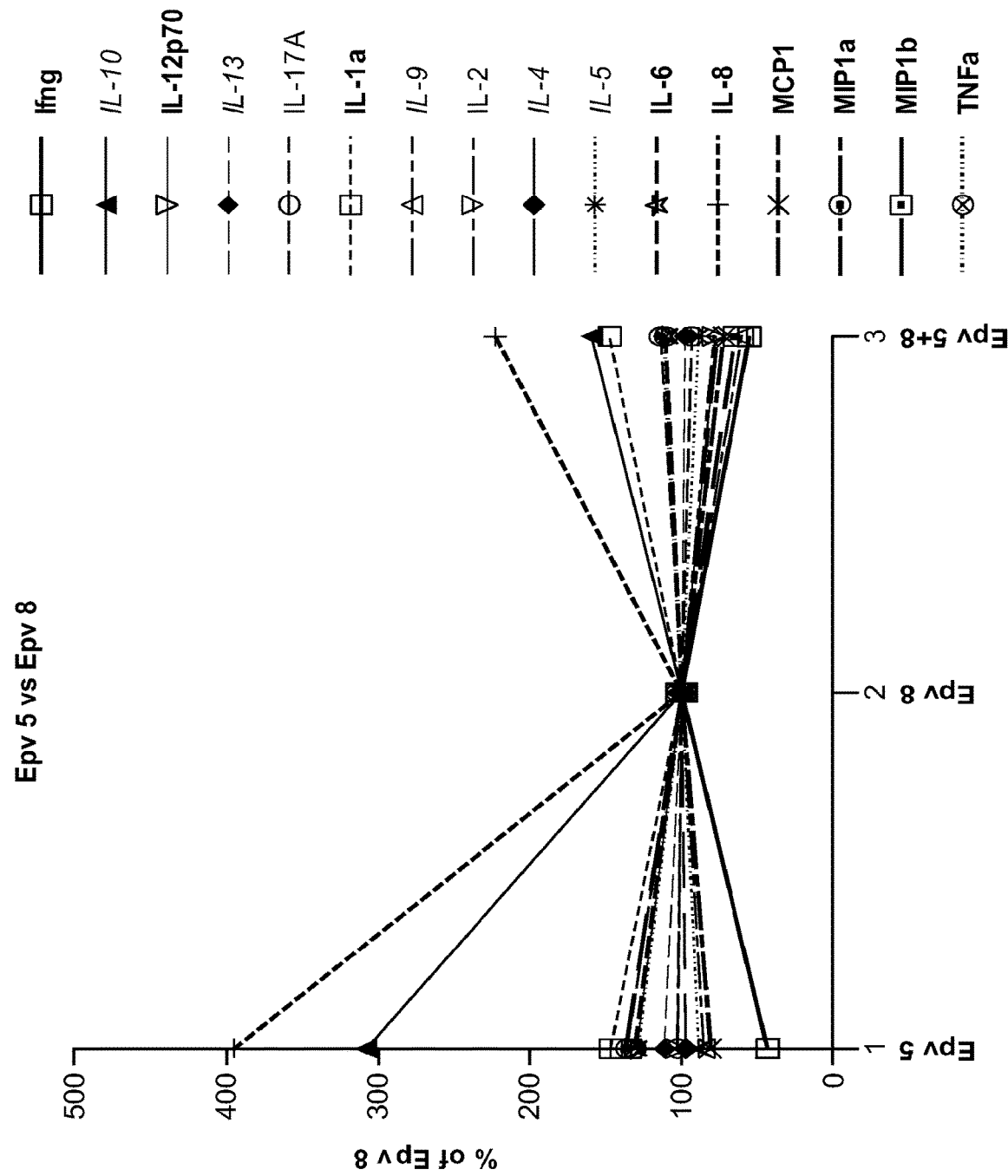
Figure 6C:
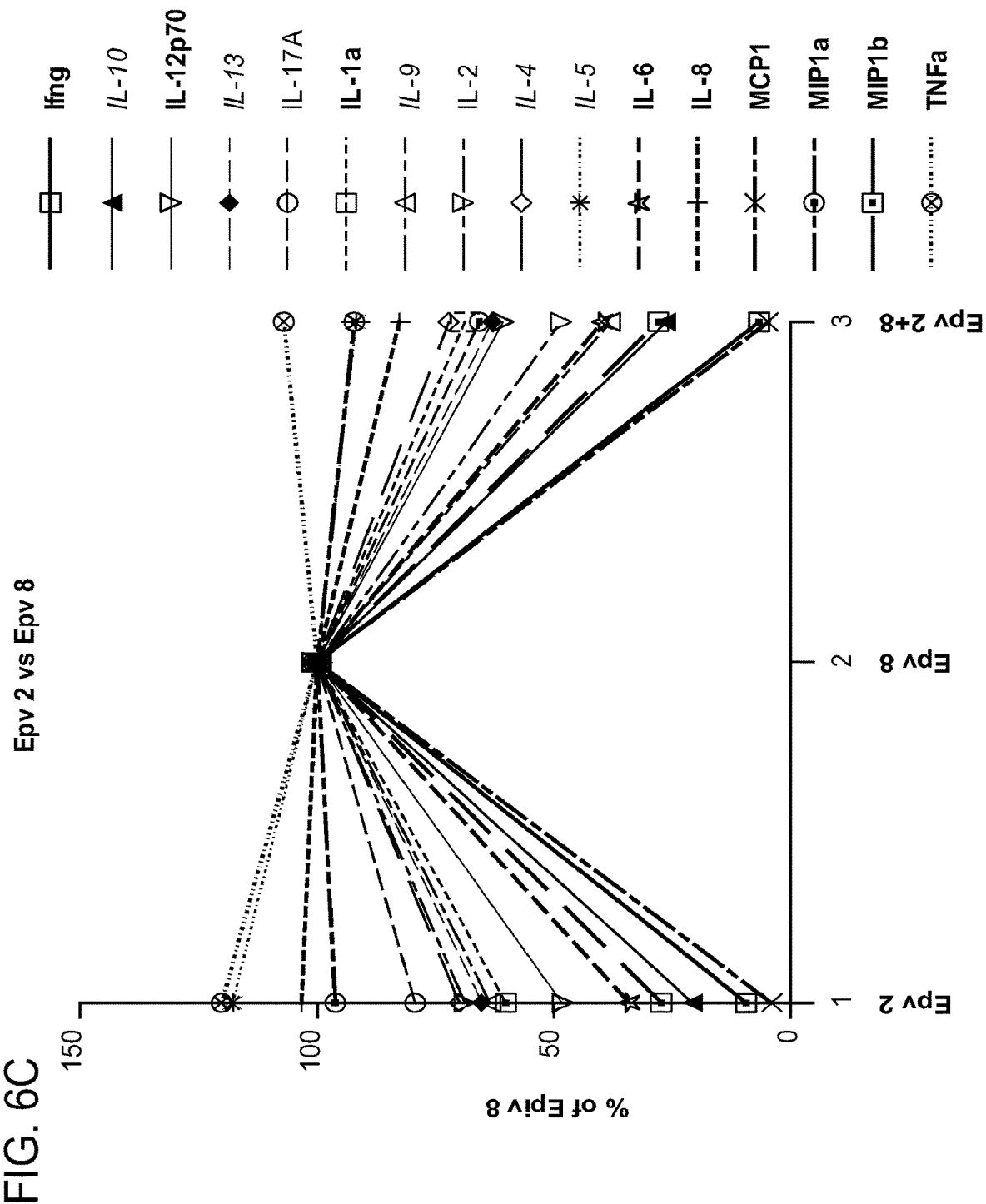
Figure 6D:
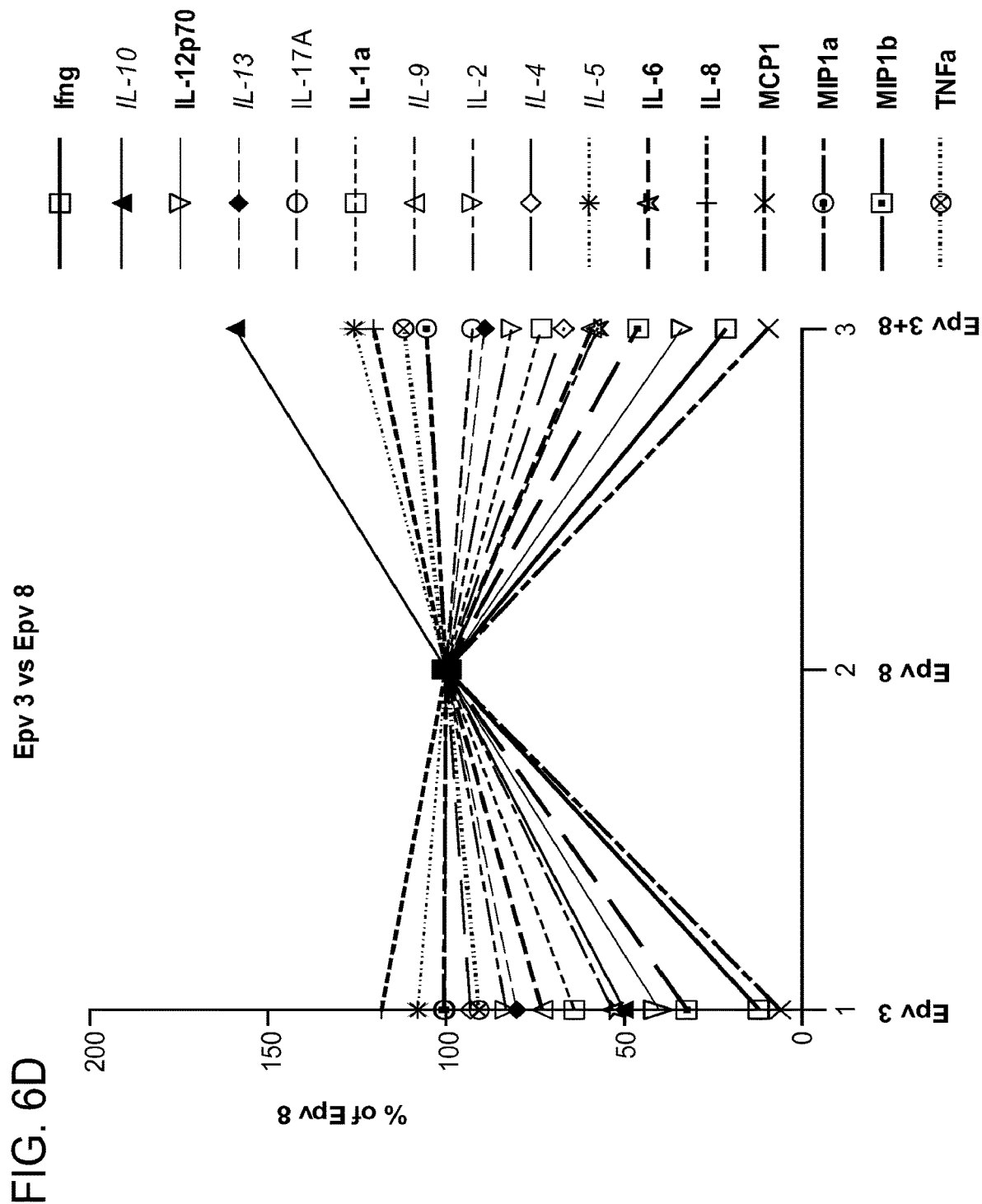
Figure 7A:
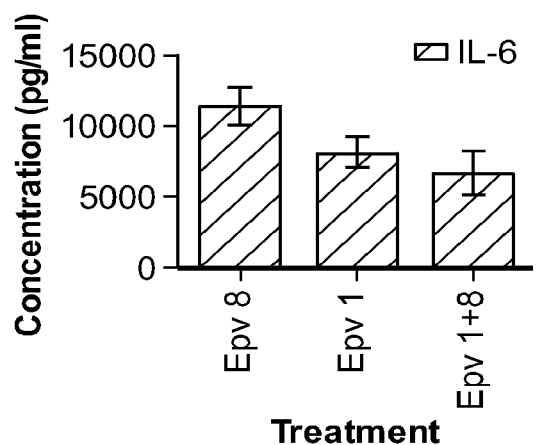
Figure 7B:
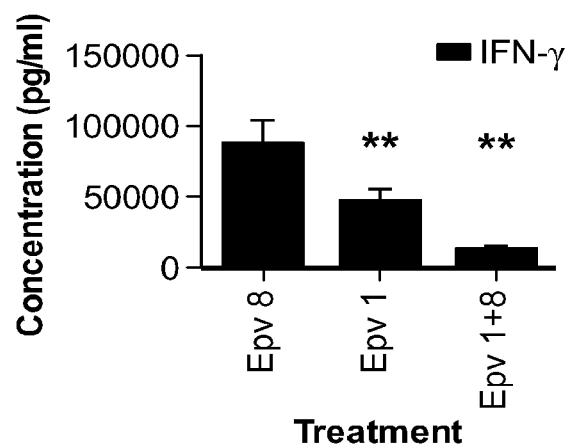
Figure 7C:
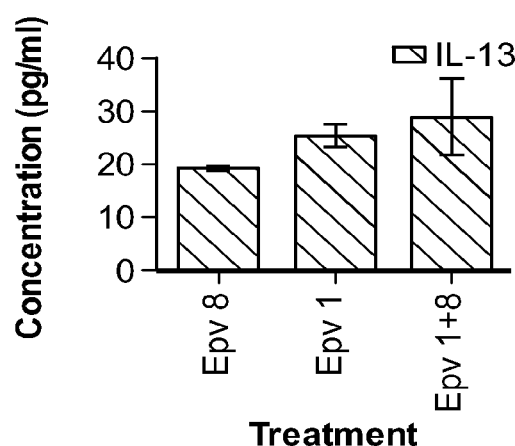
Figure 7D:
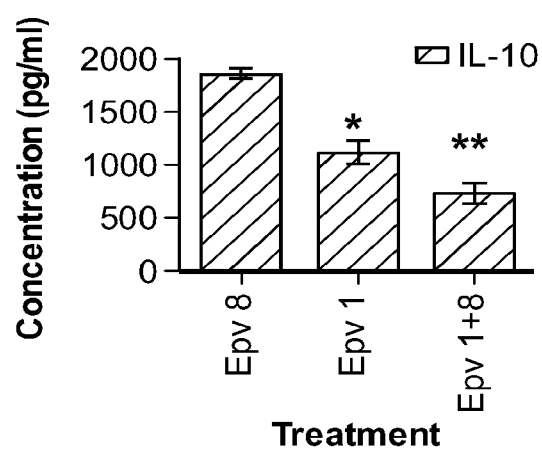
Figure 7E:
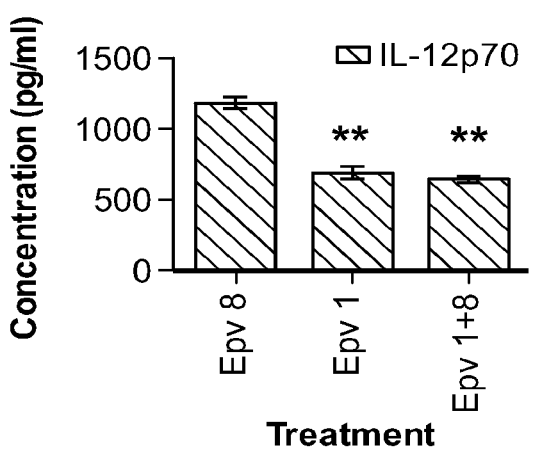
Figure 7F:
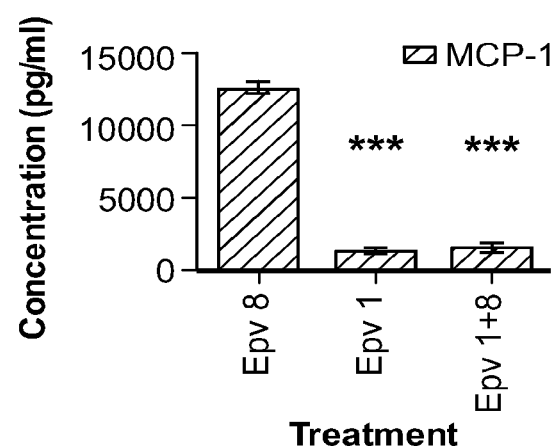
Figure 7G:
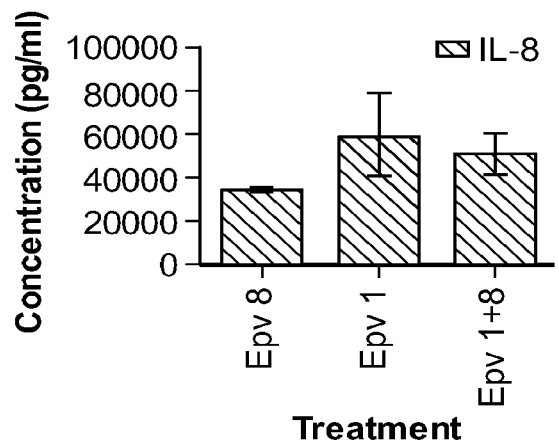
Figure 7H:
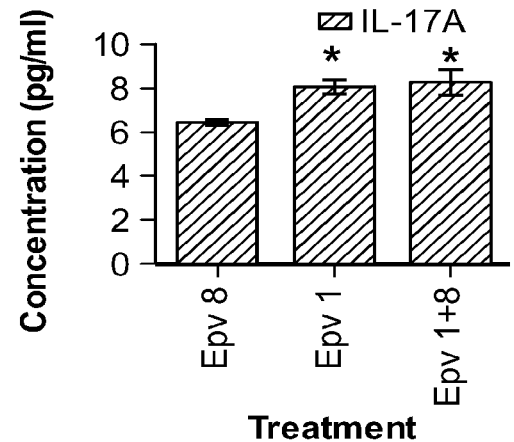
Figure 7I:
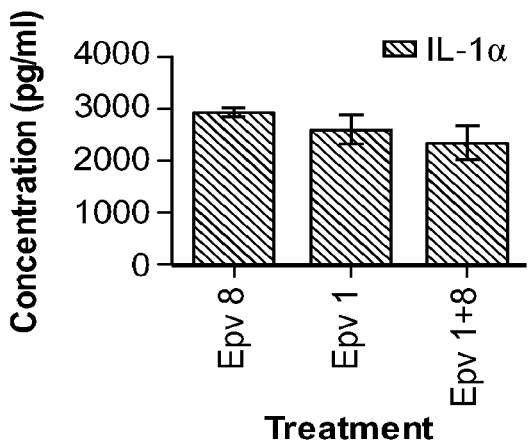
Figure 7J:
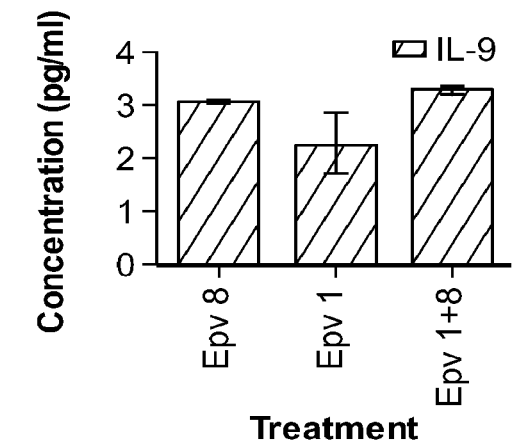
Figure 7K:
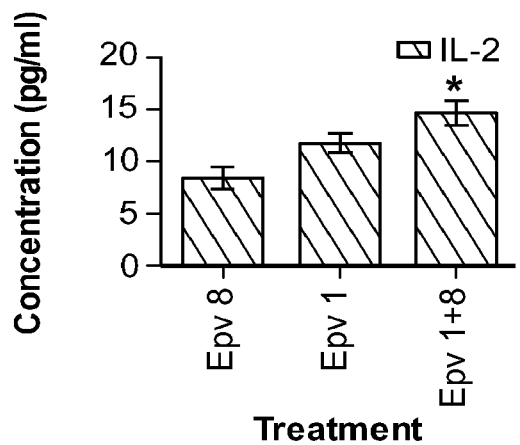
Figure 7L:
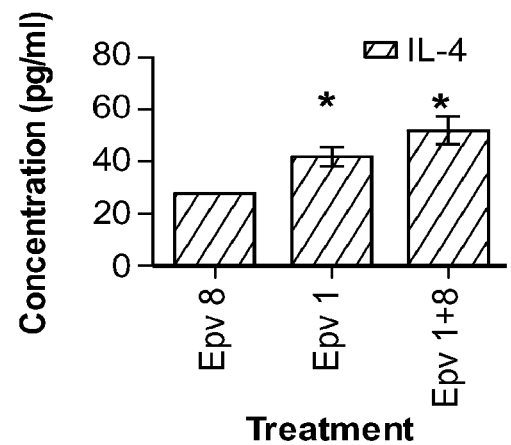
Figure 7M:
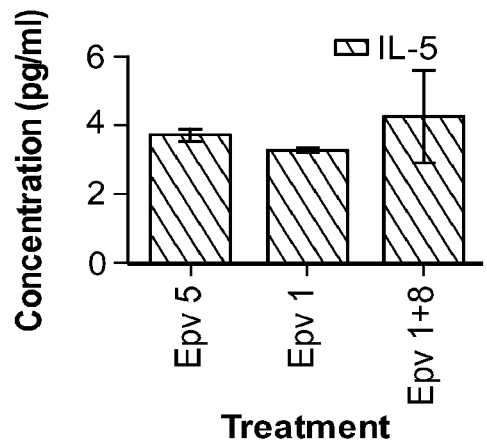
Figure 7N:
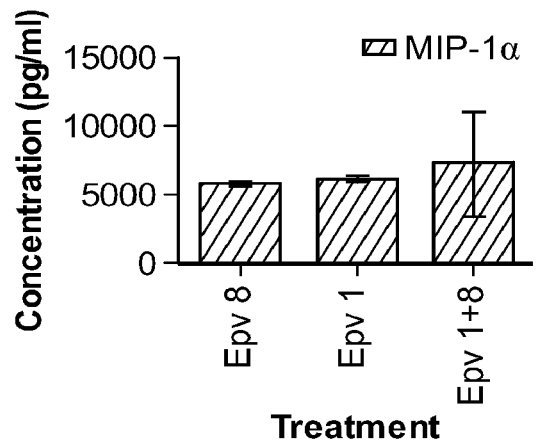
Figure 7O:
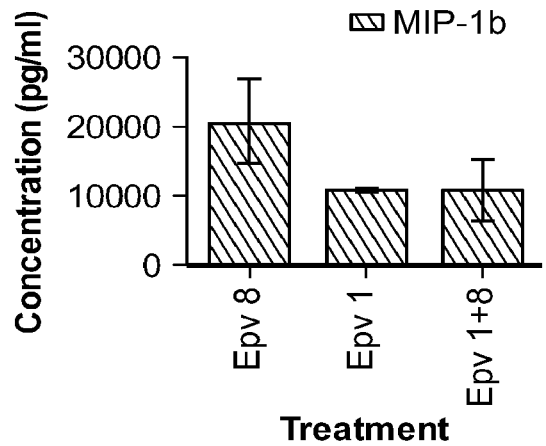
Figure 7P:
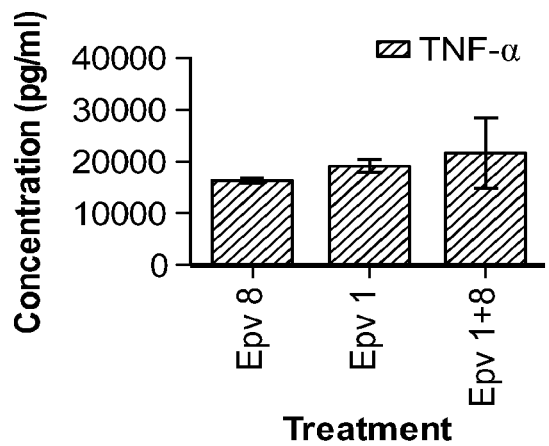
Figure 8A:
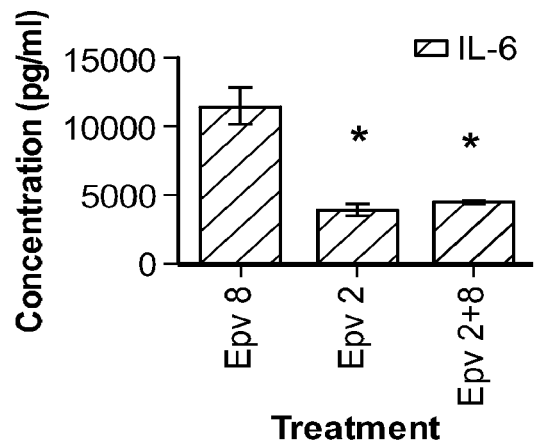
Figure 8B:
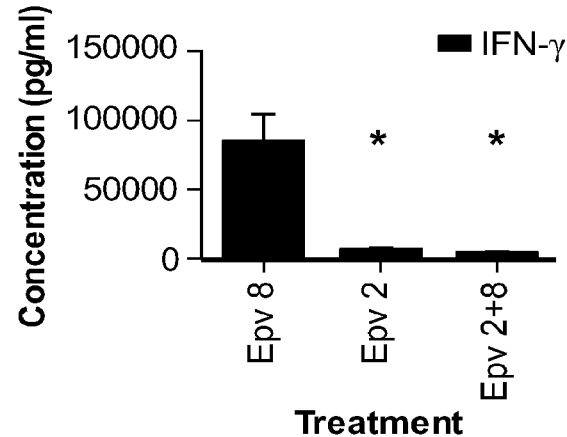
Figure 8C:
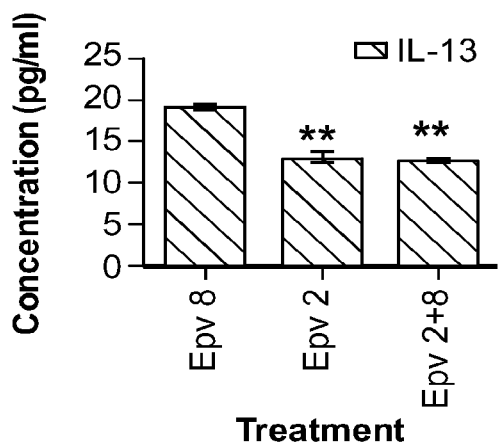
Figure 8D:
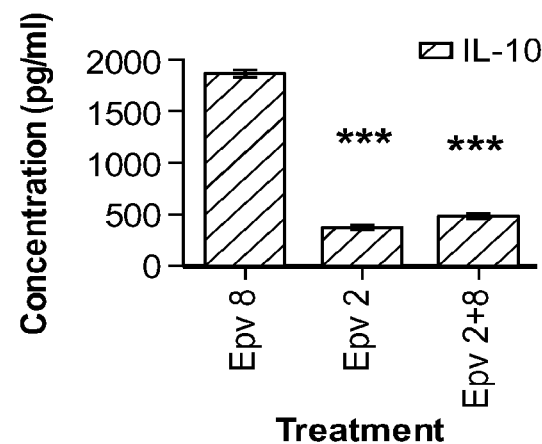
Figure 8E:
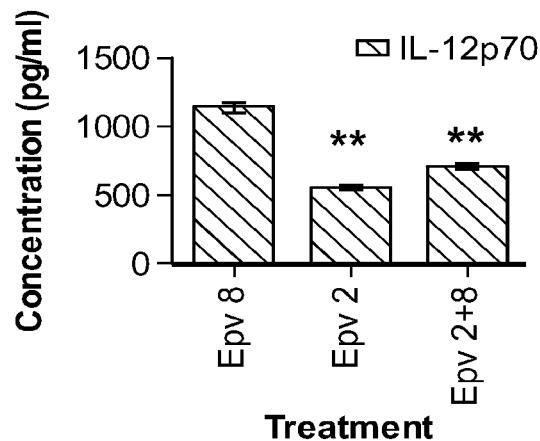
Figure 8F:
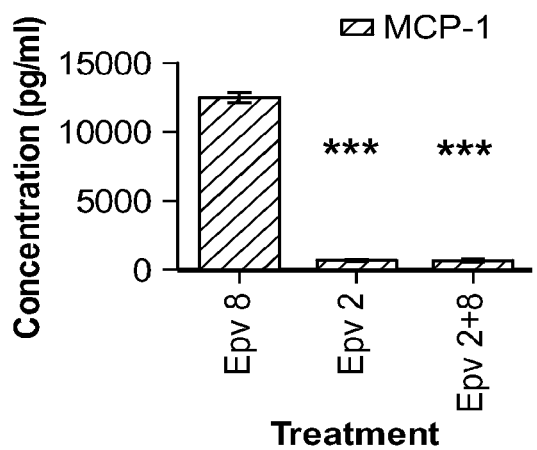
Figure 8G:
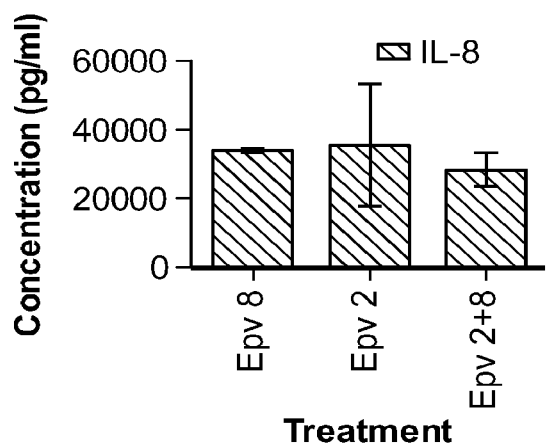
Figure 8H:
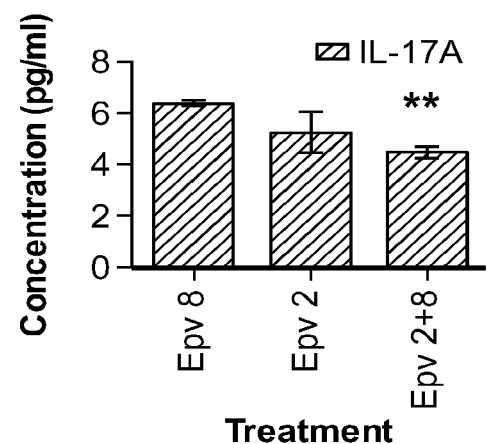
Figure 8I:
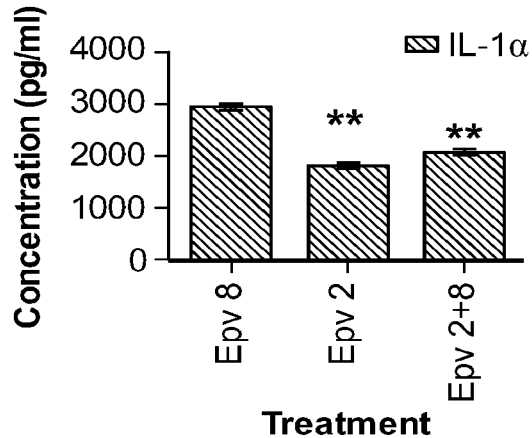
Figure 8J:
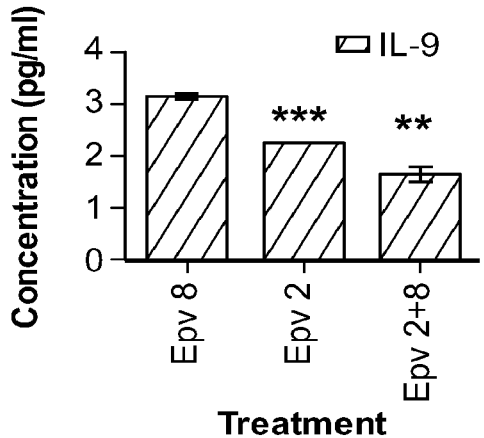
Figure 8K:
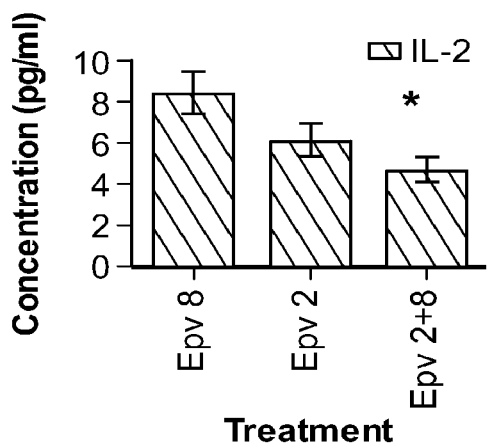
Figure 8L:
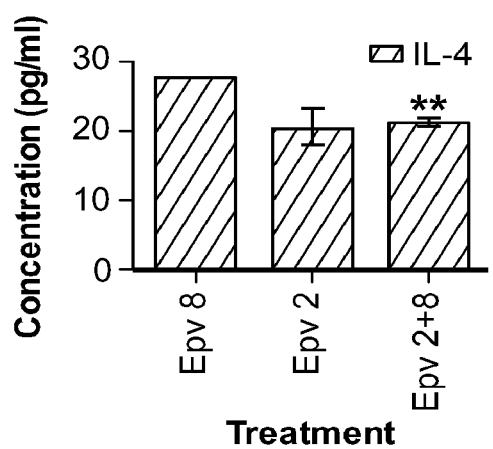
Figure 8M:
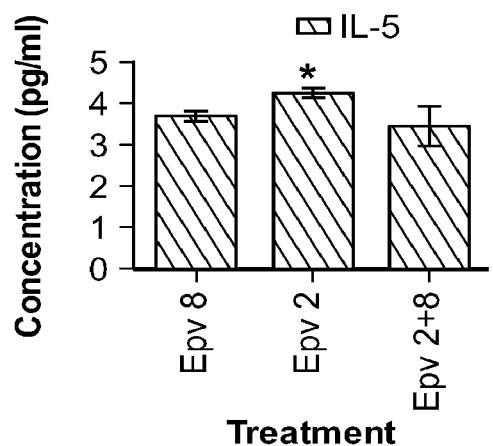
Figure 8N:
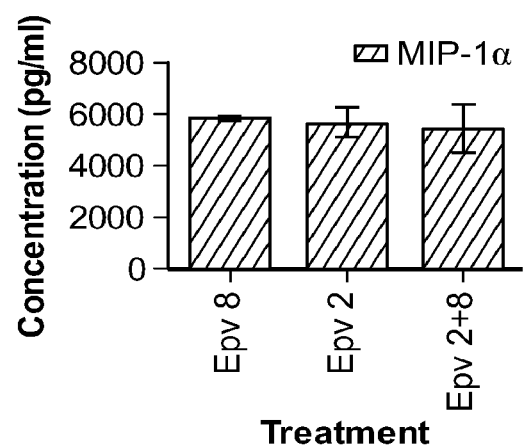
Figure 8O:
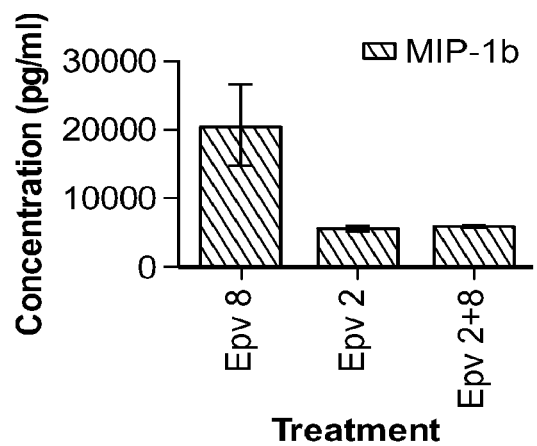
Figure 8P:
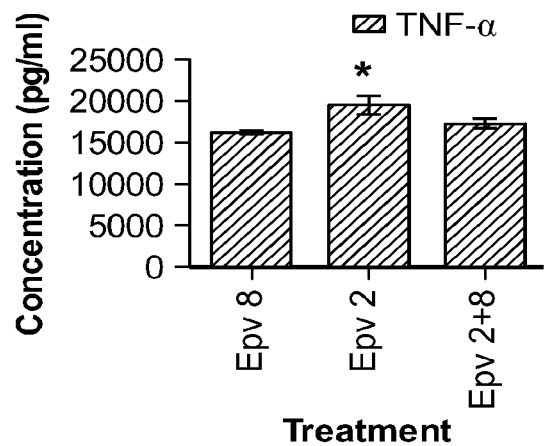
Figure 9A:
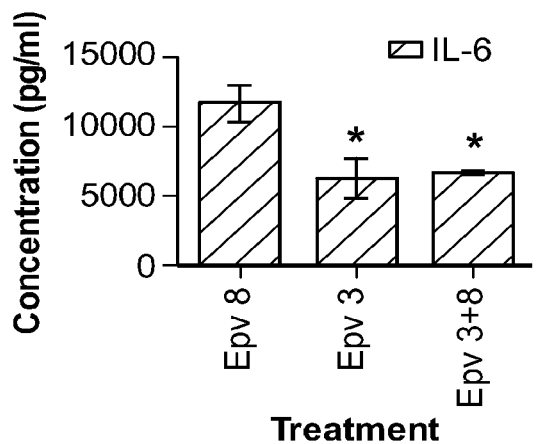
Figure 9B:
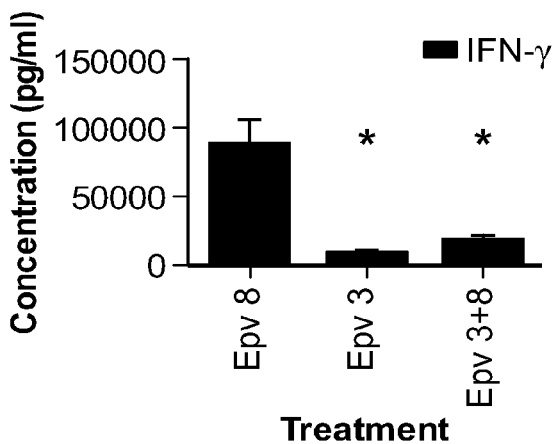
Figure 9C:
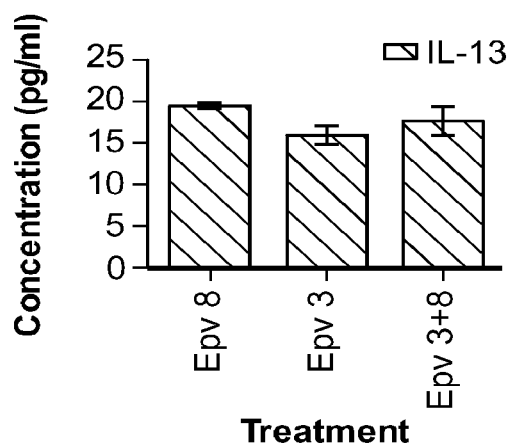
Figure 9D:
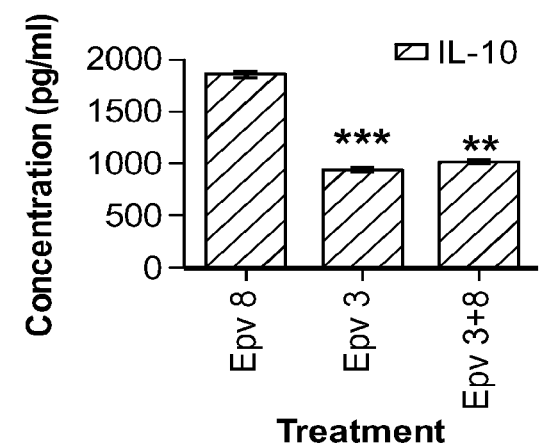
Figure 9E:
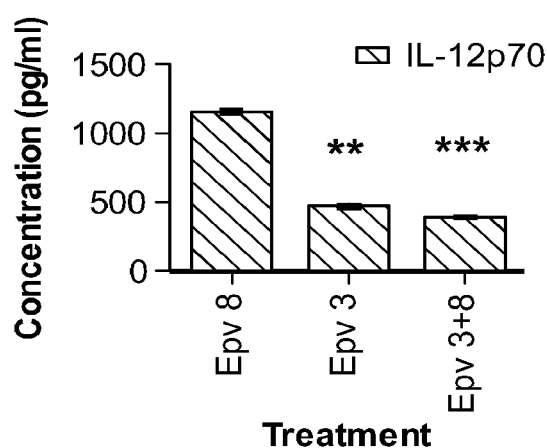
Figure 9F:
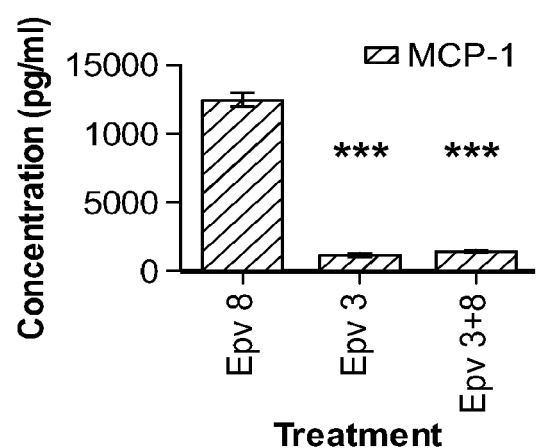
Figure 9G:
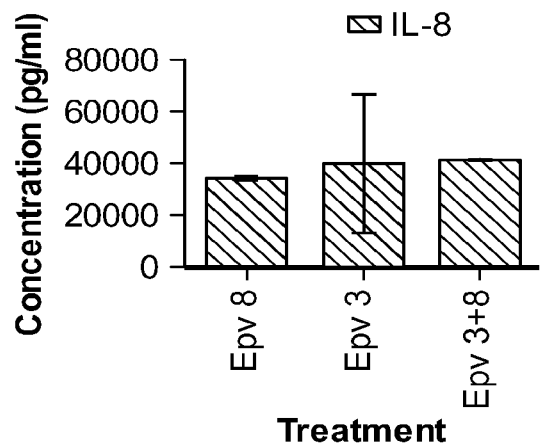
Figure 9H:
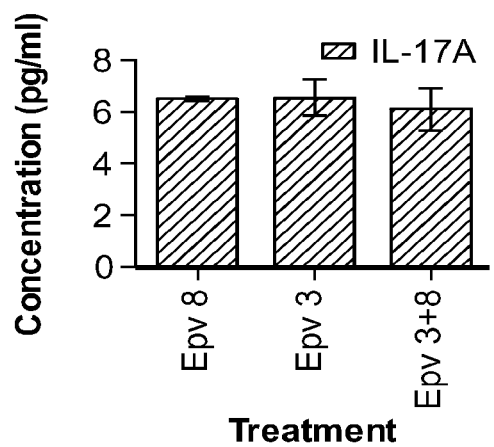
Figure 9I:
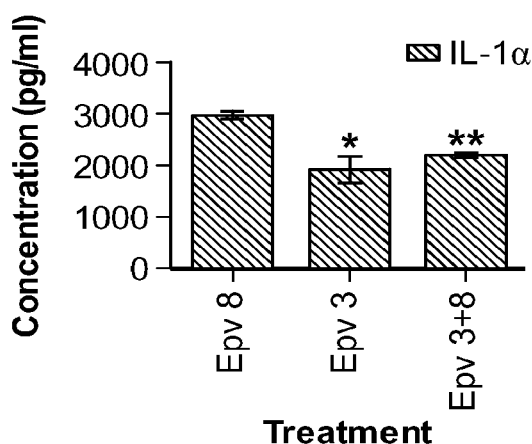
Figure 9J:
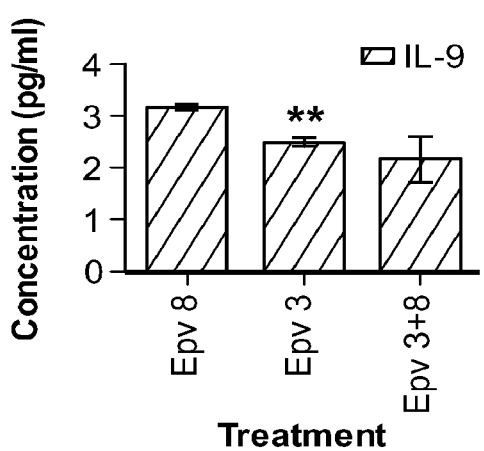
Figure 9K:
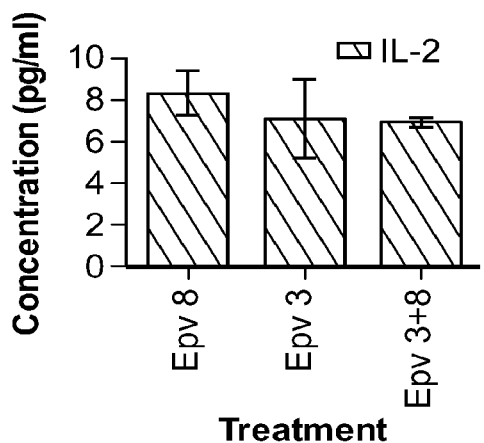
Figure 9L:
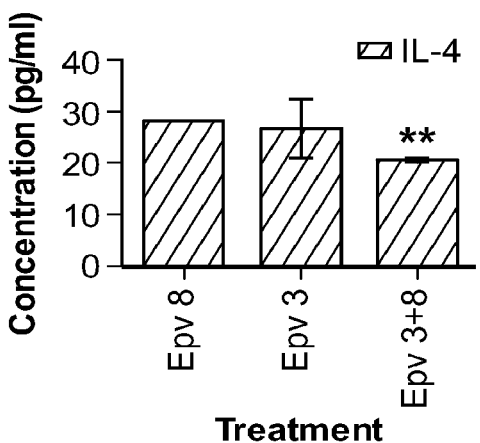
Figure 9M:
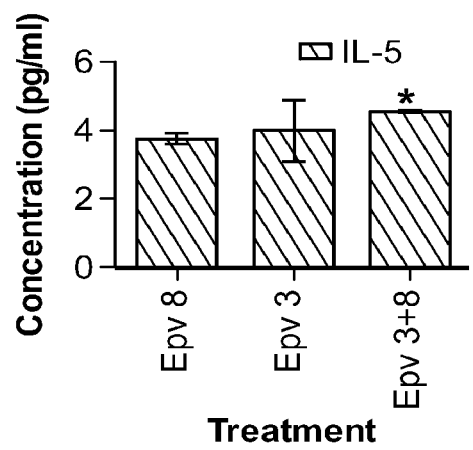
Figure 9N:
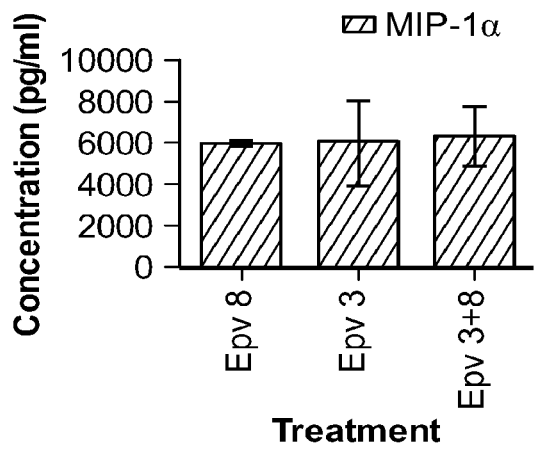
Figure 9O:
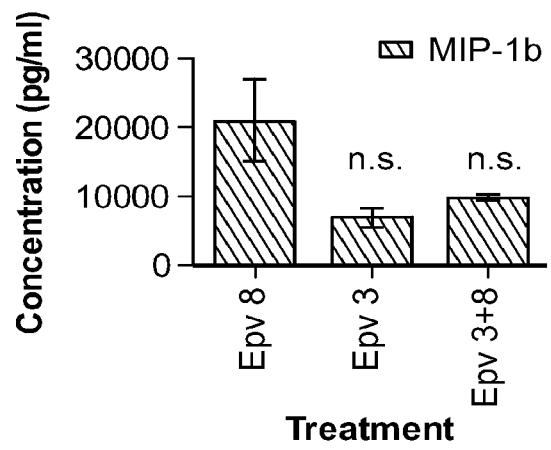
Figure 9P:
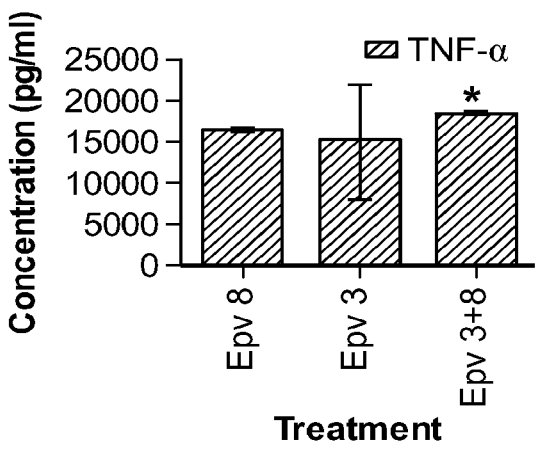
Figure 10A:
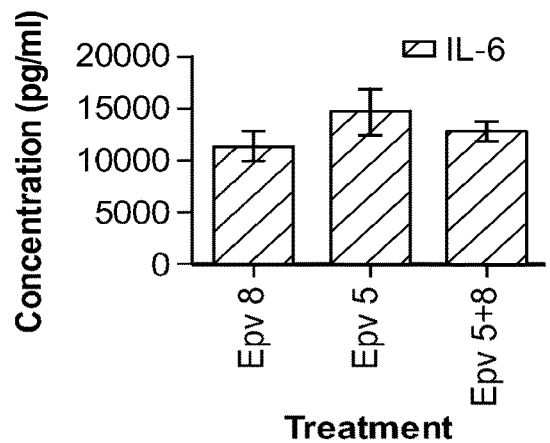
Figure 10B:
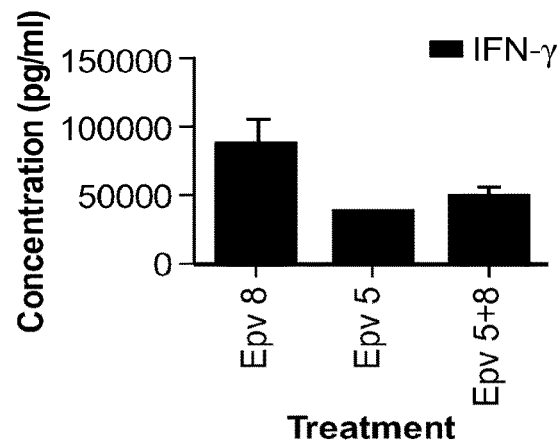
Figure 10C:
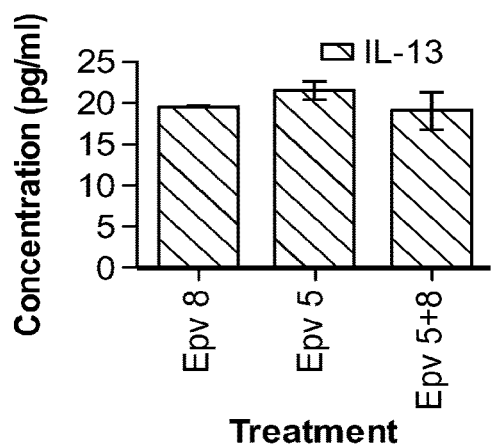
Figure 10D:
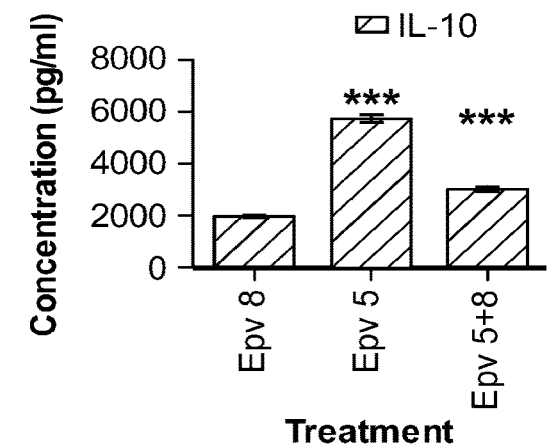
Figure 10E:
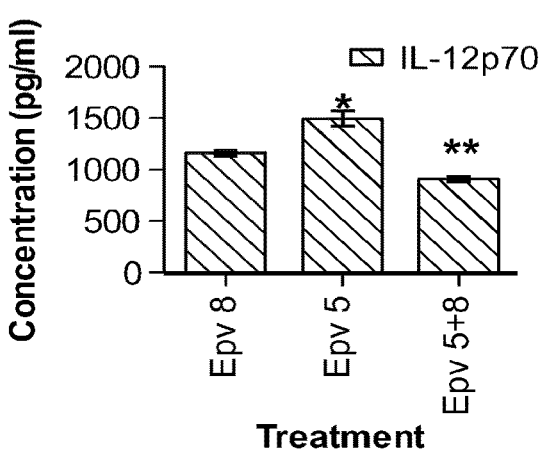
Figure 10F:
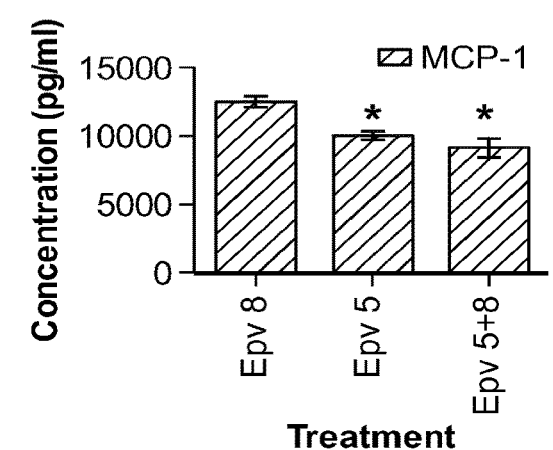
Figure 10G:
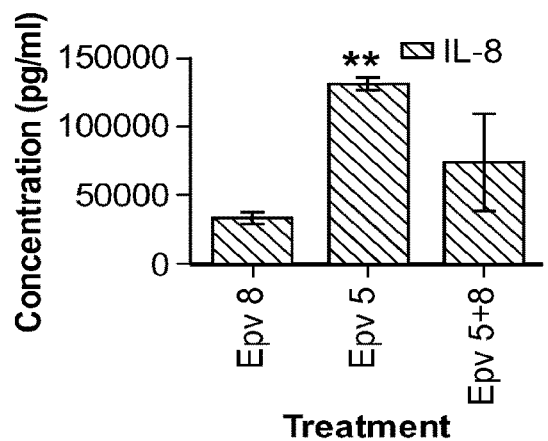
Figure 10H:
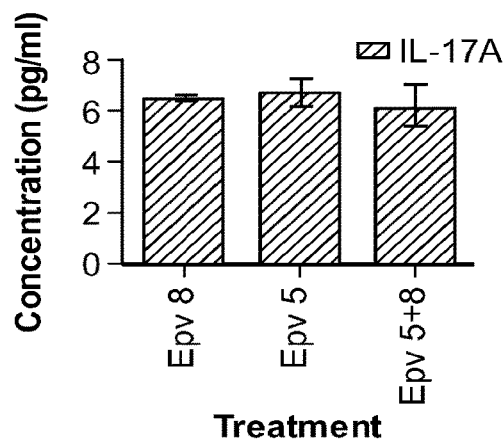
Figure 10I:
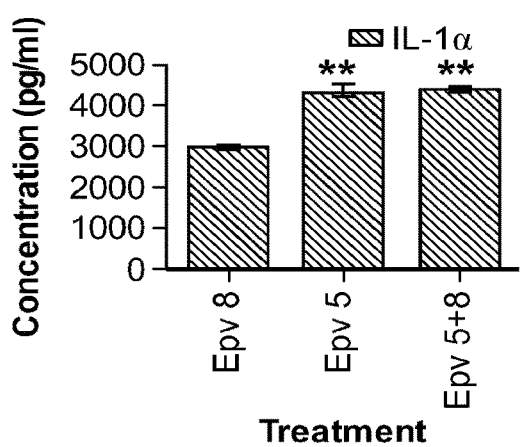
Figure 10J:
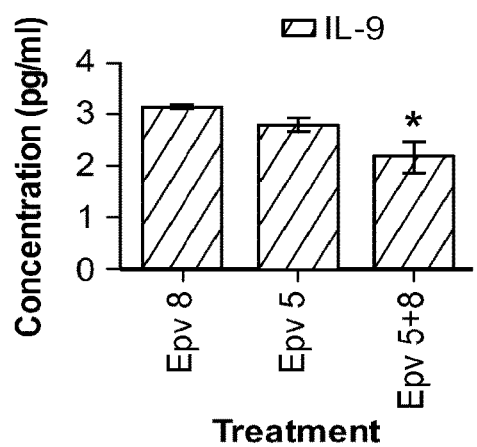
Figure 10K:
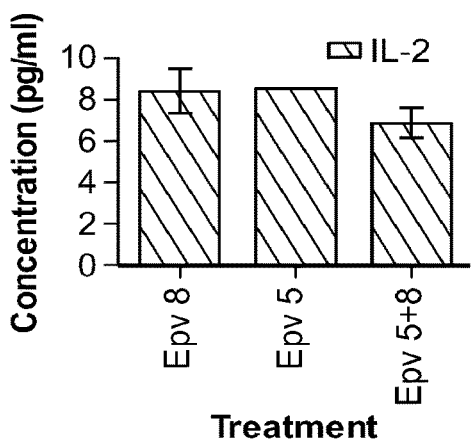
Figure 10L:
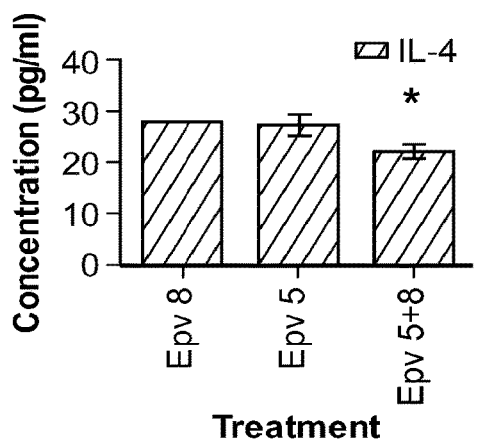
Figure 10M:
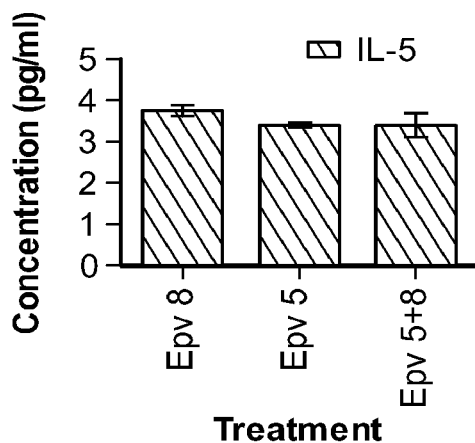
Figure 10N:
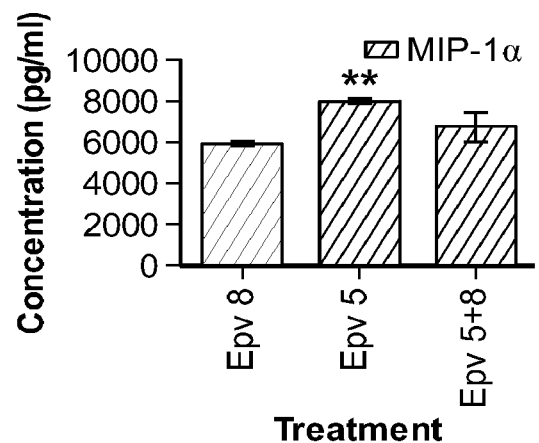
Figure 10O:
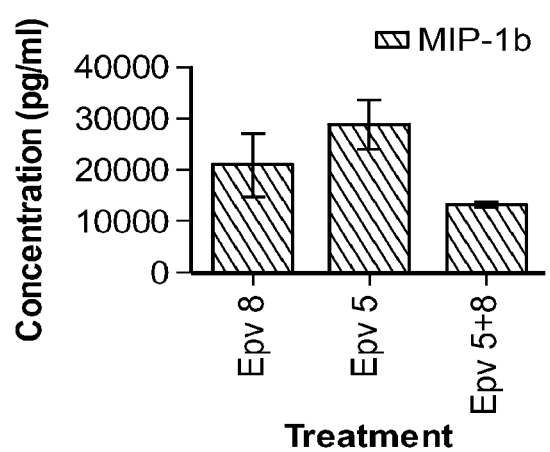
Figure 10P:
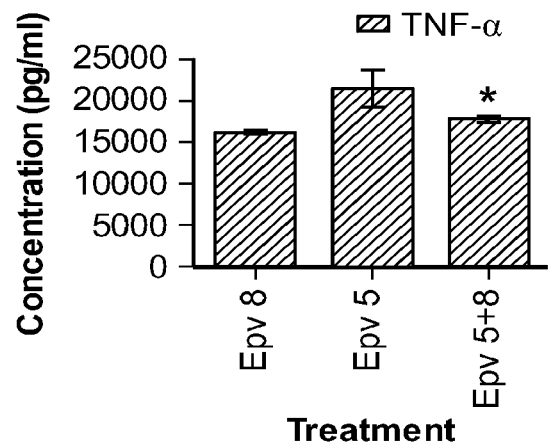

As shown in FIG. 1, C57BL/6 mice were either left untreated or were treated with xylose at 10 g/L in drinking water from day −7 to day 14; ciprofloxacin (cipro) at 0.25 g/L in drinking water from day −7 to day −2; enrofloxacin (enro) at 0.25 g/L in drinking water from day −7 to day −2; xylose+cipro or xylose+enro. Analysis of serum samples collected on days 0 and 14 showed that basal levels of serum endotoxin are present in normal mice that remained unchanged in untreated mice. Xylose treatment reduced these basal levels over time, suggesting an increase in gut barrier integrity even in normal animals. Antibiotic treatment with cipro, a broad spectrum quinolone antibiotic, or enro, an anaerobe-sparing antibiotic, led to an increase in serum endotoxin levels (measured 2 days after a 5 day course), likely due to disruption of the microbiota. Serum endotoxin levels returned to baseline over time. As shown in FIG. 1, xylose appeared to counteract the increase in serum endotoxin level caused by cipro, but not enro. The differential effect of xylose on these 2 antibiotics may relate to its ability to preserve/promote expansion of anaerobic bacteria, which are killed by cipro but not enro.

Example 2. Immunomodulatory Properties of Different Human Commensal Bacteria on Human Peripheral Blood Mononuclear Cells The microbiota of mammalian hosts is composed of bacterial species that possess both pro- and anti-inflammatory properties. In healthy individuals, a balance or state of eubiosis is maintained that supports gut barrier integrity, immune containment of commensal bacteria and promotion of a tolerogenic environment. Under disease conditions, dysbiosis characterized by an imbalance in pro- and anti-inflammatory bacteria results in local inflammation and compromised gut barrier integrity, leading to systemic inflammation and aberrant immune responses. Administration of selected probiotic bacterial strains (+/− prebiotics) that possess anti-inflammatory activity and promote immune tolerance represents an approach to correct a basic defect underlying multiple pathological conditions.

An in vitro system was developed to efficiently test the inflammatory and immunomodulatory properties of different human commensal bacteria on human peripheral blood mononuclear cells (PBMCs). Experiments were carried out with 21 bacterial candidates to profile their anti-inflammatory properties against human PBMCs. The innate properties of bacteria alone on human PBMCs were tested as well as their ability to counteract the pro-inflammatory activity of *Enterococcus feacalis*.

Human PBMCs were isolated from fresh blood by density-gradient centrifugation using Ficoll (1-4). Freshly isolated PBMCs were plated at $1.5 \times 10^6$ cells per ml per well of a 24-well plate in a total volume of 2 mls RPMI-1640 medium+5% human serum, and incubated at 37° C./5% $CO_2$ with the following:
(1) 500 µl of different commensal bacteria suspensions at OD 0.8
(2) *E. faecalis* at $10^7$ colony-forming units (cfu)
(3) A combination of commensal bacteria (OD 0.8)+*E. Faecalis* ($10^7$ cfu)
(4) Complete medium alone as a negative control
(5) Bacterial lipopolysaccharide (LPS; 100 ng/ml) as an immunomodulatory "positive" control Culture supernatants were collected at 24, 48 and 72 h, and the cytokine profile was analyzed by Luminex technology according to manufacturer's instruction (EMD Millipore, Danvers, Mass.). Cytokine production was detectable in culture supernatants by 24 h with levels increasing over 48-72 h and sometimes exceeding the range of quantitation. The results are presented in FIGS. 2-5 for all time points. The 24 h time point was chosen as the optimal time point for further analysis. The 24 h results are shown as a composite in FIG. 6 and with statistical analysis on individual cytokines in FIGS. 7-10. The results represent the properties of each bacterial species against human PBMCs and their ability to counteract inflammatory stimulation with *E. faecalis* in vitro. It was found that the commensal bacteria tested have distinct immunomodulatory properties, and most appear to counteract the inflammatory activity of *E. Faecalis* for at least one cytokine.

FIG. 2 shows the time course of Th1 related cytokines that were released by human PBMCs incubated with *Ruminococcus gnavus* (Epv 1), *Eubacterium rectale* (Epv 2), *Blautia luti* (Epv 3), *Blautia wexlerae* (Epv 5) and *Enterococcus faecalis* (Epv 8), or combinations of each bacterium with *E. faecalis*. Amounts of Th1-related pro-inflammatory cytokines interferon gamma (IFN-γ), interleukin-12 p70 (IL-12p70), interleukin-6 (IL-6), interleukin-2 (IL-2) and tumor necrosis factor alpha (TNFα) released by PBMCs were measured after 24, 48 and 72 hours. As shown in FIG. 2, all commensals have unique immunomodulatory properties. As expected, *E. faecalis* induced high levels of these pro-inflammatory cytokines. By comparison, most of the other bacterial candidates induced lower levels of Th1-related cytokines and were able to counteract the induction of one or more inflammatory cytokines by *E. faecalis*. In particular, *Blautia luti* (Epv 3), showed minimal induction of Th1-related cytokines on its own and was most effective in counteracting induction of these cytokines by *E. faecalis* (Epv 8). This profile is desirable for disease indications which are primarily driven by Th1 immune responses, such as GVHD.

FIG. 3 shows the time course of Th2 related cytokines that were released in cells treated with *R. gnavus* (Epv 1), *E. rectale*(Epv 2), *B. luti* (Epv 3), *B. wexlerae* (Epv 5) and *E. faecalis* (Epv 8), or combinations thereof. Amounts of anti-inflammatory cytokines interleukin-13 (IL-13), interleukin-4 (IL-4) and interleukin-5 (IL-5) released by PBMCs were measured after 24, 48 and 72 hours. Each bacterium displayed detectable pattern of cytokine induction and ability to modulate the effect of *E. faecalis*. Th2-related cytokines are beneficial in counteracting Th1 responses. Bacteria capable of promoting Th2 cytokine release are therefore of interest in Th1-driven diseases. *R. gnavus* appeared the most active in terms of eliciting Th2 cytokine on its own or in the presence of *E. faecalis*.

FIG. 4 shows the time course of Th9, Th17 and Treg cytokines that were released in cells treated with *R. gnavus* (Epv 1), *E. rectale*(Epv 2), *B. luti* (Epv 3), *B. wexlerae* (Epv 5) and *E. faecalis* (Epv 8), or combinations thereof. Amounts of interleukin-9 (IL-9), interleukin-17 (IL-17) and interleukin-10 (IL-10) released by PBMCs were measured after 24, 48 and 72 hours. The activity of IL-9 and IL-17 is context-dependent in that these cytokines can be beneficial under some conditions but detrimental under other conditions depending on the mechanisms responsible for disease pathogenesis. For example, IL-17 is expected to contribute to disease pathogenesis in GVHD but could provide a benefit in Th2-driven disorders. IL-10 produced by regulatory T cells (Treg) is generally immunosuppressive and is expected to provide a benefit in most inflammatory disorders whether Th1- or Th2-driven. As shown in FIG. 4, all bacterial candidates elicited IL-9 and IL-17 to varying degrees and *B. wexlerae* (Epv 5) was the most potent in inducing IL-10.

FIG. 5 shows the time course of monocyte, macrophage and neutrophil-related inflammatory cytokines that were released by PBMCs treated with *R. gnavus* (Epv 1), *E. rectale* (Epv 2), *B. luti* (Epv 3), *B. wexlerae* (Epv 5) and *E. faecalis* (Epv 8), or combinations thereof. Amounts of monocyte chemotactic protein 1 (MCP-1), macrophage inflammatory protein 1β (MIP1β), macrophage inflammatory protein 1α (MIP1α), regulated on activation, normal T expressed and secreted protein (RANTES), interleukin-1 α (IL-1 α), interleukin-1β (IL1β), interferon α2 (IFN-α2) and interleukin-8 (IL-8) that were released were measured after 24, 48 and 72 hours. In general, these cytokines contribute to inflammation by innate immune effector cells. The bacteria tested showed different degrees of induction and effects on *E. faecalis*. Overall, *E. rectale*(Epv 2) and *B. luti* (Epv 3) were the least inflammatory and the most effective at countering the effect of *E. faecalis* (Epv 8).

A composite illustration of the secretion of each of the pro-inflammatory and anti-inflammatory cytokines described above in the presence of each commensal alone or in combination with EPV8 is graphed relative to the pro-inflammatory bacterial strain E. faecalis (Epv 8) in FIG. 6. In the context of GVHD, IFNγ (IFNg), IL-12p70, IL-1α (IL-1α), IL-6, IL-8, MCP1, MIP1α(MIP1a), MIP1β (MIP1b) and TNFα (TNFa) are considered pro-inflammatory cytokines. IL-10, IL-13, IL-9, IL-4 and IL-5 are considered anti-inflammatory cytokines. IL-17 (IL-17A), IL-9 and IL-2 have context dependent activity. The results are shown as a percentage of Epv 8, where cytokine levels in the presence of E. faecalis after 24 hours is set at 100%. Each commensal has a unique signature and each one added alone to human PBMCs appeared to be less inflammatory than E. fecalis (below 100% for pro-inflammatory cytokines), except for B. wexlerae (Epv 5). When added to PBMCs in combination with E. faecalis, most commensals tested (except for Epv 5) also counteracted the pro-inflammatory activity of E. faecalis (below 100% for pro-inflammatory cytokines).

FIGS. 7-10 detail individual cytokine profiles of PBMCs following exposure to various commensals, alone or in combination with the pro-inflammatory bacterium E. faecalis (Epv8). In particular, FIG. 7 shows the effect of R. gnavus (EPV1) on cytokine concentration (pg/ml) either alone or in combination with Epv 8 (E. faecalis).

FIG. 8 shows the effect of E. rectale(EPV 2) on cytokine concentration (pg/ml) either alone or in combination with Epv 8 (E. faecalis). FIG. 9 shows the effect of B. luti (EPV 3) on cytokine concentration (pg/ml) either alone or in combination with Epv 8 (E. faecalis). FIG. 10 shows the effect of B. wexlerae (EPV 5) on cytokine concentration (pg/ml) either alone or in combination with Epv 8 (E. faecalis).

Overall, the foregoing data indicate that, among the bacteria tested, EPV3 has a significantly desirable anti-inflammatory profile for a Th-1-driven condition, such as GVHD while EPV5 has a suboptimal anti-inflammatory profile for GVHD. As shown in FIG. 11, EPV3 has relatively low intrinsic inflammatory activity compared to EPV 8 and is able to reduce the induction of pro-inflammatory cytokines by EPV 8, including IL-6, MCP-1, IL-12p70, and IFNγ which are believed to contribute to the pathogenesis of GVHD. By comparison, EPV 5 is similar to EPV 8 in terms of induction of pro-inflammatory cytokines and shows little ability to counteract the induction of pro-inflammatory cytokines by EPV 8.

Additional bacteria were profiled using this methodology including: Clostridium leptum (EPV 6), Blautia faecis (EPV15), Blautia/Ruminococcus obeum ATCC 29174 (EPV 20), Blautia product ATCC 27340 (EPV 21), Blautia coccoides ATCC 29236 (EPV 22), Blautia hydrogenotrophica ATCC BAA-2371 (EPV-23) and Blautia Hansenii ATCC27752 (EPV 24). Strains freshly isolated by Epiva from the stool of a normal healthy volunteer were also profiled and included: Eubacterium rectale (EPV 35), a previously uncultured Blautia, similar to GQ898099_s S1-5 (EPV 47), a previously uncultured Blautia, similar to SJTU_C_14_16 (EPV 51), Blautia wexlerae (SJ-TU_B_09_77) (EPV 52), Blautia luti ELU0087-T13-S-NI_000247 (EPV 54), Blautia wexlerae WAL 14507 (EPV 64), Blautia obeum (EPV 78), Ruminococcus gnavus (EPV 102) and Blautia luti (BlnIX) (EPV 114). Results focusing on key pro-inflammatory (IL-12p70, IFN□, IP-10, IL-1RA) and anti-inflammatory (IL-10, IL-4, IL-13) cytokines are shown in FIGS. 12-27. As observed with the initial set of bacterial candidates, each isolate displayed a defined signature. Candidates for treatment of autoimmune or inflammatory disorders, such as GVHD, displayed low induction of pro-inflammatory cytokines and/or positive induction of anti-inflammatory cytokines, and had ability to counteract the inflammatory activity of E. faecalis. Bacterial candidates meeting these criteria include, for example, EPV 35, 51, 78 and 114.

Taken together, these results show that commensals have distinct immunomodulatory properties and display a definable signature in terms of their ability to induce cytokines in human host cells, or counteract the pro-inflammatory activity of another bacterium (E. faecalis). Accordingly, bacterial compositions may be selected in order to achieve a desired modulation of pro- and anti-inflammatory cytokines. For example, anti-inflammatory bacterial strains may be selected based on their ability to reduce key pro-inflammatory cytokines such as interferon gamma, IL-12p70, IP-10 and IL-1RA and/or increase anti-inflammatory cytokines such as IL-13, IL-10 and IL-4.

Example 3. Effect of Commensal Human Bacteria on T-Cell Polarization

In order to determine whether exposure to commensal bacteria may polarize T cells toward a particular phenotype, flow cytometry analysis was performed on human PBMCs cultured with various commensal bacteria as described above. The cells recovered from culture were washed in phosphate-buffered saline and stained with a cocktail of fluorescently labeled antibodies against specific cell surface protein markers to allow for the detection of Th1 cells ($CXCR3^+CCR6^-$), Th2 cells ($CXCR3^-CCR6^-$), Th17 cells ($CXCR3^-CCR6^+$) and Tregs ($CD25^+CD127^{lo}$). Negative control wells contained PBMCs in culture medium alone and positive control wells contained PBMCs+LPS (100 ng/ml) as a known immune stimulus. The commensal bacteria examined included: Epv 1: R. gnavus; Epv 3: B. luti; Epv 2: E. rectale; Epv 5: B. wexlerae; Epv. 8: E. faecalis; Epv 20: B. obeum, ATCC 29174; Epv 21: B. product, ATCC 27340; Epv 24: B. hansenii, ATCC 27752. As shown in FIG. 28, exposure of human PBMCs to bacteria did result in a shift in the relative proportion of T cell populations compared to the PBMCs alone (control) although statistical significance was not achieved in every case. Overall, most bacteria tested caused an increase in the proportion of T cells with a regulatory phenotype (Tregs) with EPV 21 and EPV 24 having the greatest impact and EPV8 (E. faecalis) causing little or no increase in Tregs. Most bacteria also caused a decrease in the proportion of Th17 cells, an increase in Th2 cells and had little or no effect on the proportion of Th1 cells. This type of analysis indicates that commensal bacteria can modulate the proportions of effector T cell types and can be used to select the desired phenotype for a given disease application. For example, the optimal T cell profile to address pro-inflammatory disorders such as GVHD would consist of ↑Treg, ↓Th17, ↓ or unchanged Th1, and ↑Th2. This phenotype was induced by many of the bacteria tested.

Example 4. Pattern of Carbon Source Utilization by Commensal Bacteria

Modulation of the Modulation of the microbiota to correct a dysbiosis associated with pathological conditions can potentially be achieved through administration of bacteria (or bacterial combinations) and prebiotic(s) as a carbon source to promote endogenous expansion of beneficial bacteria. Alternatively, prebiotics can be administered in combination with bacteria to promote their growth or create a favorable environment for their growth. Profiling of carbon source usage by bacterial isolates can be used to customize and optimize selection of prebiotics for particular bacterial strains. Profiling of carbon source usage was conducted on 21 anaerobic commensal bacteria (Table 6) using 96 well plates from Biolog (Hayward, Calif.) where each well contains a different carbon source for a total of 192 different carbon sources (PM01 and PM02A plates). The carbon sources tested are listed in Table 7. The assay was conducted according to manufacturer's instructions. Briefly, pre-cultured bacteria were suspended in Biolog assay medium at a 750 nm optical density (OD) of 0.3-0.4 and 100 µl of the suspension was transferred to each well of the 96 well PM01 and PM02 assay plates. The plates were then incubated at 37° C. in an anaerobic chamber for 24 hr or longer. The amount of growth on each carbon source was evaluated by measuring the optical density (OD) of each well at 750 nm. The results are summarized in FIG. 29, and indicate that each individual strain displays a unique pattern of carbon source usage. Interestingly, different isolates of the same species (e.g. B. luti and B. wexlerae) show related (albeit distinct) patterns. Overall, these results indicate that characterization of carbon source usage for profiling of bacterial candidates allows optimal selection of prebiotics. Preferred prebiotics can be selected which increase the growth (indicated by an increase in optical density) of bacterial species contained in probiotic compositions.

Example 5. Normal Human Volunteer Study of a Prebiotic Formulation Containing Xylose D-xylose is a carbon source generally preferred by anaerobic bacteria. Preliminary results in the mouse indicate that it may act to promote gut barrier integrity (FIG. 1). It is also used as a carbon source by several bacterial strains (FIG. 29) that were determined to possess a desirable immunological profile for target indications such as GVHD (FIG. 19, 25, 27). A parallel, double-blind, 5 cohort escalation food safety study was conducted to examine D-xylose in normal human volunteers. The study was a double-blind, single-center, parallel group study designed to evaluate the tolerability and potential microbiome changes induced by ingestion of D-xylose at 5 different amounts in healthy, adult volunteers enrolled at 1 study center in the United States (US).

Subjects were screened for eligibility within 21 days prior to the first planned ingestion of study sweetener on Day 1 (Baseline). Within each of 5 cohorts, eligible subjects were randomly assigned in a double-blinded, 6:2 ratio to ingest either D-xylose or the GRAS sweetener Splenda® (control), dissolved into 2 to 6 oz of sterile water and ingested TID with meals for a total of 82 ingestions taken over 28 consecutive days. D-xylose ingestion amounts ranged from 1 to 15 g TID (total daily amount of 3 to 45 g), and all subjects randomized to Splenda® ingested 1 dissolved, commercially available packet TID (3 packets total per day).

Subjects returned to the study center weekly on Days 8, 15, 22, and 28 for ingestion, tolerability, and compliance evaluations. Safety was evaluated on a continual basis through adverse events (AE) monitoring, clinical laboratory measurements, vital sign monitoring, physical examinations, electrocardiograms (ECGs), telephone follow-up, and electronic subject ingestion diaries. Stool was collected pre-ingestion and at pre-specified time points, and post-ingestion samples were evaluated for changes in the gut microbiome compared with Baseline for all subjects. For subjects who consented to further sampling, additional stool specimens were used to potentially isolate living bacteria that could be categorized for research and potential commercialization purposes. Serum and urine were collected for measurement of D-xylose levels and pharmacokinetic (PK) assessments and PK/pharmacodynamics (PD) correlations. Telephone follow-up was conducted as needed, but minimally once per week. The total duration for each participant was up to 60 days, including the Screening period (Day −21 to 0), the ingestion period (Day 1 to 28), and an End-of-Study (EOS) follow-up visit conducted 7 (±3) days after the last ingestion of study sweetener.

Criteria for Evaluation

Safety

Safety was evaluated on a continual basis through AE monitoring, clinical laboratory measurements, vital sign monitoring, physical examinations, ECGs, telephone follow-up, and electronic subject ingestion diaries.

Immunology and Other Assessments

Stool was collected at pre-specified pre- and post-ingestion time points and post-ingestion samples were evaluated for changes in the gut microbiome compared with Baseline. Additional optional specimens were collected to potentially isolate living bacteria that could be categorized for research and potential commercialization purposes.

Blood was collected at pre-specified pre- and post-ingestion time points to evaluate C-reactive protein (CRP), serum cytokines (tumor necrosis factor alpha [TNF-α], interleukin [IL]-2, IL-6, interferon gamma [IFN-γ], and IL-10), and T-cell markers CD3, CD4, CD8, CD25, and FOXP3. Plasma was also stored and may be tested for biomarkers and/or metabolic markers for up to 7 years.

Pharmacokinetics

Blood and urine were collected at pre-specified pre- and post-ingestion time points to measure D-xylose levels and to characterize the systemic absorption profiles of D-xylose.

Statistical Methods

Statistical analyses were conducted using SAS®, Version 9.2 (SAS Institute, Inc., Cary, N.C., USA). The sample size calculations were empiric and based on an estimation of normal healthy volunteer variability in reported symptoms and side effects and not on a statistical method. A weighted randomization scheme was implemented such that more subjects were enrolled at the higher D-xylose amounts to account for potential toxicity-related effects that could have resulted in withdrawal and/or analysis ineligibility, and to enable collection of more data at ingestion amounts for which limited data were available.

Analysis Populations

The safety population comprised all subjects who ingested any amount of study sweetener.

Safety

AEs were coded using the Medical Dictionary for Regulatory Activities (MedDRA), Version 18.0 (Northrup Grumman Corporation, Chantilly, Va., USA), and summarized by cohort. Laboratory, vital sign, and physical examination data were summarized by cohort using descriptive statistics over time, including statistics for changes from Baseline. ECG findings were also summarized by cohort over time as well as using frequency counts and percentages, as normal or abnormal, with the relevance of abnormalities categorized by clinical significance.

Immunology and Other Assessments

Stool sample compliance was summarized by cohort, using the following calculation for each subject:

$$\text{Percentage compliance} = \frac{\text{Total number of stool samples collected}}{\text{Total number of stool samples expected}} \times 100$$

A total of 7 stool samples were expected to be collected for each subject. Evaluation of changes in the gut microbiome were evaluated in stool samples through taxonomic classification, relative and statistical differential abundance analyses by cohort and time point, an alpha diversity analysis calculated using the Shannon diversity index by cohort and time point, a beta diversity analysis using Bray-Curtis dissimilarity and Unifrac distance by subject and time point, and a principal coordinates analysis using the beta diversity data.

Summary statistics (n, mean, standard deviation, median, minimum, and maximum) were presented for serum concentrations of CRP, flow cytometry T-cell markers (CD3, CD4, CD8, CD25, and FOXP3), and cytokines (TNF-α, IL-2, IL-6, IFN-γ, and IL-10) as per their nominal time points.

Pharmacokinetics

Phoenix® WinNonLin®, Version 6.2.1, was used for PK analyses.

Serum D-xylose concentrations were summarized by cohort using nominal sample times according to actual amount received using summary statistics (n, coefficient of variation [CV], mean, standard deviation [SD], median, minimum, and maximum). Evidence for the occurrence of steady-state was assessed graphically by comparing the time course of either trough or 2-hour post-ingestion serum concentrations of D-xylose as different levels of D-xylose. Accumulation was assessed by comparing the 2-hour post-first-ingestion serum levels with those observed at Week 2 (Day 15) and Week 4 (Day 28).

The total amount of D-xylose excreted in urine was analyzed for all subjects over 5 hours post-ingestion and pooled for analysis; the pooling for analysis reflected the subject mean within a given time of collection (e.g., Day 15 and then Day 28) sorted by ingested amount. Urine PK parameters for D-xylose levels included $Ae_{(0-t)}$ (cumulative amount of sweetener recovered in urine) and percent sweetener amount excreted over a 5-hour period.

Summary of Results

Forty-eight subjects were randomized to ingest either 1 packet of commercially-available Splenda® TID (n=12) or D-xylose TID at the following ingestion amounts (n=36 total):

1 g: 6 subjects
2 g: 6 subjects
8 g: 7 subjects
12.5 g: 8 subjects
15 g: 9 subjects Over the 28-day ingestion period, study sweetener ingestion compliance was >90% for all subjects. Two subjects (4.2%) discontinued from the study prematurely; primary reasons for discontinuation were a protocol violation (positive urine drug screen) and withdrawal of consent. The proportion of males (47.9%) and females (52.1%) was balanced, and the majority of subjects were White (89.6%) and not Hispanic or Latino (77.1%). Subject ages spanned a wide range, with a median of 38.3 (range 22.5 to 60.5) years for the combined D-xylose cohorts and 43.6 (range 24.9 to 64.3) years for the Splenda® cohort.

Safety

D-xylose and Splenda® were both well tolerated, with no new safety concerns identified. One subject required a D-xylose reduction from 15 g to 12.5 g TID at the Week 1 (Day 8) visit due to AEs of moderate abdominal distension, diarrhea, and GI pain; no other modifications to sweetener ingestion amounts were implemented.

Overall, 17 subjects (35.4%) experienced at least 1 AE, including a higher proportion of subjects who ingested any amount of D-xylose (14 subjects [38.9%]) than Splenda® (3 subjects [25.0%]). Reported AE rates increased with increasing D-xylose ingestion amounts, with incidences ranging from 16.7% in subjects who ingested the 2 lowest amounts (1 and 2 g TID) to 66.7% in subjects who ingested the highest amount (15 g TID). AEs reported for more than 1 subject in the D-xylose cohorts included diarrhea (3 subjects [8.3%]) and flatulence and GI pain (2 subjects [5.6%] each). AEs in the Splenda® cohort included abdominal distension, flatulence, increased blood creatinine, infrequent bowel movements, and rhinitis. The incidence of AEs was highest during Weeks 1 and 2 (Days 2 through 15), regardless of sweetener type or ingestion amount. During this 2-week period, 18 subjects overall (37.5%) experienced AEs, compared with 7 subjects (14.6%) overall who experienced AEs either on Day 1 or after Week 2.

All AEs were mild in severity with the exception of moderate AEs reported for 4 subjects (11.1%) in the D-xylose cohorts. These moderate AEs included abdominal distension, concussion/post-concussion syndrome, diarrhea, GI pain, increased blood bilirubin, and neutropenia.

No SAEs, severe AEs, or subject deaths were reported. One subject in the 8 g TID D-xylose cohort experienced non-serious, moderate AEs of concussion and post-concussion syndrome that were noted to have contributed to study discontinuation; however, this subject's primary reason for discontinuation was withdrawal of consent.

GI-related AEs, which were of special interest, were reported for 7 subjects (19.4%) in the D-xylose cohorts and 2 subjects (16.7%) in the Splenda® cohort. GI-related events were mild for all but 1 subject in the 15 g TID D-xylose cohort who experienced moderate GI-related AEs of abdominal distension, diarrhea, and GI pain that required reduction of the D-xylose ingestion amount to 12.5 g TID.

Eleven subjects (22.9%) experienced at least 1 AE that was considered by the Investigator to be related to study sweetener, including 9 subjects (25.0%) in the D-xylose cohorts and 2 subjects (16.7%) in the Splenda® cohort. The incidence of sweetener-related AEs appeared to increase with increasing D-xylose ingestion amounts. Sweetener-related AEs reported for more than 1 subject in the D-xylose cohorts included diarrhea (3 subjects [8.3%]) and flatulence and GI pain (2 subjects [5.6%] each). Sweetener-related AEs reported in the Splenda® cohort were abdominal distension, flatulence, and infrequent bowel movements.

No fluctuations in clinical laboratory measurements over time were considered to be clinically meaningful. Categorical shifts from Baseline that occurred in >10% of subjects in either the combined D-xylose or Splenda® cohorts included decreased or increased glucose (27.7% D-xylose and 16.7% Splenda®) and decreased absolute neutrophil count (ANC) (13.9% and 8.3%); these shifts were not associated with sweetener type or ingestion amount.

Immunology and Other Assessments

To assess the effect of D-xylose on the gut microbiome, this study incorporated an analysis of alpha diversity, beta diversity, and differentially abundant taxa. These factors were assessed both across cohorts and over time. Regardless of sweetener ingestion amount, no apparent significant impact on the intra-sample alpha diversity of the gut microbiome was observed, and no significant changes in community composition were observed over time on study. Numerous taxa were identified as differentially abundant, but these findings may reflect the relatively small sample sizes in each cohort.

Across all D-xylose cohorts, 8.3% of subjects with normal serum CRP at Baseline experienced at least 1 post-ingestion CRP value >2.9 mg/L. A substantially higher proportion of subjects in the Splenda® cohort (41.7%) had normal serum CRP at Baseline and experienced at least 1 post-ingestion CRP value >2.9 mg/L. None of the post-ingestion CRP values for any subject were deemed clinically significant.

Because most individual cytokine data points were below the limit of quantitation (BLQ) and therefore set to zero, cytokine summary statistics were limited and did not indicate any consistent or clinically meaningful changes over time for either sweetener or any D-xylose ingestion amount. There was a trend for reduced levels of serum interferon gamma over time in the 2 g and 15 g D-xylose cohorts (FIG. 30). No consistent or clinically meaningful changes over time in total T-cells or any T-cell subsets were observed for either sweetener or any D-xylose ingestion amount.

Pharmacokinetics

Serum D-xylose concentrations increased linearly with increasing ingestion amounts. Little to no accumulation of serum D-xylose occurred at Day 15 following 1 g to 12.5 g TID ingestion, while an approximately 1.9-fold accumulation ratio was observed in the 15 mg TID cohort (although variability was high). On Day 28, the accumulation ratio ranged from 1.08 to 1.31 following 1 g to 12.5 g TID ingestion and 1.68 following 15 g TID ingestion, although variability was moderate to high in all but the 8 g TID cohort.

In the 1 g TID cohort, approximately 40% of the ingested amount of D-xylose was recovered in urine within 5 hours post-ingestion on Days 1, 15, and 28. In the 2 g through 15 g TID cohorts, between 23% and 32% of the ingested amount of D-xylose was recovered in urine within 5 hours post-ingestion on Days 1, 15, and 28. The fraction excreted in urine was similar among Days 1, 15, and 28.

A review of the time course of serum D-xylose concentrations and the corresponding urinary excretion profiles indicated high ingestion compliance.

Changes in the Gut Microbiome

A total of 344 stool samples were collected in OMNIgene•GUT collection kits and shipped to the GenoFIND laboratory for DNA extraction and V3-V4 16S amplicon sequencing. There were no major shifts in the microbiome alpha diversity between the different treatment groups (absolute number of OTUs, abundance of OTUs) or over time on study. There was an overall decrease in the Chao diversity index over time (indicator of community richness—# of singleton, doubleton OTUs), as shown in FIG. 31. Numerous taxa were identified as differentially abundant, but this finding may be attributable to the relatively small sample sizes of each cohort. Similar observations were made in the mouse study, e.g., xylose treatment did not cause major shifts in the gut microbiome but showed some differences at the family level. Overall, these results suggest that, under the conditions tested in normal individuals and normal mice, ingestion of xylose exerts subtle changes in the gut microbiome. The impact of xylose on the microbiome under disease conditions remains to be determined.

Taken together, the results of this trial show that D-xylose is safe and well-tolerated, and indicate that prebiotic formulations containing xylose may reduce inflammation in a subject, resulting in reduction of serum levels of pro-inflammatory cytokines.

Example 6. Distal Augmentation

The trillions of organisms forming the microbiome function as an organ system interconnected throughout the body. The possibility that modification of the microbiome in a given physical location may influence the microbiome at other sites in the body (distal augmentation) was investigated. Seven week old C57Bl/6 female mice were acclimatized for 7 days prior to the start of the study by daily handling and shuffling between cages. All mice were housed at three mice per cage in individually vented cages (Thoren, Hazleton, Pa.). At day 0, baseline fresh fecal pellets, and vaginal lavages with 100 μL of sterile double-distilled water were collected and immediately frozen at −80° C. for microbiome analysis. After baseline collection, mice were given to drink either autoclaved water (N=6) or 0.5 mg/L of the antibiotic vancomycin in autoclaved water (N=6) ad libitum. Water alone is not expected to influence the microbiome and acted as a negative control. Oral vancomycin is poorly absorbed from the gut and its ingestion does not result in significant levels of drug in the body (Rao et al, 2011). The impact of oral vancomycin is therefore expected to be limited to the gastrointestinal tract such that microbiome changes elsewhere in the body (e.g. vagina) would be attributable to distal augmentation. At day 6, fresh fecal pellets and vaginal lavages with 100 μL of sterile double-distilled water were collected and immediately stored at −80° C. for microbiome analysis.

Isolation and sequencing of microbial DNA from the stool and vaginal samples was performed by DNA Genotek (Ottawa, ON, Canada). The V3-V4 region of the 16S ribosomal subunit was amplified with custom PCR primers and sequenced on an Illumina MiSeq to a minimum acceptable read depth of 25,000 sequences per sample. The widely accepted read depth requirement for accurate taxonomic profiling is 15,000-100,000 reads (Illumina, 2014). A closed-reference taxonomic classification was performed, where each sequence was aligned to the SILVA reference database, version 123. Sequences were aligned using the UCLUST algorithm included in QIIME version 1.9.1 (Caporaso et al., 2010). A minimum threshold of 97% sequence identity was used to classify sequences according to representative sequences in the database. At 97% sequence identity, each OTU represents a genetically unique group of biological organisms. These OTU's were then assigned a curated taxonomic label based on the seven level SILVA taxonomy.

As expected, oral vancomycin treatment had a strong impact on the microbiome of the gut. As shown by principal component analysis (PCA) at the family level, the day 0 to day 6 pattern in fecal samples was clearly different in the control vs oral vancomycin group (FIG. 32). Interestingly, the day 0 to day 6 pattern in the vaginal samples also showed an overall difference between the PBS and oral vancomycin groups even though the vaginal environment is not exposed to vancomycin following oral administration of the antibiotic (FIG. 32). In addition, some bacterial species were detected at low frequency in vaginal samples of the vancomycin-treated group at day 6 (median abundance of approximately 0.00002%) that were not present at day 0 (Table 8). These results support the concept of distal augmentation whereby modification of the microbiome at one site also has an impact at a distal site(s). This finding opens the possibility of modulating the microbiome, for example at the level of the gut, to effect therapeutic changes in the microbiome at other sites, for example the lung.

Example 7. Provision of Fecal Material

Fresh fecal samples are obtained from healthy human donors who have been screened for general good health and for the absence of infectious diseases, and meet inclusion and exclusion criteria, inclusion criteria include being in good general health, without significant medical history, physical examination findings, or clinical laboratory abnormalities, regular bowel movements with stool appearance typically Type 2, 3, 4, 5 or 6 on the Bristol Stool Scale, and having a BMI ≥18 kg/m$^2$ and ≤25 kg/m$^2$. Exclusion criteria generally include significant chronic or acute medical conditions including renal, hepatic, pulmonary, gastrointestinal, cardiovascular, genitourinary, endocrine, immunologic, metabolic, neurologic or hematological disease, a family history of, inflammatory bowel disease including Crohn's disease and ulcerative colitis, Irritable bowel syndrome, colon, stomach or other gastrointestinal malignancies, or gastrointestinal polyposis syndromes, or recent use of yogurt or commercial probiotic materials in which an organism(s) is a primary component. Samples are collected directly using a commode specimen collection system, which contains a plastic support placed on the toilet seat and a collection container that rests on the support. Feces are deposited into the container, and the lid is then placed on the container and sealed tightly. The sample is then delivered on ice within 1-4 hours for processing. Samples are mixed with a sterile disposable tool, and 2-4 g aliquots are weighed and placed into tubes and flash frozen in a dry ice/ethanol bath. Aliquots are frozen at −80 degrees Celsius until use.

Optionally, the fecal material is suspended in a solution, and/or fibrous and/or particulate materials are removed. A frozen aliquot containing a known weight of feces is removed from storage at −80 degrees Celsius and allowed to thaw at room temperature. Sterile 1×PBS is added to create a 10% w/v suspension, and vigorous vortexing is performed to suspend the fecal material until the material appeared homogeneous. The material is then left to sit for 10 minutes at room temperature to sediment fibrous and particulate matter. The suspension above the sediment is then carefully removed into a new tube and contains a purified spore population. Optionally, the suspension is then centrifuged at a low speed, e.g., 1000× g, for 5 minutes to pellet particulate matter including fibers. The pellet is discarded and the supernatant, which contained vegetative organisms and spores, is removed into a new tube. The supernatant is then centrifuged at 6000×g for 10 minutes to pellet the vegetative organisms and spores. The pellet is then resuspended in 1×PBS with vigorous vortexing until the material appears homogenous.

Example 8. Spore Purification from Alcohol Treatment of Fecal Material

A 10% w/v suspension of human fecal material in PBS is mixed with absolute ethanol in a 1:1 ratio and vortexed to mix for 1 minute. The suspension is incubated at 37 degrees Celsius for 1 hour. After incubation the suspension is centrifuged at 13,000 rpm for 5 minutes to pellet spores. The supernatant is discarded and the pellet is resuspended in an equal volume of PBS. Glycerol is added to a final concentration of 15% and then the purified spore fraction is stored at −80 degrees Celsius.

Example 9. Generation of a Spore Preparation from Alcohol Treatment of Fecal Material A 10% w/v suspension of human fecal material in PBS is mixed with absolute ethanol in a 1:1 ratio and vortexed to mix for 1 minute. The suspension is incubated at 37 degrees Celsius for 1 hour. After incubation the suspension is centrifuged at 13,000 rpm for 5 minutes to concentrate spores into a pellet containing a purified spore-containing preparation. The supernatant is discarded and the pellet resuspended in an equal volume of PBS. Glycerol is added to a final concentration of 15% and then the purified spore preparation is stored at −80 degrees Celsius.

Example 10. Spore Purification from Thermal Treatment of Fecal Material

A 10% w/v suspension of human fecal material in PBS is incubated in a water bath at 80 degrees Celsius for 30 minutes. Glycerol is added to a final concentration of 15% and then the enriched spore containing material is stored at −80 degrees Celsius.

Example 11. Spore Purification from Alcohol Treatment and Thermal Treatment of Fecal Material A 10% w/v suspension of human feces in PBS is mixed with absolute ethanol in a 1:1 ratio and vortexed to mix for 1 minute. The suspension is incubated in a water bath under aerobic conditions at 37 degrees Celsius for 1 hour. After incubation the suspension is centrifuged at 13,000 rpm for 5 minutes to pellet spores. The supernatant is discarded and the pellet is resuspended in equal volume PBS. The ethanol treated spore population is then incubated in a water bath at 80 degrees Celsius for 30 minutes. Glycerol is added to a final concentration of 15% and the purified spore fraction is stored at −80 C.

Example 12. Construction of Binary and Ternary Combinations in a High-Throughput 96-Well Format To allow high-throughput screening of binary and ternary combinations, vials of −80° C. glycerol stock banks are thawed and diluted to 1e8 CFU/mL, Each strain is then diluted 10× (to a final concentration of 1e7 CFU/mL of each strain) into 200 uL of PBS+15% glycerol in the wells of a 96-well plate. Plates are then frozen at −80° C. When needed for the assay, plates are removed from −80° C. and thawed at room temperature under anaerobic conditions when testing in a plate assay with various pathogens.

Example 13. Spore Purification from Detergent Treatment of Fecal Material

A 10% w/v suspension of human feces in PBS is prepared to contain a final concentration of 0.5 to 2% Triton X-100. After shaking incubation for 30 minutes at 25 to 37 degrees Celsius, the sample is centrifuged at 1000 g for 5-10 minutes to pellet particulate matter and large cells. The bacterial entities are recovered in the supernatant fraction, where the purified spore population is optionally further treated, such as in Example 11. Without being bound by theory, detergent addition to the fecal mixture produces better spore populations, at least in part by enhancing separation of the spores from particulates thereby resulting in higher yields of spores. In some embodiments, the purified spore population is further treated, such as by thermal treatment and/or ethanol treatment as described above.

Example 14. Spore Purification by Chromatographic Separation of Fecal Material

A spore-enriched population such as obtained from Examples 7-12 above, is mixed with NaCl to a final concentration of 4M total salt and contacted with octyl Sepharose 4 Fast Flow to bind the hydrophobic spore fraction. The resin is washed with 4M NaCl to remove less hydrophobic components, and the spores are eluted with distilled water, and the desired enriched spore fraction is collected via UV absorbance.

Example 15. Spore Purification by Filtration of Fecal Material

A spore-enriched population such as obtained from Examples 8-13 above is diluted 1:10 with PBS, and placed in the reservoir vessel of a tangential flow microfiltration system. A 0.2 μm pore size mixed cellulose ester hydrophilic tangential flow filter is connected to the reservoir such as by a tubing loop. The diluted spore preparation is recirculated through the loop by pumping, and the pressure gradient across the walls of the microfilter forces the supernatant liquid through the filter pores. By appropriate selection of the filter pore size the desired bacterial entities are retained, while smaller contaminants such as cellular debris, and other contaminants in feces such as bacteriophage pass through the filter. Fresh PBS buffer is added to the reservoir periodically to enhance the washout of the contaminants. At the end of the diafiltration, the spores are concentrated approximately ten-fold to the original concentration. The purified spores are collected from the reservoir and stored as provided herein.

Example 16. Characterization of Purified Spore Populations

Counts of viable spores are determined by performing 10 fold serial dilutions in PBS and plating to Brucella Blood Agar Petri plates or applicable solid media. Plates are incubated at 37 degrees Celsius for 2 days. Colonies are counted from a dilution plate with 50-400 colonies and used to back-calculate the number of viable spores in the population. The ability to germinate into vegetative bacteria is also demonstrated. Visual counts are determined by phase contrast microscopy. A spore preparation is either diluted in PBS or concentrated by centrifugation, and a 5 microliter aliquot is placed into a Petroff Hauser counting chamber for visualization at 400× magnification. Spores are counted within ten 0.05 mm×0.05 mm grids and an average spore count per grid is determined and used to calculate a spore count per ml of preparation. Lipopolysaccharide (LPS) reduction in purified spore populations is measured using a Limulus amebocyte lysate (LAL) assay such as the commercially available ToxinSensor™ Chromogenic LAL Endotoxin Assay Kit (GenScript, Piscataway, N.J.) or other standard methods known to those skilled in the art.

Example 17. Quantification of *C. difficile* Using Quantitative PCR (qPCR)

A. Standard Curve Preparation

The standard curve is generated from a well on each assay plate containing only pathogenic *C. difficile* grown in SweetB+FosIn media as provided herein and quantified by selective spot plating. Serial dilutions of the culture are performed in sterile phosphate-buffered saline. Genomic DNA is extracted from the standard curve samples along with the other wells.

B. Genomic DNA Extraction

Genomic DNA is extracted from 5 μl of each sample using a dilution, freeze/thaw, and heat lysis protocol. 5 μL of thawed samples are added to 45 μL of UltraPure water (Life Technologies, Carlsbad, Calif.) and mixed by pipetting. The plates with diluted samples are frozen at −20° C. until use for qPCR which includes a heated lysis step prior to amplification. Alternatively the genomic DNA could be isolated using the Mo Bio Powersoil®-htp 96 Well Soil DNA Isolation Kit (Mo Bio Laboratories, Carlsbad, Calif.), Mo Bio Powersoil® DNA Isolation Kit (Mo Bio Laboratories, Carlsbad, Calif.), or the QIAamp DNA Stool Mini Kit (QIAGEN, Valencia, Calif.) according to the manufacturer's instructions.

C. qPCR Composition and Conditions

The qPCR reaction mixture contained 1× SsoAdvanced Universal Probes Supermix, 900 nM of Wr-tcdB-F primer (AGCAGTTGAATATAGTGGTTTAGTTAGAGTTG, Coralville, Iowa), 900 nM of Wr-tcdB-R primer (CATGCTTTTTTAGTTTCTGGATTGAA, IDT, Coralville, Iowa), 250 nM of Wr-tcdB-P probe (6FAM-CATCCAGTCTCAATTGTATATGTTTCTCCA-MGB, Life Technologies, Grand Island, N.Y.), and Molecular Biology Grade Water (Mo Bio Laboratories, Carlsbad, Calif.) to 18 μl (Primers adapted from: Wroblewski, D. et al., Rapid Molecular Characterization of *Clostridium difficile* and Assessment of Populations of *C. difficile* in Stool Specimens, Journal of Clinical Microbiology 47:2142-2148 (2009)). This reaction mixture is aliquoted to wells of a Hard-shell Low-Profile Thin Wall 96-well Skirted PCR Plate (BioRad, Hercules, Calif.). To this reaction mixture, 2 μl of diluted, frozen, and thawed samples are added and the plate sealed with a Microseal 'B' Adhesive Seal (BioRad, Hercules, Calif.). The qPCR is performed on a BioRad C1000™ Thermal Cycler equipped with a CFX96™ Real-Time System (BioRad, Hercules, Calif.). The thermocycling conditions are 95° C. for 15 minutes followed by 45 cycles of 95° C. for 5 seconds, 60° C. for 30 seconds, and fluorescent readings of the FAM channel. Alternatively, the qPCR could be performed with other standard methods known to those skilled in the art.

Example 18, 16S Sequencing to Determine Operational Taxonomic Unit (OTU)

Method for Determining 16S Sequence

OTUs may be defined either by full 16S sequencing of the rDNA gene, by sequencing of a specific hypervariable region of this gene (i.e. V1, V2, V3, V4, V5, V6, V7, V8, or V9), or by sequencing of any combination of hypervariable regions from this gene (e.g. V1-3 or V3-5). The bacterial 16S rDNA is approximately 1500 nucleotides in length and is used in reconstructing the evolutionary relationships and sequence similarity of one bacterial isolate to another using phylogenetic approaches. 16S sequences are used for phylogenetic reconstruction as they are in general highly conserved, but contain specific hypervariable regions that harbor sufficient nucleotide diversity to differentiate genera and species of most microbes.

rDNA gene sequencing methods are applicable to both the analysis of non-enriched samples, but also for identification of microbes after enrichment steps that either enrich the microbes of interest from the microbial composition and/or the nucleic acids that harbor the appropriate rDNA gene sequences as described below. For example, enrichment treatments prior to 16S rDNA gene characterization will increase the sensitivity of 16S as well as other molecular-based characterization nucleic acid purified from the microbes.

Using well known techniques, in order to determine the full 16S sequence or the sequence of any hypervariable region of the 16S rRNA sequence, genomic DNA is extracted from a bacterial sample, the 16S rDNA (full region or specific hypervariable regions) amplified using polymerase chain reaction (PCR), the PCR products cleaned, and nucleotide sequences delineated to determine the genetic composition of 16S gene or subdomain of the gene. If full 16S sequencing is performed, the sequencing method used may be, but is not limited to, Sanger sequencing. If one or more hypervariable regions are used, such as the V4 region, the sequencing may be, but is not limited to being, performed using the Sanger method or using a next-generation sequencing method, such as an Illumina (sequencing by synthesis) method using barcoded primers allowing for multiplex reactions.

Method for Determining 18S rDNA and ITS Gene Sequence

Methods to assign and identify fungal OTUs by genetic means can be accomplished by analyzing 18S sequences and the internal transcribed spacer (ITS). The rRNA of fungi that forms the core of the ribosome is transcribed as a signal gene and consists of the 8S, 5.8S and 28S regions with ITS4 and 5 between the 8S and 5.8S and 5.8S and 28S regions, respectively. These two intercistronic segments between the 18S and 5.8S and 5.8S and 28S regions are removed by splicing and contain significant variation between species for barcoding purposes as previously described (Schoch et al Nuclear ribosomal internal transcribed spacer (ITS) region as a universal DNA barcode marker for Fungi. PNAS 109:6241-6246. 2012). 18S rDNA is traditionally used for phylogenetic reconstruction however the ITS can serve this function as it is generally highly conserved but contains hypervariable regions that harbor sufficient nucleotide diversity to differentiate genera and species of most fungus.

Using well known techniques, in order to determine the full 18S and ITS sequences or a smaller hypervariable section of these sequences, genomic DNA is extracted from a microbial sample, the rDNA amplified using polymerase chain reaction (PCR), the PCR products cleaned, and nucleotide sequences delineated to determine the genetic composition rDNA gene or subdomain of the gene. The sequencing method used may be, but is not limited to, Sanger sequencing or using a next-generation sequencing method, such as an Illumina (sequencing by synthesis) method using barcoded primers allowing for multiplex reactions.

Method for Determining Other Marker Gene Sequences

In addition to the 16S rRNA gene, one may define an OTU by sequencing a selected set of genes that are known to be marker genes for a given species or taxonomic group of OTUs. These genes may alternatively be assayed using a PCR-based screening strategy. As example, various strains of pathogenic *Escherichia coli* can be distinguished using DNAs from the genes that encode heat-labile (LTI, LTIIa, and LTIIb) and heat-stable (STI and STII) toxins, verotoxin types 1, 2, and 2e (VT1, VT2, and VT2e, respectively), cytotoxic necrotizing factors (CNF1 and CNF2), attaching and effacing mechanisms (eaeA), enteroaggregative mechanisms (Eagg), and enteroinvasive mechanisms (Einv). The optimal genes to utilize for taxonomic assignment of OTUs by use of marker genes will be familiar to one with ordinary skill of the art of sequence based taxonomic identification.

Genomic DNA Extraction

Genomic DNA is extracted from pure microbial cultures using a hot alkaline lysis method. 1 μl of microbial culture is added to 9 μl of Lysis Buffer (25 mM NaOH, 0.2 mM EDTA) and the mixture is incubated at 95° C. for 30 minutes. Subsequently, the samples are cooled to 4° C. and neutralized by the addition of 10 μl of Neutralization Buffer (40 mM Tris-HCl) and then diluted 10-fold in Elution Buffer (10 mM Tris-HCl). Alternatively, genomic DNA is extracted from pure microbial cultures using commercially available kits such as the Mo Bio Ultraclean® Microbial DNA Isolation Kit (Mo Bio Laboratories, Carlsbad, Calif.) or by standard methods known to those skilled in the art. For fungal samples, DNA extraction can be performed by methods described previously (US20120135127) for producing lysates from fungal fruiting bodies by mechanical grinding methods.

Amplification of 16S Sequences for Downstream Sanger Sequencing

To amplify bacterial 16S rDNA, 2 μl of extracted gDNA is added to a 20 μl final volume PCR reaction. For full-length 16 sequencing the PCR reaction also contains 1× HotMasterMix (5PRIME, Gaithersburg, Md.), 250 nM of 27f (AGRGTTTGATCMTGGCTCAG, IDT, Coralville, Iowa), and 250 nM of 1492r (TACGGYTACCTTGTTAYGACTT, IDT, Coralville, Iowa), with PCR Water (Mo Bio Laboratories, Carlsbad, Calif.) for the balance of the volume. Alternatively, other universal bacterial primers or thermostable polymerases known to those skilled in the art are used. For example primers are available to those skilled in the art for the sequencing of the "V1-V9 regions" of the 16S rRNA. These regions refer to the first through ninth hypervariable regions of the 16S rRNA gene that are used for genetic typing of bacterial samples. These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. Brosius et al., Complete nucleotide sequence of a 16S ribosomal RNA gene from *Escherichia coli*, PNAS 75(10):4801-4805 (1978).

In some embodiments, OTUs may be defined either by full 16S sequencing of the rRNA gene, by sequencing of a specific hypervariable region of this gene (i.e., V1, V2, V3, V4, V5, V6, V7, V8, or V9), or by sequencing any combination of hypervariable regions from this gene (e.g., V1-3 or V3-5). In one embodiment, the V1, V2, and V3 regions are used to characterize an OTU. In another embodiment, the V3, V4, and V5 regions are used to characterize an OTU. In another embodiment, the V4 region is used to characterize an OTU. A person of ordinary skill in the art can identify the specific hypervariable regions of a candidate 16S rRNA by comparing the candidate sequence in question to the reference sequence and identifying the hypervariable regions based on similarity to the reference hypervariable regions.

The PCR is performed on commercially available thermocyclers such as a BioRad MyCycler™ Thermal Cycler (BioRad, Hercules, Calif.). The reactions are run at 94° C. for 2 minutes followed by 30 cycles of 94° C. for 30 seconds, 51° C. for 30 seconds, and 68° C. for 1 minute 30 seconds, followed by a 7 minute extension at 72° C. and an indefinite hold at 4° C. Following PCR, gel electrophoresis of a portion of the reaction products is used to confirm successful amplification of a ~1.5 kb product.

To remove nucleotides and oligonucleotides from the PCR products, 2 µl of HT ExoSap-IT (Affymetrix, Santa Clara, Calif.) is added to 5 µl of PCR product followed by a 15 minute incubation at 37° C. and then a 15 minute inactivation at 80° C.

Amplification of 16S Sequences for Downstream Characterization by Massively Parallel Sequencing Technologies Amplification performed for downstream sequencing by short read technologies such as Illumina require amplification using primers known to those skilled in the art that additionally include a sequence-based barcoded tag. As example, to amplify the 16s hypervariable region V4 region of bacterial 16S rDNA, 2 µl of extracted gDNA is added to a 20 µl final volume PCR reaction. The PCR reaction also contains 1× HotMasterMix (5PRIME, Gaithersburg, Md.), 200 nM of V4_515f_adapt (AATGATACGGCGACCACCGAGATCTACACTATG

GTAATTGTGTGCCAGCMGCCGCGGTAA,

IDT, Coralville, Iowa), and 200 nM of barcoded 806rbc (CAAGCAGAAGACGGCATACGAGAT_12bpGolayBarcode

AGTCAGTCAGCCGGACTACHVGGGTWTCTAAT,

IDT, Coralville, Iowa), with PCR Water (Mo Bio Laboratories, Carlsbad, Calif.) for the balance of the volume. These primers incorporate barcoded adapters for Illumina sequencing by synthesis. Optionally, identical replicate, triplicate, or quadruplicate reactions may be performed. Alternatively other universal bacterial primers or thermostable polymerases known to those skilled in the art are used to obtain different amplification and sequencing error rates as well as results on alternative sequencing technologies.

The PCR amplification is performed on commercially available thermocyclers such as a BioRad MyCycler™ Thermal Cycler (BioRad, Hercules, Calif.). The reactions are run at 94° C. for 3 minutes followed by 25 cycles of 94° C. for 45 seconds, 50° C. for 1 minute, and 72° C. for 1 minute 30 seconds, followed by a 10 minute extension at 72° C. and a indefinite hold at 4° C. Following PCR, gel electrophoresis of a portion of the reaction products is used to confirm successful amplification of a ~1.5 kb product. PCR cleanup is performed as specified in the previous example.

Sanger Sequencing of Target Amplicons from Pure Homogeneous Samples

To detect nucleic acids for each sample, two sequencing reactions are performed to generate a forward and reverse sequencing read. For full-length 16s sequencing primers 27f and 1492r are used. 40 ng of ExoSap-IT-cleaned PCR products are mixed with 25 pmol of sequencing primer and Mo Bio Molecular Biology Grade Water (Mo Bio Laboratories, Carlsbad, Calif.) to 15 µl total volume. This reaction is submitted to a commercial sequencing organization such as Genewiz (South Plainfield, N.J.) for Sanger sequencing.

In order to determine the full 16S sequence or the sequence of any hypervariable region of the 16S rRNA sequence, genomic DNA is extracted from a bacterial sample, the 16S rDNA (full region or specific hypervariable regions) is amplified using polymerase chain reaction (PCR), the PCR products are cleaned, and nucleotide sequences delineated to determine the genetic composition of 16S gene or subdomain of the gene. If full 16S sequencing is performed, the sequencing method used may be, but is not limited to, Sanger sequencing. If one or more hypervariable regions are used, such as the V4-V5 region, the sequencing may be, but is not limited to being, performed using the Sanger method or using a next-generation sequencing method, such as an Illumina (sequencing by synthesis) method using barcoded primers allowing for multiplex reactions.

Amplification of 18S and ITS Regions for Downstream Sequencing and Characterization To amplify the 18S or ITS regions, 2 µL fungal DNA were amplified in a final volume of 30 µL with 15 µL AmpliTaq Gold 360 Mastermix, PCR primers, and water. The forward and reverse primers for PCR of the ITS region are 5'-TCCTCCGCTTATTGATATGC-3' and 5'-GGAAGTAAAAGTCGTAACAAGG-3' and are added at 0.2 uM concentration each. The forward and reverse primers for the 18S region are 5'-GTAGTCATATGCTTGTCTC-3' and 5'-CTTCCGTCAATTCCTTTAAG-3' and are added at 0.4 uM concentration each. PCR is performed with the following protocol: 95C for 10 min, 35 cycles of 95C for 15 seconds, 52C for 30 seconds, 72C for 1.5s; and finally 72C for 7 minutes followed by storage at 4C. All forward primers contained the M13F-20 sequencing primer, and reverse primers included the M13R-27 sequencing primer. PCR products (3 µL) were enzymatically cleaned before cycle sequencing with 1 µL ExoSap-IT and 1 µL Tris EDTA and incubated at 37° C. for 20 min followed by 80° C. for 15 min. Cycle sequencing reactions contained 5 µL cleaned PCR product, 2 µL BigDye Terminator v3.1 Ready Reaction Mix, 1 µL 5× Sequencing Buffer, 1.6 pmol of appropriate sequencing primers designed by one skilled in the art, and water in a final volume of 10 µL. The standard cycle sequencing protocol is 27 cycles of 10 s at 96° C., 5 s at 50° C., 4 min at 60° C., and hold at 4° C. Sequencing cleaning is performed with the BigDye XTerminator Purification Kit as recommended by the manufacturer for 10-µL volumes. The genetic sequence of the resulting 18S and ITS sequences is performed using methods familiar to one with ordinary skill in the art using either Sanger sequencing technology or next-generation sequencing technologies such as but not limited to Illumina.

Preparation of Extracted Nucleic Acids for Metagenomic Characterization by Massively Parallel Sequencing Technologies Extracted nucleic acids (DNA or RNA) are purified and prepared by downstream sequencing using standard methods familiar to one with ordinary skill in the art and as described by the sequencing technology's manufactures instructions for library preparation. In short, RNA or DNA are purified using standard purification kits such as but not limited to Qiagen's RNeasy Kit or Promega's Genomic DNA purification kit. For RNA, the RNA is converted to cDNA prior to sequence library construction. Following purification of nucleic acids, RNA is converted to cDNA using reverse transcription technology such as but not limited to Nugen Ovation RNA-Seq System or Illumina Truseq as per the manufacturer's instructions. Extracted DNA or transcribed cDNA are sheared using physical (e.g., Hydroshear), acoustic (e.g., Covaris), or molecular (e.g., Nextera) technologies and then size selected as per the sequencing technologies manufacturer's recommendations. Following size selection, nucleic acids are prepared for sequencing as per the manufacturer's instructions for sample indexing and sequencing adapter ligation using methods familiar to one with ordinary skill in the art of genomic sequencing.

Massively Parallel Sequencing of Target Amplicons from Heterogeneous Samples

DNA Quantification & Library Construction. The cleaned PCR amplification products are quantified using the Quant-iT™ PicoGreen® dsDNA Assay Kit (Life Technologies, Grand Island, N.Y.) according to the manufacturer's instructions. Following quantification, the barcoded cleaned PCR products are combined such that each distinct PCR product is at an equimolar ratio to create a prepared Illumina library.

Nucleic Acid Detection. The prepared library is sequenced on Illumina HiSeq or MiSeq sequencers (Illumina, San Diego, Calif.) with cluster generation, template hybridization, isothermal amplification, linearization, blocking and denaturation and hybridization of the sequencing primers performed according to the manufacturer's instructions. 16SV4SeqFw (TATGGTAAT-TGTGTGCCAGCMGCCGCGGTAA), 16SV4SeqRev (AGTCAGTCAGCCGGACTACHVGGGTWTCTAAT), and 16SV4Index (ATT-AGAWACCCBDGTAGTCCGGCTGACTGACT) (IDT, Coralville, Iowa) are used for sequencing. Other sequencing technologies can be used such as but not limited to 454, Pacific Biosciences, Helicos, Ion Torrent, and Nanopore using protocols that are standard to someone skilled in the art of genomic sequencing.

Example 19. Data Analysis, Sequence Annotation and Taxonomic Characterization

Primary Read Annotation

Nucleic acid sequences are analyzed to define taxonomic assignments using sequence similarity and phylogenetic placement methods or a combination of the two strategies. A similar approach is used to annotate protein names, protein function, transcription factor names, and any other classification schema for nucleic acid sequences. Sequence similarity based methods include those familiar to individuals skilled in the art including, but not limited to, BLAST, BLASTx, tBLASTn, tBLASTx, RDP-classifier, DNAclust, and various implementations of these algorithms such as Qiime or Mothur. These methods rely on mapping a sequence read to a reference database and selecting the match with the best score and e-value. Common databases include, but are not limited to the Human Microbiome Project, NCBI non-redundant database, Greengenes, RDP, and Silva for taxonomic assignments. For functional assignments reads are mapped to various functional databases such as but not limited to COG, KEGG, BioCyc, and MetaCyc. Further functional annotations can be derived from 16S taxonomic annotations using programs such as PICRUST (M. Langille, et al 2013. Nature Biotechnology 31, 814-821). Phylogenetic methods can be used in combination with sequence similarity methods to improve the calling accuracy of an annotation or taxonomic assignment. Here tree topologies and nodal structure are used to refine the resolution of the analysis. In this approach we analyze nucleic acid sequences using one of numerous sequence similarity approaches and leverage phylogenetic methods that are well known to those skilled in the art, including but not limited to maximum likelihood phylogenetic reconstruction (see e.g. Liu K, Linder C R, and Warnow T. 2011. RAxML and FastTree: Comparing Two Methods for Large-Scale Maximum Likelihood Phylogeny Estimation. PLoS ONE 6: e27731. McGuire G, Denham MC, and Balding D J. 2001. Models of sequence evolution for DNA sequences containing gaps. Mol. Biol. Evol 18: 481-490. Wròbel B. 2008. Statistical measures of uncertainty for branches in phylogenetic trees inferred from molecular sequences by using model-based methods. J. Appl. Genet. 49: 49-67.) Sequence reads are placed into a reference phylogeny comprised of appropriate reference sequences. Annotations are made based on the placement of the read in the phylogenetic tree. The certainty or significance of the OTU annotation is defined based on the OTU's sequence similarity to a reference nucleic acid sequence and the proximity of the OTU sequence relative to one or more reference sequences in the phylogeny. As an example, the specificity of a taxonomic assignment is defined with confidence at the level of Family, Genus, Species, or Strain with the confidence determined based on the position of bootstrap supported branches in the reference phylogenetic tree relative to the placement of the OTU sequence being interrogated. Nucleic acid sequences can be assigned functional annotations using the methods described above.

In some embodiments, microbial clades are assigned using databases including, but not limited to, MetaPhlAn. Microbial diversity is quantified using the Shannon diversity index following closed-reference operational taxonomic unit picking. Phylogenetic abundance comparisons are performed in order to identify biomarkers of GVHD-related mortality using linear discriminant analysis (LDA) effect size (LEfSe) analysis, using a logarithmic LDA cutoff of 2.0.

Clade Assignments

The ability of 16S-V4 OTU identification to assign an OTU as a specific species depends in part on the resolving power of the 16S-V4 region of the 16S gene for a particular species or group of species. Both the density of available reference 16S sequences for different regions of the tree as well as the inherent variability in the 16S gene between different species will determine the definitiveness of a taxonomic annotation. Given the topological nature of a phylogenetic tree and the fact that tree represents hierarchical relationships of OTUs to one another based on their sequence similarity and an underlying evolutionary model, taxonomic annotations of a read can be rolled up to a higher level using a clade-based assignment procedure (Table 1). Using this approach, clades are defined based on the topology of a phylogenetic tree that is constructed from full-length 16S sequences using maximum likelihood or other phylogenetic models familiar to individuals with ordinary skill in the art of phylogenetics. Clades are constructed to ensure that all OTUs in a given clade are: (i) within a specified number of bootstrap supported nodes from one another (generally, 1-5 bootstraps), and (ii) share a defined percent similarity, e.g., within a 5% genetic similarity (for 16S molecular data typically set to 95%-97% sequence similarity). OTUs that are within the same clade can be distinguished as genetically and phylogenetically distinct from OTUs in a different clade based on 16S-V4 sequence data. OTUs falling within the same clade are evolutionarily closely related and may or may not be distinguishable from one another using 16S-V4 sequence data. The power of clade based analysis is that members of the same clade, due to their evolutionary relatedness, are likely to play similar functional roles in a microbial ecology such as that found in the human gut or vagina. Compositions substituting one species with another from the same clade are likely to have conserved ecological function and therefore are useful in the present invention. Notably in addition to 16S-V4 sequences, clade-based analysis can be used to analyze 18S, ITS, and other genetic sequences.

Notably, 1.6S sequences of isolates of a given OTU are phylogenetically placed within their respective clades, sometimes in conflict with the microbiological-based assignment of species and genus that may have preceded 16S-based assignment. Discrepancies between taxonomic assignment based on microbiological characteristics versus genetic sequencing are known to exist from the literature.

For a given network ecology or functional network ecology one can define a set of OTUs from the network's representative clades.

Metagenomic Read Annotation

Metagenomic or whole genome shotgun sequence data is annotated as described above, with the additional step that sequences are either clustered or assembled prior to annotation. Following sequence characterization as described above, sequence reads are demultiplexed using the indexing (i.e. barcodes). Following demultiplexing sequence reads are either: (i) clustered using a rapid clustering algorithm such as but not limited to UCLUST (http://drive5.com/usearch/manual/uclust_algo.html) or hash methods such VICUNA (Xiao Yang, Patrick Charlebois, Sante Gnerre, Matthew G Coole, Niall J. Lennon, Joshua Z. Levin, James Qu, Elizabeth M. Ryan, Michael C. Zody, and Matthew R. Henn, 2012. De novo assembly of highly diverse viral populations. BMC Genomics 13:475). Following clustering a representative read for each cluster is identified based and analyzed as described above in "Primary Read Annotation". The result of the primary annotation is then applied to all reads in a given cluster. (ii) A second strategy for metagenomic sequence analysis is genome assembly followed by annotation of genomic assemblies using a platform such as but not limited to MetAMOS (T J. Treangen et al. 2013 Geneome Biology 14:R2), HUMAaN (Abubucker S, Segata N, Goll J, Schubert A M, kard J, Cantarel B L, Rodriguez-Mueller B, Zucker J, Thiagarajan M, Henrissat B, et al. 2012. Metabolic Reconstruction for Metagenomic Data and Its Application to the Human Microbiome ed. J. A. Eisen. PLoS Computational Biology 8: e1002358) and other methods familiar to one with ordinary skill in the art.

Example 20. OTU Identification Using Microbial Culturing Techniques

The identity of the bacterial species which grew up from a complex fraction can be determined in multiple ways. First, individual colonies can be picked into liquid media in a 96 well format, grown up and saved as 15% glycerol stocks at −80° C. Aliquots of the cultures can be placed into cell lysis buffer and colony PCR methods can be used to amplify and sequence the 16S rDNA gene (Example 18). Alternatively, colonies may be streaked to purity in several passages on solid media. Well separated colonies are streaked onto the fresh plates of the same kind and incubated for 48-72 hours at 37° C. The process is repeated multiple times in order to ensure purity. Pure cultures can be analyzed by phenotypic- or sequence-based methods, including 16S rDNA amplification and sequencing as described in Example 18. Sequence characterization of pure isolates or mixed communities e.g. plate scrapes and spore fractions can also include whole genome shotgun sequencing. The latter is valuable to determine the presence of genes associated with sporulation, antibiotic resistance, pathogenicity, and virulence. Colonies can also be scraped from plates en masse and sequenced using a massively parallel sequencing method as described in Example 7. such that individual 16S signatures can be identified in a complex mixture. Optionally, the sample can be sequenced prior to germination (if appropriate DNA isolation procedures are used to lyse and release the DNA from spores) in order to compare the diversity of germinable species with the total number of species in a spore sample. As an alternative or complementary approach to 16S analysis, MALDI-TOF-mass spec can also be used for species identification (Barreau M, Pagnier I, La. Scola B. 2013. Improving the identification of anaerobes in the clinical microbiology laboratory through MALDI-TOF mass spectrometry. Anaerobe 22: 123-125).

Example 21. Microbiological Strain Identification Approaches

Pure bacterial isolates can be identified using microbiological methods as described in Wadsworth-KTL Anaerobic Microbiology Manual (Jouseimies-Somer H, Summanen P H, Citron D, Baron E, Wexler H M, Finegold S M. 2002. Wadsworth-KTL Anaerobic Bacteriology Manual), and The Manual of Clinical Microbiology (ASM Press, 10th Edition). These methods rely on phenotypes of strains and include Gram-staining to confirm Gram positive or negative staining behavior of the cell envelope, observance of colony morphologies on solid media, motility, cell morphology observed microscopically at 60× or 100× magnification including the presence of bacterial endospores and flagella. Biochemical tests that discriminate between genera and species are performed using appropriate selective and differential agars and/or commercially available kits for identification of Gram negative and Gram positive bacteria and yeast, for example, RapID tests (Remel) or API tests (bioMerieux). Similar identification tests can also be performed using instrumentation such as the Vitek 2 system (bioMerieux). Phenotypic tests that discriminate between genera and species and strains (for example the ability to use various carbon and nitrogen sources) can also be performed using growth and metabolic activity detection methods, for example the Biolog Microbial identification microplates. The profile of short chain fatty acid production during fermentation of particular carbon sources can also be used as a way to discriminate between species (Wadsworth-KTL Anaerobic Microbiology Manual, Jousimies-Somer, et al 2002). MALDI-TOF-mass spectrometry can also be used for species identification (as reviewed in Anaerobe 22:123).

Example 22. Construction of an In Vitro Assay to Screen for Combinations of Microbes Inhibitory to the Growth of Pathogenic *E. coli*

The in vitro assay is used to screen for combinations of bacteria inhibitory to the growth of *E. coli* by modifying the media used for growth of the pathogen inoculum. One of several choices of media is used for growth of the pathogen such as Reinforced Clostridial Media (RCM), Brain Heart Infusion Broth (BM) or Luria Bertani Broth (LB) (also known as Lysogeny Broth). *E. coli* is quantified by using alternative selective media specific for *E. coli* or using qPCR probes specific for the pathogen. For example, aerobic growth on MacConkey lactose medium selects for enteric Gram negatives, including *E. coli*. qPCR is conducted using probes specific for the shiga toxin of pathogenic *E. coli*.

Example 23. Construction of an In Vitro Assay to Screen for Combinations of Microbes Inhibitory to the Growth of Vancomycin-Resistant Enterococcus (VRE)

The in vitro assay is used to screen for combinations of bacteria inhibitory to the growth of Vancomycin-Resistant Enterococcus spp. (VRE) by modifying the media used for growth of the pathogen inoculum. Several choices of media are used for growth of the pathogen such as Reinforced Clostridial. Media (RCM), Brain Heart Infusion Broth (BHI) or Luria Bertani Broth (LB). VRE is quantified by using alternative selective media specific for VRE or using qPCR probes specific for the pathogen. For example, m-Enterococcus agar containing sodium azide is selective for *Enterococcus* spp. and a small number of other species. Probes specific to the van genes conferring vancomycin resistance are used in the qPCR.

Example 24. Testing of Bacterial Composition Against *Salmonella*

The in vitro assay is used to screen for combinations of bacteria inhibitory to the growth of *Salmonella* spp. by modifying the media used for growth of the pathogen inoculum. Several choices of media are used for growth of the pathogen such as Reinforced Clostridial Media (RCM), Brain Heart Infusion Broth (BHI) or Luria Bertani Broth (LB). *Salmonella* spp. are quantified by using alternative selective media specific for *Salmonella* spp. or using qPCR probes specific for the pathogen. For example, MacConkey agar is used to select for *Salmonella* spp. and the invA gene is targeted with qPCR probes; this gene encodes an invasion protein carried by many pathogenic *Salmonella* spp. and is used in invading eukaryotic cells.

Example 25, Method of Preparing the Bacterial Composition for Administration to a Subject Two or more strains that comprise the bacterial composition are independently cultured and mixed together before administration. Both strains are independently be grown at 37° C., pH 7, in a GMM or other animal-products-free medium, pre-reduced with 1 g/L cysteine HCl. After each strain reaches a sufficient biomass, it is preserved for banking by adding 15% glycerol and then frozen at $-80°$ C. in 1 ml cryotubes.

Each strain is then be cultivated to a concentration of $10^{10}$ CFU/mL, then concentrated 20-fold by tangential flow microfiltration; the spent medium is exchanged by diafiltering with a preservative medium consisting of 2% gelatin, 100 mM trehalose, and 10 mM sodium phosphate buffer, or other suitable preservative medium. The suspension is freeze-dried to a powder and titrated.

After drying, the powder is blended with microcrystalline cellulose and magnesium stearate and formulated into a 250 mg gelatin capsule containing 10 mg of lyophilized powder ($10^8$ to $10^{11}$ bacteria), 160 mg microcrystalline cellulose, 77.5 mg gelatin, and 2.5 mg magnesium stearate.

A bacterial composition can be derived by selectively fractionating the desired bacterial OTUs from a raw material such as but not limited to stool. As example we prepared a 10% w/v suspension of human stool material in PBS that is filtered, centrifuged at low speed, and then the supernate containing spores is mixed with absolute ethanol in a 1:1 ratio and vortexed to mix. The suspension is incubated at room temperature for 1 hour. After incubation the suspension is centrifuged at high speed to concentrate spores into a pellet containing a purified spore-containing preparation. The supernate is discarded and the pellet resuspended in an equal mass of glycerol, and the purified spore preparation is placed into capsules and stored at $-80$ degrees Celsius; this preparation is referred to as an ethanol-treated spore population.

Example 26. Method of Treating a Subject with a Bacterial Composition

A subject has suffered from recurrent bouts of *C. difficile*. In the most recent acute phase of illness, the subject is treated with an antibiotic sufficient to ameliorate the symptoms of the illness. In order to prevent another relapse of *C. difficile*, the subject is administered one of the present bacterial compositions. Specifically, the subject is administered one of the present bacterial compositions at a dose in the range of $1e10^7$ to $1e10^{12}$ in a lyophilized form, in a gelatin capsule containing 10 mg of lyophilized bacteria and stabilizing components. The subject takes the capsule by mouth and resumes a normal diet after 4, 8, 12, or 24 hours. In another embodiment, the subject may take the capsule by mouth before, during, or immediately after a meal. In a further embodiment, the subject takes the dose daily for a specified period of time.

Stool is collected before and after treatment. In one embodiment stool is collected at 1 day, 3 days, 1 week, and 1 month after administration. The presence of *C. difficile* is found in the stool before administration of the bacterial composition, but stool collections after administration show reducing (such as at least 50% less, 60%, 70%, 80%, 90%, or 95%) to no detectable levels of *C. difficile*, as measured by qPCR, as described above. ELISA for toxin protein or traditional microbiological identification techniques may also be used.

As another measure of subject success, a positive response may be defined as absence of diarrhea, which itself is defined as 3 or more loose or watery stools per day for at least 2 consecutive days or 8 or more loose or watery stools in 48 hours, or persisting diarrhea (due to other causes) with repeating (three times) negative stool tests for toxins of *C. difficile*.

Treatment failure is defined as persisting diarrhea with a positive *C. difficile* toxin stool test or no reduction in levels of *C. difficile*, as measured by qPCR sequencing. ELISA or traditional microbiological identification techniques may also be used.

Example 27. Microbiological Strain Identification Approaches

Pure bacterial isolates are identified using microbiological methods as described in Wadsworth-KTL Anaerobic Microbiology Manual (Jouseimies-Somer H, Summanen P H, Citron D, Baron E, Wexler H M, Finegold S M. 2002. Wadsworth-KTL Anaerobic Bacteriology Manual), and The Manual of Clinical Microbiology (ASM Press, 10th Edition). These methods rely on phenotypes of strains and include Gram-staining to confirm Gram positive or negative staining behavior of the cell envelope, observance of colony morphologies on solid media, motility, cell morphology observed microscopically at 60× or 100× magnification including the presence of bacterial endospores and flagella. Biochemical tests that discriminate between genera and species are performed using appropriate selective and differential agars and/or commercially available kits for identification of Gram negative and Gram positive bacteria and yeast, for example, RapID tests (Remel) or API tests (bioMerieux). Similar identification tests can also be performed using instrumentation such as the Vitek 2 system (bioMerieux). Phenotypic tests that discriminate between genera and species and strains (for example the ability to use various carbon and nitrogen sources) can also be performed using growth and metabolic activity detection methods, for example the Biolog Microbial identification microplates. The profile of short chain fatty acid production during fermentation of particular carbon sources can also be used as a way to discriminate between species (Wadsworth-KTL Anaerobic Microbiology Manual, Jousimies-Somer, et al 2002). MALDI-TOF-mass spectrometry can also be used for species identification (as reviewed in Anaerobe 22:123).

Example 28. Computational Prediction of Network Ecologies

Source data comprising a genomic-based characterization of a microbiome of individual samples are used as input computationally delineate network ecologies that would have biological properties that are characteristic of a state of health and could catalyze a shift from a state of microbial dysbiosis to a state of health. Applicants obtained 16S and metagenomic sequence datasets from public data repositories (see e.g. The Human Microbiome Project Consortium. 2012. Structure, function and diversity of the healthy human microbiome. Nature 486: 207-214. Data accessible at URL: hmpdacc.org) and MetaHit Project (Arumugam M, Raes J, Pelletier E, Paslier D L, Yamada T, Mende D R, Fernandes G R, Tap J, Bruls T, Batto J-M, et al. 2011. Enterotypes of the human gut microbiome. Nature 473: 174-180. Data accessible at URL: metahit.eu) for relevant microbiome studies in multiple disease indications including CDAD, Type 2 Diabetes, Ulcerative Colitis, and Irritable Bowel Disease, or generated data sets from samples directly using the methods described in Examples 18 and 19 and further described in the literature (see e.g. Aagaard K, Riehle K, Ma J, Segata N, Mistretta T-A, Coarfa C, Raza S, Rosenbaum S, Van den Veyver I, Milosavljevic A, et al. 2012. A Metagenomic Approach to Characterization of the Vaginal Microbiome Signature in Pregnancy ed. A. J. Ratner. PLoS ONE 7: e36466. Jumpstart Consortium Human Microbiome Project Data Generation Working Group. 2012. Evaluation of 16S rDNA-Based Community Profiling for Human Microbiome Research ed. J. Ravel. PLoS ONE 7: e39315. The Human Microbiome Project Consortium. 2012. Structure, function and diversity of the healthy human microbiome. Nature 486: 207-214). Nucleic acid sequences are analyzed and taxonomic and phylogenetic assignments of specific OTUs are made using sequence similarity and phylogenetic methods that are well known to those skilled in the art, including but not limited to maximum likelihood phylogenetic reconstruction (see e.g. Liu K, Linder C R, and Warnow T. 2011. RAxML and FastTree: Comparing Two Methods for Large-Scale Maximum Likelihood Phylogeny Estimation. PLoS ONE 6: e27731. McGuire G, Denham M C, and Balding D J. 2001. Models of sequence evolution for DNA sequences containing gaps. Mol. Biol. Evol 18: 481-490. Wròbel B. 2008. Statistical measures of uncertainty for branches in phylogenetic trees inferred from molecular sequences by using model-based methods. J. Appl. Genet. 49: 49-67.) From these taxonomic assignments OTUs and clades in the dataset are defined using the method described in Examples 18 and 19. The certainty of the OTU call is defined based on the OTU's sequence similarity to a reference nucleic acid sequence and the proximity of the OTU sequence relative to one or more reference sequences in the phylogeny. The specificity of an OTU's taxonomic and phlylogenetic assignment determines whether the match is assigned at the level of Family, Genus, Species, or Strain, and the confidence of this assignment is determined based on the position of bootstrap supported branches in the reference phylogenetic tree relative to the placement of the OTU sequence being interrogated. In addition, microbial OTU assignments may be obtained from assignments made in peer-reviewed publications.

Applicants designated individual subject samples to biologically relevant sample phenotypes such as but not limited to "healthy state," "recurrent *Clostridium difficile* infection," "Crohn's disease," "Insulin Resistance," "Obesity," "Type 2 diabetes," "Ulcerative Colitis". In one embodiment samples are assigned to "health" and "disease" phenotypes. In another embodiment, samples are assigned higher resolution phenotype such as but not limited to: "health:human", "health:mouse", "health:human microbiome project", "health:microbiota donor", "health:microbiota recipient", "disease:microbiota recipient", or "disease:no treatment", "disease:human", or "disease:mouse". In another embodiment, samples where assigned to higher resolution phenotypes, such as but not limited to those defined that characterize phenotypes specific to samples from fecal donors and patients who received a fecal microbial transplant from these donors.

In another embodiment, other phenotypes that define a category of disease or health that represents the underlying state of the population under study can be used. Applicants then computationally determined the microbial network ecologies for each phenotype using the OTU and Clade assignments that comprise the microbial profile for each sample and the algorithms described above in the Section entitled "Method of Determining Network Ecologies."

Importantly, Network Ecologies that represent a state of health in one disease indication can represent states of health in additional disease states. Additionally, Keystone OTUs found in a network associated with health for different disease indications can overlap. Applicants found that a large number of network ecologies overlapped particularly between those associated with health in the cases of CDAD and Type 2 Diabetes despite the analysis of substantially different genomic data sets for the two diseases.

Example 29. Identification of Network Classes, Keystone OTUs, Clades, and Functional Modalities Identification of Keystone OTUs, Clades and Functions The human body is an ecosystem in which the microbiota and the microbiome play a significant role in the basic healthy function of human systems (e.g. metabolic, immunological, and neurological). The microbiota and resulting microbiome comprise an ecology of microorganisms that co-exist within single subjects interacting with one another and their host (i.e., the mammalian subject) to form a dynamic unit with inherent biodiversity and functional characteristics. Within these networks of interacting microbes (i.e. ecologies), particular members can contribute more significantly than others; as such these members are also found in many different ecologies, and the loss of these microbes from the ecology can have a significant impact on the functional capabilities of the specific ecology. Robert Paine coined the concept "Keystone Species" in 1969 (see Paine R T. 1969. A note on trophic complexity and community stability. The American Naturalist 103: 91-93) to describe the existence of such lynchpin species that are integral to a given ecosystem regardless of their abundance in the ecological community. Paine originally describe the role of the starfish *Pisaster ochraceus* in marine systems and since the concept has been experimentally validated in numerous ecosystems.

Keystone OTUs, Phylogenetic Clades (a.k.a. Clades), and/or Functions (for example, but not limited to, KEGG Orthology Pathways) are computationally-derived by analysis of network ecologies elucidated from a defined set of samples that share a specific phenotype. Keystone OTUs, Clades and/or Functions are defined as all Nodes within a defined set of networks that meet two or more of the following criteria. Using Criterion 1, the node is frequently observed in networks, and the networks in which the node is observed are found in a large number of individual subjects; the frequency of occurrence of these Nodes in networks and the pervasiveness of the networks in individuals indicates these Nodes perform an important biological function in many individuals. Using Criterion 2, the node is frequently observed in networks, and the Node is observed contains a large number of edges connecting it to other nodes in the network. These Nodes are thus "super-connectors", meaning that they form a nucleus of a majority of networks and as such have high biological significance with respect to their functional contributions to a given ecology.

In another embodiment a Keystone Node is defined as one that occurs in a sample phenotype of interest such as but not limited to "health" and simultaneously does not occur in a sample phenotype that is not of interest such as but not limited to "disease." Optionally, a Keystone Node is defined as one that is shown to be significantly different from what is observed using permuted test datasets to measure significance. In another embodiment of Criterion 2 Keystone OTUs, Clades, or Functions can be defined using a hierarchical clustering method that clusters Networks based on their OTU, Clade, or functional pathways. Statistically significant branch points in the hierarchy are defined based on the topological overlap measure; this measure is a highly robust measure of network interconnectedness (Langfelder P, Zhang B, Horvath S. 2008. Defining clusters from a hierarchical cluster tree: the Dynamic Tree Cut package for R. Bioinformatics 24: 719-720). Once these branch points are defined the Keystones are delineated as OTUs, clades or functional pathways that are found consistently across all networks in all or a subset of the network clusters.

Importantly, we identify the absence of Keystone OTUs in multiple particular disease states, indicating that bacterial compositions comprised of specific sets of Keystone OTUs are likely to have utility in multiple disease indications.

Example 30. Network Analysis Across Multiple Data Sets and Selection of Target Network Ecologies with Capacity to Sporulate One can select Network Ecologies and/or Network Class Ecologies as lead targets by defining networks with a specific biological function or activity such as sporulation. Networks Ecologies or Network Class Ecologies are first selected as described above. In one example, all Network Ecologies or Network Class Ecologies that contain at least one OTU that is capable of forming spores are targeted. In another example, all Network Ecologies or Network Class Ecologies that contain at least one OTU that is capable of forming spores, and that are comprised of at least 50%, 75%, or 100% Keystone OTUs are targeted. Keystone OTUs are selected as described above. OTUs are defined as spore formers using either phenotypic assays (see e.g. Stackebrandt and Hippe. Taxonomy and Systematics. In Clostridia. Biotechnology and Medical Applications) or genetic assays (see e.g. Abecasis A B, Serrano M, Alves R, Quintais L, Pereira-Leal J B, and Henriques A O. 2013. A genomic signature and the identification of new sporulation genes. J. Bacteriol.; Paredes-Sabja D, Setlow P, and Sarker M R. 2011. Germination of spores of Bacillales and Clostridiales species: mechanisms and proteins involved. Trends Microbiol. 19: 85-94).

Clade membership of bacterial OTUs is based on 16S sequence data. Clades are defined based on the topology of a phylogenetic tree that is constructed from full-length 16S sequences using maximum likelihood methods familiar to individuals with ordinary skill in the art of phylogenetics. Clades are constructed to ensure that all OTUs in a given clade are: (i) within a specified number of bootstrap supported nodes from one another, and (ii) within 5% genetic similarity. OTUs that are within the same clade can be distinguished as genetically and phylogenetically distinct from OTUs in a different clade based on 16S-V4 sequence data, while OTUs falling within the same clade are closely related. OTUs falling within the same clade are evolutionarily closely related and may or may not be distinguishable from one another using 16S-V4 sequence data. Members of the same clade, due to their evolutionary relatedness, play similar functional roles in a microbial ecology such as that found in the human gut. Compositions substituting one species with another from the same clade are likely to have conserved ecological function and therefore are useful in the present invention. All OTUs are denoted as to their putative capacity to form spores and whether they are a Pathogen or Pathobiont (see Definitions for description of "Pathobiont"). NIAID Priority Pathogens are denoted as 'Category-A', 'Category-B', or 'Category-C', and Opportunistic Pathogens are denoted as 'OP'. OTUs that are not pathogenic or for which their ability to exist as a pathogen is unknown are denoted as 'N'. The 'SEQ ID Number' denotes the identifier of the OTU in the Sequence Listing File and 'Public DB Accession' denotes the identifier of the OTU in a public sequence repository. For SEQ ID NOs referenced in Table 1, reference is made to e.g., WO2014/121304, which is incorporated by reference herein in its entirety.

Example 31: Selection of Patients and Method for Specimen Collection

Paired stool samples and blood specimens are collected and stored weekly over the course of the transplant hospitalization including prior to conditioning, as well as on days 0, 7, 14, 21, 30, 60, and 100. For Chronic GVHD, samples are collected post GVHD at day 105, day 120, day 180.

Skin, lung, vaginal and oral samples are obtained as well pre- and post-transplant. Intestinal biopsies samples are saved from patients subjected to such analysis. Stool samples from patients are stored at 4° C. for <24 h before eezing at −80° C. GVHD is diagnosed clinically, confirmed pathologically by biopsy whenever possible, and classified according to standard criteria. Patients are evaluated for acute GVHD based on historical consensus criteria as described previously (see Rowlings P A, Przepiorka D, Klein J P, et al. IBMTR Severity Index for grading acute graft-versus-host disease: retrospective comparison with Glucksberg grade. Br J Haematol. 1997). Cases of GVHD are further categorized by treatment with or without systemic steroids (prednisone or methylprednisolone, 0.5 mg/kg daily or higher). Cause of death is determined using a standard algorithm where outcomes are prioritized in the following order: 1) primary disease recurrence, 2) graft failure, 3) GVHD, 4) infection, and 5) organ failure. Thus in patients without disease recurrence or graft failure, those who are being treated for GVHD at the time of death are considered to have succumbed to GVHD-related mortality, including those who died from infections.

Example 32. Cross Niche Analysis of Microbiome

DNA is extracted from samples from various sites—gut, blood, lung, vaginal, oral and skin. Extracted DNA is subjected to 16S, ITS or 18S sequencing as described elsewhere. Nucleic acid sequences are analyzed to define taxonomic assignments using sequence similarity and phylogenetic placement methods or a combination of the two strategies. These methods map a sequence read to a reference database and selecting the match with the best score and e-value. Common databases include, but are not limited to the Human Microbiome Project, NCBI non-redundant database, Greengenes, RDP, and Silva for taxonomic assignments. Microbial clades are assigned using databases including but not limited to MetaPhlAn. Phylogenetic abundance comparisons are performed using linear discriminant analysis (LDA) effect size (LEfSe) analysis, using a logarithmic LDA cutoff of 2.0. Taxonomic and phylogenetic abundance data from various niches is then subjected to comparative analysis to identify microbes that are unique to each site vs those that overlap between two or more sites.

Example 33. Selection of Microbes to be Used for Mitigating GVHD and Other Immune Based Diseases Based on Microbiome Analysis Candidate microbes to be used for mitigating GVHD and other immune based disorder are selected based on microbiome analysis of samples from single or multiple niche. For example, microbes that are highly abundant in patients who do not succumb to GVHD or are alive post bone marrow transplantation are associated with low or no GVHD incidence and survival post GVHD. These microbes could be abundant at a single site such as the gut. Alternatively, these microbes are also abundant at another site in addition such as the skin, lung, vagina and oral or at all of these sites within a diseased subject. Alternatively, microbes are selected based on their abundance at one site such as the gut and not at other sites. These microbes are then tested in in vitro and in vivo models to test their ability to inhibit inappropriate immune responses and reduce inflammation at multiple disease target sites such as but not limited to gut, liver, kidney, lung and skin.

Example 34. Selection of a Metabolically Altered Organism Based on Prebiotic Fermentation Bacterial isolates or evolved laboratory strains are inoculated in 25 ml of Versa TREK REDOX 2 broth (Trek Diagnostic Systems) supplemented with 30% sterile-filtered cow rumen fluid and prebiotic of interest incubated under anaerobic conditions for 2 days at 37° C. Following incubation, cultures are centrifuged at 6000 rpm for 10 min. Supernatants, uninoculated medium, or standards of short chain fatty acids (e.g., acetate, propionate, butyrate (Sigma-Aldrich) are injected into a Perkin Elmer Autosystem XL Gas Chromatograph containing a Supelco packed column (Sigma-Aldrich) according to the manufacturer's protocol (Dairy One Cooperative) (Foditsch C et al., 2014. Isolation and Characterization of Faecalibacterium prausnitzii from Calves and Piglets. PLoS One. 9(12): e116455). Bacterial isolates are selected with maximal short chain fatty acid (e.g., butyrate) production. Similar kind of analysis is done to access impact of prebiotics on other bacterial metabolite production such as but not limited to secondary bile acids.

Example 35. Mouse Model to Study the Impact of Microbiome in Acute Graft Versus Host Disease A number of experimental models for studying acute GVHD exist and involve the transplantation of T-cell-depleted bone marrow supplemented with varying numbers and phenotypic classes of donor lymphocytes (either splenocytes or lymph node T cells) into lethally irradiated recipients. The severity of aGvHD depends on several factors–1) the dose and type of T-cell subsets (i.e. CD4+, CD8+ or TReg cells), 2) Irradiation dose, 3) Genetic disparities (MHC, miHAs), 4) Variation in environmental pathogens between labs and in mice from different suppliers. Allogeneic GVHD mouse models can be MHC-mismatched and miHA-mismatched. The more recently developed xenogeneic GVHD mouse models involve transplantation of human cells into immunodeficient mice. Both these models are extensively in Schroeder and DiPersio, 2011 Disease Models & Mechanisms.

To study the impact of microbiome on acute GVHD using the allogeneic GVHD mouse models, recipient mice such as BALB/c (H2d) or C57BL/6 (H2b) mice are treated with a gut-decontaminating antibiotic cocktail (ampicillin and vancomycin) to mimic microbiota injury that occurs in allo BMT patients. Mice are then exposed to a myeloablative dose of total body irradiation (TBI, 11 Gy) and then transplanted by intravenous injection with bone marrow and purified T cells from fully MHC-mismatched C57/Bl6 (H2b) or B10.BR mice respectively. Alternatively, xenogeneic GVHD mouse models are utilized where the immunodeficient NOD.scid (IL-2Rγc)−/−(NOG) or NOD.scid (Il2rgmut) (NSG) mice are treated with a gut-decontaminating antibiotic cocktail (ampicillin and vancomycin), transplanted with human PBMCs by I.V. or I.P. injection and subsequently exposed to a myeloablative dose of total body irradiation (2.5 Gy).

Example 36. Murine Model to Study the Impact of Microbiome in Chronic Graft Versus Host Disease Current mouse models of cGvHD (Schroeder and DiPersio, 2011) can be broadly divided into sclerodermatous (pro-fibrotic) models, autoantibody-mediated (lupus-like) models and a more recently reported model in which thymic function is defective (Sakoda et al., 2007; Chu and Gress, 2008). Herein is an example with a validated sclerodermatous (pro-fibrotic) models model. Recipient mice BALB/c (H2d) or C57/Bl6 (H2b) are treated with a gut-decontaminating antibiotic cocktail (ampicillin and vancomycin) to mimic microbiota injury that occurs in allo BMT patients. Mice are then exposed to a myeloablative dose of total body irradiation (700-900 cGy ore 900-1100 cGy respectively) and then transplanted by intravenous injection with bone marrow and purified T cells or splenocytes from B10.D2 (H2c) or LP/J (H2b) mice respectively.

Example 37. Culturing and Banking Bacterial Isolates from Mouse or Human Feces Entire stool specimens are collected and homogenized in 1-3 volumes of 0.05% peptone using a sterile stainless steel blender with 1-3 volumes of peptone. Approximately 1 gram of the specimen is serially diluted (10-fold) in pre-reduced, anaerobically sterilized (PRAS) dilution blanks (Anaerobe Systems). A separate ~1 gram aliquot is weight, dried in a vacuum over, and re-weighed in order to calculate counts on a dry-weight basis. To select for Clostridiales bacteria, including *Blautia* species, 100 µL of the homogenized stool sample dilution series is plated on Brain-Heart Infusion blood agar (SBA, Becton Dickinson) supplemented with 4 µg/mL trimethoprim (Sigma Chemical) and 1 µg/mL sulfamethoxazole (Sigma), Brucella Blood Agar (BAP, Anaeobe Systems), CDC ANA blood agar, (BBL Microbiology Systems), and egg yolk agar (EYA, Anaerobe Systems) (Finegold S M, Molitoris D, Song Y, Liu C, Vaisanen M L, Bolte E, McTeague M, Sandler R, Wexler H, Marlowe E M, Collins M D, Lawson P A, Summanen P, Baysallar M, Tomzynski T J, Read E, Johnson E, Rolfe R, Nasir P, Shah H, Haake D A, Manning P, Kaul A, 2002. Gastrointestinal microflora studies in late-onset autism. Clin Infect Dis 1:35). To select for spore-formers, the dilutions may be heated at 70-80° C. for 10-20 minutes and plated in the same manner as the non-heated homogenized stool samples. After 5 days of growth at 37° C. in an anaerobic chamber, single colonies are selected. The colony purification process is repeated by restreaking select single colonies, growing as described above, and selecting again for single colonies. Single colonies are frozen in 15%-25% glycerol in 1 mL cryotubes and stored at −80° C.

Example 38. Administration of Bacterial Isolates, with or without Prebiotics, to Mitigate Experimental Acute GVHD BALB/c (H2d) or C57BL/6 mice in the case of allogeneic models and NOD.scid (IL-2Rγc)-/-(NOG) or NOD.scid (Il2rgmut) (NSG) in the case of xenogeneic models are treated with oral vancomycin and ampicillin. Following decontamination, mice are housed in autoclaved conditions (caging, bedding, water and food) to eliminate nearly all endogenous bacteria present within the flora of mice. Mice are then treated by gavage with a liquid suspension of the cultured bacterial isolate, optionally with one or more prebiotic carbohydrates. Mice are then exposed to a myeloablative dose of total body irradiation and then transplanted by intravenous injection with bone marrow and purified T cells from fully MHC-mismatched C57/Bl6 (H2b) or B10.BR mice for allogeneic models and human PBMCs for xenogeneic models. Effect on organ pathology, weight and overall survival is measured as described.

Example 39. Administration of Bacterial Isolates, with or without Prebiotics, to Mitigate Experimental Chronic GVHD Recipient mice BALB/c (H2d) or C57/Bl6 (H2b) are treated with a gut-decontaminating antibiotic cocktail (ampicillin and vancomycin). Following decontamination, mice are housed in autoclaved conditions (caging, bedding, water and food) to eliminate nearly all endogenous bacteria present within the flora of mice. Mice are then treated by gavage with a liquid suspension of the cultured bacterial isolate in addition to one or more prebiotic carbohydrates. Mice are then exposed to a myeloablative dose of total body irradiation and then transplanted by intravenous injection with bone marrow and purified T cells or splenocytes from B10.D2 (H2c) or LP/J (H2b) mice respectively. Mice are evaluated for fibrotic changes in the dermis, which can involve the lung, liver and salivary glands beginning day 30 post transplantation.

Example 40. GVHD Clinical and Histological Scoring

Mice are monitored daily for survival and weekly for GVHD clinical scores (see Cooke, K. R., L. Kobzik, T. R. Martin, J. Brewer, J. Delmonte Jr., J. M. Crawford, and J. L. Ferrara. 1996. An experimental model of idiopathic pneumonia syndrome after bone marrow transplantation: I. The roles of minor H antigens and endotoxin. Blood. 88:3230-3239). Small intestine, large intestine, and liver samples are evaluated histologically for evidence of GVHD and scored as previously described (see Hill, G. R., J. M. Crawford, K. R. Cooke, Y. S. Brinson, L. Pan, and J. L. Ferrara. 1997. Total body irradiation and acute graft-versus-host disease: the role of gastrointestinal damage and inflammatory cytokines. Blood. 90:3204-3213).

Example 41. Measuring Paneth Cell Numbers and Functionality

The small intestinal lumens of adult mice are rinsed with ice-cold water and segmented. Crypts are eluted by first turning the segments inside out and then shaking them in PBS containing 30 mM EDTA and lacking $Ca^{2+}$ and $Mg^{2+}$. The eluted villi and crypts are pelleted at 700×g, resuspended in PBS, and transferred to siliconized microfuge tubes using capillary pipettes. The crypts are resuspended in iPIPES buffer (10 mM PIPES (pH 7.4) and 137 mM NaCl) in preparation of exposure to secretory stimuli.

Crypts are incubated in 30 µl of iPIPES containing 1000 bacterial (Clostridiales) CFU per crypt for 30 min at 37° C. Cellular components are pelleted by brief centrifugation, and supernatants transferred to sterile microfuge tubes and stored at −20° C. This method may be scaled up using up to ~3000 crypts in 2 ml iPIPES (plus or minus Clostridiales bacteria). Crypts are pelleted and 10 µL of the supernatants are analyzed for bactericidal activity against Clostriales and *Enterococcus* bacteria in liquid culture or on agar plates. Proteins are extracted from the rest of the supernatant as well as the crypts using 30% acetic acid. Total protein extracted from each fraction was resolved by AU-PAGE and subjected to western blot analysis using anti-cryptdin-1 as follows. Proteins from AU-PAGE are transferred to a nitrocellulose membrane. The membrane is then blocked with 5% skim milk, incubated sequentially with anti-rabbit mouse cryptdin-1 (1:500), horseradish peroxidase-conjugated anti-rabbit IgG (1:20,000) and chemiluminescent substrate (SuperSignal, Pierce, Rockland, I L), and visualized (Ayabe T, Satchell D P, Wilson C L, Parks W C, Selsted M E, Ouellette A J, 2000. Secretion of microbicidal a-defensins by intestinal Paneth cells in response to bacteria. Nature Immunology 1:113-118).

Example 42. Measuring Intestinal Crypt Regeneration by Organoid Growth

Organoid formation may be used as a proxy for intestinal crypt regeneration as follows:
Lgr5-EGFP-IRES-CreERT2 knock-in (B6.129P2-Lgr5tm1(cre/ERT2)Cle/J, JAX mice #008875) and ROS A26-tdTomato (B6.Cg-Gt(ROSA)26Sortm14(CAG-tdTomato)Hze/J, JAX mice #007914) mice are purchased from the Jackson Laboratory (Bar Harbor, Me., USA) and crossed to produce Lgr5-EGFP-IRES-CreERT2/ROSA26-tdTomato mice (LRT mice). The obtain persistent labeling of Lgr5+ stem cells with tdTomato (as well as tdTomato-labeled progeny of Lgr5+ stem cells), the LRT mice are administered 4-hydroxytamoxifen (4-OHT; Sigma Aldrich) intraperitoneally, once, at 10-20 days old.

To obtain single crypt cells for in vitro analyses, the LRT mice are sacrificed at 3-5 weeks old, and the duodenum and jejunum (10 cm from the stomach) are harvested and rinsed three times with cold phosphate-buffered saline (PBS−). The intestinal tubes are opened longitudinally and the villi are scraped using a coverslip, then washed three times in cold 1× PBS−. The intestinal tubes are cut into 2-3 mm pieces and suspended and extensively washed in 1×PBS−+2% fetal bovine serum (FBS). Then, the 2-3-mm pieces are treated with 50 mM EDTA/1×PBS− for 30 min at 4° C. on a rocking platform to dissociate the crypts from the intestinal tubes. The dissociated crypts are passed through a 70-µm cell strainer, washed once with 1×PBS−, and treated with TrypLE Express (Life Technologies, Carlsbad, Calif., USA) for 30 min at 37° C. Then, the dissociated cells are passed through a 40-µm strainer and subsequently, through a 20-µm strainer. The strained cells are pelleted, resuspended in 1×PBS−+2% FBS, and used as single crypt cells.

The isolated single crypt cells are cultured in organoid medium [advanced DMEM/F12 supplemented with 1× GlutaMAX, 10 mM HEPES, 1× penicillin/streptomycin, 1×N2, 1×B27 (all obtained from Life Technologies, Carlsbad, Calif., USA), N-acetylcysteine (Sigma-Aldrich, St Louis, Mo., USA, 1 mM), murine epidermal growth factor (Life Technologies, Carlsbad, Calif., USA, 50 ng/ml), murine Noggin (Peprotech, Rocky Hill, N.J., USA, 100 ng/ml), and murine R-Spondin I (R&D Systems, Minneapolis, Minn., USA, 1 µg/ml)]. During the first two days of culturing 10 µM of Rho kinase inhibitor Y-27632 (Sigma-Aldrich, St Louis, Mo., USA) is added.

350 µM of organoid medium is added into wells of 48-well plates, and then single crypt cells are plated to the wells (1×105 cells/10 µl 1×PBS−+2% FBS per well). Matrigel (BD, Franklin Lakes, N.J., USA) is added to a final concentration of 10%. The organoid medium is replenished every day for the first 3 days and every 2-3 days thereafter. The cells are incubated in a humidified CO2 incubator at 37° C. After 12 days, the number of organoids is counted by phase-contrast microscopy with a 4× objective (Yamauchi M, Otsuka K, Kondo H, Hamada N, Tomita M, Takahashi M, Nakasono S, Iwasaki T, Yoshida K, 2014. A novel in vitro survival assay of small intestinal stem cells after exposure to ionizing radiation. J Radiat Res. 55:381-390).

To investigate organoid growth over time, time-lapse microscopy is performed using a confocal laser microscope (C1si, Nikon, Japan) and images are analyzed using ImageJ software (National Institutes of Health, Bethesda, Md., USA).

Example 43. Measuring Intestinal Crypt Regeneration by Quantitative Real Time PCR Alternatively, C57BL/6J mice may be used to study intestinal regeneration using a real time PCR (qPCR) method. Duodenum and jejunum are harvested as described in Example 20 and cut into 1 cm small pieces. The tissue pieces are placed in a FastPrep-24 Lysing Matrix D tubes (MP Biomedicals, Solon, Ohio) filled with 600 µL of RLT lysis buffer (Qiagen, Valencia, Calif.). Next, 6 µL β-mercaptoethanol (Sigma-Aldrich, St. Louis, Mo.) is added to the lysing tubes. And total RNA is isolated from the lysed samples using the Qiagen RNeasy Mini Kit according to the manufacturer's instructions. Complimentary DNA is made using a High Capacity cDNA Reverse Transcription Kit (Applied Biosystems, Foster City, Calif.) according to the manufacturer's instructions. qPCR is performed on cDNA samples in triplicate using an Applied Biosystems StepOne Plus system. Individual probes for Lgr5(Mm00438890_m1), Ascl2 (Mm01268891_g1), Bmi1(Mm03053308_g1), Olfm4 (Mm01320260_m1), and mTert(Mm01352136_m1) from Applied Biosystems are used and data analyzed using a relative standard curve method normalized to β-actin (Mm00607939_s1; Applied Biosystems). Actively cycling intestinal stem cells are labeled by Lgr5, Ascl2, and Olfm4, whereas slowly cycling (quiescent) intestinal stem cells are labeled by mTert and Bmi1 (Dehmer J J, Garrison A P, Speck K E, Dekaney C M, Van Landeghem L, Sun X, Henning S J, Helmrath M A, 2011. Expansion of intestinal epithelial stem cells during murine development. PLoS One. 6:e27070).

Example 44. Measurement of Transepithelial Electrical Resistance

The following protocol is preferentially used for monocultures of intestinal epithelial cells but may also be applied to epithelial cells derived from other organs such as the vagina or liver. Monolayers of epithelial cells (e.g., Caco-2) are obtained from the ATCC or from patient biopsy and maintained in Dulbeco's Modified Eagle Medium with 10% fetal bovine serum or RPMI 1640 with 10% fetal bovine serum.

A monolayer is formed by seeding epithelial cells grown to 80-90% confluency (~10^5 cells/cm2) on transwell plates (Corning) and incubating the plates between at 37° C. and 5% CO2. The cells are incubated for 10 days, during which they are fed with fresh medium (basolaterally and/or apically) every other day. The integrity of the cell layer is assessed by transepithelial electrical resistance (TEER)

using Millicell-ERS equipment (Millipore) and a World Precision Instruments probe (WPI according to the manufacturers' instructions.

Example 45. Dye-Based Evaluation of Epithelial Integrity

Cells from ATCC or patient biopsy are treated as in Example 43. Instead of measuring TEER, the transwell plates are disassembled and each filter well is treated with 75 µL 100 µg/mL of the non-membrane permeable dye Lucifer Yellow (Sigma) in Hank's Buffered Salt Solution (HBSS) buffer, pH 7.4 (Invitrogen). Next, 250 µL of HBSS buffer, pH 7.4 is added to the bottom wells and the transwell plates are reassembled and then incubated for 2 hours with shaking (60 rpm) at room temperature. Lucifer yellow fluorescence is measured using a Cytofluor II fluorometer at an excitation wavelength of 485 nm and an emission wavelength of 530 nm Permeability is calculated based on the percentage of Lucifer Yellow that leaked from the apical chamber to the basolateral chamber of the transwell plates.

Example 46. Method for Measuring Intestinal Permeability Based on Citrulline Production by Enterocytes Recently, it was shown that citrulline appeared to be particularly useful to detect gut damage, as blood concentrations of this amino acid directly reflect functioning small intestinal cell mass (Crenn P, Vahedi K, Lavergne-Slove A, Cynober L, Matuchansky C, Messing B. Plasma citrulline: a marker of enterocyte mass in villous atrophy-associated small bowel disease. Gastroenterology 2003). Blood is collected in heparin from each patient through the central venous catheter before starting therapy and on each Monday, Wednesday and Friday thereafter until discharge. Plasma is prepared and stored at −80 1C for later analysis. Citrulline concentrations (mM) are measured by a standard procedure for determining amino acid concentrations using high-performance liquid chromatography (Shimadzu, Kyoto, Japan) as described in Herbers et al., 2008. Bacteraemia coincides with low citrulline concentrations after high-dose melphalan in autologous HSCT recipients. Bone Marrow Transplant. 42:345-349.

Example 47. Method for Measuring Levels of Microbes in Distal Organs (Liver, Thymus, Lungs, Kidneys)

Liver, thymus, lungs, and kidneys from mice that had received transplants are removed aseptically and homogenized in 200 uL sterile saline 0.9%. Then, 100 uL is cultured aerobically on blood agar and deMan-Rogosa-Sharp agar plates (Difco, Detroit, Mich.), blood agar supplemented for anaerobes, chocolate blood agar, MacConkey agar, and Sabouraud agar for 24 hours in room air supplemented with 10% CO2; colony-forming units are counted and numbers adjusted to weight. Alternatively, genomic DNA from the bacteria is extracted and 16S rDNA sequencing is performed as described Example 48. Method for Measuring Effect of Microbes, with or without Prebiotics, on Bacterial Metabolites Such as SCFA Levels Short-chain fatty acids (SCFA), which are produced by many bacteria as a byproduct of carbohydrate fermentation. SCFA have been found to be important modulators of the immune system. They are abundantly produced bacteria from the Class Clostridia. To evaluate the effect of administered bacterial composition, optionally with one or more prebiotics, on SCFA, fecal pellets are collected to quantify SCFA levels, particularly acetate, propionate, or butyrate. SCFAs, creatines, and hydroxy-SCFAs are quantified by alkalinizing stool samples, obtaining fingerprints of the metabolic composition of the sample using 1D 1H NMR on a Bruker Avance-600 MHz Spectrometer, and analyzing with supervised multivariate statistical methods using Chenomx NMR Suite software.

Example 49. Administration of Bacterial Metabolites Such as SCFA to Mitigate GVHD Sodium acetate (150 mM) is delivered via the drinking water of mice beginning 2 weeks prior to BMT. Mice are then irradiated and transplanted with continued supplementation of sodium acetate. Mice are euthanized to evaluate for pathological evidence of GVHD, as well as to quantify and characterize large intestinal Tregs and alloreactive effector T cells by surface staining or intracellular staining followed by flow cytometry on days 14 and 28.

Example 50. Extraction and Purification of Immunomodulatory Oligosaccharides from Plants Store-bought plants are cut, lyophilized, and ground into powder. The powder (~500 grams) is extracted three times with 2 L of ethanol, and the concentrated extract was collected, lyophilized, and resuspended with 1 L of distilled water at 85° C. The water-soluble portion is precipitated by four volumes of ethanol at 4° C. to yield polysaccharides. Peptides are removed from this sample by treating with Pronase (Roche Applied Science). The resulting sample is run over a Bio-Gel P-6 gel filtration column (1.5×90 cm) and eluted with distilled water containing 0.02% sodium azide at a flow rate of 0.5 ml/min. All chromatographic fractions containing carbohydrates are analyzed by a phenol-sulfuric acid method (e.g., Masuko T, Minami A, lisaki N, Majima T, Nishimura S-I, Lee Y C, 2005. Carbohydrate analysis by a phenol-sulfuric acid method in microplate format. 339:69-72) and quantitated by measuring the optical density at 490 nm (Tsai C-C, Lin C-R, Tsai H-Y, Chen C-J, Li W-T, Yu H-M, Ke Y-Y, Hsieh W-Y, Chang C-Y, Wu C-Y, Chen S-T, Wong C-H, 2013. The Immunologically Active Oligosaccharides Isolated from Wheatgrass Modulate Monocytes via Toll-like Receptor-2 Signaling. 288:17689-17697).

Example 51. Selection of Oligosaccharides to Augment Gut Microbiome

The ability of bacterial isolates to grow on a panel of simple and complex carbohydrates is evaluated using a phenotypic array whose composition has been previously described previously (Martens E C, Lowe E C, Chiang H, Pudlo N A, Wu M, et al. 2011. Recognition and degradation of plant cell wall polysaccharides by two human gut symbionts. PLoS Biol 9: e1001221). Growth measurements are collected in duplicate over the course of 3 days at 37° C. under anaerobic conditions. A total of three independent experiments are performed for each species tested (n=6 growth profiles/substrate/species). Total growth ($A_{tot}$) is calculated from each growth curve as the difference between the maximum and minimum optical densities ($OD_{600}$) observed (i.e., $A_{max}-A_{min}$). Growth rates are calculated as total growth divided by time ($A_{tot}/(t_{max}-t_{min})$), where tmax and tmin correspond to the time-points at which Amax and Amin, respectively, are collected.

Example 52. Administration of Carbohydrates to Mitigate Experimental GVHD

Carbohydrates such as xylose are delivered via the drinking water of mice beginning 2 weeks prior to BMT. Mice are then irradiated and transplanted with continued supplementation of xylose. Mice are euthanized to evaluate for pathological evidence of GVHD, as well as to quantify and characterize large intestinal Tregs and alloreactive effector T cells by surface staining or intracellular staining followed by flow cytometry on days 14 and 28. This method may be applied monosaccharides, disaccharides, oligosaccharides, polysaccharides, and mixtures thereof.

Example 53. Preventing Graft Versus Host Disease in a Subject

To determine efficacy in preventing GVHD, subjects undergoing allogeneic hematopoietic stem cell transplantation are selected. GVHD prophylactic regimen is administered on day −1, where day 0 is day of transplantation or day −1 plus day 17. One arm of the study includes the test article, second arm test article plus standard of care and the third arm is standard of care alone. Standard GVHD prophylaxis consists of cyclosporine twice a day starting on day −1 with target trough levels >200 ng/mL in combination with short course of methotrexate (15 mg/sqm on day +1 and 10 mg/sqm on days +3 and +6). Most patients transplanted from unrelated donors received anti-T-cell globulin (ATG Fresenius) at a low dose of 5 mg/kg on days −3 to −1. To estimate the prophylactic and therapeutic effect of test article, the patients are carefully monitored and documented for the presentation of acute and chronic GVHD symptoms, the time of onset, the severity of the symptoms, the responsiveness to treatment, and the occurrence of infections. Stool and blood samples are collected at pretreatment, day 4, day 14, day 28, 3 months, and 6 months.

Example 54. Treating Acute Graft Versus Host Disease in a Subject

To determine the efficacy of treating acute GVHD, test article is administered to a subject with clinical signs of acute GVHD as described elsewhere. Test article is orally administered daily either alone or in conjunction with standard of care. At the time of test article administration, subjects are at least 10 days post allogeneic hematopoietic cell transplantation, have GI symptoms consistent with Grade II GVHD, and have endoscopic evidence of GVHD. The diagnosis of GVHD is confirmed by biopsy of the intestine (esophagus, stomach, small intestine, or colon) or skin. Stool, blood and other samples are collected prior to administration of test article day −2 and day +1, day +7 and Day +10. To evaluate therapeutic effect of test article, the patients are carefully monitored and documented for the presentation of acute GVHD symptoms, the severity of the symptoms, the responsiveness to treatment, and the occurrence of infections.

Example 55. Treating Chronic Graft Versus Host Disease in a Subject

Chronic GVHD presents anytime starting day 100 post bone marrow transplantation. Conventional treatment of chronic GVHD requires prolonged periods of systemic immunosuppressive therapy with potent drugs such as corticosteroids and cyclosporine. Agents such as mycophenolate mofetil, rapamycin (sirolimus), imatinib and rituximab are used in patients with steroid-refractory chronic GVHD. To determine the efficacy of treating chronic GVHD, test article is administered to a subject with clinical signs of chronic GVHD as described elsewhere. Test article is orally administered daily either alone or in conjunction standard of care. At the time of test article administration, subjects are at least 100 days post allogeneic hematopoietic cell transplantation, have symptoms consistent with chronic GVHD.

Example 56. Immunomodulation of Autologous BMT Recipients

Subjects undergoing autologous hematopoietic stem cell transplantation are selected. Test article is administered on day −1, where day 0 is day of transplantation or day −1 plus day 17. Subjects are monitored clinical signs of infections, functionality of organs as well as success of graft uptake or engraftment. Engraftment is measured by assessing graft versus tumor effect. Other outcomes that are measured include neutropenic recovery which is assessed by measurement total blood counts.

Example 57. Prevention Solid Organ Transplant Rejection in a Rat Model

Recipient LBN rats ranged in weight from 325 to 350 grams. ACI donor weights ranged from 200-250 grams. Test article is administered to rats using oral gavage. The treatment started the day before transplant and the entire treatment period ranged from 12 to 27 days. Control rats received saline. Twenty four hours after test article administration, the heterotopic heart transplant is performed. The hearts are transplanted using a modification of the technique of Ono and Lindsey (J. of Thoracic and Cardiovascular Surgery, 57, 225-229 (1969). The rats are palpated daily and asystole defined the day of rejection.

Example 58. Immunomodulation of Solid Organ Transplant Recipients

Here is a method of preventing graft rejection in a recipient of a transplanted solid organ, by administering to said mammalian recipient an effective graft rejection preventative amount of test article. Transplanted solid organ may include a kidney, heart, skin, a lung, a liver, a pancreas, an intestine, an endocrine gland, a bladder, or a skeletal muscle. Test article is administered pre-transplant at least 24 hours before transplant and after transplant beginning 24 hours after transplant and then on day 3, day, 5 and day 15. Patients are closely monitored for clinical signs and symptoms of transplant rejection as well as complications such as infections. Stool and blood samples are collected before transplantation, day 3, day 5, day 15 and day 21 and subsequently subjected to microbiome analysis. Immune response is monitored by clinical symptoms as well as biochemical analysis of the serum such as measurement of cytokine levels.

Example 59. Inhibition of Antigen Presenting Cells

Peripheral blood mononuclear cells (PBMC) are prepared by density gradient centrifugation on Ficoll-Paque (Pharmacia). Aliquots of cells are frozen in 90% FCS with 10%

DMSO and stored in liquid nitrogen. After thawing, the cells are ished twice with MSC medium (DMEM with low glucose and 10% FCS) and re-suspended in assay medium (ISCOVE'S with 25 mM Hepes, 1 mM sodium pyruvate, 100 µM non-essential amino acids, 100 U/ml penicillin, 100 µm/ml streptomycin, 0.25 µg/ml amphotericin B, $5.5 \times 10^{-5}$M 2-mercaptoethanol (all reagents from GibcoBLR) and 5% human AB serum (Sigma, MLR tested)). To prepare monocyte derived dendritic cells (moDCs), PBMCs are plated and adherent fraction is enriched for a. CD11c+ DCs by CD11c MACS sorting. Microbes or microbes pre-incubated with prebiotics or microbial metabolites to be tested are incubated with CD11c+ moDCs for 4-10 h. Following incubation period, effect of DC maturation is measured by staining and FACS analysis by looking at markers such as CD40, CD80, CD86 PD-L1 and PD-L2. Endocytic capacity is measured by FITC-dextran incubation followed by FACS analysis). Cytokine production e.g. IL-10, IL-4, IL-12 is analyzed by ELISA or intracellular staining. Effect on naïve T cell stimulation is analyzed by co-cultured by the moDCs preincubated with test article with naïve T cells isolated from PBMCs as described. T cell activation status is analyzed by surface staining followed by FACS analysis for CD3, CD4, CD25.

Example 60. Inhibition of Alloreactivation by a Microbial Composition Using Mixed Lymphocyte Reaction (MLR) Assays In Vitro Peripheral blood mononuclear cells (PBMC) are prepared by density gradient centrifugation on Ficoll-Paque (Pharmacia). Aliquots of cells are frozen in 90% FCS with 10% DMSO and stored in liquid nitrogen. After thawing, the cells are ished twice with MSC medium (DMEM with low glucose and 10% FCS) and re-suspended in assay medium (ISCOVE'S with 25 mM Hepes, 1 mM sodium pyruvate, 100 µM non-essential amino acids, 100 U/ml penicillin, 100 µm/ml streptomycin, 0.25 µg/ml amphotericin B, $5.5 \times 10^{-5}$M 2-mercaptoethanol (all reagents from GibcoBLR) and 5% human AB serum (Sigma, MLR tested)). To prepare the T cell-enriched fraction, PBMCs from donor X are depleted of monocytes and B cells by immunomagnetic negative selection. PBMCs are incubated with mouse anti-human CD19 and CD14 mAbs (no azide/low endotoxin (NA/LE) format) followed by biotin-conjugated goat anti-mouse IgG (multiple adsorption) Ab (all reagents from Pharmingen) and streptavidin microbeads (Miltenyi Biotec). Cells are then separated using a magnetic cell sorter (MACS, Miltenyi Biotec). PBMC from donor Y are X-ray irradiated with 3600 rad (12 min at 70 kV) using Cabinet X ray system (Faxitron X ray, Buffalo Grove, Ill.). To prepare monocyte derived dendritic cells (moDCs), PBMCs are plated and adherent fraction is enriched for a. CD11c+ DCs by CD11c MACS sorting. T cells ($15 \times 10^6$/dish) from donor X are cultured in 10 cm tissue culture dishes with PBMC/moDCs ($15 \times 10^6$ cells/dish) from donor Y for 7 days. The cells are incubated at 37° C. in 5% $CO_2$ atmosphere for 7 days. Various concentrations of microbial composition or microbes pre-incubated with sugars are added to T cells activated in the MLR for 3 days at 37° C. in 5% $CO_2$ atmosphere. In control cultures activated T cells are cultured without any test agent. At the end of co-culture period, T cells are recovered. CD8 cells are depleted by negative immunomagnetic selection with anti-CD8 MicroBeads (Miltenyi Biotec). Aliquots of cells collected before and after depletion are stained with anti-CD4-PE and anti-CD8-APC antibodies (Caltag) and analyzed by FACS. T cell activation status is analyzed by surface staining followed by FACS analysis for CD3, CD4, CD25. Phenotypic analysis for regulatory T cell differentiation is done by surface staining for CD3, CD4, CD25, CD127 and Foxp3 intracellular staining followed by FACS analysis. Cytokine Analysis for various cytokines including IL-6, TNF-alpha is done by ELISA or BD™ Cytometric Bead Array. To assess T cell proliferation status cultures are pulsed with [$H^3$]TdR (Amersham) (5 Ci/mmol, 1 µCi/well) for 18 hours immediately after plating, or incubated for 1, 2, 3 or 4 days and then pulsed with [$H^3$]TdR) for an additional 18 hours. Cultures are collected using Harvester 96 (Tomtec), filters are analyzed using Microbeta Trilux liquid scintillation and luminescence counter (E.G.& G Wallac). To assess T cell proliferation status cultures are pulsed with [$H^3$]TdR (Amersham) (5 Ci/mmol, 1 µCi/well) for 18 hours immediately after plating, or incubated for 1, 2, 3 or 4 days and then pulsed with [$H^3$]TdR) for an additional 18 hours. Cultures are collected using Harvester 96 (Tomtec), filters are analyzed using Microbeta Trilux liquid scintillation and luminescence counter (E.G.& G Wallac). To assess effect on cytotoxic capacity of CD8+ cells, at the end of co-culture period, CD8+ cells are sorted by MACS. CD8+ T cells are then co-incubated with target cells such as hepatocytes and $^{51}$Cromium for 4-16 h. After incubation period, level of $^{51}$Cromium in supernanat is measured to gauge cytotoxic activity.

Example 61. Inhibition of PHA Induced T Cell Proliferation and T Cell Activation by a Microbial Composition Using Mixed Lymphocyte Reaction (MLR) Assays In Vitro $5 \times 10^4$ T cells are stimulated with PHA (5 µg/ml) and then test article added at various concentrations. Alternatively, T cells are first incubated with test article and then activated with PHA. T cell activation status is analyzed by surface staining followed by FACS analysis for CD3, CD4, CD25. To assess T cell proliferation status cultures are pulsed with [$H^3$]TdR (Amersham) (5 Ci/mmol, 1 µCi/well) for 18 hours immediately after plating, or incubated for 1, 2, 3 or 4 days and then pulsed with [$H^3$]TdR) for an additional 18 hours. Cultures are collected using Harvester 96 (Tomtec), filters are analyzed using Microbeta Trilux liquid scintillation and luminescence counter (E.G.& G Wallac).

Example 62. Culturing and Banking Bacterial Isolates from Mouse or Human Feces

Entire stool specimens are collected and homogenized in 1-3 volumes of 0.05% peptone using a sterile stainless steel blender with 1-3 volumes of peptone. Approximately 1 gram of the specimen is serially diluted (10-fold) in pre-reduced, anaerobically sterilized (PRAS) dilution blanks (Anaerobe Systems). A separate ~1 gram aliquot is weight, dried in a vacuum over, and re-weighed in order to calculate counts on a dry-weight basis. To select for Clostridiales bacteria, including *Blautia* species, 100 µL of the homogenized stool sample dilution series is plated on Brain-Heart Infusion blood agar (SBA, Becton Dickinson) supplemented with 4 µg/mL trimethoprim (Sigma Chemical) and 1 µg/mL sulfamethoxazole (Sigma), Brucella Blood Agar (BAP, Anaeobe Systems), CDC ANA blood agar, (BBL Microbiology Systems), and egg yolk agar (EYA, Anaerobe Systems) (Finegold S M, Molitoris D, Song Y, Liu C, Vaisanen M L, Bolte E, McTeague M, Sandler R, Wexler H, Marlowe E M, Collins M D, Lawson P A, Summanen P, Baysallar M, Tomzynski T J, Read E, Johnson E, Rolfe R, Nasir P, Shah H, Haake D A, Manning P, Kaul A, 2002. Gastrointestinal microflora studies in late-onset autism. Clin Infect Dis 1:35). To select for spore-formers, the dilutions may be heated at 70-80° C. for 10-20 minutes and plated in the same manner as the non-heated homogenized stool samples. After 5 days of growth at 37° C. in an anaerobic chamber, single colonies are selected. The colony purification process is repeated by restreaking select single colonies, growing as described above, and selecting again for single colonies. Single colonies are frozen in 15%-25% glycerol in 1 mL cryotubes and stored at −80° C.

Example 63. Sampling of Human Vaginal Microflora

The vaginal microflora were collected in duplicate from the left and right sides of the vaginal sidewall using FLOQSwabs® (Copan Diagnostics, USA) (Jacobson J., et al. 2014. Vaginal microbiome changes with levonorgestrel intrauterine system placement. Contraception. 90(2): 130-135). To control for variables that can alter the vaginal microbiome, samples were collected at the same time of a woman's menstrual cycle (i.e., one week into the menstrual cycle) and patients were tested for pregnancy and for recent sexual activity (using a prostate-specific antigen membrane test).

Example 64. Sampling of Human Lung Microflora

Bronchoscopy was performed using endotracheal tube (Combicath™, Bio-Medical Instruments, USA). Using a syringe, Normal Saline at 1 mg/kg was lavaged into the right middle lobe of the lung. For adult patients, 2-5 mL of bronchoalveolar lavage fluid (BALF) was collected into a sterile sputum trap. For children ages three and older, 2 mL was collected; mL was collected from children 1-3 years old; 0.5 mL of RALF was collected from children under the age of one. Within ten minutes of sample collection, the sample was transferred from the sterile sputum trap to a sterile container and frozen and stored at −80° C.

Example 65. Preparation of Bacterial Suspension

A human microbiome sample from stool, saliva, or tissue is obtained from a healthy, normal subjects or subjects suffering from a particular condition which enriches their microbiome for unique and desirable species. The sample is diluted to produce a 10-50% slurry in saline+glycerol solution (0.9% (w/v) NaCl, 10% (w/w) glycerol) and placed in a filter membrane-containing stomaching bag. The material is then homogenized and removed from the filtered side of the bag producing the bacterial suspension. Alternatively, a blender is used and filtering is performed after the blending. A low speed centrifugation step is used as an alternative to filtering to remove the large, non-bacterial components of the suspension. The bacterial suspension is tittered by producing serial dilutions differing by a log and plating on BBA agar and growing at 37 C in anaerobic conditions. Colonies are considered countable at between 10-400 colonies per plate and triplicates are plated for each dilution. The bacterial suspension is flash frozen and stored at −80 C for future use.

Isolation of Spore Formers

To isolate the subpopulation of spore formers, the bacterial slurry is treated with 100% ethanol to generate a 50% ethanol slurry for 1 hr. Alternatively a heat treatment of 50 C for 30 minutes is added to inactivate the bacteria that are not capable of forming spores. The 50% ethanol suspension is then pelleted by centrifugation (13,000 rpm for 5 min) and the pellet is washed with equal 10× volume of saline and 10% glycerol 3 times to remove the excess ethanol. The final spore fraction is snap frozen in liquid nitrogen in a solution of injection grade saline and 10% glycerol for subsequent use and stored at −80 C.

Alternatively, a 10% w/v suspension of human fecal material in PBS is incubated in a water bath at 80 degrees Celsius for 30 minutes. Glycerol is added to a final concentration of 15% and then the enriched spore containing material is stored at −80 degrees Celsius.

Alternatively, a 10% w/v suspension of human feces in PBS is prepared to contain a final concentration of 0.5 to 2% Triton X-100. After shaking incubation for 30 minutes at 25 to 37 degrees Celsius, the sample is centrifuged at 1000 g for 5-10 minutes to pellet particulate matter and large cells. The bacterial entities are recovered in the supernatant fraction, where the purified spore population is optionally further treated, such as by thermal treatment and/or ethanol treatment as described above.

Example 66. Determining Titer of Bacteria

Counts of viable bacteria are determined by performing 10-fold serial dilutions in PBS and plating to Brucella Blood Agar Petri plates or other applicable solid media known to one skilled in the art (see. e.g. The Manual of Clinical Microbiology ASM Press, 10th Edition or Atlas, Handbook of Microbiological Media, 4th ed, ASM Press, 2010). Plates are incubated at 37 degrees Celsius for 2 days. Colonies are counted from a dilution plate with 50-400 colonies and used to back-calculate the number of viable bacteria in the population. Visual counts are determined by phase contrast microscopy for further morphological identification.

Alternatively, optical density measurements of bacteria containing media is used to determine a the concentration of bacteria by comparing to a standard curve of known concentrations of bacteria that have previously measured optical densities in culture.

Bacteria are also isolated and quantified by cell sorting techniques known to one skilled in the art (e.g. see Nebe-von-Caron, G., Stephens, P. J. & Hewitt, C. J. Analysis of bacterial function by multi-color fluorescence flow cytometry and single cell sorting. Journal of Microbiological Methods, 2000). With this technique surface antibodies are raised to specific markers of a desired bacteria and they are incubated, washed, and imaged via flow cytometry to count bacteria in a complex mixture of other bacteria or tissue.

Example 67. FFAB Culturing and Banking Fungal Isolates

Microbial samples e.g. fecal sample; skin swab sample, are washed and homogenized in PBS. Samples are then serially diluted and fivefold dilutions are spread-plated in triplicate on Sobour and dextrose agar, potato dextrose agar, malt agar, and yeast peptone dextrose (YPD) agar each supplemented with chloramphenicol (40 μg/ml) and kanamycin (50 μg/ml). Alternatively, cultures can be grown in liquid conditions on Sabouraud Dextrose Broth (SDB; EMD chemicals) at 37° C., 30° C. and 20° C. and subsequently plated to enrich for yeast fractions. Plates are incubated both aerobically and anaerobically for 48 hours at 37° C., 30° C., and 20° C. and subsequent colonies are counted. Random colonies are selected with different morphologies and are re-streaked three times to obtain a pure culture. Cultures can then be grown up in liquid culture as described above, placed in 10% glycerol and stored at −80° C. for banking purposes. A sample of culture can be submitted for genetic analysis by extracting DNA and performing 18S and ITS identification as described herein Example 68. Measurement of Metabolites with Mass Spectrometry To determine the prebiotics in a complex media enabling specific growth, fractionation and mass spectrometry techniques are used to identify prebiotics compounds in media responsible for specific growth. Basically, bacteria are grown in media that has been fractionated by HPLC using standard techniques, and fractions are tested for their ability to promote growth. The fractions that promote growth are further fractionated or metabolites in the media are identified using HPLC-MS techniques described below. Furthermore, any metabolomics on tissues, fresh or spent media, blood, or mammalian excretions are determined using methods described herein. Unbiased methods exist to determine the relative concentration of metabolites in a sample and are known to one skilled in the art. Gas or liquid chromatography combined with mass spectrometry demonstrate the amounts and identities of various metabolites in the aforementioned samples and are further validated by obtaining pure metabolites and running on through the same LC-MS systems.

Gas Chromatography Mass Spectrometry

Polar metabolites and fatty acids are extracted using monophasic or biphasic systems of organic solvents and an aqueous sample as previously described (Metallo et al., 2012, Fendt et al., 2013). Derivatization of both polar metabolites and fatty acids has been described previously (Metallo et al., 2012). Briefly, polar metabolites are derivatized to form methoxime-tBDMS derivatives by incubation with 2% methoxylamine hydrochloride (MP Biomedicals) in pyridine (or MOX reagent (Thermo Scientific) followed by addition of N-tert-butyldimethylsilyl-N-methyltrifluoroacetamide (MTBSTFA) with 1% tert-butyldimethylchlorosilane (t-BDMCS) (Regis Technologies). Non-polar fractions, including triacylglycerides and phospholipids are saponified to free fatty acids and esterified to form fatty acid methyl esters either by incubation with 2% H2SO4 in methanol or by using Methyl-8 reagent (Thermo Scientific). Derivatized samples are analysed by GC-MS using a DB-35MS column (30 m×0.25 mm i.d.×0.25 μm, Agilent J&W Scientific) installed in an Agilent 7890A gas chromatograph (GC) interfaced with an Agilent 5975C mass spectrometer (MS). Mass isotopomer distributions are determined by integrating metabolite ion fragments and corrected for natural abundance using algorithms adapted from Fernandez et al. (Fernandez et al., 1996).

Liquid Chromatography Mass Spectrometry of Polar Metabolites

After extraction, samples are transferred to a polypropylene vial and samples are analysed using a Q Exactive Benchtop LC-MS/MS (Thermo Fisher Scientific). Chromatographic separation is achieved by injecting 2 uL of sample on a SeQuant ZIC-pHILIC Polymeric column (2.1× 150 mm 5 uM, EMD Millipore). Flow rate is set to 100 uL/min, column compartment is set to 25C, and autosampler sample tray is set to 4° C. Mobile Phase A consists of 20 mM Ammonium Carbonate, 0.1% Ammonium Hydroxide in 100% Water. Mobile Phase B is 100% Acetonitrile. The mobile phase gradient (% B) is as follows: 0 min 80%, 5 min 80%, 30 min 20%, 31 min 80%, 42 min 80%. All mobile phase is introduced into the Ion Max source equipped with a HESI II probe set with the following parameters: Sheath Gas=40, Aux Gas=15, Sweep Gas=1, Spray Voltage=3.1 kV, Capillary Temperature=275C, S-lens RF level=40, Heater Temp=350C. Metabolites are monitored in negative or positive mode using full scan or a targeted selected ion monitoring (tSIM) method. For tSIM methods, raw counts are corrected for quadropole bias by measuring the quadropole bias experimentally in a set of adjacent runs of samples at natural abundance. Quadropole bias is measured for all species by monitoring the measured vs. theoretical m1/m0 ratio at natural abundance of all species with m-1, m0, m1, and m2 centred scans. Quadropole bias-corrected counts are additionally corrected for natural abundance to obtain the final mass isotopomer distribution for each compound in each sample.

Example 69. Selection of Oligosaceharides to Augment Gut Microbiome or the Growth of Administered Microbes The ability of bacterial isolates to grow on a panel of simple and complex carbohydrates is evaluated using a phenotypic array whose composition has been previously described previously (Martens E C, Lowe E C, Chiang H, Pudlo N A, Wu M, et al. 2011. Recognition and degradation of plant cell wall polysaccharides by two human gut symbionts. Biol 9: e1001221). Bacteria isolates are removed from a frozen stock and grown in synthetic minimal media overnight and washed in PBS twice to ensure minimal transfer of residual materials. They are then grown in synthetic minimal media with various prebiotic substrates as specified by the manufacturer. Growth measurements [(optical density at 600 nm ($OD_{600}$)] are collected every 30 min in duplicate over the course of 3 days at 37° C. under anaerobic conditions. A total of three independent experiments are performed for each species tested (n=6 growth profiles/substrate/species). Total growth ($A_{tot}$) is calculated from each growth curve as the difference between the maximum and minimum optical densities ($OD_{600}$) observed (i.e., $A_{max}-A_{min}$). Growth rates are calculated as total growth divided by time ($A_{tot}/(t_{max}-t_{min})$), where $t_{max}$ and $t_{min}$ correspond to the time-points at which $A_{max}$ and $A_{min}$, respectively, were collected.

This may be followed by a step to ensure that the selected oligosaccharide(s) promote the growth of the healthy-state gut microbiota and/or the microbe(s) comprising a therapeutic composition without augmenting the growth of microbes associated with an autoimmune or inflammatory disease state. By testing oligosaccharides against a panel of bacteria (individually or in groups) overrepresented in a selected autoimmune or inflammatory condition, a prebiotic that selectively allows enhanced growth of healthy-state bacteria over disease-state bacteria is selected.

Example 70. Validating Selective Prebiotics Enhance the Growth of Bacteria in the Blood of Mammalian Subjects Four cohorts of 8, 6-8 week old Balb/c wildtype male mice acquired and fed a normal diet. One cohort is injected with 100 ul of 1E4 CFU/ml of the bacterial composition containing 100 ul 0.1 mg/ml prebiotic mixture, the second cohort is injected with 100 ul of 1E4 CFU/ml of the bacterial composition alone, the third is injected with 100 ul 0.1 mg/ml of a prebiotic mixture and the final cohort serves as a vehicle control cohort injected with vehicle via tail vein.

The mice cohorts are then readily bleed at 1 hr, 2 hrs 4 hrs 6 hrs 12 hrs and 24 hrs after the initial administration. At 24 hours gross necropsy is performed and the organs including the lymph nodes, lungs, liver, pancreas, colon, kidneys, esophagus, mammary glands, prostate, bladder, and blood samples are assessed for the amount of the administered bacteria by qPCR primers designed for the bacteria injected. The samples are normalized to the vehicle control and the biodistribution of the bacteria is assessed demonstrating the ability of the prebiotic to alter the distribution of the administered bacteria when compared with the bacteria administered alone. Additional the experiment is repeated with oral administration of the bacteria at 1E10 CFU/ml and prebiotic mixture administered at 10 mg/ml via gavage. The prebiotic mixture demonstrates the ability to both enhance the level of the bacteria observed in blood and other organs including the lungs, kidneys, liver, colon, pancreas.

16s analysis is further performed to assess the effects on cohorts of bacteria not present in bacterial composition administered. Comparing the combined bacteria and prebiotic composition to the other cohorts shows the enhanced growth observed in a mammalian subject. The blood is also submitted for metabolomics with the pure prebiotic composition administered as a control to demonstrate appropriate utilization and production of specific bacterial metabolites not present in compositions containing the combination of bacteria and prebiotic.

Example 71. Selection of Immunomodulatory Carbohydrates or Fungal Species

A carbohydrate, library is selected based on production by bacteria associated with a healthy microbiome or bacteria associated with a disease state including but not limited to Type 1 Diabetes, Graft-Versus-Host Disease, Crohn's Disease, Celiac Disease, and Irritable Bowel Syndrome. In some embodiments, the carbohydrates are functionalized with an amine linker at the reducing end of the sugar and dissolved in phosphate buffer (50 mM $NaH_4PO_4$, pH 8.5) at a concentration of 1 mM. In other embodiments, the carbohydrates are functionalized with a thiol linker at the reducing end of the sugar and dissolved in PBS (pH 7.4; including an equimolar amount of tris(2-carboxyethyl)phosphine hydrochloride (Thermo Scientific) at a concentration of 1 mM. The compounds are robotically printed in triplicates using a piezoelectric spotting device (S3, Scienion) onto epoxy functionalized microarray slides (sciChip Epoxy, Scienion) in 60% relative humidity, at 23° C. The slides are placed in a humidified chamber for 18 hours and then stored in an anhydrous environment.

Prior to using the microarray, the slides are washed three times with water, incubated with 100 mM ethanolamine in 50 mM $NaH_2PO_4$ buffer (pH 9) at 50° C. for 1 hour, rinsed again three times with water, and finally dried by centrifugation. The microarray slides are blocked with blocking buffer (10 mM HEPES, 1 mM $CaCl_2$), 1 mM $MgCl_2$, 2% BSA) at room temperature for 1 hour and washed three times with lectin buffer (10 mM HEPES, 1 mM $CaCl_2$), 1 mM $MgCl_2$) for 5 min. 1 µg of C-type lectin receptor-binding protein sample, diluted in lectin buffer supplemented with 0.01% Tweet 20, is applied and the slides are incubated for 1 hour at room temperature. The arrays are washed three times with lectin buffer for 5 min and monoclonal mouse anti-human IgG1-AlexaFluor 488 (Invitrogen, Carlsbad, Calif.) is applied at a 1:100 dilution in lectin buffer with 0.5% BSA at room temperature for 1 hour. The slides are then washed twice with lectin buffer and once with distilled water, spun at 1000 rpm for 5 min, and scanned with a Genepix scanner 7 (Molecular Devices, Sunnyvale, Calif., USA). Binding affinities are determined by measuring the mean fluorescent intensities (MFI) using Genepix Pro 7 (Molecular Devices, Sunnyvale, Calif., USA) (Maglinao M, Eriksson M, Schlegel M K, Zimmermann S, Johannssen T, Götze S, Seeberger P H, Lepenies B, 2014. A platform to screen for C-type lectin receptor-binding carbohydrates and their potential for cell-specific targeting and immune modulation, Journal of Controlled Release, 175:36-42). Ligands for C-type lectin receptors are often fungal in origin, and thus in addition to being a selection mechanism for carbohydrates, this method also serves as a selection mechanism for immunomodulatory fungal species.

Example 72. Co-Culture of Bacteria Plus Prebiotic and Host-Cells and Analysis of Host Cell Cytokine Response The following work is done in the presence and absence (as a control) of one or more selected prebiotic carbohydrates. This assay may be used to test or confirm the ability of a prebiotic-bacterium pair to elicit an immunomodulatory response such that the production or release of proinflammatory cytokines decreases and/or the production or release of anti-inflammatory cytokines increases, may be used to evaluate the difference in cytokine response in the presence or absence of a prebiotic mixture, and/or may be used to evaluate an array of prebiotic candidates. Clostridales bacteria are obtained from the ATCC or purified from a human donor and cultured in brain-heart infusion broth at 37° C. The bacteria are harvested by centrifugation (3000 g, 15 minutes) after 24 hours of stationary growth. To test the effects of spores on human intestinal cells and/or human peripheral blood mononuclear cells (huPBMC), bacteria are first heat killed (95° C., 30 minutes) before the centrifugation step. Bacteria (or spores) are washed three times with 1×PBS (pH 7.2, Gibco BRL) and subsequently diluted to obtain final cell densities of $10^6$ and $10^7$ colony forming units (cfu)/ml in RPMI 1640 medium (Gibco BRL).

Human enterocyte-like CaCO-2 cells (passage 60-65) are seeded at a density of $2.5 \times 10^5$ cells/ml on 25 mm cell culture inserts (0.4 µm nucleopore size; Becton Dickinson). The inserts are placed into six well tissue culture plates (Nunc) and cultured 18-22 days at 37° C./10% $CO_2$ in DMEM (glutamine, high glucose; Amimed) supplemented with 20% decomplemented fetal calf serum (56° C., 30 minutes; Amimed), 1% MEM non-essential amino acids (Gibco BRL), 10 µg/ml gentamycin (Gibco BRL), and 0.1% penicillin/streptomycin (10 000 IU/ml/10 000 UG/ml; Gibco BRL). The cell culture medium is changed every second day until the cells are fully differentiated. Transepithelial electrical resistance (TEER) is determined continuously in confluent CaCO-2 monolayers using a MultiCell-ERS voltmeter/ohmmeter or as described in Example 44.

Tissue culture inserts covered with CaCO-2 cell monolayers are washed twice with prewarmed RPMI 1640 medium and transferred to six well tissue culture plates. 2 mL culture medium is added to the apical and basolateral compartments of the transwell cell culture system.

Next, the apical surface of CaCO-2 monolayers is challenged by addition of $10^6$ or $10^7$ cfu/ml of Clostridiales bacteria or spores, in the absence of gentamicin. After four hours, gentamicin is added (at 150 µg/mL) to stop bacterial growth and metabolite secretion. CaCO-2 cells are stimulated with the bacteria or spores for 6-36 hours in a 37° C., 10% $CO_2$ incubator. Then the CaCO-2 cells are collected, washed once with cold 1×PBS (pH 7.2), and lysed in denaturation solution for RNA extraction (Micro RNA Isolation Kit, Stratagene). Cellular lysates are stored at −20° C. and cell culture supernatants are collected from the apical compartment and frozen at −20° C. The immune response of CaCO-2 cells is monitored by analysis of cytokine gene transcription (TNF-α, IL-8, monocyte chemoattracting protein 1 (MCP-1), TGF-β, IL-12, IFN-γ, IL-4, IL-10) using a reverse transcription-polymerase chain reaction (RT-PCR) technique and determination of cytokine secretion in cell culture supernatants using an ELISA (Haller D, Bode C, Hammes W P, Pfeifer A M A, Schiffrin E J, Blum S, 2000. Non-pathogenic bacteria elicit a differential cytokine response by intestinal epithelial cell/leucocyte co-cultures. Gut. 47:79-97).

Example 73. Analysis of Microbially-Produced Short Chain Fatty Acids and Lactic Acid Microbes may be selected for administration to a patient based on its fermentation products. Microbes may be selected for their ability to produce immunosuppressive short chain fatty acids such as propionate (propionic acid) and/or butyrate (butyric acid). Such analysis is also used to pair microbes with a prebiotic carbohydrate such that the prebiotic carbohydrate is a substrate for the production of the desired immunosuppressive fermentation products.

5 M stock solutions of standards [formic acid (FA), acetic acid (AA), propionic acid (PA), butyric acid (BA), valerie acid, iso-caproic acid, D/L-lactic acid (D/L-LA), 2-ethyl-butyric acid and pimelic acid (Sigma Aldrich)] are made up in HPLC-grade water (VWR). A 0.2M succinic acid (SA) internal standard is prepared in HPLC-grade water with NaOH (Sigma. Aldrich) to promote dissolution. Combined working solutions (WS, containing FA, AA, PA, BA and LA) of 0.5 M and 0.05 M are prepared by diluting the stock solution appropriately with HPLC-grade water. Standard solutions of 0.1 M in water/methanol. (50/50, v/v) are prepared for valerie acid, iso-caproic acid, 2-ethyl-butyric acid and pimelic acid.

Microbes are purchased or purified from human donors or patients as described in Examples 18 and 36 and are grown in M2GSC medium. The M2GSC medium is at pH 6 and contains, per 100 mL: 30 mL of rumen fluid, 1 g of casitone, 0.25 of yeast extract, 0.2 g of glucose, 0.2 g of cellobiose, 0.2 g of soluble starch, 0.045 g of $K_2HPO_4$, 0.045 g of $KH_2PO_4$, 0.09 g of $(NH_4)_2SO_4$, 0.09 g of NaCl, 0.009 g of $MgSO_4.7H_2O$, 0.009 g of $CaCl_2$, 0.1 mg of resazurin, 0.4 g of $NaHCO_3$ and 0.1 g of cystein hydrochloride.

For analysis of microbially-produced short chain fatty acids, 1 supernatant from the microbial cultures is placed in a pyrex extraction tube. 50 µL of the SA stock solution is added as an internal standard to each standard sample or experimental sample. The samples are vortexed and equilibrated at room temperature for 5 minutes. Then, 100 µL of concentrated HCl (VWR) is added, followed by vortexing for 15 seconds. The samples are extracted for 20 min by gently rolling using 5 mL of diethylether (VWR). After centrifugation (5 min, 3500 rpm), the supernatant is transferred to another pyrex extraction tube and 500 µL of a 1 M solution of NaOH is added. The samples are extracted again for 20 min, followed by a centrifugation step. The aqueous phase is transferred to an autosampler vial and 100 µL of concentrated HCl is added. After vortexing, a 10 µL aliquot is injected onto the HPLC-UV apparatus, which comprises a P4000 gradient pump with vacuum degassing, an AS3000 autosampler (10° C.), an UV6000 detector, and a SN4000 module (Thermo Separations Products, Thermo Scientific).

Chromatographic separation is performed as described in De Baere S., Eeckhaut V., Steppe M., De Maesschalck C., De Backer P., Van Immerseel F., Croubels S., 2013. Development of a HPLC-UV method for the quantitative determination of four short-chain fatty acids and lactic acid produced by intestinal bacteria during in vitro fermentation. Journal of Pharmaceutical and Biomedical Analysis. 80:107-115.

Example 74. Method of Preparing the Microbial and Prebiotic Composition for Administration to a Patient One strain of bacteria or fungi is independently cultured and mixed together with a selected prebiotic carbohydrate before administration. The strain is grown at 37° C., pH 7, in a GMM or other animal-products-free medium, pre-reduced with 3 g/L cysteineYHCl. After each strain reaches a sufficient biomass, it is preserved for banking by adding 15% glycerol and then frozen at −80° C. in 1 mL cryotubes. The strain is then cultivated to a concentration of 10^10 CFU/mL, then concentrated 20-fold by tangential flow microfiltration. The spent medium is exchanged by diafiltering with a preservative medium consisting of 2% gelatin, 100 mM trehalose, and 10 mM sodium phosphate buffer, or other suitable preservative medium. The suspension is freeze-dried to a powder and titrated.

After drying, the powder is blended with microcrystalline cellulose and magnesium stearate and formulated into a 250 mg gelatin capsule containing 10 mg of lyophilized powder ($10^8$ to $10^{11}$ bacteria), 160 mg microcrystalline cellulose, 77.5 rag gelatin, and 2.5 mg magnesium stearate, and the prebiotic mixture. The prebiotic mixture is in powder form and is mixed with the microbial composition in a ratio of prebiotic:microbe of about 3:1, 2:1, 1:1, 1:2, 1:3, 1:5, 1:10, 1:15, 1:20, 1:25, 1:30, 1:35, 1:40, 1:45, 1:50, 1:55, 1:60, 1:70, 1:80, 1:90, 1:100, or 1:500.

Example 75. A Rat Model for Radiation- and Chemotherapy-Induced Mucositis

Eighteen female Wistar rats of 150-200 grams, aged 14-16 weeks, may be obtained from the Central Animal Research Facility, Manipal University, Manipal (License No. 9411999 CPCSEA). The rats are housed in polycarbonate cages and were provided free access to standard rat food and filtered water. After one week adaptation to the environment, rats are subjected to chemotherapy by orally administering busulfan (Sigma-Aldrich Co. LLC, St. Louis, Mo., USA) at 6 mg/kg for four days. To administer infrared radiation to the rats, the tail flick apparatus (model 37360, Ugo Basile Sri, Comerio, Va., Italy) is used. The rats are anesthetized with light ether and the dorsal surface of the tongue is exposed to IR radiation of intensity 40 mV/cm² for 5 second on the first and fourth clays of treatment with busulfan (Patel A, Rajesh S Chandrashekar V M, Rathnam S, Shah K, Rao C M, Nandakumar K, 2013. A rat model against chemotherapy plus radiation-induced mucositis. Saudi Pharmaceutical Journal. 21:399-403).

Example 76. A Mouse Model for Bone Marrow Transplantation

Female C57BL/6 and B6D2F1 mice are purchased from the Jackson Laboratory (Bar Harbor, Me., USA). Bone marrow is harvested from the femurs and tibias of 12-20 week old mice. Before receiving transplantation, B6D2F1 mice are given 14 Gy total body irradiation ($^{137}$Cs source). Irradiation is done twice, three hours apart. 5×10 6 bone marrow cells are supplemented with 2×10 6 nylon-wool nonadherent splenetic T cells from C57BL/6 mice and resuspended in Leibovitz's L15 medium (Life Technologies Inc., New York USA) and transplanted by tail vein infusion (0.25 mL) into B6D2F1 mice (Cooke K R, Gerbitz A, Crawford J M, Teshmia T, Hill G R, Tesolin A, Rossignol D P, Ferrara J L M 2001. LPS antagonism reduces graft-versus-host disease and preserves graft-versus-host leukemia after experimental bone marrow transplantation. The Journal of Clinical Investigation. 107:1581-1589).

Example 77. A Mouse Model for Studying Gut Microbiome in Graft Versus Host Disease Blood from healthy human donors is collected in a tube containing sodium heparin. The blood is diluted in an equal volume of $Ca^{2+}$- and $Mg^{2+}$-free phosphate buffered saline with 2% v/v fetal bovine serum and centrifuged at room temperate at 200× g for 10 minutes. The white "buffy coat" layer is removed to yield human peripheral mononuclear cells (huPBMCs), washed five times in RPMI 1640, and diluted (2×10$^6$ cells/mL) in RPMI 1640 with decomplemented 20% human AB serum (56° C., 30 minutes, Sigma) and 150 µg/mL gentamicin.

At 4- to 5 weeks old, the Rag2$^{-/-}$γc$^{-/-}$ mice (purchased from Taconic) are pretreated with liposome-clodronate Medisch Centrum) and sublethally irradiated (1 Cay/6 g), then transplanted intraperitoneally with 3.0×10' huPBMCs. After 4 weeks, these humanized mice sublethally irradiated and, one day later, are injected intravenously with 1.0×10$^7$ allogeneic huPBMCs (1 Cy/6 g). The transplanted mice are monitored daily for GVHD symptoms including weight loss, temperature changes, and diarrhea. (Meng J, Liu Y, Liu U Liu M, Xiang Z, Lam K-T, Lewis D B, Lau Y-L, Tu W, 2013. Human CD8$^+$ Regulatory T Cells Inhibit GVHD and Preserve General Immunity in Humanized Mice Sci Transl Med 5:168ra9.)

Example 78. Detection of Bacteria in Antigen-Presenting Cells

The following methods may be applied to assess the persistence of dysbiotic or disease-associated bacteria. Optionally, these methods may be applied to assess immunomodulatory behavior of bacteria administered to a patient or of bacteria associated with the patient's natural "healthy" microbiome.

Dendritic cells (DCs) are isolated from bone marrow or blood according to standard methods or kit protocols (e.g., Inaba K, Swiggard W J, Steinman R M, Romani N, Schuler G, 2001. Isolation of dendritic cells. Current Protocols in Immunology. Chapter 3:Unit3.7) or are obtained from the ATCC.

GFP-expressing Clostridiales bacteria are made using the pGLO™ Bacterial Transformation Kit (BioRad, USA) according to the manufacturer's instructions.

To evaluate bacterial entrance into and/or presence in DCs, 250,000 DCs are seeded on a round cover slip in complete RPMI-1640 medium and are then infected with GFP-expressing Clostridiales bacteria. After 1 hour of infection, the cells are washed twice with ice-cold PBS. To kill extracellular bacteria, the cells are incubated in complete RPMI-1640 medium supplemented with 50 µm/ml gentamicin for 2-3 hours. Cells are fixed and permeabilized for 10 min at −20° C. with 100% methanol and blocked for 1 hour with PBS plus 3% bovine serum albumin. After incubation, the cover slips is washed three times, mounted on microscope slides and analyzed on a confocal microscope (e.g., a fluoview FV100 Olympus confocal microscope). The number of cells containing intracellular bacteria are counted and normalized to the total number of cells in the field. Z-stack analysis (using 0.5 µm steps) is used to discern intracellular bacteria from extracellular bacteria (Bueno S M, Wozniak A, Leiva E D, Riquelme S A, Carreño Hardt W D, Riedel C A, Kalergis A M, 2010. Salmonella pathogenicity island 1 differentially modulates bacterial entry to dendritic and non-phagocytic cells. Immunology. 130:273-87). To detect bacteria outside of dendritic cells, confocal microscopy may be performed in which immunospecific antibioties to the GFP-expressing bacteria are visualized.

Additionally or alternatively, gentamicin protection assays are used to evaluate bacterial survival inside DCs. Overnight cultures of Clostriadles bacteria are subcultured until they reached an OD600 of 0.5-0.7 and are then washed and resuspended in ice-cold PBS. The DCs are infected with bacteria a multiplicity of infection (MOI) equal to 25 for 1 hour. The DCs are washed and extracellular bacteria are killed by incubating the DCs for 2 hours with 50 µm/ml gentamicin (Sigma-Aldrich). To recover intracellular bacteria, 10,000 live cells are counted and lysed for 15 min with 0.1% Triton-X-100 in PBS. The lysed cells are seeded on Luria-Bertani agar plates and incubated for 12-16 hours at 37° C. to count intracellular bacteria as colony-forming units (CFUs). Data from gentamicin protection assays are normalized as the percentage of recovered CFUs relative to the maximum amount obtained in each experiment (defined as 100%) (Bueno S M, Wozniak A, Leiva E D, Riquelme S A, Carreño L J, Hardt W D, Riedel C A, Kalergis A M, 2010. Salmonella pathogenicity island 1 differentially modulates bacterial entry to dendritic and non-phagocytic cells. Immunology. 130:273-87). The methods described above may also be performed in substantially the same manner, using macrophages (obtained from the ATCC) in place of DCs.

Example 79. Detection of Bacteria in MLN, PLN and Spleen

Radiolabeled bacteria may be detected in organs and serve as an indicator of bacterial translocation in an animal model.

To prepare radiolabeled bacteria, the following steps are repeated three times: A bacterial sample (e.g., Escherichia coli ATCC-10536) is obtained from the ATCC and grown overnight in an appropriate medium (e.g., trypticasein agar). The next day, the strain is transferred to a tube containing 10 mL of sterile saline solution. The bacterial concentration is adjusted to 11% of transmittance in a spectrophotometer at 580 nm, corresponding to a CFU/mL of approximately 10$^8$. Two mL of the bacterial suspension is incubated in tubes containing 1 mL of stannous chloride solution (580 µM, pH 7.0) at 37° C. for 10 minutes. After incubation, 37.0-55.5 MBq of $^{99m}$Tc obtained by elution from the sterile $^{99}$Mo/$^{99m}$Tc generator (IPEN/Brazil) is added, and the sample is incubated for 10 minutes at 37° C. The tubes are centrifuged at 3000 g for 25 minutes.

Once repeated three times, the radioactivity of the supernatant and precipitate is measured using a dose calibrator (CRC-25R Dose Calibrator; Capintec, Ramsey, N.J.), and the labeling efficiency is calculated by dividing the cpm of the precipitate by the total cpm (precipitate plus supernatant) and multiplying by 100%.

Adult Swiss male mice are fed standard chow. If the experiment calls for the assessment of a treatment (e.g., supplementation with citrulline, microbial composition, and/or an immunomodulatory or prebiotic carbohydrate), the mice fed standard chow plus treatment are compared with mice only fed standard chow. The mice are administered 0.1 mL of a suspension containing 1.8 MBq of the $^{99m}$Tc-labeled bacteria ($10^7$ CFU/mL), by gavage. One to two days later, the animals were euthanized, and the mesenteric lymph nodes (MLNs), popliteal lymph notes (PLNs), and spleen are removed, weighed, and placed in tubes. Incorporated radioactivity is assessed using a counter with an NaI (Tl) crystal (ANSR; Abbott, Chicago, Ill.) and normalized to the organ's weight (Batista M A, Nicoli J R, Martins Fdos S, Machado, J A, Arantes R M, Quinino I E, Correia M I, Cardoso V N, 2012. Pretreatment with citrulline improves gut barrier after intestinal obstruction in mice. JPEN J Parenter Enteral Nutr. 36:69-76).

Example 80. Measuring Intestinal Integrity by Zonulin ELISA

Age-matched male diabetes-prone and diabetes-resistant rats are anesthetized with ketamine and killed at increasing ages (20, 50, 75, and >100 days) by exsanguination. The rat abdominal wall is opened, small intestinal loops are isolated, and intraluminal lavage is performed by instillation of 0.5 ml of PBS into the proximal small intestine followed by aspiration. The aspirate is stored at −80° C. until a zonulin ELISA is performed as follows. Plastic microliter plates (Costar, Cambridge, Mass.) are coated with polyclonal rabbit, zonulin-specific anti-Zot antibodies (dilution 1:100) overnight at 4° C. and are then blocked by incubation with 0.05% PBS-Tween 20 for 15 min at room temperature. A standard curve is made by serial dilution of zonulin (0.78-50 ng/ml) in 0.05% PBS-Tween 20. Equal amounts of the standards and experimental samples are aliquotted into the microtiter plate wells and incubated for 1 hour at room temperature. Unbound zonulin is removed by washing, and the wells are incubated by agitation with biotinylated anti-Zot antibodies for 1 hour at room temperature. A color reaction is developed by adding 100 μl of Extra-Avidin (Sigma) diluted 1:20,000 in 0.1 M Tris.HCl, 1 mM MgCl$_2$, 1% BSA, pH 7.3, for 15 min, followed by incubation with 100 μl of a 1 mg/ml of p-nitrophenyl-phosphate substrate (Sigma) solution. Absorbance at 405 nm is read after 30 min (Watts T, Berti I, Sapone A, Gerarduzzi T, Not T, Zielke R, and Fasano A, 2005. Role of the intestinal tight junction modular zonulin in the pathogenesis of type I diabetes in BB diabetic-prone rats. PNAS. 102:2916-2921).

Example 81. Measuring Intestinal Integrity by Western Blot of Tight Junction Proteins Intestinal integrity may also be evaluated by measuring tight junction protein levels by Western blot. In this case, primary antibodies for occluding and zona occludins-1 (Grand Island, N.Y.), primary antibodies for claudin-1 and claudin-2 (Santa Cruz Biotechnology, CA), and secondary antibodies (fluorescein-conjugated goat anti-mouse and goat anti-rabbit from Santa Cruz Biotechnology, CA) are used. One centimeter sections of mid-jujunal intestine are harvested from an appropriate animal model (e.g., rat or mouse) and immediately homogenized in 1 mL ice-cold RIPA-buffer (50 mM TRIS-HCl, pH 7.4, 150 mM NaCl, 1 mM DTT, 0.5 mM EDTA, 1.0% NP40, 0.5% sodium deoxycholate, 0.1% SDS, 2 mM phenylmethylsulfonyl fluoride, 20 μg/ml aprotinin, 2 μg/ml leupeptin and 2 mM sodium orthovanadate). Tissue lysates are sonicated, incubated on ice for 20 min and centrifuged at 4° C., and the resulting supernatants are collected for immunoprecipitation. The protein concentration of the supernatants is measured using the techniques known to one skilled in the art, including but not limited to a Bradford assay. The samples are boiled for 5 min and then 2 μg of protein from each sample is loaded into the lanes of a 10% acrylamide gel. Following electrophoresis, the proteins are transferred onto nitrocellulose filters, which are then incubated with primary antibodies directed against occludin, zona-occludin-1, claudin-1, and/or claudin-2 overnight at 4° C. The filters are then washed with 1×TBST and incubated with secondary antibodies conjugated with horseradish peroxidase (HRP) for one hour at room temperature. Immunocomplexes for each of the tight junction proteins are then detected by chemiluminescence (Alaish S M, Smith A D, Timmons J, Greenspon J, Eyvazzadeh D, Murphy E, Shea-Donahue T, Cirimotich S, Mongodin E, Zhao A, Fasano A, Nataro J P, Cross A, 2013. Gut microbiota, tight junction protein expression, intestinal resistance, bacterial translocation and mortality following cholestasis depend on the genetic background of the host. Gut Microbes. 4:292-305).

Example 82. Measurement of Intestinal Permeability in a Mouse Model for Alcoholism Eight-week-old male C57BL/6N mice are fed a modified Lieber-DeCarli liquid diet containing ethanol (35% of total calories) or containing no ethanol for one week and then gradually increasing amounts of ethanol (to a maximum of 35% total calories) over the course of 3-4 days. After eight weeks of ethanol feeding, the mice are fasted overnight, anesthetized intraperitonially with sodium-pentobarbital (nembutal, 80 mg/kg), and whole intestinal samples are collected and weighed. The freshly isolated intestinal segments (duodenum, jejunum, ileum) are placed in Krebs-Henseleit bicarbonate buffer and then used for ex vivo intestinal permeability assay as follows. One end of the gut segment is ligated with suture, and 200 μl of fluorescent dextran-FITC (FD-4; M.W. 4,000, 40 mg/ml) is injected into the lumen using a gavage needle. The other end of the gut segment is ligated to form a gut sac. The gut sac is rinse in Krebs-Henseleit bicarbonate buffer and placed in 4 ml of fresh buffer, then incubated at 37° C. for 20 minutes. The FD-4 that penetrated from the lumen into the buffer is measured with a spectrofluorometer using an excitation wave length of 485 nm and an emission wave length of 530 nm (Kirpich I A, Feng W, Wang Y, Lie Y, Barker D F, Barve S S, McClain C J, 2011. The Type of Dietary Fat Modulates Intestinal Tight Junction Integrity, Gut Permeability, and Hepatic Toll-Like Receptor Expression in a Mouse Model of Alcoholic Liver Disease. Alcoholism: Clinical and Experimental Research. 36:835-846).

Example 83. Detection of Bacteria in Distal Organs

A fragment from a liver or spleen biopsy 15 minutes after reperfusion is moved to a sterile tube containing thioglycolate and the immediately cultured on a medium including but not limited to blood agar, blood agar supplemented for anaerobes, chocolate blood agar, MacConkey agar, and Sabouraud agar. Bacteria are purified as described (Example 18) or using other medium as described in Example 36 and 16S rDNA sequencing is performed as described (Examples 7, 31, 62-65), Example 84: Distal Effects of Microbiota It has been determined that the presence of certain probiotics in the microbiome plays a role in the therapeutic effectiveness of certain immunomodulatory cancer therapies, including anti-PD-1 and anti-CTLA-4 antibodies. In particular, it has been found that the addition of certain bacteria to the gut of a subject enhances the activity of these checkpoint inhibitors, resulting in increased anti-tumor T cell responses and inhibition of tumor growth (See Vétizou, et al. Science, Nov. 5, 2015, science.aad1329 and Sivan et al. Science, Nov. 5, 2015, science.aac4255).

In particular, it has been shown that oral administration of Bifidobacterium or Bacteroides probiotics, but not Lactobacillusincreases the responsiveness to checkpoint inhibitor therapy in cancer (Sivan et al., Vetizou et al). Anti-PD-1 and anti-CTLA-4 antibody therapies relieve a block, or checkpoint, that otherwise limits anti-tumor immunity. Checkpoint inhibition by these antibodies results in an increase in anti-tumor T cell immune responses, and more effective killing of cancer cells. Tumors have also been shown to be surrounded by microbiomes that are different from the microbiome in normal adjacent tissues, as a result of the interaction between the immune system and the cancer. The observation that addition of certain bacteria to the gut leads to an effect on the immune system and on the growth of tumors at a distal site suggests a concomitant impact on the tumor microbiome at these distal site(s).

In order for the immune cells induced by the combination of a checkpoint inhibitor and certain gut bacteria to have an effect, the cells must travel to the tumor site, altering both the immune and tumor environments, which will alter the tumor microbiome as well. Thus, the presence of bacteria introduced in the gut leads to an alteration in the microbiome of tumors at a distal site. The above studies support the distal effects of microbials, and the role of certain bacteria in the effectiveness of certain cancer therapies.

REFERENCES

1. Bischoff, S C, Giovanni, B, Buuman, W, Ockhuizen, T, Schulzke, J-D, Serino, M, Tilg, H, Watson, A and Wells, J M. Intestinal permeability—a new target for disease prevention and therapy. BMC Gastroenterology. 14: 189, 2014.
2. Boyum, A. Isolation of mononuclear cells and granulocytes from human blood. Scand. J. Clin. Lab. Invest. 21, Suppl 97 (Paper IV), 77-89, 1968.
3. Boyum A. Isolation of lymphocytes, granulocytes and macrophages. Scand J Immunol. (Suppl 5):9-15, 1976.
4. Bach M K, Brashler J R. Isolation of subpopulations of lymphocytic cells by the use of isotonically balanced solutions of Ficoll. I. Development of methods and demonstration of the existence of a large but finite number of subpopulations. Exp Cell Res. 61:387-96, 1970.
5. Fotino, M., Merson, E. J. and Allen, F. H. Micromethod for rapid separation of lymphocytes from peripheral blood. Ann. Clin. Lab. Sci. 1:131-133, 1971.
6. Hsiao, E Y, McBride, S W, Hsien, S, Sharon G, Hyde, E R, McCue T, Codelli, J A, Chow, J, Reisman, S E, Petrosino, J F, Patterson, P H and Mazmanian, S K. Microbiota modulate behavioral and physiological abnormalities associated with neurodevelopmental disorders. Cell, 155: 1451-1463, 2013.
7. Caporaso, J. G., Kuczynski, J., Stombaugh, J., Bittinger, K., Bushman, F. D., Costello, E. K., Knight, R. (2010). QIIME allows analysis of high-throughput community sequencing data. Nature methods, 7 (5), 335-336. doi: 10.1038/nmeth.f.303
8. Illumina. (2014). Frequently Asked Questions: 16S Metagenomic Sequencing. Retrieved from http://www.illumina.com/content/dam/illuminamarketing/documents/products/other/16smetagenomics-faq-1270-2014-003.pdf
9. Rao S, Kupfer Y, Pagala M, Chapnick E and Tessler S. (2011). Systemic absorption of oral vancomycin in patients with Clostridium difficile infection. Scand J Infect Dis 5: 386-388.

TABLE 1

| | | | | | |
|---|---|---|---|---|---|
| | | See, e.g., WO2014/121304 | | | |
| OTU | SEQ ID Number | Public DB Accession | Clade | Spore Former | Pathogen Status |
| Eubacterium saburreum | 858 | AB525414 | clade__178 | Y | N |
| Eubacterium sp. oral clone IR009 | 866 | AY349376 | clade__178 | Y | N |
| Lachnospiraceae bacterium ICM62 | 1061 | HQ616401 | clade__178 | Y | N |
| Lachnospiraceae bacterium MSX33 | 1062 | HQ616384 | clade__178 | Y | N |
| Lachnospiraceae bacterium oral taxon 107 | 1063 | ADDS01000069 | clade__178 | Y | N |
| Alicyclobacillus acidocaldarius | 122 | NR__074721 | clade__179 | Y | N |
| Clostridium baratii | 555 | NR__029229 | clade__223 | Y | N |
| Clostridium colicanis | 576 | FJ957863 | clade__223 | Y | N |
| Clostridium paraputrificum | 611 | AB536771 | clade__223 | Y | N |
| Clostridium sardiniense | 621 | NR__041006 | clade__223 | Y | N |
| Eubacterium budayi | 837 | NR__024682 | clade__223 | Y | N |
| Eubacterium moniliforme | 851 | HF558373 | clade__223 | Y | N |
| Eubacterium multiforme | 852 | NR__024683 | clade__223 | Y | N |
| Eubacterium nitritogenes | 853 | NR__024684 | clade__223 | Y | N |
| Anoxybacillus flavithermus | 173 | NR__074667 | clade__238 | Y | N |
| Bacillus aerophilus | 196 | NR__042339 | clade__238 | Y | N |
| Bacillus aestuarii | 197 | GQ980243 | clade__238 | Y | N |
| Bacillus amyloliquefaciens | 199 | NR__075005 | clade__238 | Y | N |
| Bacillus anthracis | 200 | AAEN01000020 | clade__238 | Y | Category-A |
| Bacillus atrophaeus | 201 | NR__075016 | clade__238 | Y | OP |
| Bacillus badius | 202 | NR__036893 | clade__238 | Y | OP |
| Bacillus cereus | 203 | ABDJ01000015 | clade__238 | Y | OP |
| Bacillus circulans | 204 | AB271747 | clade__238 | Y | OP |

TABLE 1-continued

See, e.g., WO2014/121304

| OTU | SEQ ID Number | Public DB Accession | Clade | Spore Former | Pathogen Status |
|---|---|---|---|---|---|
| *Bacillus firmus* | 207 | NR_025842 | clade_238 | Y | OP |
| *Bacillus flexus* | 208 | NR_024691 | clade_238 | Y | OP |
| *Bacillus fordii* | 209 | NR_025786 | clade_238 | Y | OP |
| *Bacillus halmapalus* | 211 | NR_026144 | clade_238 | Y | OP |
| *Bacillus herbersteinensis* | 213 | NR_042286 | clade_238 | Y | OP |
| *Bacillus idriensis* | 215 | NR_043268 | clade_238 | Y | OP |
| *Bacillus lentus* | 216 | NR_040792 | clade_238 | Y | OP |
| *Bacillus licheniformis* | 217 | NC_006270 | clade_238 | Y | OP |
| *Bacillus megaterium* | 218 | GU252124 | clade_238 | Y | OP |
| *Bacillus nealsonii* | 219 | NR_044546 | clade_238 | Y | OP |
| *Bacillus niabensis* | 220 | NR_043334 | clade_238 | Y | OP |
| *Bacillus niacini* | 221 | NR_024695 | clade_238 | Y | OP |
| *Bacillus pocheonensis* | 222 | NR_041377 | clade_238 | Y | OP |
| *Bacillus pumilus* | 223 | NR_074977 | clade_238 | Y | OP |
| *Bacillus safensis* | 224 | JQ624766 | clade_238 | Y | OP |
| *Bacillus simplex* | 225 | NR_042136 | clade_238 | Y | OP |
| *Bacillus sonorensis* | 226 | NR_025130 | clade_238 | Y | OP |
| *Bacillus* sp. 10403023 MM10403188 | 227 | CAET01000089 | clade_238 | Y | OP |
| *Bacillus* sp. 2_A_57_CT2 | 230 | ACWD01000095 | clade_238 | Y | OP |
| *Bacillus* sp. 2008724126 | 228 | GU252108 | clade_238 | Y | OP |
| *Bacillus* sp. 2008724139 | 229 | GU252111 | clade_238 | Y | OP |
| *Bacillus* sp. 7_16AIA | 231 | FN397518 | clade_238 | Y | OP |
| *Bacillus* sp. AP8 | 233 | JX101689 | clade_238 | Y | OP |
| *Bacillus* sp. B27(2008) | 234 | EU362173 | clade_238 | Y | OP |
| *Bacillus* sp. BT1B_CT2 | 235 | ACWC01000034 | clade_238 | Y | OP |
| *Bacillus* sp. GB1.1 | 236 | FJ897765 | clade_238 | Y | OP |
| *Bacillus* sp. GB9 | 237 | FJ897766 | clade_238 | Y | OP |
| *Bacillus* sp. HU19.1 | 238 | FJ897769 | clade_238 | Y | OP |
| *Bacillus* sp. HU29 | 239 | FJ897771 | clade_238 | Y | OP |
| *Bacillus* sp. HU33.1 | 240 | FJ897772 | clade_238 | Y | OP |
| *Bacillus* sp. JC6 | 241 | JF824800 | clade_238 | Y | OP |
| *Bacillus* sp. oral taxon F79 | 248 | HM099654 | clade_238 | Y | OP |
| *Bacillus* sp. SRC_DSF1 | 243 | GU797283 | clade_238 | Y | OP |
| *Bacillus* sp. SRC_DSF10 | 242 | GU797292 | clade_238 | Y | OP |
| *Bacillus* sp. SRC_DSF2 | 244 | GU797284 | clade_238 | Y | OP |
| *Bacillus* sp. SRC_DSF6 | 245 | GU797288 | clade_238 | Y | OP |
| *Bacillus* sp. tc09 | 249 | HQ844242 | clade_238 | Y | OP |
| *Bacillus* sp. zh168 | 250 | FJ851424 | clade_238 | Y | OP |
| *Bacillus sphaericus* | 251 | DQ286318 | clade_238 | Y | OP |
| *Bacillus sporothermodurans* | 252 | NR_026010 | clade_238 | Y | OP |
| *Bacillus subtilis* | 253 | EU627588 | clade_238 | Y | OP |
| *Bacillus thermoamylovorans* | 254 | NR_029151 | clade_238 | Y | OP |
| *Bacillus thuringiensis* | 255 | NC_008600 | clade_238 | Y | OP |
| *Bacillus weihenstephanensis* | 256 | NR_074926 | clade_238 | Y | OP |
| *Geobacillus kaustophilus* | 933 | NR_074989 | clade_238 | Y | N |
| *Geobacillus stearothermophilus* | 936 | NR_040794 | clade_238 | Y | N |
| *Geobacillus thermodenitrificans* | 938 | NR_074976 | clade_238 | Y | N |
| *Geobacillus thermoglucosidasius* | 939 | NR_043022 | clade_238 | Y | N |
| *Lysinibacillus sphaericus* | 1193 | NR_074883 | clade_238 | Y | N |
| Clostridiales sp. SS3_4 | 543 | AY305316 | clade_246 | Y | N |
| *Clostridium beijerinckii* | 557 | NR_074434 | clade_252 | Y | N |
| *Clostridium botulinum* | 560 | NC_010723 | clade_252 | Y | Category-A |
| *Clostridium butyricum* | 561 | ABDT01000017 | clade_252 | Y | N |
| *Clostridium chauvoei* | 568 | EU106372 | clade_252 | Y | N |
| *Clostridium favososporum* | 582 | X76749 | clade_252 | Y | N |
| *Clostridium histolyticum* | 592 | HF558362 | clade_252 | Y | N |
| *Clostridium isatidis* | 597 | NR_026347 | clade_252 | Y | N |
| *Clostridium limosum* | 602 | FR870444 | clade_252 | Y | N |
| *Clostridium sartagoforme* | 622 | NR_026490 | clade_252 | Y | N |
| *Clostridium septicum* | 624 | NR_026020 | clade_252 | Y | N |
| *Clostridium* sp. 7_2_43FAA | 626 | ACDK01000101 | clade_252 | Y | N |
| *Clostridium sporogenes* | 645 | ABKW02000003 | clade_252 | Y | N |
| *Clostridium tertium* | 653 | Y18174 | clade_252 | Y | N |
| *Clostridium carnis* | 564 | NR_044716 | clade_253 | Y | N |
| *Clostridium celatum* | 565 | X77844 | clade_253 | Y | N |
| *Clostridium disporicum* | 579 | NR_026491 | clade_253 | Y | N |
| *Clostridium gasigenes* | 585 | NR_024945 | clade_253 | Y | N |
| *Clostridium quinii* | 616 | NR_026149 | clade_253 | Y | N |
| *Clostridium hylemonae* | 593 | AB023973 | clade_260 | Y | N |
| *Clostridium scindens* | 623 | AF262238 | clade_260 | Y | N |
| Lachnospiraceae bacterium 5_1_57FAA | 1054 | ACTR01000020 | clade_260 | Y | N |
| *Clostridium glycyrrhizinilyticum* | 588 | AB233029 | clade_262 | Y | N |
| *Clostridium nexile* | 607 | X73443 | clade_262 | Y | N |
| *Coprococcus comes* | 674 | ABVR01000038 | clade_262 | Y | N |
| Lachnospiraceae bacterium 1_1_57FAA | 1048 | ACTM01000065 | clade_262 | Y | N |

TABLE 1-continued

See, e.g., WO2014/121304

| OTU | SEQ ID Number | Public DB Accession | Clade | Spore Former | Pathogen Status |
|---|---|---|---|---|---|
| Lachnospiraceae bacterium 1_4_56FAA | 1049 | ACTN01000028 | clade_262 | Y | N |
| Lachnospiraceae bacterium 8_1_57FAA | 1057 | ACWQ01000079 | clade_262 | Y | N |
| Ruminococcus lactaris | 1663 | ABOU02000049 | clade_262 | Y | N |
| Ruminococcus torques | 1670 | AAVP02000002 | clade_262 | Y | N |
| Paenibacillus lautus | 1397 | NR_040882 | clade_270 | Y | N |
| Paenibacillus polymyxa | 1399 | NR_037006 | clade_270 | Y | N |
| Paenibacillus sp. HGF5 | 1402 | AEXS01000095 | clade_270 | Y | N |
| Paenibacillus sp. HGF7 | 1403 | AFDH01000147 | clade_270 | Y | N |
| Eubacterium sp. oral clone JI012 | 868 | AY349379 | clade_298 | Y | N |
| Alicyclobacillus contaminans | 124 | NR_041475 | clade_301 | Y | N |
| Alicyclobacillus herbarius | 126 | NR_024753 | clade_301 | Y | N |
| Alicyclobacillus pomorum | 127 | NR_024801 | clade_301 | Y | N |
| Blautia coccoides | 373 | AB571656 | clade_309 | Y | N |
| Blautia glucerasea | 374 | AB588023 | clade_309 | Y | N |
| Blautia glucerasei | 375 | AB439724 | clade_309 | Y | N |
| Blautia hansenii | 376 | ABYU02000037 | clade_309 | Y | N |
| Blautia luti | 378 | AB691576 | clade_309 | Y | N |
| Blautia producta | 379 | AB600998 | clade_309 | Y | N |
| Blautia schinkii | 380 | NR_026312 | clade_309 | Y | N |
| Blautia sp. M25 | 381 | HM626178 | clade_309 | Y | N |
| Blautia stercoris | 382 | HM626177 | clade_309 | Y | N |
| Blautia wexlerae | 383 | EF036467 | clade_309 | Y | N |
| Bryantella formatexigens | 439 | ACCL02000018 | clade_309 | Y | N |
| Clostridium coccoides | 573 | EF025906 | clade_309 | Y | N |
| Eubacterium cellulosolvens | 839 | AY178842 | clade_309 | Y | N |
| Lachnospiraceae bacterium 6_1_63FAA | 1056 | ACTV01000014 | clade_309 | Y | N |
| Ruminococcus hansenii | 1662 | M59114 | clade_309 | Y | N |
| Ruminococcus obeum | 1664 | AY169419 | clade_309 | Y | N |
| Ruminococcus sp. 5_1_39BFAA | 1666 | ACII01000172 | clade_309 | Y | N |
| Ruminococcus sp. K_1 | 1669 | AB222208 | clade_309 | Y | N |
| Syntrophococcus sucromutans | 1911 | NR_036869 | clade_309 | Y | N |
| Bacillus alcalophilus | 198 | X76436 | clade_327 | Y | N |
| Bacillus clausii | 205 | FN397477 | clade_327 | Y | OP |
| Bacillus gelatini | 210 | NR_025595 | clade_327 | Y | OP |
| Bacillus halodurans | 212 | AY144582 | clade_327 | Y | OP |
| Bacillus sp. oral taxon F26 | 246 | HM099642 | clade_327 | Y | OP |
| Clostridium innocuum | 595 | M23732 | clade_351 | Y | N |
| Clostridium sp. HGF2 | 628 | AENW01000022 | clade_351 | Y | N |
| Clostridium perfringens | 612 | ABDW01000023 | clade_353 | Y | Category-B |
| Sarcina ventriculi | 1687 | NR_026146 | clade_353 | Y | N |
| Clostridium bartlettii | 556 | ABEZ02000012 | clade_354 | Y | N |
| Clostridium bifermentans | 558 | X73437 | clade_354 | Y | N |
| Clostridium ghonii | 586 | AB542933 | clade_354 | Y | N |
| Clostridium glycolicum | 587 | FJ384385 | clade_354 | Y | N |
| Clostridium mayombei | 605 | FR733682 | clade_354 | Y | N |
| Clostridium sordellii | 625 | AB448946 | clade_354 | Y | N |
| Clostridium sp. MT4 E | 635 | FJ159523 | clade_354 | Y | N |
| Eubacterium tenue | 872 | M59118 | clade_354 | Y | N |
| Clostridium argentinense | 553 | NR_029232 | clade_355 | Y | N |
| Clostridium sp. JC122 | 630 | CAEV01000127 | clade_355 | Y | N |
| Clostridium sp. NMBHI_1 | 636 | JN093130 | clade_355 | Y | N |
| Clostridium subterminale | 650 | NR_041795 | clade_355 | Y | N |
| Clostridium sulfidigenes | 651 | NR_044161 | clade_355 | Y | N |
| Dorea formicigenerans | 773 | AAXA02000006 | clade_360 | Y | N |
| Dorea longicatena | 774 | AJ132842 | clade_360 | Y | N |
| Lachnospiraceae bacterium 2_1_46FAA | 1050 | ADLB01000035 | clade_360 | Y | N |
| Lachnospiraceae bacterium 2_1_58FAA | 1051 | ACTO01000052 | clade_360 | Y | N |
| Lachnospiraceae bacterium 4_1_37FAA | 1053 | ADCR01000030 | clade_360 | Y | N |
| Lachnospiraceae bacterium 9_1_43BFAA | 1058 | ACTX01000023 | clade_360 | Y | N |
| Ruminococcus gnavus | 1661 | X94967 | clade_360 | Y | N |
| Ruminococcus sp. ID8 | 1668 | AY960564 | clade_360 | Y | N |
| Blautia hydrogenotrophica | 377 | ACBZ01000217 | clade_368 | Y | N |
| Lactonifactor longoviformis | 1147 | DQ100449 | clade_368 | Y | N |
| Robinsoniella peoriensis | 1633 | AF445258 | clade_368 | Y | N |
| Eubacterium infirmum | 849 | U13039 | clade_384 | Y | N |
| Eubacterium sp. WAL 14571 | 864 | FJ687606 | clade_384 | Y | N |
| Erysipelotrichaceae bacterium 5_2_54FAA | 823 | ACZW01000054 | clade_385 | Y | N |
| Eubacterium biforme | 835 | ABYT01000002 | clade_385 | Y | N |
| Eubacterium cylindroides | 842 | FP929041 | clade_385 | Y | N |
| Eubacterium dolichum | 844 | L34682 | clade_385 | Y | N |
| Eubacterium sp. 3_1_31 | 861 | ACTL01000045 | clade_385 | Y | N |
| Eubacterium tortuosum | 873 | NR_044648 | clade_385 | Y | N |
| Bulleidia extructa | 441 | ADFR01000011 | clade_388 | Y | N |
| Solobacterium moorei | 1739 | AECQ01000039 | clade_388 | Y | N |
| Coprococcus catus | 673 | EU266552 | clade_393 | Y | N |

TABLE 1-continued

See, e.g., WO2014/121304

| OTU | SEQ ID Number | Public DB Accession | Clade | Spore Former | Pathogen Status |
|---|---|---|---|---|---|
| Lachnospiraceae bacterium oral taxon F15 | 1064 | HM099641 | clade_393 | Y | N |
| Clostridium cochlearium | 574 | NR_044717 | clade_395 | Y | N |
| Clostridium malenominatum | 604 | FR749893 | clade_395 | Y | N |
| Clostridium tetani | 654 | NC_004557 | clade_395 | Y | N |
| Acetivibrio ethanolgignens | 6 | FR749897 | clade_396 | Y | N |
| Anaerosporobacter mobilis | 161 | NR_042953 | clade_396 | Y | N |
| Bacteroides pectinophilus | 288 | ABVQ01000036 | clade_396 | Y | N |
| Clostridium aminovalericum | 551 | NR_029245 | clade_396 | Y | N |
| Clostridium phytofermentans | 613 | NR_074652 | clade_396 | Y | N |
| Eubacterium hallii | 848 | L34621 | clade_396 | Y | N |
| Eubacterium xylanophilum | 875 | L34628 | clade_396 | Y | N |
| Ruminococcus callidus | 1658 | NR_029160 | clade_406 | Y | N |
| Ruminococcus champanellensis | 1659 | FP929052 | clade_406 | Y | N |
| Ruminococcus sp. 18P13 | 1665 | AJ515913 | clade_406 | Y | N |
| Ruminococcus sp. 9SE51 | 1667 | FM954974 | clade_406 | Y | N |
| Anaerostipes caccae | 162 | ABAX03000023 | clade_408 | Y | N |
| Anaerostipes sp. 3_2_56FAA | 163 | ACWB01000002 | clade_408 | Y | N |
| Clostridiales bacterium 1_7_47FAA | 541 | ABQR01000074 | clade_408 | Y | N |
| Clostridiales sp. SM4_1 | 542 | FP929060 | clade_408 | Y | N |
| Clostridiales sp. SSC_2 | 544 | FP929061 | clade_408 | Y | N |
| Clostridium aerotolerans | 546 | X76163 | clade_408 | Y | N |
| Clostridium aldenense | 547 | NR_043680 | clade_408 | Y | N |
| Clostridium algidixylanolyticum | 550 | NR_028726 | clade_408 | Y | N |
| Clostridium amygdalinum | 552 | AY353957 | clade_408 | Y | N |
| Clostridium asparagiforme | 554 | ACCJ01000522 | clade_408 | Y | N |
| Clostridium bolteae | 559 | ABCC02000039 | clade_408 | Y | N |
| Clostridium celerecrescens | 566 | JQ246092 | clade_408 | Y | N |
| Clostridium citroniae | 569 | ADLJ01000059 | clade_408 | Y | N |
| Clostridium clostridiiformes | 571 | M59089 | clade_408 | Y | N |
| Clostridium clostridioforme | 572 | NR_044715 | clade_408 | Y | N |
| Clostridium hathewayi | 590 | AY552788 | clade_408 | Y | N |
| Clostridium indolis | 594 | AF028351 | clade_408 | Y | N |
| Clostridium lavalense | 600 | EF564277 | clade_408 | Y | N |
| Clostridium saccharolyticum | 620 | CP002109 | clade_408 | Y | N |
| Clostridium sp. M62_1 | 633 | ACFX02000046 | clade_408 | Y | N |
| Clostridium sp. SS2_1 | 638 | ABGC03000041 | clade_408 | Y | N |
| Clostridium sphenoides | 643 | X73449 | clade_408 | Y | N |
| Clostridium symbiosum | 652 | ADLQ01000114 | clade_408 | Y | N |
| Clostridium xylanolyticum | 658 | NR_037068 | clade_408 | Y | N |
| Eubacterium hadrum | 847 | FR749933 | clade_408 | Y | N |
| Lachnospiraceae bacterium 3_1_57FAA_CT1 | 1052 | ACTP01000124 | clade_408 | Y | N |
| Lachnospiraceae bacterium 5_1_63FAA | 1055 | ACTS01000081 | clade_408 | Y | N |
| Lachnospiraceae bacterium A4 | 1059 | DQ789118 | clade_408 | Y | N |
| Lachnospiraceae bacterium DJF VP30 | 1060 | EU728771 | clade_408 | Y | N |
| Lachnospiraceae genomosp. C1 | 1065 | AY278618 | clade_408 | Y | N |
| Clostridium difficile | 578 | NC_013315 | clade_409 | Y | OP |
| Eubacterium sp. AS15b | 862 | HQ616364 | clade_428 | Y | N |
| Eubacterium sp. OBRC9 | 863 | HQ616354 | clade_428 | Y | N |
| Eubacterium sp. oral clone OH3A | 871 | AY947497 | clade_428 | Y | N |
| Eubacterium yurii | 876 | AEES01000073 | clade_428 | Y | N |
| Clostridium acetobutylicum | 545 | NR_074511 | clade_430 | Y | N |
| Clostridium algidicarnis | 549 | NR_041746 | clade_430 | Y | N |
| Clostridium cadaveris | 562 | AB542932 | clade_430 | Y | N |
| Clostridium carboxidivorans | 563 | FR733710 | clade_430 | Y | N |
| Clostridium estertheticum | 580 | NR_042153 | clade_430 | Y | N |
| Clostridium fallax | 581 | NR_044714 | clade_430 | Y | N |
| Clostridium felsineum | 583 | AF270502 | clade_430 | Y | N |
| Clostridium frigidicarnis | 584 | NR_024919 | clade_430 | Y | N |
| Clostridium kluyveri | 598 | NR_074165 | clade_430 | Y | N |
| Clostridium magnum | 603 | X77835 | clade_430 | Y | N |
| Clostridium putrefaciens | 615 | NR_024995 | clade_430 | Y | N |
| Clostridium sp. HPB_46 | 629 | AY862516 | clade_430 | Y | N |
| Clostridium tyrobutyricum | 656 | NR_044718 | clade_430 | Y | N |
| Sutterella parvirubra | 1899 | AB300989 | clade_432 | Y | N |
| Acetanaerobacterium elongatum | 4 | NR_042930 | clade_439 | Y | N |
| Clostridium cellulosi | 567 | NR_044624 | clade_439 | Y | N |
| Ethanoligenens harbinense | 832 | AY675965 | clade_439 | Y | N |
| Eubacterium rectale | 856 | FP929042 | clade_444 | Y | N |
| Eubacterium sp. oral clone GI038 | 865 | AY349374 | clade_444 | Y | N |
| Lachnobacterium bovis | 1045 | GU324407 | clade_444 | Y | N |
| Roseburia cecicola | 1634 | GU233441 | clade_444 | Y | N |
| Roseburia faecalis | 1635 | AY804149 | clade_444 | Y | N |
| Roseburia faecis | 1636 | AY305310 | clade_444 | Y | N |
| Roseburia hominis | 1637 | AJ270482 | clade_444 | Y | N |
| Roseburia intestinalis | 1638 | FP929050 | clade_444 | Y | N |

TABLE 1-continued

See, e.g., WO2014/121304

| OTU | SEQ ID Number | Public DB Accession | Clade | Spore Former | Pathogen Status |
|---|---|---|---|---|---|
| *Roseburia inulinivorans* | 1639 | AJ270473 | clade_444 | Y | N |
| *Brevibacillus brevis* | 410 | NR_041524 | clade_448 | Y | N |
| *Brevibacillus laterosporus* | 414 | NR_037005 | clade_448 | Y | N |
| *Bacillus coagulans* | 206 | DQ297928 | clade_451 | Y | OP |
| *Sporolactobacillus inulinus* | 1752 | NR_040962 | clade_451 | Y | N |
| *Kocuria palustris* | 1041 | EU333884 | clade_453 | Y | N |
| *Nocardia farcinica* | 1353 | NC_006361 | clade_455 | Y | N |
| *Bacillus* sp. oral taxon F28 | 247 | HM099650 | clade_456 | Y | OP |
| *Catenibacterium mitsuokai* | 495 | AB030224 | clade_469 | Y | N |
| *Clostridium* sp. TM_40 | 640 | AB249652 | clade_469 | Y | N |
| *Coprobacillus cateniformis* | 670 | AB030218 | clade_469 | Y | N |
| *Coprobacillus* sp. 29_1 | 671 | ADKX01000057 | clade_469 | Y | N |
| *Clostridium rectum* | 618 | NR_029271 | clade_470 | Y | N |
| *Eubacterium nodatum* | 854 | U13041 | clade_476 | Y | N |
| *Eubacterium saphenum* | 859 | NR_026031 | clade_476 | Y | N |
| *Eubacterium* sp. oral clone JH012 | 867 | AY349373 | clade_476 | Y | N |
| *Eubacterium* sp. oral clone JS001 | 870 | AY349378 | clade_476 | Y | N |
| *Faecalibacterium prausnitzii* | 880 | ACOP02000011 | clade_478 | Y | N |
| *Gemmiger formicilis* | 932 | GU562446 | clade_478 | Y | N |
| *Subdoligranulum variabile* | 1896 | AJ518869 | clade_478 | Y | N |
| Clostridiaceae bacterium JC13 | 532 | JF824807 | clade_479 | Y | N |
| *Clostridium* sp. MLG055 | 634 | AF304435 | clade_479 | Y | N |
| Erysipelotrichaceae bacterium 3_1_53 | 822 | ACTJ01000113 | clade_479 | Y | N |
| *Clostridium cocleatum* | 575 | NR_026495 | clade_481 | Y | N |
| *Clostridium ramosum* | 617 | M23731 | clade_481 | Y | N |
| *Clostridium saccharogumia* | 619 | DQ100445 | clade_481 | Y | N |
| *Clostridium spiroforme* | 644 | X73441 | clade_481 | Y | N |
| *Coprobacillus* sp. D7 | 672 | ACDT01000199 | clade_481 | Y | N |
| Clostridiales bacterium SY8519 | 535 | AB477431 | clade_482 | Y | N |
| *Clostridium* sp. SY8519 | 639 | AP012212 | clade_482 | Y | N |
| *Eubacterium ramulus* | 855 | AJ011522 | clade_482 | Y | N |
| *Erysipelothrix inopinata* | 819 | NR_025594 | clade_485 | Y | N |
| *Erysipelothrix rhusiopathiae* | 820 | ACLK01000021 | clade_485 | Y | N |
| *Erysipelothrix tonsillarum* | 821 | NR_040871 | clade_485 | Y | N |
| *Holdemania filiformis* | 1004 | Y11466 | clade_485 | Y | N |
| Mollicutes bacterium pACH93 | 1258 | AY297808 | clade_485 | Y | N |
| *Coxiella burnetii* | 736 | CP000890 | clade_486 | Y | Category-B |
| *Clostridium hiranonis* | 591 | AB023970 | clade_487 | Y | N |
| *Clostridium irregulare* | 596 | NR_029249 | clade_487 | Y | N |
| *Clostridium orbiscindens* | 609 | Y18187 | clade_494 | Y | N |
| *Clostridium* sp. NML 04A032 | 637 | EU815224 | clade_494 | Y | N |
| *Flavonifractor plautii* | 886 | AY724678 | clade_494 | Y | N |
| *Pseudoflavonifractor capillosus* | 1591 | AY136666 | clade_494 | Y | N |
| Ruminococcaceae bacterium D16 | 1655 | ADDX01000083 | clade_494 | Y | N |
| *Acetivibrio cellulolyticus* | 5 | NR_025917 | clade_495 | Y | N |
| *Clostridium aldrichii* | 548 | NR_026099 | clade_495 | Y | N |
| *Clostridium clariflavum* | 570 | NR_041235 | clade_495 | Y | N |
| *Clostridium stercorarium* | 647 | NR_025100 | clade_495 | Y | N |
| *Clostridium straminisolvens* | 649 | NR_024829 | clade_495 | Y | N |
| *Clostridium thermocellum* | 655 | NR_074629 | clade_495 | Y | N |
| *Fusobacterium nucleatum* | 901 | ADVK01000034 | clade_497 | Y | N |
| *Eubacterium barkeri* | 834 | NR_044661 | clade_512 | Y | N |
| *Eubacterium callanderi* | 838 | NR_026330 | clade_512 | Y | N |
| *Eubacterium limosum* | 850 | CP002273 | clade_512 | Y | N |
| *Anaerotruncus colihominis* | 164 | ABGD02000021 | clade_516 | Y | N |
| *Clostridium methylpentosum* | 606 | ACEC01000059 | clade_516 | Y | N |
| *Clostridium* sp. YIT 12070 | 642 | AB491208 | clade_516 | Y | N |
| *Hydrogenoanaerobacterium saccharovorans* | 1005 | NR_044425 | clade_516 | Y | N |
| *Ruminococcus albus* | 1656 | AY445600 | clade_516 | Y | N |
| *Ruminococcus flavefaciens* | 1660 | NR_025931 | clade_516 | Y | N |
| *Clostridium haemolyticum* | 589 | NR_024749 | clade_517 | Y | N |
| *Clostridium novyi* | 608 | NR_074343 | clade_517 | Y | N |
| *Clostridium* sp. LMG 16094 | 632 | X95274 | clade_517 | Y | N |
| *Eubacterium ventriosum* | 874 | L34421 | clade_519 | Y | N |
| *Bacteroides galacturonicus* | 280 | DQ497994 | clade_522 | Y | N |
| *Eubacterium eligens* | 845 | CP001104 | clade_522 | Y | N |
| *Lachnospira multipara* | 1046 | FR733699 | clade_522 | Y | N |
| *Lachnospira pectinoschiza* | 1047 | L14675 | clade_522 | Y | N |
| *Lactobacillus rogosae* | 1114 | GU269544 | clade_522 | Y | N |
| *Bacillus horti* | 214 | NR_036860 | clade_527 | Y | OP |
| *Bacillus* sp. 9_3AIA | 232 | FN397519 | clade_527 | Y | OP |
| *Eubacterium brachy* | 836 | U13038 | clade_533 | Y | N |
| *Filifactor alocis* | 881 | CP002390 | clade_533 | Y | N |
| *Filifactor villosus* | 882 | NR_041928 | clade_533 | Y | N |
| *Clostridium leptum* | 601 | AJ305238 | clade_537 | Y | N |

TABLE 1-continued

See, e.g., WO2014/121304

| OTU | SEQ ID Number | Public DB Accession | Clade | Spore Former | Pathogen Status |
|---|---|---|---|---|---|
| *Clostridium* sp. YIT 12069 | 641 | AB491207 | clade_537 | Y | N |
| *Clostridium sporosphaeroides* | 646 | NR_044835 | clade_537 | Y | N |
| *Eubacterium coprostanoligenes* | 841 | HM037995 | clade_537 | Y | N |
| *Ruminococcus bromii* | 1657 | EU266549 | clade_537 | Y | N |
| *Eubacterium siraeum* | 860 | ABCA03000054 | clade_538 | Y | N |
| *Clostridium viride* | 657 | NR_026204 | clade_540 | Y | N |
| *Oscillibacter* sp. G2 | 1386 | HM626173 | clade_540 | Y | N |
| *Oscillibacter valericigenes* | 1387 | NR_074793 | clade_540 | Y | N |
| *Oscillospira guilliermondii* | 1388 | AB040495 | clade_540 | Y | N |
| *Butyrivibrio crossotus* | 455 | ABWN01000012 | clade_543 | Y | N |
| *Clostridium* sp. L2_50 | 631 | AAYW02000018 | clade_543 | Y | N |
| *Coprococcus eutactus* | 675 | EF031543 | clade_543 | Y | N |
| *Coprococcus* sp. ART55_1 | 676 | AY350746 | clade_543 | Y | N |
| *Eubacterium ruminantium* | 857 | NR_024661 | clade_543 | Y | N |
| *Collinsella aerofaciens* | 659 | AAVN02000007 | clade_553 | Y | N |
| *Alkaliphilus metalliredigenes* | 137 | AY137848 | clade_554 | Y | N |
| *Alkaliphilus oremlandii* | 138 | NR_043674 | clade_554 | Y | N |
| *Clostridium sticklandii* | 648 | L04167 | clade_554 | Y | N |
| *Turicibacter sanguinis* | 1965 | AF349724 | clade_555 | Y | N |
| *Fulvimonas* sp. NML 060897 | 892 | EF589680 | clade_557 | Y | N |
| *Desulfitobacterium frappieri* | 753 | AJ276701 | clade_560 | Y | N |
| *Desulfitobacterium hafniense* | 754 | NR_074996 | clade_560 | Y | N |
| *Desulfotomaculum nigrificans* | 756 | NR_044832 | clade_560 | Y | N |
| *Lutispora thermophila* | 1191 | NR_041236 | clade_564 | Y | N |
| *Brachyspira pilosicoli* | 405 | NR_075069 | clade_565 | Y | N |
| *Eggerthella lenta* | 778 | AF292375 | clade_566 | Y | N |
| *Streptomyces albus* | 1888 | AJ697941 | clade_566 | Y | N |
| Chlamydiales bacterium NS11 | 505 | JN606074 | clade_567 | Y | N |
| *Anaerofustis stercorihominis* | 159 | ABIL02000005 | clade_570 | Y | N |
| *Butyricicoccus pullicaecorum* | 453 | HH793440 | clade_572 | Y | N |
| *Eubacterium desmolans* | 843 | NR_044644 | clade_572 | Y | N |
| *Papillibacter cinnamivorans* | 1415 | NR_025025 | clade_572 | Y | N |
| *Sporobacter termitidis* | 1751 | NR_044972 | clade_572 | Y | N |
| *Deferribacteres* sp. oral clone JV006 | 744 | AY349371 | clade_575 | Y | N |
| *Clostridium colinum* | 577 | NR_026151 | clade_576 | Y | N |
| *Clostridium lactatifermentans* | 599 | NR_025651 | clade_576 | Y | N |
| *Clostridium piliforme* | 614 | D14639 | clade_576 | Y | N |
| *Saccharomonospora viridis* | 1671 | X54286 | clade_579 | Y | N |
| *Thermobifida fusca* | 1921 | NC_007333 | clade_579 | Y | N |
| *Leptospira licerasiae* | 1164 | EF612284 | clade_585 | Y | OP |
| *Moorella thermoacetica* | 1259 | NR_075001 | clade_590 | Y | N |
| *Thermoanaerobacter pseudethanolicus* | 1920 | CP000924 | clade_590 | Y | N |
| *Flexistipes sinusarabici* | 888 | NR_074881 | clade_591 | Y | N |
| *Gloeobacter violaceus* | 942 | NR_074282 | clade_596 | Y | N |
| *Eubacterium* sp. oral clone JN088 | 869 | AY349377 | clade_90 | Y | N |
| *Clostridium oroticum* | 610 | FR749922 | clade_96 | Y | N |
| *Clostridium* sp. D5 | 627 | ADBG01000142 | clade_96 | Y | N |
| *Eubacterium contortum* | 840 | FR749946 | clade_96 | Y | N |
| *Eubacterium fissicatena* | 846 | FR749935 | clade_96 | Y | N |
| *Corynebacterium coyleae* | 692 | X96497 | clade_100 | N | N |
| *Corynebacterium mucifaciens* | 711 | NR_026396 | clade_100 | N | N |
| *Corynebacterium ureicelerivorans* | 733 | AM397636 | clade_100 | N | N |
| *Corynebacterium appendicis* | 684 | NR_028951 | clade_102 | N | N |
| *Corynebacterium genitalium* | 698 | ACLJ01000031 | clade_102 | N | N |
| *Corynebacterium glaucum* | 699 | NR_028971 | clade_102 | N | N |
| *Corynebacterium imitans* | 703 | AF537597 | clade_102 | N | N |
| *Corynebacterium riegelii* | 719 | EU848548 | clade_102 | N | N |
| *Corynebacterium* sp. L_2012475 | 723 | HE575405 | clade_102 | N | N |
| *Corynebacterium* sp. NML 93_0481 | 724 | GU238409 | clade_102 | N | N |
| *Corynebacterium sundsvallense* | 728 | Y09655 | clade_102 | N | N |
| *Corynebacterium tuscaniae* | 730 | AY677186 | clade_102 | N | N |
| *Prevotella maculosa* | 1504 | AGEK01000035 | clade_104 | N | N |
| *Prevotella oris* | 1513 | ADDV01000091 | clade_104 | N | N |
| *Prevotella salivae* | 1517 | AB108826 | clade_104 | N | N |
| *Prevotella* sp. ICM55 | 1521 | HQ616399 | clade_104 | N | N |
| *Prevotella* sp. oral clone AA020 | 1528 | AY005057 | clade_104 | N | N |
| *Prevotella* sp. oral clone GI032 | 1538 | AY349396 | clade_104 | N | N |
| *Prevotella* sp. oral taxon G70 | 1558 | GU432179 | clade_104 | N | N |
| *Prevotella corporis* | 1491 | L16465 | clade_105 | N | N |
| *Bacteroides* sp. 4_1_36 | 312 | ACTC01000133 | clade_110 | N | N |
| *Bacteroides* sp. AR20 | 315 | AF139524 | clade_110 | N | N |
| *Bacteroides* sp. D20 | 319 | ACPT01000052 | clade_110 | N | N |
| *Bacteroides* sp. F_4 | 322 | AB470322 | clade_110 | N | N |
| *Bacteroides uniformis* | 329 | AB050110 | clade_110 | N | N |
| *Prevotella nanceiensis* | 1510 | JN867228 | clade_127 | N | N |

TABLE 1-continued

See, e.g., WO2014/121304

| OTU | SEQ ID Number | Public DB Accession | Clade | Spore Former | Pathogen Status |
|---|---|---|---|---|---|
| *Prevotella* sp. oral taxon 299 | 1548 | ACWZ01000026 | clade_127 | N | N |
| *Prevotella bergensis* | 1485 | ACKS01000100 | clade_128 | N | N |
| *Prevotella buccalis* | 1489 | JN867261 | clade_129 | N | N |
| *Prevotella timonensis* | 1564 | ADEF01000012 | clade_129 | N | N |
| *Prevotella oralis* | 1512 | AEPE01000021 | clade_130 | N | N |
| *Prevotella* sp. SEQ072 | 1525 | JN867238 | clade_130 | N | N |
| *Leuconostoc carnosum* | 1177 | NR_040811 | clade_135 | N | N |
| *Leuconostoc gasicomitatum* | 1179 | FN822744 | clade_135 | N | N |
| *Leuconostoc inhae* | 1180 | NR_025204 | clade_135 | N | N |
| *Leuconostoc kimchii* | 1181 | NR_075014 | clade_135 | N | N |
| *Edwardsiella tarda* | 777 | CP002154 | clade_139 | N | N |
| *Photorhabdus asymbiotica* | 1466 | Z76752 | clade_139 | N | N |
| *Psychrobacter arcticus* | 1607 | CP000082 | clade_141 | N | N |
| *Psychrobacter cibarius* | 1608 | HQ698586 | clade_141 | N | N |
| *Psychrobacter cryohalolentis* | 1609 | CP000323 | clade_141 | N | N |
| *Psychrobacter faecalis* | 1610 | HQ698566 | clade_141 | N | N |
| *Psychrobacter nivimaris* | 1611 | HQ698587 | clade_141 | N | N |
| *Psychrobacter pulmonis* | 1612 | HQ698582 | clade_141 | N | N |
| *Pseudomonas aeruginosa* | 1592 | AABQ07000001 | clade_154 | N | N |
| *Pseudomonas* sp. 2_1_26 | 1600 | ACWU01000257 | clade_154 | N | N |
| *Corynebacterium confusum* | 691 | Y15886 | clade_158 | N | N |
| *Corynebacterium propinquum* | 712 | NR_037038 | clade_158 | N | N |
| *Corynebacterium pseudodiphtheriticum* | 713 | X84258 | clade_158 | N | N |
| *Bartonella bacilliformis* | 338 | NC_008783 | clade_159 | N | N |
| *Bartonella grahamii* | 339 | CP001562 | clade_159 | N | N |
| *Bartonella henselae* | 340 | NC_005956 | clade_159 | N | N |
| *Bartonella quintana* | 341 | BX897700 | clade_159 | N | N |
| *Bartonella tamiae* | 342 | EF672728 | clade_159 | N | N |
| *Bartonella washoensis* | 343 | FJ719017 | clade_159 | N | N |
| *Brucella abortus* | 430 | ACBJ01000075 | clade_159 | N | Category-B |
| *Brucella canis* | 431 | NR_044652 | clade_159 | N | Category-B |
| *Brucella ceti* | 432 | ACJD01000006 | clade_159 | N | Category-B |
| *Brucella melitensis* | 433 | AE009462 | clade_159 | N | Category-B |
| *Brucella microti* | 434 | NR_042549 | clade_159 | N | Category-B |
| *Brucella ovis* | 435 | NC_009504 | clade_159 | N | Category-B |
| *Brucella* sp. 83_13 | 436 | ACBQ01000040 | clade_159 | N | Category-B |
| *Brucella* sp. BO1 | 437 | EU053207 | clade_159 | N | Category-B |
| *Brucella suis* | 438 | ACBK01000034 | clade_159 | N | Category-B |
| *Ochrobactrum anthropi* | 1360 | NC_009667 | clade_159 | N | N |
| *Ochrobactrum intermedium* | 1361 | ACQA01000001 | clade_159 | N | N |
| *Ochrobactrum pseudintermedium* | 1362 | DQ365921 | clade_159 | N | N |
| *Prevotella* genomsp. C2 | 1496 | AY278625 | clade_164 | N | N |
| *Prevotella multisaccharivorax* | 1509 | AFJE01000016 | clade_164 | N | N |
| *Prevotella* sp. oral clone IDR_CEC_0055 | 1543 | AY550997 | clade_164 | N | N |
| *Prevotella* sp. oral taxon 292 | 1547 | GQ422735 | clade_164 | N | N |
| *Prevotella* sp. oral taxon 300 | 1549 | GU409549 | clade_164 | N | N |
| *Prevotella marshii* | 1505 | AEEI01000070 | clade_166 | N | N |
| *Prevotella* sp. oral clone IK053 | 1544 | AY349401 | clade_166 | N | N |
| *Prevotella* sp. oral taxon 781 | 1554 | GQ422744 | clade_166 | N | N |
| *Prevotella stercorea* | 1562 | AB244774 | clade_166 | N | N |
| *Prevotella brevis* | 1487 | NR_041954 | clade_167 | N | N |
| *Prevotella ruminicola* | 1516 | CP002006 | clade_167 | N | N |
| *Prevotella* sp. sp24 | 1560 | AB003384 | clade_167 | N | N |
| *Prevotella* sp. sp34 | 1561 | AB003385 | clade_167 | N | N |
| *Prevotella albensis* | 1483 | NR_025300 | clade_168 | N | N |
| *Prevotella copri* | 1490 | ACBX02000014 | clade_168 | N | N |
| *Prevotella oulorum* | 1514 | L16472 | clade_168 | N | N |
| *Prevotella* sp. BI_42 | 1518 | AJ581354 | clade_168 | N | N |
| *Prevotella* sp. oral clone P4PB_83 P2 | 1546 | AY207050 | clade_168 | N | N |
| *Prevotella* sp. oral taxon G60 | 1557 | GU432133 | clade_168 | N | N |
| *Prevotella amnii* | 1484 | AB547670 | clade_169 | N | N |
| *Bacteroides caccae* | 268 | EU136686 | clade_170 | N | N |
| *Bacteroides finegoldii* | 277 | AB222699 | clade_170 | N | N |
| *Bacteroides intestinalis* | 283 | ABJL02000006 | clade_171 | N | N |
| *Bacteroides* sp. XB44A | 326 | AM230649 | clade_171 | N | N |
| Bifidobacteriaceae genomsp. C1 | 345 | AY278612 | clade_172 | N | N |
| *Bifidobacterium adolescentis* | 346 | AAXD02000018 | clade_172 | N | N |
| *Bifidobacterium angulatum* | 347 | ABYS02000004 | clade_172 | N | N |
| *Bifidobacterium animalis* | 348 | CP001606 | clade_172 | N | N |
| *Bifidobacterium breve* | 350 | CP002743 | clade_172 | N | N |
| *Bifidobacterium catenulatum* | 351 | ABXY01000019 | clade_172 | N | N |
| *Bifidobacterium dentium* | 352 | CP001750 | clade_172 | N | OP |
| *Bifidobacterium gallicum* | 353 | ABXB03000004 | clade_172 | N | N |
| *Bifidobacterium infantis* | 354 | AY151398 | clade_172 | N | N |
| *Bifidobacterium kashiwanohense* | 355 | AB491757 | clade_172 | N | N |

TABLE 1-continued

See, e.g., WO2014/121304

| OTU | SEQ ID Number | Public DB Accession | Clade | Spore Former | Pathogen Status |
|---|---|---|---|---|---|
| *Bifidobacterium longum* | 356 | ABQQ01000041 | clade_172 | N | N |
| *Bifidobacterium pseudocatenulatum* | 357 | ABXX02000002 | clade_172 | N | N |
| *Bifidobacterium pseudolongum* | 358 | NR_043442 | clade_172 | N | N |
| *Bifidobacterium scardovii* | 359 | AJ307005 | clade_172 | N | N |
| *Bifidobacterium* sp. HM2 | 360 | AB425276 | clade_172 | N | N |
| *Bifidobacterium* sp. HMLN12 | 361 | JF519685 | clade_172 | N | N |
| *Bifidobacterium* sp. M45 | 362 | HM626176 | clade_172 | N | N |
| *Bifidobacterium* sp. MSX5B | 363 | HQ616382 | clade_172 | N | N |
| *Bifidobacterium* sp. TM_7 | 364 | AB218972 | clade_172 | N | N |
| *Bifidobacterium thermophilum* | 365 | DQ340557 | clade_172 | N | N |
| *Leuconostoc citreum* | 1178 | AM157444 | clade_175 | N | N |
| *Leuconostoc lactis* | 1182 | NR_040823 | clade_175 | N | N |
| *Alicyclobacillus acidoterrestris* | 123 | NR_040844 | clade_179 | N | N |
| *Alicyclobacillus cycloheptanicus* | 125 | NR_024754 | clade_179 | N | N |
| *Acinetobacter baumannii* | 27 | ACYQ01000014 | clade_181 | N | N |
| *Acinetobacter calcoaceticus* | 28 | AM157426 | clade_181 | N | N |
| *Acinetobacter* genomosp. C1 | 29 | AY278636 | clade_181 | N | N |
| *Acinetobacter haemolyticus* | 30 | ADMT01000017 | clade_181 | N | N |
| *Acinetobacter johnsonii* | 31 | ACPL01000162 | clade_181 | N | N |
| *Acinetobacter junii* | 32 | ACPM01000135 | clade_181 | N | N |
| *Acinetobacter lwoffii* | 33 | ACPN01000204 | clade_181 | N | N |
| *Acinetobacter parvus* | 34 | AIEB01000124 | clade_181 | N | N |
| *Acinetobacter schindleri* | 36 | NR_025412 | clade_181 | N | N |
| *Acinetobacter* sp. 56A1 | 37 | GQ178049 | clade_181 | N | N |
| *Acinetobacter* sp. CIP 101934 | 38 | JQ638573 | clade_181 | N | N |
| *Acinetobacter* sp. CIP 102143 | 39 | JQ638578 | clade_181 | N | N |
| *Acinetobacter* sp. M16_22 | 41 | HM366447 | clade_181 | N | N |
| *Acinetobacter* sp. RUH2624 | 42 | ACQF01000094 | clade_181 | N | N |
| *Acinetobacter* sp. SH024 | 43 | ADCH01000068 | clade_181 | N | N |
| *Lactobacillus jensenii* | 1092 | ACQD01000066 | clade_182 | N | N |
| *Alcaligenes faecalis* | 119 | AB680368 | clade_183 | N | N |
| *Alcaligenes* sp. CO14 | 120 | DQ643040 | clade_183 | N | N |
| *Alcaligenes* sp. S3 | 121 | HQ262549 | clade_183 | N | N |
| *Oligella ureolytica* | 1366 | NR_041998 | clade_183 | N | N |
| *Oligella urethralis* | 1367 | NR_041753 | clade_183 | N | N |
| *Eikenella corrodens* | 784 | ACEA01000028 | clade_185 | N | N |
| *Kingella denitrificans* | 1019 | AEWV01000047 | clade_185 | N | N |
| *Kingella* genomosp. P1 oral cone MB2_C20 | 1020 | DQ003616 | clade_185 | N | N |
| *Kingella kingae* | 1021 | AFHS01000073 | clade_185 | N | N |
| *Kingella oralis* | 1022 | ACJW02000005 | clade_185 | N | N |
| *Kingella* sp. oral clone ID059 | 1023 | AY349381 | clade_185 | N | N |
| *Neisseria elongata* | 1330 | ADBF01000003 | clade_185 | N | N |
| *Neisseria* genomosp. P2 oral clone MB5_P15 | 1332 | DQ003630 | clade_185 | N | N |
| *Neisseria* sp. oral clone JC012 | 1345 | AY349388 | clade_185 | N | N |
| *Neisseria* sp. SMC_A9199 | 1342 | FJ763637 | clade_185 | N | N |
| *Simonsiella muelleri* | 1731 | ADCY01000105 | clade_185 | N | N |
| *Corynebacterium glucuronolyticum* | 700 | ABYP01000081 | clade_193 | N | N |
| *Corynebacterium pyruviciproducens* | 716 | FJ185225 | clade_193 | N | N |
| *Rothia aeria* | 1649 | DQ673320 | clade_194 | N | N |
| *Rothia dentocariosa* | 1650 | ADDW01000024 | clade_194 | N | N |
| *Rothia* sp. oral taxon 188 | 1653 | GU470892 | clade_194 | N | N |
| *Corynebacterium accolens* | 681 | ACGD01000048 | clade_195 | N | N |
| *Corynebacterium macginleyi* | 707 | AB359393 | clade_195 | N | N |
| *Corynebacterium pseudogenitalium* | 714 | ABYQ01000237 | clade_195 | N | N |
| *Corynebacterium tuberculostearicum* | 729 | ACVP01000009 | clade_195 | N | N |
| *Lactobacillus casei* | 1074 | CP000423 | clade_198 | N | N |
| *Lactobacillus paracasei* | 1106 | ABQV01000067 | clade_198 | N | N |
| *Lactobacillus zeae* | 1143 | NR_037122 | clade_198 | N | N |
| *Prevotella dentalis* | 1492 | AB547678 | clade_205 | N | N |
| *Prevotella* sp. oral clone ASCG10 | 1529 | AY923148 | clade_206 | N | N |
| *Prevotella* sp. oral clone HF050 | 1541 | AY349399 | clade_206 | N | N |
| *Prevotella* sp. oral clone ID019 | 1542 | AY349400 | clade_206 | N | N |
| *Prevotella* sp. oral clone IK062 | 1545 | AY349402 | clade_206 | N | N |
| *Prevotella* genomosp. P9 oral clone MB7_G16 | 1499 | DQ003633 | clade_207 | N | N |
| *Prevotella* sp. oral clone AU069 | 1531 | AY005062 | clade_207 | N | N |
| *Prevotella* sp. oral clone CY006 | 1532 | AY005063 | clade_207 | N | N |
| *Prevotella* sp. oral clone FL019 | 1534 | AY349392 | clade_207 | N | N |
| *Actinomyces* genomosp. C1 | 56 | AY278610 | clade_212 | N | N |
| *Actinomyces* genomosp. C2 | 57 | AY278611 | clade_212 | N | N |
| *Actinomyces* genomosp. P1 oral clone MB6_C03 | 58 | DQ003632 | clade_212 | N | N |
| *Actinomyces georgiae* | 59 | GU561319 | clade_212 | N | N |
| *Actinomyces israelii* | 60 | AF479270 | clade_212 | N | N |
| *Actinomyces massiliensis* | 61 | AB545934 | clade_212 | N | N |
| *Actinomyces meyeri* | 62 | GU561321 | clade_212 | N | N |
| *Actinomyces odontolyticus* | 66 | ACYT01000123 | clade_212 | N | N |

TABLE 1-continued

See, e.g., WO2014/121304

| OTU | SEQ ID Number | Public DB Accession | Clade | Spore Former | Pathogen Status |
|---|---|---|---|---|---|
| *Actinomyces orihominis* | 68 | AJ575186 | clade_212 | N | N |
| *Actinomyces* sp. CCUG 37290 | 71 | AJ234058 | clade_212 | N | N |
| *Actinomyces* sp. ICM34 | 75 | HQ616391 | clade_212 | N | N |
| *Actinomyces* sp. ICM41 | 76 | HQ616392 | clade_212 | N | N |
| *Actinomyces* sp. ICM47 | 77 | HQ616395 | clade_212 | N | N |
| *Actinomyces* sp. ICM54 | 78 | HQ616398 | clade_212 | N | N |
| *Actinomyces* sp. oral clone IP081 | 87 | AY349366 | clade_212 | N | N |
| *Actinomyces* sp. oral taxon 178 | 91 | AEUH01000060 | clade_212 | N | N |
| *Actinomyces* sp. oral taxon 180 | 92 | AEPP01000041 | clade_212 | N | N |
| *Actinomyces* sp. TeJ5 | 80 | GU561315 | clade_212 | N | N |
| *Haematobacter* sp. BC14248 | 968 | GU396991 | clade_213 | N | N |
| *Paracoccus denitrificans* | 1424 | CP000490 | clade_213 | N | N |
| *Paracoccus marcusii* | 1425 | NR_044922 | clade_213 | N | N |
| *Grimontia hollisae* | 967 | ADAQ01000013 | clade_216 | N | N |
| *Shewanella putrefaciens* | 1723 | CP002457 | clade_216 | N | N |
| *Afipia* genomosp. 4 | 111 | EU117385 | clade_217 | N | N |
| *Rhodopseudomonas palustris* | 1626 | CP000301 | clade_217 | N | N |
| *Methylobacterium extorquens* | 1223 | NC_010172 | clade_218 | N | N |
| *Methylobacterium podarium* | 1224 | AY468363 | clade_218 | N | N |
| *Methylobacterium radiotolerans* | 1225 | GU294320 | clade_218 | N | N |
| *Methylobacterium* sp. 1sub | 1226 | AY468371 | clade_218 | N | N |
| *Methylobacterium* sp. MM4 | 1227 | AY468370 | clade_218 | N | N |
| *Achromobacter denitrificans* | 18 | NR_042021 | clade_224 | N | N |
| *Achromobacter piechaudii* | 19 | ADMS01000149 | clade_224 | N | N |
| *Achromobacter xylosoxidans* | 20 | ACRC01000072 | clade_224 | N | N |
| *Bordetella bronchiseptica* | 384 | NR_025949 | clade_224 | N | OP |
| *Bordetella holmesii* | 385 | AB683187 | clade_224 | N | OP |
| *Bordetella parapertussis* | 386 | NR_025950 | clade_224 | N | OP |
| *Bordetella pertussis* | 387 | BX640418 | clade_224 | N | OP |
| *Microbacterium chocolatum* | 1230 | NR_037045 | clade_225 | N | N |
| *Microbacterium flavescens* | 1231 | EU714363 | clade_225 | N | N |
| *Microbacterium lacticum* | 1233 | EU714351 | clade_225 | N | N |
| *Microbacterium oleivorans* | 1234 | EU714381 | clade_225 | N | N |
| *Microbacterium oxydans* | 1235 | EU714348 | clade_225 | N | N |
| *Microbacterium paraoxydans* | 1236 | AJ491806 | clade_225 | N | N |
| *Microbacterium phyllosphaerae* | 1237 | EU714359 | clade_225 | N | N |
| *Microbacterium schleiferi* | 1238 | NR_044936 | clade_225 | N | N |
| *Microbacterium* sp. 768 | 1239 | EU714378 | clade_225 | N | N |
| *Microbacterium* sp. oral strain C24KA | 1240 | AF287752 | clade_225 | N | N |
| *Microbacterium testaceum* | 1241 | EU714365 | clade_225 | N | N |
| *Corynebacterium atypicum* | 686 | NR_025540 | clade_229 | N | N |
| *Corynebacterium mastitidis* | 708 | AB359395 | clade_229 | N | N |
| *Corynebacterium* sp. NML 97_0186 | 725 | GU238411 | clade_229 | N | N |
| *Mycobacterium elephantis* | 1275 | AF385898 | clade_237 | N | OP |
| *Mycobacterium paraterrae* | 1288 | EU919229 | clade_237 | N | OP |
| *Mycobacterium phlei* | 1289 | GU142920 | clade_237 | N | OP |
| *Mycobacterium* sp. 1776 | 1293 | EU703152 | clade_237 | N | N |
| *Mycobacterium* sp. 1781 | 1294 | EU703147 | clade_237 | N | N |
| *Mycobacterium* sp. AQ1GA4 | 1297 | HM210417 | clade_237 | N | N |
| *Mycobacterium* sp. GN_10546 | 1299 | FJ497243 | clade_237 | N | N |
| *Mycobacterium* sp. GN_10827 | 1300 | FJ497247 | clade_237 | N | N |
| *Mycobacterium* sp. GN_11124 | 1301 | FJ652846 | clade_237 | N | N |
| *Mycobacterium* sp. GN_9188 | 1302 | FJ497240 | clade_237 | N | N |
| *Mycobacterium* sp. GR_2007_210 | 1303 | FJ555538 | clade_237 | N | N |
| *Anoxybacillus contaminans* | 172 | NR_029006 | clade_238 | N | N |
| *Bacillus aeolius* | 195 | NR_025557 | clade_238 | N | N |
| *Brevibacterium frigoritolerans* | 422 | NR_042639 | clade_238 | N | N |
| *Geobacillus* sp. E263 | 934 | DQ647387 | clade_238 | N | N |
| *Geobacillus* sp. WCH70 | 935 | CP001638 | clade_238 | N | N |
| *Geobacillus thermocatenulatus* | 937 | NR_043020 | clade_238 | N | N |
| *Geobacillus thermoleovorans* | 940 | NR_074931 | clade_238 | N | N |
| *Lysinibacillus fusiformis* | 1192 | FN397522 | clade_238 | N | N |
| *Planomicrobium koreense* | 1468 | NR_025011 | clade_238 | N | N |
| *Sporosarcina newyorkensis* | 1754 | AFPZ01000142 | clade_238 | N | N |
| *Sporosarcina* sp. 2681 | 1755 | GU994081 | clade_238 | N | N |
| *Ureibacillus composti* | 1968 | NR_043746 | clade_238 | N | N |
| *Ureibacillus suwonensis* | 1969 | NR_043232 | clade_238 | N | N |
| *Ureibacillus terrenus* | 1970 | NR_025394 | clade_238 | N | N |
| *Ureibacillus thermophilus* | 1971 | NR_043747 | clade_238 | N | N |
| *Ureibacillus thermosphaericus* | 1972 | NR_040961 | clade_238 | N | N |
| *Prevotella micans* | 1507 | AGWK01000061 | clade_239 | N | N |
| *Prevotella* sp. oral clone DA058 | 1533 | AY005065 | clade_239 | N | N |
| *Prevotella* sp. SEQ053 | 1523 | JN867222 | clade_239 | N | N |
| *Treponema socranskii* | 1937 | NR_024868 | clade_240 | N | OP |
| *Treponema* sp. 6:H:D15A_4 | 1938 | AY005083 | clade_240 | N | N |

TABLE 1-continued

See, e.g., WO2014/121304

| OTU | SEQ ID Number | Public DB Accession | Clade | Spore Former | Pathogen Status |
|---|---|---|---|---|---|
| *Treponema* sp. oral taxon 265 | 1953 | GU408850 | clade_240 | N | N |
| *Treponema* sp. oral taxon G85 | 1958 | GU432215 | clade_240 | N | N |
| *Porphyromonas endodontalis* | 1472 | ACNN01000021 | clade_241 | N | N |
| *Porphyromonas* sp. oral clone BB134 | 1478 | AY005068 | clade_241 | N | N |
| *Porphyromonas* sp. oral clone F016 | 1479 | AY005069 | clade_241 | N | N |
| *Porphyromonas* sp. oral clone P2PB_52 P1 | 1480 | AY207054 | clade_241 | N | N |
| *Porphyromonas* sp. oral clone P4GB_100 P2 | 1481 | AY207057 | clade_241 | N | N |
| *Acidovorax* sp. 98_63833 | 26 | AY258065 | clade_245 | N | N |
| Comamonadaceae bacterium NML000135 | 663 | JN585335 | clade_245 | N | N |
| Comamonadaceae bacterium NML790751 | 664 | JN585331 | clade_245 | N | N |
| Comamonadaceae bacterium NML910035 | 665 | JN585332 | clade_245 | N | N |
| Comamonadaceae bacterium NML910036 | 666 | JN585333 | clade_245 | N | N |
| *Comamonas* sp. NSP5 | 668 | AB076850 | clade_245 | N | N |
| *Delftia acidovorans* | 748 | CP000884 | clade_245 | N | N |
| *Xenophilus aerolatus* | 2018 | JN585329 | clade_245 | N | N |
| *Oribacterium* sp. oral taxon 078 | 1380 | ACIQ02000009 | clade_246 | N | N |
| *Oribacterium* sp. oral taxon 102 | 1381 | GQ422713 | clade_246 | N | N |
| *Weissella cibaria* | 2007 | NR_036924 | clade_247 | N | N |
| *Weissella confusa* | 2008 | NR_040816 | clade_247 | N | N |
| *Weissella hellenica* | 2009 | AB680902 | clade_247 | N | N |
| *Weissella kandleri* | 2010 | NR_044659 | clade_247 | N | N |
| *Weissella koreensis* | 2011 | NR_075058 | clade_247 | N | N |
| *Weissella paramesenteroides* | 2012 | ACKU01000017 | clade_247 | N | N |
| *Weissella* sp. KLDS 7.0701 | 2013 | EU600924 | clade_247 | N | N |
| *Mobiluncus curtisii* | 1251 | AEPZ01000013 | clade_249 | N | N |
| *Enhydrobacter aerosaccus* | 785 | ACYI01000081 | clade_256 | N | N |
| *Moraxella osloensis* | 1262 | JN175341 | clade_256 | N | N |
| *Moraxella* sp. GM2 | 1264 | JF837191 | clade_256 | N | N |
| *Brevibacterium casei* | 420 | JF951998 | clade_257 | N | N |
| *Brevibacterium epidermidis* | 421 | NR_029262 | clade_257 | N | N |
| *Brevibacterium sanguinis* | 426 | NR_028016 | clade_257 | N | N |
| *Brevibacterium* sp. H15 | 427 | AB177640 | clade_257 | N | N |
| *Acinetobacter radioresistens* | 35 | ACVR01000010 | clade_261 | N | N |
| *Lactobacillus alimentarius* | 1068 | NR_044701 | clade_263 | N | N |
| *Lactobacillus farciminis* | 1082 | NR_044707 | clade_263 | N | N |
| *Lactobacillus kimchii* | 1097 | NR_025045 | clade_263 | N | N |
| *Lactobacillus nodensis* | 1101 | NR_041629 | clade_263 | N | N |
| *Lactobacillus tucceti* | 1138 | NR_042194 | clade_263 | N | N |
| *Pseudomonas mendocina* | 1595 | AAUL01000021 | clade_265 | N | N |
| *Pseudomonas pseudoalcaligenes* | 1598 | NR_037000 | clade_265 | N | N |
| *Pseudomonas* sp. NP522b | 1602 | EU723211 | clade_265 | N | N |
| *Pseudomonas stutzeri* | 1603 | AM905854 | clade_265 | N | N |
| *Paenibacillus barcinonensis* | 1390 | NR_042272 | clade_270 | N | N |
| *Paenibacillus barengoltzii* | 1391 | NR_042756 | clade_270 | N | N |
| *Paenibacillus chibensis* | 1392 | NR_040885 | clade_270 | N | N |
| *Paenibacillus cookii* | 1393 | NR_025372 | clade_270 | N | N |
| *Paenibacillus durus* | 1394 | NR_037017 | clade_270 | N | N |
| *Paenibacillus glucanolyticus* | 1395 | D78470 | clade_270 | N | N |
| *Paenibacillus lactis* | 1396 | NR_025739 | clade_270 | N | N |
| *Paenibacillus pabuli* | 1398 | NR_040853 | clade_270 | N | N |
| *Paenibacillus popilliae* | 1400 | NR_040888 | clade_270 | N | N |
| *Paenibacillus* sp. CIP 101062 | 1401 | HM212646 | clade_270 | N | N |
| *Paenibacillus* sp. JC66 | 1404 | JF824808 | clade_270 | N | N |
| *Paenibacillus* sp. R_27413 | 1405 | HE586333 | clade_270 | N | N |
| *Paenibacillus* sp. R_27422 | 1406 | HE586338 | clade_270 | N | N |
| *Paenibacillus timonensis* | 1408 | NR_042844 | clade_270 | N | N |
| *Rothia mucilaginosa* | 1651 | ACVO01000020 | clade_271 | N | N |
| *Rothia nasimurium* | 1652 | NR_025310 | clade_271 | N | N |
| *Prevotella* sp. oral taxon 302 | 1550 | ACZK01000043 | clade_280 | N | N |
| *Prevotella* sp. oral taxon F68 | 1556 | HM099652 | clade_280 | N | N |
| *Prevotella tannerae* | 1563 | ACIJ02000018 | clade_280 | N | N |
| Prevotellaceae bacterium P4P_62 P1 | 1566 | AY207061 | clade_280 | N | N |
| *Porphyromonas asaccharolytica* | 1471 | AENO01000048 | clade_281 | N | N |
| *Porphyromonas gingivalis* | 1473 | AE015924 | clade_281 | N | N |
| *Porphyromonas macacae* | 1475 | NR_025908 | clade_281 | N | N |
| *Porphyromonas* sp. UQD 301 | 1477 | EU012301 | clade_281 | N | N |
| *Porphyromonas uenonis* | 1482 | ACLR01000152 | clade_281 | N | N |
| *Leptotrichia buccalis* | 1165 | CP001685 | clade_282 | N | N |
| *Leptotrichia hofstadii* | 1168 | ACVB02000032 | clade_282 | N | N |
| *Leptotrichia* sp. oral clone HE012 | 1173 | AY349386 | clade_282 | N | N |
| *Leptotrichia* sp. oral taxon 223 | 1176 | GU408547 | clade_282 | N | N |
| *Bacteroides fluxus* | 278 | AFBN01000029 | clade_285 | N | N |
| *Bacteroides helcogenes* | 281 | CP002352 | clade_285 | N | N |
| *Parabacteroides johnsonii* | 1419 | ABYH01000014 | clade_286 | N | N |
| *Parabacteroides merdae* | 1420 | EU136685 | clade_286 | N | N |

TABLE 1-continued

See, e.g., WO2014/121304

| OTU | SEQ ID Number | Public DB Accession | Clade | Spore Former | Pathogen Status |
|---|---|---|---|---|---|
| *Treponema denticola* | 1926 | ADEC01000002 | clade_288 | N | OP |
| *Treponema* genomosp. P5 oral clone MB3_P23 | 1929 | DQ003624 | clade_288 | N | N |
| *Treponema putidum* | 1935 | AJ543428 | clade_288 | N | OP |
| *Treponema* sp. oral clone P2PB_53 P3 | 1942 | AY207055 | clade_288 | N | N |
| *Treponema* sp. oral taxon 247 | 1949 | GU408748 | clade_288 | N | N |
| *Treponema* sp. oral taxon 250 | 1950 | GU408776 | clade_288 | N | N |
| *Treponema* sp. oral taxon 251 | 1951 | GU408781 | clade_288 | N | N |
| *Anaerococcus hydrogenalis* | 144 | ABXA01000039 | clade_289 | N | N |
| *Anaerococcus* sp. 8404299 | 148 | HM587318 | clade_289 | N | N |
| *Anaerococcus* sp. gpac215 | 156 | AM176540 | clade_289 | N | N |
| *Anaerococcus vaginalis* | 158 | ACXU01000016 | clade_289 | N | N |
| *Propionibacterium acidipropionici* | 1569 | NC_019395 | clade_290 | N | N |
| *Propionibacterium avidum* | 1571 | AJ003055 | clade_290 | N | N |
| *Propionibacterium granulosum* | 1573 | FJ785716 | clade_290 | N | N |
| *Propionibacterium jensenii* | 1574 | NR_042269 | clade_290 | N | N |
| *Propionibacterium propionicum* | 1575 | NR_025277 | clade_290 | N | N |
| *Propionibacterium* sp. H456 | 1577 | AB177643 | clade_290 | N | N |
| *Propionibacterium thoenii* | 1581 | NR_042270 | clade_290 | N | N |
| *Bifidobacterium bifidum* | 349 | ABQP01000027 | clade_293 | N | N |
| *Leuconostoc mesenteroides* | 1183 | ACKV01000113 | clade_295 | N | N |
| *Leuconostoc pseudomesenteroides* | 1184 | NR_040814 | clade_295 | N | N |
| *Johnsonella ignava* | 1016 | X87152 | clade_298 | N | N |
| *Propionibacterium acnes* | 1570 | ADJM01000010 | clade_299 | N | N |
| *Propionibacterium* sp. 434_HC2 | 1576 | AFIL01000035 | clade_299 | N | N |
| *Propionibacterium* sp. LG | 1578 | AY354921 | clade_299 | N | N |
| *Propionibacterium* sp. S555a | 1579 | AB264622 | clade_299 | N | N |
| *Alicyclobacillus* sp. CCUG 53762 | 128 | HE613268 | clade_301 | N | N |
| *Actinomyces cardiffensis* | 53 | GU470888 | clade_303 | N | N |
| *Actinomyces funkei* | 55 | HQ906497 | clade_303 | N | N |
| *Actinomyces* sp. HKU31 | 74 | HQ335393 | clade_303 | N | N |
| *Actinomyces* sp. oral taxon C55 | 94 | HM099646 | clade_303 | N | N |
| *Kerstersia gyiorum* | 1018 | NR_025669 | clade_307 | N | N |
| *Pigmentiphaga daeguensis* | 1467 | JN585327 | clade_307 | N | N |
| *Aeromonas allosaccharophila* | 104 | S39232 | clade_308 | N | N |
| *Aeromonas enteropelogenes* | 105 | X71121 | clade_308 | N | N |
| *Aeromonas hydrophila* | 106 | NC_008570 | clade_308 | N | N |
| *Aeromonas jandaei* | 107 | X60413 | clade_308 | N | N |
| *Aeromonas salmonicida* | 108 | NC_009348 | clade_308 | N | N |
| *Aeromonas trota* | 109 | X60415 | clade_308 | N | N |
| *Aeromonas veronii* | 110 | NR_044845 | clade_308 | N | N |
| *Marvinbryantia formatexigens* | 1196 | AJ505973 | clade_309 | N | N |
| *Rhodobacter* sp. oral taxon C30 | 1620 | HM099648 | clade_310 | N | N |
| *Rhodobacter sphaeroides* | 1621 | CP000144 | clade_310 | N | N |
| *Lactobacillus antri* | 1071 | ACLL01000037 | clade_313 | N | N |
| *Lactobacillus coleohominis* | 1076 | ACOH01000030 | clade_313 | N | N |
| *Lactobacillus fermentum* | 1083 | CP002033 | clade_313 | N | N |
| *Lactobacillus gastricus* | 1085 | AICN01000060 | clade_313 | N | N |
| *Lactobacillus mucosae* | 1099 | FR693800 | clade_313 | N | N |
| *Lactobacillus oris* | 1103 | AEKL01000077 | clade_313 | N | N |
| *Lactobacillus pontis* | 1111 | HM218420 | clade_313 | N | N |
| *Lactobacillus reuteri* | 1112 | ACGW02000012 | clade_313 | N | N |
| *Lactobacillus* sp. KLDS 1.0707 | 1127 | EU600911 | clade_313 | N | N |
| *Lactobacillus* sp. KLDS 1.0709 | 1128 | EU600913 | clade_313 | N | N |
| *Lactobacillus* sp. KLDS 1.0711 | 1129 | EU600915 | clade_313 | N | N |
| *Lactobacillus* sp. KLDS 1.0713 | 1131 | EU600917 | clade_313 | N | N |
| *Lactobacillus* sp. KLDS 1.0716 | 1132 | EU600921 | clade_313 | N | N |
| *Lactobacillus* sp. KLDS 1.0718 | 1133 | EU600922 | clade_313 | N | N |
| *Lactobacillus* sp. oral taxon 052 | 1137 | GQ422710 | clade_313 | N | N |
| *Lactobacillus vaginalis* | 1140 | ACGV01000168 | clade_313 | N | N |
| *Brevibacterium aurantiacum* | 419 | NR_044854 | clade_314 | N | N |
| *Brevibacterium linens* | 423 | AJ315491 | clade_314 | N | N |
| *Lactobacillus pentosus* | 1108 | JN813103 | clade_315 | N | N |
| *Lactobacillus plantarum* | 1110 | ACGZ02000033 | clade_315 | N | N |
| *Lactobacillus* sp. KLDS 1.0702 | 1123 | EU600906 | clade_315 | N | N |
| *Lactobacillus* sp. KLDS 1.0703 | 1124 | EU600907 | clade_315 | N | N |
| *Lactobacillus* sp. KLDS 1.0704 | 1125 | EU600908 | clade_315 | N | N |
| *Lactobacillus* sp. KLDS 1.0705 | 1126 | EU600909 | clade_315 | N | N |
| *Agrobacterium radiobacter* | 115 | CP000628 | clade_316 | N | N |
| *Agrobacterium tumefaciens* | 116 | AJ389893 | clade_316 | N | N |
| *Corynebacterium argentoratense* | 685 | EF463055 | clade_317 | N | N |
| *Corynebacterium diphtheriae* | 693 | NC_002935 | clade_317 | N | OP |
| *Corynebacterium pseudotuberculosis* | 715 | NR_037070 | clade_317 | N | N |
| *Corynebacterium renale* | 717 | NR_037069 | clade_317 | N | N |
| *Corynebacterium ulcerans* | 731 | NR_074467 | clade_317 | N | N |
| *Aurantimonas coralicida* | 191 | AY065627 | clade_318 | N | N |

TABLE 1-continued

See, e.g., WO2014/121304

| OTU | SEQ ID Number | Public DB Accession | Clade | Spore Former | Pathogen Status |
|---|---|---|---|---|---|
| *Aureimonas altamirensis* | 192 | FN658986 | clade_318 | N | N |
| *Lactobacillus acidipiscis* | 1066 | NR_024718 | clade_320 | N | N |
| *Lactobacillus salivarius* | 1117 | AEBA01000145 | clade_320 | N | N |
| *Lactobacillus* sp. KLDS 1.0719 | 1134 | EU600923 | clade_320 | N | N |
| *Lactobacillus buchneri* | 1073 | ACGH01000101 | clade_321 | N | N |
| *Lactobacillus* genomosp. C1 | 1086 | AY278619 | clade_321 | N | N |
| *Lactobacillus* genomosp. C2 | 1087 | AY278620 | clade_321 | N | N |
| *Lactobacillus hilgardii* | 1089 | ACGP01000200 | clade_321 | N | N |
| *Lactobacillus kefiri* | 1096 | NR_042230 | clade_321 | N | N |
| *Lactobacillus parabuchneri* | 1105 | NR_041294 | clade_321 | N | N |
| *Lactobacillus parakefiri* | 1107 | NR_029039 | clade_321 | N | N |
| *Lactobacillus curvatus* | 1079 | NR_042437 | clade_322 | N | N |
| *Lactobacillus sakei* | 1116 | DQ989236 | clade_322 | N | N |
| *Aneurinibacillus aneurinilyticus* | 167 | AB101592 | clade_323 | N | N |
| *Aneurinibacillus danicus* | 168 | NR_028657 | clade_323 | N | N |
| *Aneurinibacillus migulanus* | 169 | NR_036799 | clade_323 | N | N |
| *Aneurinibacillus terranovensis* | 170 | NR_042271 | clade_323 | N | N |
| *Staphylococcus aureus* | 1757 | CP002643 | clade_325 | N | Category-B |
| *Staphylococcus auricularis* | 1758 | JQ624774 | clade_325 | N | N |
| *Staphylococcus capitis* | 1759 | ACFR01000029 | clade_325 | N | N |
| *Staphylococcus caprae* | 1760 | ACRH01000033 | clade_325 | N | N |
| *Staphylococcus carnosus* | 1761 | NR_075003 | clade_325 | N | N |
| *Staphylococcus cohnii* | 1762 | JN175375 | clade_325 | N | N |
| *Staphylococcus condimenti* | 1763 | NR_029345 | clade_325 | N | N |
| *Staphylococcus epidermidis* | 1764 | ACHE01000056 | clade_325 | N | N |
| *Staphylococcus equorum* | 1765 | NR_027520 | clade_325 | N | N |
| *Staphylococcus haemolyticus* | 1767 | NC_007168 | clade_325 | N | N |
| *Staphylococcus hominis* | 1768 | AM157418 | clade_325 | N | N |
| *Staphylococcus lugdunensis* | 1769 | AEQA01000024 | clade_325 | N | N |
| *Staphylococcus pasteuri* | 1770 | FJ189773 | clade_325 | N | N |
| *Staphylococcus pseudintermedius* | 1771 | CP002439 | clade_325 | N | N |
| *Staphylococcus saccharolyticus* | 1772 | NR_029158 | clade_325 | N | N |
| *Staphylococcus saprophyticus* | 1773 | NC_007350 | clade_325 | N | N |
| *Staphylococcus* sp. clone bottae7 | 1777 | AF467424 | clade_325 | N | N |
| *Staphylococcus* sp. H292 | 1775 | AB177642 | clade_325 | N | N |
| *Staphylococcus* sp. H780 | 1776 | AB177644 | clade_325 | N | N |
| *Staphylococcus succinus* | 1778 | NR_028667 | clade_325 | N | N |
| *Staphylococcus warneri* | 1780 | ACPZ01000009 | clade_325 | N | N |
| *Staphylococcus xylosus* | 1781 | AY395016 | clade_325 | N | N |
| *Cardiobacterium hominis* | 490 | ACKY01000036 | clade_326 | N | N |
| *Cardiobacterium valvarum* | 491 | NR_028847 | clade_326 | N | N |
| *Pseudomonas fluorescens* | 1593 | AY622220 | clade_326 | N | N |
| *Pseudomonas gessardii* | 1594 | FJ943496 | clade_326 | N | N |
| *Pseudomonas monteilii* | 1596 | NR_024910 | clade_326 | N | N |
| *Pseudomonas poae* | 1597 | GU188951 | clade_326 | N | N |
| *Pseudomonas putida* | 1599 | AF094741 | clade_326 | N | N |
| *Pseudomonas* sp. G1229 | 1601 | DQ910482 | clade_326 | N | N |
| *Pseudomonas tolaasii* | 1604 | AF320988 | clade_326 | N | N |
| *Pseudomonas viridiflava* | 1605 | NR_042764 | clade_326 | N | N |
| *Listeria grayi* | 1185 | ACCR02000003 | clade_328 | N | OP |
| *Listeria innocua* | 1186 | JF967625 | clade_328 | N | N |
| *Listeria ivanovii* | 1187 | X56151 | clade_328 | N | N |
| *Listeria monocytogenes* | 1188 | CP002003 | clade_328 | N | Category-B |
| *Listeria welshimeri* | 1189 | AM263198 | clade_328 | N | OP |
| *Capnocytophaga* sp. oral clone ASCH05 | 484 | AY923149 | clade_333 | N | N |
| *Capnocytophaga sputigena* | 489 | ABZV01000054 | clade_333 | N | N |
| *Leptotrichia* genomosp. C1 | 1166 | AY278621 | clade_334 | N | N |
| *Leptotrichia shahii* | 1169 | AY029806 | clade_334 | N | N |
| *Leptotrichia* sp. neutropenicPatient | 1170 | AF189244 | clade_334 | N | N |
| *Leptotrichia* sp. oral clone GT018 | 1171 | AY349384 | clade_334 | N | N |
| *Leptotrichia* sp. oral clone GT020 | 1172 | AY349385 | clade_334 | N | N |
| *Bacteroides* sp. 20_3 | 296 | ACRQ01000064 | clade_335 | N | N |
| *Bacteroides* sp. 3_1_19 | 307 | ADCJ01000062 | clade_335 | N | N |
| *Bacteroides* sp. 3_2_5 | 311 | ACIB01000079 | clade_335 | N | N |
| *Parabacteroides distasonis* | 1416 | CP000140 | clade_335 | N | N |
| *Parabacteroides goldsteinii* | 1417 | AY974070 | clade_335 | N | N |
| *Parabacteroides gordonii* | 1418 | AB470344 | clade_335 | N | N |
| *Parabacteroides* sp. D13 | 1421 | ACPW01000017 | clade_335 | N | N |
| *Capnocytophaga* genomosp. C1 | 477 | AY278613 | clade_336 | N | N |
| *Capnocytophaga ochracea* | 480 | AEOH01000054 | clade_336 | N | N |
| *Capnocytophaga* sp. GEJ8 | 481 | GU561335 | clade_336 | N | N |
| *Capnocytophaga* sp. oral strain A47ROY | 486 | AY005077 | clade_336 | N | N |
| *Capnocytophaga* sp. S1b | 482 | U42009 | clade_336 | N | N |
| *Paraprevotella clara* | 1426 | AFFY01000068 | clade_336 | N | N |
| *Bacteroides heparinolyticus* | 282 | JN867284 | clade_338 | N | N |

TABLE 1-continued

See, e.g., WO2014/121304

| OTU | SEQ ID Number | Public DB Accession | Clade | Spore Former | Pathogen Status |
|---|---|---|---|---|---|
| *Prevotella heparinolytica* | 1500 | GQ422742 | clade_338 | N | N |
| *Treponema* genomosp. P4 oral clone MB2_G19 | 1928 | DQ003618 | clade_339 | N | N |
| *Treponema* genomosp. P6 oral clone MB4_G11 | 1930 | DQ003625 | clade_339 | N | N |
| *Treponema* sp. oral taxon 254 | 1952 | GU408803 | clade_339 | N | N |
| *Treponema* sp. oral taxon 508 | 1956 | GU413616 | clade_339 | N | N |
| *Treponema* sp. oral taxon 518 | 1957 | GU413640 | clade_339 | N | N |
| *Chlamydia muridarum* | 502 | AE002160 | clade_341 | N | OP |
| *Chlamydia trachomatis* | 504 | U68443 | clade_341 | N | OP |
| *Chlamydia psittaci* | 503 | NR_036864 | clade_342 | N | Category-B |
| *Chlamydophila pneumoniae* | 509 | NC_002179 | clade_342 | N | OP |
| *Chlamydophila psittaci* | 510 | D85712 | clade_342 | N | OP |
| *Anaerococcus octavius* | 146 | NR_026360 | clade_343 | N | N |
| *Anaerococcus* sp. 8405254 | 149 | HM587319 | clade_343 | N | N |
| *Anaerococcus* sp. 9401487 | 150 | HM587322 | clade_343 | N | N |
| *Anaerococcus* sp. 9403502 | 151 | HM587325 | clade_343 | N | N |
| *Gardnerella vaginalis* | 923 | CP001849 | clade_344 | N | N |
| *Campylobacter lari* | 466 | CP000932 | clade_346 | N | OP |
| *Anaerobiospirillum succiniciproducens* | 142 | NR_026075 | clade_347 | N | N |
| *Anaerobiospirillum thomasii* | 143 | AJ420985 | clade_347 | N | N |
| *Ruminobacter amylophilus* | 1654 | NR_026450 | clade_347 | N | N |
| *Succinatimonas hippei* | 1897 | AEVO01000027 | clade_347 | N | N |
| *Actinomyces europaeus* | 54 | NR_026363 | clade_348 | N | N |
| *Actinomyces* sp. oral clone GU009 | 82 | AY349361 | clade_348 | N | N |
| *Moraxella catarrhalis* | 1260 | CP002005 | clade_349 | N | N |
| *Moraxella lincolnii* | 1261 | FR822735 | clade_349 | N | N |
| *Moraxella* sp. 16285 | 1263 | JF682466 | clade_349 | N | N |
| *Psychrobacter* sp. 13983 | 1613 | HM212668 | clade_349 | N | N |
| *Actinobaculum massiliae* | 49 | AF487679 | clade_350 | N | N |
| *Actinobaculum schaalii* | 50 | AY957507 | clade_350 | N | N |
| *Actinobaculum* sp. BM#101342 | 51 | AY282578 | clade_350 | N | N |
| *Actinobaculum* sp. P2P_19 P1 | 52 | AY207066 | clade_350 | N | N |
| *Actinomyces* sp. oral clone IO076 | 84 | AY349363 | clade_350 | N | N |
| *Actinomyces* sp. oral taxon 848 | 93 | ACUY01000072 | clade_350 | N | N |
| *Actinomyces neuii* | 65 | X71862 | clade_352 | N | N |
| *Mobiluncus mulieris* | 1252 | ACKW01000035 | clade_352 | N | N |
| *Blastomonas natatoria* | 372 | NR_040824 | clade_356 | N | N |
| *Novosphingobium aromaticivorans* | 1357 | AAAV03000008 | clade_356 | N | N |
| *Sphingomonas* sp. oral clone FI012 | 1745 | AY349411 | clade_356 | N | N |
| *Sphingopyxis alaskensis* | 1749 | CP000356 | clade_356 | N | N |
| *Oxalobacter formigenes* | 1389 | ACDQ01000020 | clade_357 | N | N |
| *Veillonella atypica* | 1974 | AEDS01000059 | clade_358 | N | N |
| *Veillonella dispar* | 1975 | ACIK02000021 | clade_358 | N | N |
| *Veillonella* genomosp. P1 oral clone MB5_P17 | 1976 | DQ003631 | clade_358 | N | N |
| *Veillonella parvula* | 1978 | ADFU01000009 | clade_358 | N | N |
| *Veillonella* sp. 3_1_44 | 1979 | ADCV01000019 | clade_358 | N | N |
| *Veillonella* sp. 6_1_27 | 1980 | ADCW01000016 | clade_358 | N | N |
| *Veillonella* sp. ACP1 | 1981 | HQ616359 | clade_358 | N | N |
| *Veillonella* sp. AS16 | 1982 | HQ616365 | clade_358 | N | N |
| *Veillonella* sp. BS32b | 1983 | HQ616368 | clade_358 | N | N |
| *Veillonella* sp. ICM51a | 1984 | HQ616396 | clade_358 | N | N |
| *Veillonella* sp. MSA12 | 1985 | HQ616381 | clade_358 | N | N |
| *Veillonella* sp. NVG 100cf | 1986 | EF108443 | clade_358 | N | N |
| *Veillonella* sp. OK11 | 1987 | JN695650 | clade_358 | N | N |
| *Veillonella* sp. oral clone ASCG01 | 1990 | AY923144 | clade_358 | N | N |
| *Veillonella* sp. oral clone ASCG02 | 1991 | AY953257 | clade_358 | N | N |
| *Veillonella* sp. oral clone OH1A | 1992 | AY947495 | clade_358 | N | N |
| *Veillonella* sp. oral taxon 158 | 1993 | AENU01000007 | clade_358 | N | N |
| *Kocuria marina* | 1040 | GQ260086 | clade_365 | N | N |
| *Kocuria rhizophila* | 1042 | AY030315 | clade_365 | N | N |
| *Kocuria rosea* | 1043 | X87756 | clade_365 | N | N |
| *Kocuria varians* | 1044 | AF542074 | clade_365 | N | N |
| Clostridiaceae bacterium END_2 | 531 | EF451053 | clade_368 | N | N |
| *Micrococcus antarcticus* | 1242 | NR_025285 | clade_371 | N | N |
| *Micrococcus luteus* | 1243 | NR_075062 | clade_371 | N | N |
| *Micrococcus lylae* | 1244 | NR_026200 | clade_371 | N | N |
| *Micrococcus* sp. 185 | 1245 | EU714334 | clade_371 | N | N |
| *Lactobacillus brevis* | 1072 | EU194349 | clade_372 | N | N |
| *Lactobacillus parabrevis* | 1104 | NR_042456 | clade_372 | N | N |
| *Pediococcus acidilactici* | 1436 | ACXB01000026 | clade_372 | N | N |
| *Pediococcus pentosaceus* | 1437 | NR_075052 | clade_372 | N | N |
| *Lactobacillus dextrinicus* | 1081 | NR_036861 | clade_373 | N | N |
| *Lactobacillus perolens* | 1109 | NR_029360 | clade_373 | N | N |
| *Lactobacillus rhamnosus* | 1113 | ABWJ01000068 | clade_373 | N | N |
| *Lactobacillus saniviri* | 1118 | AB602569 | clade_373 | N | N |
| *Lactobacillus* sp. BT6 | 1121 | HQ616370 | clade_373 | N | N |

TABLE 1-continued

See, e.g., WO2014/121304

| OTU | SEQ ID Number | Public DB Accession | Clade | Spore Former | Pathogen Status |
|---|---|---|---|---|---|
| *Mycobacterium mageritense* | 1282 | FR798914 | clade_374 | N | OP |
| *Mycobacterium neoaurum* | 1286 | AF268445 | clade_374 | N | OP |
| *Mycobacterium smegmatis* | 1291 | CP000480 | clade_374 | N | OP |
| *Mycobacterium* sp. HE5 | 1304 | AJ012738 | clade_374 | N | N |
| *Dysgonomonas gadei* | 775 | ADLV01000001 | clade_377 | N | N |
| *Dysgonomonas mossii* | 776 | ADLW01000023 | clade_377 | N | N |
| *Porphyromonas levii* | 1474 | NR_025907 | clade_377 | N | N |
| *Porphyromonas somerae* | 1476 | AB547667 | clade_377 | N | N |
| *Bacteroides barnesiae* | 267 | NR_041446 | clade_378 | N | N |
| *Bacteroides coprocola* | 272 | ABIY02000050 | clade_378 | N | N |
| *Bacteroides coprophilus* | 273 | ACBW01000012 | clade_378 | N | N |
| *Bacteroides dorei* | 274 | ABWZ01000093 | clade_378 | N | N |
| *Bacteroides massiliensis* | 284 | AB200226 | clade_378 | N | N |
| *Bacteroides plebeius* | 289 | AB200218 | clade_378 | N | N |
| *Bacteroides* sp. 3_1_33FAA | 309 | ACPS01000085 | clade_378 | N | N |
| *Bacteroides* sp. 3_1_40A | 310 | ACRT01000136 | clade_378 | N | N |
| *Bacteroides* sp. 4_3_47FAA | 313 | ACDR02000029 | clade_378 | N | N |
| *Bacteroides* sp. 9_1_42FAA | 314 | ACAA01000096 | clade_378 | N | N |
| *Bacteroides* sp. NB_8 | 323 | AB117565 | clade_378 | N | N |
| *Bacteroides vulgatus* | 331 | CP000139 | clade_378 | N | N |
| *Bacteroides ovatus* | 287 | ACWH01000036 | clade_38 | N | N |
| *Bacteroides* sp. 1_1_30 | 294 | ADCL01000128 | clade_38 | N | N |
| *Bacteroides* sp. 2_1_22 | 297 | ACPQ01000117 | clade_38 | N | N |
| *Bacteroides* sp. 2_2_4 | 299 | ABZZ01000168 | clade_38 | N | N |
| *Bacteroides* sp. 3_1_23 | 308 | ACRS01000081 | clade_38 | N | N |
| *Bacteroides* sp. D1 | 318 | ACAB02000030 | clade_38 | N | N |
| *Bacteroides* sp. D2 | 321 | ACGA01000077 | clade_38 | N | N |
| *Bacteroides* sp. D22 | 320 | ADCK01000151 | clade_38 | N | N |
| *Bacteroides xylanisolvens* | 332 | ADKP01000087 | clade_38 | N | N |
| *Treponema lecithinolyticum* | 1931 | NR_026247 | clade_380 | N | OP |
| *Treponema parvum* | 1933 | AF302937 | clade_380 | N | OP |
| *Treponema* sp. oral clone JU025 | 1940 | AY349417 | clade_380 | N | N |
| *Treponema* sp. oral taxon 270 | 1954 | GQ422733 | clade_380 | N | N |
| *Parascardovia denticolens* | 1428 | ADEB01000020 | clade_381 | N | N |
| *Scardovia inopinata* | 1688 | AB029087 | clade_381 | N | N |
| *Scardovia wiggsiae* | 1689 | AY278626 | clade_381 | N | N |
| Clostridiales bacterium 9400853 | 533 | HM587320 | clade_384 | N | N |
| *Mogibacterium diversum* | 1254 | NR_027191 | clade_384 | N | N |
| *Mogibacterium neglectum* | 1255 | NR_027203 | clade_384 | N | N |
| *Mogibacterium pumilum* | 1256 | NR_028608 | clade_384 | N | N |
| *Mogibacterium timidum* | 1257 | Z36296 | clade_384 | N | N |
| *Borrelia burgdorferi* | 389 | ABGI01000001 | clade_386 | N | OP |
| *Borrelia garinii* | 392 | ABJV01000001 | clade_386 | N | OP |
| *Borrelia* sp. NE49 | 397 | AJ224142 | clade_386 | N | OP |
| *Caldimonas manganoxidans* | 457 | NR_040787 | clade_387 | N | N |
| Comamonadaceae bacterium oral taxon F47 | 667 | HM099651 | clade_387 | N | N |
| *Lautropia mirabilis* | 1149 | AEQP01000026 | clade_387 | N | N |
| *Lautropia* sp. oral clone AP009 | 1150 | AY005030 | clade_387 | N | N |
| *Peptoniphilus asaccharolyticus* | 1441 | D14145 | clade_389 | N | N |
| *Peptoniphilus duerdenii* | 1442 | EU526290 | clade_389 | N | N |
| *Peptoniphilus harei* | 1443 | NR_026358 | clade_389 | N | N |
| *Peptoniphilus indolicus* | 1444 | AY153431 | clade_389 | N | N |
| *Peptoniphilus lacrimalis* | 1446 | ADDO01000050 | clade_389 | N | N |
| *Peptoniphilus* sp. gpac077 | 1450 | AM176527 | clade_389 | N | N |
| *Peptoniphilus* sp. JC140 | 1447 | JF824803 | clade_389 | N | N |
| *Peptoniphilus* sp. oral taxon 386 | 1452 | ADCS01000031 | clade_389 | N | N |
| *Peptoniphilus* sp. oral taxon 836 | 1453 | AEAA01000090 | clade_389 | N | N |
| Peptostreptococcaceae bacterium ph1 | 1454 | JN837495 | clade_389 | N | N |
| *Dialister pneumosintes* | 765 | HM596297 | clade_390 | N | N |
| *Dialister* sp. oral taxon 502 | 767 | GQ422739 | clade_390 | N | N |
| *Cupriavidus metallidurans* | 741 | GU230889 | clade_391 | N | N |
| *Herbaspirillum seropedicae* | 1001 | CP002039 | clade_391 | N | N |
| *Herbaspirillum* sp. JC206 | 1002 | JN657219 | clade_391 | N | N |
| *Janthinobacterium* sp. SY12 | 1015 | EF455530 | clade_391 | N | N |
| *Massilia* sp. CCUG 43427A | 1197 | FR773700 | clade_391 | N | N |
| *Ralstonia pickettii* | 1615 | NC_010682 | clade_391 | N | N |
| *Ralstonia* sp. 5_7_47FAA | 1616 | ACUF01000076 | clade_391 | N | N |
| *Francisella novicida* | 889 | ABSS01000002 | clade_392 | N | N |
| *Francisella philomiragia* | 890 | AY928394 | clade_392 | N | N |
| *Francisella tularensis* | 891 | ABAZ01000082 | clade_392 | N | Category-A |
| *Ignatzschineria indica* | 1009 | HQ823562 | clade_392 | N | N |
| *Ignatzschineria* sp. NML 95_0260 | 1010 | HQ823559 | clade_392 | N | N |
| *Streptococcus mutans* | 1814 | AP010655 | clade_394 | N | N |
| *Lactobacillus gasseri* | 1084 | ACOZ01000018 | clade_398 | N | N |
| *Lactobacillus hominis* | 1090 | FR681902 | clade_398 | N | N |

TABLE 1-continued

See, e.g., WO2014/121304

| OTU | SEQ ID Number | Public DB Accession | Clade | Spore Former | Pathogen Status |
|---|---|---|---|---|---|
| *Lactobacillus iners* | 1091 | AEKJ01000002 | clade_398 | N | N |
| *Lactobacillus johnsonii* | 1093 | AE017198 | clade_398 | N | N |
| *Lactobacillus senioris* | 1119 | AB602570 | clade_398 | N | N |
| *Lactobacillus* sp. oral clone HT002 | 1135 | AY349382 | clade_398 | N | N |
| *Weissella beninensis* | 2006 | EU439435 | clade_398 | N | N |
| *Sphingomonas echinoides* | 1744 | NR_024700 | clade_399 | N | N |
| *Sphingomonas* sp. oral taxon A09 | 1747 | HM099639 | clade_399 | N | N |
| *Sphingomonas* sp. oral taxon F71 | 1748 | HM099645 | clade_399 | N | N |
| *Zymomonas mobilis* | 2032 | NR_074274 | clade_399 | N | N |
| *Arcanobacterium haemolyticum* | 174 | NR_025347 | clade_400 | N | N |
| *Arcanobacterium pyogenes* | 175 | GU585578 | clade_400 | N | N |
| *Trueperella pyogenes* | 1962 | NR_044858 | clade_400 | N | N |
| *Lactococcus garvieae* | 1144 | AF061005 | clade_401 | N | N |
| *Lactococcus lactis* | 1145 | CP002365 | clade_401 | N | N |
| *Brevibacterium mcbrellneri* | 424 | ADNU01000076 | clade_402 | N | N |
| *Brevibacterium paucivorans* | 425 | EU086796 | clade_402 | N | N |
| *Brevibacterium* sp. JC43 | 428 | JF824806 | clade_402 | N | N |
| *Selenomonas artemidis* | 1692 | HM596274 | clade_403 | N | N |
| *Selenomonas* sp. FOBRC9 | 1704 | HQ616378 | clade_403 | N | N |
| *Selenomonas* sp. oral taxon 137 | 1715 | AENV01000007 | clade_403 | N | N |
| *Desmospora activa* | 751 | AM940019 | clade_404 | N | N |
| *Desmospora* sp. 8437 | 752 | AFHT01000143 | clade_404 | N | N |
| *Paenibacillus* sp. oral taxon F45 | 1407 | HM099647 | clade_404 | N | N |
| *Corynebacterium ammoniagenes* | 682 | ADNS01000011 | clade_405 | N | N |
| *Corynebacterium aurimucosum* | 687 | ACLH01000041 | clade_405 | N | N |
| *Corynebacterium bovis* | 688 | AF537590 | clade_405 | N | N |
| *Corynebacterium canis* | 689 | GQ871934 | clade_405 | N | N |
| *Corynebacterium casei* | 690 | NR_025101 | clade_405 | N | N |
| *Corynebacterium durum* | 694 | Z97069 | clade_405 | N | N |
| *Corynebacterium efficiens* | 695 | ACLI01000121 | clade_405 | N | N |
| *Corynebacterium falsenii* | 696 | Y13024 | clade_405 | N | N |
| *Corynebacterium flavescens* | 697 | NR_037040 | clade_405 | N | N |
| *Corynebacterium glutamicum* | 701 | BA000036 | clade_405 | N | N |
| *Corynebacterium jeikeium* | 704 | ACYW01000001 | clade_405 | N | OP |
| *Corynebacterium kroppenstedtii* | 705 | NR_026380 | clade_405 | N | N |
| *Corynebacterium lipophiloflavum* | 706 | ACHJ01000075 | clade_405 | N | N |
| *Corynebacterium matruchotii* | 709 | ACSH02000003 | clade_405 | N | N |
| *Corynebacterium minutissimum* | 710 | X82064 | clade_405 | N | N |
| *Corynebacterium resistens* | 718 | ADGN01000058 | clade_405 | N | N |
| *Corynebacterium simulans* | 720 | AF537604 | clade_405 | N | N |
| *Corynebacterium singulare* | 721 | NR_026394 | clade_405 | N | N |
| *Corynebacterium* sp. 1 ex sheep | 722 | Y13427 | clade_405 | N | N |
| *Corynebacterium* sp. NML 99_0018 | 726 | GU238413 | clade_405 | N | N |
| *Corynebacterium striatum* | 727 | ACGE01000001 | clade_405 | N | OP |
| *Corynebacterium urealyticum* | 732 | X81913 | clade_405 | N | OP |
| *Corynebacterium variabile* | 734 | NR_025314 | clade_405 | N | N |
| *Aerococcus sanguinicola* | 98 | AY837833 | clade_407 | N | N |
| *Aerococcus urinae* | 99 | CP002512 | clade_407 | N | N |
| *Aerococcus urinaeequi* | 100 | NR_043443 | clade_407 | N | N |
| *Aerococcus viridans* | 101 | ADNT01000041 | clade_407 | N | N |
| *Fusobacterium naviforme* | 898 | HQ223106 | clade_408 | N | N |
| *Moryella indoligenes* | 1268 | AF527773 | clade_408 | N | N |
| *Selenomonas* genomosp. P5 | 1697 | AY341820 | clade_410 | N | N |
| *Selenomonas* sp. oral clone IQ048 | 1710 | AY349408 | clade_410 | N | N |
| *Selenomonas sputigena* | 1717 | ACKP02000033 | clade_410 | N | N |
| *Hyphomicrobium sulfonivorans* | 1007 | AY468372 | clade_411 | N | N |
| *Methylocella silvestris* | 1228 | NR_074237 | clade_411 | N | N |
| *Legionella pneumophila* | 1153 | NC_002942 | clade_412 | N | OP |
| *Lactobacillus coryniformis* | 1077 | NR_044705 | clade_413 | N | N |
| *Arthrobacter agilis* | 178 | NR_026198 | clade_414 | N | N |
| *Arthrobacter arilaitensis* | 179 | NR_074608 | clade_414 | N | N |
| *Arthrobacter bergerei* | 180 | NR_025612 | clade_414 | N | N |
| *Arthrobacter globiformis* | 181 | NR_026187 | clade_414 | N | N |
| *Arthrobacter nicotianae* | 182 | NR_026190 | clade_414 | N | N |
| *Mycobacterium abscessus* | 1269 | AGQU01000002 | clade_418 | N | OP |
| *Mycobacterium chelonae* | 1273 | AB548610 | clade_418 | N | OP |
| *Bacteroides salanitronis* | 291 | CP002530 | clade_419 | N | N |
| *Paraprevotella xylaniphila* | 1427 | AFBR01000011 | clade_419 | N | N |
| *Barnesiella intestinihominis* | 336 | AB370251 | clade_420 | N | N |
| *Barnesiella viscericola* | 337 | NR_041508 | clade_420 | N | N |
| *Parabacteroides* sp. NS31_3 | 1422 | JN029805 | clade_420 | N | N |
| *Porphyromonadaceae* bacterium NML 060648 | 1470 | EF184292 | clade_420 | N | N |
| *Tannerella forsythia* | 1913 | CP003191 | clade_420 | N | N |
| *Tannerella* sp. 6_1_58FAA_CT1 | 1914 | ACWX01000068 | clade_420 | N | N |
| *Mycoplasma amphoriforme* | 1311 | AY531656 | clade_421 | N | N |

TABLE 1-continued

See, e.g., WO2014/121304

| OTU | SEQ ID Number | Public DB Accession | Clade | Spore Former | Pathogen Status |
|---|---|---|---|---|---|
| *Mycoplasma genitalium* | 1317 | L43967 | clade_421 | N | N |
| *Mycoplasma pneumoniae* | 1322 | NC_000912 | clade_421 | N | N |
| *Mycoplasma penetrans* | 1321 | NC_004432 | clade_422 | N | N |
| *Ureaplasma parvum* | 1966 | AE002127 | clade_422 | N | N |
| *Ureaplasma urealyticum* | 1967 | AAYN01000002 | clade_422 | N | N |
| *Treponema* genomosp. P1 | 1927 | AY341822 | clade_425 | N | N |
| *Treponema* sp. oral taxon 228 | 1943 | GU408580 | clade_425 | N | N |
| *Treponema* sp. oral taxon 230 | 1944 | GU408603 | clade_425 | N | N |
| *Treponema* sp. oral taxon 231 | 1945 | GU408631 | clade_425 | N | N |
| *Treponema* sp. oral taxon 232 | 1946 | GU408646 | clade_425 | N | N |
| *Treponema* sp. oral taxon 235 | 1947 | GU408673 | clade_425 | N | N |
| *Treponema* sp. ovine footrot | 1959 | AJ010951 | clade_425 | N | N |
| *Treponema vincentii* | 1960 | ACYH01000036 | clade_425 | N | OP |
| Burkholderiales bacterium 1_1_47 | 452 | ADCQ01000066 | clade_432 | N | OP |
| *Parasutterella excrementihominis* | 1429 | AFBP01000029 | clade_432 | N | N |
| *Parasutterella secunda* | 1430 | AB491209 | clade_432 | N | N |
| *Sutterella morbirenis* | 1898 | AJ832129 | clade_432 | N | N |
| *Sutterella sanguinus* | 1900 | AJ748647 | clade_432 | N | N |
| *Sutterella* sp. YIT 12072 | 1901 | AB491210 | clade_432 | N | N |
| *Sutterella stercoricanis* | 1902 | NR_025600 | clade_432 | N | N |
| *Sutterella wadsworthensis* | 1903 | ADMF01000048 | clade_432 | N | N |
| *Propionibacterium freudenreichii* | 1572 | NR_036972 | clade_433 | N | N |
| *Propionibacterium* sp. oral taxon 192 | 1580 | GQ422728 | clade_433 | N | N |
| *Tessaracoccus* sp. oral taxon F04 | 1917 | HM099640 | clade_433 | N | N |
| *Peptoniphilus ivorii* | 1445 | Y07840 | clade_434 | N | N |
| *Peptoniphilus* sp. gpac007 | 1448 | AM176517 | clade_434 | N | N |
| *Peptoniphilus* sp. gpac018A | 1449 | AM176519 | clade_434 | N | N |
| *Peptoniphilus* sp. gpac148 | 1451 | AM176535 | clade_434 | N | N |
| *Flexispira rappini* | 887 | AY126479 | clade_436 | N | N |
| *Helicobacter bilis* | 993 | ACDN01000023 | clade_436 | N | N |
| *Helicobacter cinaedi* | 995 | ABQT01000054 | clade_436 | N | N |
| *Helicobacter* sp. None | 998 | U44756 | clade_436 | N | N |
| *Brevundimonas subvibrioides* | 429 | CP002102 | clade_438 | N | N |
| *Hyphomonas neptunium* | 1008 | NR_074092 | clade_438 | N | N |
| *Phenylobacterium zucineum* | 1465 | AY628697 | clade_438 | N | N |
| *Streptococcus downei* | 1793 | AEKN01000002 | clade_441 | N | N |
| *Streptococcus* sp. SHV515 | 1848 | Y07601 | clade_441 | N | N |
| *Acinetobacter* sp. CIP 53.82 | 40 | JQ638584 | clade_443 | N | N |
| *Halomonas elongata* | 990 | NR_074782 | clade_443 | N | N |
| *Halomonas johnsoniae* | 991 | FR775979 | clade_443 | N | N |
| *Butyrivibrio fibrisolvens* | 456 | U41172 | clade_444 | N | N |
| *Roseburia* sp. 11SE37 | 1640 | FM954975 | clade_444 | N | N |
| *Roseburia* sp. 11SE38 | 1641 | FM954976 | clade_444 | N | N |
| *Shuttleworthia satelles* | 1728 | ACIP02000004 | clade_444 | N | N |
| *Shuttleworthia* sp. MSX8B | 1729 | HQ616383 | clade_444 | N | N |
| *Shuttleworthia* sp. oral taxon G69 | 1730 | GU432167 | clade_444 | N | N |
| *Bdellovibrio* sp. MPA | 344 | AY294215 | clade_445 | N | N |
| *Desulfobulbus* sp. oral clone CH031 | 755 | AY005036 | clade_445 | N | N |
| *Desulfovibrio desulfuricans* | 757 | DQ092636 | clade_445 | N | N |
| *Desulfovibrio fairfieldensis* | 758 | U42221 | clade_445 | N | N |
| *Desulfovibrio piger* | 759 | AF192152 | clade_445 | N | N |
| *Desulfovibrio* sp. 3_1_syn3 | 760 | ADDR01000239 | clade_445 | N | N |
| *Geobacter bemidjiensis* | 941 | CP001124 | clade_445 | N | N |
| *Brachybacterium alimentarium* | 401 | NR_026269 | clade_446 | N | N |
| *Brachybacterium conglomeratum* | 402 | AB537169 | clade_446 | N | N |
| *Brachybacterium tyrofermentans* | 403 | NR_026272 | clade_446 | N | N |
| *Dermabacter hominis* | 749 | FJ263375 | clade_446 | N | N |
| *Aneurinibacillus thermoaerophilus* | 171 | NR_029303 | clade_448 | N | N |
| *Brevibacillus agri* | 409 | NR_040983 | clade_448 | N | N |
| *Brevibacillus centrosporus* | 411 | NR_043414 | clade_448 | N | N |
| *Brevibacillus choshinensis* | 412 | NR_040980 | clade_448 | N | N |
| *Brevibacillus invocatus* | 413 | NR_041836 | clade_448 | N | N |
| *Brevibacillus parabrevis* | 415 | NR_040981 | clade_448 | N | N |
| *Brevibacillus reuszeri* | 416 | NR_040982 | clade_448 | N | N |
| *Brevibacillus* sp. phR | 417 | JN837488 | clade_448 | N | N |
| *Brevibacillus thermoruber* | 418 | NR_026514 | clade_448 | N | N |
| *Lactobacillus murinus* | 1100 | NR_042231 | clade_449 | N | N |
| *Lactobacillus oeni* | 1102 | NR_043095 | clade_449 | N | N |
| *Lactobacillus ruminis* | 1115 | ACGS02000043 | clade_449 | N | N |
| *Lactobacillus vini* | 1141 | NR_042196 | clade_449 | N | N |
| *Gemella haemolysans* | 924 | ACDZ02000012 | clade_450 | N | N |
| *Gemella morbillorum* | 925 | NR_025904 | clade_450 | N | N |
| *Gemella morbillorum* | 926 | ACRX01000010 | clade_450 | N | N |
| *Gemella sanguinis* | 927 | ACRY01000057 | clade_450 | N | N |
| *Gemella* sp. oral clone ASCE02 | 929 | AY923133 | clade_450 | N | N |

TABLE 1-continued

See, e.g., WO2014/121304

| OTU | SEQ ID Number | Public DB Accession | Clade | Spore Former | Pathogen Status |
|---|---|---|---|---|---|
| Gemella sp. oral clone ASCF04 | 930 | AY923139 | clade_450 | N | N |
| Gemella sp. oral clone ASCF12 | 931 | AY923143 | clade_450 | N | N |
| Gemella sp. WAL 1945J | 928 | EU427463 | clade_450 | N | N |
| Sporolactobacillus nakayamae | 1753 | NR_042247 | clade_451 | N | N |
| Gluconacetobacter entanii | 945 | NR_028909 | clade_452 | N | N |
| Gluconacetobacter europaeus | 946 | NR_026513 | clade_452 | N | N |
| Gluconacetobacter hansenii | 947 | NR_026133 | clade_452 | N | N |
| Gluconacetobacter oboediens | 949 | NR_041295 | clade_452 | N | N |
| Gluconacetobacter xylinus | 950 | NR_074338 | clade_452 | N | N |
| Auritibacter ignavus | 193 | FN554542 | clade_453 | N | N |
| Dermacoccus sp. Ellin185 | 750 | AEIQ01000090 | clade_453 | N | N |
| Janibacter limosus | 1013 | NR_026362 | clade_453 | N | N |
| Janibacter melonis | 1014 | EF063716 | clade_453 | N | N |
| Acetobacter aceti | 7 | NR_026121 | clade_454 | N | N |
| Acetobacter fabarum | 8 | NR_042678 | clade_454 | N | N |
| Acetobacter lovaniensis | 9 | NR_040832 | clade_454 | N | N |
| Acetobacter malorum | 10 | NR_025513 | clade_454 | N | N |
| Acetobacter orientalis | 11 | NR_028625 | clade_454 | N | N |
| Acetobacter pasteurianus | 12 | NR_026107 | clade_454 | N | N |
| Acetobacter pomorum | 13 | NR_042112 | clade_454 | N | N |
| Acetobacter syzygii | 14 | NR_040868 | clade_454 | N | N |
| Acetobacter tropicalis | 15 | NR_036881 | clade_454 | N | N |
| Gluconacetobacter azotocaptans | 943 | NR_028767 | clade_454 | N | N |
| Gluconacetobacter diazotrophicus | 944 | NR_074292 | clade_454 | N | N |
| Gluconacetobacter johannae | 948 | NR_024959 | clade_454 | N | N |
| Nocardia brasiliensis | 1351 | AIHV01000038 | clade_455 | N | N |
| Nocardia cyriacigeorgica | 1352 | HQ009486 | clade_455 | N | N |
| Nocardia puris | 1354 | NR_028994 | clade_455 | N | N |
| Nocardia sp. 01_Je_025 | 1355 | GU574059 | clade_455 | N | N |
| Rhodococcus equi | 1623 | ADNW01000058 | clade_455 | N | N |
| Oceanobacillus caeni | 1358 | NR_041533 | clade_456 | N | N |
| Oceanobacillus sp. Ndiop | 1359 | CAER01000083 | clade_456 | N | N |
| Ornithinibacillus bavariensis | 1384 | NR_044923 | clade_456 | N | N |
| Ornithinibacillus sp. 7_10AIA | 1385 | FN397526 | clade_456 | N | N |
| Virgibacillus proomii | 2005 | NR_025308 | clade_456 | N | N |
| Corynebacterium amycolatum | 683 | ABZU01000033 | clade_457 | N | OP |
| Corynebacterium hansenii | 702 | AM946639 | clade_457 | N | N |
| Corynebacterium xerosis | 735 | FN179330 | clade_457 | N | OP |
| Staphylococcaceae bacterium NML 92_0017 | 1756 | AY841362 | clade_458 | N | N |
| Staphylococcus fleurettii | 1766 | NR_041326 | clade_458 | N | N |
| Staphylococcus sciuri | 1774 | NR_025520 | clade_458 | N | N |
| Staphylococcus vitulinus | 1779 | NR_024670 | clade_458 | N | N |
| Stenotrophomonas maltophilia | 1782 | AAVZ01000005 | clade_459 | N | N |
| Stenotrophomonas sp. FG_6 | 1783 | EF017810 | clade_459 | N | N |
| Mycobacterium africanum | 1270 | AF480605 | clade_46 | N | OP |
| Mycobacterium alsiensis | 1271 | AJ938169 | clade_46 | N | OP |
| Mycobacterium avium | 1272 | CP000479 | clade_46 | N | OP |
| Mycobacterium colombiense | 1274 | AM062764 | clade_46 | N | OP |
| Mycobacterium gordonae | 1276 | GU142930 | clade_46 | N | OP |
| Mycobacterium intracellulare | 1277 | GQ153276 | clade_46 | N | OP |
| Mycobacterium kansasii | 1278 | AF480601 | clade_46 | N | OP |
| Mycobacterium lacus | 1279 | NR_025175 | clade_46 | N | OP |
| Mycobacterium leprae | 1280 | FM211192 | clade_46 | N | OP |
| Mycobacterium lepromatosis | 1281 | EU203590 | clade_46 | N | OP |
| Mycobacterium mantenii | 1283 | FJ042897 | clade_46 | N | OP |
| Mycobacterium marinum | 1284 | NC_010612 | clade_46 | N | OP |
| Mycobacterium microti | 1285 | NR_025234 | clade_46 | N | OP |
| Mycobacterium parascrofulaceum | 1287 | ADNV01000350 | clade_46 | N | OP |
| Mycobacterium seoulense | 1290 | DQ536403 | clade_46 | N | OP |
| Mycobacterium sp. 1761 | 1292 | EU703150 | clade_46 | N | N |
| Mycobacterium sp. 1791 | 1295 | EU703148 | clade_46 | N | N |
| Mycobacterium sp. 1797 | 1296 | EU703149 | clade_46 | N | N |
| Mycobacterium sp. B10_07.09.0206 | 1298 | HQ174245 | clade_46 | N | N |
| Mycobacterium sp. NLA001000736 | 1305 | HM627011 | clade_46 | N | N |
| Mycobacterium sp. W | 1306 | DQ437715 | clade_46 | N | N |
| Mycobacterium tuberculosis | 1307 | CP001658 | clade_46 | N | Category-C |
| Mycobacterium ulcerans | 1308 | AB548725 | clade_46 | N | OP |
| Mycobacterium vulneris | 1309 | EU834055 | clade_46 | N | OP |
| Xanthomonas campestris | 2016 | EF101975 | clade_461 | N | N |
| Xanthomonas sp. kmd_489 | 2017 | EU723184 | clade_461 | N | N |
| Dietzia natronolimnaea | 769 | GQ870426 | clade_462 | N | N |
| Dietzia sp. BBDP51 | 770 | DQ337512 | clade_462 | N | N |
| Dietzia sp. CA149 | 771 | GQ870422 | clade_462 | N | N |
| Dietzia timorensis | 772 | GQ870424 | clade_462 | N | N |
| Gordonia bronchialis | 951 | NR_027594 | clade_463 | N | N |

TABLE 1-continued

See, e.g., WO2014/121304

| OTU | SEQ ID Number | Public DB Accession | Clade | Spore Former | Pathogen Status |
|---|---|---|---|---|---|
| *Gordonia polyisoprenivorans* | 952 | DQ385609 | clade_463 | N | N |
| *Gordonia* sp. KTR9 | 953 | DQ068383 | clade_463 | N | N |
| *Gordonia sputi* | 954 | FJ536304 | clade_463 | N | N |
| *Gordonia terrae* | 955 | GQ848239 | clade_463 | N | N |
| *Leptotrichia goodfellowii* | 1167 | ADAD01000110 | clade_465 | N | N |
| *Leptotrichia* sp. oral clone IK040 | 1174 | AY349387 | clade_465 | N | N |
| *Leptotrichia* sp. oral clone P2PB_51 P1 | 1175 | AY207053 | clade_465 | N | N |
| *Bacteroidales* genomosp. P7 oral clone MB3_P19 | 264 | DQ003623 | clade_466 | N | N |
| *Butyricimonas virosa* | 454 | AB443949 | clade_466 | N | N |
| *Odoribacter laneus* | 1363 | AB490805 | clade_466 | N | N |
| *Odoribacter splanchnicus* | 1364 | CP002544 | clade_466 | N | N |
| *Capnocytophaga gingivalis* | 478 | ACLQ01000011 | clade_467 | N | N |
| *Capnocytophaga granulosa* | 479 | X97248 | clade_467 | N | N |
| *Capnocytophaga* sp. oral clone AH015 | 483 | AY005074 | clade_467 | N | N |
| *Capnocytophaga* sp. oral strain S3 | 487 | AY005073 | clade_467 | N | N |
| *Capnocytophaga* sp. oral taxon 338 | 488 | AEXX01000050 | clade_467 | N | N |
| *Capnocytophaga canimorsus* | 476 | CP002113 | clade_468 | N | N |
| *Capnocytophaga* sp. oral clone ID062 | 485 | AY349368 | clade_468 | N | N |
| *Lactobacillus catenaformis* | 1075 | M23729 | clade_469 | N | N |
| *Lactobacillus vitulinus* | 1142 | NR_041305 | clade_469 | N | N |
| *Cetobacterium somerae* | 501 | AJ438155 | clade_470 | N | N |
| *Fusobacterium gonidiaformans* | 896 | ACET01000043 | clade_470 | N | N |
| *Fusobacterium mortiferum* | 897 | ACDB02000034 | clade_470 | N | N |
| *Fusobacterium necrogenes* | 899 | X55408 | clade_470 | N | N |
| *Fusobacterium necrophorum* | 900 | AM905356 | clade_470 | N | N |
| *Fusobacterium* sp. 12_1B | 905 | AGWJ01000070 | clade_470 | N | N |
| *Fusobacterium* sp. 3_1_5R | 911 | ACDD01000078 | clade_470 | N | N |
| *Fusobacterium* sp. D12 | 918 | ACDG02000036 | clade_470 | N | N |
| *Fusobacterium ulcerans* | 921 | ACDH01000090 | clade_470 | N | N |
| *Fusobacterium varium* | 922 | ACIE01000009 | clade_470 | N | N |
| *Mycoplasma arthritidis* | 1312 | NC_011025 | clade_473 | N | N |
| *Mycoplasma faucium* | 1314 | NR_024983 | clade_473 | N | N |
| *Mycoplasma hominis* | 1318 | AF443616 | clade_473 | N | N |
| *Mycoplasma orale* | 1319 | AY796060 | clade_473 | N | N |
| *Mycoplasma salivarium* | 1324 | M24661 | clade_473 | N | N |
| *Mitsuokella jalaludinii* | 1247 | NR_028840 | clade_474 | N | N |
| *Mitsuokella multacida* | 1248 | ABWK02000005 | clade_474 | N | N |
| *Mitsuokella* sp. oral taxon 521 | 1249 | GU413658 | clade_474 | N | N |
| *Mitsuokella* sp. oral taxon G68 | 1250 | GU432166 | clade_474 | N | N |
| *Selenomonas* genomosp. C1 | 1695 | AY278627 | clade_474 | N | N |
| *Selenomonas* genomosp. P8 oral clone MB5_P06 | 1700 | DQ003628 | clade_474 | N | N |
| *Selenomonas ruminantium* | 1703 | NR_075026 | clade_474 | N | N |
| *Veillonellaceae* bacterium oral taxon 131 | 1994 | GU402916 | clade_474 | N | N |
| *Alloscardovia omnicolens* | 139 | NR_042583 | clade_475 | N | N |
| *Alloscardovia* sp. OB7196 | 140 | AB425070 | clade_475 | N | N |
| *Bifidobacterium urinalis* | 366 | AJ278695 | clade_475 | N | N |
| *Prevotella loescheii* | 1503 | JN867231 | clade_48 | N | N |
| *Prevotella* sp. oral clone ASCG12 | 1530 | DQ272511 | clade_48 | N | N |
| *Prevotella* sp. oral clone GU027 | 1540 | AY349398 | clade_48 | N | N |
| *Prevotella* sp. oral taxon 472 | 1553 | ACZS01000106 | clade_48 | N | N |
| *Selenomonas dianae* | 1693 | GQ422719 | clade_480 | N | N |
| *Selenomonas flueggei* | 1694 | AF287803 | clade_480 | N | N |
| *Selenomonas* genomosp. C2 | 1696 | AY278628 | clade_480 | N | N |
| *Selenomonas* genomosp. P6 oral clone MB3_C41 | 1698 | DQ003636 | clade_480 | N | N |
| *Selenomonas* genomosp. P7 oral clone MB5_C08 | 1699 | DQ003627 | clade_480 | N | N |
| *Selenomonas infelix* | 1701 | AF287802 | clade_480 | N | N |
| *Selenomonas noxia* | 1702 | GU470909 | clade_480 | N | N |
| *Selenomonas* sp. oral clone FT050 | 1705 | AY349403 | clade_480 | N | N |
| *Selenomonas* sp. oral clone GI064 | 1706 | AY349404 | clade_480 | N | N |
| *Selenomonas* sp. oral clone GT010 | 1707 | AY349405 | clade_480 | N | N |
| *Selenomonas* sp. oral clone HU051 | 1708 | AY349406 | clade_480 | N | N |
| *Selenomonas* sp. oral clone IK004 | 1709 | AY349407 | clade_480 | N | N |
| *Selenomonas* sp. oral clone JI021 | 1711 | AY349409 | clade_480 | N | N |
| *Selenomonas* sp. oral clone JS031 | 1712 | AY349410 | clade_480 | N | N |
| *Selenomonas* sp. oral clone OH4A | 1713 | AY947498 | clade_480 | N | N |
| *Selenomonas* sp. oral clone P2PA_80 P4 | 1714 | AY207052 | clade_480 | N | N |
| *Selenomonas* sp. oral taxon 149 | 1716 | AEEJ01000007 | clade_480 | N | N |
| *Veillonellaceae* bacterium oral taxon 155 | 1995 | GU470897 | clade_480 | N | N |
| *Agrococcus jenensis* | 117 | NR_026275 | clade_484 | N | N |
| *Microbacterium gubbeenense* | 1232 | NR_025098 | clade_484 | N | N |
| *Pseudoclavibacter* sp. Timone | 1590 | FJ375951 | clade_484 | N | N |
| *Tropheryma whipplei* | 1961 | BX251412 | clade_484 | N | N |
| *Zimmermannella bifida* | 2031 | AB012592 | clade_484 | N | N |
| *Legionella hackeliae* | 1151 | M36028 | clade_486 | N | OP |
| *Legionella longbeachae* | 1152 | M36029 | clade_486 | N | OP |

TABLE 1-continued

See, e.g., WO2014/121304

| OTU | SEQ ID Number | Public DB Accession | Clade | Spore Former | Pathogen Status |
|---|---|---|---|---|---|
| *Legionella* sp. D3923 | 1154 | JN380999 | clade_486 | N | OP |
| *Legionella* sp. D4088 | 1155 | JN381012 | clade_486 | N | OP |
| *Legionella* sp. H63 | 1156 | JF831047 | clade_486 | N | OP |
| *Legionella* sp. NML 93L054 | 1157 | GU062706 | clade_486 | N | OP |
| *Legionella steelei* | 1158 | HQ398202 | clade_486 | N | OP |
| *Tatlockia micdadei* | 1915 | M36032 | clade_486 | N | N |
| *Helicobacter pullorum* | 996 | ABQU01000097 | clade_489 | N | N |
| *Acetobacteraceae bacterium* AT 5844 | 16 | AGEZ01000040 | clade_490 | N | N |
| *Roseomonas cervicalis* | 1643 | ADVL01000363 | clade_490 | N | N |
| *Roseomonas mucosa* | 1644 | NR_028857 | clade_490 | N | N |
| *Roseomonas* sp. NML94_0193 | 1645 | AF533357 | clade_490 | N | N |
| *Roseomonas* sp. NML97_0121 | 1646 | AF533359 | clade_490 | N | N |
| *Roseomonas* sp. NML98_0009 | 1647 | AF533358 | clade_490 | N | N |
| *Roseomonas* sp. NML98_0157 | 1648 | AF533360 | clade_490 | N | N |
| *Rickettsia akari* | 1627 | CP000847 | clade_492 | N | OP |
| *Rickettsia conorii* | 1628 | AE008647 | clade_492 | N | OP |
| *Rickettsia prowazekii* | 1629 | M21789 | clade_492 | N | Category-B |
| *Rickettsia rickettsii* | 1630 | NC_010263 | clade_492 | N | OP |
| *Rickettsia slovaca* | 1631 | L36224 | clade_492 | N | OP |
| *Rickettsia typhi* | 1632 | AE017197 | clade_492 | N | OP |
| *Anaeroglobus geminatus* | 160 | AGCJ01000054 | clade_493 | N | N |
| *Megasphaera* genomosp. C1 | 1201 | AY278622 | clade_493 | N | N |
| *Megasphaera micronuciformis* | 1203 | AECS01000020 | clade_493 | N | N |
| *Clostridiales* genomosp. BVAB3 | 540 | CP001850 | clade_495 | N | N |
| *Tsukamurella paurometabola* | 1963 | X80628 | clade_496 | N | N |
| *Tsukamurella tyrosinosolvens* | 1964 | AB478958 | clade_496 | N | N |
| *Abiotrophia para_adiacens* | 2 | AB022027 | clade_497 | N | N |
| *Carnobacterium divergens* | 492 | NR_044706 | clade_497 | N | N |
| *Carnobacterium maltaromaticum* | 493 | NC_019425 | clade_497 | N | N |
| *Enterococcus avium* | 800 | AF133535 | clade_497 | N | N |
| *Enterococcus caccae* | 801 | AY943820 | clade_497 | N | N |
| *Enterococcus casseliflavus* | 802 | AEWT01000047 | clade_497 | N | N |
| *Enterococcus durans* | 803 | AJ276354 | clade_497 | N | N |
| *Enterococcus faecalis* | 804 | AE016830 | clade_497 | N | N |
| *Enterococcus faecium* | 805 | AM157434 | clade_497 | N | N |
| *Enterococcus gallinarum* | 806 | AB269767 | clade_497 | N | N |
| *Enterococcus gilvus* | 807 | AY033814 | clade_497 | N | N |
| *Enterococcus hawaiiensis* | 808 | AY321377 | clade_497 | N | N |
| *Enterococcus hirae* | 809 | AF061011 | clade_497 | N | N |
| *Enterococcus italicus* | 810 | AEPV01000109 | clade_497 | N | N |
| *Enterococcus mundtii* | 811 | NR_024906 | clade_497 | N | N |
| *Enterococcus raffinosus* | 812 | FN600541 | clade_497 | N | N |
| *Enterococcus* sp. BV2CASA2 | 813 | JN809766 | clade_497 | N | N |
| *Enterococcus* sp. CCRI_16620 | 814 | GU457263 | clade_497 | N | N |
| *Enterococcus* sp. F95 | 815 | FJ463817 | clade_497 | N | N |
| *Enterococcus* sp. RfL6 | 816 | AJ133478 | clade_497 | N | N |
| *Enterococcus thailandicus* | 817 | AY321376 | clade_497 | N | N |
| *Fusobacterium canifelinum* | 893 | AY162222 | clade_497 | N | N |
| *Fusobacterium* genomosp. C1 | 894 | AY278616 | clade_497 | N | N |
| *Fusobacterium* genomosp. C2 | 895 | AY278617 | clade_497 | N | N |
| *Fusobacterium periodonticum* | 902 | ACJY01000002 | clade_497 | N | N |
| *Fusobacterium* sp. 1_1_41FAA | 906 | ADGG01000053 | clade_497 | N | N |
| *Fusobacterium* sp. 11_3_2 | 904 | ACUO01000052 | clade_497 | N | N |
| *Fusobacterium* sp. 2_1_31 | 907 | ACDC02000018 | clade_497 | N | N |
| *Fusobacterium* sp. 3_1_27 | 908 | ADGF01000045 | clade_497 | N | N |
| *Fusobacterium* sp. 3_1_33 | 909 | ACQE01000178 | clade_497 | N | N |
| *Fusobacterium* sp. 3_1_36A2 | 910 | ACPU01000044 | clade_497 | N | N |
| *Fusobacterium* sp. AC18 | 912 | HQ616357 | clade_497 | N | N |
| *Fusobacterium* sp. ACB2 | 913 | HQ616358 | clade_497 | N | N |
| *Fusobacterium* sp. AS2 | 914 | HQ616361 | clade_497 | N | N |
| *Fusobacterium* sp. CM1 | 915 | HQ616371 | clade_497 | N | N |
| *Fusobacterium* sp. CM21 | 916 | HQ616375 | clade_497 | N | N |
| *Fusobacterium* sp. CM22 | 917 | HQ616376 | clade_497 | N | N |
| *Fusobacterium* sp. oral clone ASCF06 | 919 | AY923141 | clade_497 | N | N |
| *Fusobacterium* sp. oral clone ASCF11 | 920 | AY953256 | clade_497 | N | N |
| *Granulicatella adiacens* | 959 | ACKZ01000002 | clade_497 | N | N |
| *Granulicatella elegans* | 960 | AB252689 | clade_497 | N | N |
| *Granulicatella paradiacens* | 961 | AY879298 | clade_497 | N | N |
| *Granulicatella* sp. oral clone ASC02 | 963 | AY923126 | clade_497 | N | N |
| *Granulicatella* sp. oral clone ASCA05 | 964 | DQ341469 | clade_497 | N | N |
| *Granulicatella* sp. oral clone ASCB09 | 965 | AY953251 | clade_497 | N | N |
| *Granulicatella* sp. oral clone ASCG05 | 966 | AY923146 | clade_497 | N | N |
| *Tetragenococcus halophilus* | 1918 | NR_075020 | clade_497 | N | N |
| *Tetragenococcus koreensis* | 1919 | NR_043113 | clade_497 | N | N |
| *Vagococcus fluvialis* | 1973 | NR_026489 | clade_497 | N | N |

TABLE 1-continued

See, e.g., WO2014/121304

| OTU | SEQ ID Number | Public DB Accession | Clade | Spore Former | Pathogen Status |
|---|---|---|---|---|---|
| *Chryseobacterium anthropi* | 514 | AM982793 | clade_498 | N | N |
| *Chryseobacterium gleum* | 515 | ACKQ02000003 | clade_498 | N | N |
| *Chryseobacterium hominis* | 516 | NR_042517 | clade_498 | N | N |
| *Treponema refringens* | 1936 | AF426101 | clade_499 | N | OP |
| *Treponema* sp. oral clone JU031 | 1941 | AY349416 | clade_499 | N | N |
| *Treponema* sp. oral taxon 239 | 1948 | GU408738 | clade_499 | N | N |
| *Treponema* sp. oral taxon 271 | 1955 | GU408871 | clade_499 | N | N |
| *Alistipes finegoldii* | 129 | NR_043064 | clade_500 | N | N |
| *Alistipes onderdonkii* | 131 | NR_043318 | clade_500 | N | N |
| *Alistipes putredinis* | 132 | ABFK02000017 | clade_500 | N | N |
| *Alistipes shahii* | 133 | FP929032 | clade_500 | N | N |
| *Alistipes* sp. HGB5 | 134 | AENZ01000082 | clade_500 | N | N |
| *Alistipes* sp. JC50 | 135 | JF824804 | clade_500 | N | N |
| *Alistipes* sp. RMA 9912 | 136 | GQ140629 | clade_500 | N | N |
| *Mycoplasma agalactiae* | 1310 | AF010477 | clade_501 | N | N |
| *Mycoplasma bovoculi* | 1313 | NR_025987 | clade_501 | N | N |
| *Mycoplasma fermentans* | 1315 | CP002458 | clade_501 | N | N |
| *Mycoplasma flocculare* | 1316 | X62699 | clade_501 | N | N |
| *Mycoplasma ovipneumoniae* | 1320 | NR_025989 | clade_501 | N | N |
| *Arcobacter butzleri* | 176 | AEPT01000071 | clade_502 | N | N |
| *Arcobacter cryaerophilus* | 177 | NR_025905 | clade_502 | N | N |
| *Campylobacter curvus* | 461 | NC_009715 | clade_502 | N | OP |
| *Campylobacter rectus* | 467 | ACFU01000050 | clade_502 | N | OP |
| *Campylobacter showae* | 468 | ACVQ01000030 | clade_502 | N | OP |
| *Campylobacter* sp. FOBRC14 | 469 | HQ616379 | clade_502 | N | OP |
| *Campylobacter* sp. FOBRC15 | 470 | HQ616380 | clade_502 | N | OP |
| *Campylobacter* sp. oral clone BB120 | 471 | AY005038 | clade_502 | N | OP |
| *Campylobacter sputorum* | 472 | NR_044839 | clade_502 | N | OP |
| *Bacteroides ureolyticus* | 330 | GQ167666 | clade_504 | N | N |
| *Campylobacter gracilis* | 463 | ACYG01000026 | clade_504 | N | OP |
| *Campylobacter hominis* | 464 | NC_009714 | clade_504 | N | OP |
| *Dialister invisus* | 762 | ACIM02000001 | clade_506 | N | N |
| *Dialister micraerophilus* | 763 | AFBB01000028 | clade_506 | N | N |
| *Dialister microaerophilus* | 764 | AENT01000008 | clade_506 | N | N |
| *Dialister propionicifaciens* | 766 | NR_043231 | clade_506 | N | N |
| *Dialister succinatiphilus* | 768 | AB370249 | clade_506 | N | N |
| *Megasphaera elsdenii* | 1200 | AY038996 | clade_506 | N | N |
| *Megasphaera* genomosp. type_1 | 1202 | ADGP01000010 | clade_506 | N | N |
| *Megasphaera* sp. BLPYG_07 | 1204 | HM990964 | clade_506 | N | N |
| *Megasphaera* sp. UPII 199_6 | 1205 | AFIJ01000040 | clade_506 | N | N |
| *Chromobacterium violaceum* | 513 | NC_005085 | clade_507 | N | N |
| *Laribacter hongkongensis* | 1148 | CP001154 | clade_507 | N | N |
| *Methylophilus* sp. ECd5 | 1229 | AY436794 | clade_507 | N | N |
| *Finegoldia magna* | 883 | ACHM02000001 | clade_509 | N | N |
| *Parvimonas micra* | 1431 | AB729072 | clade_509 | N | N |
| *Parvimonas* sp. oral taxon 110 | 1432 | AFII01000002 | clade_509 | N | N |
| *Peptostreptococcus micros* | 1456 | AM176538 | clade_509 | N | N |
| *Peptostreptococcus* sp. oral clone FJ023 | 1460 | AY349390 | clade_509 | N | N |
| *Peptostreptococcus* sp. P4P_31 P3 | 1458 | AY207059 | clade_509 | N | N |
| *Helicobacter pylori* | 997 | CP000012 | clade_510 | N | OP |
| *Anaplasma marginale* | 165 | ABOR01000019 | clade_511 | N | N |
| *Anaplasma phagocytophilum* | 166 | NC_007797 | clade_511 | N | N |
| *Ehrlichia chaffeensis* | 783 | AAIF01000035 | clade_511 | N | OP |
| *Neorickettsia risticii* | 1349 | CP001431 | clade_511 | N | N |
| *Neorickettsia sennetsu* | 1350 | NC_007798 | clade_511 | N | N |
| *Pseudoramibacter alactolyticus* | 1606 | AB036759 | clade_512 | N | N |
| *Veillonella montpellierensis* | 1977 | AF473836 | clade_513 | N | N |
| *Veillonella* sp. oral clone ASCA08 | 1988 | AY923118 | clade_513 | N | N |
| *Veillonella* sp. oral clone ASCB03 | 1989 | AY923122 | clade_513 | N | N |
| *Inquilinus limosus* | 1012 | NR_029046 | clade_514 | N | N |
| *Sphingomonas* sp. oral clone FZ016 | 1746 | AY349412 | clade_514 | N | N |
| *Anaerococcus lactolyticus* | 145 | ABYO01000217 | clade_515 | N | N |
| *Anaerococcus prevotii* | 147 | CP001708 | clade_515 | N | N |
| *Anaerococcus* sp. gpac104 | 152 | AM176528 | clade_515 | N | N |
| *Anaerococcus* sp. gpac126 | 153 | AM176530 | clade_515 | N | N |
| *Anaerococcus* sp. gpac155 | 154 | AM176536 | clade_515 | N | N |
| *Anaerococcus* sp. gpac199 | 155 | AM176539 | clade_515 | N | N |
| *Anaerococcus tetradius* | 157 | ACGC01000107 | clade_515 | N | N |
| *Bacteroides coagulans* | 271 | AB547639 | clade_515 | N | N |
| *Clostridiales* bacterium 9403326 | 534 | HM587324 | clade_515 | N | N |
| *Clostridiales* bacterium ph2 | 539 | JN837487 | clade_515 | N | N |
| *Peptostreptococcus* sp. 9succ1 | 1457 | X90471 | clade_515 | N | N |
| *Peptostreptococcus* sp. oral clone AP24 | 1459 | AB175072 | clade_515 | N | N |
| *Tissierella praeacuta* | 1924 | NR_044860 | clade_515 | N | N |
| *Helicobacter canadensis* | 994 | ABQS01000108 | clade_518 | N | N |

TABLE 1-continued

See, e.g., WO2014/121304

| OTU | SEQ ID Number | Public DB Accession | Clade | Spore Former | Pathogen Status |
|---|---|---|---|---|---|
| *Peptostreptococcus anaerobius* | 1455 | AY326462 | clade_520 | N | N |
| *Peptostreptococcus stomatis* | 1461 | ADGQ01000048 | clade_520 | N | N |
| *Bilophila wadsworthia* | 367 | ADCP01000166 | clade_521 | N | N |
| *Desulfovibrio vulgaris* | 761 | NR_074897 | clade_521 | N | N |
| *Actinomyces nasicola* | 64 | AJ508455 | clade_523 | N | N |
| *Cellulosimicrobium funkei* | 500 | AY501364 | clade_523 | N | N |
| *Lactococcus raffinolactis* | 1146 | NR_044359 | clade_524 | N | N |
| Bacteroidales genomosp. P1 | 258 | AY341819 | clade_529 | N | N |
| Bacteroidales genomosp. P2 oral clone MB1_G13 | 259 | DQ003613 | clade_529 | N | N |
| Bacteroidales genomosp. P3 oral clone MB1_G34 | 260 | DQ003615 | clade_529 | N | N |
| Bacteroidales genomosp. P4 oral clone MB2_G17 | 261 | DQ003617 | clade_529 | N | N |
| Bacteroidales genomosp. P5 oral clone MB2_P04 | 262 | DQ003619 | clade_529 | N | N |
| Bacteroidales genomosp. P6 oral clone MB3_C19 | 263 | DQ003634 | clade_529 | N | N |
| Bacteroidales genomosp. P8 oral clone MB4_G15 | 265 | DQ003626 | clade_529 | N | N |
| Bacteroidetes bacterium oral taxon D27 | 333 | HM099638 | clade_530 | N | N |
| Bacteroidetes bacterium oral taxon F31 | 334 | HM099643 | clade_530 | N | N |
| Bacteroidetes bacterium oral taxon F44 | 335 | HM099649 | clade_530 | N | N |
| *Flavobacterium* sp. NF2_1 | 885 | FJ195988 | clade_530 | N | N |
| *Myroides odoratimimus* | 1326 | NR_042354 | clade_530 | N | N |
| *Myroides* sp. MY15 | 1327 | GU253339 | clade_530 | N | N |
| Chlamydiales bacterium NS16 | 507 | JN606076 | clade_531 | N | N |
| *Chlamydophila pecorum* | 508 | D88317 | clade_531 | N | OP |
| *Parachlamydia* sp. UWE25 | 1423 | BX908798 | clade_531 | N | N |
| *Fusobacterium russii* | 903 | NR_044687 | clade_532 | N | N |
| *Streptobacillus moniliformis* | 1784 | NR_027615 | clade_532 | N | N |
| Eubacteriaceae bacterium P4P_50 P4 | 833 | AY207060 | clade_533 | N | N |
| *Abiotrophia defectiva* | 1 | ACIN02000016 | clade_534 | N | N |
| *Abiotrophia* sp. oral clone P4PA_155 P1 | 3 | AY207063 | clade_534 | N | N |
| *Catonella* genomosp. P1 oral clone MB5_P12 | 496 | DQ003629 | clade_534 | N | N |
| *Catonella morbi* | 497 | ACIL02000016 | clade_534 | N | N |
| *Catonella* sp. oral clone FL037 | 498 | AY349369 | clade_534 | N | N |
| *Eremococcus coleocola* | 818 | AENN01000008 | clade_534 | N | N |
| *Facklamia hominis* | 879 | Y10772 | clade_534 | N | N |
| *Granulicatella* sp. M658_99_3 | 962 | AJ271861 | clade_534 | N | N |
| *Campylobacter coli* | 459 | AAFL01000004 | clade_535 | N | OP |
| *Campylobacter concisus* | 460 | CP000792 | clade_535 | N | OP |
| *Campylobacter fetus* | 462 | ACLG01001177 | clade_535 | N | OP |
| *Campylobacter jejuni* | 465 | AL139074 | clade_535 | N | Category-B |
| *Campylobacter upsaliensis* | 473 | AEPU01000040 | clade_535 | N | OP |
| *Atopobium minutum* | 183 | HM007583 | clade_539 | N | N |
| *Atopobium parvulum* | 184 | CP001721 | clade_539 | N | N |
| *Atopobium rimae* | 185 | ACFE01000007 | clade_539 | N | N |
| *Atopobium* sp. BS2 | 186 | HQ616367 | clade_539 | N | N |
| *Atopobium* sp. F0209 | 187 | EU592966 | clade_539 | N | N |
| *Atopobium* sp. ICM42b10 | 188 | HQ616393 | clade_539 | N | N |
| *Atopobium* sp. ICM57 | 189 | HQ616400 | clade_539 | N | N |
| *Atopobium vaginae* | 190 | AEDQ01000024 | clade_539 | N | N |
| Coriobacteriaceae bacterium BV3Ac1 | 677 | JN809768 | clade_539 | N | N |
| *Actinomyces naeslundii* | 63 | X81062 | clade_54 | N | N |
| *Actinomyces oricola* | 67 | NR_025559 | clade_54 | N | N |
| *Actinomyces oris* | 69 | BABV01000070 | clade_54 | N | N |
| *Actinomyces* sp. 7400942 | 70 | EU484334 | clade_54 | N | N |
| *Actinomyces* sp. ChDC B197 | 72 | AF543275 | clade_54 | N | N |
| *Actinomyces* sp. GEJ15 | 73 | GU561313 | clade_54 | N | N |
| *Actinomyces* sp. M2231_94_1 | 79 | AJ234063 | clade_54 | N | N |
| *Actinomyces* sp. oral clone GU067 | 83 | AY349362 | clade_54 | N | N |
| *Actinomyces* sp. oral clone IO077 | 85 | AY349364 | clade_54 | N | N |
| *Actinomyces* sp. oral clone IP073 | 86 | AY349365 | clade_54 | N | N |
| *Actinomyces* sp. oral clone JA063 | 88 | AY349367 | clade_54 | N | N |
| *Actinomyces* sp. oral taxon 170 | 89 | AFBL01000010 | clade_54 | N | N |
| *Actinomyces* sp. oral taxon 171 | 90 | AECW01000034 | clade_54 | N | N |
| *Actinomyces urogenitalis* | 95 | ACFH01000038 | clade_54 | N | N |
| *Actinomyces viscosus* | 96 | ACRE01000096 | clade_54 | N | N |
| *Orientia tsutsugamushi* | 1383 | AP008981 | clade_541 | N | OP |
| *Megamonas funiformis* | 1198 | AB300988 | clade_542 | N | N |
| *Megamonas hypermegale* | 1199 | AJ420107 | clade_542 | N | N |
| *Aeromicrobium marinum* | 102 | NR_025681 | clade_544 | N | N |
| *Aeromicrobium* sp. JC14 | 103 | JF824798 | clade_544 | N | N |
| *Luteococcus sanguinis* | 1190 | NR_025507 | clade_544 | N | N |
| Propionibacteriaceae bacterium NML 02_0265 | 1568 | EF599122 | clade_544 | N | N |
| *Rhodococcus corynebacterioides* | 1622 | X80615 | clade_546 | N | N |
| *Rhodococcus erythropolis* | 1624 | ACNO01000030 | clade_546 | N | N |
| *Rhodococcus fascians* | 1625 | NR_037021 | clade_546 | N | N |
| *Segniliparus rotundus* | 1690 | CP001958 | clade_546 | N | N |
| *Segniliparus rugosus* | 1691 | ACZI01000025 | clade_546 | N | N |

TABLE 1-continued

See, e.g., WO2014/121304

| OTU | SEQ ID Number | Public DB Accession | Clade | Spore Former | Pathogen Status |
|---|---|---|---|---|---|
| *Exiguobacterium acetylicum* | 878 | FJ970034 | clade_547 | N | N |
| *Macrococcus caseolyticus* | 1194 | NR_074941 | clade_547 | N | N |
| *Streptomyces* sp. 1 AIP_2009 | 1890 | FJ176782 | clade_548 | N | N |
| *Streptomyces* sp. SD 524 | 1892 | EU544234 | clade_548 | N | N |
| *Streptomyces* sp. SD 528 | 1893 | EU544233 | clade_548 | N | N |
| *Streptomyces thermoviolaceus* | 1895 | NR_027616 | clade_548 | N | N |
| *Borrelia afzelii* | 388 | ABCU01000001 | clade_549 | N | OP |
| *Borrelia crocidurae* | 390 | DQ057990 | clade_549 | N | OP |
| *Borrelia duttonii* | 391 | NC_011229 | clade_549 | N | OP |
| *Borrelia hermsii* | 393 | AY597657 | clade_549 | N | OP |
| *Borrelia hispanica* | 394 | DQ057988 | clade_549 | N | OP |
| *Borrelia persica* | 395 | HM161645 | clade_549 | N | OP |
| *Borrelia recurrentis* | 396 | AF107367 | clade_549 | N | OP |
| *Borrelia spielmanii* | 398 | ABKB01000002 | clade_549 | N | OP |
| *Borrelia turicatae* | 399 | NC_008710 | clade_549 | N | OP |
| *Borrelia valaisiana* | 400 | ABCY01000002 | clade_549 | N | OP |
| *Providencia alcalifaciens* | 1586 | ABXW01000071 | clade_55 | N | N |
| *Providencia rettgeri* | 1587 | AM040492 | clade_55 | N | N |
| *Providencia rustigianii* | 1588 | AM040489 | clade_55 | N | N |
| *Providencia stuartii* | 1589 | AF008581 | clade_55 | N | N |
| *Treponema pallidum* | 1932 | CP001752 | clade_550 | N | OP |
| *Treponema phagedenis* | 1934 | AEFH01000172 | clade_550 | N | N |
| *Treponema* sp. clone DDKL_4 | 1939 | Y08894 | clade_550 | N | N |
| *Acholeplasma laidlawii* | 17 | NR_074448 | clade_551 | N | N |
| *Mycoplasma putrefaciens* | 1323 | U26055 | clade_551 | N | N |
| Mycoplasmataceae genomosp. P1 oral clone MB1_G23 | 1325 | DQ003614 | clade_551 | N | N |
| *Spiroplasma insolitum* | 1750 | NR_025705 | clade_551 | N | N |
| *Collinsella intestinalis* | 660 | ABXH02000037 | clade_553 | N | N |
| *Collinsella stercoris* | 661 | ABXJ01000150 | clade_553 | N | N |
| *Collinsella tanakaei* | 662 | AB490807 | clade_553 | N | N |
| *Caminicella sporogenes* | 458 | NR_025485 | clade_554 | N | N |
| *Acidaminococcus fermentans* | 21 | CP001859 | clade_556 | N | N |
| *Acidaminococcus intestini* | 22 | CP003058 | clade_556 | N | N |
| *Acidaminococcus* sp. D21 | 23 | ACGB01000071 | clade_556 | N | N |
| *Phascolarctobacterium faecium* | 1462 | NR_026111 | clade_556 | N | N |
| *Phascolarctobacterium* sp. YIT 12068 | 1463 | AB490812 | clade_556 | N | N |
| *Phascolarctobacterium succinatutens* | 1464 | AB490811 | clade_556 | N | N |
| *Acidithiobacillus ferrivorans* | 25 | NR_074660 | clade_557 | N | N |
| Xanthomonadaceae bacterium NML 03_0222 | 2015 | EU313791 | clade_557 | N | N |
| *Catabacter hongkongensis* | 494 | AB671763 | clade_558 | N | N |
| *Christensenella minuta* | 512 | AB490809 | clade_558 | N | N |
| Clostridiales bacterium oral clone P4PA_66 P1 | 536 | AY207065 | clade_558 | N | N |
| Clostridiales bacterium oral taxon 093 | 537 | GQ422712 | clade_558 | N | N |
| *Heliobacterium modesticaldum* | 1000 | NR_074517 | clade_560 | N | N |
| *Alistipes indistinctus* | 130 | AB490804 | clade_561 | N | N |
| Bacteroidales bacterium ph 8 | 257 | JN837494 | clade_561 | N | N |
| Candidates *Sulcia muelleri* | 475 | CP002163 | clade_561 | N | N |
| *Cytophaga xylanolytica* | 742 | FR733683 | clade_561 | N | N |
| Flavobacteriaceae genomosp. C1 | 884 | AY278614 | clade_561 | N | N |
| *Gramella forsetii* | 958 | NR_074707 | clade_561 | N | N |
| *Sphingobacterium faecium* | 1740 | NR_025537 | clade_562 | N | N |
| *Sphingobacterium mizutaii* | 1741 | JF708889 | clade_562 | N | N |
| *Sphingobacterium multivorum* | 1742 | NR_040953 | clade_562 | N | N |
| *Sphingobacterium spiritivorum* | 1743 | ACHA02000013 | clade_562 | N | N |
| *Jonquetella anthropi* | 1017 | ACOO02000004 | clade_563 | N | N |
| *Pyramidobacter piscolens* | 1614 | AY207056 | clade_563 | N | N |
| *Synergistes* genomosp. C1 | 1904 | AY278615 | clade_563 | N | N |
| *Synergistes* sp. RMA 14551 | 1905 | DQ412722 | clade_563 | N | N |
| Synergistetes bacterium ADV897 | 1906 | GQ258968 | clade_563 | N | N |
| Candidates *Arthromitus* sp. SFB_mouse_Yit | 474 | NR_074460 | clade_564 | N | N |
| *Gracilibacter thermotolerans* | 957 | NR_043559 | clade_564 | N | N |
| *Brachyspira aalborgi* | 404 | FM178386 | clade_565 | N | N |
| *Brachyspira* sp. HIS3 | 406 | FM178387 | clade_565 | N | N |
| *Brachyspira* sp. HIS4 | 407 | FM178388 | clade_565 | N | N |
| *Brachyspira* sp. HIS5 | 408 | FM178389 | clade_565 | N | N |
| *Adlercreutzia equolifaciens* | 97 | AB306661 | clade_566 | N | N |
| Coriobacteriaceae bacterium JC110 | 678 | CAEM01000062 | clade_566 | N | N |
| Coriobacteriaceae bacterium phI | 679 | JN837493 | clade_566 | N | N |
| *Cryptobacterium curtum* | 740 | GQ422741 | clade_566 | N | N |
| *Eggerthella sinensis* | 779 | AY321958 | clade_566 | N | N |
| *Eggerthella* sp. 1_3_56FAA | 780 | ACWN01000099 | clade_566 | N | N |
| *Eggerthella* sp. HGA1 | 781 | AEXR01000021 | clade_566 | N | N |
| *Eggerthella* sp. YY7918 | 782 | AP012211 | clade_566 | N | N |
| *Gordonibacter pamelaeae* | 680 | AM886059 | clade_566 | N | N |

TABLE 1-continued

See, e.g., WO2014/121304

| OTU | SEQ ID Number | Public DB Accession | Clade | Spore Former | Pathogen Status |
|---|---|---|---|---|---|
| *Gordonibacter pamelaeae* | 956 | FP929047 | clade_566 | N | N |
| *Slackia equolifaciens* | 1732 | EU377663 | clade_566 | N | N |
| *Slackia exigua* | 1733 | ACUX01000029 | clade_566 | N | N |
| *Slackia faecicanis* | 1734 | NR_042220 | clade_566 | N | N |
| *Slackia heliotrinireducens* | 1735 | NR_074439 | clade_566 | N | N |
| *Slackia isoflavoniconvertens* | 1736 | AB566418 | clade_566 | N | N |
| *Slackia piriformis* | 1737 | AB490806 | clade_566 | N | N |
| *Slackia* sp. NATTS | 1738 | AB505075 | clade_566 | N | N |
| Chlamydiales bacterium NS13 | 506 | JN606075 | clade_567 | N | N |
| Victivallaceae bacterium NML 080035 | 2003 | FJ394915 | clade_567 | N | N |
| *Victivallis vadensis* | 2004 | ABDE02000010 | clade_567 | N | N |
| *Streptomyces griseus* | 1889 | NR_074787 | clade_573 | N | N |
| *Streptomyces* sp. SD 511 | 1891 | EU544231 | clade_573 | N | N |
| *Streptomyces* sp. SD 534 | 1894 | EU544232 | clade_573 | N | N |
| *Cloacibacillus evryensis* | 530 | GQ258966 | clade_575 | N | N |
| Deferribacteres sp. oral clone JV001 | 743 | AY349370 | clade_575 | N | N |
| Deferribacteres sp. oral clone JV023 | 745 | AY349372 | clade_575 | N | N |
| Synergistetes bacterium LBVCM1157 | 1907 | GQ258969 | clade_575 | N | N |
| Synergistetes bacterium oral taxon 362 | 1909 | GU410752 | clade_575 | N | N |
| Synergistetes bacterium oral taxon D48 | 1910 | GU430992 | clade_575 | N | N |
| *Peptococcus* sp. oral clone JM048 | 1439 | AY349389 | clade_576 | N | N |
| *Helicobacter winghamensis* | 999 | ACDO01000013 | clade_577 | N | N |
| *Wolinella succinogenes* | 2014 | BX571657 | clade_577 | N | N |
| *Olsenella* genomosp. C1 | 1368 | AY278623 | clade_578 | N | N |
| *Olsenella profusa* | 1369 | FN178466 | clade_578 | N | N |
| *Olsenella* sp. F0004 | 1370 | EU592964 | clade_578 | N | N |
| *Olsenella* sp. oral taxon 809 | 1371 | ACVE01000002 | clade_578 | N | N |
| *Olsenella uli* | 1372 | CP002106 | clade_578 | N | N |
| *Nocardiopsis dassonvillei* | 1356 | CP002041 | clade_579 | N | N |
| *Peptococcus niger* | 1438 | NR_029221 | clade_580 | N | N |
| *Peptococcus* sp. oral taxon 167 | 1440 | GQ422727 | clade_580 | N | N |
| *Akkermansia muciniphila* | 118 | CP001071 | clade_583 | N | N |
| *Opitutus terrae* | 1373 | NR_074978 | clade_583 | N | N |
| Clostridiales bacterium oral taxon F32 | 538 | HM099644 | clade_584 | N | N |
| *Leptospira borgpetersenii* | 1161 | NC_008508 | clade_585 | N | OP |
| *Leptospira broomii* | 1162 | NR_043200 | clade_585 | N | OP |
| *Leptospira interrogans* | 1163 | NC_005823 | clade_585 | N | OP |
| *Methanobrevibacter gottschalkii* | 1213 | NR_044789 | clade_587 | N | N |
| *Methanobrevibacter millerae* | 1214 | NR_042785 | clade_587 | N | N |
| *Methanobrevibacter oralis* | 1216 | HE654003 | clade_587 | N | N |
| *Methanobrevibacter thaueri* | 1219 | NR_044787 | clade_587 | N | N |
| *Methanobrevibacter smithii* | 1218 | ABYV02000002 | clade_588 | N | N |
| *Deinococcus radiodurans* | 746 | AE000513 | clade_589 | N | N |
| *Deinococcus* sp. R_43890 | 747 | FR682752 | clade_589 | N | N |
| *Thermus aquaticus* | 1923 | NR_025900 | clade_589 | N | N |
| *Actinomyces* sp. c109 | 81 | AB167239 | clade_590 | N | N |
| Syntrophomonadaceae genomosp. P1 | 1912 | AY341821 | clade_590 | N | N |
| *Anaerobaculum hydrogeniformans* | 141 | ACJX02000009 | clade_591 | N | N |
| *Microcystis aeruginosa* | 1246 | NC_010296 | clade_592 | N | N |
| *Prochlorococcus marinus* | 1567 | CP000551 | clade_592 | N | N |
| *Methanobrevibacter acididurans* | 1208 | NR_028779 | clade_593 | N | N |
| *Methanobrevibacter arboriphilus* | 1209 | NR_042783 | clade_593 | N | N |
| *Methanobrevibacter curvatus* | 1210 | NR_044796 | clade_593 | N | N |
| *Methanobrevibacter cuticularis* | 1211 | NR_044776 | clade_593 | N | N |
| *Methanobrevibacter filiformis* | 1212 | NR_044801 | clade_593 | N | N |
| *Methanobrevibacter woesei* | 1220 | NR_044788 | clade_593 | N | N |
| *Roseiflexus castenholzii* | 1642 | CP000804 | clade_594 | N | N |
| *Methanobrevibacter olleyae* | 1215 | NR_043024 | clade_595 | N | N |
| *Methanobrevibacter ruminantium* | 1217 | NR_042784 | clade_595 | N | N |
| *Methanobrevibacter wolinii* | 1221 | NR_044790 | clade_595 | N | N |
| *Methanosphaera stadtmanae* | 1222 | AY196684 | clade_595 | N | N |
| *Chloroflexi* genomosp. P1 | 511 | AY331414 | clade_596 | N | N |
| *Halorubrum lipolyticum* | 992 | AB477978 | clade_597 | N | N |
| *Methanobacterium formicicum* | 1207 | NR_025028 | clade_597 | N | N |
| *Acidilobus saccharovorans* | 24 | AY350586 | clade_598 | N | N |
| *Hyperthermus butylicus* | 1006 | CP000493 | clade_598 | N | N |
| *Ignicoccus islandicus* | 1011 | X99562 | clade_598 | N | N |
| *Metallosphaera sedula* | 1206 | D26491 | clade_598 | N | N |
| *Thermofilum pendens* | 1922 | X14835 | clade_598 | N | N |
| *Prevotella melaninogenica* | 1506 | CP002122 | clade_6 | N | N |
| *Prevotella* sp. ICM1 | 1520 | HQ616385 | clade_6 | N | N |
| *Prevotella* sp. oral clone FU048 | 1535 | AY349393 | clade_6 | N | N |
| *Prevotella* sp. oral clone GI030 | 1537 | AY349395 | clade_6 | N | N |
| *Prevotella* sp. SEQ116 | 1526 | JN867246 | clade_6 | N | N |
| *Streptococcus anginosus* | 1787 | AECT01000011 | clade_60 | N | N |

TABLE 1-continued

See, e.g., WO2014/121304

| OTU | SEQ ID Number | Public DB Accession | Clade | Spore Former | Pathogen Status |
|---|---|---|---|---|---|
| *Streptococcus milleri* | 1812 | X81023 | clade_60 | N | N |
| *Streptococcus* sp. 16362 | 1829 | JN590019 | clade_60 | N | N |
| *Streptococcus* sp. 69130 | 1832 | X78825 | clade_60 | N | N |
| *Streptococcus* sp. AC15 | 1833 | HQ616356 | clade_60 | N | N |
| *Streptococcus* sp. CM7 | 1839 | HQ616373 | clade_60 | N | N |
| *Streptococcus* sp. OBRC6 | 1847 | HQ616352 | clade_60 | N | N |
| *Burkholderia ambifaria* | 442 | AAUZ01000009 | clade_61 | N | OP |
| *Burkholderia cenocepacia* | 443 | AAHI01000060 | clade_61 | N | OP |
| *Burkholderia cepacia* | 444 | NR_041719 | clade_61 | N | OP |
| *Burkholderia mallei* | 445 | CP000547 | clade_61 | N | Category-B |
| *Burkholderia multivorans* | 446 | NC_010086 | clade_61 | N | OP |
| *Burkholderia oklahomensis* | 447 | DQ108388 | clade_61 | N | OP |
| *Burkholderia pseudomallei* | 448 | CP001408 | clade_61 | N | Category-B |
| *Burkholderia rhizoxinica* | 449 | HQ005410 | clade_61 | N | OP |
| *Burkholderia* sp. 383 | 450 | CP000151 | clade_61 | N | OP |
| *Burkholderia xenovorans* | 451 | U86373 | clade_61 | N | OP |
| *Prevotella buccae* | 1488 | ACRB01000001 | clade_62 | N | N |
| *Prevotella* genomosp. P8 oral clone MB3_P13 | 1498 | DQ003622 | clade_62 | N | N |
| *Prevotella* sp. oral clone FW035 | 1536 | AY349394 | clade_62 | N | N |
| *Prevotella bivia* | 1486 | ADFO01000096 | clade_63 | N | N |
| *Prevotella disiens* | 1494 | AEDO01000026 | clade_64 | N | N |
| *Bacteroides faecis* | 276 | GQ496624 | clade_65 | N | N |
| *Bacteroides fragilis* | 279 | AP006841 | clade_65 | N | N |
| *Bacteroides nordii* | 285 | NR_043017 | clade_65 | N | N |
| *Bacteroides salyersiae* | 292 | EU136690 | clade_65 | N | N |
| *Bacteroides* sp. 1_1_14 | 293 | ACRP01000155 | clade_65 | N | N |
| *Bacteroides* sp. 1_1_6 | 295 | ACIC01000215 | clade_65 | N | N |
| *Bacteroides* sp. 2_1_56FAA | 298 | ACWI01000065 | clade_65 | N | N |
| *Bacteroides* sp. AR29 | 316 | AF139525 | clade_65 | N | N |
| *Bacteroides* sp. B2 | 317 | EU722733 | clade_65 | N | N |
| *Bacteroides thetaiotaomicron* | 328 | NR_074277 | clade_65 | N | N |
| *Actinobacillus minor* | 45 | ACFT01000025 | clade_69 | N | N |
| *Haemophilas parasuis* | 978 | GU226366 | clade_69 | N | N |
| *Vibrio cholerae* | 1996 | AAUR01000095 | clade_71 | N | Category-B |
| *Vibrio fluvialis* | 1997 | X76335 | clade_71 | N | Category-B |
| *Vibrio furnissii* | 1998 | CP002377 | clade_71 | N | Category-B |
| *Vibrio mimicus* | 1999 | ADAF01000001 | clade_71 | N | Category-B |
| *Vibrio parahaemolyticus* | 2000 | AAWQ01000116 | clade_71 | N | Category-B |
| *Vibrio* sp. RC341 | 2001 | ACZT01000024 | clade_71 | N | Category-B |
| *Vibrio vulnificus* | 2002 | AE016796 | clade_71 | N | Category-B |
| *Lactobacillus acidophilus* | 1067 | CP000033 | clade_72 | N | N |
| *Lactobacillus amylolyticus* | 1069 | ADNY01000006 | clade_72 | N | N |
| *Lactobacillus amylovorus* | 1070 | CP002338 | clade_72 | N | N |
| *Lactobacillus crispatus* | 1078 | ACOG01000151 | clade_72 | N | N |
| *Lactobacillus delbrueckii* | 1080 | CP002341 | clade_72 | N | N |
| *Lactobacillus helveticus* | 1088 | ACLM01000202 | clade_72 | N | N |
| *Lactobacillus kalixensis* | 1094 | NR_029083 | clade_72 | N | N |
| *Lactobacillus kefiranofaciens* | 1095 | NR_042440 | clade_72 | N | N |
| *Lactobacillus leichmannii* | 1098 | JX986966 | clade_72 | N | N |
| *Lactobacillus* sp. 66c | 1120 | FR681900 | clade_72 | N | N |
| *Lactobacillus* sp. KLDS 1.0701 | 1122 | EU600905 | clade_72 | N | N |
| *Lactobacillus* sp. KLDS 1.0712 | 1130 | EU600916 | clade_72 | N | N |
| *Lactobacillus* sp. oral clone HT070 | 1136 | AY349383 | clade_72 | N | N |
| *Lactobacillus ultunensis* | 1139 | ACGU01000081 | clade_72 | N | N |
| *Prevotella intermedia* | 1502 | AF414829 | clade_81 | N | N |
| *Prevotella nigrescens* | 1511 | AFPX01000069 | clade_81 | N | N |
| *Prevotella pallens* | 1515 | AFPY01000135 | clade_81 | N | N |
| *Prevotella* sp. oral taxon 310 | 1551 | GQ422737 | clade_81 | N | N |
| *Prevotella* genomosp. C1 | 1495 | AY278624 | clade_82 | N | N |
| *Prevotella* sp. CM38 | 1519 | HQ610181 | clade_82 | N | N |
| *Prevotella* sp. oral taxon 317 | 1552 | ACQH01000158 | clade_82 | N | N |
| *Prevotella* sp. SG12 | 1527 | GU561343 | clade_82 | N | N |
| *Prevotella denticola* | 1493 | CP002589 | clade_83 | N | N |
| *Prevotella* genomosp. P7 oral clone MB2_P31 | 1497 | DQ003620 | clade_83 | N | N |
| *Prevotella histicola* | 1501 | JN867315 | clade_83 | N | N |
| *Prevotella multiformis* | 1508 | AEWX01000054 | clade_83 | N | N |
| *Prevotella* sp. JCM 6330 | 1522 | AB547699 | clade_83 | N | N |
| *Prevotella* sp. oral clone GI059 | 1539 | AY349397 | clade_83 | N | N |
| *Prevotella* sp. oral taxon 782 | 1555 | GQ422745 | clade_83 | N | N |
| *Prevotella* sp. oral taxon G71 | 1559 | GU432180 | clade_83 | N | N |
| *Prevotella* sp. SEQ065 | 1524 | JN867234 | clade_83 | N | N |
| *Prevotella veroralis* | 1565 | ACVA01000027 | clade_83 | N | N |
| *Bacteroides acidifaciens* | 266 | NR_028607 | clade_85 | N | N |
| *Bacteroides cellulosilyticus* | 269 | ACCH01000108 | clade_85 | N | N |
| *Bacteroides clarus* | 270 | AFBM01000011 | clade_85 | N | N |

TABLE 1-continued

See, e.g., WO2014/121304

| OTU | SEQ ID Number | Public DB Accession | Clade | Spore Former | Pathogen Status |
|---|---|---|---|---|---|
| *Bacteroides eggerthii* | 275 | ACWG01000065 | clade_85 | N | N |
| *Bacteroides oleiciplenus* | 286 | AB547644 | clade_85 | N | N |
| *Bacteroides pyogenes* | 290 | NR_041280 | clade_85 | N | N |
| *Bacteroides* sp. 315_5 | 300 | FJ848547 | clade_85 | N | N |
| *Bacteroides* sp. 31SF15 | 301 | AJ583248 | clade_85 | N | N |
| *Bacteroides* sp. 31SF18 | 302 | AJ583249 | clade_85 | N | N |
| *Bacteroides* sp. 35AE31 | 303 | AJ583244 | clade_85 | N | N |
| *Bacteroides* sp. 35AE37 | 304 | AJ583245 | clade_85 | N | N |
| *Bacteroides* sp. 35BE34 | 305 | AJ583246 | clade_85 | N | N |
| *Bacteroides* sp. 35BE35 | 306 | AJ583247 | clade_85 | N | N |
| *Bacteroides* sp. WH2 | 324 | AY895180 | clade_85 | N | N |
| *Bacteroides* sp. XB12B | 325 | AM230648 | clade_85 | N | N |
| *Bacteroides* stercoris | 327 | ABFZ02000022 | clade_85 | N | N |
| *Actinobacillus pleuropneumoniae* | 46 | NR_074857 | clade_88 | N | N |
| *Actinobacillus ureae* | 48 | AEVG01000167 | clade_88 | N | N |
| *Haemophilus aegyptius* | 969 | AFBC01000053 | clade_88 | N | N |
| *Haemophilus ducreyi* | 970 | AE017143 | clade_88 | N | OP |
| *Haemophilus haemolyticus* | 973 | JN175335 | clade_88 | N | N |
| *Haemophilus influenzae* | 974 | AADP01000001 | clade_88 | N | OP |
| *Haemophilus parahaemolyticus* | 975 | GU561425 | clade_88 | N | N |
| *Haemophilus parainfluenzae* | 976 | AEWU01000024 | clade_88 | N | N |
| *Haemophilus paraphrophaemolyticus* | 977 | M75076 | clade_88 | N | N |
| *Haemophilus somnus* | 979 | NC_008309 | clade_88 | N | N |
| *Haemophilus* sp. 70334 | 980 | HQ680854 | clade_88 | N | N |
| *Haemophilus* sp. HK445 | 981 | FJ685624 | clade_88 | N | N |
| *Haemophilus* sp. oral clone ASCA07 | 982 | AY923117 | clade_88 | N | N |
| *Haemophilus* sp. oral clone ASCG06 | 983 | AY923147 | clade_88 | N | N |
| *Haemophilus* sp. oral clone BJ021 | 984 | AY005034 | clade_88 | N | N |
| *Haemophilus* sp. oral clone BJ095 | 985 | AY005033 | clade_88 | N | N |
| *Haemophilus* sp. oral taxon 851 | 987 | AGRK01000004 | clade_88 | N | N |
| *Haemophilus sputorum* | 988 | AFNK01000005 | clade_88 | N | N |
| *Histophilus somni* | 1003 | AF549387 | clade_88 | N | N |
| *Mannheimia haemolytica* | 1195 | ACZX01000102 | clade_88 | N | N |
| *Pasteurella bettyae* | 1433 | L06088 | clade_88 | N | N |
| *Moellerella wisconsensis* | 1253 | JN175344 | clade_89 | N | N |
| *Morganella morganii* | 1265 | AJ301681 | clade_89 | N | N |
| *Morganella* sp. JB_T16 | 1266 | AJ781005 | clade_89 | N | N |
| *Proteus mirabilis* | 1582 | ACLE01000013 | clade_89 | N | N |
| *Proteus penneri* | 1583 | ABVP01000020 | clade_89 | N | N |
| *Proteus* sp. HS7514 | 1584 | DQ512963 | clade_89 | N | N |
| *Proteus vulgaris* | 1585 | AJ233425 | clade_89 | N | N |
| *Oribacterium sinus* | 1374 | ACKX1000142 | clade_90 | N | N |
| *Oribacterium* sp. ACB1 | 1375 | HM120210 | clade_90 | N | N |
| *Oribacterium* sp. ACB7 | 1376 | HM120211 | clade_90 | N | N |
| *Oribacterium* sp. CM12 | 1377 | HQ616374 | clade_90 | N | N |
| *Oribacterium* sp. ICM51 | 1378 | HQ616397 | clade_90 | N | N |
| *Oribacterium* sp. OBRC12 | 1379 | HQ616355 | clade_90 | N | N |
| *Oribacterium* sp. oral taxon 108 | 1382 | AFIH01000001 | clade_90 | N | N |
| *Actinobacillus actinomycetemcomitans* | 44 | AY362885 | clade_92 | N | N |
| *Actinobacillus succinogenes* | 47 | CP000746 | clade_92 | N | N |
| *Aggregatibacter actinomycetemcomitans* | 112 | CP001733 | clade_92 | N | N |
| *Aggregatibacter aphrophilus* | 113 | CP001607 | clade_92 | N | N |
| *Aggregatibacter segnis* | 114 | AEPS01000017 | clade_92 | N | N |
| *Averyella dalhousiensis* | 194 | DQ481464 | clade_92 | N | N |
| Bisgaard Taxon | 368 | AY683487 | clade_92 | N | N |
| Bisgaard Taxon | 369 | AY683489 | clade_92 | N | N |
| Bisgaard Taxon | 370 | AY683491 | clade_92 | N | N |
| Bisgaard Taxon | 371 | AY683492 | clade_92 | N | N |
| *Buchnera aphidicola* | 440 | NR_074609 | clade_92 | N | N |
| *Cedecea davisae* | 499 | AF493976 | clade_92 | N | N |
| *Citrobacter amalonaticus* | 517 | FR870441 | clade_92 | N | N |
| *Citrobacter braakii* | 518 | NR_028687 | clade_92 | N | N |
| *Citrobacter farmeri* | 519 | AF025371 | clade_92 | N | N |
| *Citrobacter freundii* | 520 | NR_028894 | clade_92 | N | N |
| *Citrobacter gillenii* | 521 | AF025367 | clade_92 | N | N |
| *Citrobacter koseri* | 522 | NC_009792 | clade_92 | N | N |
| *Citrobacter murliniae* | 523 | AF025369 | clade_92 | N | N |
| *Citrobacter rodentium* | 524 | NR_074903 | clade_92 | N | N |
| *Citrobacter sedlakii* | 525 | AF025364 | clade_92 | N | N |
| *Citrobacter* sp. 30_2 | 526 | ACDJ01000053 | clade_92 | N | N |
| *Citrobacter* sp. KMSI_3 | 527 | GQ468398 | clade_92 | N | N |
| *Citrobacter werkmanii* | 528 | AF025373 | clade_92 | N | N |
| *Citrobacter youngae* | 529 | ABWL02000011 | clade_92 | N | N |
| *Cronobacter malonaticus* | 737 | GU122174 | clade_92 | N | N |
| *Cronobacter sakazakii* | 738 | NC_009778 | clade_92 | N | N |

TABLE 1-continued

See, e.g., WO2014/121304

| OTU | SEQ ID Number | Public DB Accession | Clade | Spore Former | Pathogen Status |
|---|---|---|---|---|---|
| *Cronobacter turicensis* | 739 | FN543093 | clade_92 | N | N |
| *Enterobacter aerogenes* | 786 | AJ251468 | clade_92 | N | N |
| *Enterobacter asburiae* | 787 | NR_024640 | clade_92 | N | N |
| *Enterobacter cancerogenus* | 788 | Z96078 | clade_92 | N | N |
| *Enterobacter cloacae* | 789 | FP929040 | clade_92 | N | N |
| *Enterobacter cowanii* | 790 | NR_025566 | clade_92 | N | N |
| *Enterobacter hormaechei* | 791 | AFHR01000079 | clade_92 | N | N |
| *Enterobacter* sp. 247BMC | 792 | HQ122932 | clade_92 | N | N |
| *Enterobacter* sp. 638 | 793 | NR_074777 | clade_92 | N | N |
| *Enterobacter* sp. JC163 | 794 | JN657217 | clade_92 | N | N |
| *Enterobacter* sp. SCSS | 795 | HM007811 | clade_92 | N | N |
| *Enterobacter* sp. TSE38 | 796 | HM156134 | clade_92 | N | N |
| Enterobacteriaceae bacterium 9_2_54FAA | 797 | ADCU01000033 | clade_92 | N | N |
| Enterobacteriaceae bacterium CF01Ent_1 | 798 | AJ489826 | clade_92 | N | N |
| Enterobacteriaceae bacterium Smarlab 3302238 | 799 | AY538694 | clade_92 | N | N |
| *Escherichia albertii* | 824 | ABKX01000012 | clade_92 | N | N |
| *Escherichia coli* | 825 | NC_008563 | clade_92 | N | Category-B |
| *Escherichia fergusonii* | 826 | CU928158 | clade_92 | N | N |
| *Escherichia hermannii* | 827 | HQ407266 | clade_92 | N | N |
| *Escherichia* sp. 1_1_43 | 828 | ACID01000033 | clade_92 | N | N |
| *Escherichia* sp. 4_1_40B | 829 | ACDM02000056 | clade_92 | N | N |
| *Escherichia* sp. B4 | 830 | EU722735 | clade_92 | N | N |
| *Escherichia vulneris* | 831 | NR_041927 | clade_92 | N | N |
| *Ewingella americana* | 877 | JN175329 | clade_92 | N | N |
| *Haemophilus* genomosp. P2 oral clone MB3_C24 | 971 | DQ003621 | clade_92 | N | N |
| *Haemophilus* genomosp. P3 oral clone MB3_C38 | 972 | DQ003635 | clade_92 | N | N |
| *Haemophilus* sp. oral clone JM053 | 986 | AY349380 | clade_92 | N | N |
| *Hafnia alvei* | 989 | DQ412565 | clade_92 | N | N |
| *Klebsiella oxytoca* | 1024 | AY292871 | clade_92 | N | OP |
| *Klebsiella pneumoniae* | 1025 | CP000647 | clade_92 | N | OP |
| *Klebsiella* sp. AS10 | 1026 | HQ616362 | clade_92 | N | N |
| *Klebsiella* sp. Co9935 | 1027 | DQ068764 | clade_92 | N | N |
| *Klebsiella* sp. enrichment culture clone SRC_DSD25 | 1036 | HM195210 | clade_92 | N | N |
| *Klebsiella* sp. OBRC7 | 1028 | HQ616353 | clade_92 | N | N |
| *Klebsiella* sp. SP_BA | 1029 | FJ999767 | clade_92 | N | N |
| *Klebsiella* sp. SRC_DSD1 | 1033 | GU797254 | clade_92 | N | N |
| *Klebsiella* sp. SRC_DSD11 | 1030 | GU797263 | clade_92 | N | N |
| *Klebsiella* sp. SRC_DSD12 | 1031 | GU797264 | clade_92 | N | N |
| *Klebsiella* sp. SRC_DSD15 | 1032 | GU797267 | clade_92 | N | N |
| *Klebsiella* sp. SRC_DSD2 | 1034 | GU797253 | clade_92 | N | N |
| *Klebsiella* sp. SRC_DSD6 | 1035 | GU797258 | clade_92 | N | N |
| *Klebsiella variicola* | 1037 | CP001891 | clade_92 | N | N |
| *Kluyvera ascorbata* | 1038 | NR_028677 | clade_92 | N | N |
| *Kluyvera cryocrescens* | 1039 | NR_028803 | clade_92 | N | N |
| *Leminorella grimontii* | 1159 | AJ233421 | clade_92 | N | N |
| *Leminorella richardii* | 1160 | HF558368 | clade_92 | N | N |
| *Pantoea agglomerans* | 1409 | AY335552 | clade_92 | N | N |
| *Pantoea ananatis* | 1410 | CP001875 | clade_92 | N | N |
| *Pantoea brenneri* | 1411 | EU216735 | clade_92 | N | N |
| *Pantoea citrea* | 1412 | EF688008 | clade_92 | N | N |
| *Pantoea conspicua* | 1413 | EU216737 | clade_92 | N | N |
| *Pantoea septica* | 1414 | EU216734 | clade_92 | N | N |
| *Pasteurella dagmatis* | 1434 | ACZR01000003 | clade_92 | N | N |
| *Pasteurella multocida* | 1435 | NC_002663 | clade_92 | N | N |
| *Plesiomonas shigelloides* | 1469 | X60418 | clade_92 | N | N |
| *Raoultella ornithinolytica* | 1617 | AB364958 | clade_92 | N | N |
| *Raoultella planticola* | 1618 | AF129443 | clade_92 | N | N |
| *Raoultella terrigena* | 1619 | NR_037085 | clade_92 | N | N |
| *Salmonella bongori* | 1683 | NR_041699 | clade_92 | N | Category-B |
| *Salmonella enterica* | 1672 | NC_011149 | clade_92 | N | Category-B |
| *Salmonella enterica* | 1673 | NC_011205 | clade_92 | N | Category-B |
| *Salmonella enterica* | 1674 | DQ344532 | clade_92 | N | Category-B |
| *Salmonella enterica* | 1675 | ABEH02000004 | clade_92 | N | Category-B |
| *Salmonella enterica* | 1676 | ABAK02000001 | clade_92 | N | Category-B |
| *Salmonella enterica* | 1677 | NC_011080 | clade_92 | N | Category-B |
| *Salmonella enterica* | 1678 | EU118094 | clade_92 | N | Category-B |
| *Salmonella enterica* | 1679 | NC_011094 | clade_92 | N | Category-B |
| *Salmonella enterica* | 1680 | AE014613 | clade_92 | N | Category-B |
| *Salmonella enterica* | 1682 | ABFH02000001 | clade_92 | N | Category-B |
| *Salmonella enterica* | 1684 | ABEM01000001 | clade_92 | N | Category-B |
| *Salmonella enterica* | 1685 | ABAM02000001 | clade_92 | N | Category-B |
| *Salmonella typhimurium* | 1681 | DQ344533 | clade_92 | N | Category-B |
| *Salmonella typhimurium* | 1686 | AF170176 | clade_92 | N | Category-B |
| *Serratia fonticola* | 1718 | NR_025339 | clade_92 | N | N |
| *Serratia liquefaciens* | 1719 | NR_042062 | clade_92 | N | N |

TABLE 1-continued

See, e.g., WO2014/121304

| OTU | SEQ ID Number | Public DB Accession | Clade | Spore Former | Pathogen Status |
|---|---|---|---|---|---|
| *Serratia marcescens* | 1720 | GU826157 | clade_92 | N | N |
| *Serratia odorifera* | 1721 | ADBY01000001 | clade_92 | N | N |
| *Serratia proteamaculans* | 1722 | AAUN01000015 | clade_92 | N | N |
| *Shigella boydii* | 1724 | AAKA01000007 | clade_92 | N | Category-B |
| *Shigella dysenteriae* | 1725 | NC_007606 | clade_92 | N | Category-B |
| *Shigella flexneri* | 1726 | AE005674 | clade_92 | N | Category-B |
| *Shigella sonnei* | 1727 | NC_007384 | clade_92 | N | Category-B |
| *Tatumella ptyseos* | 1916 | NR_025342 | clade_92 | N | N |
| *Trabulsiella guamensis* | 1925 | AYS73830 | clade_92 | N | N |
| *Yersinia aldovae* | 2019 | AJ871363 | clade_92 | N | OP |
| *Yersinia aleksiciae* | 2020 | AJ627597 | clade_92 | N | OP |
| *Yersinia bercovieri* | 2021 | AF366377 | clade_92 | N | OP |
| *Yersinia enterocolitica* | 2022 | FR729477 | clade_92 | N | Category-B |
| *Yersinia frederiksenii* | 2023 | AF366379 | clade_92 | N | OP |
| *Yersinia intermedia* | 2024 | AF366380 | clade_92 | N | OP |
| *Yersinia kristensenii* | 2025 | ACCA01000078 | clade_92 | N | OP |
| *Yersinia mollaretii* | 2026 | NR_027546 | clade_92 | N | OP |
| *Yersinia pestis* | 2027 | AE013632 | clade_92 | N | Category-A |
| *Yersinia pseudotuberculosis* | 2028 | NC_009708 | clade_92 | N | OP |
| *Yersinia rohdei* | 2029 | ACCD01000071 | clade_92 | N | OP |
| *Yokenella regensburgei* | 2030 | AB273739 | clade_92 | N | N |
| *Conchiformibius kuhniae* | 669 | NR_041821 | clade_94 | N | N |
| *Morococcus cerebrosus* | 1267 | JN175352 | clade_94 | N | N |
| *Neisseria bacilliformis* | 1328 | AFAY01000058 | clade_94 | N | N |
| *Neisseria cinerea* | 1329 | ACDY01000037 | clade_94 | N | N |
| *Neisseria flavescens* | 1331 | ACQV01000025 | clade_94 | N | N |
| *Neisseria gonorrhoeae* | 1333 | CP002440 | clade_94 | N | OP |
| *Neisseria lactamica* | 1334 | ACEQ01000095 | clade_94 | N | N |
| *Neisseria macacae* | 1335 | AFQE01000146 | clade_94 | N | N |
| *Neisseria meningitidis* | 1336 | NC_003112 | clade_94 | N | OP |
| *Neisseria mucosa* | 1337 | ACDX01000110 | clade_94 | N | N |
| *Neisseria pharyngis* | 1338 | AJ239281 | clade_94 | N | N |
| *Neisseria polysaccharea* | 1339 | ADBE01000137 | clade_94 | N | N |
| *Neisseria sicca* | 1340 | ACKO02000016 | clade_94 | N | N |
| *Neisseria* sp. KEM232 | 1341 | GQ203291 | clade_94 | N | N |
| *Neisseria* sp. oral clone AP132 | 1344 | AY005027 | clade_94 | N | N |
| *Neisseria* sp. oral strain B33KA | 1346 | AY005028 | clade_94 | N | N |
| *Neisseria* sp. oral taxon 014 | 1347 | ADEA01000039 | clade_94 | N | N |
| *Neisseria* sp. TM10_1 | 1343 | DQ279352 | clade_94 | N | N |
| *Neisseria subflava* | 1348 | ACEO01000067 | clade_94 | N | N |
| *Okadaella gastrococcus* | 1365 | HQ699465 | clade_98 | N | N |
| *Streptococcus agalactiae* | 1785 | AAJO01000130 | clade_98 | N | N |
| *Streptococcus alactolyticus* | 1786 | NR_041781 | clade_98 | N | N |
| *Streptococcus australis* | 1788 | AEQR01000024 | clade_98 | N | N |
| *Streptococcus bovis* | 1789 | AEEL01000030 | clade_98 | N | N |
| *Streptococcus canis* | 1790 | AJ413203 | clade_98 | N | N |
| *Streptococcus constellatus* | 1791 | AY277942 | clade_98 | N | N |
| *Streptococcus cristatus* | 1792 | AEVC01000028 | clade_98 | N | N |
| *Streptococcus dysgalactiae* | 1794 | AP010935 | clade_98 | N | N |
| *Streptococcus equi* | 1795 | CP001129 | clade_98 | N | N |
| *Streptococcus equinus* | 1796 | AEVB01000043 | clade_98 | N | N |
| *Streptococcus gallolyticus* | 1797 | FR824043 | clade_98 | N | N |
| *Streptococcus* genomosp. C1 | 1798 | AY278629 | clade_98 | N | N |
| *Streptococcus* genomosp. C2 | 1799 | AY278630 | clade_98 | N | N |
| *Streptococcus* genomosp. C3 | 1800 | AY278631 | clade_98 | N | N |
| *Streptococcus* genomosp. C4 | 1801 | AY278632 | clade_98 | N | N |
| *Streptococcus* genomosp. C5 | 1802 | AY278633 | clade_98 | N | N |
| *Streptococcus* genomosp. C6 | 1803 | AY278634 | clade_98 | N | N |
| *Streptococcus* genomosp. C7 | 1804 | AY278635 | clade_98 | N | N |
| *Streptococcus* genomosp. C8 | 1805 | AY278609 | clade_98 | N | N |
| *Streptococcus gordonii* | 1806 | NC_009785 | clade_98 | N | N |
| *Streptococcus infantarius* | 1807 | ABJK02000017 | clade_98 | N | N |
| *Streptococcus infantis* | 1808 | AFNN01000024 | clade_98 | N | N |
| *Streptococcus intermedius* | 1809 | NR_028736 | clade_98 | N | N |
| *Streptococcus lutetiensis* | 1810 | NR_037096 | clade_98 | N | N |
| *Streptococcus massiliensis* | 1811 | AY769997 | clade_98 | N | N |
| *Streptococcus mitis* | 1813 | AM157420 | clade_98 | N | N |
| *Streptococcus oligofermentans* | 1815 | AY099095 | clade_98 | N | N |
| *Streptococcus oralis* | 1816 | ADMV01000001 | clade_98 | N | N |
| *Streptococcus parasanguinis* | 1817 | AEKM01000012 | clade_98 | N | N |
| *Streptococcus pasteurianus* | 1818 | AP012054 | clade_98 | N | N |
| *Streptococcus peroris* | 1819 | AEVF01000016 | clade_98 | N | N |
| *Streptococcus pneumoniae* | 1820 | AE008537 | clade_98 | N | N |
| *Streptococcus porcinus* | 1821 | EF121439 | clade_98 | N | N |
| *Streptococcus pseudopneumoniae* | 1822 | FJ827123 | clade_98 | N | N |

TABLE 1-continued

See, e.g., WO2014/121304

| OTU | SEQ ID Number | Public DB Accession | Clade | Spore Former | Pathogen Status |
|---|---|---|---|---|---|
| *Streptococcus pseudoporcinus* | 1823 | AENS01000003 | clade_98 | N | N |
| *Streptococcus pyogenes* | 1824 | AE006496 | clade_98 | N | OP |
| *Streptococcus ratti* | 1825 | X58304 | clade_98 | N | N |
| *Streptococcus sanguinis* | 1827 | NR_074974 | clade_98 | N | N |
| *Streptococcus sinensis* | 1828 | AF432857 | clade_98 | N | N |
| *Streptococcus* sp. 2_1_36FAA | 1831 | ACOI01000028 | clade_98 | N | N |
| *Streptococcus* sp. 2285_97 | 1830 | AJ131965 | clade_98 | N | N |
| *Streptococcus* sp. ACS2 | 1834 | HQ616360 | clade_98 | N | N |
| *Streptococcus* sp. AS20 | 1835 | HQ616366 | clade_98 | N | N |
| *Streptococcus* sp. BS35a | 1836 | HQ616369 | clade_98 | N | N |
| *Streptococcus* sp. C150 | 1837 | ACRI01000045 | clade_98 | N | N |
| *Streptococcus* sp. CM6 | 1838 | HQ616372 | clade_98 | N | N |
| *Streptococcus* sp. ICM10 | 1840 | HQ616389 | clade_98 | N | N |
| *Streptococcus* sp. ICM12 | 1841 | HQ616390 | clade_98 | N | N |
| *Streptococcus* sp. ICM2 | 1842 | HQ616386 | clade_98 | N | N |
| *Streptococcus* sp. ICM4 | 1844 | HQ616387 | clade_98 | N | N |
| *Streptococcus* sp. ICM45 | 1843 | HQ616394 | clade_98 | N | N |
| *Streptococcus* sp. M143 | 1845 | ACRK01000025 | clade_98 | N | N |
| *Streptococcus* sp. M334 | 1846 | ACRL01000052 | clade_98 | N | N |
| *Streptococcus* sp. oral clone ASB02 | 1849 | AY923121 | clade_98 | N | N |
| *Streptococcus* sp. oral clone ASCA03 | 1850 | DQ272504 | clade_98 | N | N |
| *Streptococcus* sp. oral clone ASCA04 | 1851 | AY923116 | clade_98 | N | N |
| *Streptococcus* sp. oral clone ASCA09 | 1852 | AY923119 | clade_98 | N | N |
| *Streptococcus* sp. oral clone ASCB04 | 1853 | AY923123 | clade_98 | N | N |
| *Streptococcus* sp. oral clone ASCB06 | 1854 | AY923124 | clade_98 | N | N |
| *Streptococcus* sp. oral clone ASCC04 | 1855 | AY923127 | clade_98 | N | N |
| *Streptococcus* sp. oral clone ASCC05 | 1856 | AY923128 | clade_98 | N | N |
| *Streptococcus* sp. oral clone ASCC12 | 1857 | DQ272507 | clade_98 | N | N |
| *Streptococcus* sp. oral clone ASCD01 | 1858 | AY923129 | clade_98 | N | N |
| *Streptococcus* sp. oral clone ASCD09 | 1859 | AY923130 | clade_98 | N | N |
| *Streptococcus* sp. oral clone ASCD10 | 1860 | DQ272509 | clade_98 | N | N |
| *Streptococcus* sp. oral clone ASCE03 | 1861 | AY923134 | clade_98 | N | N |
| *Streptococcus* sp. oral clone ASCE04 | 1862 | AY953253 | clade_98 | N | N |
| *Streptococcus* sp. oral clone ASCE05 | 1863 | DQ272510 | clade_98 | N | N |
| *Streptococcus* sp. oral clone ASCE06 | 1864 | AY923135 | clade_98 | N | N |
| *Streptococcus* sp. oral clone ASCE09 | 1865 | AY923136 | clade_98 | N | N |
| *Streptococcus* sp. oral clone ASCE10 | 1866 | AY923137 | clade_98 | N | N |
| *Streptococcus* sp. oral clone ASCE12 | 1867 | AY923138 | clade_98 | N | N |
| *Streptococcus* sp. oral clone ASCF05 | 1868 | AY923140 | clade_98 | N | N |
| *Streptococcus* sp. oral clone ASCF07 | 1869 | AY953255 | clade_98 | N | N |
| *Streptococcus* sp. oral clone ASCF09 | 1870 | AY923142 | clade_98 | N | N |
| *Streptococcus* sp. oral clone ASCG04 | 1871 | AY923145 | clade_98 | N | N |
| *Streptococcus* sp. oral clone BW009 | 1872 | AY005042 | clade_98 | N | N |
| *Streptococcus* sp. oral clone CH016 | 1873 | AY005044 | clade_98 | N | N |
| *Streptococcus* sp. oral clone GK051 | 1874 | AY349413 | clade_98 | N | N |
| *Streptococcus* sp. oral clone GM006 | 1875 | AY349414 | clade_98 | N | N |
| *Streptococcus* sp. oral clone P2PA_41 P2 | 1876 | AY207051 | clade_98 | N | N |
| *Streptococcus* sp. oral clone P4PA_30 P4 | 1877 | AY207064 | clade_98 | N | N |
| *Streptococcus* sp. oral taxon 071 | 1878 | AEEP01000019 | clade_98 | N | N |
| *Streptococcus* sp. oral taxon G59 | 1879 | GU432132 | clade_98 | N | N |
| *Streptococcus* sp. oral taxon G62 | 1880 | GU432146 | clade_98 | N | N |
| *Streptococcus* sp. oral taxon G63 | 1881 | GU432150 | clade_98 | N | N |
| *Streptococcus suis* | 1882 | FM252032 | clade_98 | N | N |
| *Streptococcus thermophilus* | 1883 | CP000419 | clade_98 | N | N |
| *Streptococcus salivarius* | 1826 | AGBV01000001 | clade_98 | N | N |
| *Streptococcus uberis* | 1884 | HQ391900 | clade_98 | N | N |
| *Streptococcus urinalis* | 1885 | DQ303194 | clade_98 | N | N |
| *Streptococcus vestibularis* | 1886 | AEKO01000008 | clade_98 | N | N |
| *Streptococcus viridans* | 1887 | AF076036 | clade_98 | N | N |
| Synergistetes bacterium oral clone 03 5 D05 | 1908 | GU227192 | clade_98 | N | N |

TABLE 1A

Exemplary Immunomodulatory Bacterial Species

*Alkaliphilus metalliredigens*
*Ammonifex degensii*
*Anaerofustis stercorihominis*
*Anaerostipes caccae*
*Anaerotruncus colihominis*
*Bacillus amyloliquefaciens*
*Bacillus anthracis*
*Bacillus cellulosilyticus*
*Bacillus cereus*
*Bacillus clausii*
*Bacillus coagulans*
*Bacillus cytotoxicus*
*Bacillus halodurans*
*Bacillus licheniformis*

TABLE 1A-continued

| Exemplary Immunomodulatory Bacterial Species |
| --- |
| *Bacillus pumilus* |
| *Bacillus subtilis* |
| *Bacillus thuringiensis* |
| *Bacillus weihenstephanensis* |
| *Blautia* (*Ruminococcus*) *hansenii* |
| *Blautia* (*Ruminococcus*) *obeum* |
| *Brevibacillus brevis* |
| *Bryantella formatexigens* |
| *Caldicellulosiruptor saccharolyticus* |
| *Candidatus Desulforudis audaxviator* |
| *Carboxydibrachium pacificum* |
| *Carboxydothermus hydrogenoformans* |
| *Clostridium acetobutylicum* |
| *Clostridium asparagiforme* |
| *Clostridium bartlettii* |
| *Clostridium beijerinckii* |
| *Clostridium bolteae* |
| *Clostridium botulinum* A str. ATCC 19397 |
| *Clostridium botulinum* B str. Eklund 17B |
| *Clostridium butyricum* pathogenic E4 str. BoNT BL5262 |
| *Clostridium carboxidivorans* |
| *Clostridium cellulolyticum* |
| *Clostridium cellulovorans* |
| *Clostridium difficile* |
| *Clostridium* (*Hungatella*) *hathewayi* |
| *Clostridium hylemonae* |
| *Clostridium kluyveri* |
| *Clostridium leptum* |
| *Clostridium methylpentosum* |
| *Clostridium* (*Tyzzerella*) *nexile* |
| *Clostridium novyi* NT |
| *Clostridium papyrosolvens* |
| *Clostridium perfringens* |
| *Clostridium phytofermentans* ISDg |
| *Clostridium scindens* |
| *Clostridium* sp. 7_2_43FAA |
| *Clostridium sporogenes* |
| *Clostridium tetani* |
| *Clostridium thermocellum* |
| *Coprococcus comes* |
| *Desulfotomaculum reducens* |
| *Dorea longicatena* |
| *Eubacterium eligens* |
| *Eubacterium hallii* |
| *Eubacterium rectale* |
| *Eubacterium ventriosum* |
| *Faecalibacterium prausnitzii* |
| *Geobacillus kaustophilus* |
| *Geobacillus* sp. G11MC16 |
| *Geobacillus thermodenitrificans* |
| *Heliobacterium modesticaldum* |
| *Lysinibacillus sphaericus* |
| *Oceanobacillus iheyensis* |
| *Paenibacillus* sp. JDR-2 |
| *Pelotomaculum thermopropionicum* |
| *Roseburia intestinalis* |
| *Ruminococcus bromii* |
| *Ruminococcus gnavus* |
| *Ruminococcus torques* |
| *Subdoligranulum variabile* |
| *Symbiobacterium thermophilum* |
| *Thermoanaerobacter italicus* |
| *Thermoanaerobacter tengcongensis* |
| *Thermoanaerobacterium thermosaccharolyticum* |
| *Thermosinus carboxydivorans* |

TABLE 1B

| Exemplary Bacteria Useful in the Present Invention |
| --- |
| *Acidaminococcus intestini* |
| *Acinetobacter baumannii* |
| *Acinetobacter lwoffii* |
| *Akkermansia muciniphila* |
| *Alistipes putredinis* |

TABLE 1B-continued

| Exemplary Bacteria Useful in the Present Invention |
| --- |
| *Alistipes shahii* |
| *Anaerostipes hadrus* |
| *Anaerotruncus colihominis* |
| *Bacteroides caccae* |
| *Bacteroides cellulosilyticus* |
| *Bacteroides dorei* |
| *Bacteroides eggerthii* |
| *Bacteroides finegoldii* |
| *Bacteroides fragilis* |
| *Bacteroides massiliensis* |
| *Bacteroides ovatus* |
| *Bacteroides salanitronis* |
| *Bacteroides salyersiae* |
| *Bacteroides* sp. 1_1_6 |
| *Bacteroides* sp. 3_1_23 |
| *Bacteroides* sp. D20 |
| *Bacteroides thetaiotaomicron* |
| *Bacteroides uniformis* |
| *Bacteroides vulgatus* |
| *Bifidobacterium adolescentis* |
| *Bifidobacterium bifidum* |
| *Bifidobacterium breve* |
| *Bifidobacterium faecale* |
| *Bifidobacterium kashiwanohense* |
| *Bifidobacterium longum* subsp. *longum* |
| *Bifidobacterium pseudocatenulatum* |
| *Bifidobacterium stercoris* |
| *Blautia* (*Ruminococcus*) *coccoides* |
| *Blautia faecis* |
| *Blautia glucerasea* |
| *Blautia* (*Ruminococcus*) *hansenii* |
| *Blautia hydrogenotrophica* (*Ruminococcus hydrogenotrophicus*) |
| *Blautia* (*Ruminococcus*) *luti* |
| *Blautia* (*Ruminococcus*) *obeum* |
| *Blautia producta* (*Ruminococcus productus*) |
| *Blautia* (*Ruminococcus*) *schinkii* |
| *Blautia stercoris* |
| *Blautia* uncultured bacterium clone BKLE_a03_2 (GenBank: EU469501.1) |
| *Blautia* uncultured bacterium clone SJTU_B_14_30 (GenBank: EF402926.1) |
| *Blautia* uncultured bacterium clone SJTU_C_14_16 (GenBank: EF404657.1) |
| *Blautia* uncultured bacterium clone S1-5 (GenBank: GQ898099.1) |
| *Blautia* uncultured PAC000178_s (www.ezbiocloud.net/eztaxon/hierarchy?m=browse&k=PAC000178&d=2) |
| *Blautia wexlerae* |
| *Candidatus Arthromitus* sp. SFB-mouse-Yit |
| *Catenibacterium mitsuokai* |
| Clostridiaceae bacterium (*Dielma fastidiosa*) JC13 |
| Clostridiales bacterium 1_7_47FAA |
| *Clostridium asparagiforme* |
| *Clostridium bolteae* |
| *Clostridium clostridioforme* |
| *Clostridium glycyrrhizinilyticum* |
| *Clostridium* (*Hungatella*) *hathewayi* |
| *Clostridium histolyticum* |
| *Clostridium indolis* |
| *Clostridium leptum* |
| *Clostridium* (*Tyzzerella*) *nexile* |
| *Clostridium perfringens* |
| *Clostridium* (*Erysipelatoclostridium*) *ramosum* |
| *Clostridium scindens* |
| *Clostridium* sp. 14774 |
| *Clostridium* sp. 7_3_54FAA |
| *Clostridium* sp. HGF2 |
| *Clostridium symbiosum* |
| *Collinsella aerofaciens* |
| *Collinsella intestinalis* |
| *Coprobacillus* sp. D7 |
| *Coprococcus catus* |
| *Coprococcus comes* |
| *Dorea formicigenerans* |
| *Dorea longicatena* |
| *Enterococcus faecalis* |
| *Enterococcus faecium* |
| Erysipelotrichaceae bacterium 3_1_53 |
| *Escherichia coli* |

TABLE 1B-continued

Exemplary Bacteria Useful in the Present Invention

Escherichia coli S88
Eubacterium eligens
Eubacterium fissicatena
Eubacterium ramulus
Eubacterium rectale
Faecalibacterium prausnitzii
Flavonifractor plautii
Fusobacterium mortiferum
Fusobacterium nucleatum
Holdemania filiformis
Hydrogenoanaerobacterium saccharovorans
Klebsiella oxytoca
Lachnospiraceae bacterium 3_1_57FAA_CT1
Lachnospiraceae bacterium 7_1_58FAA
Lachnospiraceae bacterium 5_1_57FAA
Lactobacillus casei
Lactobacillus rhamnosus
Lactobacillus ruminis
Lactococcus casei
Odoribacter splanchnicus
Oscillibacter valericigenes
Parabacteroides gordonii
Parabacteroides johnsonii
Parabacteroides merdae
Pediococcus acidilactici
Peptostreptococcus asaccharolyticus
Propionibacterium granulosum
Roseburia intestinalis
Roseburia inulinivorans
Ruminococcus faecis
Ruminococcus gnavus
Ruminococcus sp. ID8
Ruminococcus torques
Slackia piriformis
Staphylococcus epidermidis
Staphylococcus saprophyticus
Streptococcus cristatus
Streptococcus dysgalactiae subsp. equisimilis
Streptococcus infantis
Streptococcus oralis
Streptococcus sanguinis
Streptococcus viridans
Streptococcus thermophilus
Veillonella dispar

TABLE 1C

Exemplary Bacteria Useful in the Present Invention

Anaerotruncus colihominis strain 13
Blautia producta strain 6
Clostridium bolteae strain 7
Clostridiaceae bacterium JC13 strain 8
Clostridiales bacterium 1_7_47FAA strain 28
Clostridium sp. 7_3_54FAA strain 16
Clostridium asparagiforme strain 15
Clostridium clostridioforme
Clostridium (Hungatella) hathewayi strain 4
Clostridium indolis strain 9
Clostridium (Erysipelatoclostridium) ramosum strain 18
Clostridium scindens strain 26
Clostridium sp. 14774 strain 1
Eubacterium fissicatena strain 21
Hydrogenoanaerobacterium saccharovorans
Lachnospiraceae bacterium 3_1_57FAA strain 27
Lachnospiraceae bacterium 3_1_57FAA strain 29
Lachnospiraceae bacterium 7_1_58FAA strain 3
Oscillibacter valericigenes
Ruminococcus sp. ID8 strain 14

TABLE 1D

Exemplary Bacteria Useful in the Present Invention

Bacteroides caccae
Bacteroides eggerthii
Bacteroides ovatus
Bacteroides sp. 1_1_6
Bacteroides sp. 3_1_23
Bacteroides sp. D20
Bacteroides vulgatus
Bifidobacterium adolescentis
Bifidobacterium pseudocatenulatum
Blautia (Ruminococcus) obeum
Blautia producta (Ruminococcus productus)
Blautia (Ruminococcus) schinkii
Clostridium (Hungatella) hathewayi
Clostridium (Tyzzerella) nexile
Clostridium sp. HGF2
Clostridium symbiosum
Collinsella aerofaciens
Coprobacillus sp. D7
Coprococcus catus
Coprococcus comes
Dorea formicigenerans
Dorea longicatena
Enterococcus faecalis
Erysipelotrichaceae bacterium 3_1_53
Escherichia coli
Escherichia coli S88
Eubacterium eligens
Eubacterium rectale
Faecalibacterium prausnitzii
Lachnospiraceae bacterium 5_1_57FAA
Odoribacter splanchnicus
Parabacteroides merdae
Roseburia intestinalis
Ruminococcus torques
Streptococcus thermophilus

TABLE 1E

Exemplary Bacteria Useful in the Present Invention

Akkermansia muciniphila
Enterococcus faecalis
Klebsiella oxytoca
Lactobacillus rhamnosus
Staphylococcus epidermidis
Streptococcus viridans
Veillonella dispar

TABLE 1F

Exemplary Bacteria Useful in the Present Invention

Acinetobacter baumannii
Acinetobacter lwoffii
Akkermansia muciniphila
Alistipes shahii
Anaerotruncus colihominis
Bacteroides caccae
Bacteroides dorei
Bacteroides eggerthii
Bacteroides finegoldii
Bacteroides fragilis
Bacteroides massiliensis
Bacteroides ovatus
Bacteroides salanitronis
Bacteroides sp. 1_1_6
Bacteroides sp. 3_1_23
Bacteroides sp. D20
Bacteroides thetaiotaomicron
Bacteroides uniformis
Bacteroides vulgatus
Bifidobacterium adolescentis
Bifidobacterium breve

TABLE 1F-continued

Exemplary Bacteria Useful in the Present Invention

*Bifidobacterium pseudocatenulatum*
*Blautia (Ruminococcus) coccoides*
*Blautia faecis*
*Blautia glucerasea*
*Blautia (Ruminococcus) hansenii*
*Blautia hydrogenotrophica (Ruminococcus hydrogenotrophicus)*
*Blautia (Ruminococcus) luti*
*Blautia (Ruminococcus) obeum*
*Blautia producta (Ruminococcus productus)*
*Blautia (Ruminococcus) schinkii*
*Blautia stercoris*
*Blautia wexlerae*
*Candidatus Arthromitus* sp. SFB-mouse-Yit
Clostridiaceae bacterium (*Dielma fastidiosa*) JC13
Clostridiales bacterium 1_7_47FAA
*Clostridium asparagiforme*
*Clostridium bolteae*
*Clostridium clostridioforme*
*Clostridium (Hungatella) hathewayi*
*Clostridium histolyticum*
*Clostridium indolis*
*Clostridium leptum*
*Clostridium (Tyzzerella) nexile*
*Clostridium perfringens*
*Clostridium (Erysipelatoclostridium) ramosum*
*Clostridium scindens*
*Clostridium* sp. 14774
*Clostridium* sp. 7_3_54FAA
*Clostridium* sp. HGF2
*Clostridium symbiosum*
*Collinsella aerofaciens*
*Coprobacillus* sp. D7
*Coprococcus catus*
*Coprococcus comes*
*Dorea formicigenerans*
*Dorea longicatena*
*Enterococcus faecium*
Erysipelotrichaceae bacterium 3_1_53
*Escherichia coli*
*Escherichia coli* S88
*Eubacterium eligens*
*Eubacterium fissicatena*
*Eubacterium rectale*
*Faecalibacterium prausnitzii*
*Fusobacterium mortiferum*
*Fusobacterium nucleatum*
*Hydrogenoanaerobacterium saccharovorans*
Lachnospiraceae bacterium 3_1_57FAA_CT1
Lachnospiraceae bacterium 7_1_58FAA
Lachnospiraceae bacterium 5_1_57FAA
*Lactobacillus casei*
*Lactococcus casei*
*Odoribacter splanchnicus*
*Oscillibacter valericigenes*
*Parabacteroides johnsonii*
*Parabacteroides merdae*
*Pediococcus acidilactici*
*Peptostreptococcus asaccharolyticus*
*Propionibacterium granulosum*
*Roseburia intestinalis*
*Ruminococcus gnavus*
*Ruminococcus* sp. ID8
*Ruminococcus torques*
*Staphylococcus saprophyticus*
*Streptococcus thermophilus*

TABLE 2A

Species identified as germinable and sporulatable by colony picking

| OTU | BBA | GAM + FOS/ inulin | M2GSC | Sweet B + FOS/ Inulin | Sweet GAM | Total |
|---|---|---|---|---|---|---|
| *Blautia producta* | 1 | | | | | 1 |
| *Clostridium bartlettii* | 4 | | 1 | | | 5 |
| *Clostridium bolteae* | 2 | | | 5 | 1 | 8 |
| *Clostridium botulinum* | | | | 5 | | 5 |
| *Clostridium butyricum* | 37 | 43 | 8 | 1 | 33 | 122 |
| *Clostridium celatum* | 4 | | | | 1 | 5 |
| *Clostridium clostridioforme* | 1 | | | | 1 | 2 |
| *Clostridium disporicum* | 26 | 26 | 22 | 33 | 50 | 157 |
| *Clostridium glycolicum* | 4 | 9 | 14 | | | 27 |
| *Clostridium mayombei* | 2 | 2 | | | | 4 |
| *Clostridium paraputrificum* | 8 | 8 | 33 | 16 | 6 | 71 |
| *Clostridium sordellii* | | | 14 | | | 14 |
| *Clostridium* sp. 7_2_43FAA | | 1 | | | | 1 |
| *Clostridium symbiosum* | 3 | | | | | 3 |
| *Clostridium tertium* | | 1 | | 1 | | 2 |
| (blank) | | 2 | | 31 | | 33 |
| Totals | 92 | 92 | 92 | 92 | 92 | 460 |

TABLE 2B

Species identified as germinable by 16S colony pick approach

Clostridium_paraputrificum
Clostridium_disporicum
Clostridium_glycolicum
Clostridium_bartlettii
Clostridium_butyricum
Ruminococcus_bromii
Lachnospiraceae_bacterium_2_1_58FAA
Eubacterium_hadrum
Turicibacter_sanguinis
Lachnospiraceae_bacterium_oral_taxon_F15
Clostridium_perfringens
Clostridium_bifermentans
Roseburia_sp_11SE37
Clostridium_quinii
Ruminococcus_lactaris
Clostridium_botulinum
Clostridium_tyrobutyricum
Blautia_hansenii
Clostridium_kluyveri
Clostridium_sp_JC122
Clostridium_hylemonae
Clostridium_celatum
Clostridium_straminisolvens
Clostridium_orbiscindens
Roseburia_cecicola
Eubacterium_tenue
Clostridium_sp_7_2_43FAA
Lachnospiraceae_bacterium_4_1_37FAA
Eubacterium_rectale
Clostridium_viride
Ruminococcus_sp_K_1
Clostridium_symbiosum
Ruminococcus_torques
Clostridium_algidicarnis

TABLE 2C

Species identified as sporulatable by 16S NGS approach

Clostridium_paraputrificum
Clostridium_bartlettii
Lachnospiraceae_bacterium_2_1_58FAA

TABLE 2C-continued

Species identified as sporulatable by 16S NGS approach

Clostridium_disporicum
Ruminococcus_bromii
Eubacterium_hadrum
Clostridium_butyricum
Roseburia_sp_11SE37
Clostridium_perfringens
Clostridium_glycolicum
Clostridium_hylemonae
Clostridium_orbiscindens
Ruminococcus_lactaris
Clostridium_symbiosum
Lachnospiraceae_bacterium_oral_taxon_F15
Blautia_hansenii
Turicibacter_sanguinis
Clostridium_straminisolvens
Clostridium_botulinum
Lachnospiraceae_bacterium_4_1_37FAA
Roseburia_cecicola
Ruminococcus_sp_K_1
Clostridium_bifermentans
Eubacterium_rectale
Clostridium_quinii
Clostridium_viride
Clostridium_kluyveri
Clostridium_tyrobutyricum
Oscillibacter_sp_G2
Clostridium_sp_JC122
Lachnospiraceae_bacterium_3_1_57FAA
Clostridium_aldenense
Ruminococcus_torques
Clostridium_sp_7_2_43FAA
Clostridium_celatum
Eubacterium_sp_WAL_14571
Eubacterium_tenue
Lachnospiraceae_bacterium_5_1_57FAA
Clostridium_clostridioforme
Clostridium_sp_YIT_12070
Blautia_sp_M25
Anaerostipes_caccae
Roseburia_inulinivorans
Clostridium_sp_D5
Clostridium_asparagiforme
Coprobacillus_sp_D7
Clostridium_sp_HGF2
Clostridium_citroniae
Clostridium_difficile
Oscillibacter_valericigenes
Clostridium_algidicarnis

TABLE 3

Criteria for stages of acute GVHD
ORGAN

Skin <25% 25-50% >50% or Generalized
(maculopapular rush generalised erythroderma with extent, % of
body erythroderma bullous formation surface area) or desquamation
Liver 34-50 51-102 103-255 >255
(bilirubin mmol L) [2-3] [3-6] [6-15] [>15]
[bilirubin mg/dL] ø) (or AST 150-750 U/L)
Gut >30 mL kg or >60 mL/kg or >90 mL/kg or >2000 mL/day
or (daily diarrhea >500 mL (2) >1000 mL >1500 mL
severe abdominal volume) pain with or without ileus

TABLE 4

COGs for Identifying Prebiotic Activities

| COG ID | COG NAME | COG CATEGORY |
|---|---|---|
| COG0022 | Pyruvate/2-oxoglutarate/acetoin dehydrogenase complex, dehydrogenase (E1) component | C |
| COG0039 | Malate/lactate dehydrogenase | C |
| COG0045 | Succinyl-CoA synthetase, beta subunit | C |
| COG0055 | FoF1-type ATP synthase, beta subunit | C |
| COG0056 | FoF1-type ATP synthase, alpha subunit | C |
| COG0074 | Succinyl-CoA synthetase, alpha subunit | C |
| COG0114 | Fumarate hydratase class II | C |
| COG0224 | FoF1-type ATP synthase, gamma subunit | C |
| COG0240 | Glycerol-3-phosphate dehydrogenase | C |
| COG0243 | Anaerobic selenocysteine-containing dehydrogenase | C |
| COG0247 | Fe—S oxidoreductase | C |
| COG0277 | FAD/FMN-containing dehydrogenase | C |
| COG0280 | Phosphotransacetylase | C |
| COG0281 | Malic enzyme | C |
| COG0282 | Acetate kinase | C |
| COG0348 | Polyferredoxin | C |
| COG0355 | FoF1-type ATP synthase, epsilon subunit | C |
| COG0356 | FoF1-type ATP synthase, membrane subunit a | C |
| COG0371 | Glycerol dehydrogenase or related enzyme, iron-containing ADH family | C |
| COG0372 | Citrate synthase | C |
| COG0374 | Ni, Fe-hydrogenase I large subunit | C |
| COG0377 | NADH: ubiquinone oxidoreductase 20 kD subunit (chhain B) or related Fe—S oxidoreductase | C |
| COG0426 | Flavorubredoxin | C |
| COG0427 | Acyl-CoA hydrolase | C |
| COG0431 | NAD(P)H-dependent FMN reductase | C |
| COG0435 | Glutathionyl-hydroquinone reductase | C |
| COG0437 | Fe—S-cluster-containing dehydrogenase component | C |
| COG0479 | Succinate dehydrogenase/fumarate reductase, Fe—S protein subunit | C |
| COG0508 | Pyruvate/2-oxoglutarate dehydrogenase complex, dihydrolipoamide acyltransferase (E2) component | C |
| COG0538 | Isocitrate dehydrogenase | C |
| COG0546 | Phosphoglycolate phosphatase, HAD superfamily | C |

TABLE 4-continued

COGs for Identifying Prebiotic Activities

| COG ID | COG NAME | COG CATEGORY |
|---|---|---|
| COG0554 | Glycerol kinase | C |
| COG0567 | 2-oxoglutarate dehydrogenase complex, dehydrogenase (E1) component, and related enzymes | C |
| COG0578 | Glycerol-3-phosphate dehydrogenase | C |
| COG0633 | Ferredoxin | C |
| COG0636 | FoF1-type ATP synthase, membrane subunit c/Archaeal/vacuolar-type H+-ATPase, subunit K | |
| COG0644 | Dehydrogenase (flavoprotein) | C |
| COG0649 | NADH: ubiquinone oxidoreductase 49 kD subunit (chain D) | C |
| COG0650 | Formate hydrogenlyase subunit 4 | C |
| COG0655 | Multimeric flavodoxin WrbA | C |
| COG0674 | Pyruvate: ferredoxin oxidoreductase or related 2-oxoacid: ferredoxin oxidoreductase, alpha subunit | C |
| COG0680 | Ni, Fe-hydrogenase maturation factor | C |
| COG0711 | FoF1-type ATP synthase, membrane subunit b or b' | C |
| COG0712 | FoF1-type ATP synthase, delta subunit | C |
| COG0713 | NADH: ubiquinone oxidoreductase subunit 11 or 4L (chain K) | C |
| COG0716 | Flavodoxin | C |
| COG0723 | Rieske Fe—S protein | C |
| COG0778 | Nitroreductase | C |
| COG0838 | NADH: ubiquinone oxidoreductase subunit 3 (chain A) | C |
| COG0839 | NADH: ubiquinone oxidoreductase subunit 6 (chain J) | C |
| COG0843 | Heme/copper-type cytochrome/quinol oxidase, subunit 1 | C |
| COG0852 | NADH: ubiquinone oxidoreductase 27 kD subunit (chain C) | C |
| COG1005 | NADH: ubiquinone oxidoreductase subunit 1 (chain H) | C |
| COG1007 | NADH: ubiquinone oxidoreductase subunit 2 (chain N) | C |
| COG1008 | NADH: ubiquinone oxidoreductase subunit 4 (chain M) | C |
| COG1012 | Acyl-CoA reductase or other NAD-dependent aldehyde dehydrogenase | C |
| COG1013 | Pyruvate: ferredoxin oxidoreductase or related 2-oxoacid: ferredoxin oxidoreductase, beta subunit | C |
| COG1014 | Pyruvate: ferredoxin oxidoreductase or related 2-oxoacid: ferredoxin oxidoreductase, gamma subunit | C |
| COG1017 | Hemoglobin-like flavoprotein | C |
| COG1018 | Ferredoxin-NADP reductase | C |
| COG1029 | Formylmethanofuran dehydrogenase subunit B | C |
| COG1034 | NADH dehydrogenase/NADH: ubiquinone oxidoreductase 75 kD subunit (chain G) | C |
| COG1035 | Coenzyme F420-reducing hydrogenase, beta subunit | C |
| COG1036 | Archaeal flavoprotein | C |
| COG1038 | Pyruvate carboxylase | C |
| COG1042 | Acyl-CoA synthetase (NDP forming) | C |
| COG1048 | Aconitase A | C |
| COG1049 | Aconitase B | C |
| COG1053 | Succinate dehydrogenase/fumarate reductase, flavoprotein subunit | C |
| COG1071 | TPP-dependent pyruvate or acetoin dehydrogenase subunit alpha | C |
| COG1139 | L-lactate utilization protein LutB, contains a ferredoxin-type domain | C |
| COG1141 | Ferredoxin | C |
| COG1142 | Fe—S-cluster-containing hydrogenase component 2 | C |
| COG1143 | Formate hydrogenlyase subunit 6/NADH: ubiquinone oxidoreductase 23 kD subunit (chain I) | C |
| COG1144 | Pyruvate: ferredoxin oxidoreductase or related 2-oxoacid: ferredoxin oxidoreductase, delta subunit | C |
| COG1145 | Ferredoxin | C |
| COG1148 | Heterodisulfide reductase, subunit A (polyferredoxin) | C |
| COG1150 | Heterodisulfide reductase, subunit C | C |
| COG1152 | CO dehydrogenase/acetyl-CoA synthase alpha subunit | C |
| COG1153 | Formylmethanofuran dehydrogenase subunit D | C |
| COG1155 | Archaeal/vacuolar-type H+-ATPase catalytic subunit A/Vma1 | C |
| COG1156 | Archaeal/vacuolar-type H+-ATPase subunit B/Vma2 | C |
| COG1182 | FMN-dependent NADH-azoreductase | C |
| COG1229 | Formylmethanofuran dehydrogenase subunit A | C |
| COG1249 | Pyruvate/2-oxoglutarate dehydrogenase complex, dihydrolipoamide dehydrogenase (E3) component or related enzyme | C |
| COG1251 | NAD(P)H-nitrite reductase, large subunit | C |
| COG1252 | NADH dehydrogenase, FAD-containing subunit | C |
| COG1254 | Acylphosphatase | C |
| COG1269 | Archaeal/vacuolar-type H+-ATPase subunit I/STV1 | C |
| COG1271 | Cytochrome bd-type quinol oxidase, subunit 1 | C |
| COG1274 | Phosphoenolpyruvate carboxykinase, GTP-dependent | C |
| COG1282 | NAD/NADP transhydrogenase beta subunit | C |
| COG1290 | Cytochrome b subunit of the bc complex | C |
| COG1294 | Cytochrome bd-type quinol oxidase, subunit 2 | C |

TABLE 4-continued

COGs for Identifying Prebiotic Activities

| COG ID | COG NAME | COG CATEGORY |
|---|---|---|
| COG1301 | Na+/H+-dicarboxylate symporter | C |
| COG1319 | CO or xanthine dehydrogenase, FAD-binding subunit | C |
| COG1347 | Na+-transporting NADH: ubiquinone oxidoreductase, subunit NqrD | C |
| COG1359 | Quinol monooxygenase YgiN | C |
| COG1390 | Archaeal/vacuolar-type H+-ATPase subunit E/Vma4 | C |
| COG1394 | Archaeal/vacuolar-type H+-ATPase subunit D/Vma8 | C |
| COG1436 | Archaeal/vacuolar-type H+-ATPase subunit F/Vma7 | C |
| COG1454 | Alcohol dehydrogenase, class IV | C |
| COG1456 | CO dehydrogenase/acetyl-CoA synthase gamma subunit (corrinoid Fe—S protein) | C |
| COG1526 | Formate dehydrogenase assembly factor FdhD | C |
| COG1527 | Archaeal/vacuolar-type H+-ATPase subunit C/Vma6 | C |
| COG1529 | CO or xanthine dehydrogenase, Mo-binding subunit | C |
| COG1556 | L-lactate utilization protein LutC, contains LUD domain | C |
| COG1584 | Succinate-acetate transporter protein | C |
| COG1592 | Rubrerythrin | C |
| COG1614 | CO dehydrogenase/acetyl-CoA synthase beta subunit | C |
| COG1620 | L-lactate permease | C |
| COG1622 | Heme/copper-type cytochrome/quinol oxidase, subunit 2 | C |
| COG1625 | Fe—S oxidoreductase, related to NifB/MoaA family | C |
| COG1679 | Predicted aconitase | C |
| COG1726 | Na+-transporting NADH: ubiquinone oxidoreductase, subunit NqrA | C |
| COG1740 | Ni, Fe-hydrogenase I small subunit | C |
| COG1757 | Na+/H+ antiporter NhaC | C |
| COG1773 | Rubredoxin | C |
| COG1795 | Formaldehyde-activating enzyme nesessary for methanogenesis | C |
| COG1805 | Na+-transporting NADH: ubiquinone oxidoreductase, subunit NqrB | C |
| COG1838 | Tartrate dehydratase beta subunit/Fumarate hydratase class I, C-terminal domain | C |
| COG1845 | Heme/copper-type cytochrome/quinol oxidase, subunit 3 | C |
| COG1853 | NADH-FMN oxidoreductase RutF, flavin reductase (DIM6/NTAB) family | C |
| COG1866 | Phosphoenolpyruvate carboxykinase, ATP-dependent | C |
| COG1880 | CO dehydrogenase/acetyl-CoA synthase epsilon subunit | C |
| COG1882 | Pyruvate-formate lyase | C |
| COG1883 | Na+-transporting methylmalonyl-CoA/oxaloacetate decarboxylase, beta subunit | C |
| COG1894 | NADH: ubiquinone oxidoreductase, NADH-binding 51 kD subunit (chain F) | C |
| COG1902 | 2,4-dienoyl-CoA reductase or related NADH-dependent reductase, Old Yellow Enzyme (OYE) family | C |
| COG1905 | NADH: ubiquinone oxidoreductase 24 kD subunit (chain E) | C |
| COG1908 | Coenzyme F420-reducing hydrogenase, delta subunit | C |
| COG1927 | F420-dependent methylenetetrahydromethanopterin dehydrogenase | C |
| COG1941 | Coenzyme F420-reducing hydrogenase, gamma subunit | C |
| COG1951 | Tartrate dehydratase alpha subunit/Fumarate hydratase class I, N-terminal domain | C |
| COG1969 | Ni, Fe-hydrogenase I cytochrome b subunit | C |
| COG1979 | Alcohol dehydrogenase YqhD, Fe-dependent ADH family | C |
| COG2009 | Succinate dehydrogenase/fumarate reductase, cytochrome b subunit | C |
| COG2010 | Cytochrome c, mono- and diheme variants | C |
| COG2025 | Electron transfer flavoprotein, alpha subunit | C |
| COG2033 | Desulfoferrodoxin, superoxide reductase-like (SORL) domain | C |
| COG2037 | Formylmethanofuran: tetrahydromethanopterin formyltransferase | C |
| COG2041 | Periplasmic DMSO/TMAO reductase YedYZ, molybdopterin-dependent catalytic subunit | C |
| COG2048 | Heterodisulfide reductase, subunit B | C |
| COG2055 | Malate/lactate/ureidoglycolate dehydrogenase, LDH2 family | C |
| COG2069 | CO dehydrogenase/acetyl-CoA synthase delta subunit (corrinoid Fe—S protein) | C |
| COG2080 | Aerobic-type carbon monoxide dehydrogenase, small subunit, CoxS/CutS family | C |
| COG2086 | Electron transfer flavoprotein, alpha and beta subunits | C |
| COG2142 | Succinate dehydrogenase, hydrophobic anchor subunit | C |
| COG2191 | Formylmethanofuran dehydrogenase subunit E | C |
| COG2209 | Na+-transporting NADH: ubiquinone oxidoreductase, subunit NqrE | C |
| COG2210 | Peroxiredoxin family protein | C |
| COG2218 | Formylmethanofuran dehydrogenase subunit C | C |
| COG2224 | Isocitrate lyase | C |
| COG2225 | Malate synthase | C |

TABLE 4-continued

COGs for Identifying Prebiotic Activities

| COG ID | COG NAME | COG CATEGORY |
|---|---|---|
| COG2326 | Polyphosphate kinase 2, PPK2 family | C |
| COG2352 | Phosphoenolpyruvate carboxylase | C |
| COG2414 | Aldehyde: ferredoxin oxidoreductase | C |
| COG2421 | Acetamidase/formamidase | C |
| COG2440 | Ferredoxin-like protein FixX | C |
| COG2609 | Pyruvate dehydrogenase complex, dehydrogenase (E1) component | C |
| COG2717 | Periplasmic DMSO/TMAO reductase YedYZ, heme-binding membrane subunit | C |
| COG2811 | Archaeal/vacuolar-type H+-ATPase subunit H | C |
| COG2828 | 2-Methylaconitate cis-trans-isomerase PrpF (2-methyl citrate pathway) | C |
| COG2838 | Monomeric isocitrate dehydrogenase | C |
| COG2851 | Mg2+/citrate symporter | C |
| COG2857 | Cytochrome c1 | C |
| COG2863 | Cytochrome c553 | C |
| COG2864 | Cytochrome b subunit of formate dehydrogenase | C |
| COG2869 | Na+-transporting NADH: ubiquinone oxidoreductase, subunit NqrC | C |
| COG2871 | Na+-transporting NADH: ubiquinone oxidoreductase, subunit NqrF | C |
| COG2878 | Na+-translocating ferredoxin: NAD+ oxidoreductase RNF, RnfB subunit | C |
| COG2993 | Cbb3-type cytochrome oxidase, cytochrome c subunit | C |
| COG3005 | Tetraheme cytochrome c subunit of nitrate or TMAO reductase | C |
| COG3029 | Fumarate reductase subunit C | C |
| COG3038 | Cytochrome b561 | C |
| COG3051 | Citrate lyase, alpha subunit | C |
| COG3052 | Citrate lyase, gamma subunit | C |
| COG3053 | Citrate lyase synthetase | C |
| COG3069 | C4-dicarboxylate transporter | C |
| COG3080 | Fumarate reductase subunit D | C |
| COG3125 | Heme/copper-type cytochrome/quinol oxidase, subunit 4 | C |
| COG3181 | Tripartite-type tricarboxylate transporter, receptor component TctC | C |
| COG3202 | ATP/ADP translocase | C |
| COG3241 | Azurin | C |
| COG3245 | Cytochrome c5 | C |
| COG3258 | Cytochrome c | C |
| COG3259 | Coenzyme F420-reducing hydrogenase, alpha subunit | C |
| COG3260 | Ni, Fe-hydrogenase III small subunit | C |
| COG3261 | Ni, Fe-hydrogenase III large subunit | C |
| COG3262 | Ni, Fe-hydrogenase III component G | C |
| COG3278 | Cbb3-type cytochrome oxidase, subunit 1 | C |
| COG3288 | NAD/NADP transhydrogenase alpha subunit | C |
| COG3302 | DMSO reductase anchor subunit | C |
| COG3312 | FoF1-type ATP synthase assembly protein I | C |
| COG3411 | (2Fe—2S) ferredoxin | C |
| COG3426 | Butyrate kinase | C |
| COG3427 | Carbon monoxide dehydrogenase subunit G | C |
| COG3474 | Cytochrome c2 | C |
| COG3493 | Na+/citrate or Na+/malate symporter | C |
| COG3630 | Na+-transporting methylmalonyl-CoA/oxaloacetate decarboxylase, gamma subunit | C |
| COG3658 | Cytochrome b | C |
| COG3761 | NADH: ubiquinone oxidoreductase 17.2 kD subunit | C |
| COG3783 | Soluble cytochrome b562 | C |
| COG3794 | Plastocyanin | C |
| COG3808 | Na+ or H+-translocating membrane pyrophosphatase | C |
| COG3909 | Cytochrome c556 | C |
| COG3978 | Acetolactate synthase small subunit, contains ACT domain | C |
| COG4036 | Energy-converting hydrogenase Eha subunit G | C |
| COG4037 | Energy-converting hydrogenase Eha subunit F | C |
| COG4038 | Energy-converting hydrogenase Eha subunit E | C |
| COG4039 | Energy-converting hydrogenase Eha subunit C | C |
| COG4041 | Energy-converting hydrogenase Eha subunit B | C |
| COG4042 | Energy-converting hydrogenase Eha subunit A | C |
| COG4074 | 5,10-methenyltetrahydromethanopterin hydrogenase | C |
| COG4078 | Energy-converting hydrogenase Eha subunit H | C |
| COG4106 | Trans-aconitate methyltransferase | C |
| COG4147 | Na+(or H+)/acetate symporter ActP | C |
| COG4221 | NADP-dependent 3-hydroxy acid dehydrogenase YdfG | C |
| COG4231 | TPP-dependent indolepyruvate ferredoxin oxidoreductase, alpha subunit | C |
| COG4237 | Hydrogenase-4 membrane subunit HyfE | C |
| COG4459 | Periplasmic nitrate reductase system, NapE component | C |

TABLE 4-continued

COGs for Identifying Prebiotic Activities

| COG ID | COG NAME | COG CATEGORY |
|---|---|---|
| COG4624 | Iron only hydrogenase large subunit, C-terminal domain | C |
| COG4654 | Cytochrome c551/c552 | C |
| COG4656 | Na+-translocating ferredoxin: NAD+ oxidoreductase RNF, RnfC subunit | C |
| COG4657 | Na+-translocating ferredoxin: NAD+ oxidoreductase RNF, RnfA subunit | C |
| COG4658 | Na+-translocating ferredoxin: NAD+ oxidoreductase RNF, RnfD subunit | C |
| COG4659 | Na+-translocating ferredoxin: NAD+ oxidoreductase RNF, RnfG subunit | C |
| COG4660 | Na+-translocating ferredoxin: NAD+ oxidoreductase RNF, RnfE subunit | C |
| COG4736 | Cbb3-type cytochrome oxidase, subunit 3 | C |
| COG4802 | Ferredoxin-thioredoxin reductase, catalytic subunit | C |
| COG5012 | Methanogenic corrinoid protein MtbC1 | C |
| COG5016 | Pyruvate/oxaloacetate carboxyltransferase | C |
| COG0021 | Transketolase | G |
| COG0033 | Phosphoglucomutase | G |
| COG0036 | Pentose-5-phosphate-3-epimerase | G |
| COG0057 | Glyceraldehyde-3-phosphate dehydrogenase/erythrose-4-phosphate dehydrogenase | G |
| COG0058 | Glucan phosphorylase | G |
| COG0120 | Ribose 5-phosphate isomerase | G |
| COG0126 | 3-phosphoglycerate kinase | G |
| COG0148 | Enolase | G |
| COG0149 | Triosephosphate isomerase | G |
| COG0153 | Galactokinase | G |
| COG0158 | Fructose-1,6-bisphosphatase | G |
| COG0166 | Glucose-6-phosphate isomerase | G |
| COG0176 | Transaldolase | G |
| COG0191 | Fructose/tagatose bisphosphate aldolase | G |
| COG0205 | 6-phosphofructokinase | G |
| COG0235 | Ribulose-5-phosphate 4-epimerase/Fuculose-1-phosphate aldolase | G |
| COG0246 | Mannitol-1-phosphate/altronate dehydrogenases | G |
| COG0269 | 3-keto-L-gulonate-6-phosphate decarboxylase | G |
| COG0279 | Phosphoheptose isomerase | G |
| COG0296 | 1,4-alpha-glucan branching enzyme | G |
| COG0297 | Glycogen synthase | G |
| COG0362 | 6-phosphogluconate dehydrogenase | G |
| COG0363 | 6-phosphogluconolactonase/Glucosamine-6-phosphate isomerase/deaminase | G |
| COG0364 | Glucose-6-phosphate 1-dehydrogenase | G |
| COG0366 | Glycosidase | G |
| COG0380 | Trehalose-6-phosphate synthase | G |
| COG0383 | Alpha-mannosidase | G |
| COG0395 | ABC-type glycerol-3-phosphate transport system, permease component | G |
| COG0406 | Broad specificity phosphatase PhoE | G |
| COG0448 | ADP-glucose pyrophosphorylase | G |
| COG0469 | Pyruvate kinase | G |
| COG0471 | Di- and tricarboxylate transporter | G |
| COG0483 | Archaeal fructose-1,6-bisphosphatase or related enzyme of inositol monophosphatase family | G |
| COG0524 | Sugar or nucleoside kinase, ribokinase family | G |
| COG0574 | Phosphoenolpyruvate synthase/pyruvate phosphate dikinase | G |
| COG0579 | L-2-hydroxyglutarate oxidase LhgO | G |
| COG0580 | Glycerol uptake facilitator and related aquaporins (Major Intrinsic Protein Family) | G |
| COG0588 | Phosphoglycerate mutase (BPG-dependent) | G |
| COG0662 | Mannose-6-phosphate isomerase, cupin superfamily | G |
| COG0676 | D-hexose-6-phosphate mutarotase | G |
| COG0696 | Phosphoglycerate mutase (BPG-independent, AlkP superfamily) | G |
| COG0698 | Ribose 5-phosphate isomerase RpiB | G |
| COG0738 | Fucose permease | G |
| COG0800 | 2-keto-3-deoxy-6-phosphogluconate aldolase | G |
| COG0837 | Glucokinase | G |
| COG1015 | Phosphopentomutase | G |
| COG1023 | 6-phosphogluconate dehydrogenase (decarboxylating) | G |
| COG1064 | D-arabinose 1-dehydrogenase, Zn-dependent alcohol dehydrogenase family | G |
| COG1069 | Ribulose kinase | G |
| COG1070 | Sugar (pentulose or hexulose) kinase | G |
| COG1080 | Phosphoenolpyruvate-protein kinase (PTS system EI component in bacteria) | G |
| COG1082 | Sugar phosphate isomerase/epimerase | G |

TABLE 4-continued

COGs for Identifying Prebiotic Activities

| COG ID | COG NAME | COG CATEGORY |
| --- | --- | --- |
| COG1085 | Galactose-1-phosphate uridylyltransferase | G |
| COG1105 | Fructose-1-phosphate kinase or kinase (PfkB) | G |
| COG1109 | Phosphomannomutase | G |
| COG1129 | ABC-type sugar transport system, ATPase component | G |
| COG1172 | Ribose/xylose/arabinose/galactoside ABC-type transport system, permease component | G |
| COG1175 | ABC-type sugar transport system, permease component | G |
| COG1216 | Glycosyltransferase, GT2 family | G |
| COG1263 | Phosphotransferase system IIC components, glucose/maltose/N-acetylglucosamine-specific | G |
| COG1264 | Phosphotransferase system IIB components | G |
| COG1299 | Phosphotransferase system, fructose-specific IIC component | G |
| COG1312 | D-mannonate dehydratase | G |
| COG1440 | Phosphotransferase system cellobiose-specific component IIB | G |
| COG1445 | Phosphotransferase system fructose-specific component IIB | G |
| COG1447 | Phosphotransferase system cellobiose-specific component IIA | G |
| COG1449 | Alpha-amylase/alpha-mannosidase, GH57 family | G |
| COG1455 | Phosphotransferase system cellobiose-specific component IIC | G |
| COG1472 | Periplasmic beta-glucosidase and related glycosidases | G |
| COG1482 | Mannose-6-phosphate isomerase, class I | G |
| COG1486 | Alpha-galactosidase/6-phospho-beta-glucosidase, family 4 of glycosyl hydrolase | G |
| COG1494 | Fructose-1,6-bisphosphatase/sedoheptulose 1,7-bisphosphatase or related protein | G |
| COG1501 | Alpha-glucosidase, glycosyl hydrolase family GH31 | G |
| COG1523 | Pullulanase/glycogen debranching enzyme | G |
| COG1543 | Predicted glycosyl hydrolase, contains GH57 and DUF1957 domains | G |
| COG1554 | Trehalose and maltose hydrolase (possible phosphorylase) | G |
| COG1593 | TRAP-type C4-dicarboxylate transport system, large permease component | G |
| COG1621 | Sucrose-6-phosphate hydrolase SacC, GH32 family | G |
| COG1626 | Neutral trehalase | G |
| COG1638 | TRAP-type C4-dicarboxylate transport system, periplasmic component | G |
| COG1640 | 4-alpha-glucanotransferase | G |
| COG1653 | ABC-type glycerol-3-phosphate transport system, periplasmic component | G |
| COG1803 | Methylglyoxal synthase | G |
| COG1819 | UDP: flavonoid glycosyltransferase YjiC, YdhE family | G |
| COG1820 | N-acetylglucosamine-6-phosphate deacetylase | G |
| COG1830 | Fructose-bisphosphate aldolase class Ia, DhnA family | G |
| COG1850 | Ribulose 1,5-bisphosphate carboxylase, large subunit, or a RuBisCO-like protein | G |
| COG1869 | D-ribose pyranose/furanose isomerase RbsD | G |
| COG1874 | Beta-galactosidase GanA | G |
| COG1877 | Trehalose-6-phosphatase | G |
| COG1879 | ABC-type sugar transport system, periplasmic component, contains N-terminal xre family HTH domain | G |
| COG1892 | Phosphoenolpyruvate carboxylase | G |
| COG1904 | Glucuronate isomerase | G |
| COG1929 | Glycerate kinase | G |
| COG1980 | Archaeal fructose 1,6-bisphosphatase | G |
| COG2017 | Galactose mutarotase or related enzyme | G |
| COG2074 | 2-phosphoglycerate kinase | G |
| COG2079 | 2-methylcitrate dehydratase PrpD | G |
| COG2115 | Xylose isomerase | G |
| COG2120 | N-acetylglucosaminyl deacetylase, LmbE family | G |
| COG2133 | Glucose/arabinose dehydrogenase, beta-propeller fold | G |
| COG2140 | Oxalate decarboxylase/archaeal phosphoglucose isomerase, cupin superfamily | G |
| COG2152 | Predicted glycosyl hydrolase, GH43/DUF377 family | G |
| COG2160 | L-arabinose isomerase | G |
| COG2182 | Maltose-binding periplasmic protein MalE | G |
| COG2190 | Phosphotransferase system IIA component | G |
| COG2211 | Na+/melibiose symporter or related transporter | G |
| COG2213 | Phosphotransferase system, mannitol-specific IIBC component | G |
| COG2220 | L-ascorbate metabolism protein UlaG, beta-lactamase superfamily | G |
| COG2271 | Sugar phosphate permease | G |
| COG2273 | Beta-glucanase, GH16 family | G |
| COG2301 | Citrate lyase beta subunit | G |
| COG2342 | Endo alpha-1,4 polygalactosaminidase, GH114 family (was erroneously annotated as Cys-tRNA synthetase) | G |
| COG2376 | Dihydroxyacetone kinase | G |
| COG2379 | Glycerate-2-kinase | G |

TABLE 4-continued

COGs for Identifying Prebiotic Activities

| COG ID | COG NAME | COG CATEGORY |
|---|---|---|
| COG2407 | L-fucose isomerase or related protein | G |
| COG2513 | 2-Methylisocitrate lyase and related enzymes, PEP mutase family | G |
| COG2704 | Anaerobic C4-dicarboxylate transporter | G |
| COG2706 | 6-phosphogluconolactonase, cycloisomerase 2 family | G |
| COG2721 | Altronate dehydratase | G |
| COG2723 | Beta-glucosidase/6-phospho-beta-glucosidase/beta-galactosidase | G |
| COG2730 | Aryl-phospho-beta-D-glucosidase BglC, GH1 family | G |
| COG2731 | Beta-galactosidase, beta subunit | G |
| COG2814 | Predicted arabinose efflux permease, MFS family | G |
| COG2861 | Uncharacterized conserved protein YibQ, putative polysaccharide deacetylase 2 family | G |
| COG2893 | Phosphotransferase system, mannose/fructose-specific component IIA | G |
| COG2942 | Mannose or cellobiose epimerase, N-acyl-D-glucosamine 2-epimerase family | G |
| COG2971 | BadF-type ATPase, related to human N-acetylglucosamine kinase | G |
| COG3001 | Fructosamine-3-kinase | G |
| COG3010 | Putative N-acetylmannosamine-6-phosphate epimerase | G |
| COG3037 | Ascorbate-specific PTS system EIIC-type component UlaA | G |
| COG3090 | TRAP-type C4-dicarboxylate transport system, small permease component | G |
| COG3250 | Beta-galactosidase/beta-glucuronidase | G |
| COG3265 | Gluconate kinase | G |
| COG3280 | Maltooligosyltrehalose synthase | G |
| COG3281 | Predicted trehalose synthase | G |
| COG3325 | Chitinase, GH18 family | G |
| COG3345 | Alpha-galactosidase | G |
| COG3347 | Rhamnose utilisation protein RhaD, predicted bifunctional aldolase and dehydrogenase | G |
| COG3386 | Sugar lactone lactonase YvrE | G |
| COG3387 | Glucoamylase (glucan-1,4-alpha-glucosidase), GH15 family | G |
| COG3405 | Endo-1,4-beta-D-glucanase Y | G |
| COG3408 | Glycogen debranching enzyme (alpha-1,6-glucosidase) | G |
| COG3414 | Phosphotransferase system, galactitol-specific IIB component | G |
| COG3429 | Glucose-6-phosphate dehydrogenase assembly protein OpcA, contains a peptidoglycan-binding domain | G |
| COG3444 | Phosphotransferase system, mannose/fructose/N-acetylgalactosamine-specific component IIB | G |
| COG3459 | Cellobiose phosphorylase | G |
| COG3469 | Chitinase | G |
| COG3507 | Beta-xylosidase | G |
| COG3525 | N-acetyl-beta-hexosaminidase | G |
| COG3534 | Alpha-L-arabinofuranosidase | G |
| COG3537 | Putative alpha-1,2-mannosidase | G |
| COG3588 | Fructose-bisphosphate aldolase class 1 | G |
| COG3594 | Fucose 4-O-acetylase or related acetyltransferase | G |
| COG3622 | Hydroxypyruvate isomerase | G |
| COG3623 | L-ribulose-5-phosphate 3-epimerase UlaE | G |
| COG3635 | 2,3-bisphosphoglycerate-independent phosphoglycerate mutase, archeal type | G |
| COG3661 | Alpha-glucuronidase | G |
| COG3664 | Beta-xylosidase | G |
| COG3669 | Alpha-L-fucosidase | G |
| COG3684 | Tagatose-1,6-bisphosphate aldolase | G |
| COG3693 | Endo-1,4-beta-xylanase, GH35 family | G |
| COG3709 | Ribose 1,5-bisphosphokinase PhnN | G |
| COG3715 | Phosphotransferase system, mannose/fructose/N-acetylgalactosamine-specific component IIC | G |
| COG3716 | Phosphotransferase system, mannose/fructose/N-acetylgalactosamine-specific component IID | G |
| COG3717 | 5-keto 4-deoxyuronate isomerase | G |
| COG3718 | 5-deoxy-D-glucuronate isomerase | G |
| COG3730 | Phosphotransferase system sorbitol-specific component IIC | G |
| COG3731 | Phosphotransferase system sorbitol-specific component IIA | G |
| COG3732 | Phosphotransferase system sorbitol-specific component IIBC | G |
| COG3734 | 2-keto-3-deoxy-galactonokinase | G |
| COG3769 | Predicted mannosyl-3-phosphoglycerate phosphatase, HAD superfamily | G |
| COG3775 | Phosphotransferase system, galactitol-specific IIC component | G |
| COG3822 | D-lyxose ketol-isomerase | G |
| COG3833 | ABC-type maltose transport system, permease component | G |
| COG3836 | 2-keto-3-deoxy-L-rhamnonate aldolase RhmA | G |
| COG3839 | ABC-type sugar transport system, ATPase component | G |
| COG3855 | Fructose-1,6-bisphosphatase | G |

TABLE 4-continued

COGs for Identifying Prebiotic Activities

| COG ID | COG NAME | COG CATEGORY |
|---|---|---|
| COG3866 | Pectate lyase | G |
| COG3867 | Arabinogalactan endo-1,4-beta-galactosidase | G |
| COG3892 | Myo-inositol catabolism protein IolC | G |
| COG3934 | Endo-1,4-beta-mannosidase | G |
| COG3936 | Membrane-bound acyltransferase YfiQ, involved in biofilm formation | G |
| COG3940 | Beta-xylosidase, GH43 family | G |
| COG3954 | Phosphoribulokinase | G |
| COG3957 | Phosphoketolase | G |
| COG3958 | Transketolase, C-terminal subunit | G |
| COG3959 | Transketolase, N-terminal subunit | G |
| COG3962 | TPP-dependent trihydroxycyclohexane-1,2-dione (THcHDO) dehydratase, myo-inositol metabolism | G |
| COG3979 | Chitodextrinase | G |
| COG4124 | Beta-mannanase | G |
| COG4130 | Predicted sugar epimerase, xylose isomerase-like family | G |
| COG4154 | L-fucose mutarotase/ribose pyranase, RbsD/FucU family | G |
| COG4193 | Beta-N-acetylglucosaminidase | G |
| COG4209 | ABC-type polysaccharide transport system, permease component | G |
| COG4211 | ABC-type glucose/galactose transport system, permease component | G |
| COG4213 | ABC-type xylose transport system, periplasmic component | G |
| COG4214 | ABC-type xylose transport system, permease component | G |
| COG4225 | Rhamnogalacturonyl hydrolase YesR | G |
| COG4284 | UDP-N-acetylglucosamine pyrophosphorylase | G |
| COG4451 | Ribulose bisphosphate carboxylase small subunit | G |
| COG4468 | Galactose-1-phosphate uridylyltransferase | G |
| COG4573 | Tagatose-1,6-bisphosphate aldolase non-catalytic subunit AgaZ/GatZ | G |
| COG4580 | Maltoporin (phage lambda and maltose receptor) | G |
| COG4632 | Exopolysaccharide biosynthesis protein related to N-acetylglucosamine-1-phosphodiester alpha-N-acety . . . | G |
| COG4668 | Mannitol/fructose-specific phosphotransferase system, IIA domain | G |
| COG4724 | Endo-beta-N-acetylglucosaminidase D | G |
| COG4806 | L-rhamnose isomerase | G |
| COG4809 | Archaeal ADP-dependent phosphofructokinase/glucokinase | G |
| COG4813 | Trehalose utilization protein | G |
| COG4833 | Predicted alpha-1,6-mannanase, GH76 family | G |
| COG4975 | Glucose uptake protein GlcU | G |
| COG4993 | Glucose dehydrogenase | G |
| COG5017 | UDP-N-acetylglucosamine transferase subunit ALG13 | G |
| COG5026 | Hexokinase | G |
| COG5263 | Glucan-binding domain (YG repeat) | G |
| COG0002 | N-acetyl-gamma-glutamylphosphate reductase | E |
| COG0006 | Xaa-Pro aminopeptidase | E |
| COG0010 | Arginase family enzyme | E |
| COG0014 | Gamma-glutamyl phosphate reductase | E |
| COG0019 | Diaminopimelate decarboxylase | E |
| COG0031 | Cysteine synthase | E |
| COG0040 | ATP phosphoribosyltransferase | E |
| COG0065 | Homoaconitase/3-isopropylmalate dehydratase large subunit | E |
| COG0066 | 3-isopropylmalate dehydratase small subunit | E |
| COG0067 | Glutamate synthase domain 1 | E |
| COG0069 | Glutamate synthase domain 2 | E |
| COG0070 | Glutamate synthase domain 3 | E |
| COG0076 | Glutamate or tyrosine decarboxylase or a related PLP-dependent protein | E |
| COG0077 | Prephenate dehydratase | E |
| COG0078 | Ornithine carbamoyltransferase | E |
| COG0079 | Histidinol-phosphate/aromatic aminotransferase or cobyric acid decarboxylase | E |
| COG0082 | Chorismate synthase | E |
| COG0083 | Homoserine kinase | E |
| COG0106 | Phosphoribosylformimino-5-aminoimidazole carboxamide ribonucleotide (ProFAR) isomerase | E |
| COG0107 | Imidazole glycerol phosphate synthase subunit HisF | E |
| COG0112 | Glycine/serine hydroxymethyltransferase | E |
| COG0118 | Imidazoleglycerol phosphate synthase glutamine amidotransferase subunit HisH | E |
| COG0119 | Isopropylmalate/homocitrate/citramalate synthases | E |
| COG0128 | 5-enolpyruvylshikimate-3-phosphate synthase | E |
| COG0131 | Imidazoleglycerol phosphate dehydratase HisB | E |
| COG0133 | Tryptophan synthase beta chain | E |
| COG0134 | Indole-3-glycerol phosphate synthase | E |

TABLE 4-continued

COGs for Identifying Prebiotic Activities

| COG ID | COG NAME | COG CATEGORY |
|---|---|---|
| COG0135 | Phosphoribosylanthranilate isomerase | E |
| COG0136 | Aspartate-semialdehyde dehydrogenase | E |
| COG0137 | Argininosuccinate synthase | E |
| COG0139 | Phosphoribosyl-AMP cyclohydrolase | E |
| COG0140 | Phosphoribosyl-ATP pyrophosphohydrolase | E |
| COG0141 | Histidinol dehydrogenase | E |
| COG0159 | Tryptophan synthase alpha chain | E |
| COG0160 | 4-aminobutyrate aminotransferase or related aminotransferase | E |
| COG0165 | Argininosuccinate lyase | E |
| COG0169 | Shikimate 5-dehydrogenase | E |
| COG0174 | Glutamine synthetase | E |
| COG0182 | Methylthioribose-1-phosphate isomerase (methionine salvage pathway), a paralog of eIF-2B alpha subunit | E |
| COG0241 | Histidinol phosphatase or a related phosphatase | E |
| COG0253 | Diaminopimelate epimerase | E |
| COG0260 | Leucyl aminopeptidase | E |
| COG0263 | Glutamate 5-kinase | E |
| COG0287 | Prephenate dehydrogenase | E |
| COG0289 | Dihydrodipicolinate reductase | E |
| COG0308 | Aminopeptidase N | E |
| COG0334 | Glutamate dehydrogenase/leucine dehydrogenase | E |
| COG0337 | 3-dehydroquinate synthetase | E |
| COG0339 | Zn-dependent oligopeptidase | E |
| COG0345 | Pyrroline-5-carboxylate reductase | E |
| COG0367 | Asparagine synthetase B (glutamine-hydrolyzing) | E |
| COG0403 | Glycine cleavage system protein P (pyridoxal-binding), N-terminal domain | E |
| COG0404 | Glycine cleavage system T protein (aminomethyltransferase) | E |
| COG0405 | Gamma-glutamyltranspeptidase | E |
| COG0410 | ABC-type branched-chain amino acid transport system, ATPase component | E |
| COG0411 | ABC-type branched-chain amino acid transport system, ATPase component | E |
| COG0421 | Spermidine synthase | E |
| COG0436 | Aspartate/methionine/tyrosine aminotransferase | E |
| COG0440 | Acetolactate synthase, small subunit | E |
| COG0460 | Homoserine dehydrogenase | E |
| COG0498 | Threonine synthase | E |
| COG0506 | Proline dehydrogenase | E |
| COG0509 | Glycine cleavage system H protein (lipoate-binding) | E |
| COG0520 | Selenocysteine lyase/Cysteine desulfurase | E |
| COG0527 | Aspartokinase | E |
| COG0531 | Amino acid transporter | E |
| COG0547 | Anthranilate phosphoribosyltransferase | E |
| COG0548 | Acetylglutamate kinase | E |
| COG0549 | Carbamate kinase | E |
| COG0559 | Branched-chain amino acid ABC-type transport system, permease component | E |
| COG0560 | Phosphoserine phosphatase | E |
| COG0591 | Na+/proline symporter | E |
| COG0620 | Methionine synthase II (cobalamin-independent) | E |
| COG0624 | Acetylornithine deacetylase/Succinyl-diaminopimelate desuccinylase or related deacylase | E |
| COG0626 | Cystathionine beta-lyase/cystathionine gamma-synthase | E |
| COG0646 | Methionine synthase I (cobalamin-dependent), methyltransferase domain | E |
| COG0665 | Glycine/D-amino acid oxidase (deaminating) | E |
| COG0683 | ABC-type branched-chain amino acid transport system, periplasmic component | E |
| COG0685 | 5,10-methylenetetrahydrofolate reductase | E |
| COG0686 | Alanine dehydrogenase | E |
| COG0687 | Spermidine/putrescine-binding periplasmic protein | E |
| COG0703 | Shikimate kinase | E |
| COG0709 | Selenophosphate synthase | E |
| COG0710 | 3-dehydroquinate dehydratase | E |
| COG0722 | 3-deoxy-D-arabino-heptulosonate 7-phosphate (DAHP) synthase | E |
| COG0747 | ABC-type transport system, periplasmic component | E |
| COG0754 | Glutathionylspermidine synthase | E |
| COG0757 | 3-dehydroquinate dehydratase | E |
| COG0765 | ABC-type amino acid transport system, permease component | E |
| COG0786 | Na+/glutamate symporter | E |
| COG0804 | Urease alpha subunit | E |
| COG0814 | Amino acid permease | E |
| COG0831 | Urease gamma subunit | E |
| COG0832 | Urease beta subunit | E |
| COG0833 | Amino acid permease | E |

TABLE 4-continued

COGs for Identifying Prebiotic Activities

| COG ID | COG NAME | COG CATEGORY |
|---|---|---|
| COG1003 | Glycine cleavage system protein P (pyridoxal-binding), C-terminal domain | E |
| COG1027 | Aspartate ammonia-lyase | E |
| COG1045 | Serine acetyltransferase | E |
| COG1104 | Cysteine sulfinate desulfinase/cysteine desulfurase or related enzyme | E |
| COG1113 | L-asparagine transporter and related permeases | E |
| COG1114 | Branched-chain amino acid permeases | E |
| COG1115 | Na+/alanine symporter | E |
| COG1125 | ABC-type proline/glycine betaine transport system, ATPase component | E |
| COG1126 | ABC-type polar amino acid transport system, ATPase component | E |
| COG1135 | ABC-type methionine transport system, ATPase component | E |
| COG1164 | Oligoendopeptidase F | E |
| COG1166 | Arginine decarboxylase (spermidine biosynthesis) | E |
| COG1171 | Threonine dehydratase | E |
| COG1174 | ABC-type proline/glycine betaine transport system, permease component | E |
| COG1176 | ABC-type spermidine/putrescine transport system, permease component I | E |
| COG1177 | ABC-type spermidine/putrescine transport system, permease component II | E |
| COG1231 | Monoamine oxidase | E |
| COG1246 | N-acetylglutamate synthase or related acetyltransferase, GNAT family | E |
| COG1247 | L-amino acid N-acyltransferase YncA | E |
| COG1279 | Arginine exporter protein ArgO | E |
| COG1280 | Threonine/homoserine/homoserine lactone efflux protein | E |
| COG1296 | Predicted branched-chain amino acid permease (azaleucine resistance) | E |
| COG1350 | Predicted alternative tryptophan synthase beta-subunit (paralog of TrpB) | E |
| COG1362 | Aspartyl aminopeptidase | E |
| COG1364 | N-acetylglutamate synthase (N-acetylornithine aminotransferase) | E |
| COG1410 | Methionine synthase I, cobalamin-binding domain | E |
| COG1446 | Isoaspartyl peptidase or L-asparaginase, Ntn-hydrolase superfamily | E |
| COG1448 | Aspartate/tyrosine/aromatic aminotransferase | E |
| COG1465 | 3-dehydroquinate synthase, class II | E |
| COG1505 | Prolyl oligopeptidase PreP, S9A serine peptidase family | E |
| COG1506 | Dipeptidyl aminopeptidase/acylaminoacyl peptidase | E |
| COG1509 | L-lysine 2,3-aminomutase (EF-P beta-lysylation pathway) | E |
| COG1586 | S-adenosylmethionine decarboxylase or arginine decarboxylase | E |
| COG1605 | Chorismate mutase | E |
| COG1685 | Archaeal shikimate kinase | E |
| COG1687 | Branched-chain amino acid transport protein AzlD | E |
| COG1748 | Saccharopine dehydrogenase, NADP-dependent | E |
| COG1760 | L-serine deaminase | E |
| COG1770 | Protease II | E |
| COG1791 | Acireductone dioxygenase (methionine salvage), cupin superfamily | E |
| COG1823 | L-cystine uptake protein TcyP, sodium: dicarboxylate symporter family | E |
| COG1834 | N-Dimethylarginine dimethylaminohydrolase | E |
| COG1878 | Kynurenine formamidase | E |
| COG1897 | Homoserine trans-succinylase | E |
| COG1945 | Pyruvoyl-dependent arginine decarboxylase (PvlArgDC) | E |
| COG1982 | Arginine/lysine/ornithine decarboxylase | E |
| COG1984 | Allophanate hydrolase subunit 2 | E |
| COG2008 | Threonine aldolase | E |
| COG2011 | ABC-type methionine transport system, permease component | E |
| COG2021 | Homoserine acetyltransferase | E |
| COG2040 | Homocysteine/selenocysteine methylase (S-methylmethionine-dependent) | E |
| COG2049 | Allophanate hydrolase subunit 1 | E |
| COG2056 | Predicted histidine transporter YuiF, NhaC family | E |
| COG2066 | Glutaminase | E |
| COG2071 | Gamma-glutamyl-gamma-aminobutyrate hydrolase PuuD (putrescine degradation), contains GATase1-like domain | E |
| COG2095 | Small neutral amino acid transporter SnatA, MarC family | E |
| COG2113 | ABC-type proline/glycine betaine transport system, periplasmic component | E |
| COG2171 | Tetrahydrodipicolinate N-succinyltransferase | E |
| COG2195 | Di- or tripeptidase | E |

TABLE 4-continued

COGs for Identifying Prebiotic Activities

| COG ID | COG NAME | COG CATEGORY |
|---|---|---|
| COG2235 | Arginine deiminase | E |
| COG2309 | Leucyl aminopeptidase (aminopeptidase T) | E |
| COG2317 | Zn-dependent carboxypeptidase, M32 family | E |
| COG2355 | Zn-dependent dipeptidase, microsomal dipeptidase homolog | E |
| COG2362 | D-aminopeptidase | E |
| COG2423 | Ornithine cyclodeaminase/archaeal alanine dehydrogenase, mu-crystallin family | E |
| COG2502 | Asparagine synthetase A | E |
| COG2515 | 1-aminocyclopropane-1-carboxylate deaminase/D-cysteine desulfhydrase, PLP-dependent ACC family | E |
| COG2716 | Glycine cleavage system regulatory protein | E |
| COG2755 | Lysophospholipase L1 or related esterase | E |
| COG2856 | Zn-dependent peptidase ImmA, M78 family | E |
| COG2873 | O-acetylhomoserine/O-acetylserine sulfhydrylase, pyridoxal phosphate-dependent | E |
| COG2876 | 3-deoxy-D-arabino-heptulosonate 7-phosphate (DAHP) synthase | E |
| COG2902 | NAD-specific glutamate dehydrogenase | E |
| COG2939 | Carboxypeptidase C (cathepsin A) | E |
| COG2957 | Agmatine/peptidylarginine deiminase | E |
| COG2981 | Uncharacterized protein involved in cysteine biosynthesis | E |
| COG2986 | Histidine ammonia-lyase | E |
| COG2987 | Urocanate hydratase | E |
| COG2988 | Succinylglutamate desuccinylase | E |
| COG3033 | Tryptophanase | E |
| COG3048 | D-serine dehydratase | E |
| COG3075 | Anaerobic glycerol-3-phosphate dehydrogenase | E |
| COG3104 | Dipeptide/tripeptide permease | E |
| COG3138 | Arginine/ornithine N-succinyltransferase beta subunit | E |
| COG3186 | Phenylalanine-4-hydroxylase | E |
| COG3192 | Ethanolamine transporter EutH, required for ethanolamine utilization at low pH | E |
| COG3200 | 3-deoxy-D-arabino-heptulosonate 7-phosphate (DAHP) synthase, class II | E |
| COG3232 | 5-carboxymethyl-2-hydroxymuconate isomerase | E |
| COG3340 | Peptidase E | E |
| COG3404 | Formiminotetrahydrofolate cyclodeaminase | E |
| COG3457 | Predicted amino acid racemase | E |
| COG3483 | Tryptophan 2,3-dioxygenase (vermilion) | E |
| COG3579 | Aminopeptidase C | E |
| COG3591 | V8-like Glu-specific endopeptidase | E |
| COG3616 | D-serine deaminase, pyridoxal phosphate-dependent | E |
| COG3633 | Na+/serine symporter | E |
| COG3643 | Glutamate formiminotransferase | E |
| COG3681 | L-cysteine desulfidase | E |
| COG3705 | ATP phosphoribosyltransferase regulatory subunit HisZ | E |
| COG3724 | Succinylarginine dihydrolase | E |
| COG3741 | N-formylglutamate amidohydrolase | E |
| COG3799 | Methylaspartate ammonia-lyase | E |
| COG3842 | ABC-type Fe3+/spermidine/putrescine transport systems, ATPase components | E |
| COG3844 | Kynureninase | E |
| COG3931 | Predicted N-formylglutamate amidohydrolase | E |
| COG3938 | Proline racemase | E |
| COG3968 | Glutamine synthetase type III | E |
| COG3977 | Alanine-alpha-ketoisovalerate (or valine-pyruvate) aminotransferase | E |
| COG4091 | Predicted homoserine dehydrogenase, contains C-terminal SAF domain | E |
| COG4126 | Asp/Glu/hydantoin racemase | E |
| COG4160 | ABC-type arginine/histidine transport system, permease component | E |
| COG4161 | ABC-type arginine transport system, ATPase component | E |
| COG4166 | ABC-type oligopeptide transport system, periplasmic component | E |
| COG4175 | ABC-type proline/glycine betaine transport system, ATPase component | E |
| COG4176 | ABC-type proline/glycine betaine transport system, permease component | E |
| COG4177 | ABC-type branched-chain amino acid transport system, permease component | E |
| COG4187 | Arginine utilization protein RocB | E |
| COG4215 | ABC-type arginine transport system, permease component | E |
| COG4229 | Enolase-phosphatase E1 involved in merthionine salvage | E |
| COG4230 | Delta 1-pyrroline-5-carboxylate dehydrogenase | E |
| COG4302 | Ethanolamine ammonia-lyase, small subunit | E |
| COG4303 | Ethanolamine ammonia-lyase, large subunit | E |
| COG4311 | Sarcosine oxidase delta subunit | E |

TABLE 4-continued

COGs for Identifying Prebiotic Activities

| COG ID | COG NAME | COG CATEGORY |
|---|---|---|
| COG4359 | 2-hydroxy-3-keto-5-methylthiopentenyl-1-phosphate phosphatase (methionine salvage) | E |
| COG4392 | Branched-chain amino acid transport protein | E |
| COG4401 | Chorismate mutase | E |
| COG4413 | Urea transporter | E |
| COG4448 | L-asparaginase II | E |
| COG4583 | Sarcosine oxidase gamma subunit | E |
| COG4597 | ABC-type amino acid transport system, permease component | E |
| COG4598 | ABC-type histidine transport system, ATPase component | E |
| COG4608 | ABC-type oligopeptide transport system, ATPase component | E |
| COG4690 | Dipeptidase | E |
| COG4766 | Ethanolamine utilization protein EutQ, cupin superfamily (function unknown) | E |
| COG4810 | Ethanolamine utilization protein EutS, ethanolamine utilization microcompartment shell protein | E |
| COG4812 | Ethanolamine utilization cobalamin adenosyltransferase | E |
| COG4816 | Ethanolamine utilization protein EutL, ethanolamine utilization microcompartment shell protein | E |
| COG4819 | Ethanolamine utilization protein EutA, possible chaperonin protecting lyase from inhibition | E |
| COG4820 | Ethanolamine utilization protein EutJ, possible chaperonin | E |
| COG4857 | 5-Methylthioribose kinase, methionine salvage pathway | E |
| COG4865 | Glutamate mutase epsilon subunit | E |
| COG4917 | Ethanolamine utilization protein EutP, contains a P-loop NTPase domain | E |
| COG4992 | Acetylornithine/succinyldiaminopimelate/putrescine aminotransferase | E |
| COG5006 | Threonine/homoserine efflux transporter RhtA | E |
| COG0020 | Undecaprenyl pyrophosphate synthase | I |
| COG0183 | Acetyl-CoA acetyltransferase | I |
| COG0204 | 1-acyl-sn-glycerol-3-phosphate acyltransferase | I |
| COG0245 | 2C-methyl-D-erythritol 2,4-cyclodiphosphate synthase | I |
| COG0331 | Malonyl CoA-acyl carrier protein transacylase | I |
| COG0332 | 3-oxoacyl-[acyl-carrier-protein] synthase III | I |
| COG0344 | Phospholipid biosynthesis protein PlsY, probable glycerol-3-phosphate acyltransferase | I |
| COG0365 | Acyl-coenzyme A synthetase/AMP-(fatty) acid ligase | I |
| COG0416 | Fatty acid/phospholipid biosynthesis enzyme | I |
| COG0439 | Biotin carboxylase | I |
| COG0446 | NADPH-dependent 2,4-dienoyl-CoA reductase, sulfur reductase, or a related oxidoreductase | I |
| COG0558 | Phosphatidylglycerophosphate synthase | I |
| COG0575 | CDP-diglyceride synthetase | I |
| COG0584 | Glycerophosphoryl diester phosphodiesterase | I |
| COG0623 | Enoyl-[acyl-carrier-protein] reductase (NADH) | I |
| COG0657 | Acetyl esterase/lipase | I |
| COG0671 | Membrane-associated phospholipid phosphatase | I |
| COG0688 | Phosphatidylserine decarboxylase | I |
| COG0736 | Phosphopantetheinyl transferase (holo-ACP synthase) | I |
| COG0743 | 1-deoxy-D-xylulose 5-phosphate reductoisomerase | I |
| COG0761 | 4-Hydroxy-3-methylbut-2-enyl diphosphate reductase IspH | I |
| COG0764 | 3-hydroxymyristoyl/3-hydroxydecanoyl-(acyl carrier protein) dehydratase | I |
| COG0777 | Acetyl-CoA carboxylase beta subunit | I |
| COG0818 | Diacylglycerol kinase | I |
| COG0821 | 4-hydroxy-3-methylbut-2-en-1-yl diphosphate synthase IspG/GcpE | I |
| COG0824 | Acyl-CoA thioesterase FadM | I |
| COG0825 | Acetyl-CoA carboxylase alpha subunit | I |
| COG1022 | Long-chain acyl-CoA synthetase (AMP-forming) | I |
| COG1024 | Enoyl-CoA hydratase/carnithine racemase | I |
| COG1075 | Triacylglycerol esterase/lipase EstA, alpha/beta hydrolase fold | I |
| COG1133 | ABC-type long-chain fatty acid transport system, fused permease and ATPase components | I |
| COG1183 | Phosphatidylserine synthase | I |
| COG1211 | 2-C-methyl-D-erythritol 4-phosphate cytidylyltransferase | I |
| COG1213 | Choline kinase | I |
| COG1250 | 3-hydroxyacyl-CoA dehydrogenase | I |
| COG1257 | Hydroxymethylglutaryl-CoA reductase | I |
| COG1260 | Myo-inositol-1-phosphate synthase | I |
| COG1267 | Phosphatidylglycerophosphatase A | I |
| COG1307 | Fatty acid-binding protein DegV (function unknown) | I |
| COG1398 | Fatty-acid desaturase | I |
| COG1443 | Isopentenyldiphosphate isomerase | I |
| COG1502 | Phosphatidylserine/phosphatidylglycerophosphate/cardiolipin synthase or related enzyme | I |

TABLE 4-continued

COGs for Identifying Prebiotic Activities

| COG ID | COG NAME | COG CATEGORY |
|---|---|---|
| COG1560 | Lauroyl/myristoyl acyltransferase | I |
| COG1562 | Phytoene/squalene synthetase | I |
| COG1577 | Mevalonate kinase | I |
| COG1607 | Acyl-CoA hydrolase | I |
| COG1608 | Isopentenyl phosphate kinase | I |
| COG1646 | Heptaprenylglyceryl phosphate synthase | I |
| COG1657 | Squalene cyclase | I |
| COG1788 | Acyl CoA: acetate/3-ketoacid CoA transferase, alpha subunit | I |
| COG1804 | Crotonobetainyl-CoA: carnitine CoA-transferase CaiB and related acyl-CoA transferases | I |
| COG1884 | Methylmalonyl-CoA mutase, N-terminal domain/subunit | I |
| COG1924 | Activator of 2-hydroxyglutaryl-CoA dehydratase (HSP70-class ATPase domain) | I |
| COG1946 | Acyl-CoA thioesterase | I |
| COG1947 | 4-diphosphocytidyl-2C-methyl-D-erythritol kinase | I |
| COG1960 | Acyl-CoA dehydrogenase related to the alkylation response protein AidB | I |
| COG1968 | Undecaprenyl pyrophosphate phosphatase UppP | I |
| COG2030 | Acyl dehydratase | I |
| COG2031 | Short chain fatty acids transporter | I |
| COG2057 | Acyl CoA: acetate/3-ketoacid CoA transferase, beta subunit | I |
| COG2067 | Long-chain fatty acid transport protein | I |
| COG2084 | 3-hydroxyisobutyrate dehydrogenase or related beta-hydroxyacid dehydrogenase | I |
| COG2134 | CDP-diacylglycerol pyrophosphatase | I |
| COG2185 | Methylmalonyl-CoA mutase, C-terminal domain/subunit (cobalamin-binding) | I |
| COG2230 | Cyclopropane fatty-acyl-phospholipid synthase and related methyltransferases | I |
| COG2246 | Putative flippase GtrA (transmembrane translocase of bactoprenol-linked glucose) | I |
| COG2267 | Lysophospholipase, alpha-beta hydrolase superfamily | I |
| COG2272 | Carboxylesterase type B | I |
| COG2854 | ABC-type transporter Mla maintaining outer membrane lipid asymmetry, periplasmic MlaC component | I |
| COG2930 | Lipid-binding SYLF domain | I |
| COG2937 | Glycerol-3-phosphate O-acyltransferase | I |
| COG3000 | Sterol desaturase/sphingolipid hydroxylase, fatty acid hydroxylase superfamily | I |
| COG3007 | Trans-2-enoyl-CoA reductase | I |
| COG3124 | Acyl carrier protein phosphodiesterase | I |
| COG3154 | Predicted lipid carrier protein YhbT, SCP2 domain | I |
| COG3239 | Fatty acid desaturase | I |
| COG3243 | Poly(3-hydroxyalkanoate) synthetase | I |
| COG3255 | Putative sterol carrier protein | I |
| COG3356 | Predicted membrane-associated lipid hydrolase, neutral ceramidase superfamily | I |
| COG3407 | Mevalonate pyrophosphate decarboxylase | I |
| COG3425 | 3-hydroxy-3-methylglutaryl CoA synthase | I |
| COG3475 | Phosphorylcholine metabolism protein LicD | I |
| COG3675 | Predicted lipase | I |
| COG3777 | Hydroxyacyl-ACP dehydratase HTD2, hotdog domain | I |
| COG3882 | Predicted enzyme involved in methoxymalonyl-ACP biosynthesis | I |
| COG3884 | Acyl-ACP thioesterase | I |
| COG3963 | Phospholipid N-methyltransferase | I |
| COG4247 | 3-phytase (myo-inositol-hexaphosphate 3-phosphohydrolase) | I |
| COG4281 | Acyl-CoA-binding protein | I |
| COG4395 | Predicted lipid-binding transport protein, Tim44 family | I |
| COG4553 | Poly-beta-hydroxyalkanoate depolymerase | I |
| COG4667 | Predicted phospholipase, patatin/cPLA2 family | I |
| COG4670 | Acyl CoA: acetate/3-ketoacid CoA transferase | I |
| COG4706 | Predicted 3-hydroxylacyl-ACP dehydratase, HotDog domain | I |
| COG4770 | Acetyl/propionyl-CoA carboxylase, alpha subunit | I |
| COG4781 | Membrane-anchored glycerophosphoryl diester phosphodiesterase (GDPDase), membrane domain | I |
| COG4799 | Acetyl-CoA carboxylase, carboxyltransferase component | I |
| COG4850 | Phosphatidate phosphatase APP1 | I |
| COG4981 | Enoyl reductase domain of yeast-type FAS1 | I |
| COG4982 | 3-oxoacyl-ACP reductase domain of yeast-type FAS1 | I |
| COG5083 | Phosphatidate phosphatase PAH1, contains Lipin and LNS2 domains. can be involved in plasmid maintenance | I |
| COG0473 | Isocitrate/isopropylmalate dehydrogenase | CE |
| COG0604 | NADPH: quinone reductase or related Zn-dependent oxidoreductase | CR |
| COG0129 | Dihydroxyacid dehydratase/phosphogluconate dehydratase | EG |

TABLE 4-continued

COGs for Identifying Prebiotic Activities

| COG ID | COG NAME | COG CATEGORY |
|---|---|---|
| COG1363 | Putative aminopeptidase FrvX | EG |
| COG0493 | NADPH-dependent glutamate synthase beta chain or related oxidoreductase | ER |
| COG1063 | Threonine dehydrogenase or related Zn-dependent dehydrogenase | ER |
| COG1168 | Bifunctional PLP-dependent enzyme with beta-cystathionase and maltose regulon repressor activities | ER |
| COG1387 | Histidinol phosphatase or related hydrolase of the PHP family | ER |
| COG3185 | 4-hydroxyphenylpyruvate dioxygenase and related hemolysins | ER |
| COG0347 | Nitrogen regulatory protein PII | TE |
| COG0834 | ABC-type amino acid transport/signal transduction system, periplasmic component/domain | ET |
| COG4677 | Pectin methylesterase and related acyl-CoA thioesterases | GI |
| COG0637 | Beta-phosphoglucomutase or related phosphatase, HAD superfamily | GR |
| COG2610 | H+/gluconate symporter or related permease | GR |
| COG1489 | DNA-binding protein, stimulates sugar fermentation | GT |
| COG1762 | Phosphotransferase system mannitol/fructose-specific IIA domain (Ntr-type) | GT |
| COG1925 | Phosphotransferase system, HPr and related phosphotransfer proteins | TG |
| COG3925 | N-terminal domain of the phosphotransferase system fructose-specific component IIB | GT |
| COG4945 | Carbohydrate-binding DOMON domain | GT |
| COG1597 | Diacylglycerol kinase family enzyme | IR |
| COG2303 | Choline dehydrogenase or related flavoprotein | IR |
| COG3240 | Phospholipase/lecithinase/hemolysin | IR |

TABLE 5

List of species enriched in alive GHVD patients:

Lactobacillus gasseri
Lactobacillus fermentum
Lactobacillus reuteri
Enterococcus faecalis
Enterococcus durans
Enterococcus villorum
Lactobacillus plantarum
Pediococcus acidilactici
Staphylococcus pasteuri
Staphylococcus cohnii
Streptococcus sanguinis
Streptococcus sinensis
Streptococcus mitis
Streptococcus sp. SCA22
Streptococcus sp. CR-3145
Streptococcus anginosus
Streptococcus mutans
Coprobacillus cateniformis
Clostridium saccharogumia
Eubacterium dolichum DSM 3991
Clostridium sp. PPf35E6
Clostridium sordelli ATCC 9714
Ruminococcus torques
Ruminococcus gnavus
Clostridium clostridioforme
Ruminococcus obeum
Blautia producta
Clostridium sp. ID5
Megasphaera micronuciformis
Veillonella parvula
Clostridium methylpentosum
Clostridium islandicum
Faecalibacterium prausnitzii
Bacteroides uniformmis
Bacteroides thetaiotaomicron
Bacteroides acidifaciens
Bacteroides ovatus
Bacteroides fragilis
Parabacteroides distasonis
Propinionibacteirum propionicum
Actinomyces hyovaginalis
Rothia mucilaginosa
Rothia aeria
Bifidobacterium breve
Scardovia inopinata
Eggerthella lenta

TABLE 6

Anaerobic bacterial species tested for carbon source usage (Biolog plates)

| Species purchased: | Species Freshly Isolated: |
|---|---|
| R. gnavus (EPV1) | Blautia luti BlnIX (EPV114) |
| E. rectale (EPV2) | Blautia luti ELU (EPV54) |
| B. luti (EPV3) | Ruminococcus gnavus (EPV102) |
| B. wexlerae (EPV5) | Blautia faecis (EPV78) |
| C. leptum (EPV6) | Ruminococcus torques (EPV76) |
| B. faecis (EPV15) | Blautia wexlerae SJTU1416 (EPV52) |
| B. obeum (EPV20) | Blautia WAL14507 (EPV64) |
| B. producta (EPV21) | Uncultured bacterium SJTU1416 (EPV51) |
| B. coccoides (EPV22) | Uncultured bacterium GQ8980099 (EPV47) |
| B. hydrogenotrophica (EPV23) | Eubacterium rectale (EPV35) |
| B. hansenii (EPV24) | |

TABLE 7

Exemplary Prebiotics/Carbon Sources

| Chemical | MoA |
|---|---|
| L-Arabinose | C-Source, carbohydrate |
| N-Acetyl-D-Glucosamine | C-Source, carbohydrate |
| D-Saccharic acid | C-Source, carboxylic acid |
| Succinic acid | C-Source, carboxylic acid |
| D-Galactose | C-Source, carbohydrate |
| L-Aspartic acid | C-Source, amino acid |

TABLE 7-continued

Exemplary Prebiotics/Carbon Sources

| Chemical | MoA |
|---|---|
| L-Proline | C-Source, amino acid |
| D-Alanine | C-Source, amino acid |
| D-Trehalose | C-Source, carbohydrate |
| D-Mannose | C-Source, carbohydrate |
| Dulcitol | C-Source, carbohydrate |
| D-Serine | C-Source, amino acid |
| D-Sorbitol | C-Source, carbohydrate |
| Glycerol | C-Source, carbohydrate |
| L-Fucose | C-Source, carbohydrate |
| D-Glucuronic acid | C-Source, carboxylic acid |
| D-Gluconic acid | C-Source, carboxylic acid |
| DL-a-Glycerol Phosphate | C-Source, carbohydrate |
| D-Xylose | C-Source, carbohydrate |
| L-Lactic acid | C-Source, carboxylic acid |
| Formic acid | C-Source, carboxylic acid |
| D-Mannitol | C-Source, carbohydrate |
| L-Glutamic acid | C-Source, amino acid |
| D-Glucose-6-Phosphate | C-Source, carbohydrate |
| D-Galactonic acid-g-Lactone | C-Source, carboxylic acid |
| DL-Malic acid | C-Source, carboxylic acid |
| D-Ribose | C-Source, carbohydrate |
| Tween 20 | C-Source, fatty acid |
| L-Rhamnose | C-Source, carbohydrate |
| D-Fructose | C-Source, carbohydrate |
| Acetic acid | C-Source, carboxylic acid |
| a-D-Glucose | C-Source, carbohydrate |
| Maltose | C-Source, carbohydrate |
| D-Melibiose | C-Source, carbohydrate |
| Thymidine | C-Source, carbohydrate |
| L-Asparagine | C-Source, amino acid |
| D-Aspartic acid | C-Source, amino acid |
| D-Glucosaminic acid | C-Source, carboxylic acid |
| 1,2-Propanediol | C-Source, alcohol |
| Tween 40 | C-Source, fatty acid |
| a-Ketoglutaric acid | C-Source, carboxylic acid |
| a-Ketobutyric acid | C-Source, carboxylic acid |
| a-Methyl-D-Galactoside | C-Source, carbohydrate |
| a-D-Lactose | C-Source, carbohydrate |
| Lactulose | C-Source, carbohydrate |
| Sucrose | C-Source, carbohydrate |
| Uridine | C-Source, carbohydrate |
| L-Glutamine | C-Source, amino acid |
| m-Tartaric acid | C-Source, carboxylic acid |
| D-Glucose-1-Phosphate | C-Source, carbohydrate |
| D-Fructose-6-Phosphate | C-Source, carbohydrate |
| Tween 80 | C-Source, fatty acid |
| a-Hydroxyglutaric acid-g-Lactone | C-Source, carboxylic acid |
| a-Hydroxybutyric acid | C-Source, carboxylic acid |
| b-Methyl-D-Glucoside | C-Source, carbohydrate |
| Adonitol | C-Source, carbohydrate |
| Maltotriose | C-Source, carbohydrate |
| 2'-Deoxyadenosine | C-Source, carbohydrate |
| Adenosine | C-Source, carbohydrate |
| Gly-Asp | C-Source, amino acid |
| Citric acid | C-Source, carboxylic acid |
| m-Inositol | C-Source, carbohydrate |
| D-Threonine | C-Source, amino acid |
| Fumaric acid | C-Source, carboxylic acid |
| Bromosuccinic acid | C-Source, carboxylic acid |
| Propionic acid | C-Source, carboxylic acid |
| Mucic acid | C-Source, carboxylic acid |
| Glycolic acid | C-Source, carboxylic acid |
| Glyoxylic acid | C-Source, carboxylic acid |
| D-Cellobiose | C-Source, carbohydrate |
| Inosine | C-Source, carbohydrate |
| Gly-Glu | C-Source, amino acid |
| Tricarballylic acid | C-Source, carboxylic acid |
| L-Serine | C-Source, amino acid |
| L-Threonine | C-Source, amino acid |
| L-Alanine | C-Source, amino acid |
| Ala-Gly | C-Source, amino acid |
| Acetoacetic acid | C-Source, carboxylic acid |
| N-Acetyl-D-Mannosamine | C-Source, carbohydrate |
| Mono-Methylsuccinate | C-Source, carboxylic acid |
| Methylpyruvate | C-Source, ester |
| D-Malic acid | C-Source, carboxylic acid |
| L-Malic acid | C-Source, carboxylic acid |
| Gly-Pro | C-Source, amino acid |
| p-Hydroxyphenyl Acetic acid | C-Source, carboxylic acid |
| m-Hydroxyphenyl Acetic acid | C-Source, carboxylic acid |
| Tyramine | C-Source, amine |
| D-Psicose | C-Source, carbohydrate |
| L-Lyxose | C-Source, carbohydrate |
| Glucuronamide | C-Source, amide |
| Pyruvic acid | C-Source, carboxylic acid |
| L-Galactonic acid-g-Lactone | C-Source, carboxylic acid |
| D-Galacturonic acid | C-Source, carboxylic acid |
| Phenylethylamine | C-Source, amine |
| 2-Aminoethanol | C-Source, alcohol |
| Negative Control | C-Source, negative control |
| Chondroitin Sulfate C | C-Source, polymer |
| a-Cyclodextrin | C-Source, polymer |
| b-Cyclodextrin | C-Source, polymer |
| g-Cyclodextrin | C-Source, polymer |
| Dextrin | C-Source, polymer |
| Gelatin | C-Source, polymer |
| Glycogen | C-Source, polymer |
| Inulin | C-Source, polymer |
| Laminarin | C-Source, polymer |
| Mannan | C-Source, polymer |
| Pectin | C-Source, polymer |
| N-Acetyl-D-Galactosamine | C-Source, carbohydrate |
| N-Acetyl-Neuraminic acid | C-Source, carboxylic acid |
| b-D-Allose | C-Source, carbohydrate |
| Amygdalin | C-Source, carbohydrate |
| D-Arabinose | C-Source, carbohydrate |
| D-Arabitol | C-Source, carbohydrate |
| L-Arabitol | C-Source, carbohydrate |
| Arbutin | C-Source, carbohydrate |
| 2-Deoxy-D-Ribose | C-Source, carbohydrate |
| i-Erythritol | C-Source, carbohydrate |
| D-Fucose | C-Source, carbohydrate |
| 3-O-b-D-Galactopyranosyl-D-Arabinose | C-Source, carbohydrate |
| Gentiobiose | C-Source, carbohydrate |
| L-Glucose | C-Source, carbohydrate |
| D-Lactitol | C-Source, carbohydrate |
| D-Melezitose | C-Source, carbohydrate |
| Maltitol | C-Source, carbohydrate |
| a-Methyl-D-Glucoside | C-Source, carbohydrate |
| b-Methyl-D-Galactoside | C-Source, carbohydrate |
| 3-Methylglucose | C-Source, carbohydrate |
| b-Methyl-D-Glucuronic acid | C-Source, carboxylic acid |
| a-Methyl-D-Mannoside | C-Source, carbohydrate |
| b-Methyl-D-Xyloside | C-Source, carbohydrate |
| Palatinose | C-Source, carbohydrate |
| D-Raffinose | C-Source, carbohydrate |
| Salicin | C-Source, carbohydrate |
| Sedoheptulosan | C-Source, carbohydrate |
| L-Sorbose | C-Source, carbohydrate |
| Stachyose | C-Source, carbohydrate |
| D-Tagatose | C-Source, carbohydrate |
| Turanose | C-Source, carbohydrate |
| Xylitol | C-Source, carbohydrate |
| N-Acetyl-D-Glucosaminitol | C-Source, carbohydrate |
| g-Amino-N-Butyric acid | C-Source, carboxylic acid |
| d-Amino Valeric acid | C-Source, carboxylic acid |
| Butyric acid | C-Source, carboxylic acid |
| Capric acid | C-Source, carboxylic acid |
| Caproic acid | C-Source, carboxylic acid |
| Citraconic acid | C-Source, carboxylic acid |
| Citramalic acid | C-Source, carboxylic acid |
| D-Glucosamine | C-Source, carbohydrate |
| 2-Hydroxybenzoic acid | C-Source, carboxylic acid |
| 4-Hydroxybenzoic acid | C-Source, carboxylic acid |
| b-Hydroxybutyric acid | C-Source, carboxylic acid |
| g-Hydroxybutyric acid | C-Source, carboxylic acid |
| a-Keto-Valeric acid | C-Source, carboxylic acid |
| Itaconic acid | C-Source, carboxylic acid |
| 5-Keto-D-Gluconic acid | C-Source, carboxylic acid |
| D-Lactic acid Methyl Ester | C-Source, ester |
| Malonic acid | C-Source, carboxylic acid |

TABLE 7-continued

Exemplary Prebiotics/Carbon Sources

| Chemical | MoA |
|---|---|
| Melibionic acid | C-Source, carbohydrate |
| Oxalic acid | C-Source, carboxylic acid |
| Oxalomalic acid | C-Source, carboxylic acid |
| Quinic acid | C-Source, carboxylic acid |
| D-Ribono-1,4-Lactone | C-Source, carboxylic acid |
| Sebacic acid | C-Source, carboxylic acid |
| Sorbic acid | C-Source, carboxylic acid |
| Succinamic acid | C-Source, carboxylic acid |
| D-Tartaric acid | C-Source, carboxylic acid |
| L-Tartaric acid | C-Source, carboxylic acid |
| Acetamide | C-Source, amide |
| L-Alaninamide | C-Source, amide |
| N-Acetyl-L-Glutamic acid | C-Source, amino acid |
| L-Arginine | C-Source, amino acid |
| Glycine | C-Source, amino acid |
| L-Histidine | C-Source, amino acid |
| L-Homoserine | C-Source, amino acid |
| Hydroxy-L-Proline | C-Source, amino acid |
| L-Isoleucine | C-Source, amino acid |
| L-Leucine | C-Source, amino acid |
| L-Lysine | C-Source, amino acid |
| L-Methionine | C-Source, amino acid |
| L-Ornithine | C-Source, amino acid |
| L-Phenylalanine | C-Source, amino acid |
| L-Pyroglutamic acid | C-Source, amino acid |
| L-Valine | C-Source, amino acid |
| D,L-Carnitine | C-Source, carboxylic acid |
| sec-Butylamine | C-Source, amine |
| D,L-Octopamine | C-Source, amine |
| Putrescine | C-Source, amine |
| Dihydroxyacetone | C-Source, alcohol |
| 2,3-Butanediol | C-Source, alcohol |
| 2,3-Butanedione | C-Source, alcohol |
| 3-Hydroxy-2-butanone | C-Source, alcohol |

TABLE 8

Bacterial Species Detected at Low Frequency in Vaginal Samples from Vancomycin-Treated Mice

| Site | Group | Taxonomy | Mean abundance day 6 (out of 10,000) | Median abundance day 6 (out of 10,000) |
|---|---|---|---|---|
| vaginal | Vancomycin | KF008552.1.1432 D_0_Bacteria; D_1_Proteobacteria; D_2_Gammaproteobacteria; D_3_Enterobacteriales; D_4_Enterobacteriaceae; D_5_Klebsiella; D_6_Klebsiella pneumoniae | 0.291242675 | 0.024255713 |
| vaginal | Vancomycin | AB740357.1.1462 D_0_Bacteria; D_1_Proteobacteria; D_2_Gammaproteobacteria; D_3_Enterobacteriales; D_4_Enterobacteriaceae; D_5_Pantoea; D_6_Pantoea sp. NCCP-532 | 1.436524722 | 0 |
| vaginal | Vancomycin | DQ799428.1.1372 D_0_Bacteria; D_1_Verrucomicrobia; D_2_Verrucomicrobiae; D_3_Verrucomicrobiales; D_4_Verrucomicrobiaceae; D_5_Akkermansia; D_6_uncultured bacterium | 0.348310693 | 0 |
| vaginal | Vancomycin | JX094996.1.1390 D_0_Bacteria; D_1_Firmicutes; D_2_Clostridia; D_3_Clostridiales; D_4_Lachnospiraceae; D_5_Blautia; D_6_uncultured bacterium | 0.348310693 | 0 |
| vaginal | Vancomycin | EU459716.1.1286 D_0_Bacteria; D_1_Firmicutes; D_2_Clostridia; D_3_Clostridiales; D_4_Lachnospiraceae; D_5_uncultured; D_6_uncultured bacterium | 0.348310693 | 0 |
| vaginal | Vancomycin | EU457230.1.1391 D_0_Bacteria; D_1_Firmicutes; D_2_Clostridia; D_3_Clostridiales; D_4_Lachnospiraceae; D_5_Incertae Sedis; D_6_uncultured bacterium | 0.696621386 | 0 |
| vaginal | Vancomycin | EU459317.1.1373 D_0_Bacteria; D_1_Firmicutes; D_2_Clostridia; D_3_Clostridiales; D_4_Clostridiaceae 1; D_5_Clostridium sensu stricto 1; D_6_uncultured bacterium | 0.348310693 | 0 |
| vaginal | Vancomycin | HM817954.1.1353 D_0_Bacteria; D_1_Firmicutes; D_2_Clostridia; D_3_Clostridiales; D_4_Lachnospiraceae; D_5_Roseburia; D_6_uncultured bacterium | 0.348310693 | 0 |

TABLE 8-continued

Bacterial Species Detected at Low Frequency in Vaginal Samples from Vancomycin-Treated Mice

| Site | Group | Taxonomy | Mean abundance day 6 (out of 10,000) | Median abundance day 6 (out of 10,000) |
|---|---|---|---|---|
| vaginal | Vancomycin | GQ134873.1.1373 D_0_Bacteria; D_1_Firmicutes; D_2_Clostridia; D_3_Clostridiales; D_4_Clostridiaceae 1; D_5_Clostridium sensu stricto 1; D_6_uncultured bacterium | 0.348310693 | 0 |
| vaginal | Vancomycin | FJ879074.1.1494 D_0_Bacteria; D_1_Firmicutes; D_2_Clostridia; D_3_Clostridiales; D_4_Lachnospiraceae; D_5_uncultured; D_6_uncultured bacterium | 0.348310693 | 0 |
| vaginal | Vancomycin | EU774816.1.1381 D_0_Bacteria; D_1_Firmicutes; D_2_Clostridia; D_3_Clostridiales; D_4_Clostridiaceae 1; D_5_Clostridium sensu stricto 1; D_6_uncultured bacterium | 0.348310693 | 0 |
| vaginal | Vancomycin | EU775614.1.1398 D_0_Bacteria; D_1_Proteobacteria; D_2_Gammaproteobacteria; D_3_Enterobacteriales; D_4_Enterobacteriaceae; D_5_Enterobacter; D_6_uncultured bacterium | 0.417063419 | 0 |

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

SEQUENCE LISTING

The patent contains a lengthy sequence listing. A copy of the sequence listing is available in electronic form from the USPTO web site (https://seqdata.uspto.gov/?pageRequest=docDetail&DocID=US11672834B2). An electronic copy of the sequence listing will also be available from the USPTO upon request and payment of the fee set forth in 37 CFR 1.19(b)(3).

What is claimed is:

1. A method of treating irritable bowel syndrome (IBS) in a human subject in need thereof, comprising administering to the subject a pharmaceutical composition comprising *Blautia hydrogenotrophica*.

2. The method of claim 1, wherein the pharmaceutical composition further comprises a pharmaceutically acceptable excipient.

3. The method of claim 1, wherein the irritable bowel syndrome (IBS) is characterized by one or more of abdominal discomfort or pain, abnormal stool passage, passage of mucus, bloating, or feeling of abdominal distension.

4. The method of claim 1, wherein the irritable bowel syndrome (IBS) is diarrhea-predominant IBS.

5. The method of claim 1, wherein the irritable bowel syndrome (IBS) is constipation-predominant IBS.

6. The method of claim 1, wherein the irritable bowel syndrome (IBS) is constipation alternating with diarrhea (alternating IBS).

7. The method of claim 1, wherein the subject has a dysbiosis.

8. The method of claim 7, wherein the dysbiosis is a gastrointestinal dysbiosis.

9. The method of claim 1, wherein the level of *Blautia hydrogenotrophica* is augmented in the gastrointestinal tract of the subject.

10. The method of claim 9, wherein the *Blautia hydrogenotrophica* engraft in the gastrointestinal tract of the subject.

11. The method of claim 1, wherein the level of a bacterial species not present in the pharmaceutical composition is augmented in the gastrointestinal tract of the subject.

12. The method of claim 1, further comprising administering a prebiotic to the subject.

13. The method of claim 12, wherein the prebiotic augments the growth of the bacterial population present in the pharmaceutical composition.

14. The method of claim 12, wherein the prebiotic comprises a monomer or polymer selected from the group consisting of arabinoxylan, xylose, soluble fiber dextran, soluble corn fiber, polydextrose, lactose, N-acetyl-lactosamine, glucose, and combinations thereof.

15. The method of claim 12, wherein the prebiotic comprises a monomer or polymer selected from the group consisting of galactose, fructose, rhamnose, mannose, uronic acids, 3'-fucosyllactose, 3'sialyllactose, 6'-sialyllactose, lacto-N-neotetraose, 2'-2'-fucosyllactose, and combinations thereof.

16. The method of claim 12, wherein the prebiotic comprises a monosaccharide selected from the group consisting of arabinose, fructose, fucose, lactose, galactose, glucose, mannose, D-xylose, xylitol, ribose, and combinations thereof.

17. The method of claim 12, wherein the prebiotic comprises a disaccharide selected from the group consisting of xylobiose, sucrose, maltose, lactose, lactulose, trehalose, cellobiose, and combinations thereof.

18. The method of claim 12, wherein the prebiotic comprises a polysaccharide, wherein the polysaccharide is xylooligosaccharide.

19. The method of claim 1, wherein the pharmaceutical composition comprises only one bacterial species.

20. The method of claim 1, wherein the method reduces inflammation in the subject.

* * * * *